US012049504B2

(12) United States Patent
Levings et al.

(10) Patent No.: US 12,049,504 B2
(45) Date of Patent: Jul. 30, 2024

(54) ANTI-HLA-A2 ANTIBODIES AND METHODS OF USING THE SAME

(71) Applicants: THE UNIVERSITY OF BRITISH COLUMBIA, Vancouver (CA); CDRD VENTURES INC., Vancouver (CA)

(72) Inventors: Megan Levings, Vancouver (CA); Paul Orban, Vancouver (CA); Nicholas Dawson, Vancouver (CA); Caroline Lamarche, Vancouver (CA); Jan Peter Bergqvist, Vancouver (CA)

(73) Assignees: The University of British Columbia; CDRD Ventures Inc.

( * ) Notice: Subject to any disclaimer, the term of this patent is extended or adjusted under 35 U.S.C. 154(b) by 773 days.

(21) Appl. No.: 16/648,967

(22) PCT Filed: Sep. 19, 2018

(86) PCT No.: PCT/CA2018/051167
§ 371 (c)(1),
(2) Date: Mar. 19, 2020

(87) PCT Pub. No.: WO2019/056099
PCT Pub. Date: Mar. 28, 2019

(65) Prior Publication Data
US 2020/0283529 A1 Sep. 10, 2020

Related U.S. Application Data

(60) Provisional application No. 62/692,386, filed on Jun. 29, 2018, provisional application No. 62/560,574, filed on Sep. 19, 2017.

(51) Int. Cl.
C07K 16/28 (2006.01)
A61K 35/17 (2015.01)
A61P 37/06 (2006.01)
C07K 14/705 (2006.01)
C07K 14/725 (2006.01)

(52) U.S. Cl.
CPC .......... *C07K 16/2833* (2013.01); *A61K 35/17* (2013.01); *A61P 37/06* (2018.01); *C07K 14/7051* (2013.01); *C07K 14/70517* (2013.01); *C07K 14/70521* (2013.01); *C07K 14/70578* (2013.01); *C07K 2317/24* (2013.01); *C07K 2317/33* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,229,275 A | 7/1993 | Goroff | |
| 5,350,674 A | 9/1994 | Boenisch et al. | |
| 5,399,346 A | 3/1995 | Anderson et al. | |
| 5,530,101 A * | 6/1996 | Queen .................. | C07K 16/465 424/143.1 |
| 5,567,610 A | 10/1996 | Borrebaeck et al. | |
| 5,580,859 A | 12/1996 | Felgner et al. | |
| 5,585,362 A | 12/1996 | Wilson | |
| 5,589,466 A | 12/1996 | Felgner et al. | |
| 5,641,870 A | 6/1997 | Rinderknecht et al. | |
| 5,677,425 A | 10/1997 | Bodmer et al. | |
| 5,858,358 A | 1/1999 | June et al. | |
| 5,883,223 A | 3/1999 | Gray | |
| 6,326,193 B1 | 12/2001 | Liu et al. | |
| 6,352,694 B1 | 3/2002 | June et al. | |
| 6,534,055 B1 | 3/2003 | June et al. | |
| 6,692,964 B1 | 2/2004 | June et al. | |
| 6,703,199 B1 | 3/2004 | Koide | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |

(Continued)

FOREIGN PATENT DOCUMENTS

| | | |
|---|---|---|
| EP | 0404097 B1 | 9/1996 |
| WO | 1993/011161 A1 | 6/1993 |

(Continued)

OTHER PUBLICATIONS

Maus et al. (Cancer Immunol Res. 2013, 1:26-31) (Year: 2013).*
Nakauchi Yusuke et al., "Effective treatment against severe graft-versus-host disease with allele-specific anti-HLA monoclonal antibody in a humanized mouse model", Experimental Hematology, Feb. 2015, vol. 43, No. 2, pp. 79-88.e1-4 (14 pp.) doi: 10.1016/j.exphem.2014.10.008.
Yamazaki Satoshi et al., "A rapid and efficient strategy to generate allele-specific anti-HLA monoclonal antibodies", Journal of Immunological Methods, Mar. 31, 2009, vol. 343, No. 1, pp. 56-60 (5 pp.), doi: 10.1016/j.jim.2009.01.007.

(Continued)

*Primary Examiner* — Sharon X Wen
(74) *Attorney, Agent, or Firm* — Steptoe LLP; Z. Ying Li; Wyan-Ching M. Lee

(57) ABSTRACT

Provided are humanized anti-HLA-A2 antibodies. In certain aspects, the humanized anti-HLA-A2 antibodies are capable of constituting an antigen binding domain of a chimeric antigen receptor (CAR), where the CAR is capable of being expressed in a human cell such that the CAR specifically binds to HLA-A2. Also provided are CARs that include the humanized anti-HLA-A2 antibodies. Modified cells including the antibodies and CARs, as well as methods of using such modified cells are also provided.

18 Claims, 38 Drawing Sheets

Specification includes a Sequence Listing.

(56) References Cited

U.S. PATENT DOCUMENTS

| | | | |
|---|---|---|---|
| 7,175,843 | B2 | 2/2007 | June et al. |
| 7,232,566 | B2 | 6/2007 | June et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 9,102,760 | B2 | 8/2015 | June et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2006/0200869 | A1 | 9/2006 | Naldini et al. |
| 2007/0036773 | A1 | 2/2007 | Cooper et al. |
| 2007/0071675 | A1 | 3/2007 | Wu et al. |
| 2011/0158957 | A1 | 6/2011 | Bonini et al. |
| 2012/0060230 | A1 | 3/2012 | Collingwood et al. |
| 2012/0321667 | A1 | 12/2012 | Sentman |
| 2014/0068797 | A1 | 3/2014 | Doudna et al. |
| 2016/0024470 | A1 | 1/2016 | Aarvak et al. |
| 2020/0283530 | A1 | 9/2020 | Zhou et al. |

FOREIGN PATENT DOCUMENTS

| | | | |
|---|---|---|---|
| WO | | 2001/029058 A1 | 4/2001 |
| WO | | 2001/077342 A1 | 10/2001 |
| WO | | 2001/096584 A2 | 12/2001 |
| WO | | 2007/065957 A2 | 6/2007 |
| WO | | 2007/110785 A2 | 10/2007 |
| WO | | 2011/058321 A1 | 5/2011 |
| WO | | 2012/138475 A1 | 10/2012 |
| WO | | 2014/020922 A1 | 2/2014 |
| WO | | 2018/001874 A1 | 1/2018 |
| WO | | 2018/183293 A1 | 10/2018 |
| WO | WO 2019/056106 | | 3/2019 |
| WO | WO 2010/137295 | | 9/2020 |

OTHER PUBLICATIONS

Larson Rebecca C. and Maus Marcela V., "Recent advances and discoveries in the mechanisms and functions of CAR T cells", Nature Reviews Cancer, Mar. 2021, vol. 21, No. 3, pp. 145-161 (17 pp.), doi: 10.1038/s41568-020-00323-z.

Dawson Nicholas Aj et al., "Systematic testing and specificity mapping of alloantigen-specific chimeric antigen receptors in regulatory T cells", Journal of Clinical Investigation Insight, Mar. 21, 2019, vol. 4, No. 6, Article e123672, doi: 10.1172/jci.insight.123672.

Dawson Nicholas Aj et al., "Systematic testing and specificity mapping of alloantigen-specific chimeric antigen receptors in regulatory T cells", Journal of Clinical Investigation Insight, Mar. 21, 2019, vol. 4, No. 6, Article e123672, doi: 10.1172/jci.insight.123672—Supplementary Figures.

Dawson A. J. Nicholas and Levings Megan K., "Antigen-specific regulatory T cells: are police CARs the answer?", Translational Research, Sep. 2017, vol. 187, pp. 53-58 (6 pp.), doi: 10.1016/j.trsl.2017.06.009.

Fan Chia-Yu et al., "De novo protein sequencing, humanization and in vitro effects of an antihuman CD34 mouse monoclonal antibody", Biochemistry Biophysics Reports (2017) vol. 9, pp. 51-60 (10 pp.), doi: 10.1016/j.obrep.2016.11.006.

Zhang Yi-Fan and Ho Mitchell, "Humanization of high-affinity antibodies targeting glypican-3 in hepatocellular carcinoma", Sep. 26, 2016, vol. 6, Article 33878, doi: 10.1038/srep33878.

Sarah E Allan et al., "Generation of potent and stable human CD4+ T regulatory cells by activation-independent expression of FOXP3", Molecular Therapy: The Journal of the American Society of Gene Therapy, Jan. 2008, vol. 16, No. 1, pp. 194-202 (9 pp.), doi: 10.1038/sj.mt.6300341.

Rodolphe Barrangou et al., "CRISPR provides acquired resistance against viruses in prokaryotes", Science, Mar. 23, 2007, vol. 315, No. 5819, pp. 1709-1712 (4 pp.), doi: 10.1126/science.1138140.

David M Barrett et al., "Relation of clinical culture method to T-cell memory status and efficacy in xenograft models of adoptive immunotherapy", NIH Public Access Author Manuscript, Cytotherapy, May 2014, vol. 16, No. 5, pp. 619-630 (12 pp.), doi: 10.1016/j.jcyt.2013.10.013.

Barbara E Bierer et al., "Cyclosporin A and FK506: molecular mechanisms of immunosuppression and probes for transplantation biology", Current Opinion in Immunology, Oct. 1993, vol. 5, No. 5, pp. 763-773 (11 pp.), doi: 10.1016/0952-7915(93)90135-f.

J Bitinaite et al., "FokI dimerization is required for DNA cleavage", Proceedings of the National Academy of Sciences of the United States of America, Sep. 1, 1998, vol. 95, No. 18, pp. 10570-10575 (6 pp.), doi: 10.1073/pnas.95.18.10570.

Dan Blat et al., "Suppression of murine colitis and its associated cancer by carcinoembryonic antigen-specific regulatory T cells", Molecular Therapy: The Journal of the American Society of Gene Therapy, May 2014, vol. 22, No. 5, pp. 1018-1028 (11 pp.), doi: 10.1038/mt.2014.41.

Jeffery A Bluestone et al., "Type 1 diabetes immunotherapy using polyclonal regulatory T cells", HHS Public Access Author Manuscript, Science Translational Medicine, Nov. 25, 2015, vol. 7, No. 315, Article 315ra189 (15 pp.), doi: 10.1126/scitranslmed.aad4134.

D A Boardman et al., "Expression of a Chimeric Antigen Receptor Specific for Donor HLA Class I Enhances the Potency of Human Regulatory T Cells in Preventing Human Skin Transplant Rejection", American Journal of Transplantation, Apr. 2017, vol. 17, No. 4, pp. 931-943 (13 pp.), doi: 10.1111/ajt.

Jens Boch et al., "Breaking the code of DNA binding specificity of TAL-type III effectors", Science, Dec. 11, 2009, vol. 326, No. 5959, pp. 1509-1512 (4 pp.), doi: 10.1126/science.1178811.

Jens Boch, "TALEs of genome targeting", Nature Biotechnology, Feb. 2011, vol. 29, No. 2, pp. 135-136 (2 pp.), doi: 10.1038/nbt.1767.

Sandrine Boissel et al., "MegaTALs: a rare-cleaving nuclease architecture for therapeutic genome engineering", Nucleic Acids Research, Feb. 2014, vol. 42, No. 4, pp. 2591-2601 (11 pp.), doi: 10.1093/nar/gkt1224.

Claudio G Brunstein et al., "Infusion of ex vivo expanded T regulatory cells in adults transplanted with umbilical cord blood: safety profile and detection kinetics", Blood, Jan. 20, 2011, vol. 117, No. 3, pp. 1061-1070 (10 pp.), doi: 10.1182/blood-2010-07-293795.

Claudio G Brunstein et al., "Adoptive transfer of umbilical cord blood-derived regulatory T cells and early viral reactivation", HHS Public Access Author Manuscript, Biology of Blood Marrow Transplantation, Aug. 2013, vol. 19, No. 8, pp. 1271-1273 (3 pp.), doi: 10.1016/j.bbmt.2013.06.004.

D R Burton, "Immunoglobulin G: functional sites", Molecular Immunology, Mar. 1985, vol. 22, No. 3, pp. 161-206 (46 pp.), doi: 10.1016/0161-5890(85)90151-8.

Dana Carroll, "Genome engineering with zinc-finger nucleases", Genetics Society of America, Aug. 2011, vol. 188, No. 4, pp. 773-782 (10 pp.), doi: 10.1534/genetics.111.131433.

Monica Casucci and Attilio Bondaza, "Suicide gene therapy to increase the safety of chimeric antigen receptor-redirected T lymphocytes", Journal of Cancer, 2011, vol. 2, pp. 378-382 (5 pp.), doi: 10.7150/jca.2.378.

Toni Cathomen and J Keith Joung, "Zinc-finger nucleases: the next generation emerges", Molecular Therapy, Jul. 2008, vol. 16, No. 7, pp. 1200-1207 (8 pp.), doi: 10.1038/mt.2008.

Tomas Cermak et al., "Efficient design and assembly of custom TALEN and other TAL effector-based constructs for DNA targeting", Nucleic Acids Research, Jul. 2011, vol. 39, No. 12, Article e82 (11 pp.), doi: 10.1093/nar/gkr218.

A S Chong and S H Khiew, "Transplantation tolerance: don't forget about the B cells", Clinical and Experimental Immunology, Aug. 2017, vol. 189, No. 2, pp. 171-180 (10 pp.), doi: 10.1111/cei.12927.

Cyrus Chothia an Arthur M Lesk, "Canonical structures for the hypervariable regions of immunoglobulins", Journal of Molecular Biology, Aug. 20, 1987, vol. 196, No. 4, pp. 901-917 (17 pp.), doi: 10.1016/0022-2836(87)90412-8.

T Clackson et al., "Making antibody fragments using phage display libraries", Nature, Aug. 15, 1991, vol. 352, No. 6336, pp. 624-628 (5 pp.), doi: 10.1038/352624a0.

(56) References Cited

OTHER PUBLICATIONS

Le Cong et al., "Multiplex genome engineering using CRISPR/Cas systems", HHS Public Access Author Manuscript, Science, Feb. 15, 2013, vol. 339, No. 6121, pp. 819-823 (5 pp.), doi: 10.1126/science.

Kenneth R Cooke et al., "An experimental model of idiopathic pneumonia syndrome after bone marrow transplantation: I. The roles of minor H antigens and endotoxin", Blood, Oct. 15, 1996, vol. 88, No. 8, pp. 3230-3239 (10 pp.).

Sarah Q Crome et al., "Natural killer cells regulate diverse T cell responses", Trends in Immunology, Jul. 2013, vol. 34, No. 7, pp. 342-349 (8 pp.), doi: 10.1016/j.it.2013.03.002.

Sarah Q Crome et al., "A distinct innate lymphoid cell population regulates tumor-associated T cells", HHS Public Access Author Manuscript, Nature Medicine, Mar. 2017, vol. 23, No. 3, pp. 368-375 (8 pp.), doi: 10.1038/nm.4278.

Juliette M K M Delhove and Waseem Qasim, "Genome-Edited T Cell Therapies", Current Stem Cell Reports, 2017, vol. 3, No. 2, pp. 124-136 (13 pp.), doi: 10.1007/s40778-017-0077-5.

Mauro Di Ianni et al., "Tregs prevent GVHD and promote immune reconstitution in HLA-haploidentical transplantation", Blood, Apr. 7, 2011, vol. 117, No. 14, pp. 3921-3928 (8 pp.), doi: 10.1182/blood-2010-10-311894.

I E Dijke et al., "Discarded Human Thymus Is a Novel Source of Stable and Long-Lived Therapeutic Regulatory T Cells", American Journal of Transplantation, Jan. 2016, vol. 16, No. 1, pp. 58-71 (14 pp.), doi: 10.1111/ajt.13456.

Yannick Doyon et al., "Enhancing zinc-finger-nuclease activity with improved obligate heterodimeric architectures", Nature Methods, Jan. 2011, vol. 8, No. 1, pp. 74-79 (6 pp.), doi: 10.1038/nmeth.1539.

Narayanasamy Elango et al., "Optimized transfection of mRNA transcribed from a d(A/T)100 tail-containing vector", Biochemical and Biophysical Research Communications, May 13, 2005, vol. 330, No. 3, pp. 958-966 (9 pp.), doi: 10.1016/j.bbrc.2005.03.067.

Kevin W Eliceiri et al., "Biological imaging software tools", NIH Publi Access Author Manuscript, Nature Methods, Jun. 28, 2012, vol. 9, No. 7, pp. 697-710 (14 pp.), doi: 10.1038/nmeth.2084.

Eran Elinav et al., "Redirection of regulatory T cells with predetermined specificity for the treatment of experimental colitis in mice", Gastroenterology, Jun. 2008, vol. 134, No. 7, pp. 2014-2024 (11 pp.), doi: 10.1053/j.gastro.2008.02.060.

Eran Elinav et al., "Amelioration of colitis by genetically engineered murine regulatory T cells redirected by antigen-specific chimeric receptor", Gastroenterology, May 2009, Volum 136, No. 5, pp. 1721-1731 (11 pp.), doi: 10.1053/j.gastro.2009.01.049.

J M Ellis et al., "Frequencies of HLA-A2 alleles in five U.S. population groups. Predominance of A*02011 and identification of HLA-A*0231", Human Immunology, Mar. 2000, vol. 61, No. 3, pp. 334-340 (7 pp.), doi: 10.1016/s0198-8859(99)00155-x.

Justin Eyquem et al., "Targeting a CAR to the TRAC locus with CRISPR/Cas9 enhances tumour rejection", HHS Public Access Author Manuscript, Nature, Mar. 2, 2017, vol. 543, No. 7643, pp. 113-117 (5 pp.), doi: 10.1038/nature21405.

Alyssa Fischer et al., "Histopathologic features of cutaneous acute graft-versus-host disease in T-cell-depleted peripheral blood stem cell transplant recipients", HHS Public Access Author Manuscript, The American Journal of Dermatopathology, Jul. 2015, vol. 37, No. 7, pp. 523-529 (7 pp.), doi: 10.1097/DAD.0000000000000357.

Moa Fransson et al., "CAR/FoxP3-engineered T regulatory cells target the CNS and suppress EAE upon intranasal delivery", Journal of Nueoinflammation, May 30, 2012, vol. 9, Article 112 (12 pp.), doi: 10.1186/1742-2094-9-112.

Binqing Fu et al., "Subsets of human natural killer cells and their regulatory effects", Immunology, Apr. 2014, vol. 141, No. 4, pp. 483-489 (7 pp.), doi: 10.1111/imm.12224.

R J Garland et al., "The use of Teflon cell culture bags to expand functionally active CD8+ cytotoxic T lymphocytes", Journal of Immunological Methods, Jul. 30, 1999, vol. 227, No. 1-2, pp. 53-63 (11 pp.), doi: 10.1016/s0022-1759(99)00068-x.

René Geissler et al., "Transcriptional Activators of Human Genes with Programmable DNA-Specificity", PLoS One, 2011, vol. 6, No. 5, Article e19509 (7 pp.), doi: 10.1371/journal.pone.0019509.

Saar Gill and Carl H June, "Going viral: chimeric antigen receptor T-cell therapy for hematological malignancies", Immunological Reviews, Jan. 2015, vol. 263, No. 1, pp. 68-89 (22 pp.), doi: 10.1111/imr.12243.

Dela Golshayan et al., "In vitro-expanded donor alloantigen-specific CD4+CD25+ regulatory T cells promote experimental transplantation tolerance", Blood, Jan. 15, 2007, vol. 109, No. 2, pp. 827-835 (9 pp.), doi: 10.1182/blood-2006-05-025460.

E Allison Green et al., "Pancreatic lymph node-derived CD4(+)CD25(+) Treg cells: highly potent regulators of diabetes that require Trance-Rank signals", Immunity, Feb. 2002, vol. 16, No. 2, pp. 183-191 (9 pp.), doi: 10.1016/s1074-7613(02)00279-0.

Btissem Grissa et al., "The CRISPRdb database and tools to display CRISPRs and to generate dictionaries of spacers and repeats", BMC Bioinformatics, May 23, 2007, vol. 8, Article 172 (10 pp.), doi: 10.1186/1471-2105-8-172.

Jing Guo et al., "Directed evolution of an enhanced and highly efficient FokI cleavage domain for zinc finger nucleases", HHS Public Access Author Manuscript, Journal of Molecular Biology, Jul. 2, 2010, vol. 400, No. 1, pp. 96-107 (12 pp.), doi: 10.1016/j.jmb.2010.04.060.

J B Haanen et al., "Selective expansion of cross-reactive CD8(+) memory T cells by viral variants", Journal of Experimental Medicine, Nov. 1, 1999, vol. 190, No. 9, pp. 1319-1328 (10 pp.), doi: 10.1084/jem.190.9.1319.

D J Henderson et al., "Comparison of the effects of FK-506, cyclosporin A and rapamycin on IL-2 production", Immunology, Jul. 1991, vol. 73, No. 3, pp. 316-321 (6 pp.).

Mariuzza, "The structural basis of antigen-antibody recognition," Ann Rev Biophys Biophys Chem (1987) 16:139-59.

Brinkmann and Kontermann, "The making of bispecific antibodies," MABS (2017) 9(2):182-212.

Walker et al., "New insights into the role of mast cells in autoimmunity: Evidence for a common mechanism of action?," Biochim Biophys Acta (2012) 1822(1):57-65.

Dijke et al., "B cells in transplantation," J Heart Lung Transplant (2016) 35(6):704-10.

Zhang et al., "Engineering CAR-T cells," Biomark Res (2017) 5(22):1-6.

Caroline A Schneider et al., "NIH Image to ImageJ: 25 years of image analysis", HHS Public Access Author Manuscript, Nature Methods, Jul. 2012, vol. 9, No. 7, pp. 671-675 (5 pp.), doi: 10.1038/nmeth.2089.

Leigh A Stephens et al., "Curing CNS autoimmune disease with myelin-reactive Foxp3+ Treg", European Journal of Immunology, Apr. 2009, vol. 39, No. 4, pp. 1108-1117 (10 pp.), doi: 10.1002/eji.200839073.

J Stepinski et al., "Synthesis and properties of mRNAs containing the novel 'anti-reverse' cap analogs 7-methyl(3'-O-methyl) GpppG and 7-methyl (3'-deoxy)GpppG", RNA, Oct. 2001, vol. 7, No. 10, pp. 1486-1495 (10 pp.).

Barry L Stoddard, "Homing endonucleases: from microbial genetic invaders to reagents for targeted DNA modification", HHS Public Access Author Manuscript, Structure, Jan. 12, 2011, vol. 19, No. 1, pp. 7-15 (9 pp.), doi: 10.1016/j.str.2010.12.003.

Michel Szczepek et al., "Structure-based redesign of the dimerization interface reduces the toxicity of zinc-finger nucleases", Nature Biotechnology, Jul. 2007, vol. 25, No. 7, pp. 786-793 (8 pp.), doi: 10.1038/nbt1317.

Ryo Takeuchi et al., "Engineering of customized meganucleases via in vitro compartmentalization and in cellulo optimization", HHS Public Access Author Manuscript, Methods in Molecular Biology, 2015, vol. 1239, pp. 105-132, doi: 10.1007/978-1-4939-1862-1_6.

Qizhi Tang et al., "In vitro-expanded antigen-specific regulatory T cells suppress autoimmune diabetes", The Journal of Experimental Medicine, Jun. 7, 2004, vol. 199, No. 11, pp. 1455-1465 (11 pp.), doi: 10.1084/jem.20040139.

Kristin V Tarbell et al., "CD25+ CD4+ T cells, expanded with dendritic cells presenting a single autoantigenic peptide, suppress

(56) References Cited

OTHER PUBLICATIONS autoimmune diabetes", The Journal of Experimental Medicine, Jun. 7, 2004, vol. 199, No. 11, pp. 1467-1477 (11 pp.), doi: 10.1084/jem.20040180.

Kristin V Tarbell et al., "Dendritic cell-expanded, islet-specific CD4+ CD25+ CD62L+ regulatory T cells restore hormoglycemia in diabetic NOD mice", The Journal of Experimental Medicine, Jan. 22, 2007, vol. 204, No. 1, pp. 191-201 (11 pp.), doi: 10.1084/jem.20061631.

J ten Berge et al., "Selective expansion of a peripheral blood CD8+ memory T cell subset expressing both granzyme B and L-selectin during primary viral infection in renal allograft recipients", Transplantation Proceedings, Dec. 1998, vol. 30, No. 8, pp. 3975-3977 (3 pp.), doi: 10.1016/s0041-1345(98)01309-8.

Hiroki Torikai et al., "Toward eliminating HLA class I expression to generate universal cells from allogeneic donors", Blood, Aug. 22, 2013, vol. 122, No. 8, pp. 1341-1349 (9 pp.), doi: 10.1182/blood-2013-03-478255.

Aurélie Trenado et al., "Ex vivo-expanded CD4+CD25+ immunoregulatory T cells prevent graft-versus-host-disease by inhibiting activation/differentiation of pathogenic T cells", Journal of Immunology, Jan. 15, 2006, vol. 176, No. 2, pp. 1266-1273 (8 pp.), doi: 10.4049/jimmunol.176.2.1266.

Piotr Trzonkowski et al., "First-in-man clinical results of the treatment of patients with graft versus host disease with human ex vivo expanded CD4+CD25+CD127-T regulatory cells", Clinical Immunology, Oct. 2009, vol. 133, No. 1, pp. 22-26 (5 pp.), doi: 10.1016/j.clim.2009.06.001.

Shengdar Q Tsai et al., "Dimeric CRISPR RNA-guided FokI nucleases for highly specific genome editing", HHS Public Access Author Manuscript, Nature Biotechnology, Jun. 2014, vol. 32, No. 6, pp. 569-576 (8 pp.), doi: 10.1038nbt.2908.

Julia Yuen-Shan Tsang et al., "Conferring indirect allospecificity on CD4+CD25+ Tregs by TCR gene transfer favors transplantation tolerance in mice", The Journal of Clinical Investigation, Nov. 2008, vol. 118, No. 11, pp. 3619-3628 (10 pp.), doi: 10.1172/JCI33185.

Kui-Tei et al., "Sensitive assay of RNA interference in *Drosophila* and Chinese hamster cultured cells using firefly uciferase gene as target", FEBS Letters, Aug. 18, 2000, vol. 479, No. 3, pp. 79-82 (4 pp.), doi: 10.1016/s0014-5793(00)01883-4.

Panayotis Verginis et al., "Induction of antigen-specific regulatory T cells in wild-type mice: visualization and targets of suppression", Proceedings of the National Academy of Sciences of the United States of America, Mar. 4, 2008, vol. 105, No. 9, pp. 3479-3484 (6 pp.), doi: 10.1073/pnas.0800149105.

Zhenguang Wang et al., "New development in CAR-T cell therapy", Journal of Hematology & Oncology, Feb. 21, 2017, vol. 10, No. 1, Article 53 (11 pp.), doi: 10.1186/s13045-017-0423-1.

Norihiro Watanabe et al., "Fine-tuning the CAR spacer improves T-cell potency", Oncoimmunology, Nov. 8, 2016, vol. 5, No. 12, Article e1253656 (14 pp.), doi: 10.1080/2162402X.2016.1253656.

N A Watkins et al., "The isolation and characterisation of human monoclonal HLA-A2 antibodies from an immune V gene phage display library", Tissue Antigens, Mar. 2000, vol. 55, No. 3, pp. 219-228 (10 pp.), doi: 10.1034/i.1399-0039.2000.550305.x.

Daniela Wesch et al., "Human gamma delta T regulatory cells in cancer: fact or fiction?", Frontiers in Immunology, Nov. 20, 2014, vol. 5, Article 598 (7 pp.), doi: 10.3389/fimmu.2014.00598.

Blake Wiedenheft et al., "RNA-guided genetic silencing systems in bacteria and archaea", Nature, Feb. 15, 2012, vol. 482, No. 7385, pp. 331-338 (8 pp.), doi: 10.1038/nature10886.

Andrew J Wood et al., "Targeted genome editing across species using ZFNs and TALENs", NIH Public Access Author Manuscript, Science, Jul. 15, 2011, vol. 333, No. 6040, p. 307, doi: 10.1126/science.1207773.

Kathryn J Wood et al., "Regulatory immune cells in transplantation", Nature Review Immunology, May 25, 2012, vol. 12, No. 6, pp. 417-430 (14 pp.), doi: 10.1038/nri3227.

Nan Zhang et al., "Regulatory T cells sequentially migrate from inflamed tissues to draining lymph nodes to suppress the alloimmune response", Immunity, Mar. 20, 2009, vol. 30, No. 3, pp. 458-469 (12 pp.), doi: 10.1016/j.immuni.2008.12.022.

Feng Zhang et al., "Programmable sequence-specific transcriptional regulation of mammalian genome using designer TAL effectors", HHS Public Access Author Manuscript, Nature Biotechnology, Feb. 2011, vol. 29, No. 2, pp. 149-153 (5 pp.), doi: 10.1038/nbt.1775.

Steven A Rosenberg et al., "Use of tumor-infiltrating lymphocytes and interleukin-2 in the immunotherapy of patients with metastatic melanoma. A preliminary report", New England Journal of Medicine, Dec. 22, 1988, vol. 319, No. 25, pp. 1676-1680 (5 pp.), doi: 10.1056/NEJM198812223192527.

Carole Guillonneau et al., "CD8+ regulatory T cells in solid organ transplantation", Current Opinion in Organ Transplantation, Dec. 2012, vol. 15, No. 6, pp. 751-756 (6 pp.), doi: 10.1097/MOT.0b013e32834016d1.

Gerardo Zapata et al., "Engineering linear F(ab')2 fragments for efficient production in *Escherichia coli* and enhanced antiproliferative activity", Protein Engineering, Design and Selection, Oct. 1995, vol. 8, No. 10, pp. 1057-1062 (6 pp.), doi: 10.1093/protein/8.10.1057.

Sofia Mumtaz et al., "Design of liposomes for circumventing the reticuloendothelial cells", Glycobiology, Nov. 1991, vol. 1, No. 5, pp. 505-510 (6 pp.), doi: 10.1093/glycob/1.5.505.

Nicolas Cougot et al., "Cap-tabolism", Trends in Biochemical Sciences, Aug. 2004, vol. 29, No. 8, pp. 436-444 (9 pp.), doi: 10.1016/j.tibs.2004.06.008.

Makiya Nishikawa and Leaf Huang, "Nonviral vectors in the new millennium: delivery barriers in gene transfer", Human Gene Therapy, May 20, 2001, vol. 12, No. 8, pp. 861-870 (10 pp.), doi: 10.1089/104303401750195836.

Lutz Riechmann et al., "Reshaping human antibodies for therapy", Nature, Mar. 24, 1988, vol. 332, No. 6162, pp. 323-327 (5 pp.), doi: 10.1038/332323a0.

Mark A Batzer et al., "Enhanced evolutionary PCR using oligonucleotides with inosine at the 3'-terminus", Nucleic Acids Research, Sep. 25, 1991, vol. 19, No. 18, p. 5081 (1 p.), doi: 10.1093/nar/19.18.5081.

Tessa Gargett and Michael P Brown, "The inducible caspase-9 suicide gene system as a 'safety switch' to limit on-target, off-tumor toxicities of chimeric antigen receptor T cells", Frontiers in Immunology, Oct. 28, 2014, vol. 5, Article 235 (7 pp.), doi: 10.3389/fphar.2014.00235.

Brian Philip et al., "A highly compact epitope-based marker/suicide gene for easier and safer T-cell therapy", Blood, Aug. 21, 2014, vol. 124, No. 8, pp. 1277-1287 (11 pp.), doi: 10.1182/blood-2014-01-545020.

Erhao Zhang and Hanmei Xu, "A new insight in chimeric antigen receptor-engineered T cells for cancer immunotherapy", Journal of Hematology and Oncology, Jan. 3, 2017, vol. 10, No. 1, pp. 1 (11 pp.), doi: 10.1186/s13045-016-0379-6.

Melissa S Jurica et al., "DNA recognition and cleavage by the LAGLIDADG homing endonuclease I-CreI", Molecular Cell, Oct. 1998, vol. 2, No. 4, pp. 469-476 (8 pp.), doi: 10.1016/s1097-2765(00)80146-x.

J Sethuraman et al., "Genes within genes: multiple LAGLIDADG homing endonucleases target the ribosomal protein S3 gene encoded within an rnl group I intron of Ophiostoma and related taxa", Molecular Biology and Evolution, Oct. 2009, vol. 26, No. 10, pp. 2299-2315 (17 pp.), doi: 10.1093/molbev/msp145.

Jacob Z Dalgaard et al., "Statistical modeling and analysis of the LAGLIDADG family of site-specific endonucleases and identification of an intein that encodes a site-specific endonuclease of the HNH family", Nucleic Acids Research, Nov. 15, 1997, vol. 25, No. 22, pp. 4626-4638 (13 pp.), doi: 10.1093/nar/25.22.4626.

Sepideh Khaleghi et al., "A caspase 8-based suicide switch induces apoptosis in nanobody-directed chimeric receptor expressing T cells", International Journal of Hematology, Apr. 2012, vol. 95, No. 4, pp. 434-444 (11 pp.), doi: 10.1007/s12185-012-1037-6.

Karen E Flick et al., "DNA binding and cleavage by the nuclear intron-encoded homing endonuclease I-PpoI", Nature, Jul. 2, 1998, vol. 394, No. 6688, pp. 96-101 (6 pp.), doi: 10.1038/27952.

Brett Chevalier et al., "Flexible DNA target site recognition by divergent homing endonuclease isoschizomers I-CreI and I-MsoI",

(56) References Cited

OTHER PUBLICATIONS

Journal of Molecular Biology, May 30, 2003, vol. 329, No. 2, pp. 253-269 (17 pp.), doi: 10.1016/s0022-2836(03)00447-9.

Brett Chevalier et al., "The LAGLIDADG Homing Endonuclease Family", 2005, In: Belfort M., Wood D.W., Stoddard B.L., Derbyshire V. (eds) Homing Endonucleases and Inteins. Nucleic Acids and Molecular Biology, vol. 16. Springer, Berlin, Heidelberg., pp. 33-47 (15 pp.), https://doi.org/10.1007/3-540-29474-0_3.

International search report issued for WO 2019/056099.

Geoffrey R Hill et al., "Total body irradiation and acute graft-versus-host disease: the role of gastrointestinal damage and inflammatory cytokines", Blood, Oct. 15, 1997, vol. 90, No. 8, pp. 3204-3213 (10 pp.).

H G Hilton and P Parham, "Direct binding to antigen-coated beads refines the specificity and cross-reactivity of four monoclonal antibodies that recognize polymorphic epitopes of HLA class I molecules", HHS Public Access Author Manuscript, Tissue Antigens. Apr. 2013, vol. 81, No. 4, pp. 212-220 (9 pp.), doi: 10.1111/tan.12095.

Megan E Himmel et al., "Helios+ and Helios- cells coexist within the natural FOXP3+ T regulatory cell subset in humans", Journal of Immunology, Mar. 1, 2013, vol. 190, No. 5, pp. 2001-2008 (8 pp.), doi: 10.4049/jimmunol.

Dirk Hockemeyer et al., "Genetic engineering of human pluripotent cells using TALE nucleases", HHS Public Access Author Manuscript, Nature Biotechnology, Jul. 7, 2011, vol. 29, No. 8, pp. 731-734 (4 pp.), doi: 10.1038/nbt.1927.

P Holliger et al., "'Diabodies': small bivalent and bispecific antibody fragments", Proceedings of the National Academy of Sciences of the United States of America, Jul. 15, 1993, vol. 90, No. 14, pp. 6444-6448 (5 pp.), doi: 10.1073/pnas.90.14.6444.

A A Hombach et al., "Redirecting human CD4+CD25+ regulatory T cells from the peripheral blood with pre-defined target specificity", Gene Therapy, Sep. 2009, vol. 16, No. 9, pp. 1088-1096 (9 pp.), doi: 10.1038/gt.2009.75.

Philippe Horvath and Rodolphe Barrangou, "CRISPR/Cas, the immune system of bacteria and archaea", Science, Jan. 8, 2010, vol. 327, No. 5962, pp. 167-170 (4 pp.), doi: 10.1126/science.1179555.

James A Hutchinson et al., "MITAP-compliant characterization of human regulatory macrophages", Transplant International, Aug. 2017, vol. 30, No. 8, pp. 765-775 (11 pp.), doi: 10.1111/tri.12988.

Fatemeh Rahimi Jamnani et al., "T cells expressing VHH-directed oligoclonal chimeric HER2 antigen receptors: towards tumor-directed oligoclonal T cell therapy", Biochimica et Biophysica Acta, Jan. 2014, vol. 1840, No. 1, pp. 378-386 (9 pp.), doi: 10.1016/j.bbagen.2013.09.029.

Olivier Joffre et al., "Prevention of acute and chronic allograft rejection with CD4+CD25+Foxp3+ regulatory T lymphocytes", Nature Medicine, Jan. 2008, vol. 14, No. 1, pp. 88-92 (5 pp.), doi: 10.1038/nm1688.

P T Jones et al., "Replacing the complementarity-determining regions in a human antibody with those from a mouse", Nature, May 29-Jun. 4, 1986, vol. 321, No. 6069, pp. 522-525 (4 pp.), doi: 10.1038/321522a0.

Benjamin S Jones et al., "Improving the safety of cell therapy products by suicide gene transfer", Frontiers in Pharmacology, Nov. 27, 2014, vol. 5, Article 254 (8 pp.), doi: 10.3389/fphar.2014.00254.

Carl H June et al., "Adoptive cellular therapy: a race to the finish line", Science Translational Medicine, Mar. 25, 2015, vol. 7, No. 280, Article 280ps7 (8 pp.), doi: 10.1126/scitranslmed.aaa3643.

Carl H June, "Adoptive T cell therapy for cancer in the clinic", Journal of Clinical Investigation, Jun. 2007, vol. 117, No. 6, pp. 1466-1476 (11 pp.), doi: 10.1172/JCI32446.

Stephen C Juvet and Li Zhang, "Double negative regulatory T cells in transplantation and autoimmunity: recent progress and future directions", Journal of Molecular and Cellular Biology, Feb. 2012, vol. 4, No. 1, pp. 48-58 (11 pp.), doi: 10.1093/jmcb/mjr043.

Jean Kanitakis, "The challenge of dermatopathological diagnosis of composite tissue allograft rejection: a review", Journal of Cutaneous Pathology, Aug. 2008, vol. 35, No. 8, pp. 738-744 (7 pp.), doi: 10.1111/i.1600-0560.2007.00889.x.

Y G Kim et al., "Hybrid restriction enzymes: zinc finger fusions to Fok I cleavage domain", Proceedings of the National Academy of Sciences of the United States of America, Feb. 6, 1996, vol. 93, No. 3, pp. 1156-1160 (5 pp.), doi: 10.1073/pnas.93.3.1156.

G Kohler and C Milstein, "Continuous cultures of fused cells secreting antibody of predefined specificity", Nature, Aug. 7, 1975, vol. 256, No. 5517, pp. 495-497 (3 pp.), doi: 10.1038/256495a0.

Ana Konvalinka and Kathryn Tinckam, "Utility of HLA Antibody Testing in Kidney Transplantation", Journal of the American Society of Nephrology, Jul. 2015, vol. 26, No. 7, pp. 1489-1502 (14 pp.), doi: 10.1681/ASN.2014080837.

Megan K Levings et al., "Human CD25(+)CD4(+) T regulatory cells suppress naive and memory T cell proliferation and can be expanded in vitro without loss of function", The Journal of Experimental Medicine, Jun. 4, 2001, vol. 193, No. 11, pp. 1295-1302 (7 pp.), doi: 10.1084/jem.193.11.1295.

Nan Li et al., "Therapeutically targeting glypican-2 via single-domain antibody-based chimeric antigen receptors and immunotoxins in neuroblastoma", Proceedings of the National Academy of Sciences, Aug. 8, 2017, vol. 114, No. 32, E6623-E6631 (9 pp.), doi: 10.1073/pnas.1706055114.

Jun Liu et al., "Calcineurin is a common target of cyclophilin-cyclosporin A and FKBP-FK506 complexes", Cell, Aug. 23, 1991, vol. 66, No. 4, pp. 807-815 (9 pp.), doi: 10.1016/0092-8674(91)90124-h.

Katherine G MacDonald et al., "Alloantigen-specific regulatory T cells generated with a chimeric antigen receptor", Journal of Clinical Investigation, Mar. 21, 2016, vol. 126, No. 4, pp. 1413-1424 (12 pp.), doi: 10.1172/JCI82771.

Kira S Makarova et al., "A putative RNA-interference-based immune system in prokaryotes: computational analysis of the predicted enzymatic machinery, functional analogies with eukaryotic RNAi, and hypothetical mechanisms of action", Biology Direct, Mar. 16, 2006, vol. 1, Article 7 (26 pp.), doi: 10.1186/1745-6150-1-7.

Natalia Marek-Trzonkowska et al., "Administration of CD4+CD25highCD127—regulatory T cells preserves β-cell function in type 1 diabetes in children", Diabetes Care, Sep. 2012, vol. 35, No. 9, pp. 1817-1820, doi: 10.2337/dc12-0038.

J D Marks et al., "By-passing immunization. Human antibodies from V-gene libraries displayed on phage", Journal of Molecular Biology, Dec. 5, 1991, vol. 222, No. 3, pp. 581-597 (17 pp.), doi: 10.1016/0022-2836(91)90498-u.

Luciano A Marraffini and Erik J Sontheimer, "CRISPR interference limits horizontal gene transfer in *Staphylococci* by targeting DNA", HHS Public Access Author Manuscript, Science, Dec. 19, 2008, vol. 322, No. 5909, pp. 1843-1845 (3 pp.), doi: 10.1126/science.1165771.

Daniela Massi et al., "A reappraisal of the histopathologic criteria for the diagnosis of cutaneous allogeneic acute graft-vs-host disease", American Journal of Clinical Pathology, Dec. 1999, vol. 112, No. 6, pp. 791-800 (10 pp.).

Emma L Masteller et al., "Expansion of functional endogenous antigen-specific CD4+CD25+ regulatory T cells from nonobese diabetic mice", Journal of Immunology, Sep. 1, 2005, vol. 175, No. 5, pp. 3053-3059 (7 pp.), doi: 10.4049/jimmunol.175.5.3053.

Alicia N McMurchy and Megan K Levings, "Suppression assays with human T regulatory cells: a technical guide", European Journal of Immunology, Jan. 2012, vol. 42, No. 1, pp. 27-34 (8 pp.), doi: 10.1002/eji.201141651.

Jeffery C Miller et al., "A Tale nuclease architecture for efficient genome editing", Nature Biotechnology, Feb. 2011, vol. 29, No. 2, pp. 143-148 (6 pp.), doi: 10.1038/nbt.1755.

Michael C Milone et al., "Chimeric receptors containing CD137 signal transduction domains mediate enhanced survival of T cells and increased antileukemic efficacy in vivo", Molecular Therapy, Aug. 2009, vol. 17, No. 8, pp. 1453-1464 (12 pp.), doi: 10.1038/mt.2009.83.

Matthew J Moscou and Adam J Bogdanove, "A simple cipher governs DNA recognition by TAL effectors", Science, Dec. 11, 2009, vol. 326, No. 5959, p. 1501, doi: 10.1126/science.1178817.

(56) References Cited

OTHER PUBLICATIONS

Genovega A Nacheva and Alfredo Berzal-Herranz, "Preventing nondesired RNA-primed RNA extension catalyzed by T7 RNA polymerase", European Journal of Biochemistry, Apr. 2003, vol. 270, No. 7, pp. 1458-1465 (8 pp.), doi: 10.1046/j.1432-1033.2003.03510.x.
Bruno Nervi et al., "Factors affecting human T cell engraftment, trafficking, and associated xenogeneic graft-vs-host disease in NOD/SCID beta2mnull mice", NIH Public Access Author Manuscript, Experimental Hematology, Dec. 2007, vol. 35, No. 12, pp. 1823-1838 (16 pp.), doi: 10.1016/j.exphem.2007.06.007.
Eiji Nishimura et al., "Induction of antigen-specific immunologic tolerance by in vivo and in vitro antigen-specific expansion of naturally arising Foxp3+CD25+CD4+ regulatory T cells", International Immunology, Aug. 2004, vol. 16, No. 8, pp. 1189-1201 (13 pp.), doi: 10.1093/intimm/dxh122.
F Noyan et al., "Prevention of Allograft Rejection by Use of Regulatory T Cells With an MHC-Specific Chimeric Antigen Receptor", American Journal of Transplantation, Apr. 2017, vol. 17, No. 4, pp. 917-930 (14 pp.), doi: 10.1111/ajt.14175.
E Ohtsuka et al., "An alternative approach to deoxyoligonucleotides as hybridization probes by insertion of deoxyinosine at ambiguous codon positions", Journal of Biological Chemistry, Mar. 10, 1985, vol. 260, No. 5, pp. 2605-2608 (4 pp.).
Mark Osborn et al., "Evaluation of TCR Gene Editing Achieved by TALENs, CRISPR/Cas9, and megaTAL Nucleases", Molecular Therapy, Mar. 2016, vol. 24, No. 3, pp. 570-581 (12 pp.), doi: 10.1038/mt.2015.197.
Gabor Papp et al., "Regulatory immune cells and functions in autoimmunity and transplantation immunology", Autoimmune Reviews, May 2017, vol. 16, No. 5, pp. 435-444 (10 pp.), doi: 10.1016/j.autrev.2017.03.011.
P Parham and F M Brodsky, "Partial purification and some properties of BB7.2. A cytotoxic monoclonal antibody with specificity for HLA-A2 and a variant of HLA-A28", Human Immunology, Dec. 1981, vol. 3, No. 4, pp. 277-299 (23 pp.), doi: 10.1016/0198-8859(81)90065-3.
Elizabeth Pennisi, "The CRISPR craze", Science, Aug. 23, 2013, vol. 341, No. 6148, pp. 833-836 (4 pp.), doi: 10.1126/science.341.6148.833.
L G Presta, "Antibody engineering", Current Opinion in Structural Biology, Aug. 1992, vol. 3, No. 4, pp. 394-398 (5 pp.), doi: 10.1016/0958-1669(92)90168-i.
Elena Provasi et al., "Editing T cell specificity towards leukemia by zinc finger nucleases and lentiviral gene transfer", HHS Public Access Author Manuscript, Nature Medicine, May 2012, vol. 18, No. 5, pp. 807-815 (9 pp.), doi: 10.1038/nm.2700.
A L Putnam et al., "Clinical grade manufacturing of human alloantigen-reactive regulatory T cells for use in transplantation", American Journal of Transplantation, Nov. 2013, vol. 13, No. 11, pp. 3010-3020 (11 pp.), doi: 10.1111/ajt.12433.
James Robinson et al., "The IPD and IMGT/HLA database: allele variant databases", Nucleic Acids Research, Jan. 2015, vol. 43, pp. D423-D431 (9 pp.), doi: 10.1093/nar/gku1161.
G M Rossolini et al., "Use of deoxyinosine-containing primers vs degenerate primers for polymerase chain reaction based on ambiguous sequence information", Molecular and Cellular Probes, Apr. 1994, vol. 8, No. 2, pp. 91-98 (8 pp.), doi: 10.1006/mcpr.1994.1013.
Michel Sadelain et al., "The basic principles of chimeric antigen receptor design", Cancer Discovery, Apr. 2013, vol. 3, No. 4, pp. 388-398 (11 pp.), doi: 10.1158/2159-8290.CD-12-0548.
Pervinder Sagoo et al., "Human regulatory T cells with alloantigen specificity are more potent inhibitors of alloimmune skin graft damage than polyclonal regulatory T cells", Science Translational Medicine, May 18, 2011, vol. 3, No. 83, Article 83ra42, doi: 10.1126/scitranslmed.3002076.
Alberto Sanchez-Fueyo et al., "Specificity of CD4+CD25+ regulatory T cell function in alloimmunity", HHS Public Access Author Manuscript, Journal of Immunology, Jan. 1, 2006, vol. 176, No. 1, pp. 329-334 (6 pp.), doi: 10.4049/jimmunol.176.1.329.
Michelle Scalley-Kim et al., "Coevolution of a homing endonuclease and its host target sequence", HHS Public Access Author Manuscript, Journal of Molecular Biology, Oct. 5, 2007, vol. 372, No. 5, pp. 1305-1319 (15 pp.), doi: 10.1016/j.jmb.2007.07.052.
E T Schenborn and R C Mierendorf Jr, "A novel transcription property of SP6 and T7 RNA polymerases: dependence on template structure" Nucleic Acids Research, Sep. 11, 1985, vol. 13, No. 17, pp. 6223-6236 (14 pp.), doi: 10.1093/nar/13.17.6223.
Thomas D Schmittgen and Kenneth J Livak, "Analyzing real-time PCR data by the comparative C(T) method", Nature Protocols, vol. 3, No. 6, pp. 1101-1108 (8 pp.), doi: 10.1038/nprot.2008.73.
U.S. Appl. No. 16/649,426, filed Mar. 20, 2020.
Altschul et al., "Basic local alignment search tool", Journal of Molecular Biology, Oct. 5, 1990, vol. 215, No. 3, pp. 403-410 (8 pp.), doi: 10.1016/S0022-2836(05)80360-2.
Delgado et al., "Enhanced tumour specificity of an anti-carcinoembrionic antigen Fab' fragment by poly(ethylene glycol) (PEG) modification", British Journal of Cancer, Jan. 1996, vol. 73, No. 2, pp. 175-182 (8 pp.), doi: 10.1038/bjc.1996.32.
Green et al., "Antigen-specific human monoclonal antibodies from mice engineered with human Ig heavy and light chain YACs", Nature Genetics, May 1994, vol. 7, No. 1, pp. 13-21 (9 pp.), doi: 10.1038/ng0594-13.
Holliger et al., "Engineered antibody fragments and the rise of single domains", Nature Biotechnology, Sep. 2005, vol. 23, No. 9, pp. 1126-1136 (11 pp.), doi: 10.1038/nbt1142.
Honegger et al., "Yet another No.ing scheme for immunoglobulin variable domains: an automatic modeling and analysis tool", Journal of Molecular Biology, Jun. 8, 2001, vol. 309, No. 3, pp. 657-670 (14 pp.), doi: 10.1006/jmbi.2001.4662.
Lefranc et al., "IMGT, the international ImMunoGeneTics database", Nucleic Acids Research, Jan. 1, 1999, vol. 27, No. 1, pp. 209-212 (4 pp.), doi: 10.1093/nar/27.1.209.
Leong et al., "Adapting pharmacokinetic properties of a humanized anti-interleukin-8 antibody for therapeutic applications using site-specific pegylation", Cytokine, Nov. 7, 2001, vol. 16, No. 3, pp. 106-119 (14 pp.), doi: 10.1006/cyto.2001.0936.
Lonberg et al., "Antigen-specific human antibodies from mice comprising four distinct genetic modifications", Nature, Apr. 28, 1994, vol. 368, No. 6474, pp. 856-859 (4 pp.), doi: 10.1038/368856a0.
McCafferty et al., "Phage antibodies: filamentous phage displaying antibody variable domains", Nature, Dec. 6, 1990, vol. 348, No. 6301, pp. 552-553 (2 pp.), doi: 10.1038/348552a0.
Morrison et al., "Chimeric human antibody molecules: mouse antigen-binding domains with human constant region domains", Proceedings of the National Academy of Sciences of the United States of America, Nov. 1984, vol. 81, No. 21, pp. 6851-6855 (5 pp.), doi: 10.1073/pnas.81.21.6851.
Queen et al., "A humanized antibody that binds to the interleukin 2 receptor," Proc. Natl. Acad. Sci. (1989) 86(24):10029-33.
Ruiz et al., "IMGT, the international ImMunoGeneTics database", Nucleic Acids Research, Jan. 1, 2000, vol. 28, No. 1, pp. 219-221 (3 pp.), doi: 10.1093/nar/28.1.219.
Scatchard, "The attractions of proteins for small molecules and ions", Annals of the New York Academy of Sciences, May 1949, vol. 51, pp. 660-672 (13 pp.) (1949) doi:10.1111/j.1749-6632.1949.tb27297.x.
Taylor et al., "Human immunoglobulin transgenes undergo rearrangement, somatic mutation and class switching in mice that lack endogenous IgM", International Immunology, Apr. 1994, vol. 6, No. 4, pp. 579-591 (13 pp.), doi: 10.1093/intimm/6.4.579.
Pan et al., "Blocking Neuropilin-1 Function Has an Additive Effect with Anti-VEGF to Inhibit Tumor Growth", Cancer Cell (2007) 11:53-67.
Brunner et al., "Cytotoxic T cells: Double-barreled shot guns", Nature Medicine (1999) 5(1):Abstract.
Rosano et al., "Recombinant Protein Expression in *Escherichia coli*: Advances and Challenges", Frontiers in Microbiology (2014) 5(172):1-17, doi: 10.3389/fmicb.2014.00172.
Macdonald, K. G et al., Alloantigen-specific regulatory T cells generated with a chimeric antigen receptor. J Clin Invest, vol. 126, Issue No. 4, pp. 1413-1424 (Apr. 2016).†

(56) References Cited

OTHER PUBLICATIONS

Parham, p et al., Partial purification and some properties of BB7.2. A cytotoxic monoclonal antibody with specificity for HLA-A2 and a variant of HLA-A28. Hum Immunol, vol. 3, Issue No. 4, pp. 277-299 (Dec. 1981).†

Dawson, N. A et al., Systematic testing and specificity mapping of alloantigen-specific chimeric antigen receptors in regulatory T cells. JCI Insight, vol. 4, Issue No. 6, p. e123672 (Mar. 2019).†

Riechmann, L et al. Reshaping human antibodies for therapy. Nature, vol. 332, Issue No. 6162, pp. 323-327 (Mar. 1988).†

Queen, C et al., A humanized antibody that binds to the interleukin 2 receptor. Proc. Natl. Acad. Sci. USA, vol. 86, Issue No. 24, p. 10029-10033 (Dec. 1989).†

\* cited by examiner
† cited by third party

D

A

B

C

D

F

G

H

A

B

C

D

A

B

E

F

G

ANTI-HLA-A2 ANTIBODIES AND METHODS OF USING THE SAME

CROSS-REFERENCE TO RELATED APPLICATIONS

This application is a national stage application under 35 U.S.C. § 371 of International Patent Application No. PCT/CA2018/051167, filed Sep. 19, 2018, which claims the benefit of U.S. Provisional Patent Application Ser. No. 62/560,574, filed Sep. 19, 2017, and U.S. Provisional Patent Application Ser. No. 62/692,386, filed Jun. 29, 2018. The disclosures of those applications are incorporated by reference herein in their entirety.

FIELD OF THE INVENTION

The present invention relates in some aspects to HLA-A2 binding molecules, in particular, to humanized anti-HLA-A2 antibodies. The present invention further relates to recombinant receptors containing such antibodies, including chimeric antigen receptors (CARs), which contain such antibodies. The disclosure further relates to genetically engineered cells expressing such receptors and antibodies, and use thereof in cell therapy.

BACKGROUND OF THE INVENTION

Class I HLA antigens are polymorphic proteins expressed on all nucleated cells and are critical targets for immune recognition in the context of transplantation. Indeed, the development of HLA class I specific T cells and/or antibodies are major risk factors for acute and chronic rejection and allograft, and the presence of pre-formed anti-donor HLA Class I antibodies can result in hyper-acute rejection (Konvalinka et al., 2015). Thus finding ways to control the immune response to HLA Class I proteins would be a major breakthrough in transplantation.

Classical HLA Class I molecules are polymorphic and encoded by many different alleles which have evolved in response to evolutionary pressure from infections. There are three loci that encode the classical HLA Class I proteins, which are named the A, B and C loci. Within the HLA-A locus, the HLA-A2 family of alleles is the largest and most diverse family, with at least 31 different HLA-A2 alleles known to exist in humans. Interestingly, contrary to many other HLA allele families, HLA-A2 is frequent in all ethnic groups, and is found in 50% of Caucasians and 35% of African-Americans (Ellis et al., 2000). Many HLA-A2 alleles differ by only 1 to 9 amino acids, with the majority of the polymorphism centered around the peptide binding groove (Hilton et al., 2013). HLA-A2 alleles are subgrouped into two main branches: those derived via interallelic gene conversion events from A*0201 or A*0205 (Ellis et al., 2000).

Adoptive immunotherapy with T regulatory (Treg) cells as a way to control unwanted immunity to HLA proteins and other antigens that drive transplant rejection is a promising treatment for allograft rejection and graft-versus-host disease (GVHD). The use of polyclonal Treg cell transfer in the prevention of graft-versus-host disease (GVHD) after allogeneic hematopoietic stem cell transplantation (HSCT) has been reported (Brunstein et al., 2011; Di Ianni et al., 2011; Trzonkowski et al., 2009). The use of Treg cell transfer in the maintenance of c-peptide levels in type 1 diabetes has also been reported (Bluestone et al., 2015; Marek-Trzonkowska et al., 2012). Notably, it has been reported that there may be a transient risk of generalized immunosuppression associated with the use of polyclonal Treg cells for such cell therapy (Brunstein et al., 2013).

Data from animal studies indicate that the potency and specificity of cell therapy with Treg cells can be significantly enhanced by the use of antigen-specific cells. For example, in models of autoimmunity, antigen-specific Treg cells are superior to polyclonal Treg cells in reducing disease: Treg cells isolated from pancreatic lymph nodes or pulsed with islet antigen are significantly better at preventing or curing type 1 diabetes than are polyclonal Treg cells (Green et al., 2002; Masteller et al., 2005; Tang et al., 2004; Tarbell et al., 2007; Tarbell et al., 2004), and Treg cells expressing an autoantigen-specific transgenic T cell receptor (TCR) are superior to polyclonal Treg cells at suppressing central nervous system inflammation in a model of experimental autoimmune encephalomyelitis (EAE) (Stephens et al., 2009). Similarly, alloantigen-specific Treg cells, enriched by alloantigen-stimulated expansion in vitro, or engineered to express a TCR transgene, are more effective than polyclonal Treg cells at preventing rejection of organ and tissue grafts (Golshayan et al., 2007; Joffre et al., 2008; Nishimura et al., 2004; Sanchez-Fueyo et al., 2006; Tsang et al., 2008). There is some evidence that Treg cells expanded with alloantigens effectively prevent GVHD (Trenado et al., 2006) and that in vivo induction of antigen-specific Treg cells promotes acceptance of hematopoietic allografts without GVHD (Verginis et al., 2008). Humanized mouse models have shown similar results: alloantigen-expanded human Treg cells are more potent suppressors of skin graft rejection than are polyclonal Treg cells (Putnam et al., 2013; Sagoo et al., 2011).

An alternate approach to over-expressing transgenic TCRs or antigen-stimulated expansion to enrich for antigen-specific T cells is the use of chimeric antigen receptors (CARs). In cell-based adoptive immunotherapy, immune cells isolated from a patient can be modified to express synthetic proteins that enable the cells to perform new therapeutic functions after they are subsequently transferred back into the patient. An example of such a synthetic protein is a CAR. An example of a currently used CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell. For example, T cells may be genetically engineered to express extracellular single-chain antibody (scFv) antigen binding domains fused to intracellular signaling domains (Gill and June, 2015; June et al., 2015). In particular, Treg cells expressing CARs specific for model antigens have been reported (Blat et al., 2014; Elinav et al., 2009; Elinav et al., 2008; Fransson et al., 2012; Hombach et al., 2009, Boardman et al., 2016; MacDonald et al., 2016; Noyan et al., 2016).

SUMMARY

Aspects of the present disclosure include anti-HLA-A2 antibodies. Chimeric antigen receptors (CARs) including an extracellular domain including any of the anti-HLA-A2 antibodies of the present disclosure are also provided. Nucleic acids encoding the anti-HLA-A2 antibodies and CARs of the present disclosure, expression vectors including same, and host cells including such expression vectors are also provided. Aspects of the present disclosure also include humanized anti-HLA-A2 antibodies. Chimeric antigen receptors (CARs) including an extracellular domain including any of the humanized anti-HLA-A2 antibodies of the present disclosure are also provided. Nucleic acids encoding the humanized anti-HLA-A2 antibodies and CARs of the present disclosure, expression vectors including same, and host cells including such expression vectors are also provided. Also provided are immune cells, e.g., immune regulatory cells, which include the CARs and/or expression vectors of the present disclosure, compositions and pharmaceutical compositions including such immune cells, kits of parts including such immune cells and/or reagents (e.g., a nucleic acid or vector encoding an anti-HLA-A antibody or CAR of the present disclosure) for making such immune cells, and methods of making such immune cells. Methods of using the anti-HLA-A2 antibodies, CARs, immune cells, and pharmaceutical compositions of the present disclosure are also provided. For example, the subject anti-HLA-A2 antibodies, CARs, immune cells (e.g., immune regulatory cells), and pharmaceutical compositions find use, e.g., in promoting immune tolerance in a subject, preventing or treating graft versus host disease (GVHD) in a subject, preventing or treating organ or tissue transplant rejection in a subject, and the like.

In some embodiments, provided is a humanized anti-HLA-A2 antibody, where the antibody is capable of constituting an antigen binding domain of a chimeric antigen receptor (CAR), where the CAR is capable of being expressed in a human cell (e.g., a human immune cell, such as a human immune regulatory cell) such that the CAR specifically binds to HLA-A2. In certain aspects, such antibodies compete for binding to HLA-A2 with an antibody including: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190.

In certain aspects, provided is a humanized anti-HLA-A2 antibody, where the antibody competes for binding to HLA-A2 with an antibody including: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190.

According to certain embodiments, a humanized anti-HLA-A2 antibody as set forth above binds to the same HLA-A2 epitope as an antibody including: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190.

In some embodiments, a humanized anti-HLA-A2 antibody of the present disclosure has less reactivity to at least one HLA-A subtype selected from one or more of HLA-A*03, HLA-A*25, HLA-A*29, HLA-A*30, HLA-A*31, HLA-A*33, HLA-A*36, HLA-A*68, and any combination thereof, as compared to a BB7.2 antibody. For example, in some embodiments, a humanized anti-HLA-A2 antibody of the present disclosure has less reactivity to at least one HLA-A subtype selected from one or more of HLA-A*25, HLA-A*29, HLA-A*30, and any combination thereof, as compared to a BB7.2 antibody.

In certain aspects, a humanized anti-HLA-A2 antibody of the present disclosure includes a heavy chain variable region including an amino acid sequence selected from the group consisting of: SYHIQ (SEQ ID NO: 1) and GYTFTSY (SEQ ID NO: 2).

According to certain embodiments, a humanized anti-HLA-A2 antibody of the present disclosure includes a heavy chain variable region including an amino acid sequence selected from the group consisting of: YPGDGS (SEQ ID NO: 4) and WIYPGDGSTX$^{10}$YX$^{12}$X$^{13}$KFX$^{16}$G (SEQ ID NO: 10), where X$^{10}$ is Q or K, X$^{12}$ is N or S, X$^{13}$ is E or Q, and X$^{16}$ is K or Q. Such an antibody may include, e.g., a heavy chain variable region including an amino acid sequence selected from the group consisting of: WIYPGDGSTQYNEKFKG (SEQ ID NO: 3) and YPGDGS (SEQ ID NO: 4). Also by way of example, such an antibody may include, e.g., a heavy chain variable region including the amino acid sequence WIYPGDGSTKYSQKFQG (SEQ ID NO: 5). In certain aspects, a humanized antibody of the present disclosure includes a heavy chain variable region including the amino acid sequence EGTYYAMDY (SEQ ID NO: 6).

In some embodiments, a humanized anti-HLA-A2 antibody of the present disclosure includes a light chain variable region including the amino acid sequence RSSQSIVHSNGNTYLE (SEQ ID NO: 7). In certain aspects, a humanized antibody of the present disclosure includes a light chain variable region including the amino acid sequence KVSNRFS (SEQ ID NO: 8). According to some embodiments, a humanized antibody of the present disclosure includes a light chain variable region including the amino acid sequence FQGSHVPRT (SEQ ID NO: 9).

In certain aspects, a humanized anti-HLA-A2 antibody of the present disclosure includes a heavy chain variable region including a framework region 1 (VH FR1) including an amino acid sequence selected from the group consisting of:

```
                                        (SEQ ID NO: 11)
QVQLVQSGAEVKKPGASVKVSCKAS
and (SEQ ID NO: 12)
QVQLVQSGAEVKKPGASVKVSCKASGYTFT.
```

According to certain embodiments, a humanized anti-HLA-A2 antibody of the present disclosure includes a heavy chain variable region including a framework region 2 (VH FR2) including an amino acid sequence selected from the group consisting of:

WVRQAPGQX$^9$LEWMGX$^{15}$ (SEQ ID NO: 13),
WVRQAPGQX$^9$LEWMGX$^{15}$WI (SEQ ID NO: 17),
HIQWVRQAPGQX$^{12}$LEWMGX$^{18}$WI (SEQ ID NO: 21), and
HIQWVRQAPGQX$^{12}$LEWMGX$^{18}$ (SEQ ID NO: 25), where:

$X^9$ is R or G and $X^{15}$ is I or absent in SEQ ID NO: 13;
$X^9$ is R or G, and $X^{15}$ is I or absent in SEQ ID NO: 17;
$X^{12}$ is R or G, and $X^{18}$ is I or absent in SEQ ID NO: 21; and
$X^{12}$ is R or G, and $X^{18}$ is I or absent in SEQ ID NO: 25.

In some embodiments, a humanized anti-HLA-A2 antibody of the present disclosure includes a heavy chain variable region including a framework region 3 (VH FR3) including an amino acid sequence selected from the group consisting of:

X$^1$VTX$^4$TX$^6$DTSX$^{10}$STAYMX$^{16}$LSX$^{19}$LRSX$^{23}$DX$^{25}$A VYYCAR (SEQ ID NO: 29),
TX$^2$YX$^4$X$^5$KFXGX$^{10}$VTX$^{13}$TX$^{15}$DTSX$^{19}$STAYMX$^{25}$ LSX$^{28}$LRSX$^{32}$DX$^{34}$AVYYCAR (SEQ ID NO: 35),
TQYNEKFKGX$^{10}$VTX$^{13}$TX$^{15}$DTSX$^{19}$STAYMX$^{25}$LS X$^{28}$LRSX$^{32}$DX$^{34}$AVYYCAR (SEQ ID NO: 36), and
TKYSQKFQGX$^{10}$VTX$^{13}$TX$^{15}$DTSX$^{19}$STAYMX$^{25}$LS X$^{28}$LRSX$^{32}$DX$^{34}$AVYYCAR (SEQ ID NO: 37), where:

$X^1$ is R or absent, $X^4$ is I or M, $X^6$ is R or A, $X^{10}$ is A, T or I, $X^{16}$ is E or L, $X^{19}$ is S or R, $X^{23}$ is E or D, and $X^{25}$ is T or M in SEQ ID NO: 29;
$X^2$ is Q or K, $X^4$ is N or S, $X^5$ is E or Q, $X^8$ is K or Q, $X^{10}$ is R or absent, $X^{13}$ is I or M, $X^{15}$ is R or A, $X^{19}$ is A, T or I, $X^{25}$ is E or L, $X^{28}$ is S or R, $X^{32}$ is E or D, and $X^{34}$ is T or M in SEQ ID NO: 35;
$X^{10}$ is R or absent, $X^{13}$ is I or M, $X^{15}$ is R or A, $X^{19}$ is A, T or I, $X^{25}$ is E or L, $X^{28}$ is S or R, $X^{32}$ is E or D, and $X^{34}$ is T or M in SEQ ID NO: 36; and
$X^{10}$ is R or absent, $X^{13}$ is I or M, $X^{15}$ is R or A, $X^{19}$ is A, T or I, $X^{25}$ is E or L, $X^{28}$ is S or R, $X^{32}$ is E or D, and $X^{34}$ is T or M in SEQ ID NO: 37.

In certain aspects, a humanized anti-HLA-A2 antibody of the present disclosure includes a heavy chain variable region including a framework region 4 (VH FR4) including the amino acid sequence WGQGTTVTVSS (SEQ ID NO: 44). According to certain embodiments, a humanized anti-HLA-A2 antibody of the present disclosure includes a heavy chain variable region including an amino acid sequence selected from the group consisting of SEQ ID NOs: 61-66.

According to certain embodiments, a humanized anti-HLA-A2 antibody of the present disclosure includes a light chain variable region including a framework region 1 (VL FR1) including the amino acid sequence DX$^2$VMTQX$^7$PLSX$^{11}$X$^{12}$VTX$^{15}$GQPASISX$^{23}$ (SEQ ID NO: 46), where $X^2$ is V or I, $X^7$ is S or T, $X^{11}$ is L or S, $X^{12}$ is P or S, $X^{15}$ is L or P, and $X^{23}$ is C or F.

In some embodiments, a humanized anti-HLA-A2 antibody of the present disclosure includes a light chain variable region including a framework region 2 (VL FR2) including the amino acid sequence WX$^2$X$^3$QX$^5$PGQX$^9$PX$^{11}$X$^{12}$LIY (SEQ ID NO: 51), where $X^2$ is F or Y, $X^3$ is Q or L, $X^5$ is R or K, $X^9$ is S or P, $X^{11}$ is R or Q, and $X^{12}$ is R or L.

In certain aspects, a humanized anti-HLA-A2 antibody of the present disclosure includes a light chain variable region including a framework region 3 (VL FR3) including the amino acid sequence GVPDRFSGSGX$^{11}$GTDFTLKISRVEAEDVGVYYC (SEQ ID NO: 56), where $X^{11}$ is S or A. According to certain embodiments, a humanized anti-HLA-A2 antibody of the present disclosure includes a light chain variable region including a framework region 4 (VL FR4) including the amino acid sequence FGGGTKVEIK (SEQ ID NO: 59). In some embodiments, a humanized anti-HLA-A2 antibody of the present disclosure includes a light chain variable region including an amino acid sequence selected from the group consisting of SEQ ID NOs: 67-71. In some embodiments, a humanized anti-HLA-A2 antibody of the present disclosure is a whole antibody, a single chain antibody, a dimeric single chain antibody, a Fv, a scFv, a Fab, a F(ab)'$_2$, a defucosylated antibody, a bi-specific antibody, a diabody, a triabody, a tetrabody, an antibody fragment selected from the group consisting of a unibody, a domain antibody, and a nanobody or an antibody mimetic selected from the group consisting of an affibody, an alphabody, an armadillo repeat protein based scaffold, a knottin, a kunitz domain peptide, an affilin, an affitin, an adnectin, an atrimer, an evasin, a DARPin, an anticalin, an avimer, a fynomer, a versabody or a duocalin.

According to certain embodiments, a humanized anti-HLA-A2 antibody of the present disclosure is an scFv. For example, a humanized anti-HLA-A2 antibody of the present disclosure may be an scFv including an amino acid sequence selected from the group consisting of SEQ ID NOs: 72-91.

In some embodiments, provided is a humanized anti-HLA-A2 antibody as set forth above, where the antibody is capable of constituting an antigen binding domain of a chimeric antigen receptor (CAR), where the CAR is capable of being expressed in an immune cell (e.g., a T regulatory cell (Treg)) such that the CAR specifically binds to HLA-A2. In certain aspects, provided is a humanized anti-HLA-A2 antibody as set forth above, where the antibody is capable of constituting an antigen binding domain of a chimeric antigen receptor (CAR), where the CAR is capable of being expressed in an immune cell (e.g., a T regulatory cell (Treg)) such that the immune cell is activated by HLA-A2.

In certain aspects, provided is a nucleic acid encoding any of the humanized anti-HLA-A2 antibodies set forth above. Also provided is an expression vector and gene therapy vectors that include such a nucleic acid. A host cell including such an expression vector or a gene therapy vector is also provided.

Aspects of the present disclosure further include chimeric antigen receptors (CARs). For example, provided is a CAR including: (i) an extracellular domain including any of the humanized anti-HLA-A2 antibodies set forth above; (ii) a transmembrane domain; and (iii) a cytoplasmic domain including an intracellular signaling domain; where the CAR is capable of being expressed in an immune cell such that the CAR specifically binds to HLA-A2. Such a CAR may have less reactivity to at least one HLA-A subtype selected from one or more of HLA-A*03, HLA-A*25, HLA-A*29, HLA-A*30, HLA-A*31, HLA-A*33, HLA-A*36, HLA-A*68, and any combination thereof, as compared to a CAR including a BB7.2 antibody. For example, in some embodiments, such a CAR has less reactivity to at least one HLA-A subtype selected from one or more of HLA-A*25, HLA-A*29, HLA-A*30, and any combination thereof, as compared to a CAR including a BB7.2 antibody. A CAR of the present disclosure may be capable of being expressed in an immune cell (e.g., a T regulatory cell (Treg)) such that the immune cell is activated by HLA-A2. A CAR of the present disclosure may include a hinge region. In certain aspects, the hinge region includes a stalk region of CD8a.

A CAR of the present disclosure may include a transmembrane domain that includes a transmembrane domain of a protein selected from the group consisting of: CD3 gamma, CD3 delta, CD3 epsilon, CD3 zeta, the alpha chain of the T-cell receptor, the beta chain of the T-cell receptor, the gamma chain of the T-cell receptor, the delta chain of the T-cell receptor, CD28, CD45, CD4, CD5, CD8, CD9, CD16, CD22, CD33, CD37, CD64, CD80, CD86, CD134, CD137 and CD154, and any combination thereof. In some embodiments, the transmembrane domain includes a transmembrane domain of CD28.

According to certain embodiments, a CAR of the present disclosure includes an intracellular signaling domain that includes a functional signaling domain of a protein selected from the group consisting of: CD3 gamma, CD3 delta, CD3 epsilon, CD3 zeta, FcR gamma, FcR alpha, FcR epsilon, CD5, CD22, CD79a, CD79b, and CD66d, and any combination thereof. In some embodiments, the intracellular signaling domain includes a functional signaling domain of CD3 zeta. In certain aspects, the intracellular signaling domain further includes a costimulatory domain. Such a costimulatory domain may include a functional signaling domain of a protein selected from the group consisting of OX40, CD27, CD28, lymphocyte function-associated antigen-1 (LFA-1) (CD11a/CD18), TNFR1 (CD120a/TNFRSF1A), TNFR2 (CD120b/TNFRSFIB), CTLA-4 (CD152), CD95, ICOS (CD278), 4-1BB (CD137), CD2, CD30, CD40, PD-1, CD7, LIGHT, NKG2C, B7-H3, ICAM-1, a ligand that specifically binds with CD83, IL2ra (CD25), IL6Ra (CD126), IL-7Ra (CD127), IL-13RA1, IL-13RA2, IL-33R(IL1RL1), IL-10RA, IL-10RB, IL-4R, IL-5R (CSF2RB), ARHR, BAFF receptor, IL-21R, TGFbR1, TGFbR2, TGFbR3, common gamma chain, and any combination thereof. According to certain embodiments, the costimulatory domain includes a functional signaling domain of a protein selected from CD28 and 4-1BB. For example, the costimulatory domain may include a functional signaling domain of CD28.

Also provided are modified immune cells including any of the CARs of the present disclosure. In some embodiments, the modified immune cell is a T regulatory cell (Treg).

The present disclosure provides nucleic acids encoding any of the CARs of the present disclosure. Expression vectors including such nucleic acids are also provided, as are immune cells (e.g., T regulatory cells (Tregs)) including such expression vectors.

Compositions (e.g., pharmaceutical compositions) are also provided. In certain aspects, provided is a pharmaceutical composition including a plurality of modified immune cells or immune cells of the present disclosure. Kits of parts are also provided. In some embodiments, said kits of parts comprise in a first part immune cells of the present disclosure, and in a second part another therapeutic agent, such as, for example, an immunosuppressive agent. In some embodiments, said kits of parts comprise one or more reagents (e.g., a nucleic acid or expression vector encoding an anti-HLA-A antibody or CAR of the present disclosure) for making the cells of the present disclosure. Methods of making modified immune cells of the present disclosure are also provided. In some embodiments, such methods include transducing an immune cell with an expression vector of the present disclosure, thereby generating the modified immune cell.

Methods of using the antibodies, CARs, immune cells, modified immune cells, and pharmaceutical compositions of the present disclosure are also provided. In certain aspects, provided are methods of promoting immune tolerance in a subject, the methods including administering to the subject a pharmaceutical composition of the present disclosure, e.g., a pharmaceutical composition including a plurality of the modified immune cells or immune cells of the present disclosure. In some embodiments, the immune tolerance is tolerance to a transplanted organ or tissue. According to certain embodiments, provided are methods of preventing or treating graft versus host disease (GVHD) in a subject, the methods including administering to the subject a pharmaceutical composition of the present disclosure, e.g., a pharmaceutical composition including a plurality of the modified immune cells or immune cells of the present disclosure. In certain aspects, the subject is undergoing or has undergone a hematopoietic stem cell transplant. Also provided are methods of preventing or treating organ or tissue transplant rejection in a subject, the methods including administering to the subject a pharmaceutical composition of the present disclosure, e.g., a pharmaceutical composition including a plurality of the modified immune cells or immune cells of the present disclosure. In some embodiments, the subject is further receiving an immunosuppressive agent. According to certain embodiments, provided are methods of preventing or treating organ or tissue transplant rejection or graft versus host disease (GVHD) in a subject, the methods including administering to the subject a combination of an immune cell of the present disclosure with at least one immunosuppressive agent for inducing immune tolerance. In any of the methods of using the antibodies, CARs, immune cells, modified immune cells, and pharmaceutical compositions of the present disclosure, the subject may be human.

K562 cells (TCR), or HLA-A2-K562 cells (CAR). After 24 hours, expression of CD69, CD154, CTLA-4 and LAP was measured by flow cytometry on live CD4+ cells. (A & B) show representative histograms and (C & D) show averaged data from two independent experiments (E) ΔNGFR control/CAR Tregs were co-cultured with a 2:1 (Tregs: K562) ratio of HLA-A2-expressing K562 cells. After 16 hours, expression of CD69, CD71, CTLA-4 and LAP were measured by flow cytometry. Percent positive and fold increase over baseline (no K562) expression of CD69 and CD71. (F) Percent positive and fold increase over baseline (no K562) expression of CTLA-4 and LAP. Data are n=2-4 for each construct from at least two independent experiments. One-way ANOVA and Holm-Sidak's post-test comparing all constructs to mA2-CAR Tregs. Mean±SEM. * $p<0.05$,  $p<0.01$, * $p<0.001$, **** $p<0.0001$.

Figure 6:
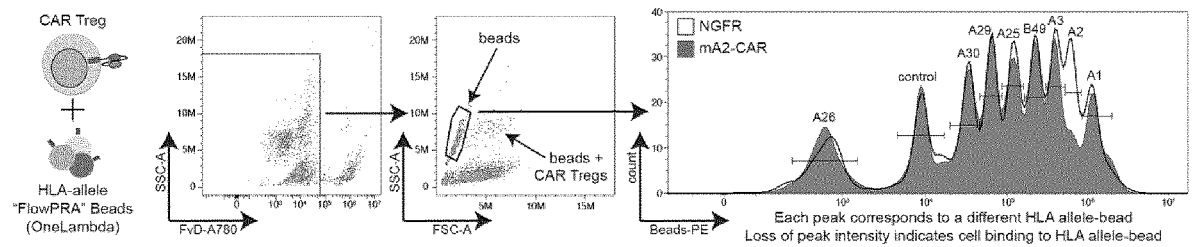
Figure 6:
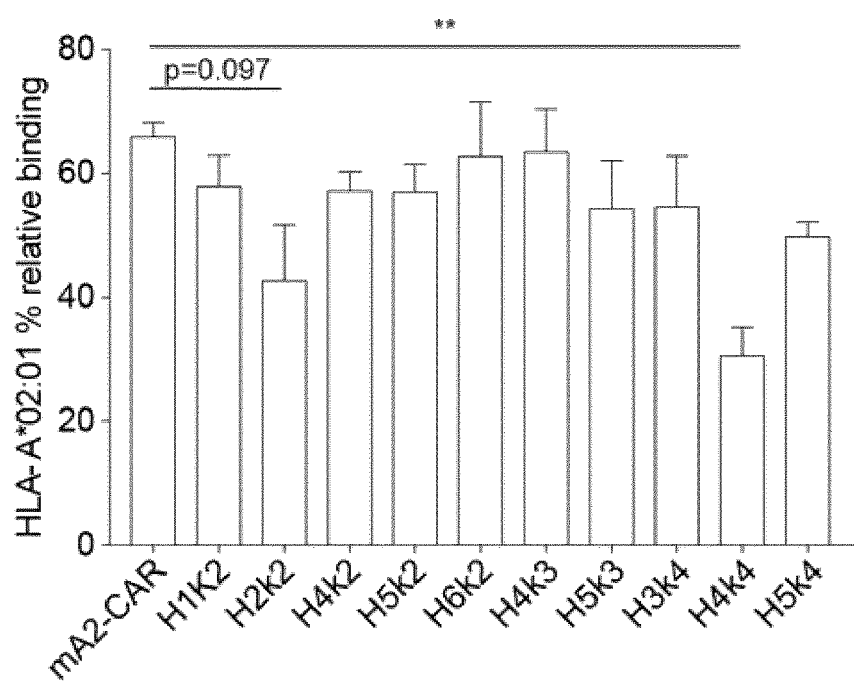
Figure 6:
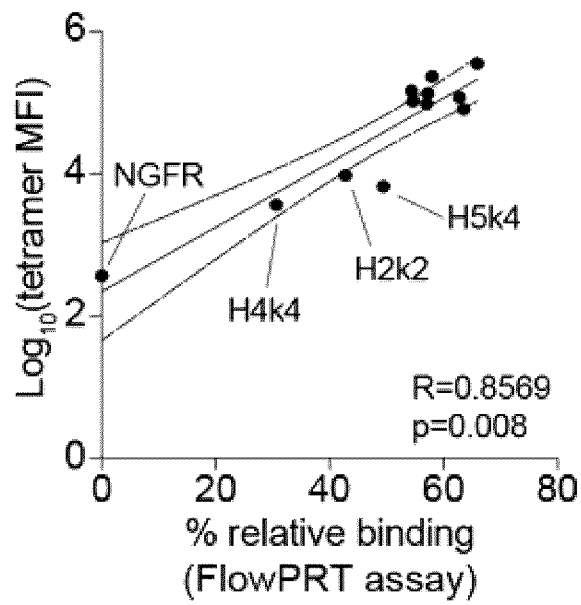
Figure 6:
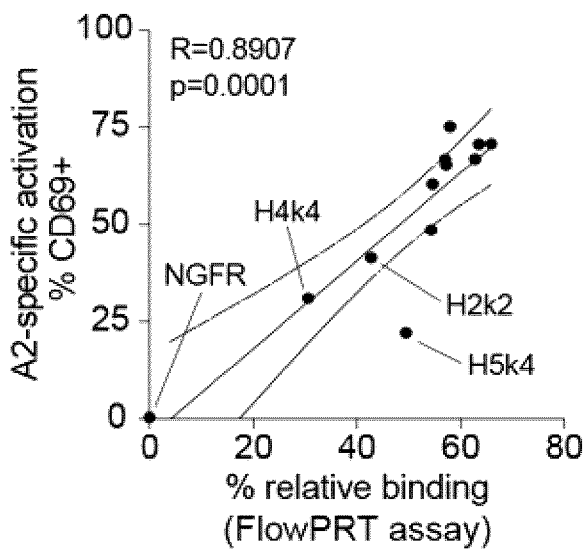
Figure 6:
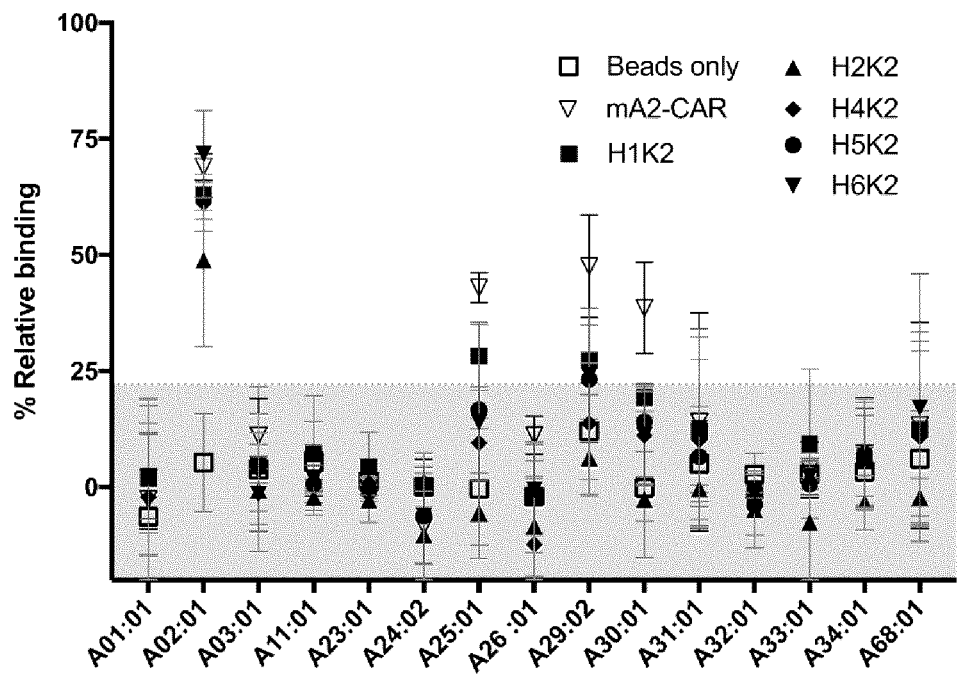
Figure 6:
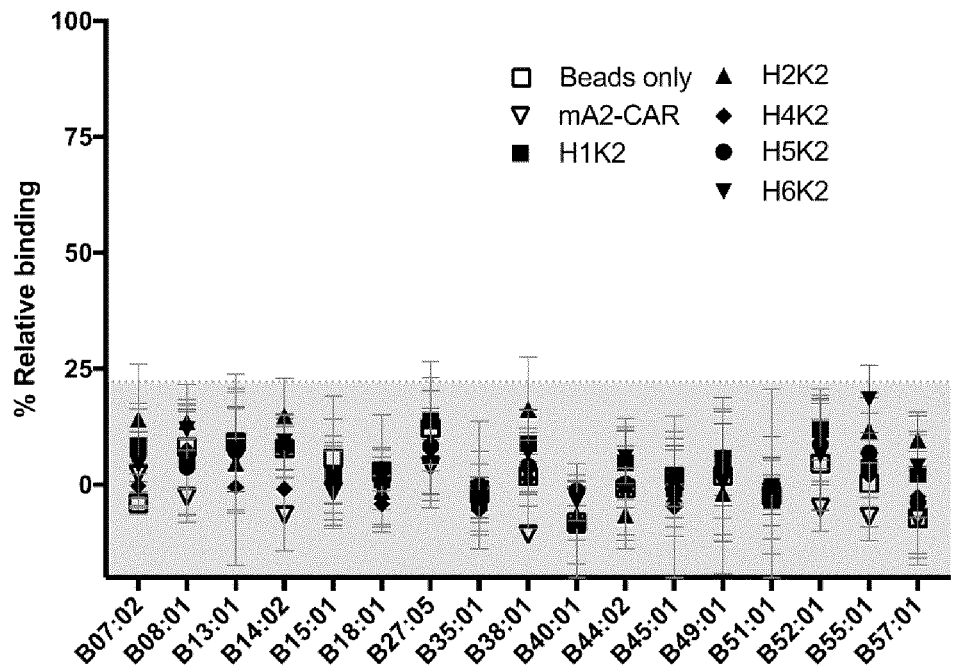
Figure 6:
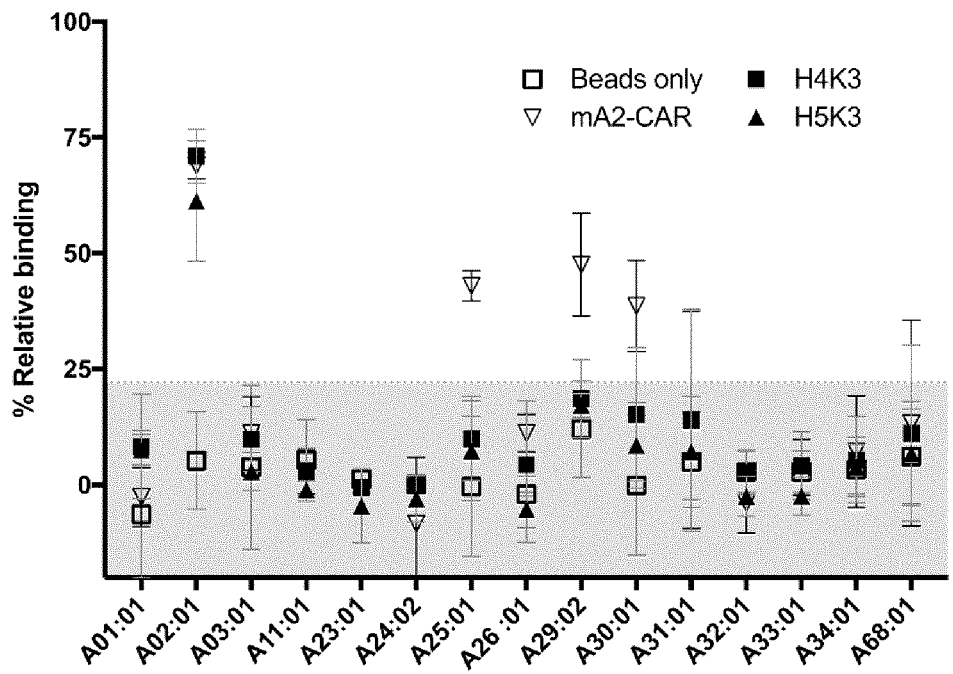
Figure 6:
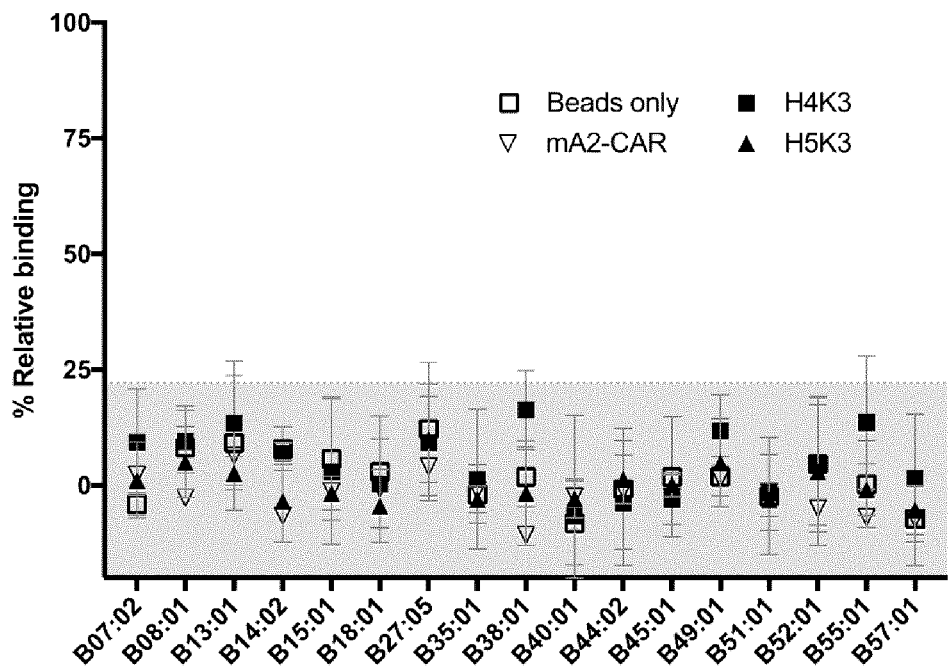
Figure 6:
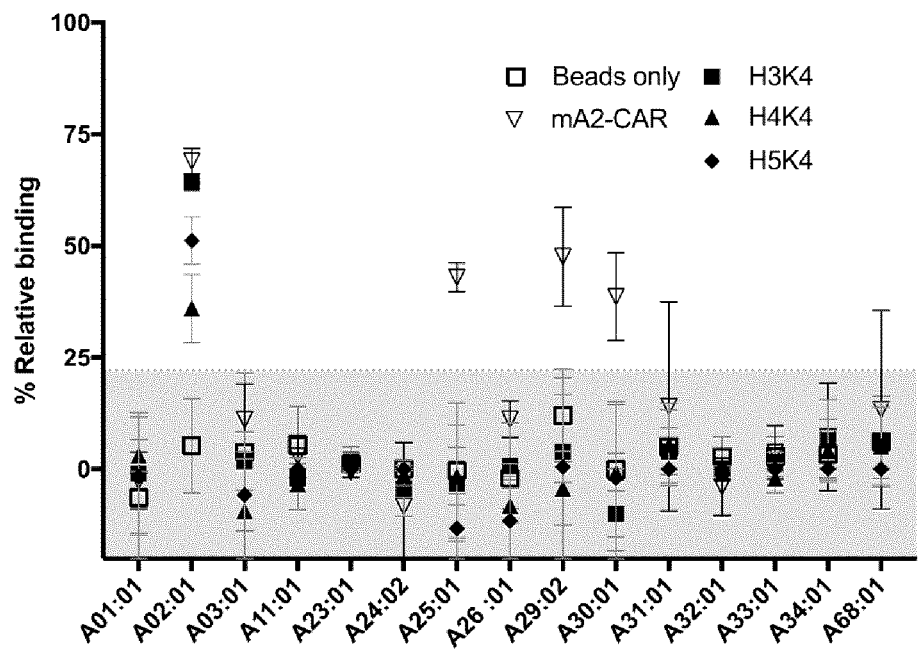
Figure 6:
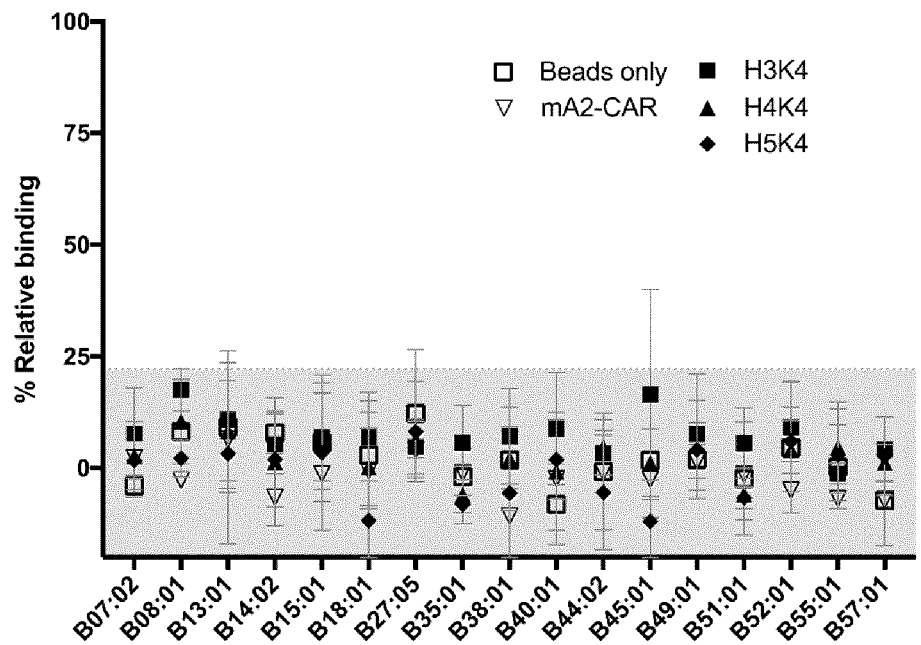
Figure 6:
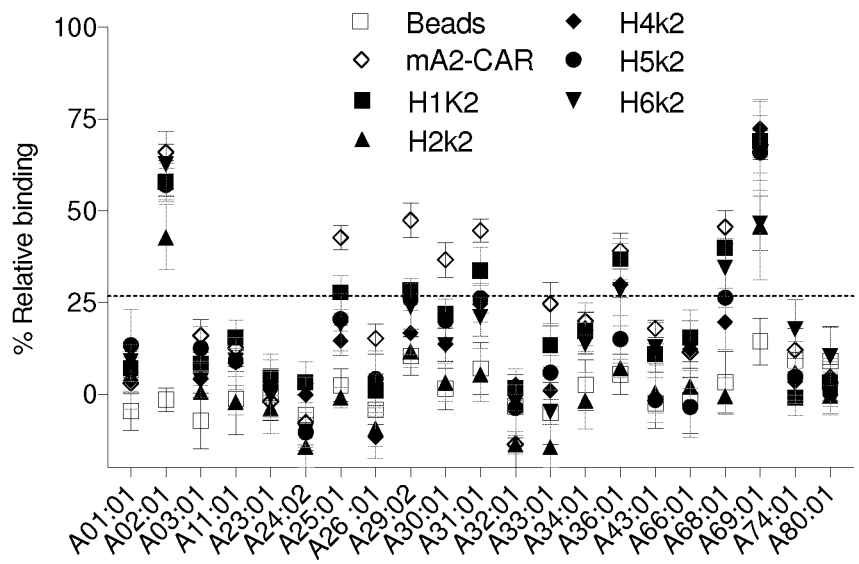
Figure 6:
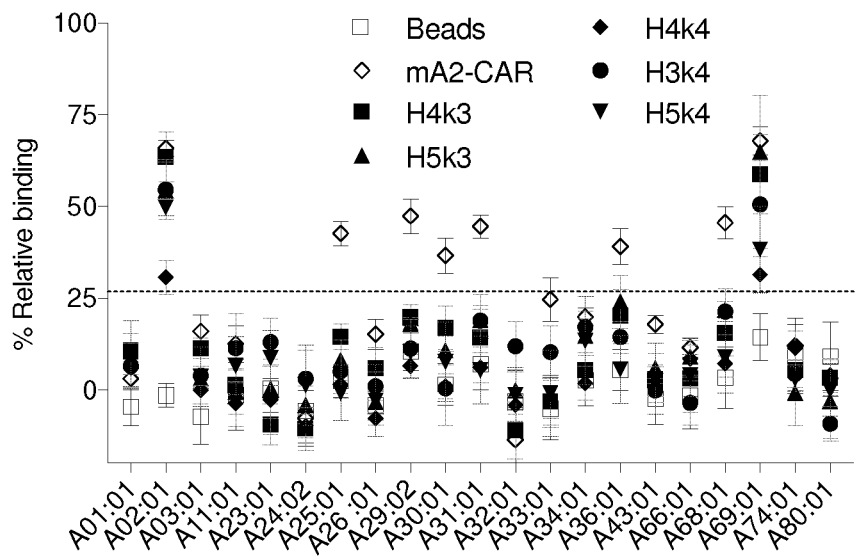
Figure 6:
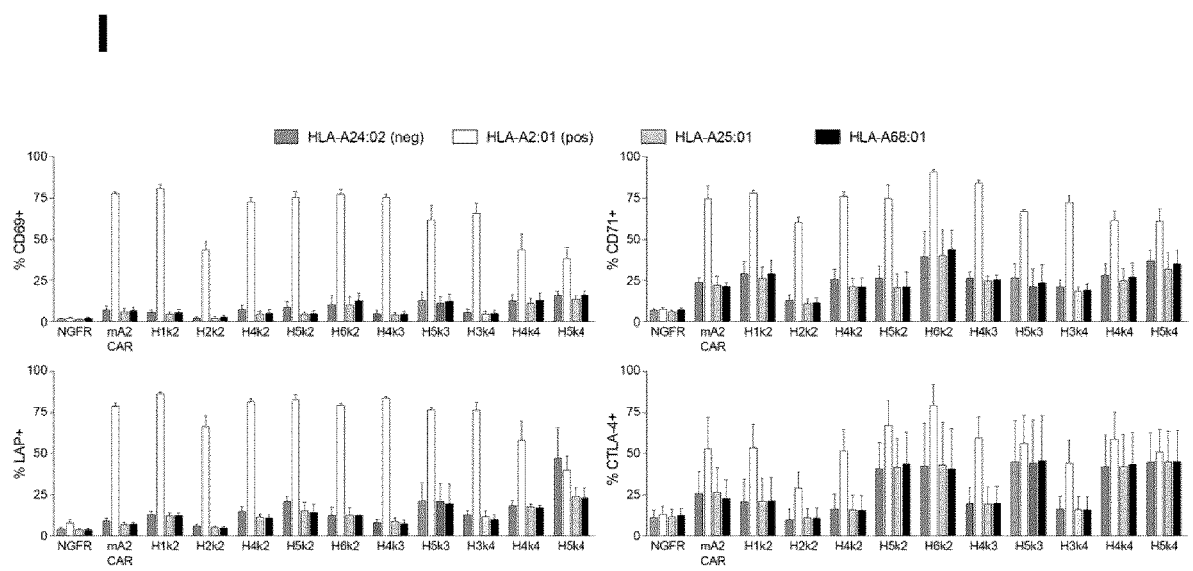

FIG. 6. Determination of cross-reactivity of humanized anti-HLA-A2 CARs with common HLA-A and HLA-B allelic variants. (A) show the schematic diagram of the experimental set up and gating strategy for the FlowPRT cell assay. ΔNGFR$^+$ Tregs expressing the indicated humanized CARs were incubated with Flow Panel Reactive Single Antigen beads and a fixable viability dye for 30 minutes at room temperature. Samples were then washed, fixed and analyzed via flow cytometry. (B) Binding to HLA-A*02:01-coated beads for each m/hA2-CAR Treg relative to binding of a ΔNGFR Treg control. (C & D) Correlation between the mean of HLA-A*02:01 binding measured by the FlowPRT cell assay and either (C) HLA-A*02:01-tetramer MFI evaluated by flow cytometry or (D) the increase in proportion of CD69+ cells 16 h after co-culture with HLA-A*02:01 versus negative control HLA-A*24:01 K562 cells. Data in E, F, G & H show the percent binding relative to control Tregs expressing only truncated NGFR, normalized for the number of HLA negative beads collected by the cytometer. Data points above the shaded grey area (E, F & G) or the horizontal dotted line (H) represent values that were more than two standard deviations from the mean of the bead-only control and thus statistically significant ($p<0.05$). Data are the average of three independent experiments. (I) ΔNGFR or m/hA2-CAR Tregs were co-cultured with the indicated K562 cells transduced to express selected HLA-A alleles. After 16 hours, expression of CD69, CD71, LAP and CTLA-4 was measured on live CD4$^+$ T cells. n=2-6 from at least 2 independent experiments. Statistical significance determined by one-way ANOVA and Holm-Sidak post-test comparing to mA2-CAR. mean±SEM, ** $p<0.01$.

Figure 7:
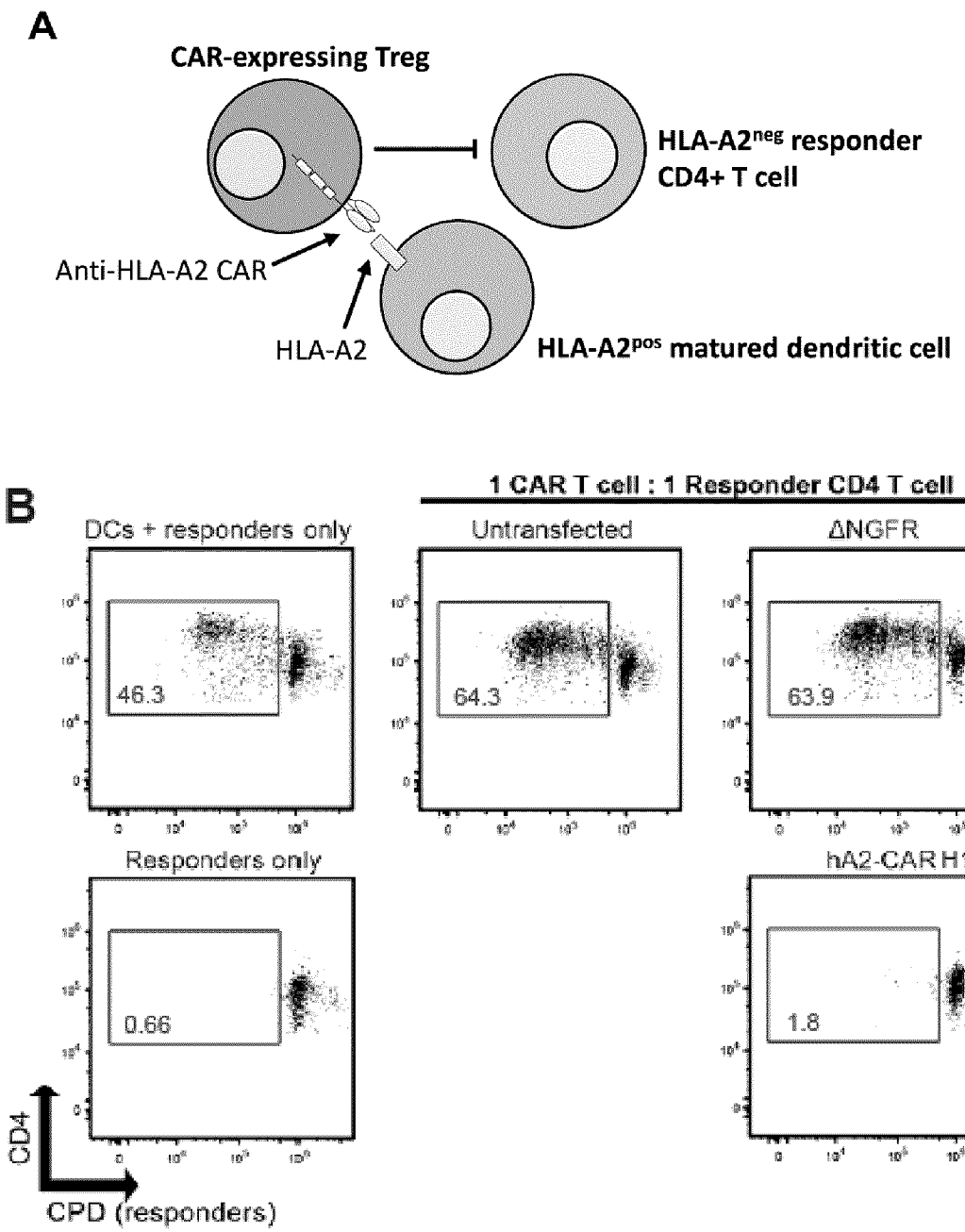
Figure 7:
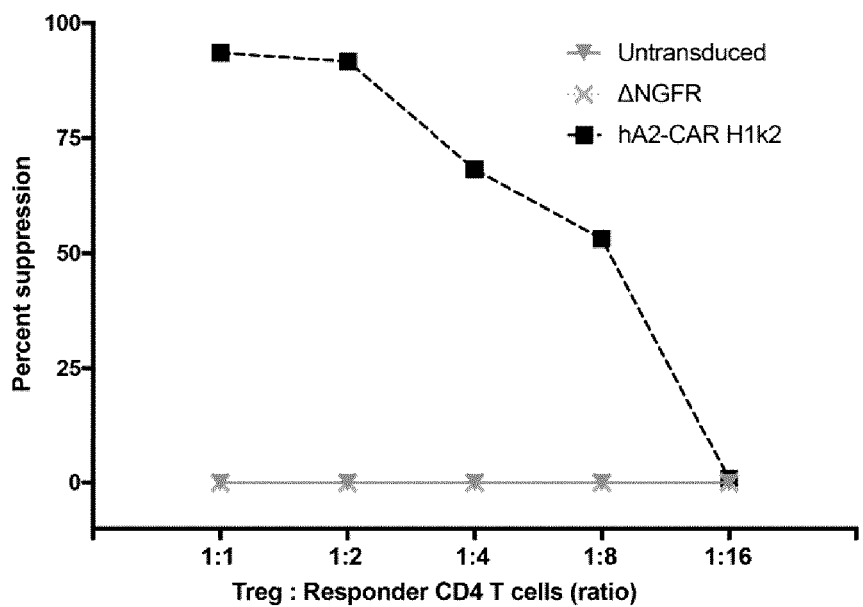
Figure 7:
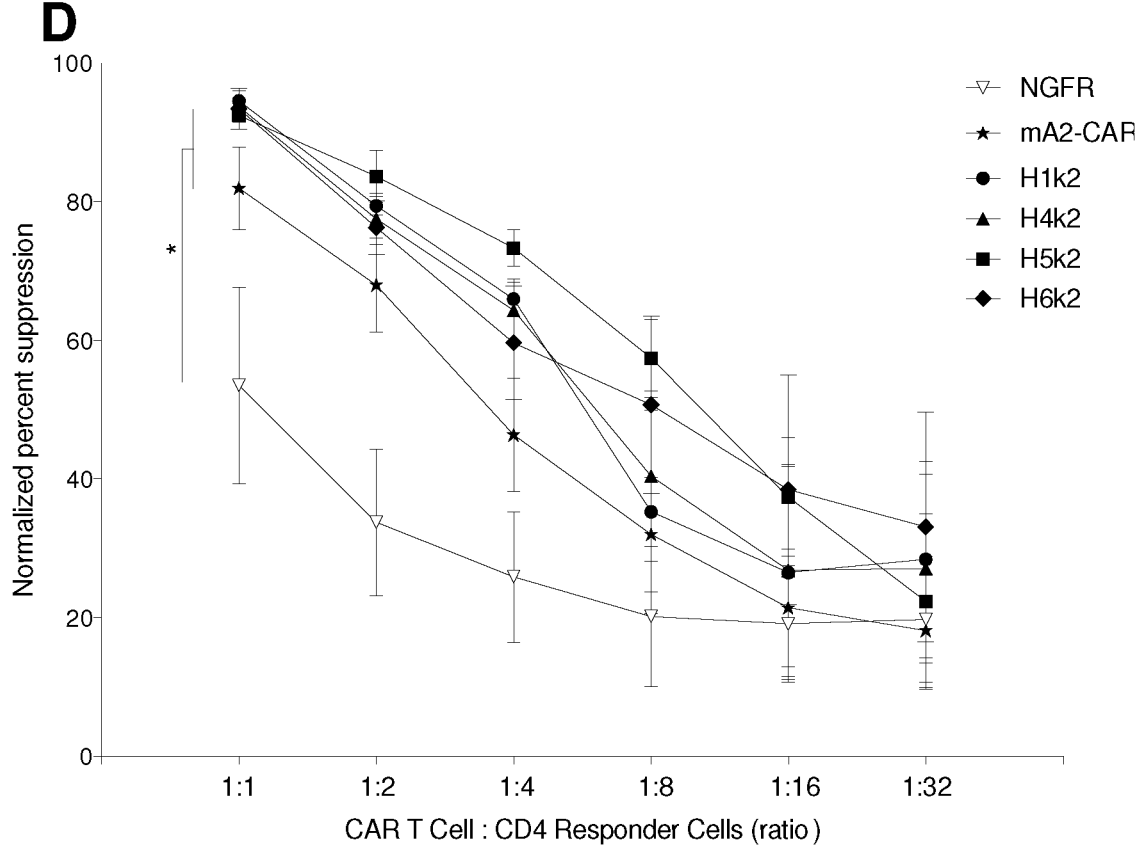
Figure 7:
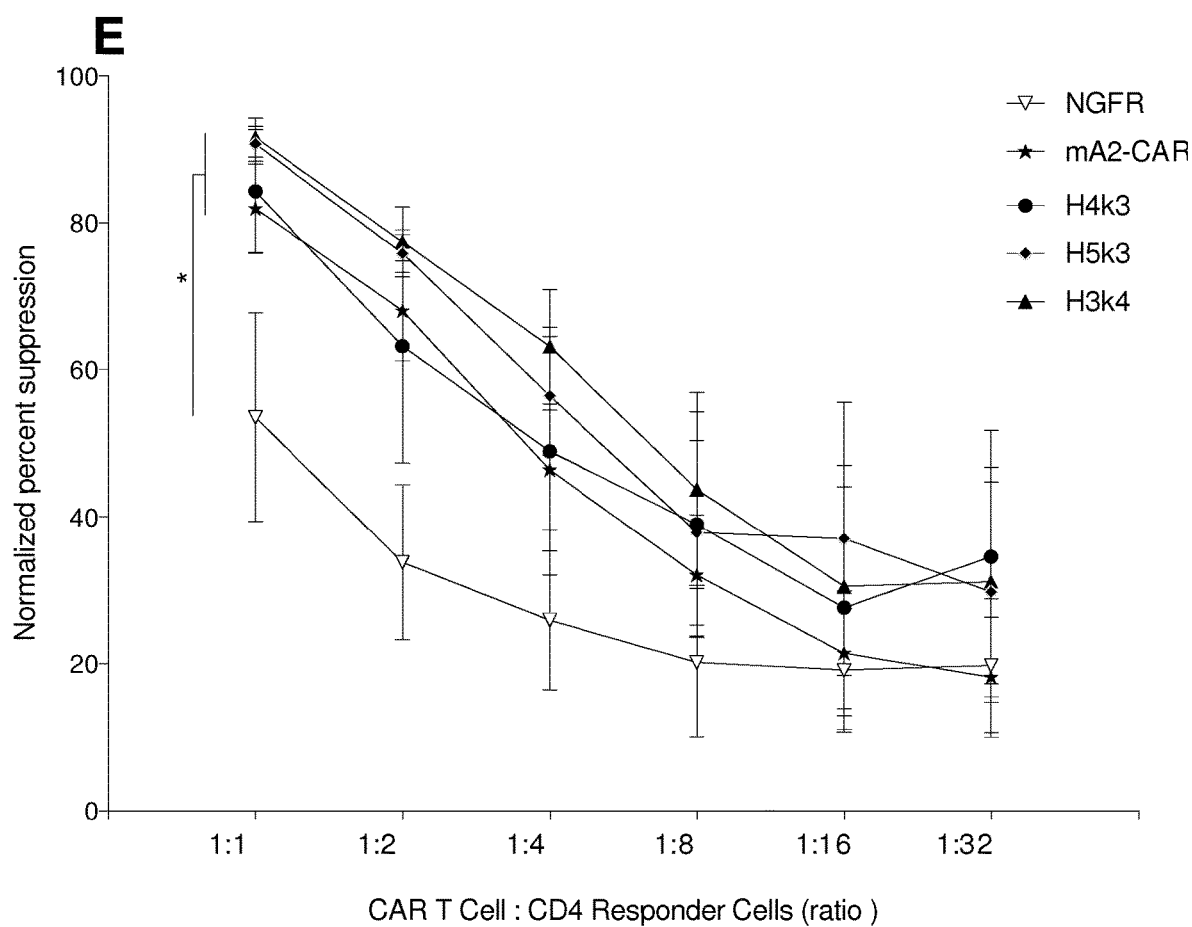

FIG. 7. Tregs expressing a humanized HLA-A2 CAR potently suppress T cell proliferation stimulated by HLA-A2$^+$ dendritic cells. (A) Schematic diagram of experiment setup. Matured HLA-A2$^+$ dendritic cells were used to stimulate with Cell Proliferation Dye (CPD)-e450-labelled HLA-A2$^{neg}$ CD4+"responder" T cells. CPD-e660-labelled Tregs which were either untransduced, or transduced with a control lenti virus encoding ΔNGFR, or Humanized A2 CAR-expressing Tregs. (B, C, D & E) The indicated ratios of cells were co-cultured for six days, then the amount of proliferation of the responder CPD-e450-labelled responder CD4$^+$ T cells was measured by flow cytometry. B shows representative dot plots and C, D and E show graphed data for multiple cell ratios. C, D and E show average data for n=3-7 from at least 3 independent experiments. Statistics were performed using a two-way ANOVA with Holm-Sidak post-test versus a ΔNGFR Treg control. * $p<0.05$, mean±SEM.

Figure 8:
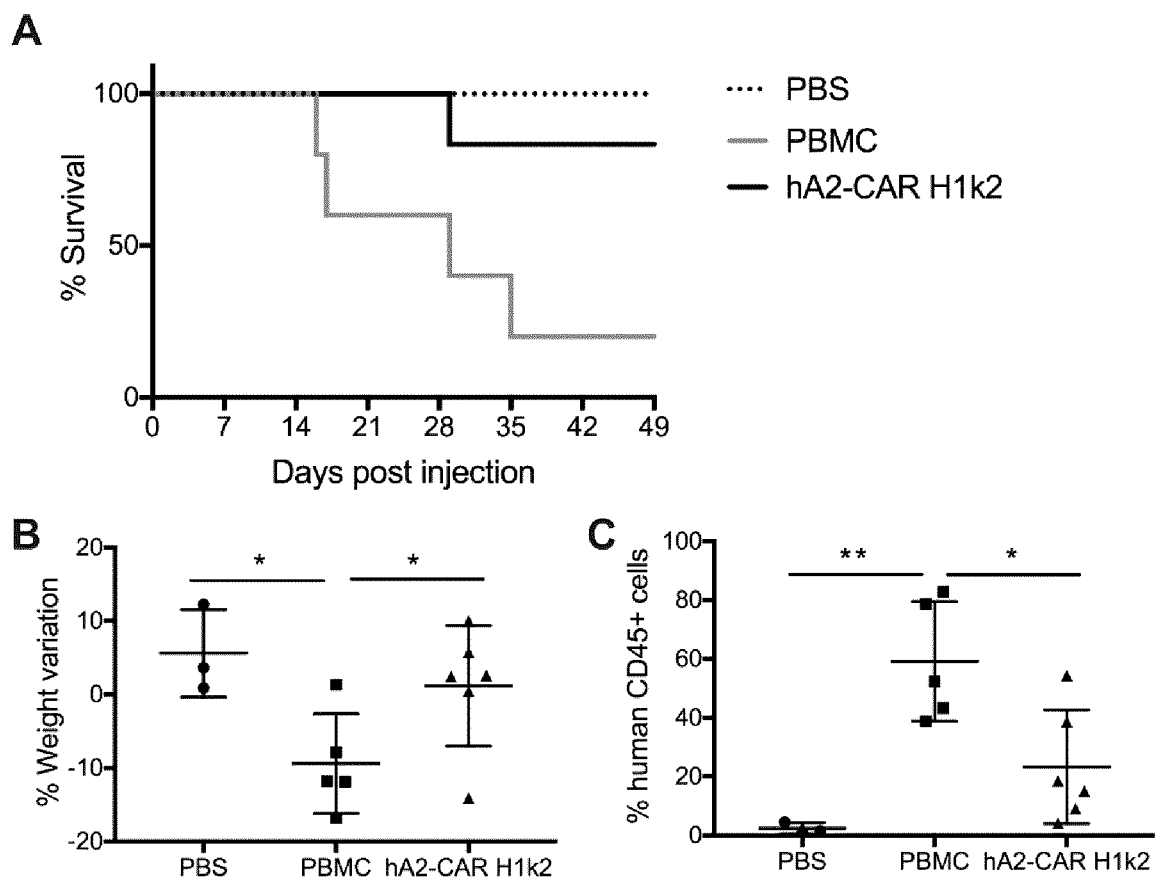
Figure 8:
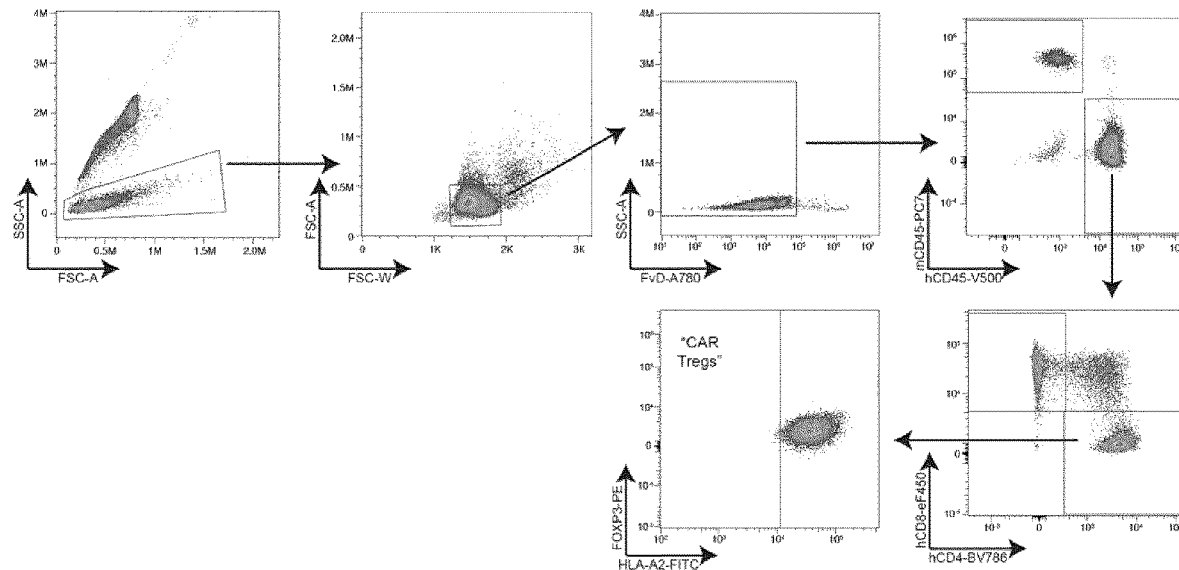
Figure 8:
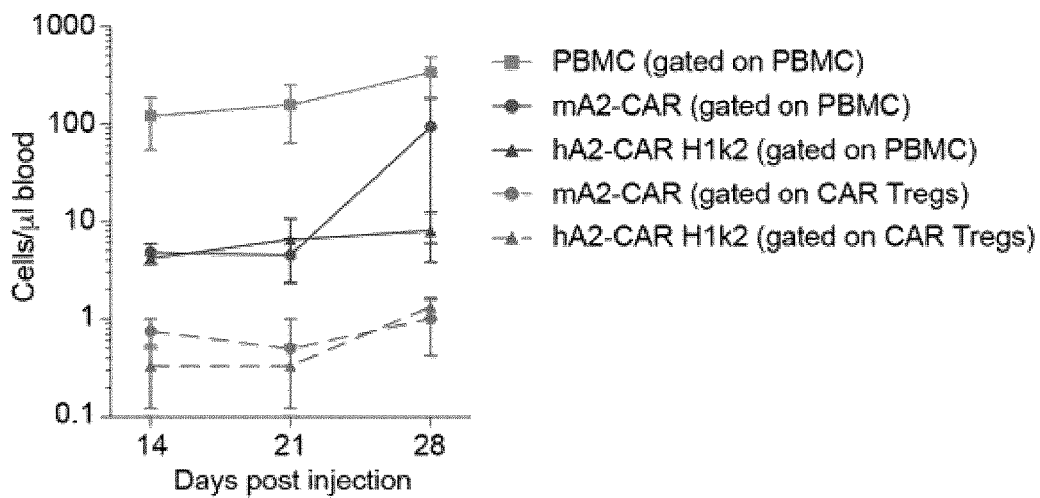

FIG. 8. Tregs expressing a humanized HLA-A2 CAR potently suppress xenogeneic graft-versus-host disease. Irradiated NSG mice were injected with PBS (n=3), 8×10$^6$ HLA-A2$^+$ PBMCs alone (n=5) or with 4×10$^6$ Hlk2 CAR-expressing Tregs (n=6). Human cell engraftment in the blood was monitored every 7 days. (A) Survival curve and (B) percent of weight change relative to the start of experiment. (C) Proportion of total mononuclear cells (live singlets) expressing human CD45 in blood. (D) Gating strategy to discriminate overall human CD45$^+$ and CAR Treg (hCD45$^+$hCD4$^+$HLA-A2$^-$) cell engraftment. (E) In-vivo cell engraftment after adoptive transfer in a xenogeneic GVHD mouse model as shown by the absolute number of PBMC and CAR Treg engraftment per μL of blood over time. The number of PBMC were calculated as hCD45+ minus total CAR Treg count as gated in D.

Figure 9:
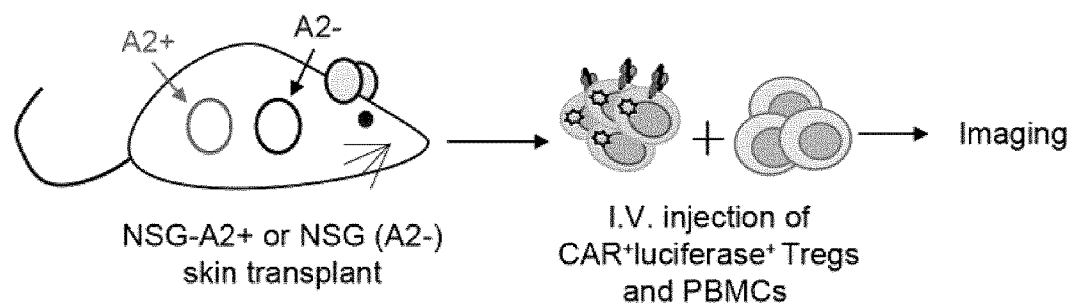
Figure 9:
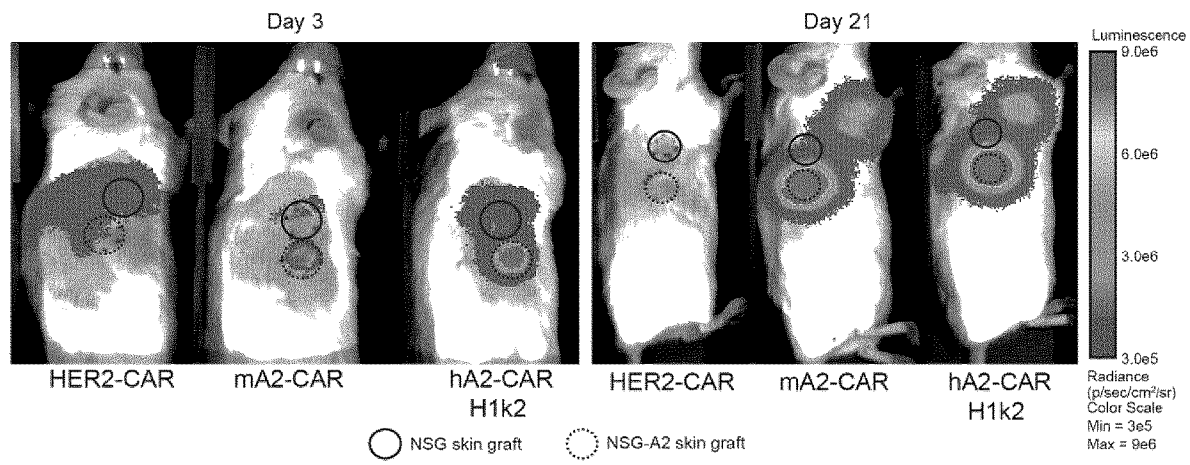
Figure 9:
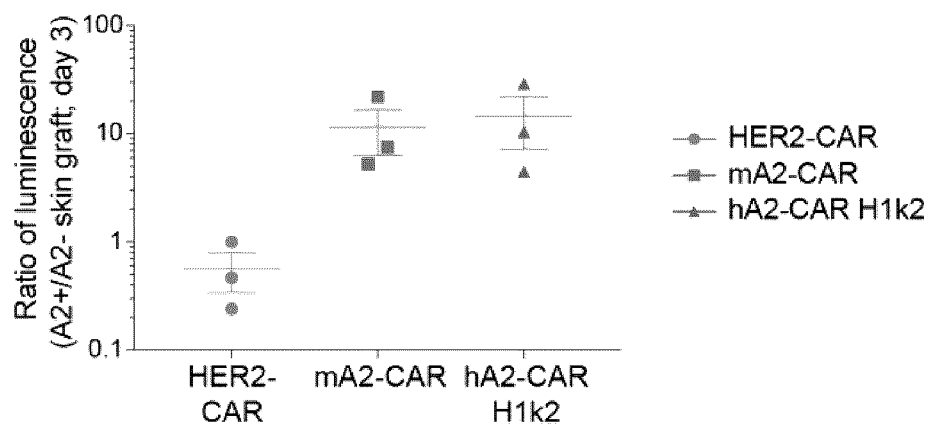
Figure 9:
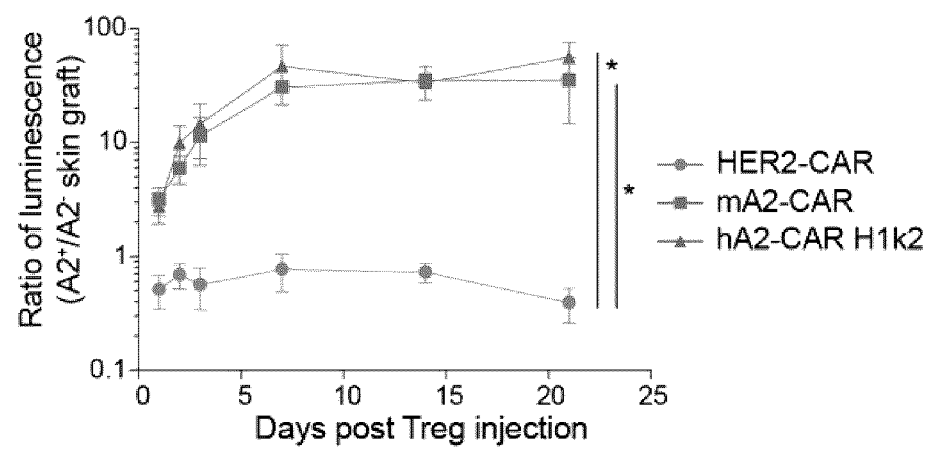

FIG. 9. Expression of m/hA2 CARs endows Tregs with rapid and persistent homing to HLA-A2:01$^+$ skin allografts. Tregs were co-transduced with lentivirus encoding luciferase and either a control HER2-CAR, mA2-CAR or hA2-CAR (Hlk2). Dual transduced cells were FACS-sorted, expanded for 5 days, then injected to NSG mice which had previously been transplanted with juxtaposed skin transplants from both NSG and NSG-HLA-A*02:01 transgenic mice. (A) Schematic representation of the experimental setup. (B) Representative luciferase imaging of skin grafts (left) 72 hours or (right) 21 days after Treg injection. Amount of luciferase radiance was quantified using the average amount of photons/sec/cm$^2$/steradian and plotted as a ratio between (C) the HLA-A*02:01-NSG and NSG skin grafts 72 hours after Treg injection or (D) over time. n=2-3 per group from three independents experiments, mean±SEM. Repeated measures ANOVA with Bonferroni correction.

Figure 10:
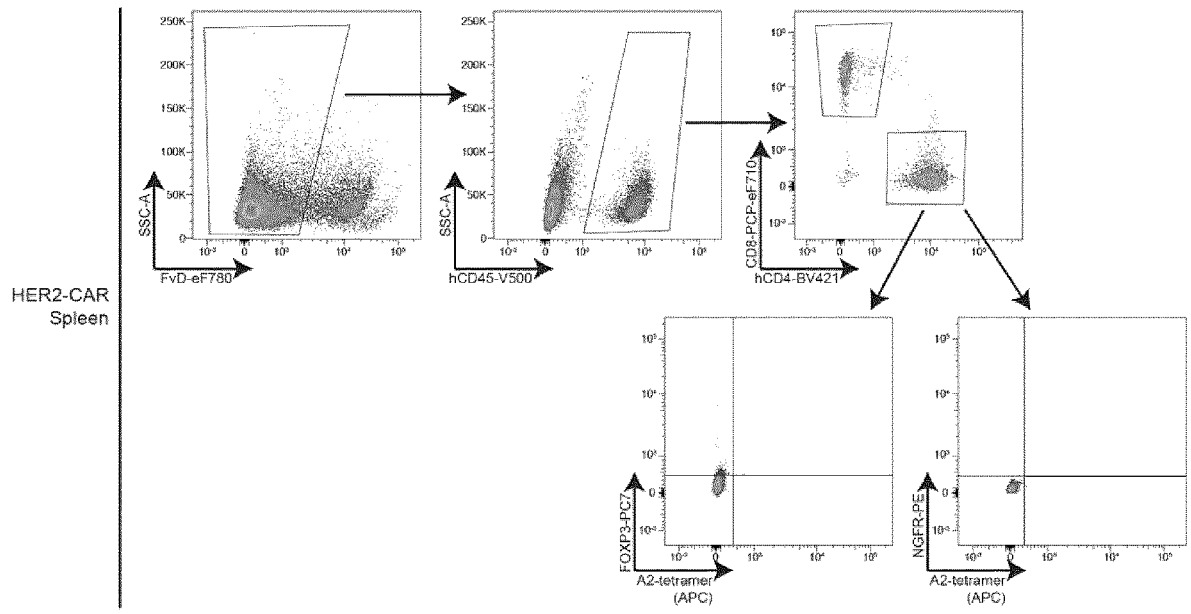
Figure 10:
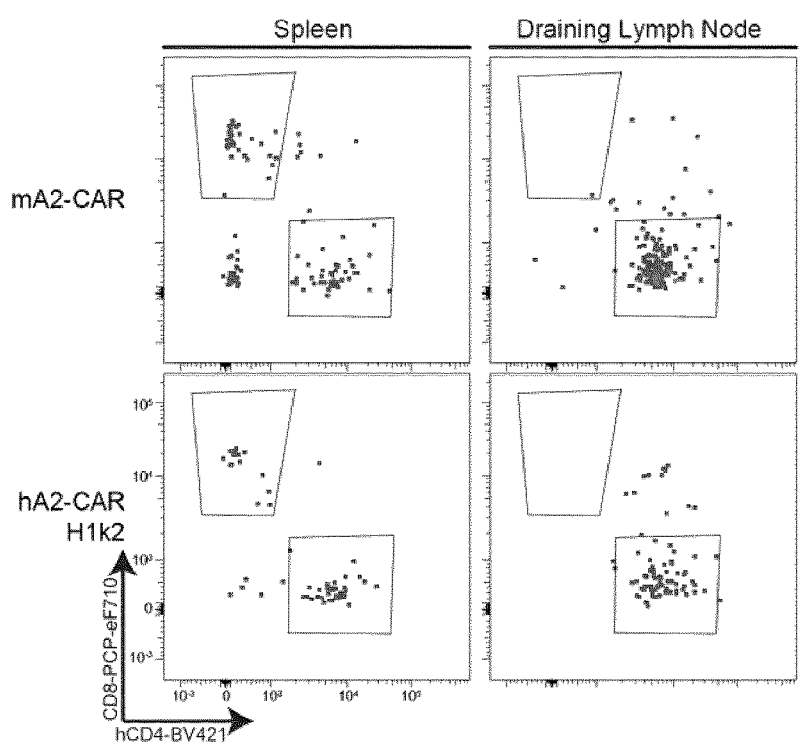
Figure 10:
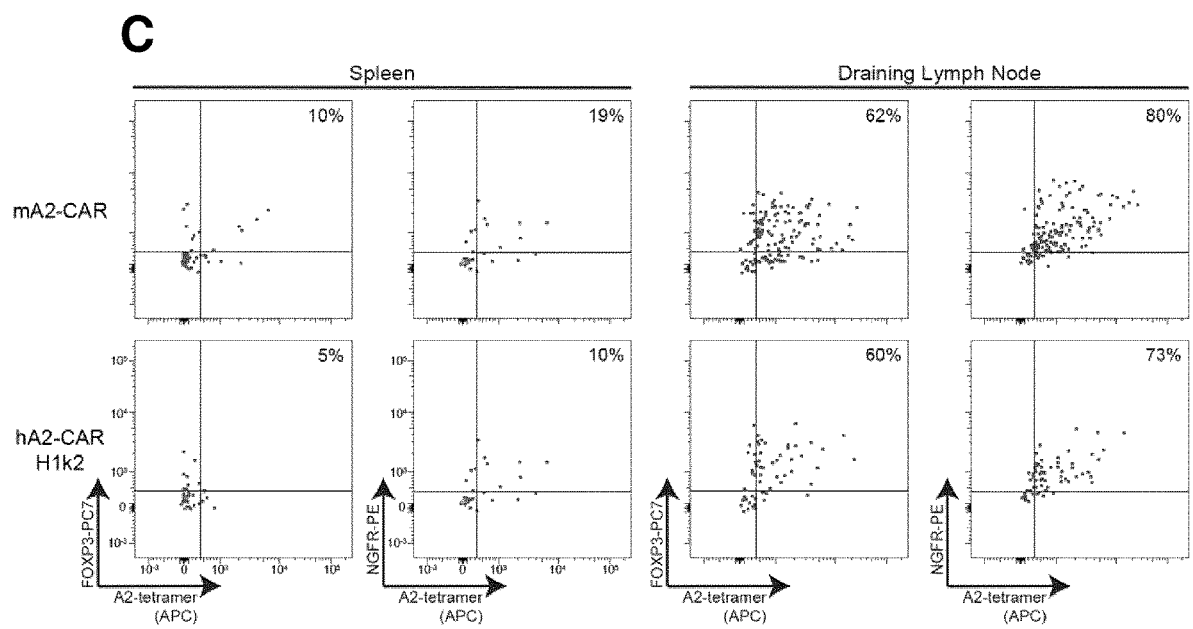

FIG. 10. Flow cytometric tracking of m/hA2 CAR Tregs with rapid and persistent homing to HLA-A2:01$^+$ skin allografts. Tregs were co-transduced with lentivirus containing luciferase and either HER2-CAR, mA2-CAR or hA2-CAR constructs, expanded and injected into transplanted NSG mice as shown in FIG. 9. (A) Pre-gating for flow cytometry plots were based on cells from the spleen of control HER2-CAR. (B) hCD4/hCD8 flow cytometry profile for the indicated constructs. Plots were pre-gated on FvD$^-$hCD45$^+$ as in (A). (C) Flow cytometry plots showing staining for m/hA2-CAR Tregs in the spleen and draining lymph node upon experiment endpoint n=1 per group from one independent experiment. * $p<0.05$.

Figure 11:
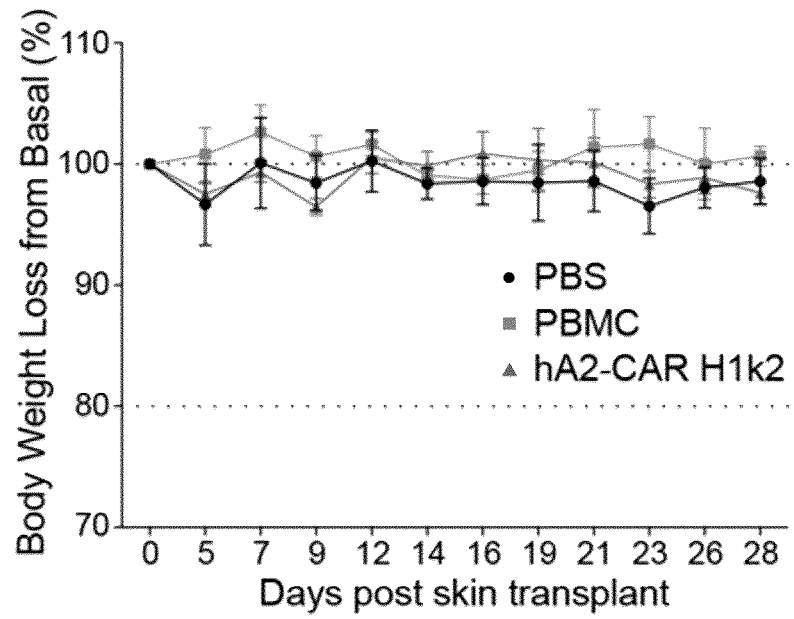
Figure 11:
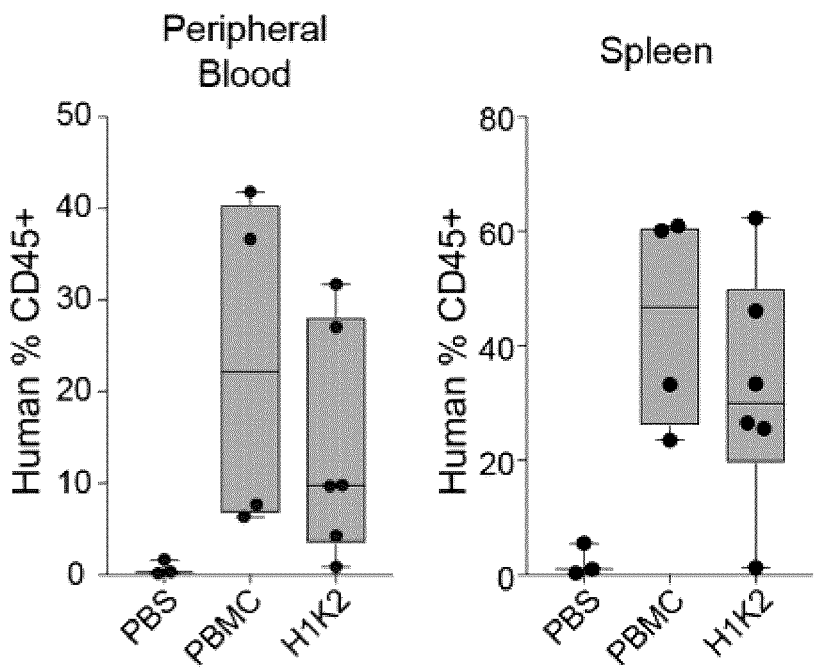
Figure 11:
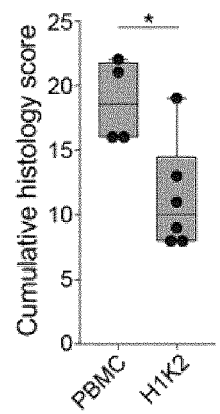
Figure 11:
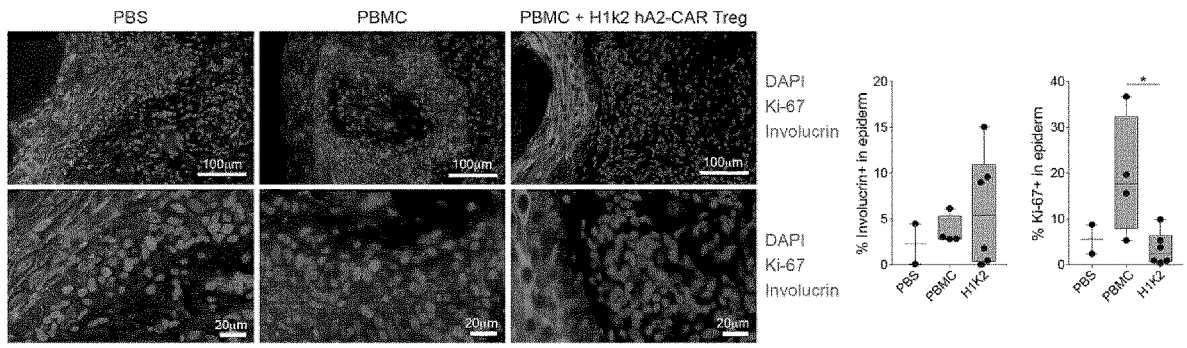
Figure 11:
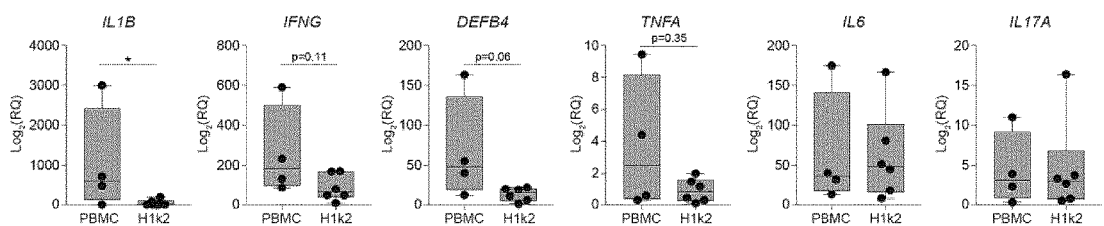
Figure 11:
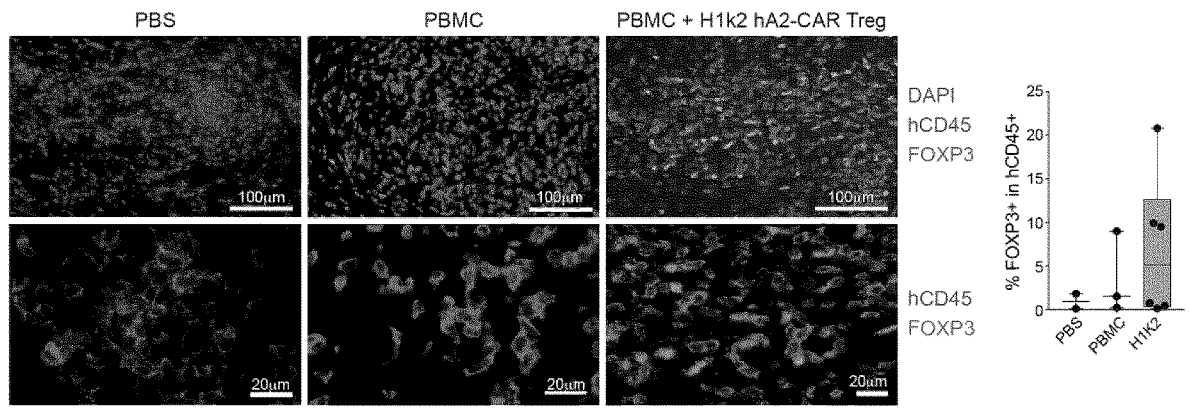
Figure 11:
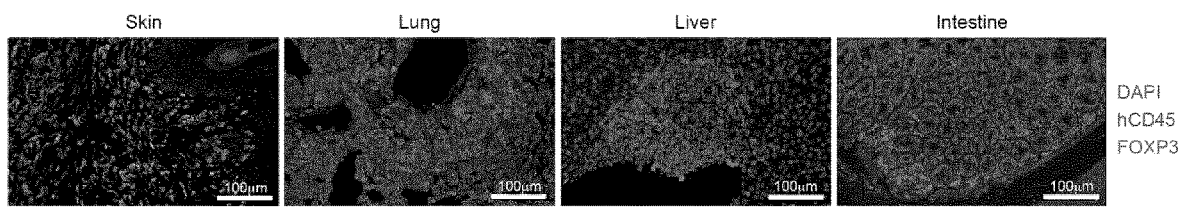

FIG. 11. hA2-CAR-Tregs diminish human skin allograft rejection. NSG mice were transplanted with HLA-A*02:01$^+$ human skin and injected three weeks later with either: PBS (n=3); HLA-A*02:01$^{neg}$ PBMCs alone (n=4) or with a 2:1 ratio of autologous H1k2 CAR Tregs (n=6). PBMC/hA2-CAR Tregs were from two individual donors, tested in one experiment. (A) Body weight was monitored thrice weekly and (B) the proportion of human CD45$^+$ cells in the blood (left) and spleen (right) was measured upon the experimental endpoint. (C) Cumulative histological score of transplanted skin sections as determined by H&E stain. (D) Transplanted skin grafts were immunostained at experiment endpoint to quantify the amount of involucrin expression and proportion of Ki-67$^+$ cells in the epidermis. (E) mRNA expression of the indicated genes within transplanted skin sections was determined by qRT-PCR. (F) Transplanted skin grafts were immunostained at experiment endpoint to quantify the proportion of FOXP3+ cells within human CD45+ cells. (G) Transplanted skin grafts, intestine, lung and liver sections were immunostained at the experiment endpoint to show the proportion of FOXP3+ cells within human CD45+ cells in each tissue. Each data point represents one mouse. Boxwhisker plots show mean±range. Statistical significance determined by two-tailed Mann-Whitney test comparing PBMC to Hlk2. * p<0.05.

Figure 12:
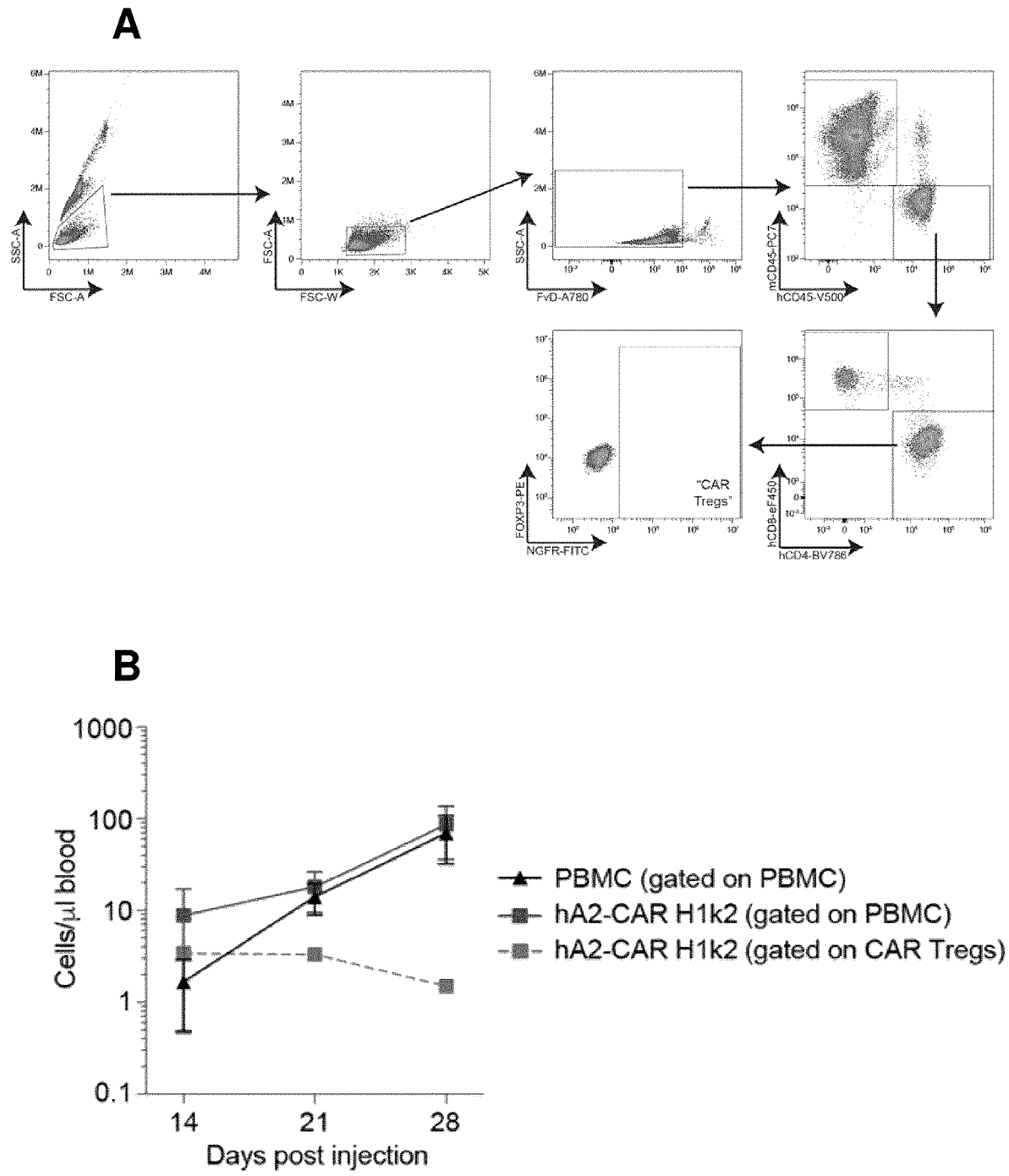

FIG. 12: Flow cytometric tracking of hA2 CAR Tregs in blood in the human skin transplant model. NSG mice were transplanted with human HLA-A*02+ skin and injected with cells as described in FIG. 11. (A) Gating strategy to discriminate overall human CD45+ (PBMC) and CAR Treg (hCD45+hCD4+NGFR+) cell engraftment. (B) Absolute number of PBMCs and CAR Treg engraftment per µL of blood over time. Number of PBMCs were calculated as hCD45+ minus total CAR Treg count, as gated in (A).

Figure 13:
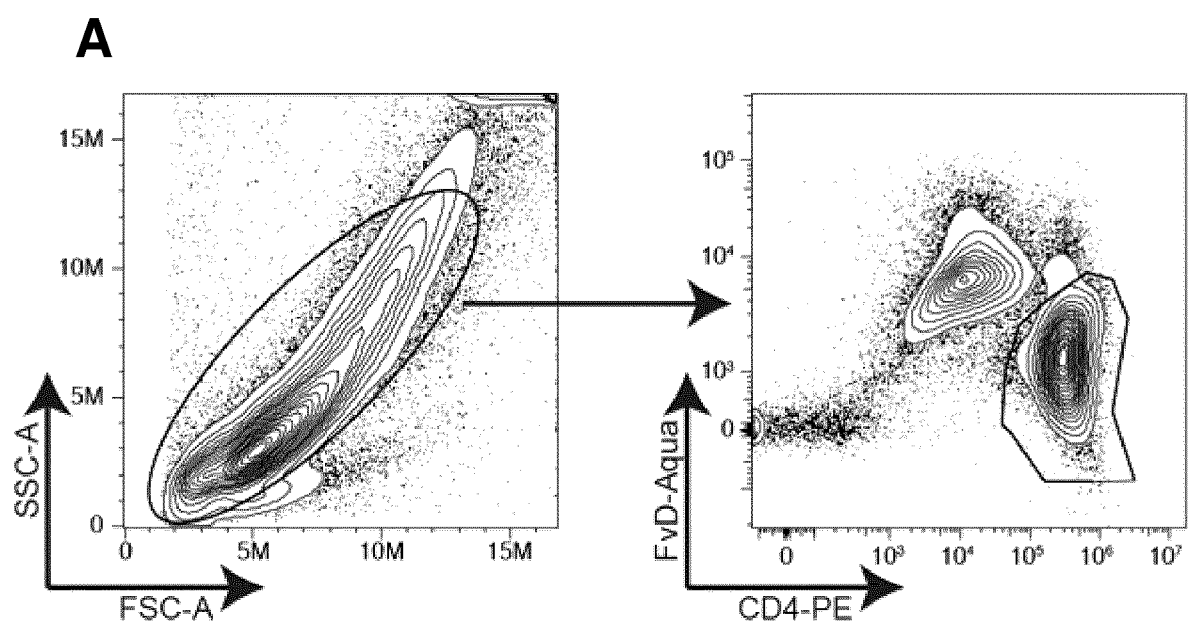
Figure 13:
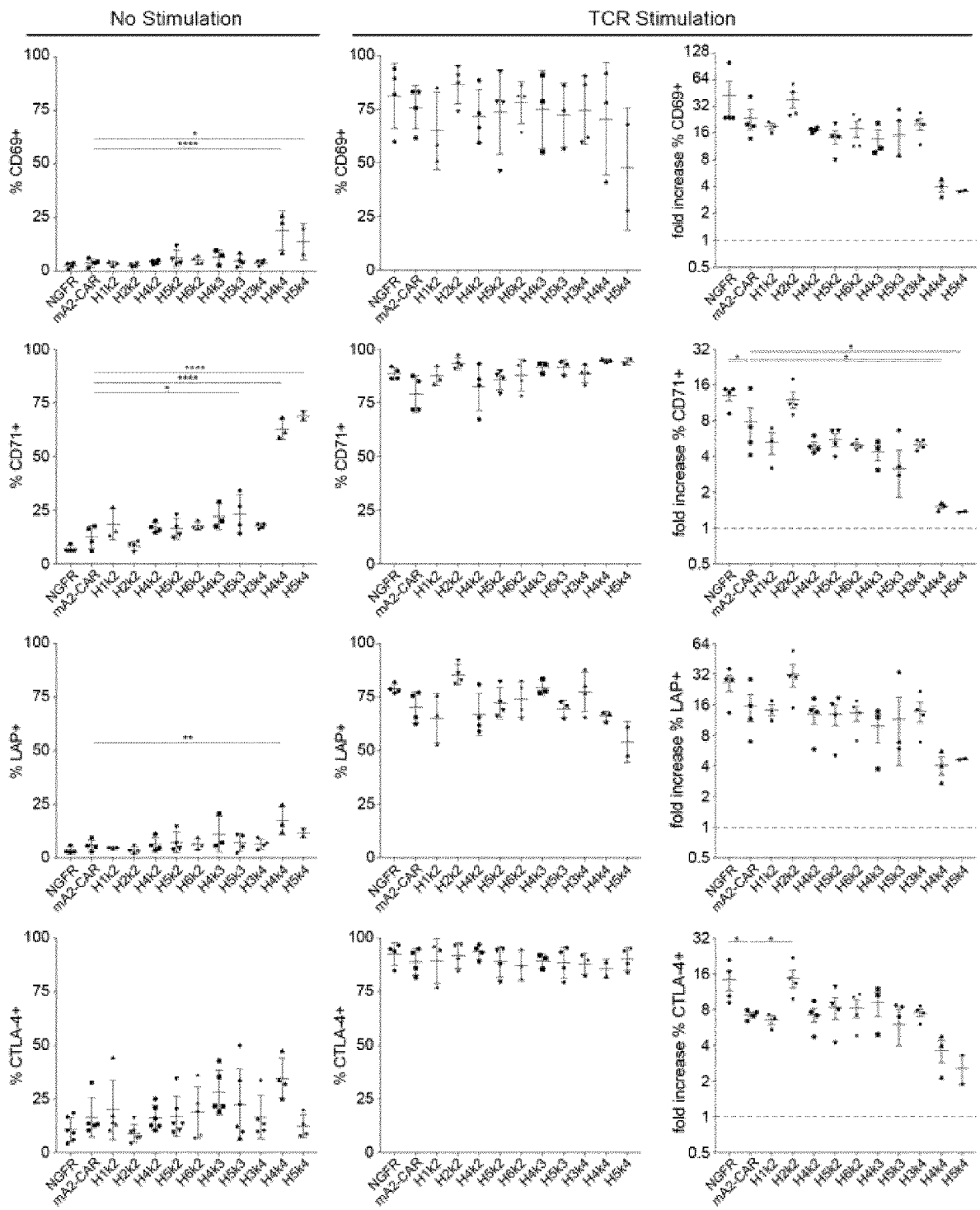

FIG. 13: Activation of hA2 CAR Tregs using artificial antigen presenting cells. ΔNGFR control/CAR Tregs were co-cultured for 16 hours with either no stimulation or a 2:1 (Tregs: K562) ratio of CD64-expressing K562 cells loaded with anti-CD3 and anti-CD28 monoclonal antibodies (TCR stimulation). (A) Example gating strategy. (B) Expression of CD69, CD71, CTLA-4 and LAP were measured by flow cytometry (left). Fold increase of each activation marker over baseline (no stimulation) was calculated (right). Data are n=2-4 for each construct from at least two independent experiments. Mean±SEM. One-way ANOVA and Holm-Sidak's multiple comparisons test comparing all constructs to mA2-CAR Tregs. * p<0.05,  p<0.01, ** p<0.0001.

DETAILED DESCRIPTION

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention pertains. Although any methods and materials similar or equivalent to those described herein can also be used in the practice or testing of the present invention, the preferred methods and materials are now described. One skilled in the art will recognize many methods and materials similar or equivalent to those described herein, which could be used in the practice of the present invention. Indeed, the present invention is in no way limited to the methods and materials described. For purposes of the present invention, the following terms are defined below. All publications mentioned herein are incorporated herein by reference to disclose and describe the methods and/or materials in connection with which the publications are cited. In the event that any definition set forth conflicts with any document incorporated herein by reference, the definition set forth below shall control.

II. Definitions

The terms "a" and "an" refer to one or to more than one of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The terms "HLA-A2" and "A2" as used herein each refer to human leukocyte antigen (HLA) proteins including cell surface proteins, encoded by the HLA-A*02 allele family at the HLA-A locus of the HLA gene complex. HLA proteins encompassed by the terms "HLA-A2" and "A2" include HLA proteins identified as belonging to the HLA-A*02 antigen type by serological testing or genotyping. Additional names for the HLA-A*02 antigen type include "HLA-A2", HLA-A02" and "HLA-A*2". Different naming systems have been developed which identify HLA proteins encoded by this family of alleles including the HLA naming system developed in 2010 by the WHO Committee for Factors of the HLA System. The terms "HLA-A2" and "A2" refer to HLA proteins encoded by alleles having designations according to this naming system which begin with "HLA-A*02:", including but not limited to designations which begin with "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11". In addition to the numerical digits which follow "HLA-A*02:", the allele designations may also contain an upper case letter, including but not limited to upper case letters "P" and "G" (e.g., HLA-A*02:01P or HLA-A*02:01:01G). The allele designations which begin with "HLA-A*02:" followed by 2, 3, or 4 additional numerical digits may constitute the complete designation or a beginning portion of the designation. The allele designations may be italicized. The terms "HLA-A2" and "A2" also refer to HLA proteins identified with designations which begin with "HLA-A*02:" according to this naming system, including but not limited to the designations "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11".

An "HLA-A subtype" as used herein refers to a protein encoded by an allele of the HLA-A gene.

The term "HLA-A*03" as used herein refers to HLA proteins including cell surface proteins, encoded by the HLA-A*03 allele family at the HLA-A locus of the HLA gene complex. HLA proteins encompassed by the term "HLA-A*03" include HLA proteins identified as belonging to the HLA-A*03 antigen type by serological testing or genotyping. Additional names for the HLA-A*03 antigen type include "HLA-A03" and "HLA-A3". The term "HLA-A*03" refers to HLA proteins encoded by alleles having designations according to the HLA naming system developed in 2010 by the WHO Committee for Factors of the HLA System which begin with "HLA-A*03:", including but not limited to designations which begin with "HLA-A*03:01", "HLA-A*03:02", "HLA-A*03:04", "HLA-A*03:05", "HLA-A*03:06", "HLA-A*03:07", "HLA-A*03:08", "HLA-A*03:09", "HLA-A*03:10", and "HLA-A*03:12". In addition to the numerical digits which follow "HLA-A*03:", the allele designations may also contain an upper case letter, including but not limited to upper case letters "P" and "G" (e.g., HLA-A*03:01P or HLA-A*03:01:01G). The allele designations which begin with "HLA-A*03:" followed by 2, 3 or 4 additional numerical digits may constitute the complete designation or a beginning portion of the designation. The allele designations may be italicized. The term "HLA-A*03" also refers to HLA proteins identified with designations which begin with "HLA-A*03:" according to this naming system, including but not limited to the designations "HLA-A*03:01", "HLA-A*03:02", "HLA-A*03:04", "HLA-A*03:05", "HLA-A*03:06", "HLA-A*03:07", "HLA-A*03:08", "HLA-A*03:09", "HLA-A*03:10", and "HLA-A*03:12".

The terms "HLA-A*25", "HLA-A25" and "A25" as used herein each refer to HLA proteins including cell surface proteins, encoded by the HLA-A*25 allele family at the HLA-A locus of the HLA gene complex. HLA proteins encompassed by the terms "HLA-A*25", "HLA-A25" and "A25" include HLA proteins identified as belonging to the HLA-A*25 antigen type by serological testing or genotyping. Additional names for the HLA-A*25 antigen type include "HLA-A25". The terms "HLA-A*25", "HLA-A25" and "A25" refer to HLA proteins encoded by alleles having designations according to the HLA naming system developed in 2010 by the WHO Committee for Factors of the HLA System which begin with "HLA-A*25:", including but not limited to designations which begin with "HLA-A*25:01", "HLA-A*25:02", "HLA-A*25:03", "HLA-A*25:04", "HLA-A*25:05", "HLA-A*25:06", "HLA-A*25:07", "HLA-A*25:08", "HLA-A*25:09", "HLA-A*25:10", and "HLA-A*25:11". In addition to the numerical digits which follow "HLA-A*25:", the allele designations may also contain an upper case letter, including but not limited to upper case letters "P" and "G" (e.g., HLA-A*25:01P or HLA-A*25:01:01G). The allele designations which begin with "HLA-A*25:" followed by 2, 3 or 4 additional numerical digits may constitute the complete designation or a beginning portion of the designation. The allele designations may be italicized. The terms "HLA-A*25", "HLA-A25" and "A25" also refer to HLA proteins identified with designations which begin with "HLA-A*25:" according to this naming system, including but not limited to the designations "HLA-A*25:01", "HLA-A*25:02", "HLA-A*25:03", "HLA-A*25:04", "HLA-A*25:05", "HLA-A*25:06", "HLA-A*25:07", "HLA-A*25:08", "HLA-A*25:09", "HLA-A*25:10", and "HLA-A*25:11".

The terms "HLA-A*29", "HLA-A29" and "A29" as used herein each refer to HLA proteins including cell surface proteins, encoded by the HLA-A*29 allele family at the HLA-A locus of the HLA gene complex. HLA proteins encompassed by the terms "HLA-A*29", "HLA-A29" and "A29" include HLA proteins identified as belonging to the HLA-A*29 antigen type by serological testing or genotyping. Additional names for the HLA-A*29 antigen type include "HLA-A29". The terms "HLA-A*29", "HLA-A29" and "A29" refer to HLA proteins encoded by alleles having designations according to the HLA naming system developed in 2010 by the WHO Committee for Factors of the HLA System which begin with "HLA-A*29:", including but not limited to designations which begin with "HLA-A*29:01", "HLA-A*29:02", "HLA-A*29:03", "HLA-A*29:04", "HLA-A*29:05", "HLA-A*29:06", "HLA-A*29:07", HLA-A*29:09", "HLA-A*29:10", and "HLA-A*29:11". In addition to the numerical digits which follow "HLA-A*29:", the allele designations may also contain an upper case letter, including but not limited to upper case letters "P" and "G" (e.g., HLA-A*29:02P or HLA-A*29:02:01G). The allele designations which begin with "HLA-A*29:" followed by 2, 3 or 4 additional numerical digits may constitute the complete designation or a beginning portion of the designation. The allele designations may be italicized. The terms "HLA-A*29", "HLA-A29" and "A29" also refer to HLA proteins identified with designations which begin with "HLA-A*29:" according to this naming system, including but not limited to the designations "HLA-A*29:01", "HLA-A*29:02", "HLA-A*29:03", "HLA-A*29:04", "HLA-A*29:05", "HLA-A*29:06", "HLA-A*29:07", "HLA-A*29:09", "HLA-A*29:10", and "HLA-A*29:11".

The terms "HLA-A*30", "HLA-A30" and "A30" as used herein each refer to HLA proteins including cell surface proteins, encoded by the HLA-A*30 allele family at the HLA-A locus of the HLA gene complex. HLA proteins encompassed by the terms "HLA-A*30", "HLA-A30" and "A30" include HLA proteins identified as belonging to the HLA-A*30 antigen type by serological testing or genotyping. Additional names for the HLA-A*30 antigen type include "HLA-A30". The terms "HLA-A*30", "HLA-A30" and "A30" refer to HLA proteins encoded by alleles having designations according to the HLA naming system developed in 2010 by the WHO Committee for Factors of the HLA System which begin with "HLA-A*30:", including but not limited to designations which begin with "HLA-A*30:01", "HLA-A*30:02", "HLA-A*30:03", "HLA-A*30:04", "HLA-A*30:06", "HLA-A*30:07", "HLA-A*30:08", "HLA-A*30:09", "HLA-A*30:10", and "HLA-A*30:11". In addition to the numerical digits which follow "HLA-A*30:", the allele designations may also contain an upper case letter, including but not limited to upper case letters "P" and "G" (e.g., HLA-A*30:01P, HLA-A*30:02P, HLA-A*30:04P, HLA-A*30:01:01G, HLA-A*30:02:01G or HLA-A*30:04:01G). The allele designations which begin with "HLA-A*30:" followed by 2, 3 or 4 additional numerical digits may constitute the complete designation or a beginning portion of the designation. The allele designations may be italicized. The terms "HLA-A*30", "HLA-A30" and "A30" also refer to HLA proteins identified with designations which begin with "HLA-A*30:" according to this naming system, including but not limited to the designations "HLA-A*30:01", "HLA-A*30:02", "HLA-A*30:03", "HLA-A*30:04", "HLA-A*30:06", "HLA-A*30:07", "HLA-A*30:08", "HLA-A*30:09", "HLA-A*30:10", and "HLA-A*30:11".

The terms "HLA-A*31", "HLA-A31" and "A31" as used herein each refer to HLA proteins including cell surface proteins, encoded by the HLA-A*31 allele family at the HLA-A locus of the HLA gene complex. HLA proteins encompassed by the terms "HLA-A*31", "HLA-A31" and "A31" include HLA proteins identified as belonging to the HLA-A*31 antigen type by serological testing or genotyping. Additional names for the HLA-A*31 antigen type include "HLA-A31". The terms "HLA-A*31", "HLA-A31" and "A31" refer to HLA proteins encoded by alleles having designations according to the HLA naming system developed in 2010 by the WHO Committee for Factors of the HLA System which begin with "HLA-A*31:", including but not limited to designations which begin with "HLA-A*31:01", "HLA-A*31:02", "HLA-A*31:03", "HLA-A*31:04", "HLA-A*31:05", "HLA-A*31:06", "HLA-A*31:07", "HLA-A*31:08", "HLA-A*31:09", "HLA-A*31:10", and "HLA-A*31:11". In addition to the numerical digits which follow "HLA-A*31:", the allele designations may also contain an upper case letter, including but not limited to upper case letters "P" and "G" (e.g., HLA-A*31:01P or HLA-A*31:01:02G). The allele designations which begin with "HLA-A*31:" followed by 2, 3 or 4 additional numerical digits may constitute the complete designation or a beginning portion of the designation. The allele designations may be italicized. The terms "HLA-A*31", "HLA-A31" and "A31" also refer to HLA proteins identified with designations which begin with "HLA-A*31:" according to this naming system, including but not limited to the designations "HLA-A*31:01", "HLA-A*31:02", "HLA-A*31:03", "HLA-A*31:04", "HLA-A*31:05", "HLA-A*31:06", "HLA-A*31:07", "HLA-A*31:08", "HLA-A*31:09", "HLA-A*31:10", and "HLA-A*31:11".

The terms "HLA-A*33", "HLA-A33" and "A33" as used herein each refer to HLA proteins including cell surface proteins, encoded by the HLA-A*33 allele family at the HLA-A locus of the HLA gene complex. HLA proteins encompassed by the terms "HLA-A*33", "HLA-A33" and "A33" include HLA proteins identified as belonging to the HLA-A*33 antigen type by serological testing or genotyping. Additional names for the HLA-A*33 antigen type include "HLA-A33". The terms "HLA-A*33", "HLA-A33" and "A33" refer to HLA proteins encoded by alleles having designations according to the HLA naming system developed in 2010 by the WHO Committee for Factors of the HLA System which begin with "HLA-A*33:", including but not limited to designations which begin with "HLA-A*33:01", "HLA-A*33:03", "HLA-A*33:04", "HLA-A*33:05", "HLA-A*33:06", "HLA-A*33:07", "HLA-A*33:08", "HLA-A*33:09", "HLA-A*33:10", and "HLA-A*33:11". In addition to the numerical digits which follow "HLA-A*33:", the allele designations may also contain an upper case letter, including but not limited to upper case letters "P" and "G" (e.g., HLA-A*33:01P or HLA-A*33:01:01G). The allele designations which begin with "HLA-A*33:" followed by 2, 3 or 4 additional numerical digits may constitute the complete designation or a beginning portion of the designation. The allele designations may be italicized. The terms "HLA-A*33", "HLA-A33" and "A33" also refer to HLA proteins identified with designations which begin with "HLA-A*33:" according to this naming system, including but not limited to the designations "HLA-A*33:01", "HLA-A*33:03", "HLA-A*33:04", "HLA-A*33:05", "HLA-A*33:06", "HLA-A*33:07", "HLA-A*33:08", "HLA-A*33:09", "HLA-A*33:10", and "HLA-A*33:11".

The terms "HLA-A*36", "HLA-A36" and "A36" as used herein each refer to HLA proteins including cell surface proteins, encoded by the HLA-A*36 allele family at the HLA-A locus of the HLA gene complex. HLA proteins encompassed by the terms "HLA-A*36", "HLA-A36" and "A36" include HLA proteins identified as belonging to the HLA-A*36 antigen type by serological testing or genotyping. Additional names for the HLA-A*36 antigen type include "HLA-A36". The terms "HLA-A*36", "HLA-A36" and "A36" refer to HLA proteins encoded by alleles having designations according to the HLA naming system developed in 2010 by the WHO Committee for Factors of the HLA System which begin with "HLA-A*36:", including but not limited to designations which begin with "HLA-A*36:01", "HLA-A*36:02", "HLA-A*36:03", "HLA-A*36:04", and "HLA-A*36:05". In addition to the numerical digits which follow "HLA-A*36:", the allele designations may also contain an upper case letter, including but not limited to upper case letters "P" and "G". The allele designations which begin with "HLA-A*36:" followed by 2, 3 or 4 additional numerical digits may constitute the complete designation or a beginning portion of the designation. The allele designations may be italicized. The terms "HLA-A*36", "HLA-A36" and "A36" also refer to HLA proteins identified with designations which begin with "HLA-A*36:" according to this naming system, including but not limited to the designations "HLA-A*36:01", "HLA-A*36:02", "HLA-A*36:03", "HLA-A*36:04", "HLA-A*36:05", and "HLA-A*36:06".

The terms "HLA-A*68", "HLA-A68" and "A68" as used herein each refer to HLA proteins including cell surface proteins, encoded by the HLA-A*68 allele family at the HLA-A locus of the HLA gene complex. HLA proteins encompassed by the terms "HLA-A*68", "HLA-A68" and "A68" include HLA proteins identified as belonging to the HLA-A*68 antigen type by serological testing or genotyping. Additional names for the HLA-A*68 antigen type include "HLA-A68". The terms "HLA-A*68", "HLA-A68" and "A68" refer to HLA proteins encoded by alleles having designations according to the HLA naming system developed in 2010 by the WHO Committee for Factors of the HLA System which begin with "HLA-A*68:", including but not limited to designations which begin with "HLA-A*68:01", "HLA-A*68:02", "HLA-A*68:03", "HLA-A*68:04", "HLA-A*68:05", "HLA-A*68:06", "HLA-A*68:07", "HLA-A*68:08", "HLA-A*68:09", and "HLA-A*68:10". In addition to the numerical digits which follow "HLA-A*68:", the allele designations may also contain an upper case letter, including but not limited to upper case letters "P" and "G" (e.g., HLA-A*68:01P, HLA-A*68:01:01G or HLA-A*68:01:02G). The allele designations which begin with "HLA-A*68:" followed by 2, 3 or 4 additional numerical digits may constitute the complete designation or a beginning portion of the designation. The allele designations may be italicized. The terms "HLA-A*68", "HLA-A68" and "A68" also refer to HLA proteins identified with designations which begin with "HLA-A*68:" according to this naming system, including but not limited to the designations "HLA-A*68:01", "HLA-A*68:02", "HLA-A*68:03", "HLA-A*68:04", "HLA-A*68:05", "HLA-A*68:06", "HLA-A*68:07", "HLA-A*68:08", "HLA-A*68:09", and "HLA-A*68:10".

Specific HLA proteins may be referred to herein using protein designations according to the HLA naming system developed in 2010 by the WHO Committee for Factors of the HLA System. For example, the term "HLA-A*02:01" as used herein refers to an HLA protein with the designation "HLA-A*02:01" according to this naming system. Similarly, the terms "HLA-A*03:01", "HLA-A*25:01", "HLA-A*29:02", "HLA-A*30:01", "HLA-A*31:01", "HLA-A*33:01", "HLA-A*36:01" and "HLA-A*68:01" refer to HLA proteins with designations "HLA-A*03:01", "HLA-A*25:01", "HLA-A*29:02", "HLA-A*30:01", "HLA-A*31:01", "HLA-A*33:01", "HLA-A*36:01" and "HLA-A*68:01", respectively.

The term "anti-HLA-A2 antibody" as used herein refers to an antibody that preferentially or specifically binds to HLA-A2.

The term "BB7.2" as used herein, refers to a murine hybridoma identified as ATCC Deposit HB-82. The BB7.2 hybridoma cells secrete a murine monoclonal antibody of IgG2b kappa isotype, which has been characterized by Parham, P. et al. and Hilton et al. (Parham, P. et al, 1981; Hilton et al., 2013). The amino acid sequences of the six complementarity determining regions (CDRs) of the monoclonal antibody secreted by BB7.2 are as follows:

```
Heavy chain CDR1 (HCDR1):
                          (SEQ ID NO: 183)
SYHIQ;

Heavy chain CDR2 (HCDR2):
                          (SEQ ID NO: 185)
WIYPGDGSTQYNEKFKG;

Heavy chain CDR3 (HCDR3):
                          (SEQ ID NO: 187)
EGTYYAMDY;

Light chain CDR1 (LCDR1):
                          (SEQ ID NO: 188)
RSSQSIVHSNGNTYLE;

Light chain CDR2 (LCDR2):
                          (SEQ ID NO: 189)
KVSNRFS;

Light chain CDR3 (LCDR3):
                          (SEQ ID NO: 190)
FQGSHVPRT.
```

As used herein, a "BB7.2 antibody" is an antibody having the VH (SEQ ID NO: 191) and VL (SEQ ID NO: 192) of the monoclonal antibody secreted by BB7.2. A BB7.2 antibody may be a whole antibody or a fragment thereof having the VH and VL of the monoclonal antibody secreted by BB7.2, such as an scFv having the VH and VL of the monoclonal antibody secreted by BB7.2.

The terms "antibodies" and "immunoglobulin" include antibodies or immunoglobulins of any isotype, fragments of antibodies which retain specific binding to antigen, including, but not limited to, Fab, Fab', F(ab')$_2$, Fv, scFv, Fd, diabodies, single domain antibodies (sdAbs), linear antibodies, single-chain antibody molecules, and multispecific antibodies formed from antibody fragments, chimeric antibodies, humanized antibodies, single-chain antibodies, and fusion proteins comprising an antigen-binding portion of an antibody and a non-antibody protein.

Antibodies can be polyclonal or monoclonal, multiple or single chain, or intact immunoglobulins, and may be derived from natural sources or from recombinant sources. Antibodies can be tetramers of immunoglobulin molecules. The basic 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for t and c isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. The five classes of immunoglobulins: IgA, IgD, IgE, IgG, and IgM have heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "VH", "$V_H$" or "H". The variable domain of the light chain may be referred to as "VL", "$V_L$" or "L". These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110- to 130-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)).

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variants thereof. In an embodiment, the intact antibody may have one or more effector functions.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include Fab, Fab', F(ab')2, Fv fragments, scFv fragments; diabodies; single domain antibodies (sdAbs); linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen. Also included among anti-HLA-A2 antibody fragments are portions of anti-HLA-A2 antibodies (and combinations of portions of anti-HLA-A2 antibodies, for example, scFv) that may be used as targeting arms, directed to an HLA-A2 antigen, in chimeric antigenic receptors of CAR-modified immune cells. Such fragments are not necessarily proteolytic fragments but rather portions of polypeptide sequences that can confer affinity for a target. Further included among anti-HLA-A2 antibody fragments are single domain antibodies (sdAbs) (see, for example, Li et al. (2017); Jamnani et al. (2014)). Such single domain antibodies may be used as targeting arms in the CAR-modified immune cells of the present invention.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and antigen-binding site. This fragment consists of a dimer of one heavy-chain variable region domain and one light-chain variable region domain in tight, non-covalent association. In a single-chain Fv (scFv) species, one heavy-chain variable domain and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. The scFv polypeptide may further comprise a polypeptide linker between the VH and VL domains which enables the scFv to form the desired structure for antigen binding. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL. For a review of scFv, see Pluckthun in The Pharmacology of Monoclonal Antibodies, vol. 113, Rosenburg and Moore eds., Springer-Verlag, New York, pp. 269-315 (1994); Antibody Engineering, ed. Borrebaeck, Oxford University Press, New York (1995). In one embodiment, an anti-HLA-A2 antibody derived scFv may be used as the targeting arm of a CAR-modified immune cell disclosed herein.

The term "adnectin", also known as monobody, is well known in the art and refers to proteins designed to bind with high affinity and specificity to antigens. They belong to the class of molecules collectively called "antibody mimetics".

The term "alphabody", refers to as Cell-Penetrating Alphabodies, refers to a type of antibody mimetics consisting of small 10 kDa proteins engineered to bind to a variety of antigens. Alphabodies are able to reach and bind to intracellular protein targets.

The term "affibody" is well known in the art and refers to affinity proteins based on a 58 amino acid residue protein domain, derived from one of the IgG binding domain of staphylococcal protein A.

The term "anticalin" is well known in the art and refers to an antibody mimetic technology, wherein the binding specificity is derived from lipocalin. Anticalin may also be formatted as dual targeting protein, called Duocalin.

The term "armadillo repeat protein-based scaffold" refers to a type of antibody mimetics corresponding to artificial peptide binding scaffolds based on armadillo repeat proteins. Armadillo repeat proteins are characterized by an armadillo domain, composed of tandem armadillo repeats of approximately 42 amino acids, which mediates interactions with peptides or proteins.

The term "avimers" is well known in the art and refers to an antibody mimetic technology. The term "DARPins" (Designed Ankyrin Repeat Proteins) is well known in the art and refers to an antibody mimetic DRP (designed repeat protein) technology developed to exploit the binding abilities of non-antibody polypeptides.

The term "diabodies" refers to small antibody fragments prepared by constructing scFv fragments with short linkers (about 5-10 residues) between the VH and VL domains such that inter-chain but not intra-chain pairing of the V domains is achieved, resulting in a bivalent fragment, i.e., fragment having two antigen binding sites. Bispecific diabodies are heterodimers of two "crossover" scFv fragments in which the VH and VL domains of the two antibodies are present on different polypeptide chains. Diabodies are described more fully in, for example, EP 0404097; WO 93/11161; and Holliger et al., Proc. Natl. Acad. Sci. USA, 90:6444-6448 (1993).

The term "evasin" is well known in the art and refers to a class of chemokine-binding proteins.

The term "fynomer" is well known in the art and refers to proteins that belong to the class of antibody mimetic. They are attractive binding molecules due to their high thermal stability and reduced immunogenicity.

The term "knottin" (that may also be referred to as inhibitor cystine not) refers to an antibody mimetic comprising a protein structural motif containing three disulfide bridges.

The term "kunitz domain peptide" refers to a type of antibody mimetics, and is based on the active domains of proteins inhibiting the function of proteases.

The term "nanobody" is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3).

The term "unibody" is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

The term "versabody" is well known in the art and refers to another antibody mimetic technology. They are small proteins of 3-5 kDa with >15% cysteines, which form a high disulfide density scaffold, replacing the hydrophobic core the typical proteins have.

The term "flexible polypeptide linker" or "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3, n=4, n=5, n=6, n=7, n=8, n=9 and n=10. In another embodiment, the flexible polypeptide linker is a Gly/Ser linker and comprises the amino acid sequence (Gly-Gly-Gly-Gly-Ser)$_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, (Gly$_4$Ser)$_4$ or (Gly$_4$Ser)$_3$. In another embodiment, the linkers include multiple repeats of (Gly$_2$Ser), (GlySer) or (Gly$_3$Ser). Also included within the scope of the invention are linkers described in WO2012/138475, incorporated herein by reference).

The term "heavy chain," refers to the larger of the two types of polypeptide chains present in antibody molecules in their naturally occurring conformations, and which normally determines the class to which the antibody belongs.

The term "light chain," refers to the smaller of the two types of polypeptide chains present in antibody molecules in their naturally occurring conformations. Kappa (κ) and lambda (λ) light chains refer to the two major antibody light chain isotypes.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., 1991). Chothia refers instead to the location of the structural loops (Chothia et al., 1987). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below. The residues from each of these hypervariable regions are noted below.

| Loop | Kabat | AbM | Chothia | Contact |
|------|-------|-----|---------|---------|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32 . . . 34 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

The terms "hypervariable region" and "complementarity determining region" and their respective abbreviations (HVR, HV, CDR) are used interchangeably herein. Further, the following pairs of terms are also used interchangeably herein:

"VH CDR1" and "HCDR1";
"VH CDR2" and "HCDR2";
"VH CDR3" and "HCDR3";
"VL CDR1" and "LCDR1";
"VL CDR2" and "LCDR2"; and
"VL CDR3" and "LCDR3".

Hypervariable regions may comprise "extended hypervariable regions" as follows: 24-36 or 24-34 (L), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al. (Kabat et al., 1991) for each of these definitions.

"Framework" or "FR" residues are those variable domain residues other than the hypervariable region residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., (Kabat et al., 1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., 1991). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system.

The term "specifically binds," refers to a ligand (e.g., a humanized anti-HLA-A2 antibody) which recognizes and binds with a cognate binding partner (e.g., HLA-A2) protein present in a sample, but which ligand does not substantially recognize or bind other molecules in the sample. Non-specific binding would refer to binding with an affinity of less than $10^{-7}$ M, e.g., binding with an affinity of $10^{-6}$ M, $10^{-5}$ M, $10^{-4}$ M, etc.

An antibody that "specifically binds" an antigen or epitope of interest is one that binds the antigen or epitope with sufficient affinity that is measurably different from a non-specific interaction. Specific binding can be measured, for example, by determining binding of a molecule compared to binding of a control molecule.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The term "antigen" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized or can be derived from a biological sample, or might be a macromolecule besides a polypeptide. Such a biological sample can include, but is not limited to a tissue sample, a tumor sample, a cell or a fluid with other biological components.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive", "preferentially binds" and "specifically binds" are used interchangeably herein with respect to antibodies and fragments thereof. Anti-HLA-A2 antibodies of the invention, including humanized anti-HLA-A2 antibodies, as well as fragments thereof as such term is used herein, specifically bind to HLA-A2.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than $10^{-7}$ M, e.g., binding with an affinity of $10^{-6}$ M, $10^{-5}$ M, $10^{-4}$ M, etc.

The term "reactivity" as used herein refers to the ability of an antibody to react with (that is, bind to) a molecule (e.g., specifically bind to the molecule). A first antibody has "less reactivity" to a molecule (e.g., an HLA molecule) than a second antibody when the first antibody exhibits reduced binding to the molecule as compared to the second antibody.

Approaches for readily comparing the reactivities of first and second antibodies to one or more particular HLA molecules are known. One example approach is provided in the Examples section herein, where FlowPRA® Single Antigen beads (One Lambda) were employed to interrogate antibodies for the ability to react with (or bind to) particular HLA molecules. Such flow cytometric approaches are amenable to high-throughput antibody reactivity analyses.

As used herein, the term "hinge region" refers to a flexible polypeptide connector region (also referred to herein as "hinge" or "spacer") providing structural flexibility and spacing to flanking polypeptide regions and can consist of natural or synthetic polypeptides. A hinge region may influence the potency of an immune cell expressing a CAR (see for example Watanabe et al. (2016)). A "hinge region" derived from an immunoglobulin (e.g., IgG1) is generally defined as stretching from $Glu_{216}$ to $Pro_{230}$ of human IgG1 (Burton (1985) Molec. Immunol., 22:161-206). Hinge regions of other IgG isotypes may be aligned with the IgG1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include complete hinge region derived from an antibody of a different class or subclass from that of the CH1 domain. The term "hinge region" can also include regions derived from CD8 and other receptors that provide a similar function in providing flexibility and spacing to flanking regions.

As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells ($CD4^+$ cells), $CD8^+$ T-cells (e.g., cytotoxic $CD8^+$ T cell, regulatory $CD8^+$ T cell), T-regulatory cells (Treg), gamma-delta T cells, and double negative T cells.

A "cytotoxic cell" includes cytotoxic $CD8^+$ T cells, natural-killer (NK) cells, and neutrophils, which cells are capable of mediating cytotoxicity responses.

As used herein, the term "regulatory immune cell" refers to an immune cell that acts in a "regulatory" way to suppress activation of the immune system and thereby maintains immune system homeostasis and tolerance to self-antigens. "Regulatory immune cells" may also have effects on non-immune cells that result in an improved clinical state such as promoting tissue repair or regeneration. Regulatory immune cells may include regulatory T cells, $CD4^+$ regulatory T cells, $CD8^+$ regulatory T cells, regulatory γδ T cells, regulatory DN T cells, regulatory B cells, regulatory NK cells, regulatory macrophages, and regulatory dendritic cells.

"Regulatory T lymphocyte", "regulatory T cell,", "T regulatory cell", "Treg cell" or "Treg," as used in the present specification and claims are synonymous and are intended to have its standard definition as used in the art. Treg cells are a specialized subpopulation of T cells that act in a "regulatory" way to suppress activation of the immune system and thereby maintain immune system homeostasis and tolerance to self-antigens. Tregs have sometimes been referred to as suppressor T-cells. Treg cells are often, but not always, characterized by expression of the forkhead family transcription factor Foxp3 (forkhead box p3). They may also express CD4 or CD8 surface proteins. They usually also express CD25. As used in the present specification and claims, and unless otherwise specified, Tregs include "natural" Tregs which develop in the thymus, induced/adaptive/peripheral Tregs that arise via a differentiation process which takes place outside the thymus (e.g. in tissues or secondary lymphoid organs, or in the laboratory setting under defined culture conditions), and Tregs that have been created using recombinant DNA technology, for example by engineered expression of FOXP3. Naturally-occurring Treg cells ($CD4^+CD25+Foxp3+$) arise like all other T cells in the thymus. In contrast, induced/adaptive/peripheral Treg cells (which include $CD4^+CD25+Foxp3+$Tregs, Tr1 cells, Th3 cells and others) arise outside the thymus. One way to induce Tregs is by exposure of T effector cells to IL-10 or TGF-β. T-cells may also be converted to Treg cells by transfection or transduction of the Foxp3 gene into a mixed population of T-cells. A T-cell that is caused to express Foxp3 adopts the Treg phenotype and such recombinant Tregs are also defined herein as "Tregs".

As used herein, the term "immune effector cell" refers to a cell of the immune system which is in a form that is capable of mounting a specific immune response.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

The term "rejection" refers to a state in which a transplanted organ or tissue is not accepted by the body of the recipient. Rejection results from the recipient's immune system attacking the transplanted organ or tissue. Rejection can occur days to weeks after transplantation (acute) or months to years after transplantation (chronic).

The term "graft-versus-host disease" or "GVHD" as used herein refers to a medical complication following the receipt of transplanted tissue from a genetically different person. Immune cells in the donated tissue (the graft) recognize the recipient (the host) as foreign. The transplanted immune cells then attack the host's body cells. GVHD is commonly associated with stem cell transplant; however, the term includes GVHD arising from other forms of tissue graft. GVHD may also occur after a blood transfusion.

As used herein, the term "immunological tolerance" or "immune tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological or immune tolerance occurs when immunological or immune tolerance is preferentially invoked against certain antigens in comparison with others.

As used herein, the term "operational tolerance" refers to a clinical situation where there is a stable graft function lacking histological signs of rejection, including acute or chronic rejection, in the absence of any immunosuppressive drug therapies for at least 1 year, in an immunocompetent host capable of responding to other challenges including infections.

As used herein, the term "immune accommodation" refers to a condition of a transplant recipient in which an organ or tissue transplant functions normally despite the presence of antibodies in the recipient which are specific for the organ or tissue transplant.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

As used herein, the terms "treatment," "treating," and the like, refer to obtaining a desired pharmacologic and/or physiologic effect. The effect may be therapeutic in terms of a partial or complete cure for a disease and/or adverse effect attributable to the disease. "Treatment," as used herein, covers any treatment of a disease in a mammal, e.g., in a human, and includes relieving the disease, i.e., causing regression of the disease and/or amelioration of one or more symptoms of the disease.

As used herein, the terms "prevention, "prevent," "preventing," and the like, mean to provide prophylactic or protective treatment for a disease or disease state. The effect may be prophylactic in terms of completely or partially preventing a disease or symptom thereof. "Prevention," as used herein, covers any prophylactic effect on a disease in a mammal, e.g., in a human, and includes: (a) preventing the disease from occurring in a subject which may be predisposed to the disease but has not yet been diagnosed as having it; and (b) inhibiting the disease, i.e., arresting its development.

The terms "patient," "subject," "individual," "host," and the like are used interchangeably herein, and refer to any animal, or cells thereof whether in vitro or in situ, amenable to the methods described herein. The terms "patient," "subject," "individual," "host," and the like are intended to include living organisms in which an immune response can be elicited (e.g., mammals). Examples of "patient," "subject," "individual," "host," include murines (e.g., rats, mice), lagomorphs (e.g., rabbits), non-human primates, humans, canines, felines, ungulates (e.g., equines, bovines, ovines, porcines, caprines), etc. and transgenic species thereof. In certain non-limiting embodiments, the patient, subject, host, or individual is a human.

The term "effective amount" or "therapeutically effective amount" are used interchangeably herein, and refers to the amount of a therapeutic agent, or combined amounts of more than one therapeutic agent, that will elicit the biological or medical response of a tissue, system, or subject that is being sought by the researcher, veterinarian, medical doctor or other clinician. The term "therapeutically effective amount" includes that amount of a therapeutic agent that, when administered, is sufficient to prevent development of, or alleviate to some extent, one or more of the signs or symptoms of the disorder or disease being treated. The therapeutically effective amount will vary depending on the therapeutic agent, the disease and its severity and the age, weight, etc., of the subject to be treated.

The term "activation" as used herein, refers to the state of a T cell (e.g., a regulatory T cell) that has been sufficiently stimulated to induce a detectable cellular response. Activation can also be associated with detectable effector function (s) such as cytokine production or suppressive activity. The term "activated" regulatory T cells refers to, among other things, regulatory T cells that are capable of suppressing an immune response.

The term "chimeric antigen receptor" or alternatively a "CAR" refers to a recombinant polypeptide construct comprising an extracellular domain comprising an antigen binding domain; a transmembrane domain; and a cytoplasmic domain comprising an intracellular signaling domain. In one embodiment, the CAR optionally comprises a hinge. The terms "chimeric receptor" or "chimeric antigen receptor" or "CAR" may in particular refer to one polypeptide or to a set of polypeptides, typically two in the simplest embodiments, which when in an immune cell, provides the cell with specificity for a target ligand and with intracellular signal generation. In some embodiments, the set of polypeptides are contiguous with each other. In some embodiments, the chimeric receptor is a chimeric fusion protein comprising the set of polypeptides. In some embodiments, the set of polypeptides include a dimerization switch that, upon the presence of a dimerization molecule, can couple the polypeptides to one another, e.g., can couple a ligand binding domain to an intracellular signaling domain. In one embodiment, the chimeric receptor comprises an optional leader sequence at the amino-terminus (N-ter) of the chimeric receptor fusion protein. In one embodiment, the chimeric receptor further comprises a leader sequence at the N-terminus of the extracellular ligand binding domain, wherein the leader sequence is optionally cleaved from the ligand binding domain during cellular processing and localization of the chimeric receptor to the cellular membrane.

The term "signaling domain" refers to the functional portion of a protein which acts by transmitting information within the cell to regulate cellular activity via defined signaling pathways by generating second messengers or functioning as effectors by responding to such messengers.

The term "autologous" refers to any material derived from the same subject to whom it is later to be re-introduced into the subject.

The term "allogeneic" refers to any material derived from a different subject of the same species as the subject to whom the material is introduced. Two or more subjects are said to be allogeneic to one another when the genes at one or more loci are not identical. In some aspects, allogeneic material from subjects of the same species may be sufficiently unlike genetically to interact antigenically. The term "allograft" refers to a graft derived from a different subject of the same species.

The term "xenogeneic" refers to any material derived from a subject of a different species. The term "xenograft" refers to a graft derived from a subject of a different species.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, cell, and/or composition of the invention or be shipped together with a container which contains the nucleic acid, peptide, cell and/or composition. Alternatively, the instructional material may be shipped separately from the container with the intention that the instructional material and the nucleic acid, peptide, cell and/or composition be used cooperatively by the recipient.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution", or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "conservative sequence modification" refers to an amino acid modification that does not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as upregulation or downregulation of cytokines and cell surface proteins, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for example, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif (ITAM).

The term "antigen presenting cell" or "APC" refers to an immune system cell such as an accessory cell (e.g., a B cell, a dendritic cell, macrophages, Langerhans cells and the like) that can display an antigen complexed with major histocompatibility complexes (MHCs) on its surface for recognition by certain lymphocytes such as T cells. T cells may recognize these complexes using their T cell receptors (TCRs). Antigen presenting cells may process antigens for display in conjunction with MHCs. The term "antigen presenting cell" or "APC" as used herein includes states where the APCs are displaying an antigen and states where the APCs are not displaying an antigen. In some instances, APCs process antigens and present them to T cells. In other instances, T cells may recognize APCs in the absence of antigen presentation where the TCR directly binds to the MHC protein. For example, in the context of transplantation, APCs may directly stimulate T cells via expression of foreign MHC proteins.

An "intracellular signaling domain," as the term is used herein, refers to an intracellular portion of a CAR. The intracellular signaling domain generates a signal that promotes an immune effector function of the CAR containing cell, e.g., a CAR Treg cell. Examples of immune effector function, e.g., in a CAR Treg cell, may include suppression or downregulation of the effector function of other immune cells. Other immune cells includes any type of leukocytes, for example (but not limited to) T cells, B cells, NK cells. In addition, the immune effector function of Tregs may include effects on non-immune cells that result in an improved clinical state such as promoting tissue repair or regeneration.

The term "zeta" or alternatively "zeta chain", or "CD3-zeta" is defined as the protein provided as GenBan Acc. No. BAG36664.1, or the equivalent residues from a non-human species, e.g., mouse, rodent, monkey, ape and the like, and a "zeta stimulatory domain" or a "CD3-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

"Co-stimulatory ligand," as the term is used herein, includes a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, a ligand, including an antibody, that specifically binds with a co-stimulatory molecule present on a T cell, such as, but not limited to, an MHC class I molecule, BTLA, a Toll ligand receptor, OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, GITR, HVEM, SLAMF7, NKp80, CD160, IL2ra, IL6Ra, IL-7Ra, IL-13RA1/RA2, IL-33R(IL1RL1), IL-10RA/RB, IL-4R, IL-5R (CSF2RB), ARHR, BAFF receptor, IL-21R, TGFbR1/2/3, common gamma chain, a ligand that specifically binds with CD83, and any combination thereof.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Costimulatory molecules include, but are not limited to an MHC class I molecule, BTLA, a Toll ligand receptor, OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, GITR, HVEM, SLAMF7, NKp80, CD160, IL2ra, IL6Ra, IL-7Ra, IL-13RA1/RA2, IL-33R(IL1RL1), IL-10RA/RB, IL-4R, IL-5R (CSF2RB), ARHR, BAFF receptor, IL-21R, TGFbR1/2/3, common gamma chain, a ligand that specifically binds with CD83, and any combination thereof.

A "costimulatory intracellular signaling domain" or "costimulatory domain" can be the intracellular portion of a costimulatory molecule. Examples of such molecules include an MHC class I molecule, BTLA, a Toll ligand receptor, OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, GITR, HVEM, SLAMF7, NKp80, CD160, IL2ra, IL6Ra, IL-7Ra, IL-13RA1/RA2, IL-33R(IL1RL1), IL-10RA/RB, IL-4R, IL-5R (CSF2RB), ARHR, BAFF receptor, IL-21R, TGFbR1/2/3, common gamma chain, a ligand that specifically binds with CD83, and the like.

A "co-stimulatory signal," as used herein, refers to a signal, which in combination with a primary signal, such as TCR/CD3 ligation, leads to T cell proliferation and/or upregulation or downregulation of key molecules.

The intracellular signaling domain can comprise the entire intracellular portion, or the entire native intracellular signaling domain, of the molecule from which it is derived, or a functional fragment thereof.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a nucleotide sequence or nucleic acid sequence encoding an amino acid sequence includes all nucleotide or nucleic acid sequences that are degenerate versions of each other and that encode the same amino acid sequence. The phrase nucleotide sequence or nucleic acid sequence that encodes a protein or a RNA may also include introns to the extent that the nucleotide or nucleic acid sequence encoding the protein may in some version contain an intron(s).

A "transplant," as used herein, refers to cells, tissue, or an organ that is introduced into a subject. The source of the transplanted material can be cultured cells, cells from another subject, or cells from the same subject (e.g., after the cells are cultured in vitro). Exemplary organ transplants are kidney, liver, heart, lung, and pancreas. An exemplary tissue transplant is islets. An exemplary cell transplant is allogeneic hematopoietic stem cell transplantation.

The term "exogenous" refers to any material introduced from or produced outside an organism, cell, tissue or system.

The term "expression" refers to the transcription and/or translation of a particular nucleotide sequence driven by a promoter.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, scFv, Fab, scFab, sdAb, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

A "human" immunoglobulin, antibody or antibody fragment refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intradermal, intranodal, intramedullary, intraperitoneal, intravenous (i.v.), intramuscular (i.m.), or intrasternal injection, intratumoral, or infusion techniques.

The terms "nucleic acid" or "polynucleotide", used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Thus, unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Various aspects of the invention can be presented throughout this disclosure in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

III. Anti-HLA-A2 Antibodies

In one aspect, the present invention provides anti-HLA-A2 antibodies. Exemplary antibodies include monoclonal antibodies, polyclonal antibodies, recombinant antibodies, chimeric antibodies, human antibodies, humanized antibodies, and antigen binding fragments thereof.

In one embodiment, the invention provides humanized anti-HLA-A2 antibodies. The humanized anti-HLA-A2 antibodies provided herein bind specifically to HLA-A2. In one embodiment, the humanized anti-HLA-A2 antibodies provided herein bind specifically to HLA-A*02:01. As would be appreciated by one skilled in the art, the ability of an antibody to bind to HLA-A2 may be detected through the use of techniques known in the art. For example, binding of an antibody to HLA-A2 may be detected through the use of an HLA-A2 tetramer as exemplified herein. In one embodiment, the humanized anti-HLA-A2 antibodies provided herein compete for binding to HLA-A2 with an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the humanized anti-HLA-A2 antibodies provided herein bind to the same HLA-A2 epitope as an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the humanized anti-HLA-A2 antibodies provided herein compete for binding to HLA-A2 with a BB7.2 antibody.

In one embodiment, the humanized anti-HLA-A2 antibodies provided herein bind to the same HLA-A2 epitope as a BB7.2 antibody. In one embodiment, the humanized anti-HLA-A2 antibodies provided herein have less reactivity to at least one HLA-A subtype selected from one or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from two or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from three or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from four or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from five or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from six or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from seven or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from each of HLA-A*03, HLA-A*25, HLA-A*29, HLA-A*30, HLA-A*31, HLA-A*33, HLA-A*36, HLA-A*68, as compared to a BB7.2 antibody. In one embodiment, the humanized anti-HLA-A2 antibodies provided herein have less reactivity to at least one HLA-A subtype selected from one or more of HLA-A*25, HLA-A*29, HLA-A*30, as compared to a BB7.2 antibody. In one embodiment, the humanized anti-HLA-A2 antibodies provided herein have less reactivity to at least one HLA-A subtype selected from two or more of HLA-A*25, HLA-A*29, HLA-A*30, as compared to a BB7.2 antibody. In one embodiment, the humanized anti-HLA-A2 antibodies provided herein have less reactivity to at least one HLA-A subtype selected from each of HLA-A*25, HLA-A*29, HLA-A*30, as compared to a BB7.2 antibody. In one embodiment, the humanized anti-HLA-A2 antibodies provided herein have less reactivity to at least one of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least two of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least three of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least four of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least five of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least six of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least seven of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the humanized anti-HLA-A2 antibodies provided herein have less reactivity to at least one of HLA-A*25:01, HLA-A*29:02, and HLA-A*30:01, as compared to a BB7.2 antibody. In one embodiment, the humanized anti-HLA-A2 antibodies provided herein have less reactivity to at least two of HLA-A*25:01, HLA-A*29:02, and HLA-A*30:01, as compared to a BB7.2 antibody. In one embodiment, the humanized anti-HLA-A2 antibodies provided herein have less reactivity to HLA-A*25:01, HLA-A*29:02, and HLA-A*30:01, as compared to a BB7.2 antibody. In one embodiment, the humanized anti-HLA-A2 antibodies provided herein have less reactivity to HLA-A*25:01 as compared to a BB7.2 antibody. In one embodiment, the humanized anti-HLA-A2 antibodies provided herein have less reactivity to HLA-A*29:02 as compared to a BB7.2 antibody. In one embodiment, the humanized anti-HLA-A2 antibodies provided herein have less reactivity to HLA-A*30:01 as compared to a BB7.2 antibody. In one embodiment, the humanized anti-HLA-A2 antibodies provided herein have less reactivity to HLA-A*03:01 as compared to a BB7.2 antibody. In one embodiment, the humanized anti-HLA-A2 antibodies provided herein have less reactivity to HLA-A*31:01 as compared to a BB7.2 antibody. In one embodiment, the humanized anti-HLA-A2 antibodies provided herein have less reactivity to HLA-A*33:01 as compared to a BB7.2 antibody. In one embodiment, the humanized anti-HLA-A2 antibodies provided herein have less reactivity to HLA-A*36:01 as compared to a BB7.2 antibody. In one embodiment, the humanized anti-HLA-A2 antibodies provided herein have less reactivity to HLA-A*68:01 as compared to a BB7.2 antibody. The BB7.2 antibody may be isolated from the BB7.2 hybridoma (ATCC Deposit No. HB-82).

Techniques for determining the reactivity of the humanized anti-HLA-A2 antibodies to HLA-A subtypes would be known to those of ordinary skill in the art. For example, the reactivity of the humanized anti-HLA-A2 antibodies to HLA-A subtypes may be determined by a single antigen bead assay. Such single antigen bead assays are commercially available (e.g., FlowPRA Single Antigen Antibody; ONE LAMBDA).

In one embodiment, the humanized anti-HLA-A2 antibodies provided herein have less reactivity to at least one HLA-A subtype selected from one or more of HLA-A*03, HLA-A*25, HLA-A*29, HLA-A*30, HLA-A*31, HLA-A*33, HLA-A*36, HLA-A*68, and any combination thereof, as compared to a BB7.2 antibody, e.g., as compared to a BB7.2 scFv when measured in the conditions of Test A. For example, in some embodiments, the humanized anti-HLA-A2 antibodies provided herein have less reactivity to at least one HLA-A subtype selected from one or more of HLA-A*25, HLA-A*29, HLA-A*30, and any combination thereof, as compared to a BB7.2 antibody, e.g., as compared to a BB7.2 scFv when measured in the conditions of Test A.

Test A:

$0.25 \cdot 10^6$ T cells expressing a CAR comprising the humanized anti-HLA-A2 antibody or a BB7.2 antibody, e.g., a BB7.2 scFv (mA2 CAR)) are incubated with FlowPRA single antigen antibody beads panel (FL1HD01, FL1HD02, FL1HD03, FL1HD04, FL1HD06 and FL1HD08, One Lambda) and fixable viability dye (FVD, ThermoFisher, 65-0865-14, eBioscience) for 30 minutes at room temperature. Samples are washed, fixed with 0.5% formaldehyde and analyzed via flow cytometry. Two hundred negative control beads are acquired per sample. Beads alone were used as a negative control. For analysis, dead cells are first eliminated using the fixable viability dye. Single antigen beads are then gated after exclusion of dead cells and doublets. Then, the number of beads per HLA is determined by their respective PE intensity peak. Data are normalized by multiplying the number of beads of interest in each HLA-peak by 200, divided by the number of negative beads in the sample. For each HLA-peak the percent relative binding of CAR Tregs compared to control (non-CAR-expressing cells) is determined by subtracting the number of beads in the CAR-Treg from the number of beads in the control sample then dividing the average number of beads in the non-CAR-expressing control, times 100.

In one embodiment, the humanized anti-HLA-A2 antibody of the invention has a reactivity to at least one HLA-A subtype selected from the group comprising HLA-A*03, HLA-A*25, HLA-A*29, HLA-A*30, HLA-A*30, HLA-A*31, HLA-A*33, HLA-A*36, HLA-A*68 statistically inferior to a BB7.2 antibody, e.g., when measured in the conditions of Test A.

In one embodiment, the anti-HLA-A2 antibody of the invention has a reactivity to at least one HLA-A subtype selected from the group comprising HLA-A*25, HLA-A*29, HLA-A*30 statistically inferior to a BB7.2 antibody, e.g., when measured in the conditions of Test A.

In one embodiment, the term "statistically inferior" means that the reactivity (for example, the relative binding in the conditions of Test A) measured for the anti-HLA-A2 antibody of the invention is inferior to the reactivity measured for a BB7.2 antibody with a p value of at most about 0.05, preferably of at most about 0.01, more preferably of at most about 0.005, and even more preferably of at most about 0.001, in particular when analyzed by 2-way ANOVA, Dunnett post-test.

In one embodiment, the anti-HLA-A2 antibody of the invention has a reactivity to at least one HLA-A subtype selected from the group comprising HLA-A*03, HLA-A*25, HLA-A*29, HLA-A*30, HLA-A*30, HLA-A*31, HLA-A*33, HLA-A*36, HLA-A*68 inferior to a BB7.2 antibody In some embodiments, such an anti-HLA-A2 antibody has a relative binding for at least one HLA-A subtype selected from the group comprising HLA-A*03, HLA-A*25, HLA-A*29, HLA-A*30, HLA-A*30, HLA-A*31, HLA-A*33, HLA-A*36, HLA-A*68 inferior to a BB7.2 antibody when measured in the conditions of Test A. In certain aspects, the relative binding measured for such a anti-HLA-A2 antibody is at most about 90%, 80%, 70%, 60%, 50%, 40%, 30%, 20%, 10% or less of the relative binding measured for a BB7.2 antibody.

In one embodiment, the anti-HLA-A2 antibody of the invention has a reactivity to at least one HLA-A subtype selected from the group comprising HLA-A*25, HLA-A*29, HLA-A*30 inferior to a BB7.2 antibody In some embodiments, such an anti-HLA-A2 antibody has a relative binding for at least one HLA-A subtype selected from the group comprising HLA-A*25, HLA-A*29, HLA-A*30 inferior to a BB7.2 antibody when measured in the conditions of Test A. In certain aspects, the relative binding measured for such an anti-HLA-A2 antibody is at most about 90%, 80%, 70%, 60%, 50%, 40%, 30%, 20%, 10% or less of the relative binding measured for a BB7.2 antibody.

Further, humanized anti-HLA-A2 antibodies provided herein with antigen binding activity, are capable of constituting antigen binding domains of chimeric antigen receptors (CARs), wherein such CARs are capable of being expressed in human cells such that the CARs specifically bind to HLA-A2. In one embodiment, the CARs specifically bind to HLA-A*02:01. As would be appreciated by one skilled in the art, the ability of a CAR to bind to HLA-A2 may be detected through the use of techniques known in the art. For example, binding of a CAR to HLA-A2 may be detected through the use of an HLA-A2 tetramer as exemplified herein. In one embodiment, the human cell is an immune cell. In one embodiment, the immune cell is a regulatory immune cell. In one embodiment, the immune cell is a T regulatory cell (Treg). In one embodiment, the immune cell is a T cell. In one embodiment, the T cell is a Treg. Further, humanized anti-HLA-A2 antibodies provided herein with antigen binding activity, are capable of constituting antigen binding domains of chimeric antigen receptors (CARs), wherein such CARs are capable of being expressed in a T regulatory cell (Treg) such that the CARs specifically bind to HLA-A2. In one embodiment, the CARs specifically bind to HLA-A*02:01. In one embodiment, the Treg is a human Treg.

In one embodiment, the humanized anti-HLA-A2 antibody is capable of constituting an antigen binding domain of a CAR, wherein such CAR is capable of being expressed in an immune cell such that the immune cell is activated by HLA-A2. In one embodiment, the immune cell is activated by HLA-A*02:01. In one embodiment, the immune cell is a regulatory immune cell. In one embodiment, the immune cell is a T regulatory cell (Treg). In one embodiment, the immune cell is a T cell. In one embodiment, the T cell is a Treg. In one embodiment, the immune cell is a human immune cell. In one embodiment, the regulatory immune cell is a human regulatory immune cell. In one embodiment, the T cell is a human T cell. In one embodiment, the Treg is a human Treg.

In one embodiment, the humanized anti-HLA-A2 antibody comprises a heavy chain variable region comprising an amino acid sequence selected from the group consisting of: SYHIQ (SEQ ID NO: 1) and GYTFTSY (SEQ ID NO: 2).

In one embodiment, the humanized anti-HLA-A2 antibody comprises a heavy chain variable region comprising a complementarity determining region 1 (VH CDR1) selected from SEQ ID NOs: 1-2. In one embodiment, the humanized anti-HLA-A2 antibody comprises a heavy chain variable region comprising a VH CDR1 set forth by SEQ ID NO: 1. In one embodiment, the humanized anti-HLA-A2 antibody comprises a heavy chain variable region comprising a VH CDR1 set forth by SEQ ID NO: 2.

In one embodiment, the humanized anti-HLA-A2 antibody comprises a heavy chain variable region comprising an amino acid sequence selected from the group consisting of: YPGDGS (SEQ ID NO: 4) and WIYPGDGSTX$^{10}$YX$^{12}$X$^{13}$KFX$^{16}$G (SEQ ID NO: 10), wherein in SEQ ID NO: 10, the amino acid at position 10 (X$^{10}$) is Q or K, the amino acid at position 12 (X$^{12}$) is N or S, the amino acid at position 13 (X$^{13}$) is E or Q, and the amino acid at position 16 (X$^{16}$) is K or Q.

In one embodiment, the humanized anti-HLA-A2 antibody comprises a heavy chain variable region comprising the amino acid sequence WIYPGDGSTX$^{10}$YX$^{12}$X$^{13}$KFX$^{16}$G (SEQ ID NO: 10), wherein the amino acid at position 10 (X$^{10}$) is Q or K, the amino acid at position 12 (X$^{12}$) is N or S, the amino acid at position 13 (X$^{13}$) is E or Q, and the amino acid at position 16 (X$^{16}$) is K or Q.

In one embodiment, the humanized anti-HLA-A2 antibody comprises a heavy chain variable region comprising a complementarity determining region 2 (VH CDR2) comprising an amino acid sequence selected from the group consisting of: YPGDGS (SEQ ID NO: 4) and WIYPGDGSTX$^{10}$YX$^{12}$X$^{13}$KFX$^{16}$G (SEQ ID NO: 10), wherein in SEQ ID NO: 10, the amino acid at position 10 (X$^{10}$) is Q or K, the amino acid at position 12 (X$^{12}$) is N or S, the amino acid at position 13 (X$^{13}$) is E or Q, and the amino acid at position 16 (X$^{16}$) is K or Q. In one embodiment, the humanized anti-HLA-A2 antibody comprises a heavy chain variable region comprising a complementarity determining region 2 (VH CDR2) comprising the amino acid sequence WIYPGDGSTX$^{10}$YX$^{12}$X$^{13}$KFX$^{16}$G (SEQ ID NO: 10), wherein the amino acid at position 10 (X$^{10}$) is Q or K, the amino acid at position 12 (X$^{12}$) is N or S, the amino acid at position 13 (X$^{13}$) is E or Q, and the amino acid at position 16 (X$^{16}$) is K or Q. In one embodiment, the heavy chain variable region comprises a VH CDR2 comprising an amino acid sequence set forth in SEQ ID NO: 10, wherein the amino acid at position 10 is Q or K, the amino acid at position 12 is S, the amino acid at position 13 is Q, and the amino acid at position 16 is Q. In one embodiment, the heavy chain variable region comprises a VH CDR2 comprising an amino acid sequence set forth in SEQ ID NO: 10, wherein the amino acid at position 10 is K, the amino acid at position 12 is N or S, the amino acid at position 13 is Q, and the amino acid at position 16 is Q. In one embodiment, the heavy chain variable region comprises a VH CDR2 comprising an amino acid sequence set forth in SEQ ID NO: 10, wherein the amino acid at position 10 is K, the amino acid at position 12 is S, the amino acid at position 13 is E or Q, and the amino acid at position 16 is Q. In one embodiment, the heavy chain variable region comprises a VH CDR2 comprising an amino acid sequence set forth in SEQ ID NO: 10, wherein the amino acid at position 10 is K, the amino acid at position 12 is S, the amino acid at position 13 is Q, and the amino acid at position 16 is K or Q. In one embodiment, the heavy chain variable region comprises a VH CDR2 comprising an amino acid sequence set forth in SEQ ID NO: 10, wherein the amino acid at position 10 is Q or K, the amino acid at position 12 is N or S, the amino acid at position 13 is Q, and the amino acid at position 16 is Q. In one embodiment, the heavy chain variable region comprises a VH CDR2 comprising an amino acid sequence set forth in SEQ ID NO: 10, wherein the amino acid at position 10 is Q or K, the amino acid at position 12 is S, the amino acid at position 13 is E or Q, and the amino acid at position 16 is Q. In one embodiment, the heavy chain variable region comprises a VH CDR2 comprising an amino acid sequence set forth in SEQ ID NO: 10, wherein the amino acid at position 10 is Q or K, the amino acid at position 12 is S, the amino acid at position 13 is Q, and the amino acid at position 16 is K or Q. In one embodiment, the heavy chain variable region comprises a VH CDR2 comprising an amino acid sequence set forth in SEQ ID NO: 10, wherein the amino acid at position 10 is K, the amino acid at position 12 is N or S, the amino acid at position 13 is E or Q, and the amino acid at position 16 is Q. In one embodiment, the heavy chain variable region comprises a VH CDR2 comprising an amino acid sequence set forth in SEQ ID NO: 10, wherein the amino acid at position 10 is K, the amino acid at position 12 is N or S, the amino acid at position 13 is Q, and the amino acid at position 16 is K or Q. In one embodiment, the heavy chain variable region comprises a VH CDR2 comprising an amino acid sequence set forth in SEQ ID NO: 10, wherein the amino acid at position 10 is K, the amino acid at position 12 is S, the amino acid at position 13 is E or Q, and the amino acid at position 16 is K or Q. In one embodiment, the heavy chain variable region comprises a VH CDR2 comprising an amino acid sequence set forth in SEQ ID NO: 10, wherein the amino acid at position 10 is Q or K, the amino acid at position 12 is N or S, the amino acid at position 13 is E or Q, and the amino acid at position 16 is Q. In one embodiment, the heavy chain variable region comprises a VH CDR2 comprising an amino acid sequence set forth in SEQ ID NO: 10, wherein the amino acid at position 10 is Q or K, the amino acid at position 12 is N or S, the amino acid at position 13 is Q, and the amino acid at position 16 is K or Q. In one embodiment, the heavy chain variable region comprises a VH CDR2 comprising an amino acid sequence set forth in SEQ ID NO: 10, wherein the amino acid at position 10 is Q or K, the amino acid at position 12 is S, the amino acid at position 13 is E or Q, and the amino acid at position 16 is K or Q. In one embodiment, the heavy chain variable region comprises a VH CDR2 comprising an amino acid sequence set forth in SEQ ID NO: 10, wherein the amino acid at position 10 is K, the amino acid at position 12 is N or S, the amino acid at position 13 is E or Q, and the amino acid at position 16 is K or Q.

In one embodiment, the humanized anti-HLA-A2 antibody comprises a heavy chain variable region comprising an amino acid sequence selected from the group consisting of: WIYPGDGSTQYNEKFKG (SEQ ID NO: 3), YPGDGS (SEQ ID NO: 4), and WIYPGDGSTKYSQKFQG (SEQ ID NO: 5). In one embodiment, the humanized anti-HLA-A2 antibody comprises a heavy chain variable region comprising an amino acid sequence selected from the group consisting of: WIYPGDGSTQYNEKFKG (SEQ ID NO: 3) and YPGDGS (SEQ ID NO: 4). In one embodiment, the humanized anti-HLA-A2 antibody comprises a heavy chain variable region comprising an amino acid sequence selected from the group consisting of: YPGDGS (SEQ ID NO: 4) and WIYPGDGSTKYSQKFQG (SEQ ID NO: 5).

In one embodiment, the humanized anti-HLA-A2 antibody comprises a heavy chain variable region comprising an amino acid sequence set forth by SEQ ID NO: 3. In one embodiment, the humanized anti-HLA-A2 antibody comprises a heavy chain variable region comprising an amino acid sequence set forth by SEQ ID NO: 4. In one embodiment, the humanized anti-HLA-A2 antibody comprises a heavy chain variable region comprising an amino acid sequence set forth by SEQ ID NO: 5.

In one embodiment, the humanized anti-HLA-A2 antibody comprises a heavy chain variable region comprising a complementarity determining region 2 (VH CDR2) selected from SEQ ID NOs: 3-5. In one embodiment, the humanized anti-HLA-A2 antibody comprises a heavy chain variable region comprising a complementarity determining region 2 (VH CDR2) selected from SEQ ID NOs: 3-4. In one embodiment, the humanized anti-HLA-A2 antibody comprises a heavy chain variable region comprising a complementarity determining region 2 (VH CDR2) selected from SEQ ID NOs: 4-5. In one embodiment, the humanized anti-HLA-A2 antibody comprises a heavy chain variable region comprising a complementarity determining region 2 (VH CDR2) set forth by SEQ ID NO: 5. In one embodiment, the humanized anti-HLA-A2 antibody comprises a heavy chain variable region comprising a VH CDR2 set forth by SEQ ID NO: 3. In one embodiment, the humanized anti-HLA-A2 antibody comprises a heavy chain variable region comprising a VH CDR2 set forth by SEQ ID NO: 4.

In one embodiment, the humanized anti-HLA-A2 antibody comprises a heavy chain variable region comprising the amino acid sequence EGTYYAMDY (SEQ ID NO: 6).

In one embodiment, the humanized anti-HLA-A2 antibody comprises a heavy chain variable region comprising a complementarity determining region 3 (VH CDR3) set forth by SEQ ID NO: 6.

In one embodiment, the humanized anti-HLA-A2 antibody comprises a heavy chain variable region comprising at least one of the following CDRs:
  a VH CDR1 set forth by SEQ ID NO: 1; or
  a VH CDR2 set forth by SEQ ID NO: 10, wherein the amino acid at position 10 ($X^{10}$) is Q or K, the amino acid at position 12 ($X^{12}$) is N or S, the amino acid at position 13 ($X^{13}$) is E or Q, and the amino acid at position 16 ($X^{16}$) is K or Q; or
  a VH CDR3 set forth by SEQ ID NO: 6.

In one embodiment, the humanized anti-HLA-A2 antibody comprises a heavy chain variable region comprising at least one of the following CDRs:
  a VH CDR1 set forth by SEQ ID NO: 1; or
  a VH CDR2 set forth by SEQ ID NO: 3; or
  a VH CDR3 set forth by SEQ ID NO: 6.

In one embodiment, the humanized anti-HLA-A2 antibody comprises a heavy chain variable region comprising at least one of the following CDRs:
  a VH CDR1 set forth by SEQ ID NO: 1; or
  a VH CDR2 set forth by SEQ ID NO: 5; or
  a VH CDR3 set forth by SEQ ID NO: 6.

In one embodiment, the humanized anti-HLA-A2 antibody comprises a heavy chain variable region comprising one VH CDR1 set forth by SEQ ID NO: 1; one VH CDR2 set forth by SEQ ID NO: 10 wherein the amino acid at position 10 ($X^{10}$) is Q or K, the amino acid at position 12 ($X^{12}$) is N or S, the amino acid at position 13 ($X^{13}$) is E or Q, and the amino acid at position 16 ($X^{16}$) is K or Q; and one VH CDR3 set forth by SEQ ID NO: 6.

In one embodiment, the humanized anti-HLA-A2 antibody comprises a heavy chain variable region comprising one VH CDR1 set forth by SEQ ID NO: 1; one VH CDR2 set forth by SEQ ID NO: 3; and one VH CDR3 set forth by SEQ ID NO: 6.

In one embodiment, the humanized anti-HLA-A2 antibody comprises a heavy chain variable region comprising one VH CDR1 set forth by SEQ ID NO: 1; one VH CDR2 set forth by SEQ ID NO: 5; and one VH CDR3 set forth by SEQ ID NO: 6.

According to the present invention, any of the CDRs 1, 2 or 3 of the heavy chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 1, 3, 5, 6 and 10.

In one embodiment, the humanized anti-HLA-A2 antibody comprises a heavy chain variable region comprising at least one of the following CDRs:
 a VH CDR1 set forth by SEQ ID NO: 2; or
 a VH CDR2 set forth by SEQ ID NO: 4; or
 a VH CDR3 set forth by SEQ ID NO: 6

In one embodiment, the humanized anti-HLA-A2 antibody comprises a heavy chain variable region comprising one VH CDR1 set forth by SEQ ID NO: 2; one VH CDR2 set forth by SEQ ID NO: 4; and one VH CDR3 set forth by SEQ ID NO: 6.

According to the present invention, any of the CDRs 1, 2 or 3 of the heavy chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 2, 4 and 6.

In one embodiment, the humanized anti-HLA-A2 antibody comprises a light chain variable region comprising the amino acid sequence RSSQSIVHSNGNTYLE (SEQ ID NO: 7).

In one embodiment, the humanized anti-HLA-A2 antibody comprises a light chain variable region comprising a complementarity determining region 1 (VL CDR1) set forth by SEQ ID NO: 7.

In one embodiment, the humanized anti-HLA-A2 antibody comprises a light chain variable region comprising the amino acid sequence KVSNRFS (SEQ ID NO: 8).

In one embodiment, the humanized anti-HLA-A2 antibody comprises a light chain variable region comprising a complementarity determining region 2 (VL CDR2) set forth by SEQ ID NO: 8.

In one embodiment, the humanized anti-HLA-A2 antibody comprises a light chain variable region comprising the amino acid sequence FQGSHVPRT (SEQ ID NO: 9).

In one embodiment, the humanized anti-HLA-A2 antibody comprises a light chain variable region comprising a complementarity determining region 3 (VL CDR3) set forth by SEQ ID NO: 9.

In one embodiment, the humanized anti-HLA-A2 antibody comprises a light chain variable region comprising at least one of the following CDRs:
 a VL CDR1 set forth by SEQ ID NO: 7; or
 a VL CDR2 set forth by SEQ ID NO: 8; or
 a VL CDR3 set forth by SEQ ID NO: 9.

In one embodiment, the humanized anti-HLA-A2 antibody comprises a light chain variable region comprising one VL CDR1 set forth by SEQ ID NO: 7; one VL CDR2 set forth by SEQ ID NO: 8; and one VL CDR3 set forth by SEQ ID NO: 9.

According to the present invention, any of the CDRs 1, 2 or 3 of the light chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 7, 8 and 9.

In one embodiment, the humanized anti-HLA-A2 antibody comprises a heavy chain variable region comprising a framework region 1 (VH FR1) comprising an amino acid sequence selected from the group consisting of: QVQLVQSGAEVKKPGASVKVSCKAS (SEQ ID NO: 11) and QVQLVQSGAEVKKPGASVKVSCKASGYTFT (SEQ ID NO: 12).

In one embodiment, the humanized anti-HLA-A2 antibody comprises a heavy chain variable region comprising a framework region 1 (VH FR1) comprising the amino acid sequence QVQLVQSGAEVKKPGASVKVSCKAS (SEQ ID NO: 11). In one embodiment, the humanized anti-HLA-A2 antibody comprises a heavy chain variable region comprising a framework region 1 (VH FR1) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 11.

In one embodiment, the humanized anti-HLA-A2 antibody comprises a heavy chain variable region comprising a framework region 1 (VH FR1) comprising the amino acid sequence QVQLVQSGAEVKKPGASVKVSCKASGYTFT (SEQ ID NO: 12). In one embodiment, the humanized anti-HLA-A2 antibody comprises a heavy chain variable region comprising a framework region 1 (VH FR1) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 12.

In one embodiment, the humanized anti-HLA-A2 antibody comprises a heavy chain variable region comprising a framework region 2 (VH FR2) comprising an amino acid sequence selected from the group consisting of:
 WVRQAPGQX$^9$LEWMGX$^{15}$ (SEQ ID NO: 13),
 WVRQAPGQX$^9$LEWMGX$^{15}$WI (SEQ ID NO: 17),
 HIQWVRQAPGQX$^{12}$LEWMGX$^{18}$WI (SEQ ID NO: 21), and
 HIQWVRQAPGQX$^{12}$LEWMGX$^{18}$ (SEQ ID NO: 25),
wherein:
 $X^9$ is R or G and $X^{15}$ is I or absent in SEQ ID NO: 13;
 $X^9$ is R or G, and $X^{15}$ is I or absent in SEQ ID NO: 17;
 $X^{12}$ is R or G, and $X^{18}$ is I or absent in SEQ ID NO: 21; and
 $X^{12}$ is R or G, and $X^{18}$ is I or absent in SEQ ID NO: 25.

In one embodiment, the humanized anti-HLA-A2 antibody comprises a heavy chain variable region comprising a framework region 2 (VH FR2) comprising the amino acid sequence WVRQAPGQX$^9$LEWMGX$^{15}$ (SEQ ID NO: 13), wherein the amino acid at position 9 ($X^9$) is R or G, and the amino acid at position 15 ($X^{15}$) is I or absent.

In one embodiment, the heavy chain variable region comprises a framework region 2 (VH FR2) comprising an amino acid sequence set forth in SEQ ID NO: 13, wherein the amino acid at position 9 is R or G, and the amino acid at position 15 is absent.

In one embodiment, the heavy chain variable region comprises a framework region 2 (VH FR2) comprising an amino acid sequence set forth in SEQ ID NO: 14, 15, or 16. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 14, 15, or 16.

In one embodiment, the humanized anti-HLA-A2 antibody comprises a heavy chain variable region comprising a framework region 2 (VH FR2) comprising the amino acid sequence HIQWVRQAPGQX$^{12}$LEWMGX$^{18}$ (SEQ ID NO: 25), wherein the amino acid at position 12 (X$^{12}$) is R or G, and the amino acid at position 18 (X$^{18}$) is I or absent.

In one embodiment, the heavy chain variable region comprises a framework region 2 (VH FR2) comprising an amino acid sequence set forth in SEQ ID NO: 25, wherein the amino acid at position 12 is R or G, and the amino acid at position 18 is absent.

In one embodiment, the heavy chain variable region comprises a framework region 2 (VH FR2) comprising an amino acid sequence set forth in SEQ ID NO: 26, 27, or 28. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 26, 27, or 28.

In one embodiment, the humanized anti-HLA-A2 antibody comprises a heavy chain variable region comprising a framework region 2 (VH FR2) comprising the amino acid sequence WVRQAPGQX$^{9}$LEWMGX$^{15}$WI (SEQ ID NO: 17), wherein the amino acid at position 9 (X$^{9}$) is R or G, and the amino acid at position 15 (X$^{15}$) is I or absent.

In one embodiment, the heavy chain variable region comprises a framework region 2 (VH FR2) comprising an amino acid sequence set forth in SEQ ID NO: 17, wherein the amino acid at position 9 is R or G, and the amino acid at position 15 is absent.

In one embodiment, the heavy chain variable region comprises a framework region 2 (VH FR2) comprising an amino acid sequence set forth in SEQ ID NO: 18, 19, or 20. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 18, 19, or 20.

In one embodiment, the humanized anti-HLA-A2 antibody comprises a heavy chain variable region comprising a framework region 2 (VH FR2) comprising the amino acid sequence HIQWVRQAPGQX$^{12}$LEWMGX$^{18}$WI (SEQ ID NO: 21), wherein the amino acid at position 12 (X$^{12}$) is R or G, and the amino acid at position 18 (X$^{18}$) is I or absent.

In one embodiment, the heavy chain variable region comprises a framework region 2 (VH FR2) comprising an amino acid sequence set forth in SEQ ID NO: 21, wherein the amino acid at position 12 is R or G, and the amino acid at position 18 is absent.

In one embodiment, the heavy chain variable region comprises a framework region 2 (VH FR2) comprising an amino acid sequence set forth in SEQ ID NO: 22, 23, or 24. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 22, 23, or 24.

In one embodiment, the humanized anti-HLA-A2 antibody comprises a heavy chain variable region comprising a framework region 3 (VH FR3) comprising an amino acid sequence selected from the group consisting of:

X$^{1}$VTX$^{4}$TX$^{6}$DTSX$^{10}$STAYMX$^{16}$LSX$^{19}$LRSX$^{23}$DX$^{25}$AVYYCAR (SEQ ID NO: 29),

TX$^{2}$YX$^{4}$X$^{5}$KFX$^{8}$GX$^{10}$VTX$^{13}$TX$^{15}$DTSX$^{19}$STAYMX$^{25}$LSX$^{28}$LRSX$^{32}$DX$^{34}$AVYYCAR (SEQ ID NO: 35),

TQYNEKFKGX$^{10}$VTX$^{13}$TX$^{15}$DTSX$^{19}$STAYMX$^{25}$LSX$^{28}$LRSX$^{32}$DX$^{34}$AVYYCAR (SEQ ID NO: 36), and TKYSQKFQGX$^{10}$VTX$^{13}$TX$^{15}$DTSX$^{19}$STAYMX$^{25}$LSX$^{28}$LRSX$^{32}$DX$^{34}$AVYYC (SEQ ID NO: 37), wherein:

X$^{1}$ is R or absent, X$^{4}$ is I or M, X$^{6}$ is R or A, X$^{10}$ is A, T or I, X$^{16}$ is E or L, X$^{19}$ is S or R, X$^{23}$ is E or D, and X$^{25}$ is T or M in SEQ ID NO: 29;

X$^{2}$ is Q or K, X$^{4}$ is N or S, X$^{5}$ is E or Q, X$^{8}$ is K or Q, X$^{10}$ is R or absent, X$^{13}$ is I or M, X$^{15}$ is R or A, X$^{19}$ is A, T or I, X$^{25}$ is E or L, X$^{28}$ is S or R, X$^{32}$ is E or D, and X$^{34}$ is T or M in SEQ ID NO: 35;

X$^{10}$ is R or absent, X$^{13}$ is I or M, X$^{15}$ is R or A, X$^{19}$ is A, T or I, X$^{25}$ is E or L, X$^{28}$ is S or R, X$^{32}$ is E or D, and X$^{34}$ is T or M in SEQ ID NO: 36; and X$^{10}$ is R or absent, X$^{13}$ is I or M, X$^{15}$ is R or A, X$^{19}$ is A, T or I, X$^{25}$ is E or L, X$^{28}$ is S or R, X$^{32}$ is E or D, and X$^{34}$ is T or M in SEQ ID NO: 37.

In one embodiment, the humanized anti-HLA-A2 antibody comprises a heavy chain variable region comprising a framework region 3 (VH FR3) comprising the amino acid sequence X$^{1}$VTX$^{4}$TX$^{6}$DTSX$^{10}$STAYMX$^{16}$LSX$^{19}$LRSX$^{23}$DX$^{25}$AVYYCAR (SEQ ID NO: 29), wherein the amino acid at position 1 (X$^{1}$) is R or absent, the amino acid at position 4 (X$^{4}$) is I or M, the amino acid at position 6 (X$^{6}$) is R or A, the amino acid at position 10 (X$^{10}$) is A, T or I, the amino acid at position 16 (X$^{16}$) is E or L, the amino acid at position 19 (X$^{19}$) is S or R, the amino acid at position 23 (X$^{23}$) is E or D, and the amino acid at position 25 (X$^{25}$) is T or M.

In one embodiment, the heavy chain variable region comprises a framework region 3 (VH FR3) comprising an amino acid sequence set forth in SEQ ID NO: 29, wherein the amino acid at position 1 is R, the amino acid at position 4 is I or M, the amino acid at position 6 is R, the amino acid at position 10 is A or I, the amino acid at position 16 is E, the amino acid at position 19 is S or R, the amino acid at position 23 is E or D, and the amino acid at position 25 is T or M.

In one embodiment, the heavy chain variable region comprises a framework region 3 (VH FR3) comprising an amino acid sequence set forth by SEQ ID NO: 29, wherein the amino acid at position 1 is R, the amino acid at position 4 is I or M, the amino acid at position 6 is R, the amino acid at position 10 is A or I, the amino acid at position 16 is E, the amino acid at position 19 is S or R, the amino acid at position 23 is E or D, and the amino acid at position 25 is T.

In one embodiment, the heavy chain variable region comprises a framework region 3 (VH FR3) comprising an amino acid sequence set forth by SEQ ID NO: 29, wherein the amino acid at position 1 is R, the amino acid at position 4 is I, the amino acid at position 6 is R, the amino acid at position 10 is A, the amino acid at position 16 is E, the amino acid at position 19 is S, the amino acid at position 23 is E, and the amino acid at position 25 is T or M.

In one embodiment, the heavy chain variable region comprises a framework region 3 (VH FR3) comprising an amino acid sequence set forth in SEQ ID NO: 30, 31, 32, 33, or 34. In one embodiment, the heavy chain variable region comprises a framework region 3 (VH FR3) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 30, 31, 32, 33, or 34.

In one embodiment, the humanized anti-HLA-A2 antibody comprises a heavy chain variable region comprising a framework region 3 (VH FR3) comprising the amino acid sequence TX$^2$YX$^4$X$^5$KFX$^8$GX$^{10}$VTX$^{13}$TX$^{15}$DTSX$^{19}$STAYMX$^{25}$LSX$^{28}$LRSX$^{32}$DX$^{34}$AVYYCAR (SEQ ID NO: 35), wherein the amino acid at position 2 (X$^2$) is Q or K, the amino acid at position 4 (X$^4$) is N or S, the amino acid at position 5 (X$^5$) is E or Q, the amino acid at position 8 (X$^8$) is K or Q, the amino acid at position 10 (X$^{10}$) is R or absent, the amino acid at position 13 (X$^{13}$) is I or M, the amino acid at position 15 (X$^{15}$) is R or A, the amino acid at position 19 (X$^{19}$) is A, T or I, the amino acid at position 25 (X$^{25}$) is E or L, the amino acid at position 28 (X$^{28}$) is S or R, the amino acid at position 32 (X$^{32}$) is E or D, and the amino acid at position 34 (X$^{34}$) is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E or Q, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E or Q, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E or Q, the amino acid at position 8 is K or Q, the amino acid at position 10 is R, the amino acid at position 13 is I, the amino acid at position 15 is R, the amino acid at position 19 is A, the amino acid at position 25 is E, the amino acid at position 28 is S, the amino acid at position 32 is E, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N, the amino acid at position 5 is E, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N or S, the amino acid at position 5 is E, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N, the amino acid at position 5 is E or Q, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N, the amino acid at position 5 is E, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N, the amino acid at position 5 is E or Q, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N, the amino acid at position 5 is E, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N or S, the amino acid at position 5 is E, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N or S, the amino acid at position 5 is E, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N, the amino acid at position 5 is E or Q, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E or Q, the amino acid at position 8 is K, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N or S, the amino acid at position 5 is E, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q or K, the amino acid at position 4 is N, the amino acid at position 5 is E or Q, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 35, wherein the amino acid at position 2 is Q, the amino acid at position 4 is N or S, the amino acid at position 5 is E or Q, the amino acid at position 8 is K or Q, the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the humanized anti-HLA-A2 antibody comprises a heavy chain variable region comprising a framework region 3 (VH FR3) comprising the amino acid sequence TQYNEKFKGX$^{10}$VTX$^{13}$TX$^{15}$SDTSX$^{19}$STAYMX$^{25}$LSX$^{28}$LRSX$^{32}$DX$^{34}$ AVYYCAR (SEQ ID NO: 36), wherein the amino acid at position 10 (X$^{10}$) is R or absent, the amino acid at position 13 (X$^{13}$) is I or M, the amino acid at position 15 (X$^{15}$) is R or A, the amino acid at position 19 (X$^{19}$) is A, T or I, the amino acid at position 25 (X$^{25}$) is E or L, the amino acid at position 28 (X$^{28}$) is S or R, the amino acid at position 32 (X$^{32}$) is E or D, and the amino acid at position 34 (X$^{34}$) is T or M.

In one embodiment, the heavy chain variable region comprises a framework region 3 (VH FR3) comprising an amino acid sequence set forth in SEQ ID NO: 36, wherein the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 36, wherein the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T.

In one embodiment, the heavy chain variable region comprises a framework region 3 (VH FR3) comprising an amino acid sequence set forth in SEQ ID NO: 36, wherein the amino acid at position 10 is R, the amino acid at position 13 is I, the amino acid at position 15 is R, the amino acid at position 19 is A, the amino acid at position 25 is E, the amino acid at position 28 is S, the amino acid at position 32 is E, and the amino acid at position 34 is T or M.

In one embodiment, the humanized anti-HLA-A2 antibody comprises a heavy chain variable region comprising a framework region 3 (VH FR3) comprising the amino acid sequence TKYSQKFQGX$^{10}$VTX$^{13}$TX$^{15}$SDTSX$^{19}$STAYMX$^{25}$LSX$^{28}$LRSX$^{32}$DX$^{34}$AVYYCAR (SEQ ID NO: 37), wherein the amino acid at position 10 (X$^{10}$) is R or absent, the amino acid at position 13 (X$^{13}$) is I or M, the amino acid at position 15 (X$^{15}$) is R or A, the amino acid at position 19 (X$^{19}$) is A, T or I, the amino acid at position 25 (X$^{25}$) is E or L, the amino acid at position 28 (X$^{28}$) is S or R, the amino acid at position 32 (X$^{32}$) is E or D, and the amino acid at position 34 (X$^{34}$) is T or M.

In one embodiment, the heavy chain variable region comprises a framework region 3 (VH FR3) comprising an amino acid sequence set forth in SEQ ID NO: 37, wherein the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T or M.

In one embodiment, the heavy chain variable region comprises a framework region 3 (VH FR3) comprising an amino acid sequence set forth in SEQ ID NO: 37, wherein the amino acid at position 10 is R, the amino acid at position 13 is I or M, the amino acid at position 15 is R, the amino acid at position 19 is A or I, the amino acid at position 25 is E, the amino acid at position 28 is S or R, the amino acid at position 32 is E or D, and the amino acid at position 34 is T.

In one embodiment, the heavy chain variable region comprises a framework region 3 (VH FR3) comprising an amino acid sequence set forth in SEQ ID NO: 37, wherein the amino acid at position 10 is R, the amino acid at position 13 is I, the amino acid at position 15 is R, the amino acid at position 19 is A, the amino acid at position 25 is E, the amino acid at position 28 is S, the amino acid at position 32 is E, and the amino acid at position 34 is T or M.

In one embodiment, the heavy chain variable region comprises a framework region 3 (VH FR3) comprising an amino acid sequence set forth in SEQ ID NO: 38, 39, 40, 41, 42, or 43. In one embodiment, the heavy chain variable region comprises a framework region 3 (VH FR3) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 38, 39, 40, 41, 42, or 43.

In one embodiment, the humanized anti-HLA-A2 antibody comprises a heavy chain variable region comprising a framework region 4 (VH FR4) comprising the amino acid sequence WGQGTTVTVSS (SEQ ID NO: 44). In one embodiment, the humanized anti-HLA-A2 antibody comprises a heavy chain variable region comprising a framework region 4 (VH FR4) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 44.

In one embodiment, the heavy chain variable region comprises:
- a VH CDR1 set forth by SEQ ID NO: 1;
- a VH CDR2 set forth by SEQ ID NO: 10, wherein the amino acid at position 10 ($X^{10}$) is Q or K, the amino acid at position 12 ($X^{12}$) is N or S, the amino acid at position 13 ($X^{13}$) is E or Q, and the amino acid at position 16 ($X^{16}$) is K or Q;
- a VH CDR3 set forth by SEQ ID NO: 6;
- a VH FR1 set forth by SEQ ID NO: 12;
- a VH FR2 set forth by SEQ ID NO: 13, wherein the amino acid at position 9 ($X^9$) is R or G, and the amino acid at position 15 ($X^{15}$) is I or absent;
- a VH FR3 set forth by SEQ ID NO: 29, wherein the amino acid at position 1 ($X^1$) is R or absent, the amino acid at position 4 ($X^4$) is I or M, the amino acid at position 6 ($X^6$) is R or A, the amino acid at position 10 ($X^{10}$) is A, T or I, the amino acid at position 16 ($X^{16}$) is E or L, the amino acid at position 19 ($X^{19}$) is S or R, the amino acid at position 23 ($X^{23}$) is E or D, and the amino acid at position 25 ($X^{25}$) is T or M; and
- a VH FR4 set forth by SEQ ID NO: 44.

In one embodiment, the heavy chain variable region comprises:
- a VH CDR1 set forth by SEQ ID NO: 2;
- a VH CDR2 set forth by SEQ ID NO: 10, wherein the amino acid at position 10 ($X^{10}$) is Q or K, the amino acid at position 12 ($X^{12}$) is N or S, the amino acid at position 13 ($X^{13}$) is E or Q, and the amino acid at position 16 ($X^{16}$) is K or Q;
- a VH CDR3 set forth by SEQ ID NO: 6;
- a VH FR1 set forth by SEQ ID NO: 11;
- a VH FR2 set forth by SEQ ID NO: 25, wherein the amino acid at position 12 ($X^{12}$) is R or G, and the amino acid at position 18 ($X^{18}$) is I or absent;
- a VH FR3 set forth by SEQ ID NO: 29, wherein the amino acid at position 1 ($X^1$) is R or absent, the amino acid at position 4 ($X^4$) is I or M, the amino acid at position 6 ($X^6$) is R or A, the amino acid at position 10 ($X^{10}$) is A, T or I, the amino acid at position 16 ($X^{16}$) is E or L, the amino acid at position 19 ($X^{19}$) is S or R, the amino acid at position 23 ($X^{23}$) is E or D, and the amino acid at position 25 ($X^{25}$) is T or M; and
- a VH FR4 set forth by SEQ ID NO: 44.

In one embodiment, the heavy chain variable region comprises:
- a VH CDR1 set forth by SEQ ID NO: 2;
- a VH CDR2 set forth by SEQ ID NO: 4;
- a VH CDR3 set forth by SEQ ID NO: 6;
- a VH FR1 set forth by SEQ ID NO: 11;
- a VH FR2 set forth by SEQ ID NO: 21, wherein the amino acid at position 12 ($X^{12}$) is R or G, and the amino acid at position 18 ($X^{18}$) is I or absent;
- a VH FR3 set forth by SEQ ID NO: 35, wherein the amino acid at position 2 ($X^2$) is Q or K, the amino acid at position 4 ($X^4$) is N or S, the amino acid at position 5 ($X^5$) is E or Q, the amino acid at position 8 ($X^8$) is K or Q, the amino acid at position 10 ($X^{10}$) is R or absent, the amino acid at position 13 ($X^{13}$) is I or M, the amino acid at position 15 ($X^{15}$) is R or A, the amino acid at position 19 ($X^{19}$) is A, T or I, the amino acid at position 25 ($X^{25}$) is E or L, the amino acid at position 28 ($X^{28}$) is S or R, the amino acid at position 32 ($X^{32}$) is E or D, and the amino acid at position 34 ($X^{34}$) is T or M; and
- a VH FR4 set forth by SEQ ID NO: 44.

In one embodiment, the heavy chain variable region comprises:
- a VH CDR1 set forth by SEQ ID NO: 1;
- a VH CDR2 set forth by SEQ ID NO: 4;
- a VH CDR3 set forth by SEQ ID NO: 6;
- a VH FR1 set forth by SEQ ID NO: 12;
- a VH FR2 set forth by SEQ ID NO: 17, wherein the amino acid at position 9 ($X^9$) is R or G, and the amino acid at position 15 ($X^{15}$) is I or absent;
- a VH FR3 set forth by SEQ ID NO: 35, wherein the amino acid at position 2 ($X^2$) is Q or K, the amino acid at position 4 ($X^4$) is N or S, the amino acid at position 5 ($X^5$) is E or Q, the amino acid at position 8 ($X^8$) is K or Q, the amino acid at position 10 ($X^{10}$) is R or absent, the amino acid at position 13 ($X^{13}$) is I or M, the amino acid at position 15 ($X^{15}$) is R or A, the amino acid at position 19 ($X^{19}$) is A, T or I, the amino acid at position 25 ($X^{25}$) is E or L, the amino acid at position 28 ($X^{28}$) is S or R, the amino acid at position 32 ($X^{32}$) is E or D, and the amino acid at position 34 ($X^{34}$) is T or M; and
- a VH FR4 set forth by SEQ ID NO: 44.

In one embodiment, the humanized anti-HLA-A2 antibody comprises a heavy chain variable region comprising the amino acid sequence QVQLVQSGAEVKKPGASVKVSCKASGYTFTSYHIQWVRQAPGQX$^{44}$LEWMGX$^{50}$WIYPGDGSTX$^{60}$YX$^{62}$X$^{63}$ KFX$^{66}$G X$^{68}$VTX$^{71}$ TX⁷³DTSX⁷⁷STAYMX⁸³LSX⁸⁶LRSX⁹⁰DX⁹²AVYYCAR EGTYYAMDYWGQGTT VTVSS (SEQ ID NO: 45), wherein the amino acid at position 44 ($X^{44}$) is R or G, the amino acid at position 50 ($X^{50}$) is I or absent, the amino acid at position 60 ($X^{60}$) is Q or K, the amino acid at position 62 ($X^{62}$) is N or S, the amino acid at position 63 ($X^{63}$) is E or Q, the amino acid at position 66 ($X^{66}$) is K or Q, the amino acid at position 68 ($X^{68}$) is R or absent, the amino acid at position 71 ($X^{71}$) is I or M, the amino acid at position 73 ($X^{73}$) is R or A, the amino acid at position 77 ($X^{77}$) is A, T or I, the amino acid at position 83 ($X^{83}$) is E or L, the amino acid at position 86 ($X^{86}$) is S or R, the amino acid at position 90 ($X^{90}$) is E or D, and the amino acid at position 92 ($X^{92}$) is T or M.

In one embodiment, the heavy chain variable region comprises an amino acid sequence set forth in SEQ ID NO: 45, wherein the amino acid at position 44 is R or G; the amino acid at position 50 is absent; the amino acid at position 60 is Q or K; the amino acid at position 62 is N or S; the amino acid at position 63 is E or Q; the amino acid at position 66 is K or Q; the amino acid at position 68 is R; the amino acid at position 71 is I or M; the amino acid at position 73 is R; the amino acid at position 77 is A or I; the amino acid at position 83 is E; the amino acid at position 86 is S or R; the amino acid at position 90 is E or D; and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is N or S; the amino acid at position 63 is E or Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T.

In one embodiment, the heavy chain variable region comprises an amino acid sequence set forth in SEQ ID NO: 45, wherein the amino acid at position 44 is R, the amino acid at position 50 is absent, the amino acid at position 60 is Q or K; the amino acid at position 62 is N or S; the amino acid at position 63 is E or Q; the amino acid at position 66 is K or Q; the amino acid at position 68 is R, the amino acid at position 71 is I, the amino acid at position 73 is R, the amino acid at position 77 is A, the amino acid at position 83 is E, the amino acid at position 86 is S, the amino acid at position 90 is E, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q; the amino acid at position 62 is N; the amino acid at position 63 is E; the amino acid at position 66 is K; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q; the amino acid at position 62 is N; the amino acid at position 63 is E; the amino acid at position 66 is K; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T.

In one embodiment, the heavy chain variable region comprises an amino acid sequence set forth in SEQ ID NO: 45, wherein the amino acid at position 44 is R, the amino acid at position 50 is absent, the amino acid at position 60 is Q; the amino acid at position 62 is N; the amino acid at position 63 is E; the amino acid at position 66 is K; the amino acid at position 68 is R, the amino acid at position 71 is I, the amino acid at position 73 is R, the amino acid at position 77 is A, the amino acid at position 83 is E, the amino acid at position 86 is S, the amino acid at position 90 is E, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is S; the amino acid at position 63 is Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is S; the amino acid at position 63 is Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T.

In one embodiment, the heavy chain variable region comprises an amino acid sequence set forth in SEQ ID NO: 45, wherein the amino acid at position 44 is R, the amino acid at position 50 is absent, the amino acid at position 60 is K; the amino acid at position 62 is S; the amino acid at position 63 is Q; the amino acid at position 66 is Q; the amino acid at position 68 is R, the amino acid at position 71 is I, the amino acid at position 73 is R, the amino acid at position 77 is A, the amino acid at position 83 is E, the amino acid at position 86 is S, the amino acid at position 90 is E, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is S; the amino acid at position 63 is Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is N or S; the amino acid at position 63 is Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is S; the amino acid at position 63 is E or Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is S; the amino acid at position 63 is Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is N or S; the amino acid at position 63 is Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is S; the amino acid at position 63 is E or Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is S; the amino acid at position 63 is Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is N or S; the amino acid at position 63 is E or Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is N or S; the amino acid at position 63 is Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is S; the amino acid at position 63 is E or Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is N or S; the amino acid at position 63 is E or Q; the amino acid at position 66 is Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is N or S; the amino acid at position 63 is Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is Q or K; the amino acid at position 62 is S; the amino acid at position 63 is E or Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 45, wherein the amino acid at position 44 is R or G, the amino acid at position 50 is absent, the amino acid at position 60 is K; the amino acid at position 62 is N or S; the amino acid at position 63 is E or Q; the amino acid at position 66 is K or Q; the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the humanized anti-HLA-A2 antibody comprises a heavy chain variable region comprising an amino acid sequence set forth in SEQ ID NO: 61, 62, 63, 64, 65, or 66. In one embodiment, the humanized anti-HLA-A2 antibody comprises a heavy chain variable region comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 61, 62, 63, 64, 65, or 66.

In one embodiment, the humanized anti-HLA-A2 antibody comprises a light chain variable region comprising a framework region 1 (VL FR1) comprising the amino acid sequence DX$^2$VMTQX$^7$PLSX$^{11}$X$^{12}$VTX$^{15}$GQPASISX$^{23}$ (SEQ ID NO: 46), wherein the amino acid at position 2 (X$^2$) is V or I, the amino acid at position 7 (X$^7$) is S or T, the amino acid at position 11 (X$^{11}$) is L or S; the amino acid at position 12 (X$^{12}$) is P or S; the amino acid at position 15 (X$^{15}$) is L or P, and the amino acid at position 23 (X$^{23}$) is C or F.

In one embodiment, the light chain variable region comprises a framework region 1 (VL FR1) comprising an amino acid sequence set forth in SEQ ID NO: 46, wherein the amino acid at position 2 is V or I; the amino acid at position 7 is S or T; the amino acid at position 11 is L or S; the amino acid at position 12 is P or S; the amino acid at position 15 is L or P; and the amino acid at position 23 is C.

In one embodiment, the light chain variable region comprises a framework region 1 (VL FR1) comprising an amino acid sequence set forth in SEQ ID NO: 46, wherein the amino acid at position 2 is I; the amino acid at position 7 is T; the amino acid at position 11 is L or S; the amino acid at position 12 is P or S; the amino acid at position 15 is L or P; and the amino acid at position 23 is C.

In one embodiment, the light chain variable region comprises a framework region 1 (VL FR1) comprising an amino acid sequence set forth in SEQ ID NO: 46, wherein the amino acid at position 2 is V or I; the amino acid at position 7 is S or T; the amino acid at position 11 is L; the amino acid at position 12 is P or S; the amino acid at position 15 is L or P; and the amino acid at position 23 is C.

In one embodiment, the light chain variable region comprises a framework region 1 (VL FR1) comprising an amino acid sequence set forth in SEQ ID NO: 46, wherein the amino acid at position 2 is V or I; the amino acid at position 7 is S or T; the amino acid at position 11 is L or S; the amino acid at position 12 is P; the amino acid at position 15 is L; and the amino acid at position 23 is C.

In one embodiment, the light chain variable region comprises a framework region 1 (VL FR1) comprising an amino acid sequence set forth in SEQ ID NO: 47, 48, 49, or 50. In one embodiment, the light chain variable region comprises a framework region 1 (VL FR1) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 47, 48, 49, or 50.

In one embodiment, the humanized anti-HLA-A2 antibody comprises a light chain variable region comprising a framework region 2 (VL FR2) comprising the amino acid sequence WX$^2$X$^3$QX$^5$PGQX$^9$PX$^{11}$X$^{12}$LIY (SEQ ID NO: 51), wherein the amino acid at position 2 (X$^2$) is F or Y, the amino acid at position 3 (X$^3$) is Q or L, the amino acid at position 5 (X$^5$) is R or K, the amino acid at position 9 (X$^9$) is S or P, the amino acid at position 11 (X$^{11}$) is R or Q, and the amino acid at position 12 (X$^{12}$) is R or L.

In one embodiment, the light chain variable region comprises a framework region 2 (VL FR2) comprising the amino acid sequence set forth in SEQ ID NO: 51, wherein the amino acid at position 2 is Y, the amino acid at position 3 is Q or L, the amino acid at position 5 is R or K, the amino acid at position 9 is S or P, the amino acid at position 11 is R or Q, and the amino acid at position 12 is L.

In one embodiment, the light chain variable region comprises a framework region 2 (VL FR2) comprising the amino acid sequence set forth in SEQ ID NO: 51, wherein the amino acid at position 2 is Y, the amino acid at position 3 is Q or L, the amino acid at position 5 is R or K, the amino acid at position 9 is S, the amino acid at position 11 is R or Q, and the amino acid at position 12 is L.

In one embodiment, the light chain variable region comprises a framework region 2 (VL FR2) comprising the amino acid sequence set forth in SEQ ID NO: 51, wherein the amino acid at position 2 is Y, the amino acid at position 3 is Q, the amino acid at position 5 is R, the amino acid at position 9 is S or P, the amino acid at position 11 is R, and the amino acid at position 12 is L.

In one embodiment, the light chain variable region comprises a framework region 2 (VL FR2) comprising an amino acid sequence set forth in SEQ ID NO: 51, wherein the amino acid at position 2 is F or Y, the amino acid at position 3 is Q or L, the amino acid at position 5 is R or K, the amino acid at position 9 is S, the amino acid at position 11 is R or Q, and the amino acid at position 12 is R or L.

In one embodiment, the light chain variable region comprises a framework region 2 (VL FR2) comprising an amino acid sequence set forth in SEQ ID NO: 51, wherein the amino acid at position 2 is F or Y, the amino acid at position 3 is Q, the amino acid at position 5 is R, the amino acid at position 9 is S or P, the amino acid at position 11 is R, and the amino acid at position 12 is R or L.

In one embodiment, the light chain variable region comprises a framework region 2 (VL FR2) comprising the amino acid sequence set forth in SEQ ID NO: 52, 53, 54, or 55. In one embodiment, the light chain variable region comprises a framework region 2 (VL FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 52, 53, 54, or 55.

In one embodiment, the humanized anti-HLA-A2 antibody comprises a light chain variable region comprising a framework region 3 (VL FR3) comprising the amino acid sequence GVPDRFSGSGX$^{11}$GTDFTLKISRVEAEDVGVYYC (SEQ ID NO: 56), wherein the amino acid at position 11 (X$^{11}$) is S or A.

In one embodiment, the humanized anti-HLA-A2 antibody comprises a light chain variable region comprising a framework region 3 (VL FR3) comprising an amino acid sequence set forth in SEQ ID NO: 57 or 58. In one embodiment, the humanized anti-HLA-A2 antibody comprises a light chain variable region comprising a framework region 3 (VL FR3) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 57 or 58.

In one embodiment, the humanized anti-HLA-A2 antibody comprises a light chain variable region comprising a framework region 4 (VL FR4) comprising the amino acid sequence FGGGTKVEIK (SEQ ID NO: 59). In one embodiment, the humanized anti-HLA-A2 antibody comprises a light chain variable region comprising a framework region 4 (VL FR4) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 59.

In one embodiment, the humanized anti-HLA-A2 antibody comprises a light chain variable region comprising an amino acid sequence DX$^2$VMTQX$^7$PLSX$^{11}$X$^{12}$VTX$^{15}$GQPASISX$^{23}$RSSQSIVH SNGNTYLEWX$^{41}$X$^{42}$QX$^{44}$PGQX$^{48}$PX$^{50}$X$^{51}$LIYKVSNRF SGVPDRFSGSGX$^{72}$GTDFTLKISRVEAEDVGVYYCFQ GSHVPRTFG GGTKVEIK (SEQ ID NO: 60), wherein the amino acid at position 2 (X$^2$) is V or I, the amino acid at position 7 (X$^7$) is S or T, the amino acid at position 11 (X$^{11}$) is L or S, the amino acid at position 12 (X$^{12}$) is P or S, the amino acid at position 15 (X$^{15}$) is L or P, the amino acid at position 23 (X$^{23}$) is C or F, the amino acid at position 41 (X$^{41}$) is F or Y, the amino acid at position 42 (X$^{42}$) is Q or L, the amino acid at position 44 (X$^{44}$) is R or K, the amino acid at position 48 (X$^{48}$) is S or P, the amino acid at position 50 (X$^{50}$) is R or Q, the amino acid at position 51 (X$^{51}$) is R or L, and the amino acid at position 72 (X$^{72}$) is S or A.

In one embodiment, the light chain variable region comprises an amino acid sequence set forth in SEQ ID NO: 60, wherein the amino acid at position 2 is V or I, the amino acid at position 7 is S or T, the amino acid at position 11 is L or S, the amino acid at position 12 is P or S, the amino acid at position 15 is L or P, the amino acid at position 23 is C, the amino acid at position 41 is Y, the amino acid at position 42 is Q or L, the amino acid at position 44 is R or K, the amino acid at position 48 is S or P, the amino acid at position 50 is R or Q, the amino acid at position 51 is L, and the amino acid at position 72 is S or A.

In one embodiment, the light chain variable region comprises an amino acid sequence set forth in SEQ ID NO: 60, wherein the amino acid at position 2 is I, the amino acid at position 7 is T, the amino acid at position 11 is L or S, the amino acid at position 12 is P or S, the amino acid at position 15 is L or P, the amino acid at position 23 is C, the amino acid at position 41 is Y, the amino acid at position 42 is Q or L, the amino acid at position 44 is R or K, the amino acid at position 48 is S or P, the amino acid at position 50 is R or Q, the amino acid at position 51 is L, and the amino acid at position 72 is S or A.

In one embodiment, the light chain variable region comprises an amino acid sequence set forth in SEQ ID NO: 60, wherein the amino acid at position 2 is V or I, the amino acid at position 7 is S or T, the amino acid at position 11 is L, the amino acid at position 12 is P or S, the amino acid at position 15 is L or P, the amino acid at position 23 is C, the amino acid at position 41 is Y, the amino acid at position 42 is Q or L, the amino acid at position 44 is R or K, the amino acid at position 48 is S, the amino acid at position 50 is R or Q, the amino acid at position 51 is L, and the amino acid at position 72 is S.

In one embodiment, the light chain variable region comprises an amino acid sequence set forth in SEQ ID NO: 60, wherein the amino acid at position 2 is V or I, the amino acid at position 7 is S or T, the amino acid at position 11 is L or S, the amino acid at position 12 is P, the amino acid at position 15 is L, the amino acid at position 23 is C, the amino acid at position 41 is Y, the amino acid at position 42 is Q, the amino acid at position 44 is R, the amino acid at position 48 is S or P, the amino acid at position 50 is R, the amino acid at position 51 is L, and the amino acid at position 72 is S or A.

In one embodiment, the light chain variable region comprises an amino acid sequence set forth in SEQ ID NO: 60, wherein the amino acid at position 2 is V or I, the amino acid at position 7 is S or T, the amino acid at position 11 is L or S, the amino acid at position 12 is P or S, the amino acid at position 15 is L or P, the amino acid at position 23 is C, the amino acid at position 41 is F or Y, the amino acid at position 42 is Q or L, the amino acid at position 44 is R or K, the amino acid at position 48 is S or P, the amino acid at position 50 is R or Q, the amino acid at position 51 is R or L, and the amino acid at position 72 is S or A.

In one embodiment, the humanized anti-HLA-A2 antibody comprises a light chain variable region comprising an amino acid sequence set forth in SEQ ID NO: 67, 68, 69, 70, or 71. In one embodiment, the humanized anti-HLA-A2 antibody comprises a light chain variable region comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 67, 68, 69, 70, or 71.

In one embodiment, the humanized anti-HLA-A2 antibody is an scFv, scFab or sdAb. In one embodiment, the humanized anti-HLA-A2 antibody is an scFv or scFab. In one embodiment, the humanized anti-HLA-A2 antibody is an sdAb. In one embodiment, the humanized anti-HLA-A2 antibody is an scFab. In one embodiment, the humanized anti-HLA-A2 antibody is an scFv. In one embodiment, the humanized anti-HLA-A2 antibody is an scFv comprising an amino acid sequence set forth in SEQ ID NO: 72, 73, 74, 75, 76, 77, 78, 79, 80, 81, 82, 83, 84, 85, 86, 87, 88, 89, 90, or 91. In one embodiment, the humanized anti-HLA-A2 antibody is an scFv comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 72, 73, 74, 75, 76, 77, 78, 79, 80, 81, 82, 83, 84, 85, 86, 87, 88, 89, 90, or 91.

In one embodiment, the humanized anti-HLA-A2 antibody comprises an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to the SEQ ID NOs recited above. In one embodiment, the humanized anti-HLA-A2 antibody is an scFv or scFab comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to the SEQ ID NOs recited above.

In one aspect, the invention provides an anti-HLA antibody comprising a heavy chain variable region comprising the amino acid sequence WIYPGDGSTKYSQKFQG (SEQ ID NO: 5).

In one embodiment, said antibody is an antibody mimetic selected from the group consisting of an affibody, an alphabody, an armadillo repeat protein-based scaffold, a knottin, a kunitz domain peptide, an affilin, an affitin, an adnectin, an atrimer, an evasin, a DARPin, an anticalin, an avimer, a fynomer, a versabody and a duocalin.

The anti-HLA-A2 antibodies provided herein bind specifically to HLA-A2. In one embodiment, the anti-HLA-A2 antibodies provided herein bind specifically to HLA-A*02: 01. As would be appreciated by one skilled in the art, the ability of an antibody to bind to HLA-A2 may be detected through the use of techniques known in the art. For example, binding of an antibody to HLA-A2 may be detected through the use of an HLA-A2 tetramer as exemplified herein. In one embodiment, the anti-HLA-A2 antibodies provided herein compete for binding to HLA-A2 with an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the anti-HLA-A2 antibodies provided herein bind to the same HLA-A2 epitope as an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the anti-HLA-A2 antibodies provided herein compete for binding to HLA-A2 with a BB7.2 antibody. In one embodiment, the anti-HLA-A2 antibodies provided herein bind to the same HLA-A2 epitope as a BB7.2 antibody. In one embodiment, the anti-HLA antibody comprises a heavy chain variable region comprising a complementarity determining region 2 (VH CDR2) set forth by SEQ ID NO: 5. In one embodiment, the anti-HLA-A2 antibodies provided herein have less reactivity to at least one HLA-A subtype selected from one or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from two or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from three or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from four or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from five or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from six or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from seven or more of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from each of HLA-A*03, HLA-A*25, HLA-A*29, HLA-A*30, HLA-A*31, HLA-A*33, HLA-A*36, HLA-A*68, as compared to a BB7.2 antibody. In one embodiment, the anti-HLA-A2 antibodies provided herein have less reactivity to at least one HLA-A subtype selected from one or more of HLA-A*25, HLA-A*29, HLA-A*30, as compared to a BB7.2 antibody. In one embodiment, the anti-HLA-A2 antibodies provided herein have less reactivity to at least one HLA-A subtype selected from two or more of HLA-A*25, HLA-A*29, HLA-A*30, as compared to a BB7.2 antibody. In one embodiment, the anti-HLA-A2 antibodies provided herein have less reactivity to at least one HLA-A subtype selected from each of HLA-A*25, HLA-A*29, HLA-A*30, as compared to a BB7.2 antibody. In one embodiment, the anti-HLA-A2 antibodies provided herein have less reactivity to at least one of HLA-A*03:01, HLA-A*25:01, HLA-A*29: 02, HLA-A*30:01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least two of HLA-A*03:01, HLA-A*25:01, HLA-A*29:02, HLA-A*30: 01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least three of HLA-A*03:01, HLA-A*25:01, HLA-A*29:02, HLA-A*30:01, HLA-A*31: 01, HLA-A*33:01, HLA-A*36:01, and HLA-A*68:01, as compared to a BB7.2 antibody. In one embodiment, the anti-HLA-A2 antibodies provided herein have less reactivity to at least four of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least five of HLA-A*03:01, HLA-A*25:01, HLA-A*29:02, HLA-A*30: 01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least six of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least seven of HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to HLA-A*03:01, HLA-A*25:01, HLA-A*29:02, HLA-A*30:01, HLA-A*31:01, HLA-A*33:01, HLA-A*36:01, and HLA-A*68:01, as compared to a BB7.2 antibody. In one embodiment, the anti-HLA-A2 antibodies provided herein have less reactivity to at least one of HLA-A*25:01, HLA-A*29:02, and HLA-A*30:01, as compared to a BB7.2 antibody. In one embodiment, the anti-HLA-A2 antibodies provided herein have less reactivity to at least two of HLA-A*25:01, HLA-A*29:02, and HLA-A*30:01, as compared to a BB7.2 antibody. In one embodiment, the anti-HLA-A2 antibodies provided herein have less reactivity to HLA-A*25:01, HLA-A*29:02, and HLA-A*30:01, as compared to a BB7.2 antibody. In one embodiment, the anti-HLA-A2 antibodies provided herein have less reactivity to HLA-A*25:01 as compared to a BB7.2 antibody. In one embodiment, the anti-HLA-A2 antibodies provided herein have less reactivity to HLA-A*29:02 as compared to a BB7.2 antibody. In one embodiment, the anti-HLA-A2 antibodies provided herein have less reactivity to HLA-A*30:01 as compared to a BB7.2 antibody. In one embodiment, the anti-HLA-A2 antibodies provided herein have less reactivity to HLA-A*03:01 as compared to a BB7.2 antibody. In one embodiment, the anti-HLA-A2 antibodies provided herein have less reactivity to HLA-A*31:01 as compared to a BB7.2 antibody. In one embodiment, the anti-HLA-A2 antibodies provided herein have less reactivity to HLA-A*33:01 as compared to a BB7.2 antibody. In one embodiment, the anti-HLA-A2 antibodies provided herein have less reactivity to HLA-A*36:01 as compared to a BB7.2 antibody. In one embodiment, the anti-HLA-A2 antibodies provided herein have less reactivity to HLA-A*68:01 as compared to a BB7.2 antibody. The BB7.2 antibody may be isolated from the BB7.2 hybridoma (ATCC Deposit No. HB-82). Techniques for determining the reactivity of the anti-HLA-A2 antibodies to HLA-A subtypes would be known to those of ordinary skill in the art. For example, the reactivity of the anti-HLA-A2 antibodies to HLA-A subtypes may be determined by a single antigen bead assay. Such single antigen bead assays are commercially available (e.g., FlowPRA Single Antigen Antibody; ONE LAMBDA).

In one embodiment, the anti-HLA-A2 antibodies provided herein have less reactivity to at least one HLA-A subtype selected from one or more of HLA-A*03, HLA-A*25, HLA-A*29, HLA-A*30, HLA-A*31, HLA-A*33, HLA-A*36, HLA-A*68, and any combination thereof, as compared to a BB7.2 antibody when measured in the conditions of Test A. For example, in some embodiments, the anti-HLA-A2 antibodies provided herein have less reactivity to at least one HLA-A subtype selected from the group comprising HLA-A*25, HLA-A*29, HLA-A*30 and any combination thereof, as compared to a BB7.2 antibody when measured in the conditions of Test A.

Test A:

$0.25 \cdot 10^6$ T cells expressing a CAR comprising the anti-HLA-A2 antibody or a BB7.2 antibody (e.g., a BB7.2 scFv (mA2 CAR)) are incubated with FlowPRA single antigen antibody beads panel (FL1HD01, FL1HD02, FL1HD03, FL1HD04, FL1HD06 and FL1HD08, One Lambda) and fixable viability dye (FVD, ThermoFisher, 65-0865-14, eBioscience) for 30 minutes at room temperature. Samples are washed, fixed with 0.5% formaldehyde and analyzed via flow cytometry. Two hundred negative control beads are acquired per sample. Beads alone were used as a negative control. For analysis, dead cells are first eliminated using the fixable viability dye. Single antigen beads are then gated after exclusion of dead cells and doublets. Then, the number of beads per HLA is determined by their respective PE intensity peak. Data are normalized by multiplying the number of beads of interest in each HLA-peak by 200, divided by the number of negative beads in the sample. For each HLA-peak the percent relative binding of CAR Tregs compared to control (non-CAR-expressing cells) is determined by subtracting the number of beads in the CAR-Treg from the number of beads in the control sample then dividing the average number of beads in the non-CAR-expressing control, times 100. In one embodiment, the anti-HLA-A2 antibody of the invention has a reactivity to at least one HLA-A subtype selected from the group comprising HLA-A*03, HLA-A*25, HLA-A*29, HLA-A*30, HLA-A*31, HLA-A*33, HLA-A*36, HLA-A*68 statistically inferior to a BB7.2 antibody, e.g., when measured in the conditions of Test A.

In one embodiment, the anti-HLA-A2 antibody of the invention has a reactivity to at least one HLA-A subtype selected from the group comprising HLA-A*25, HLA-A*29, HLA-A*30 statistically inferior to a BB7.2 antibody, e.g., when measured in the conditions of Test A.

In one embodiment, the term "statistically inferior" means that the reactivity (i.e., for example, the relative binding in the conditions of Test A) measured for the anti-HLA-A2 antibody of the invention is inferior to the reactivity measured for a BB7.2 antibody with ap value of at most about 0.05, preferably of at most about 0.01, more preferably of at most about 0.005, and even more preferably of at most about 0.001, in particular when analyzed by 2-way ANOVA, Dunnett post-test.

In one embodiment, the anti-HLA-A2 antibody of the invention has a reactivity to at least one HLA-A subtype selected from the group comprising HLA-A*03, HLA-A*25, HLA-A*29, HLA-A*30, HLA-A*31, HLA-A*33, HLA-A*36, HLA-A*68 inferior to a BB7.2 antibody In some embodiments, such an anti-HLA-A2 antibody has a relative binding for at least one HLA-A subtype selected from the group comprising HLA-A*03, HLA-A*25, HLA-A*29, HLA-A*30, HLA-A*31, HLA-A*33, HLA-A*36, HLA-A*68 inferior to a BB7.2 antibody when measured in the conditions of Test A. In certain aspects, the relative binding measured for such an anti-HLA-A2 antibody is at most about 90%, 80%, 70%, 60%, 50%, 40%, 30%, 20%, 10% or less of the relative binding measured for a BB7.2 antibody.

In one embodiment, the anti-HLA-A2 antibody of the invention has a reactivity to at least one HLA-A subtype selected from the group comprising HLA-A*25, HLA-A*29, HLA-A*30 inferior to a BB7.2 antibody In some embodiments, such an anti-HLA-A2 antibody has a relative binding for at least one HLA-A subtype selected from the group comprising HLA-A*25, HLA-A*29, HLA-A*30 inferior to a BB7.2 antibody when measured in the conditions of Test A. In certain aspects, the relative binding measured for such an anti-HLA-A2 antibody is at most about 90%, 80%, 70%, 60%, 50%, 40%, 30%, 20%, 10% or less of the relative binding measured for a BB7.2 antibody.

Further, the anti-HLA-A2 antibodies provided herein with antigen binding activity, are capable of constituting antigen binding domains of CARs, wherein such CARs are capable of being expressed in human cells such that the CARs specifically bind to HLA-A2. In one embodiment, the CARs specifically bind to HLA-A*02:01. As would be appreciated by one skilled in the art, the ability of a CAR to bind to HLA-A2 may be detected through the use of techniques known in the art. For example, binding of a CAR to HLA-A2 may be detected through the use of an HLA-A2 tetramer as exemplified herein. In one embodiment, the human cell is an immune cell. In one embodiment, the immune cell is a regulatory immune cell. In one embodiment, the immune cell is a T regulatory cell (Treg). In one embodiment, the immune cell is a T cell. In one embodiment, the T cell is a Treg.

Further, anti-HLA-A2 antibodies provided herein with antigen binding activity, are capable of constituting antigen binding domains of chimeric antigen receptors (CARs), wherein such CARs are capable of being expressed in a T regulatory cell (Treg) such that the CARs specifically bind to HLA-A2. In one embodiment, the CARs specifically bind to HLA-A*02:01. In one embodiment, the Treg is a human Treg.

In one embodiment, the anti-HLA-A2 antibody is capable of constituting an antigen binding domain of a CAR, wherein such CAR is capable of being expressed in an immune cell such that the immune cell is activated by HLA-A2. In one embodiment, the immune cell is activated by HLA-A*02:01. In one embodiment, the immune cell is a regulatory immune cell. In one embodiment, the immune cell is a T regulatory cell (Treg). In one embodiment, the immune cell is a T cell. In one embodiment, the T cell is a Treg. In one embodiment, the immune cell is a human immune cell. In one embodiment, the regulatory immune cell is a human regulatory immune cell. In one embodiment, the T cell is a human T cell. In one embodiment, the Treg is a human Treg.

In one embodiment, such anti-HLA-A2 antibody comprises a heavy chain variable region comprising an amino acid sequence selected from the group consisting of: SYHIQ (SEQ ID NO: 1) and GYTFTSY (SEQ ID NO: 2).

In one embodiment, the anti-HLA-A2 antibody comprises a heavy chain variable region comprising a complementarity determining region 1 (VH CDR1) selected from SEQ ID NOs: 1-2. In one embodiment, the anti-HLA-A2 antibody comprises a heavy chain variable region comprising a VH CDR1 set forth by SEQ ID NO: 1. In one embodiment, the anti-HLA-A2 antibody comprises a heavy chain variable region comprising a VH CDR1 set forth by SEQ ID NO: 2.

In one embodiment, the anti-HLA-A2 antibody comprises a heavy chain variable region comprising the amino acid sequence EGTYYAMDY (SEQ ID NO: 6).

In one embodiment, the anti-HLA-A2 antibody comprises a heavy chain variable region comprising a complementarity determining region 3 (VH CDR3) set forth by SEQ ID NO: 6.

In one embodiment, the anti-HLA-A2 antibody comprises a heavy chain variable region comprising one VH CDR2 set forth by SEQ ID NO: 5 and at least one of the following CDRs: a VH CDR1 set forth by SEQ ID NO: 1; or a VH CDR3 set forth by SEQ ID NO: 6.

In one embodiment, the anti-HLA-A2 antibody comprises a heavy chain variable region comprising one VH CDR1 set forth by SEQ ID NO: 1; one VH CDR2 set forth by SEQ ID NO: 5; and one VH CDR3 set forth by SEQ ID NO: 6.

According to the present invention, any of the CDRs 1, 2 or 3 of the heavy chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 1, 5 and 6.

In one embodiment, the anti-HLA-A2 antibody comprises a heavy chain variable region comprising one VH CDR2 set forth by SEQ ID NO: 5 and at least one of the following CDRs: a VH CDR1 set forth by SEQ ID NO: 2; or a VH CDR3 set forth by SEQ ID NO: 6.

In one embodiment, the anti-HLA-A2 antibody comprises a heavy chain variable region comprising one VH CDR1 set forth by SEQ ID NO: 2; one VH CDR2 set forth by SEQ ID NO: 5; and one VH CDR3 set forth by SEQ ID NO: 6.

According to the present invention, any of the CDRs 1, 2 or 3 of the heavy chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 2, 5 and 6.

In one embodiment, the anti-HLA-A2 antibody comprises a light chain variable region comprising the amino acid sequence RSSQSIVHSNGNTYLE (SEQ ID NO: 7).

In one embodiment, the anti-HLA-A2 antibody comprises a light chain variable region comprising a complementarity determining region 1 (VL CDR1) set forth by SEQ ID NO: 7.

In one embodiment, the anti-HLA-A2 antibody comprises a light chain variable region comprising the amino acid sequence KVSNRFS (SEQ ID NO: 8).

In one embodiment, the anti-HLA-A2 antibody comprises a light chain variable region comprising a complementarity determining region 2 (VL CDR2) set forth by SEQ ID NO: 8.

In one embodiment, the anti-HLA-A2 antibody comprises a light chain variable region comprising the amino acid sequence FQGSHVPRT (SEQ ID NO: 9).

In one embodiment, the anti-HLA-A2 antibody comprises a light chain variable region comprising a complementarity determining region 3 (VL CDR3) set forth by SEQ ID NO: 9.

In one embodiment, the anti-HLA-A2 antibody comprises a light chain variable region comprising at least one of the following CDRs:
a VL CDR1 set forth by SEQ ID NO: 7; or
a VL CDR2 set forth by SEQ ID NO: 8; or
a VL CDR3 set forth by SEQ ID NO: 9.

In one embodiment, the anti-HLA-A2 antibody comprises a light chain variable region comprising one VL CDR1 set forth by SEQ ID NO: 7; one VL CDR2 set forth by SEQ ID NO: 8; and one VL CDR3 set forth by SEQ ID NO: 9.

According to the present invention, any of the CDRs 1, 2 or 3 of the light chain may be characterized as having an amino acid sequence that shares at least about 60%, 70%, 75%, 80%, 85%, 90%, 95%, 96%, 97%, 98%, or 99% identity with the particular sets of CDRs listed in the corresponding SEQ ID NOs: 7, 8 and 9.

In one embodiment, the anti-HLA-A2 antibody comprises a heavy chain variable region comprising a framework region 1 (VH FR1) comprising an amino acid sequence selected from the group consisting of: QVQLVQSGAEVKKPGASVKVSCKAS (SEQ ID NO: 11) and QVQLVQSGAEVKKPGASVKVSCKASGYTFT (SEQ ID NO: 12).

In one embodiment, the anti-HLA-A2 antibody thereof comprises a heavy chain variable region comprising a framework region 1 (VH FR1) comprising the amino acid sequence QVQLVQSGAEVKKPGASVKVSCKAS (SEQ ID NO: 11). In one embodiment, the anti-HLA-A2 antibody comprises a heavy chain variable region comprising a framework region 1 (VH FR1) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 11.

In one embodiment, the anti-HLA-A2 antibody comprises a heavy chain variable region comprising a framework region 1 (VH FR1) comprising the amino acid sequence QVQLVQSGAEVKKPGASVKVSCKASGYTFT (SEQ ID NO: 12). In one embodiment, the anti-HLA-A2 antibody comprises a heavy chain variable region comprising a framework region 1 (VH FR1) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 12.

In one embodiment, the anti-HLA-A2 antibody comprises a heavy chain variable region comprising a framework region 2 (VH FR2) comprising an amino acid sequence selected from the group consisting of: WVRQAPGQX$^9$LEWMGX$^{15}$ (SEQ ID NO: 13), and HIQWVRQAPGQX$^{12}$LEWMGX$^{18}$ (SEQ ID NO: 25), wherein: X$^9$ is R or G and X$^{15}$ is I or absent in SEQ ID NO: 13; and X$^{12}$ is R or G, and X$^{18}$ is I or absent in SEQ ID NO: 25.

In one embodiment, the anti-HLA-A2 antibody comprises a heavy chain variable region comprising a framework region 2 (VH FR2) comprising the amino acid sequence WVRQAPGQX$^9$LEWMGX$^{15}$ (SEQ ID NO: 13), wherein the amino acid at position 9 (X$^9$) is R or G, and the amino acid at position 15 (X$^{15}$) is I or absent.

In one embodiment, the heavy chain variable region comprises a framework region 2 (VH FR2) comprising an amino acid sequence set forth in SEQ ID NO: 13, wherein the amino acid at position 9 is R or G, and the amino acid at position 15 is absent.

In one embodiment, the heavy chain variable region comprises a framework region 2 (VH FR2) comprising an amino acid sequence set forth in SEQ ID NO: 14, 15, or 16. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 14, 15, or 16.

In one embodiment, the anti-HLA-A2 antibody comprises a heavy chain variable region comprising a framework region 2 (VH FR2) comprising the amino acid sequence HIQWVRQAPGQX$^{12}$LEWMGX$^{18}$ (SEQ ID NO: 25), wherein the amino acid at position 12 (X$^{12}$) is R or G, and the amino acid at position 18 (X$^{18}$) is I or absent.

In one embodiment, the heavy chain variable region comprises a framework region 2 (VH FR2) comprising an amino acid sequence set forth in SEQ ID NO: 25, wherein the amino acid at position 12 is R or G, and the amino acid at position 18 is absent.

In one embodiment, the heavy chain variable region comprises a framework region 2 (VH FR2) comprising an amino acid sequence set forth in SEQ ID NO: 26, 27, or 28. In one embodiment, the heavy chain variable region comprises a framework region 2 (VH FR2) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 26, 27, or 28.

In one embodiment, the anti-HLA-A2 antibody comprises a heavy chain variable region comprising a framework region 3 (VH FR3) comprising the amino acid sequence X$^1$VTX$^4$TX$^6$DTSX$^{10}$STAYMX$^{16}$LSX$^{19}$LRSX$^{23}$DX$^{25}$AVYYCAR (SEQ ID NO: 29), wherein the amino acid at position 1 (X$^1$) is R or absent, the amino acid at position 4 (X$^4$) is I or M, the amino acid at position 6 (X$^6$) is R or A, the amino acid at position 10 (X$^{10}$) is A, T or I, the amino acid at position 16 (X$^{16}$) is E or L, the amino acid at position 19 (X$^{19}$) is S or R, the amino acid at position 23 (X$^{23}$) is E or D, and the amino acid at position 25 (X$^{25}$) is T or M.

In one embodiment, the heavy chain variable region comprises a framework region 3 (VH FR3) comprising an amino acid sequence set forth in SEQ ID NO: 29, wherein the amino acid at position 1 is R, the amino acid at position 4 is I or M, the amino acid at position 6 is R, the amino acid at position 10 is A or I, the amino acid at position 16 is E, the amino acid at position 19 is S or R, the amino acid at position 23 is E or D, and the amino acid at position 25 is T or M.

In one embodiment, the heavy chain variable region comprises a framework region 3 (VH FR3) comprising an amino acid sequence set forth by SEQ ID NO: 29, wherein the amino acid at position 1 is R, the amino acid at position 4 is I or M, the amino acid at position 6 is R, the amino acid at position 10 is A or I, the amino acid at position 16 is E, the amino acid at position 19 is S or R, the amino acid at position 23 is E or D, and the amino acid at position 25 is T.

In one embodiment, the heavy chain variable region comprises a framework region 3 (VH FR3) comprising an amino acid sequence set forth by SEQ ID NO: 29, wherein the amino acid at position 1 is R, the amino acid at position 4 is I, the amino acid at position 6 is R, the amino acid at position 10 is A, the amino acid at position 16 is E, the amino acid at position 19 is S, the amino acid at position 23 is E, and the amino acid at position 25 is T or M.

In one embodiment, the heavy chain variable region comprises a framework region 3 (VH FR3) comprising an amino acid sequence set forth in SEQ ID NO: 30, 31, 32, 33, or 34. In one embodiment, the heavy chain variable region comprises a framework region 3 (VH FR3) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 30, 31, 32, 33, or 34.

In one embodiment, the anti-HLA-A2 antibody comprises a heavy chain variable region comprising a framework region 4 (VH FR4) comprising the amino acid sequence WGQGTTVTVSS (SEQ ID NO: 44). In one embodiment, the anti-HLA-A2 antibody comprises a heavy chain variable region comprising a framework region 4 (VH FR4) comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 44.

In one embodiment, the heavy chain variable region comprises:
  a VH CDR1 set forth by SEQ ID NO: 1;
  a VH CDR2 set forth by SEQ ID NO: 5;
  a VH CDR3 set forth by SEQ ID NO: 6;
  a VH FR1 set forth by SEQ ID NO: 12;
  a VH FR2 set forth by SEQ ID NO: 13, wherein the amino acid at position 9 (X$^9$) is R or G, and the amino acid at position 15 (X$^{15}$) is I or absent;
  a VH FR3 set forth by SEQ ID NO: 29, wherein the amino acid at position 1 (X$^1$) is R or absent, the amino acid at position 4 (X$^4$) is I or M, the amino acid at position 6 (X$^6$) is R or A, the amino acid at position 10 (X$^{10}$) is A, T or I, the amino acid at position 16 (X$^{16}$) is E or L, the amino acid at position 19 (X$^{19}$) is S or R, the amino acid at position 23 (X$^{23}$) is E or D, and the amino acid at position 25 (X$^{25}$) is T or M; and a VH FR4 set forth by SEQ ID NO: 44.

In one embodiment, the heavy chain variable region comprises:
  a VH CDR1 set forth by SEQ ID NO: 2;
  a VH CDR2 set forth by SEQ ID NO: 5;
  a VH CDR3 set forth by SEQ ID NO: 6;
  a VH FR1 set forth by SEQ ID NO: 11;

a VH FR2 set forth by SEQ ID NO: 25, wherein the amino acid at position 12 ($X^{12}$) is R or G, and the amino acid at position 18 ($X^{18}$) is I or absent;
a VH FR3 set forth by SEQ ID NO: 29, wherein the amino acid at position 1 ($X^1$) is R or absent, the amino acid at position 4 ($X^4$) is I or M, the amino acid at position 6 ($X^6$) is R or A, the amino acid at position 10 ($X^{10}$) is A, T or I, the amino acid at position 16 ($X^{16}$) is E or L, the amino acid at position 19 ($X^{19}$) is S or R, the amino acid at position 23 ($X^{23}$) is E or D, and the amino acid at position 25 ($X^{25}$) is T or M; and a VH FR4 set forth by SEQ ID NO: 44.

In one embodiment, the anti-HLA-A2 antibody comprises a heavy chain variable region comprising an amino acid sequence QVQLVQSGAEVKKPGASVKVSCKASGYTFTSYHIQWVRQAPGQX$^{44}$LEWMGX$^{50}$WIYPGDGSTKYSQKFQGX$^{68}$VTX$^{71}$TX$^{73}$DTSX$^{77}$STAYMX$^3$LSX$^6$LRSX$^{90}$DX$^{92}$AVYYCAREGTYYAMDYWGQGTTVTVSS (SEQ ID NO: 92), wherein the amino acid at position 44 is R or G, the amino acid at position 50 is I or absent, the amino acid at position 68 is R or absent, the amino acid at position 71 is I or M, the amino acid at position 73 is R or A, the amino acid at position 77 is A, T or I, the amino acid at position 83 is E or L, the amino acid at position 86 is S or R, the amino acid at position 90 is E or D, and the amino acid at position 92 is T or M.

In one embodiment, the heavy chain variable region comprises an amino acid sequence set forth in SEQ ID NO: 92, wherein the amino acid at position 44 is R or G, the amino acid at position 50 is absent, the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T or M.

In one embodiment, the heavy chain variable region comprises an amino acid sequence set forth in SEQ ID NO: 92, wherein the amino acid at position 44 is R or G, the amino acid at position 50 is absent, the amino acid at position 68 is R, the amino acid at position 71 is I or M, the amino acid at position 73 is R, the amino acid at position 77 is A or I, the amino acid at position 83 is E, the amino acid at position 86 is S or R, the amino acid at position 90 is E or D, and the amino acid at position 92 is T.

In one embodiment, the heavy chain variable region comprises an amino acid sequence set forth in SEQ ID NO: 92, wherein the amino acid at position 44 is R, the amino acid at position 50 is absent, the amino acid at position 68 is R, the amino acid at position 71 is I, the amino acid at position 73 is R, the amino acid at position 77 is A, the amino acid at position 83 is E, the amino acid at position 86 is S, the amino acid at position 90 is E, and the amino acid at position 92 is T or M.

In one embodiment, the anti-HLA-A2 antibody comprises a heavy chain variable region comprising an amino acid sequence set forth in SEQ ID NO: 66. In one embodiment, the anti-HLA-A2 antibody comprises a heavy chain variable region comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 66.

In one embodiment, the anti-HLA-A2 antibody comprises a light chain variable region as defined anywhere herein. For example, in one embodiment, the anti-HLA-A2 antibody may comprise a light chain variable region as defined anywhere herein for the humanized anti-HLA-A2 antibody.

In one embodiment, the anti-HLA-A2 antibody is an scFv, scFab or sdAb. In one embodiment, the anti-HLA-A2 antibody is an scFv or scFab. In one embodiment, the anti-HLA-A2 antibody is an sdAb. In one embodiment, the anti-HLA-A2 antibody is an scFab. In one embodiment, the anti-HLA-A2 antibody is an scFv. In one embodiment, the anti-HLA-A2 antibody is an scFv comprising an amino acid sequence set forth in SEQ ID NO: 91. In one embodiment, the anti-HLA-A2 antibody is an scFv comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 91.

In one embodiment, the anti-HLA-A2 antibody is a humanized anti-HLA-A2 antibody. In one embodiment, the anti-HLA-A2 antibody is a human antibody. In one embodiment, the anti-HLA-A2 antibody is a non-humanized antibody. In one embodiment, the anti-HLA-A2 antibody is a non-human antibody.

In one embodiment, the anti-HLA-A2 antibody comprises an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to the SEQ ID NOs recited above. In one embodiment, the anti-HLA-A2 antibody is an scFv or scFab comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to the SEQ ID NOs recited above. Also provided is a composition comprising, consisting essentially of, or consisting of, at least one anti-HLA-A2 antibody of the invention.

As used herein, "consisting essentially of", with reference to a composition, means that at least one anti-HLA-A2 antibody of the invention as described here above is the only one therapeutic agent or agent with a biologic activity within said composition.

In another embodiment, there is provided a pharmaceutical composition comprising at least one anti-HLA-A2 antibody of the invention, and a pharmaceutically acceptable carrier.

In one embodiment, the anti-HLA-A2 antibody is a humanized anti-HLA-A2 antibody.

Examples of pharmaceutically acceptable carriers include, but are not limited to, media, solvents, coatings, isotonic and absorption delaying agents, additives, stabilizers, preservatives, surfactants, substances which inhibit enzymatic degradation, alcohols, pH controlling agents, antioxidants; chelating agents such as EDTA or glutathione; adjuvants (e.g., aluminum hydroxide); preservatives and propellants.

Examples of pharmaceutically acceptable media include, but are not limited to, water, neutral buffered saline, phosphate buffered saline, normal saline or other physiologically buffered saline, or other solvent such as glycol, glycerol, and oil such as olive oil or an injectable organic ester. A pharmaceutically acceptable medium can also contain liposomes or micelles.

Examples of coating materials include, but are not limited to, lecithin.

Examples of isotonic agents include, but are not limited to, sugars, sodium chloride, and the like.

Examples of agents that delay absorption include, but are not limited to, aluminum monostearate and gelatin.

Examples of additives include, but are not limited to, mannitol, dextran, carbohydrates (such as, for example, glucose, mannose, sucrose or dextrans); glycine, lactose or polyvinylpyrrolidone or other additives such as antioxidants or inert gas, stabilizers or recombinant proteins (e. g. human serum albumin) suitable for in vivo administration. Examples of suitable stabilizers include, but are not limited to, sucrose, gelatin, peptone, digested protein extracts such as NZ-Amine or NZ-Amine AS.

Pharmaceutically acceptable carriers that may be used in these compositions further include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylenepolyoxypropylene-block polymers, polyethylene glycol and wool fat.

Also provided is a medicament comprising, consisting or consisting essentially of at least one anti-HLA-A2 antibody of the invention, as described hereinabove. In one embodiment, the anti-HLA-A2 antibody is a humanized anti-HLA-A2 antibody.

IV. Chimeric Antigen Receptors (CARs)

In one aspect, the present invention provides chimeric antigen receptors (CARs). CARs are chimeric protein molecules that combine antibody-based specificity for a target antigen with an immune cell receptor-activating intracellular domain.

The CARs of the invention comprise an extracellular domain that specifically binds to HLA-A2. The extracellular domain comprises an anti-HLA-A2 antibody of the invention. In one embodiment, the anti-HLA-A2 antibody is a humanized anti-HLA-A2 antibody. The CARs of the invention further comprise a transmembrane domain and a cytoplasmic domain comprising an intracellular signaling domain. In one embodiment, the CARs of the invention are capable of being expressed in a human cell such that the CARs specifically bind to HLA-A2. In other embodiments, the CARs of the invention are capable of being expressed in an immune cell such that the CARs specifically bind to HLA-A2. In one embodiment, the CARs specifically bind to HLA-A*02:01. As would be appreciated by one skilled in the art, the ability of a CAR to bind to HLA-A2 may be detected through the use of techniques known in the art. For example, binding of a CAR to HLA-A2 may be detected through the use of an HLA-A2 tetramer as exemplified herein. In one embodiment, the CARs provided herein have less reactivity to at least one HLA-A subtype selected from one or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from two or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from three or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from four or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from five or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from six or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from seven or more of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from each of HLA-A*03, HLA-A*25, HLA-A*29, HLA-A*30, HLA-A*31, HLA-A*33, HLA-A*36, HLA-A*68, as compared to a CAR comprising a BB7.2 antibody. In one embodiment, the CARs provided herein have less reactivity to at least one HLA-A subtype selected from one or more of HLA-A*25, HLA-A*29, HLA-A*30, as compared to a CAR comprising a BB7.2 antibody. In one embodiment, the CARs provided herein have less reactivity to at least one HLA-A subtype selected from two or more of HLA-A*25, HLA-A*29, HLA-A*30, as compared to a CAR comprising a BB7.2 antibody. In one embodiment, the CARs provided herein have less reactivity to at least one HLA-A subtype selected from each of HLA-A*25, HLA-A*29, HLA-A*30, as compared to a CAR comprising a BB7.2 antibody. In one embodiment, the CARs provided herein have less reactivity to at least one of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least two of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least three of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least four of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least five of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least six of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least seven of HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to HLA-A*03:01, HLA-A*25:01, HLA-A*29:02, HLA-A*30:01, HLA-A*31:01, HLA-A*33:01, HLA-A*36:01, and HLA-A*68:01, as compared to a CAR comprising a BB7.2 antibody. In one embodiment, the CARs provided herein have less reactivity to at least one of HLA-A*25:01, HLA-A*29:02, and HLA-A*30:01, as compared to a CAR comprising a BB7.2 antibody. In one embodiment, the CARs provided herein have less reactivity to at least two of HLA-A*25:01, HLA-A*29:02, and HLA-A*30:01, as compared to a CAR comprising a BB7.2 antibody. In one embodiment, the CARs provided herein have less reactivity to HLA-A*25:01, HLA-A*29:02, and HLA-A*30:01, as compared to a CAR comprising a BB7.2 antibody. In one embodiment, the CARs provided herein have less reactivity to HLA-A*25:01 as compared to a CAR comprising a BB7.2 antibody. In one embodiment, the CARs provided herein have less reactivity to HLA-A*29:02 as compared to a CAR comprising a BB7.2 antibody. In one embodiment, the CARs provided herein have less reactivity to HLA-A*30:01 as compared to a CAR comprising a BB7.2 antibody. In one embodiment, the CARs provided herein have less reactivity to HLA-A*03:01 as compared to a CAR comprising a BB7.2 antibody. In one embodiment, the CARs provided herein have less reactivity to HLA-A*31:01 as compared to a CAR comprising a BB7.2 antibody. In one embodiment, the CARs provided herein have less reactivity to HLA-A*33:01 as compared to a CAR comprising a BB7.2 antibody. In one embodiment, the CARs provided herein have less reactivity to HLA-A*36:01 as compared to a CAR comprising a BB7.2 antibody. In one embodiment, the CARs provided herein have less reactivity to HLA-A*68:01 as compared to a CAR comprising a BB7.2 antibody. In one embodiment, the human cell is an immune cell. In one embodiment, the immune cell is a regulatory immune cell. In one embodiment, the immune cell is a T regulatory cell (Treg). In one embodiment, the immune cell is a T cell. In one embodiment, the T cell is a Treg.

Techniques for determining the reactivity of the CAR of the invention to HLA-A subtypes would be known to those of ordinary skill in the art. For example, the reactivity of the CAR of the invention to HLA-A subtypes may be determined by a single antigen bead assay. Such single antigen bead assays are commercially available (e.g., FlowPRA Single Antigen Antibody; ONE LAMBDA).

In one embodiment, the CAR of the invention has less reactivity to an HLA-A subtype selected from the group comprising of HLA-A*03, HLA-A*25, HLA-A*29, HLA-A*30, HLA-A*31, HLA-A*33, HLA-A*36, HLA-A*68, and any combination thereof, as compared to a CAR comprising a BB7.2 antibody, when measured in the conditions of Test A, as described hereinabove.

In one embodiment, the CAR of the invention has less reactivity to an HLA-A subtype selected from the group comprising of HLA-A*25, HLA-A*29, HLA-A*30, and any combination thereof, as compared to a CAR comprising a BB7.2 antibody, when measured in the conditions of Test A, as described hereinabove.

In one embodiment, the CAR of the invention has a reactivity to at least one HLA-A subtype selected from the group comprising HLA-A*03, HLA-A*25, HLA-A*29, HLA-A*30, HLA-A*31, HLA-A*33, HLA-A*36, HLA-A*68 statistically inferior to the one of a CAR comprising a BB7.2 antibody, e.g., when measured in the conditions of Test A.

In one embodiment, the CAR of the invention has a reactivity to at least one HLA-A subtype selected from the group comprising HLA-A*25, HLA-A*29, HLA-A*30 statistically inferior to the one of a CAR comprising a BB7.2 antibody, e.g., when measured in the conditions of Test A.

In one embodiment, the term "statistically inferior" means that the reactivity (i.e., for example, the relative binding in the conditions of Test A) measured for the CAR of the invention is inferior to the reactivity measured for a CAR comprising a BB7.2 antibody, with a p value of at most about 0.05, preferably of at most about 0.01, more preferably of at most about 0.005, and more preferably of at most about 0.001, in particular when analyzed by 2-way ANOVA, Dunnett post-test.

In one embodiment, the CAR of the invention has a reactivity to at least one HLA-A subtype selected from the group comprising HLA-A*03, HLA-A*25, HLA-A*29, HLA-A*30, HLA-A*31, HLA-A*33, HLA-A*36, HLA-A*68 inferior to a CAR comprising a BB7.2 antibody In some embodiments, such a CAR has a relative binding for at least one HLA-A subtype selected from the group comprising HLA-A*03, HLA-A*25, HLA-A*29, HLA-A*30, HLA-A*31, HLA-A*33, HLA-A*36, HLA-A*68 inferior to a CAR comprising a BB7.2 antibody when measured in the conditions of Test A. In certain aspects, the relative binding for such a CAR is at most about 90%, 80%, 70%, 60%, 50%, 40%, 30%, 20%, 10% or less of the relative binding measured for a CAR comprising a BB7.2 antibody.

In one embodiment, the CAR of the invention has a reactivity to at least one HLA-A subtype selected from the group comprising HLA-A*25, HLA-A*29, HLA-A*30 inferior to a CAR comprising a BB7.2 antibody In some embodiments, such a CAR has a relative binding for at least one HLA-A subtype selected from the group comprising HLA-A*25, HLA-A*29, HLA-A*30 inferior to a CAR comprising a BB7.2 antibody when measured in the conditions of Test A. In certain aspects, the relative binding measured for such a CAR is at most about 90%, 80%, 70%, 60%, 50%, 40%, 30%, 20%, 10% or less of the binding of a CAR comprising a BB7.2 antibody.

In one embodiment, the CAR is capable of being expressed in an immune cell such that the immune cell is activated by HLA-A2. In one embodiment, the immune cell is activated by HLA-A*02:01. In one embodiment, the immune cell is a regulatory immune cell. In one embodiment, the immune cell is a T regulatory cell (Treg). In one embodiment, the immune cell is a T cell. In one embodiment, the T cell is a Treg. In one embodiment, the immune cell is a human immune cell. In one embodiment, the regulatory immune cell is a human regulatory immune cell. In one embodiment, the T cell is a human T cell. In one embodiment, the Treg is a human Treg.

In one embodiment, the CAR competes for binding to HLA-A2 with an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the CAR binds to the same HLA-A2 epitope as an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the CAR competes for binding to HLA-A2 with the BB7.2 antibody. In one embodiment, the CAR binds to the same HLA-A2 epitope as a BB7.2 antibody. The BB7.2 antibody may be isolated from the BB7.2 hybridoma (ATCC Deposit No. HB-82).

In one embodiment, the CAR of the invention comprises: an extracellular domain, comprising an anti-HLA-A2 antibody; a transmembrane domain; and a cytoplasmic domain comprising an intracellular signaling domain. In one embodiment, the anti-HLA-A2 antibody is a humanized anti-HLA-A2 antibody.

In one embodiment, the chimeric receptor further comprises a Tag and/or a leader sequence.

In one embodiment, the chimeric receptor further comprises a tag, such as, for example, a tag for quality control, enrichment, tracking in vivo and the like. Said Tag may be localized N-terminally, C-terminally and/or internally. Examples of tags that may be used in the chimeric receptor of the invention are well known by the skilled artisan. For example, but without limitation, a tag used in the invention can be a tag selected from the group comprising or consisting of Hemagglutinin Tag, Poly Arginine Tag, Poly Histidine Tag, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag (e.g., eGFP), T7 Tag, V5 Tag and Xpress Tag.

The extracellular domain is a target-specific binding element also sometimes referred to as a targeting arm of the CAR. The extracellular domain is chosen to recognize a ligand that acts as a cell surface marker on target cells associated with a particular disease state. A CAR of the present invention is engineered to target a cell displaying HLA-A2 by engineering an appropriate extracellular domain that specifically binds to an HLA-A2 epitope. The target-specific binding element or antigen binding domain of the CAR of the present invention may be referred to herein as an anti-HLA-A2 binding domain. In some embodiments, the anti-HLA-A2 binding domain may be a humanized anti-HLA-A2 binding domain.

The transmembrane domain is attached to the extracellular domain and the cytoplasmic domain of the CAR. The transmembrane domain is capable of signaling to the intracellular signaling domain(s) of the cytoplasmic domain whenever the extracellular domain of the CAR is bound to a target.

The cytoplasmic domain which includes the intracellular signaling domain of the CAR is responsible for activation of at least one of the physiological effector functions of the immune cell (e.g., regulatory T cell) in which the CAR has been placed in. The term "effector function" refers to a specialized function of an immune cell. For example, an effector function of a regulatory T cell may include suppressing or downregulating the induction and/or proliferation of other immune cells. In addition, the effector function of Tregs may include effects on non-immune cells that result in an improved clinical state such as promoting tissue repair or regeneration. Thus, the term "intracellular signaling domain" refers to the portion of a protein which transduces the effector function signal and directs the immune cell to perform its specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In one embodiment, there may be a spacer domain (or linker or hinge) incorporated between the antigen binding domain and the transmembrane domain of the CAR or between the intracellular signaling domain and the transmembrane domain of the CAR. As defined hereinabove, spacer domain, linker and hinge are oligo- or polypeptides that function to link the transmembrane domain to, either the antigen binding domain or, the intracellular signaling domain in the polypeptide chain. A spacer domain may comprise, e.g., up to 300 amino acids, 10 to 100 amino acids, 25 to 75 amino acids, or 25 to 50 amino acids, or amino acids of any subranges or individual numerical values within these ranges.

Extracellular Domain

The extracellular domain comprises an anti-HLA-A2 antibody of the present invention. In one embodiment, the extracellular domain comprises a humanized anti-HLA-A2 antibody of the present invention.

In one embodiment, the extracellular domain comprises an anti-HLA-A2 antibody of the present invention which is an scFv, scFab or sdAb. In one embodiment, the extracellular domain comprises an anti-HLA-A2 antibody of the present invention which is an scFv or scFab. In one embodiment, the extracellular domain comprises an anti-HLA-A2 antibody of the present invention which is an sdAb. In one embodiment, the extracellular domain comprises an anti-HLA-A2 antibody of the present invention which is an scFv. In one embodiment, the extracellular domain comprises an anti-HLA-A2 antibody of the present invention which is an scFab. In one embodiment, the extracellular domain comprises any humanized anti-HLA-A2 antibody of the present invention wherein the humanized anti-HLA-A2 antibody is an scFv, scFab or sdAb. In one embodiment, the extracellular domain comprises any humanized anti-HLA-A2 antibody of the present invention wherein the humanized anti-HLA-A2 antibody is an scFv or scFab. In one embodiment, the extracellular domain comprises a humanized anti-HLA-A2 antibody of the present invention which is an sdAb. In one embodiment, the extracellular domain comprises a humanized anti-HLA-A2 antibody of the present invention which is an scFv. In one embodiment, the extracellular domain comprises a humanized anti-HLA-A2 antibody of the present invention which is an scFab.

In some embodiments, the extracellular domain may comprise a hinge, where the transmembrane domain is attached to the extracellular region of the CAR, e.g., the antigen binding domain of the CAR, via the hinge. In one embodiment, the hinge may be from a human protein. For example, in one embodiment, the hinge may be a human Ig (immunoglobulin) hinge, e.g., an IgG4 hinge, or a CD8a hinge. In some instances, the extracellular domain of the CAR of the invention may comprise a CD8a hinge. In one embodiment, the hinge region comprises a stalk region of CD8a. In one embodiment, the CD8 hinge may be encoded by the nucleic acid sequence of SEQ ID NO: 15 of U.S. Pat. No. 9,102,760. In one embodiment, the CD8 hinge may comprise the amino acid sequence of SEQ ID NO: 21 of U.S. Pat. No. 9,102,760. In another embodiment, the CD8 hinge may comprise the amino acid sequence of SEQ ID NO: 21 of U.S. Pat. No. 9,102,760. In one embodiment, the hinge or spacer may comprise the amino acid sequence of SEQ ID NO: 115 or 219 in Table 3. In one embodiment, the hinge or spacer may be encoded by a nucleic acid sequence of SEQ ID NO: 159 or 220 in Table 4.

Transmembrane Domain

The transmembrane domain may be derived either from a natural source or a synthetic source. In one embodiment, the transmembrane domain may be derived from a natural source, for example, from any membrane-bound or transmembrane protein.

In one embodiment, the transmembrane domain of the CAR may be derived from a transmembrane domain that is naturally associated with one of the domains of the CAR. In other embodiments, the transmembrane domain may be selected or modified by amino acid substitution to avoid binding of such domains to the transmembrane domain of the same or different surface membrane proteins to minimize interactions with other members of the receptor complex.

In one embodiment, the transmembrane domain may include one or more additional amino acids adjacent to the transmembrane region, e.g., one or more amino acid associated with the extracellular region of the protein from which the transmembrane is derived (e.g., 1, 2, 3, 4, 5, 6, 7, 8, 9, 10, 11, 12, 13, 14, or 15 amino acids of the extracellular region) and/or one or more additional amino acids associated with the cytoplasmic region of the protein from which the transmembrane protein is derived (e.g., 1, 2, 3, 4, 5, 6, 7, 8, 9, 10, 11, 12, 13, 14, or 15 amino acids of the cytoplasmic region).

In one embodiment, the transmembrane domain may comprise a transmembrane domain of a protein selected from the group consisting of CD3 gamma, CD3 delta, CD3 epsilon, CD3 zeta, the alpha chain of the T-cell receptor, the beta chain of the T-cell receptor, the gamma chain of the T-cell receptor, the delta chain of the T-cell receptor, CD28, CD45, CD4, CD5, CD8, CD9, CD16, CD22, CD33, CD37, CD64, CD80, CD86, CD134, CD137, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, PD1, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C and CD154, and any combination thereof. In one embodiment, the transmembrane domain may comprise a transmembrane domain of CD28. In one embodiment, the CD28 transmembrane domain is encoded by the nucleic acid sequence of SEQ ID NO: 160 in Table 4. In one embodiment, the CD28 transmembrane domain comprises the amino acid sequence of SEQ ID NO: 116 in Table 3. In another embodiment, the CD28 transmembrane domain comprises the amino acid sequence of SEQ ID NO: 116 in Table 3.

In one embodiment, the transmembrane domain may comprise a transmembrane domain of CD8. In one embodiment, the CD8 transmembrane domain is encoded by the nucleic acid sequence of SEQ ID NO: 16 of U.S. Pat. No. 9,102,760. In one embodiment, the CD8 transmembrane domain comprises the amino acid sequence of SEQ ID NO: 22 of U.S. Pat. No. 9,102,760. In another embodiment, the CD8 transmembrane domain comprises the amino acid sequence of SEQ ID NO: 22 of U.S. Pat. No. 9,102,760.

In one embodiment, the CD8 transmembrane domain is encoded by the nucleic acid sequence of SEQ ID NO: 224 in Table 4. In one embodiment, the CD8 transmembrane domain comprises the amino acid sequence of SEQ ID NO: 223 in Table 3.

In other embodiments, the transmembrane domain may be synthetic, in which case it may comprise predominantly hydrophobic residues including leucine and valine. In one embodiment, a triplet of phenylalanine, tryptophan and valine may be found at each end of a synthetic transmembrane domain.

In one embodiment, a short oligo- or polypeptide linker may form a linkage between the transmembrane domain and the cytoplasmic domain of the CAR. In one embodiment, the linker may comprise between 1, 2, 3, 4, 5, 6, 7, 8, 9 or 10 amino acids in length. In one embodiment, the linker may comprise a glycine-serine doublet.

Cytoplasmic Domain

In one embodiment, intracellular signaling domains for use in the CAR of the invention may include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from CD3 zeta, FcR gamma, CD3 gamma, CD3 delta, CD3 epsilon, CD5, CD22, CD79a, CD79b, and CD66d. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

In one embodiment, the intracellular signaling domain comprises a functional signaling domain of a protein selected from the group consisting of CD3 gamma, CD3 delta, CD3 epsilon, CD3 zeta, FcR gamma (e.g., FCγRI, RCγRIIA, FcγRIIB1, FcγRIIB2, FcγRIIIA, or FcγRIIIB), FcR alpha (e.g., FcaRI), FcR epsilon (e.g., FccRI or FccRII), CD5, CD22, CD79a, CD79b, DAP10, DAP12 and CD66d, and any combination thereof. In one embodiment, the intracellular signaling domain comprises or consists of a primary signaling domain of CD3-zeta.

It is known that signals generated through the TCR alone may be insufficient for full activation of the T cell and that a secondary or co-stimulatory signal may also be required. Thus, in certain embodiments, T cell activation may be mediated by two classes of cytoplasmic signaling sequence: those that initiate antigen-dependent primary activation through the TCR (primary cytoplasmic signaling sequences)

and those that act in an antigen-independent manner to provide a secondary or co-stimulatory signal (secondary cytoplasmic signaling sequences). In one embodiment, the intracellular signaling domain may further comprise a costimulatory domain.

In one embodiment, the intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, a ligand that specifically binds with CD83, IL2ra (CD25), IL6Ra (CD126), IL-7Ra (CD127), IL-13RA1, IL-13RA2, IL-33R(IL1RL1), IL-10RA, IL-10RB, IL-4R, IL-5R (CSF2RB), ARHR, BAFF receptor, IL-21R, TGFbR1, TGFbR2, TGFbR3, common gamma chain, an MHC class I molecule, BTLA and a Toll ligand receptor, a ligand that specifically binds with CD83, CDS, ICAM-1, GITR, HVEM (LIGHTR), SLAMF7, NKp80 (KLRF1), NKp44, NKp30, NKp46, CD160 (BY55), CD19, CD19a, CD4, CD8alpha, CD8beta, IL2R beta, IL2R gamma, IL7R alpha, ITGA4, VLA1, CD49a, IA4, CD49D, ITGA6, VLA-6, CD49f, ITGAD, CDlld, ITGAE, CD103, ITGAL, CDlla, ITGAM, CDlib, ITGAX, CDlic, ITGB1, CD29, ITGB2, CitgbD18, ITGB7, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKG2D and the like.

The intracellular signaling sequences within the cytoplasmic portion of the CAR of the invention may be linked to each other in a random or specified order. Optionally, a short oligo- or polypeptide linker, for example, between 1 and 10 amino acids (e.g., 1, 2, 3, 4, 5, 6, 7, 8, 9, or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker.

In one embodiment, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one embodiment, the cytoplasmic domain may comprise the signaling domain of CD3-zeta and the signaling domain of CD28. In another embodiment, the cytoplasmic domain may comprise the signaling domain of CD3-zeta and the signaling domain of 4-IBB. In yet another embodiment, the cytoplasmic domain may comprise the signaling domain of CD3-zeta and the signaling domains of CD28 and 4-1BB.

In one embodiment, the cytoplasmic domain may comprise the signaling domain of CD28 and the signaling domain of CD3-zeta, wherein the signaling domain of CD28 is encoded by the nucleic acid sequence set forth in SEQ ID NO: 161 in Table 4 and the signaling domain of CD3-zeta is encoded by the nucleic acid sequence set forth in SEQ ID NO: 162 in Table 4.

In one embodiment, the cytoplasmic domain may comprise the signaling domain of CD28 and the signaling domain of CD3-zeta, wherein the signaling domain of CD28 comprises the amino acid sequence of SEQ ID NO: 117 in Table 3 and the signaling domain of CD3-zeta comprises the amino acid sequence of SEQ ID NO: 118 in Table 3.

In one embodiment, the cytoplasmic domain may comprise the signaling domain of CD28 and the signaling domain of CD3-zeta, wherein the signaling domain of CD28 comprises the amino acid sequence set forth in SEQ ID NO: 117 in Table 3 and the signaling domain of CD3-zeta comprises the amino acid sequence set forth in SEQ ID NO: 118 in Table 3.

In one embodiment, the cytoplasmic domain may comprise the signaling domain of 4-1BB and the signaling domain of CD3-zeta, wherein the signaling domain of 4-1BB is encoded by the nucleic acid sequence set forth in SEQ ID NO: 17 of U.S. Pat. No. 9,102,760 and the signaling domain of CD3-zeta is encoded by the nucleic acid sequence set forth in SEQ ID NO: 162 in Table 4.

In one embodiment, the cytoplasmic domain may comprise the signaling domain of 4-1BB and the signaling domain of CD3-zeta, wherein the signaling domain of 4-1BB comprises the amino acid sequence of SEQ ID NO: 23 of U.S. Pat. No. 9,102,760 and the signaling domain of CD3-zeta comprises the amino acid sequence of SEQ ID NO: 118 in Table 3.

In one embodiment, the cytoplasmic domain may comprise the signaling domain of 4-1BB and the signaling domain of CD3-zeta, wherein the signaling domain of 4-1BB comprises the amino acid sequence set forth in SEQ ID NO: 23 of U.S. Pat. No. 9,102,760 and the signaling domain of CD3-zeta comprises the amino acid sequence set forth in SEQ ID NO: 118 in Table 3.

In one embodiment, the CAR comprises an amino acid sequence set forth in SEQ ID NO: 119, 120, 121, 122, 123, 124, 125, 126, 127, 128, 129, 130, 131, 132, 133, 134, 135, 136, 137, 138 or 213. In one embodiment, the CAR comprises an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 119, 120, 121, 122, 123, 124, 125, 126, 127, 128, 129, 130, 131, 132, 133, 134, 135, 136, 137, 138 or 213.

V. Nucleic Acids and Vectors

In some embodiments, the invention provides a nucleic acid encoding an anti-HLA-A2 antibody of the present invention. In some embodiments, the invention provides a nucleic acid encoding a humanized anti-HLA-A2 antibody of the present invention. In some embodiments, the invention provides a nucleic acid encoding a protein comprising the amino acid sequence set forth in SEQ ID NO: 72, 73, 74, 75, 76, 77, 78, 79, 80, 81, 82, 83, 84, 85, 86, 87, 88, 89, 90, or 91. In some embodiments, the invention provides a nucleic acid encoding a protein comprising the amino acid sequence set forth in SEQ ID NO: 93, 94, 95, 96, 97, 98, 99, 100, 101, 102, 103, 104, 105, 106, 107, 108, 109, 110, 111, or 112. In some embodiments, the invention provides a nucleic acid encoding a protein comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 72, 73, 74, 75, 76, 77, 78, 79, 80, 81, 82, 83, 84, 85, 86, 87, 88, 89, 90, or 91. In some embodiments, the invention provides a nucleic acid encoding a protein comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 93, 94, 95, 96, 97, 98, 99, 100, 101, 102, 103, 104, 105, 106, 107, 108, 109, 110, 111, or 112. In some embodiments, the invention provides a nucleic acid comprising the nucleic acid sequence set forth in SEQ ID NO: 139, 140, 141, 142, 143, 144, 145, 146, 147, 148, 149, 150, 151, 152, 153, 154, 155, 156, 157, or 158. In some embodiments, the invention provides a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 139, 140, 141, 142, 143, 144, 145, 146, 147, 148, 149, 150, 151, 152, 153, 154, 155, 156, 157, or 158. In some embodiments, the invention provides a protein encoded by a nucleic acid comprising the nucleic acid sequence set forth in SEQ ID NO: 139, 140, 141, 142, 143, 144, 145, 146, 147, 148, 149, 150, 151, 152, 153, 154, 155, 156, 157, or 158. In some embodiments, the invention provides a protein encoded by a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 139, 140, 141, 142, 143, 144, 145, 146, 147, 148, 149, 150, 151, 152, 153, 154, 155, 156, 157, or 158. In some embodiments, the invention provides a nucleic acid encoding a protein comprising the amino acid sequence set forth in SEQ ID NO: 61, 62, 63, 64, 65, 66, 67, 68, 69, 70, or 71. In some embodiments, the invention provides a nucleic acid encoding a protein comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 61, 62, 63, 64, 65, 66, 67, 68, 69, 70, or 71.

In some embodiments, the invention provides a nucleic acid encoding a chimeric antigen receptor (CAR) of the present invention. The CAR-encoding nucleic acid sequences of the invention may encode CARs which comprise an extracellular domain as described anywhere herein.

The extracellular domain may comprise an anti-HLA-A2 antibody of the present invention. The extracellular domain may comprise a humanized anti-HLA-A2 antibody of the present invention. In one embodiment, the extracellular domain may further comprise a leader sequence. In one embodiment, the leader sequence comprises an amino acid sequence set forth in SEQ ID NO: 113. In one embodiment, the extracellular domain comprises a hinge region, wherein the anti-HLA-A2 binding domain is connected to the transmembrane domain by the hinge region. In one embodiment, the hinge region comprises a stalk region of CD8a.

The nucleic acid sequences of the invention may encode CARs which comprise a transmembrane domain as described anywhere herein. For example, in one embodiment, the transmembrane domain comprises a transmembrane domain of a protein selected from the group consisting of CD3 gamma, CD3 delta, CD3 epsilon, CD3 zeta, the alpha chain of the T-cell receptor, the beta chain of the T-cell receptor, the gamma chain of the T-cell receptor, the delta chain of the T-cell receptor, CD28, CD45, CD4, CD5, CD8, CD9, CD16, CD22, CD33, CD37, CD64, CD80, CD86, CD134, CD137, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, PD1, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C and CD154, and any combination thereof. In one embodiment, the transmembrane domain comprises a transmembrane domain of CD28.

The nucleic acid sequences of the invention may encode CARs which comprise a cytoplasmic domain as described anywhere herein. Furthermore, the cytoplasmic domain may comprise an intracellular signaling domain as described anywhere herein. For example, in one embodiment, the intracellular signaling domain comprises a functional signaling domain of a protein selected from the group consisting of CD3 gamma, CD3 delta, CD3 epsilon, CD3 zeta, FcR gamma (e.g., FCγRI, RCγRIIA, FcγRIIB1, FcγRIIB2, FcγRIIIA, or FcγRIIIB), FcR alpha (e.g., FccRI), FcR epsilon (e.g., FccRI or FccRII), CD5, CD22, CD79a, CD79b, DAP10, DAP12 and CD66d, and any combination thereof. In one embodiment, the intracellular signaling domain comprises a functional signaling domain of CD3 zeta. In one embodiment, the intracellular signaling domain further comprises a costimulatory domain. The costimulatory domain of the CARs encoded by the nucleic acid sequences of the invention may be a costimulatory domain as described anywhere herein. For example, in one embodiment, the costimulatory domain comprises a functional signaling domain of a protein selected from the group consisting of OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, a ligand that specifically binds with CD83, IL2ra (CD25), IL6Ra (CD126), IL-7Ra (CD127), IL-13RA1, IL-13RA2, IL-33R(IL1RL1), IL-10RA, IL-10RB, IL-4R, IL-5R (CSF2RB), ARHR, BAFF receptor, IL-21R, TGFbR1, TGFbR2, TGFbR3, common gamma chain, an MHC class I molecule, BTLA and a Toll ligand receptor, a ligand that specifically binds with CD83, CDS, ICAM-1, GITR, HVEM (LIGHTR), SLAMF7, NKp80 (KLRF1), NKp44, NKp30, NKp46, CD160 (BY55), CD19, CD19a, CD4, CD8alpha, CD8beta, IL2R beta, IL2R gamma, IL7R alpha, ITGA4, VLA1, CD49a, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CitgbD18, ITGB7, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKG2D and any combination thereof. In one embodiment, the costimulatory domain comprises a functional signaling domain of a protein selected from the group consisting of CD28, 4-1BB and a combination thereof. In one embodiment, the costimulatory domain comprises a functional signaling domain of CD28. In one embodiment, the costimulatory domain comprises a functional signaling domain of 4-1BB. In one embodiment, the sequences comprising the intracellular signaling domain are expressed in the same frame and as a single polypeptide chain.

The nucleic acid sequences of the present invention may be isolated nucleic acid sequences.

In one embodiment, the nucleic acid is provided as a messenger RNA transcript. In one embodiment, the nucleic acid is provided as a DNA construct.

In one embodiment, there is provided a recombinant DNA construct comprising sequences encoding a CAR, wherein the CAR comprises: (i) an extracellular domain comprising an anti-HLA-A2 antibody; (ii) a transmembrane domain; and (iii) a cytoplasmic domain comprising an intracellular signaling domain, wherein the encoded CAR is capable of being expressed in a human cell such that the CAR is capable of specifically binding to HLA-A2. In one embodiment, the CAR is capable of specifically binding to HLA-A*02:01. In one embodiment, the anti-HLA-A2 antibody is a humanized anti-HLA-A2 antibody. In one embodiment, the human cell is an immune cell. In one embodiment, the immune cell is a regulatory immune cell. In one embodiment, the immune cell is a T regulatory cell (Treg). In one embodiment, the immune cell is a T cell. In one embodiment, the T cell is a Treg.

In one embodiment, there is provided a recombinant DNA construct comprising sequences encoding a CAR, wherein the CAR comprises: (i) an extracellular domain comprising an anti-HLA-A2 antibody; (ii) a transmembrane domain; and (iii) a cytoplasmic domain comprising an intracellular signaling domain, wherein the encoded CAR is capable of being expressed in a T regulatory cell (Treg) such that the CAR is capable of specifically binding to HLA-A2. In one embodiment, the CAR is capable of specifically binding to HLA-A*02:01. In one embodiment, binding of a CAR to HLA-A2 may be detected through the use of an HLA-A2 tetramer as exemplified herein. In one embodiment, the anti-HLA-A2 antibody is a humanized anti-HLA-A2 antibody. In one embodiment, the Treg is a human Treg.

In one embodiment, the encoded CAR is capable of being expressed in an immune cell such that the immune cell is activated by HLA-A2. In one embodiment, the immune cell is activated by HLA-A*02:01. In one embodiment, the immune cell is a regulatory immune cell.

In one embodiment, the immune cell is a T regulatory cell (Treg). In one embodiment, the immune cell is a T cell. In one embodiment, the T cell is a Treg. In one embodiment, the immune cell is a human immune cell. In one embodiment, the regulatory immune cell is a human regulatory immune cell. In one embodiment, the T cell is a human T cell. In one embodiment, the Treg is a human Treg.

In one embodiment, the encoded CAR competes for binding to HLA-A2 with an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the encoded CAR binds to the same HLA-A2 epitope as an antibody comprising: a heavy chain complementarity determining region 1 (HCDR1) having the amino acid sequence of SEQ ID NO: 183; a heavy chain complementarity determining region 2 (HCDR2) having the amino acid sequence of SEQ ID NO: 185; a heavy chain complementarity determining region 3 (HCDR3) having the amino acid sequence of SEQ ID NO: 187; a light chain complementarity determining region 1 (LCDR1) having the amino acid sequence of SEQ ID NO: 188; a light chain complementarity determining region 2 (LCDR2) having the amino acid sequence of SEQ ID NO: 189; and a light chain complementarity determining region 3 (LCDR3) having the amino acid sequence of SEQ ID NO: 190. In one embodiment, the encoded CAR competes for binding to HLA-A2 with a BB7.2 antibody. In one embodiment, the encoded CAR binds to the same HLA-A2 epitope as a BB7.2 antibody.

In some embodiments, the invention provides a nucleic acid encoding a protein comprising the amino acid sequence set forth in SEQ ID NO: 119, 120, 121, 122, 123, 124, 125, 126, 127, 128, 129, 130, 131, 132, 133, 134, 135, 136, 137, 138 or 213. In some embodiments, the invention provides a nucleic acid encoding a protein comprising an amino acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 119, 120, 121, 122, 123, 124, 125, 126, 127, 128, 129, 130, 131, 132, 133, 134, 135, 136, 137, 138 or 213. In some embodiments, the invention provides a nucleic acid comprising the nucleic acid sequence set forth in SEQ ID NO: 163, 164, 165, 166, 167, 168, 169, 170, 171, 172, 173, 174, 175, 176, 177, 178, 179, 180, 181, 182 or 214. In some embodiments, the invention provides a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 163, 164, 165, 166, 167, 168, 169, 170, 171, 172, 173, 174, 175, 176, 177, 178, 179, 180, 181, 182 or 214. In some embodiments, the invention provides a protein encoded by a nucleic acid comprising the nucleic acid sequence set forth in SEQ ID NO: 163, 164, 165, 166, 167, 168, 169, 170, 171, 172, 173, 174, 175, 176, 177, 178, 179, 180, 181, 182 or 214. In some embodiments, the invention provides a protein encoded by a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 163, 164, 165, 166, 167, 168, 169, 170, 171, 172, 173, 174, 175, 176, 177, 178, 179, 180, 181, 182 or 214.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention further provides a vector comprising an anti-HLA-A2 antibody-encoding nucleic acid molecule or a CAR-encoding nucleic acid molecule. In one embodiment, the invention provides a vector comprising a humanized anti-HLA-A2 antibody-encoding nucleic acid molecule. In one embodiment, the invention provides vectors in which such a nucleic acid molecule is inserted.

In one embodiment, the present invention provides a vector comprising a nucleic acid sequence as described anywhere herein.

In some embodiments, the present invention provides a vector comprising a nucleic acid that encodes any of the anti-HLA-A2 antibodies described herein. In other embodiments, the present invention provides a vector comprising a nucleic acid that encodes any of the humanized anti-HLA-A2 antibodies described herein. In some embodiments, the present invention provides a vector comprising a nucleic acid comprising the nucleic acid sequence set forth in SEQ ID NO: 139, 140, 141, 142, 143, 144, 145, 146, 147, 148, 149, 150, 151, 152, 153, 154, 155, 156, 157, or 158. In some embodiments, the invention provides a vector comprising a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 139, 140, 141, 142, 143, 144, 145, 146, 147, 148, 149, 150, 151, 152, 153, 154, 155, 156, 157, or 158. In certain aspects, provided is a host cell that includes such a vector.

In one embodiment, the present invention provides a vector comprising a CAR-encoding nucleic acid of the invention. In some embodiments, the present invention provides a vector comprising a nucleic acid sequence set forth in SEQ ID NO: 163, 164, 165, 166, 167, 168, 169, 170, 171, 172, 173, 174, 175, 176, 177, 178, 179, 180, 181, 182 or 214. In some embodiments, the invention provides a vector comprising a nucleic acid comprising a nucleic acid sequence having about 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 163, 164, 165, 166, 167, 168, 169, 170, 171, 172, 173, 174, 175, 176, 177, 178, 179, 180, 181, 182 or 214.

In one embodiment, the vectors of the invention may be transduced into a cell. In one embodiment, the vectors of the invention may be transduced or engineered via non-viral vector methods into a human cell. In one embodiment, the vectors of the invention can be transduced into an immune cell. In one embodiment, the immune cell is a regulatory immune cell. In one embodiment, the immune cell is a T regulatory cell (Treg). In one embodiment, the immune cell is a T cell. In one embodiment, the T cell may be a Treg. In one embodiment, the vector is capable of expressing the CAR in mammalian immune cells. In one embodiment, the mammalian immune cell is a human immune cell. In one embodiment, the vector is capable of expressing the CAR in mammalian regulatory immune cells. In one embodiment, the mammalian regulatory immune cell is a human regulatory immune cell. In one embodiment, the vector is capable of expressing the CAR in mammalian T cells. In one embodiment, the mammalian T cells are mammalian T regulatory cells. In one embodiment, the mammalian T cell is a human T cell. In one embodiment, the mammalian T cell is a human T regulatory cell.

In one embodiment, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs.

The present invention includes retroviral and lentiviral vector constructs expressing a CAR that can be directly transduced into a cell. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

In addition to the methods described above, the following methods may be used.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector. In another embodiment, genome editing techniques such as CRISPR-Cas9 or TALEN-based techniques may be used to introduce nucleic acids encoding CARs of the present invention into the genome of recipient immune cells (Delhove, J. M. K. M., et al., 2017; Eyquem, J. et al., 2017).

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, poxviruses, and lentiviruses (see, for example, U.S. Pat. Nos. 5,350,674 and 5,585,362). In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional transcriptionally active elements, e.g., promoters and enhancers, may regulate the frequency of transcriptional initiation. Typically, regarding core promoter, these are located in the region 30-110 bp upstream of the start site, although a number of promoters have recently been shown to contain functional elements downstream of the start site as well, and enhancers elements are generally located 500-2000 bp upstream of the start site. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is Elongation Growth Factor-1α (EF-1α). Another example of a suitable promoter is phosphoglycerate kinase (PGK) promoter. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, for example, Sambrook et al., 2001). For example, a polynucleotide may be introduced into a host cell by calcium phosphate transfection. Alternatively, a host cell may be transfected with a polynucleotide such as RNA by electroporation (see, for example, WO 2007/065957).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

VI. Car-Modified Immune Cells

CAR-encoding nucleic acids of the invention may be introduced into immune cells to generate CAR-modified immune cells expressing CARs of the present invention, which modified immune cells find use as disclosed herein. CAR-modified immune cells may also be referred to herein as "CAR-engineered immune cells". In an embodiment, there is provided a modified immune cell comprising a CAR as described anywhere herein. In another embodiment, there is provided an immune cell comprising an expression vector as described anywhere herein. The immune cell may be any immune cell suitable for use in cellular therapy. In one embodiment, the immune cell may be a human immune cell.

In one embodiment, the immune cell is selected from the group consisting of a lymphocyte, a myeloid-derived cell, and any combination thereof. In one embodiment, the lymphocyte is selected from the group consisting of a T cell, a B cell, a natural killer (NK) cell, and any combination thereof. In one embodiment, the immune cell is a T cell. In one embodiment, the T cell is selected from the group consisting of a CD4$^+$ T cell, a CD8$^+$ T cell, a γδ T cell, a double negative (DN) T cell, and any combination thereof. In one embodiment, the CD4$^+$ T cell is selected from the group consisting of a T helper cell, a regulatory T cell, and any combination thereof. In one embodiment, the immune cell is a regulatory T cell. In one embodiment, the Treg is a thymus derived Treg or an adaptive or induced Treg. In one embodiment, the Treg is a CD4$^+$FOXP3$^+$ regulatory T cell or a CD4$^+$FOXP3$^-$ regulatory T cell ($T_R$1 cell). In one embodiment, the Treg is a CD4$^+$FOXP3$^+$ regulatory T cell. In one embodiment, the Treg is a CD4$^+$FOXP3$^-$ regulatory T cell ($T_R$1 cell). In one embodiment, the CD8$^+$ T cell is a cytotoxic CD8$^+$ T cell or a CD8$^+$ regulatory T cell. In one embodiment, the CD8$^+$ T cell is a CD8$^+$ regulatory T cell. In one embodiment, the CD8$^+$ regulatory T cell is selected from the group consisting of a CD8$^+$CD28$^-$ regulatory T cell, a CD8$^+$CD103$^+$ regulatory T cell, a CD8$^+$FoxP3$^+$ regulatory T cell, a CD8$^+$CD122$^+$ regulatory T cell and any combination thereof. In one embodiment, the CD8$^+$ regulatory T cell is an INFγ$^+$IL10$^+$IL34$^+$CD8$^+$CD45RC$^{low}$ regulatory T cell. In one embodiment, the γδ T cell is a regulatory γδ T cell. In one embodiment, the DN T cell is a regulatory DN T cell. In one embodiment, the immune cell is a B cell. In one embodiment, the B cell is a regulatory B cell. In one embodiment, the regulatory B cell is a CD19$^+$CD24$^{hi}$CD38$^{hi}$ B cell. In one embodiment, the NK cell is a regulatory NK cell. In one embodiment, the myeloid-derived cell is selected from the group consisting of a neutrophil, an eosinophil, a basophil, a monocyte, a macrophage, a dendritic cell, or any combination thereof. In one embodiment, the macrophage is a regulatory macrophage. In one embodiment, the dendritic cell is a regulatory dendritic cell.

In one embodiment, the immune cell is a regulatory immune cell. The immune cell may be any regulatory immune cell suitable for use in cellular therapy (see, e.g., Wood, K. J. et al., 2012; Papp, G. et al., 2017). In one embodiment, the regulatory immune cell may be a human regulatory immune cell. In one embodiment, the regulatory immune cell is selected from the group consisting of a regulatory T cell, a CD4$^+$ regulatory T cell, a CD8$^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the regulatory immune cell is a CD8$^+$ regulatory T cell (see, e.g., Guillonneau, C. et al., 2010). In one embodiment, the CD8$^+$ regulatory T cell is selected from the group consisting of a CD8$^+$CD28$^-$ regulatory T cell, a CD8$^+$CD103$^+$ regulatory T cell, a CD8$^+$FoxP3$^+$ regulatory T cell, a CD8$^+$CD122$^+$ regulatory T cell, and any combination thereof. In one embodiment, the CD8$^+$ regulatory T cell is an INFγ$^+$IL10$^+$IL34$^+$CD8$^+$CD45RC$^{low}$ regulatory T cell. In one embodiment, the regulatory immune cell is a regulatory γδ T cell (see, e.g., Wesch, D., et al., 2014). In one embodiment, the immune cell is a regulatory DN T cell (see, e.g., Juvet, S. C., et al., 2012). In one embodiment, the regulatory immune cell is a regulatory B cell (see, e.g., Chong, A. S., et al., 2017). In one embodiment, the regulatory B cell is a CD19$^+$CD24$^{hi}$CD38$^{hi}$ B cell. In one embodiment, the regulatory immune cell is a regulatory NK cell (see, e.g., Fu, B. et al., 2013; Crome, S. Q., et al., 2013; Crome, S. Q., et al., 2017). In one embodiment, the regulatory immune cell is a regulatory macrophage (see, e.g., Hutchinson, J. A., et al., 2017). In one embodiment, the regulatory immune cell is a regulatory dendritic cell. In one embodiment, the regulatory immune cell is a regulatory T cell. In one embodiment, the Treg is a thymus derived Treg or an adaptive or induced Treg. In one embodiment, the Treg is a CD4$^+$FOXP3$^+$ regulatory T cell or a CD4$^+$FOXP3$^-$ regulatory T cell ($T_R$1 cell). In one embodiment, the Treg is a CD4$^+$FOXP3$^+$ regulatory T cell. In one embodiment, the Treg is a CD4$^+$FOXP3$^-$ regulatory T cell ($T_R$1 cell).

In one embodiment, the regulatory immune cell has the following phenotype: CD4$^+$CD25$^+$, such as, for example, CD4$^+$CD25$^+$CD127$^-$, such as, for example, CD4$^+$CD25$^+$CD127$^-$CD45RA$^+$. In further embodiments, the regulatory immune cell has the following phenotype: FoxP3$^+$CD4$^+$CD25$^+$, such as, for example, FoxP3$^+$CD4$^+$CD25$^+$CD127$^-$, such as, for example, FoxP3$^+$CD4$^+$CD25$^+$CD127CD45RA$^+$.

In one embodiment, the immune regulatory cell presents at least one of the following phenotypes: CD4$^+$CD25$^+$, FoxP3$^+$, CD127$^{lo/-}$, CTLA-4$^+$, CD39$^+$, Helios$^+$, CD62L$^{+/hi}$, VLA4$^+$, LFA1$^+$, CD49$^{bint}$, ITGb$^{7int}$, PSGL-1$^+$, ICOS$^+$, GITR$^+$, PD-1$^{int}$, Perf$^{lo/-}$, CCR7$^+$. In one embodiment, the immune regulatory cell does not express Granzyme A and/or Granzyme B.

In one embodiment, the determination of the expression level of molecules is conducted by flow cytometry, immunofluorescence or image analysis, for example high content analysis. Preferably, the determination of the expression level of molecules is conducted by flow cytometry. In one embodiment, before conducting flow cytometry analysis, cells are fixed and permeabilized, thereby allowing detecting intracellular proteins.

In one embodiment, the determination of the expression level of a molecule in a cell population comprises determining the percentage of cells of the cell population expressing the molecule (i.e. cells "+" for the molecule). Preferably, said percentage of cells expressing the molecule is measured by FACS.

The terms "expressing (or +)" and "not expressing (or –)" are well known in the art and refer to the expression level of the cell marker of interest, in that the expression level of the cell marker corresponding to "+" is high or intermediate, also referred as "+/–", and the expression level of the cell marker corresponding to "–" is null.

The term "low" or "lo" or "lo/–" is well known in the art and refers to the expression level of the cell marker of interest, in that the expression level of the cell marker is low by comparison with the expression level of that cell marker in the population of cells being analyzed as a whole. More particularly, the term "lo" refers to a distinct population of cells that express the cell marker at a lower level than one or more other distinct population of cells.

The term "high" or "hi" or "bright" is well known in the art and refers to the expression level of the cell marker of interest, in that the expression level of the cell marker is high by comparison with the expression level of that cell marker in the population of cells being analyzed as a whole.

Generally, cells in the top 2, 3, 4, or 5% of staining intensity are designated "hi", with those falling in the top half of the population categorized as being "+". Those cells falling below 50%, of fluorescence intensity are designated as "lo" cells and below 5% as "–" cells.

The expression level of the cell marker of interest is determined by comparing the Median Fluorescence Intensity (MFI) of the cells from the cell population stained with fluorescently labeled antibody specific for this marker to the fluorescence intensity (FI) of the cells from the same cell population stained with fluorescently labeled antibody with an irrelevant specificity but with the same isotype, the same fluorescent probe and originated from the same specie (referred as Isotype control). The cells from the population stained with fluorescently labeled antibody specific for this marker and that show equivalent MFI or a lower MFI than the cells stained with the isotype controls are not expressing this marker and then are designated (–) or negative. The cells from the population stained with fluorescently labeled antibody specific for this marker and that show a MFI value superior to the cells stained with the isotype controls are expressing this marker and then are designated (+) or positive.

In one embodiment, the immune cell of the invention expresses at its cell surface a CAR of the invention, and another receptor (herein referred to as "second receptor"), that binds to another ligand than HLA-A2. According to the invention, this second receptor comprises an extracellular ligand binding domain, optionally a hinge, optionally a transmembrane domain, and an intracellular signaling domain, as previously described.

In one embodiment, the second receptor is endogenous (such as, for example, the endogenous TCR). In another embodiment, the second receptor is exogenous, and its expression is induced in the immune cell of the invention by transformation or transduction of a nucleic acid encoding it. Said exogenous receptor may be an exogenous TCR or a chimeric antigen receptor. Therefore, in one embodiment, the immune cell of the invention expresses two chimeric antigen receptors, wherein the first one recognizes HLA-A2, and the second one recognizes a distinct ligand.

In another embodiment, the immune cell of the invention expresses at its cell surface a CAR of the invention, and another receptor (herein referred to as "second receptor"), that binds to another epitope in HLA-A2. According to the invention, this second receptor comprises an extracellular ligand binding domain, optionally a hinge, optionally a transmembrane domain, and an intracellular signaling domain, as previously described.

In another embodiment, the immune cell of the invention expresses two CARs, wherein the first one recognizes a first epitope of HLA-A2, and the second one recognizes a distinct epitope on HLA-A2.

In one embodiment, the CAR of the invention comprises a first intracellular signaling domain, and the second receptor comprises a distinct second intracellular signaling domain. In a first embodiment, the CAR of the invention comprises a T cell primary signaling domain (such as, for example, CD3zeta), and the second receptor comprises a costimulatory signaling domain (such as, for example, of 4-1BB, CD28 or a combination of costimulatory signaling domain of 4-1BB and CD28). In a second embodiment, the CAR of the invention comprises a costimulatory signaling domain (such as, for example, of 4-1BB, CD28 or a combination of costimulatory signaling domain of 4-1BB and CD28), and the second receptor comprises a T cell primary signaling domain (such as, for example, CD3zeta).

Consequently, according to these embodiments, the complete activation of the immune cell of the invention requires both the binding of the CAR of the invention to HLA-A2, and the binding of the second receptor to the ligand to which it is directed.

In one embodiment, the ligand recognized by the second receptor is expressed or present at a diseased tissue or organ, or at a site of an autoimmune response.

Examples of ligands that may be recognized by the second receptor include, but are not limited to, food antigens from the common human diet, autoantigens, inhaled allergens, ingested allergens or contact allergens.

The term "food antigen from common human diet" refers to an immunogenic peptide, which comes from foodstuffs common for humans, such as food antigens of the following non-limiting list: bovine antigens such as lipocalin, Ca-binding S100, alpha-lactalbumin, lactoglobulins such as beta-lactoglobulin, bovine serum albumin, caseins. Food-antigens may also be atlantic salmon antigens such as parvalbumin; chicken antigens such as, for example, ovomucoid, ovalbumin, Ag22, conalbumin, lysozyme or chicken serum albumin; peanut antigens; shrimp antigens such as tropomyosin; wheat antigens such as agglutinin or gliadin; celery antigens such as celery profilin; carrot antigens such as carrot profilin; apple antigens such as thaumatin, apple lipid transfer protein, or apple profilin; pear antigens such as pear profilin, or isoflavone reductase; avocado antigens such as endochitinase; apricot antigens such as apricot lipid transfer protein; peach antigens such as peach lipid transfer protein or peach profilin; soybean antigens such as HPS, soybean profilin or (SAM22) PR-I0 prot; fragments, variants and mixtures thereof.

In one embodiment, said autoantigen is a multiple sclerosis-associated antigen, a joint-associated antigen, an eye-associated antigen, a human HSP antigen, a skin-associated antigen or an antigen involved in graft rejection or GVHD The term "multiple sclerosis-associated antigen" refers to myelin basic protein (MBP). myelin associated glycoprotein (MAG), myelin oligodendrocyte glycoprotein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

The term "joint-associated antigen" refers to citrulline-substituted cyclic and linear filaggrin peptides, type II collagen peptides, human cartilage glycoprotein 39 (HCgp39) peptides, HSP, heterogeneous nuclear ribonucleoprotein (hnRNP) A2 peptides, hnRNP B1, hnRNP D, Ro60/52, HSP60, HSP65, HSP70 and HSP90, BiP, keratin, vimentin, fibrinogen, type I, III, IV and V collagen peptides, annexin V, Glucose 6 phosphate isomerase (GPI), acetyl-calpastatin, pyruvate dehydrogenase (PDH), aldolase, topoisomerase I, snRNP, PARP, Scl-70, Scl-100, phospholipid antigens including anionic cardiolipin and phosphatidylserine, neutrally charged phosphatidylethanolamine and phosphatidylcholine, matrix metalloproteinase, fibrillin, aggreccan, fragments, variants and mixtures thereof.

The term "eye-associated antigen" refers to type II collagen, retinal arrestin, S-arrestin, interphotoreceptor retinoid-binding proteins (IRBP 1), beta-crystallin B1, retinal proteins, choroid proteins and fragments, variants and mixtures thereof.

The term "human HSP antigen" refers to human HSP60, HSP70, HSP90, fragments, variants and mixtures thereof.

Examples of skin-associated antigens include, but are not limited to, keratinocytes antigens, an antigen present in the dermis or epidermis, a melanocyte antigen (such as, for example, melanin or tyrosinase), desmoglein (e.g., desmoglein 1 or 3, that may also be referred to as Dsgl/3), BP180, BP230, plectin, integrins (e.g., integrin a4P36), collagens (e.g., collagen type VII), laminins (e.g., laminin 332 or laminin γ1), plakins (e.g., envoplakin, periplakin, or desmoplakins), keratins (e.g., KRT5, KRT8, KRT15, KRT17 and KRT31), keratin filament-associated proteins, filaggrin, comeodesmosin, and elastin.

In one embodiment, the ligand is an antigen involved in graft rejection or GVHD. Examples of such antigens include, but are not limited to, the MHC specific to the transplanted tissue or to the host, β2-microglobulin, antigens from ABO system, antigens from rhesus system (in particular antigens from the C, c, E et e and D system) and isohaemagglutinins. Other examples of antigens that may be involved in graft rejection or GVHD include, but are not limited to HLA-DR (in particular during the first six months following grafting), HLA-B (in particular during the first two years following grafting), minor histocompatibility antigens (miHA, e.g., HLA-E, HLA-F and HLA-G), HLAs corresponding to MHC class I (B, and C), HLAs corresponding to MHC class II (DP, DM, DOA, DOB, DQ, and DR) and HLAs corresponding to MHC class III (e.g., components of the complement system).

Other examples of autoantigens include, without limitation, aquaporin water channels (such as, for example, aquaporin-4 water channel (AQP4)), Hu, Ma2, collapsin response-mediator protein 5 (CRMP5), and amphiphysin, voltage-gated potassium channel (VGKC), N-methyl-d-aspartate receptor (NMDAR), α-amino-3-hydroxy-5-methyl-4-isoxazoleproprionic acid (AMPAR), thyroid peroxidase, thyroglobulin, anti-N-methyl-D-aspartate receptor (NR1 subunit), Rh blood group antigens, I antigen, desmoglein 1 or 3 (Dsgl/3), BP180, BP230, Acetylcholine nicotinic post-synaptic receptors, thyrotropin receptors, platelet integrin, GpIIb:IIIa, Collagen (such as, for example, Collagen alpha-3(IV) chain), rheumatoid factor, calpastatin, citrullinated proteins, Myelin basic protein (MBP), Myelin oligodendrocyte glycoprotein (MOG) peptides, alpha-beta-crystallin, DNA, histone, ribosomes, RNP, tissue transglutaminase (TG2), intrinsic factor, 65-kDa antigen, phosphatidylserine, ribosomal phosphoproteins, anti-neutrophil cytoplasmic antibody, Scl-70, U1-RNP, ANA, SSA, anti-SSB, anti-nuclear antibodies (ANA), antineutrophil cytoplasm antibodies (ANCA), Jo-1, antimitochondrial antibodies, gp210, p62, sp100, antiphospholipid antibodies, U1-70 kd snRNP, GQlb ganglioside, GM1, asialo GM1, GDlb, anti-smooth muscle antibodies (ASMA), anti-liver-kidney microsome-1 antibodies (ALKM-1), anti-liver cytosol antibody-1 (ALC-1), IgA antiendomysial antibodies, neutrophil granule proteins, streptococcal cell wall antigen, intrinsic factor of gastric parietal cells, insulin (IAA), glutamic acid decarboxylase (GAA or GAD) and protein tyrosine phosphatase (such as, for example, IA2 or ICA512), PLA2R1 and THSD7A1.

In one embodiment, said ligand is selected from the group comprising ovalbumin, MOG, type II collagen fragments, variants and mixtures thereof.

In one embodiment, said ligand is ovalbumin, fragments, variants and mixtures thereof.

In another embodiment, said ligand is MOG, fragments, variants and mixtures thereof.

In another embodiment, said ligand is type II collagen, fragments, variants and mixtures thereof.

In another embodiment, said ligand is IL23R, fragments, variants and mixtures thereof.

In one embodiment, the CAR of the invention further comprises an extracellular ligand binding domain recognizing a ligand distinct from HLA-A2. In one embodiment, said ligand binding domain is an antibody or an antigen binding fragment thereof.

In one embodiment, the ligand binding domain of the CAR of the invention is a multifunctional antibody recognizing multiple distinct epitopes on HLA-A2. In one embodiment, the ligand binding domain of the CAR of the invention is a bifunctional antibody recognizing two distinct epitopes on HLA-A2.

In one embodiment, the CAR of the invention comprises an extracellular ligand binding domain comprising a HLA-A2 binding domain and another ligand binding domain recognizing a ligand distinct from HLA-A2. In one embodiment, said ligand binding domain is a bifunctional antibody recognizing both HLA-A2 and the distinct ligand.

Examples of ligands distinct from HLA-A2 that may be recognized by the CAR of the invention are listed hereinabove.

In one embodiment, CAR-modified immune cells of the invention may be generated by introducing a lentiviral vector comprising a desired CAR into the cells. In one embodiment, there is provided a method of making an immune cell modified to express a CAR, wherein the method comprises transducing an immune cell with a vector as described anywhere herein, thereby generating said modified immune cell.

In one embodiment, the genetically modified immune cells of the invention are modified through the introduction of RNA. In one embodiment, an in vitro transcribed RNA CAR can be introduced in a cell as a form of transient transfection. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention.

In one embodiment, the DNA to be used for PCR contains an open reading frame. The DNA can be from a naturally occurring DNA sequence from the genome of an organism. In one embodiment, the DNA is a full-length gene of interest or a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR may be used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art.

"Forward primers" are primers that contain a region of nucleotides that are substantially complementary to nucleotides on the DNA template that are upstream of the DNA sequence that is to be amplified. "Upstream" is used herein to refer to a location 5', to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand. Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatemeric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270: 1485-65 (2003).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning is highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on RNAs also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7: 1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In one embodiment, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transposons.

In one embodiment, the immune cell of the invention is a T cell. Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation or Sepax separation system. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

Sources, Activation and Expansion of T Cells

In one embodiment, the immune cell may be a T cell. Prior to expansion and genetic modification of the T cells of the invention, a source of T cells or progenitor cells from which T cells can be made, is obtained from a subject. T cells can be obtained from any source where these cells reside including peripheral blood mononuclear cells, bone marrow, lymph node tissue, cord blood, thymus tissue, germinal centres, tissue from a site of infection, ascites, pleural effusion, spleen, tumors, and transplanted organs/tissue. In certain embodiments of the present invention, T cells can be obtained from a unit of blood collected from a subject using any number of techniques known to the skilled artisan, such as Ficoll™ separation. In one embodiment, cells from the circulating blood of a subject are obtained by apheresis. The apheresis product typically contains lymphocytes, including T cells, Tregs, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells may be washed with a wash solution (e.g., phosphate buffered saline (PBS)). As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, Mg$^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3$^+$, CD25$^+$, CD127neg, HLA-DR$^+$, CD28$^+$, CD4$^+$, CD8$^+$, CD45RA$^+$, and/or CD45RO$^+$ T cells, can be further isolated by positive or negative selection techniques. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^{hi}$, GITR$^+$, and FoxP3$^+$.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, or from samples where there are many tumor cells present (i.e., leukemic blood, tumor tissue, etc.). Such populations of cells may have therapeutic value and would be desirable to obtain.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In one embodiment, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 10 per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In certain embodiments, a blood sample or an apheresis is taken from a subject who is at risk of developing a disease, but who has not yet developed a disease, and the cells of interest are isolated and frozen for later use. In certain embodiments, the T cells may be expanded, frozen, and used at a later time. In certain embodiments, samples are collected from a subject shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain immunosuppressive treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect immune cells during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy.

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of $CD4^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above. For example, such values may include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, and 1:1 particles per T cell. In one embodiment, a ratio of particles to cells of 1:1 or less is used. In one particular embodiment, a particle: cell ratio may be 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells (e.g., Treg cells), are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used.

For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest. Such populations of cells may have therapeutic value and would be desirable to obtain in certain embodiments.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGF3, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, Immunocult (StemCell), AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one embodiment, regulatory T cell may be obtained by isolating CD4$^+$ T cells from HLA-A2$^-$ donors via RosetteSep (Stemcell) and enriched for CD25$^+$ cells (Miltenyi) prior to sorting live CD4$^+$CD127$^{lo}$CD25$^{hi}$ Tregs using a FACSAria II (BD Biosciences). Sorted Tregs may be stimulated with L cells and aCD3 mAb (OKT3; 200 ng/mL) in 1000 U/ml of IL-2.

In one embodiment of the invention, the T cells may be cultured in the presence of rapamycin in order to obtain regulatory T cells, as described for example in WO2007110785 incorporated herein by reference. Another method to generate regulatory T cells is described in US2016024470 incorporated herein by reference, where T cells are cultured with a T cell receptor (TCR)/CD3 activator such as for example TCR/CD3 antibodies, a TCR co-stimulator activator such as for example CD28, CD137 (4-1 BB), GITR, B7-1/2, CD5, ICOS, OX40, CD40 or CD137 antibodies, and rapamycin.

In one embodiment of the invention, the T cells genetically modified by expression of the CAR may also have been genetically modified by expression of at least one intracellular factor such as ROR-C, Foxo1, T-bet, or Gata 3, c-Maf, AhR. In one embodiment, the genetically modified immune cell of the invention expresses Foxo1.

In one embodiment, the genetically modified cells of the present invention can be an allogeneic immune cell, such as, for example, an allogenic T or Treg cell. For example, the allogeneic immune cell can be an immune cell lacking expression of a functional human leukocyte antigen (HLA), e.g., HLA class I and/or HLA class II, or lacking expression of a functional T cell receptor (TCR).

In one embodiment, a T cell lacking a functional TCR can be engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

In another embodiment, the genetically modified cells described herein can be engineered such that it does not express a functional HLA on its surface. For example, an immune cell described herein, can be engineered such that cell surface expression HLA, e.g., HLA class 1 and/or HLA class II or non-classical HLA molecules is downregulated.

In another embodiment, the T cell can lack a functional TCR and a functional HLA such as HLA class I and/or HLA class II.

Modified immune cells (such as, for example, modified T or Treg cells) that lack expression of a functional TCR and/HLA can be obtained by any suitable means, including a knock out or knock down of one or more subunit of TCR and/or HLA. For example, the immune cell can include a knock down of TCR and/or HLA using siRNA, shRNA, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain) (Osborn et al, "Evaluation of TCR Gene Editing Achieved by TALENs, CRISPR/Cas9, and megaTAL Nucleases" Mol Ther. 2016 March; 24(3):570-81).

In one embodiment, TCR expression and/or HLA expression can be inhibited using siRNA or shRNA that targets a nucleic acid encoding a TCR and/or HLA in a T cell. Expression of siRNA and shRNAs in T cells can be achieved using any conventional expression system, e.g., such as a lentiviral expression system. Exemplary siRNA and shRNA that downregulate expression of HLA class I and/or HLA class II genes are described, e.g., in US2007/0036773. Exemplary shRNAs that downregulate expression of components of the TCR are described, e.g., in US2012/0321667.

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) BMC Bioinformatics 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) Science 322: 1843-1845. The CRISPR/Cas system has been modified for use in gene editing (silencing, enhancing or changing specific genes) in eukaryotes such as mice or primates. Wiedenheft et al. (2012) Nature 482: 331-8. This is accomplished by introducing into the eukaryotic cell a plasmid containing a specifically designed CRISPR and one or more appropriate Cas. The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence. RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) Science 327: 167-170; Makarova et al. (2006) Biology Direct 1: 7. The spacers thus serve as templates for RNA molecules, analogously to siRNAs. Pennisi (2013) Science 341: 833-836. The CRISPR/Cas system can thus be used to edit a TCR and/or HLA gene (adding or deleting a base pair), or introducing a premature stop which thus decreases expression of a TCR and/or HLA. The CRISPR/Cas system can alternatively be used like RNA interference, turning off HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in US20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865, 406; 8,795,965; 8,771,945; and 8,697,359.

"TALEN" or "TALEN to TCR and/or HLA" or "TALEN to inhibit TCR and/or HLA" refers to a transcription activator-like effector nuclease, an artificial nuclease which can be used to edit the TCR and/or HLA. TALENs are produced artificially by fusing a TAL effector DNA binding domain to a DNA cleavage domain. Transcription activator-like effectors (TALEs) can be engineered to bind any desired DNA sequence, including a portion of the TCR and/or HLA gene. By combining an engineered TALE with a DNA cleavage domain, a restriction enzyme can be produced which is specific to any desired DNA sequence, including a TCR and/or HLA sequence. These can then be introduced into a cell, wherein they can be used for genome editing. Boch (2011) Nature Biotech. 29: 135-6; and Boch et al. (2009) Science 326: 1509-12; Moscou et al. (2009) Science 326: 3501.

TALEs are proteins secreted by *Xanthomonas* bacteria. The DNA binding domain contains a repeated, highly conserved 33-34 amino acid sequence, with the exception of the $12^{th}$ and $13^{th}$ amino acids. These two positions are highly variable, showing a strong correlation with specific nucleotide recognition. They can thus be engineered to bind to a desired DNA sequence. To produce a TALEN, a TALE protein is fused to a nuclease (N), which is a wild-type or mutated Fok1 endonuclease. Several mutations to Fok1 have been made for its use in TALENs; these, for example, improve cleavage specificity or activity. Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010) J. Mol. Biol. 200: 96. The Fok1 domain functions as a dimer, requiring two constructs with unique DNA binding domains for sites in the target genome with proper orientation and spacing. Both the number of amino acid residues between the TALE DNA binding domain and the Fok1 cleavage domain and the number of bases between the two individual TALEN binding sites appear to be important parameters for achieving high levels of activity. Miller et al. (2011) Nature Biotech. 29: 143-8. A TCR and/or HLA TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the TCR and/or HLA gene or introduce such a defect into a wt TCR and/or HLA gene, thus decreasing expression of TCR and/or HLA. TALENs specific to sequences in TCR and/or HLA can be constructed using any method known in the art, including various schemes using modular components. Zhang et al. (2011) Nature Biotech. 29: 149-53; Geibler et al. (2011) PLoS ONE 6: e19509.

"ZFN" or "Zinc Finger Nuclease" or "ZFN to TCR and/or HLA" or "ZFN to inhibit TCR and/or HLA" refer to a zinc finger nuclease, an artificial nuclease which can be used to edit the TCR and/or HLA gene. Like a TALEN, a ZFN comprises a Fok1 nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160. A zinc finger is a small protein structural motif stabilized by one or more zinc ions. A zinc finger can comprise, for example, $Cys_2His_2$, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one—hybrid systems, bacterial one—hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5. Also like a TALEN, a ZFN can create a double-stranded break in the DNA, which can create a frame-shift mutation if improperly repaired, leading to a decrease in the expression and amount of TCR and/or HLA in a cell. ZFNs can also be used with homologous recombination to mutate in the TCR and/or HLA gene. ZFNs specific to sequences in TCR and/or HLA can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; Quo et al. (2010) J. Mol. Biol. 400: 96; US2011/0158957; and US2012/0060230.

"Meganuclease" or "meganuclease to TCR and/or HLA" or "meganuclease to inhibit TCR and/or HLA" refers to a monomeric endonuclease with large (>14 base pairs) recognition sites, which can be used to edit the TCR and/or HLA gene. Meganucleases (mn) are monomeric proteins with innate nuclease activity that are derived from bacterial homing endonucleases and engineered for a unique target site. Homing endonucleases are DNA-cleaving enzymes that can generate double strand breaks at individual loci in their host genomes, and thereby drive site-specific gene conversion events. (Stoddard, Structure. 2011 Jan. 12; 19(1):7-15). Despite their small size, homing endonucleases recognize long DNA sequences (typically 20 to 30 base pairs). Homing endonucleases are extremely widespread and are found in microbes, as well as in phages and viruses. The LAGLIDADG and His-Cys box enzymes (which are the most sequence-specific of these enzymes) rely upon antiparallel 3-sheets that dock into the major grooves of their DNA target sites (Flick et al., 1998; Jurica et al., 1998). There they establish a collection of sequence-specific and non-specific contacts that are distributed nonuniformly across multiple consecutive basepairs (Chevalier et al., 2003; Scalley-Kim et al., 2007).

The LAGLIDADG homing endonuclease (LHE) family is the primary source of the engineered enzymes used for gene targeting applications. The LHE family is primarily encoded within archaea and in the chloroplast and mitochondrial genomes of algae and fungi (Chevalier et al., 2005; Dalgaard et al., 1997; Sethuraman et al., 2009). Meganucleases that possess a single conserved LAGLIDADG motif (SEQ ID NO: 85) per protein chain form homodimeric proteins that cleave palindromic and nearly palindromic DNA target sequences, while those that contain two such motifs per protein chain form larger, pseudo-symmetric monomers that can target completely asymmetric DNA sequences.

Meganucleases can be engineered to target TCR and/or HLA and thus create a double-stranded break in the DNA, which can create a frame-shift mutation if improperly repaired, leading to a decrease in the expression and amount of TCR and/or HLA in a cell.

"MegaTAL" or "megaTAL to TCR and/or HLA" or "megaTAL to inhibit TCR and/or HLA" refers to an artificial nuclease, which can be used to edit the TCR and/or HLA gene. MegaTALs are hybrid monomeric nucleases obtained through the fusion of minimal TAL (transcription activator-like) effector domains to the N-terminus of meganucleases derived from the LAGLIDADG homing endonuclease family (Nucleic Acids Res. 2014 February; 42(4):2591-601; Takeuchi et al, Methods Mol Biol. 2015; 1239:105-32. doi: 10.1007/978-1-4939-1862-1_6).

MegaTALs thus consist of a site-specific meganuclease cleavage head with additional affinity and specificity provided by a TAL effector DNA binding domain. MegaTALs can be engineered to target TCR and/or HLA and thus create a double-stranded break in the DNA, which can create a frame-shift mutation if improperly repaired, leading to a decrease in the expression and amount of HLA in a cell. A variant of the I-OnuI meganuclease (mn) was used to design a TCRα-megaTAL to knockout the T-cell receptor alpha (TCRα) gene. The TCRa mn was fused to a 10.5 repeat TALE array designed to bind a DNA sequence upstream of the TCRa mn binding site. It was found that the megaTAL targeting TCRa achieved extremely high gene disruption with no detectable off-target cleavage in human primary T-cells (Boissel et al, Nucleic Acids Res. 2014 February; 42(4):2591-601).

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117: 1466-1476 (2007). Thus, in an embodiment, the genetically modified immune cell of the invention ectopically expresses a telomerase subunit, e.g., the catalytic subunit of telomerase, e.g., TERT, e.g., hTERT. In some aspects, this disclosure provides a method of producing a CAR-expressing immune cell, comprising contacting an immune cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

VII. Therapeutic Application

The invention provides immune cells modified to express a CAR targeting an HLA-A2 antigen as a means to recruit said immune cells to sites of specific immune or inflammatory response, and to activate the immune cells to suppress the immunological activity of immune effector cells at these sites. The CAR-mediated recruitment and activation of immune cells provide a method of preventing or treating a number of immunological diseases or disorders for which such immune suppression activity is beneficial.

In one embodiment, the immune cell is a regulatory immune cell. The immune cell may be any regulatory immune cell suitable for use in cellular therapy (see, e.g., Wood, K. J. et al., 2012; Papp, G. et al., 2017). In one embodiment, the regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the immune cell is a human immune cell. In another embodiment, the regulatory immune cell is a human regulatory immune cell. In one embodiment, the human regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof.

In one embodiment, the immune cell may be a regulatory T cell. In another embodiment, the regulatory T cell may be a human regulatory T cell. Although activation of regulatory T cells is antigen-dependent, the suppressive action of these cells is antigen-, TCR-, and MHC-independent. Accordingly, expression of CARs in regulatory T cells redirects these cells and their activation to the appropriate target tissue so that they are activated in an antigen-specific manner; however, their suppressive effects take place without a need for further recognition of disease-associated-antigens. Therefore, as long as the regulatory T cells are in the correct vicinity of where immune effector cells are located and mediating their undesired effects, the redirected regulatory T cells can be triggered or activated at that location to provide their suppressive effects.

In one embodiment, the target HLA-A2 antigen may be present or expressed at a site or target tissue of an undesirable immune or inflammatory response mediated by immune effector cells.

In one embodiment, the CAR-modified immune cells of the invention may be used in the prevention or treatment of one or more diseases, disorders, symptoms, or conditions associated with organ or tissue transplant (e.g., organ or tissue rejection/dysfunction, GVHD, and/or conditions associated therewith). Transplant rejection involves the destruction of the donor's transplanted tissue by the recipient's immune cells through an immune response. An immune response is also involved in GVHD; however, in this case, the recipient's tissues are destroyed by the donor's immune cells transferred to the recipient via the transplant. Accordingly, CAR-mediated redirection and activation of immune cells provide a method of suppressing rejection of mismatched cells and/or tissues by immune effector cells in transplant recipients or inhibiting the pathogenic action of transplanted immunocompetent cells in the case of GVHD. In one embodiment, the mismatched cells and/or tissues comprise HLA-A2 mismatched cells and/or tissues.

Another embodiment of the present invention is thus a method for treating one or more diseases, disorders, symptoms, or conditions associated with organ or tissue transplant (e.g., organ or tissue rejection/dysfunction, GVHD, and/or conditions associated therewith) in a subject, wherein said method comprises administering to the subject a CAR-engineered immune cell or a composition as described herein.

In one embodiment, the method is a cell therapy method. In one embodiment, the cell therapy is autologous. In one embodiment, the cell therapy is heterologous. In one embodiment, the cell therapy is allogenic. In one embodiment, the method is a gene therapy method.

Another embodiment of the present invention is thus a CAR-engineered immune cell or a composition as described herein for use in treating one or more diseases, disorders, symptoms, or conditions associated with organ or tissue transplant (e.g., organ or tissue rejection/dysfunction, GVHD, and/or conditions associated therewith) in a subject.

The CAR-modified immune cells of the invention may be used to promote immune tolerance, operational tolerance, and/or immune accommodation in a subject. The CAR-modified immune cells of the invention may be used to promote immune tolerance, operational tolerance, and/or immune accommodation in a subject following organ or tissue transplantation. In one embodiment, there is provided a method of promoting immune tolerance, operational tolerance, and/or immune accommodation in a subject, the method comprising administering to the subject a CAR-modified immune cell as described anywhere herein. In another embodiment, there is provided a method of promoting immune tolerance, operational tolerance, and/or immune accommodation in a subject, the method comprising administering to the subject a pharmaceutical composition as described anywhere herein. In one embodiment, the use may be for promoting immune tolerance, operational tolerance, and/or immune accommodation to a transplanted organ or tissue in a subject. In one embodiment, the CAR-modified immune cell is administered at the same time as, before, or after the transplantation of the organ or tissue. In one embodiment, the CAR-modified immune cell is administered at the same time as the transplantation of the organ or tissue. In another embodiment, the CAR-modified immune cell is administered before the transplantation of the organ or tissue. In one embodiment, the CAR-modified immune cell is administered after the transplantation of the organ or tissue. In one embodiment, the immune cell is a regulatory immune cell. In one embodiment, the regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the immune cell is a regulatory T cell. In one embodiment, the immune cell is a $CD4^+$ regulatory T cell. In one embodiment, the immune cell is a human immune cell. In another embodiment, the regulatory immune cell is a human regulatory immune cell. In one embodiment, the human regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof. In another embodiment, the immune cell is a human regulatory T cell. In one embodiment, the immune cell is a human CD4+ regulatory T cell.

The CAR-modified immune cells of the present invention may be used to prevent or treat rejection of a transplanted organ or tissue. In one embodiment, the CAR-modified immune (e.g., the CAR-engineered Treg cells) cells of the present invention may be used to prevent or treat hyperacute rejection of a transplanted organ or tissue. In one embodiment, the CAR-modified immune cells (e.g., the CAR-engineered Treg cells) of the present invention may be used to prevent or treat antibody-mediated rejection of a transplanted organ or tissue. In one embodiment, the method comprises administering CAR-modified immune cells (e.g., the CAR-engineered Treg cells) of the present invention to a subject exposed to a transplanted organ or tissue. In one embodiment, the transplanted organ or tissue may encompass a bone marrow transplant, an organ transplant, a blood transfusion or any other foreign tissue or cell that is purposefully introduced into a subject. In one embodiment, the CAR-modified immune cells (e.g., the CAR-engineered Treg cells) of the present invention may be used as a therapy to inhibit graft rejection following transplantation. In one embodiment, the graft rejection may be allograft rejection. In one embodiment, the graft rejection may be xenograft rejection. In one embodiment, there is provided a method of preventing or treating organ or tissue transplant rejection in a subject, the method comprising administering to the subject a CAR-modified immune cell as described anywhere herein. In one embodiment, there is provided a method of preventing or treating organ or tissue transplant rejection in a subject, the method comprising administering to the subject a pharmaceutical composition as described anywhere herein. Another embodiment of the present invention is thus a CAR-engineered immune cell (e.g., the CAR-engineered Treg cells) of the invention, or a pharmaceutical composition comprising said immune cells, for use in preventing or treating organ or tissue transplant rejection in a subject. In one embodiment, the present invention provides a method of increasing the time period of graft survival in a subject, the method comprising administering to the subject a CAR-modified immune cell (e.g., the CAR-engineered Treg cells) as described anywhere herein. In one embodiment, the present invention provides a method of increasing the time period of graft survival in a subject, the method comprising administering to the subject a pharmaceutical composition as described anywhere herein. In one embodiment, the method provides a time period of graft survival of 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or the lifetime of the subject. In one embodiment, the subject is not undergoing any immunosuppressant agent therapies. In one embodiment, the administration of an immune cell or composition of the invention allows reducing the amount of an immunosuppressant agent therapy received by the subject. In one embodiment, the graft may be an allograft. In one embodiment, the transplant may be exposed to the CAR-modified immune cells of the present invention at the same time as, before, or after the transplantation of the transplant into the recipient. In one embodiment, the organ or tissue transplant may be a heart, heart valve, lung, kidney, liver, pancreas, intestine, skin, blood vessels, bone marrow, stem cells, bone, or, islet cells. However, the invention is not limited to a specific type of transplantation. In one embodiment, the donor transplant may be "preconditioned" or "pretreated" by treating the organ or tissue transplant prior to transplantation into the recipient with the CAR-modified immune cells of the invention in order to reduce the immunogenicity of the transplant against the recipient, thereby reducing or preventing graft rejection. In one embodiment, the transplant host or recipient is HLA-A2 negative. In one embodiment, the transplant host or recipient is HLA-A2 negative and is positive for one or two different HLA-A subtypes selected from one or two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for one HLA-A subtype selected from one of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from one or two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from one of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for one or two different HLA-A subtypes selected from one or two of HLA-A*25, HLA-A*29, HLA-A*30. In one embodiment, the transplant host or recipient is HLA-A2 negative and is positive for one HLA-A subtype selected from one of HLA-A*25, HLA-A*29, HLA-A*30. In one embodiment, the transplant host or recipient is HLA-A2 negative and is positive for two different HLA-A subtypes selected from one or two of HLA-A*25, HLA-A*29, HLA-A*30. In one embodiment, the transplant host or recipient is HLA-A2 negative and is positive for two different HLA-A subtypes selected from one of HLA-A*25, HLA-A*29, HLA-A*30. In one embodiment, the transplant host or recipient is HLA-A2 negative and is positive for two different HLA-A subtypes selected from two of HLA-A*25, HLA-A*29, HLA-A*30. In one embodiment, the transplant host or recipient is HLA-A2 negative and is positive for an HLA-A subtype of HLA-A*03. In one embodiment, the transplant host or recipient is HLA-A2 negative and is positive for an HLA-A subtype of HLA-A*25. In one embodiment, the transplant host or recipient is HLA-A2 negative and is positive for an HLA-A subtype of HLA-A*29. In one embodiment, the transplant host or recipient is HLA-A2 negative and is positive for an HLA-A subtype of HLA-A*30. In one embodiment, the transplant host or recipient is HLA-A2 negative and is positive for an HLA-A subtype of HLA-A*31. In one embodiment, the transplant host or recipient is HLA-A2 negative and is positive for an HLA-A subtype of HLA-A*33. In one embodiment, the transplant host or recipient is HLA-A2 negative and is positive for an HLA-A subtype of HLA-A*36. In one embodiment, the transplant host or recipient is HLA-A2 negative and is positive for an HLA-A subtype of HLA-A*68. In one embodiment, the transplant host or recipient is HLA-A2 negative and is positive for one or two of HLA-A*03:01, HLA-A*25:01, HLA-A*29:02, HLA-A*30:01, HLA-A*31:01, HLA-A*33:01, HLA-A*36:01, and HLA- A*68:01. In one embodiment, the transplant host or recipient is HLA-A2 negative and is positive for one of HLA-A*03:01, HLA-A*25:01, HLA-A*29:02, HLA-A*30:01, HLA-A*31:01, HLA-A*33:01, HLA-A*36:01, and HLA-A*68:01. In one embodiment, the transplant host or recipient is HLA-A2 negative and is positive for two of HLA-A*03:01, HLA-A*25:01, HLA-A*29:02, HLA-A*30:01, HLA-A*31:01, HLA-A*33:01, HLA-A*36:01, and HLA-A*68:01. In one embodiment, the transplant host or recipient is HLA-A2 negative and is positive for one or two of HLA-A*25:01, HLA-A*29:02, and HLA-A*30:01. In one embodiment, the transplant host or recipient is HLA-A2 negative and is positive for one of HLA-A*25:01, HLA-A*29:02, and HLA-A*30:01. In one embodiment, the transplant host or recipient is HLA-A2 negative and is positive for two HLA-A*25:01, HLA-A*29:02, and HLA-A*30:01. In one embodiment, the transplant host or recipient is HLA-A2 negative and is positive for HLA-A*25:01. In one embodiment, the transplant host or recipient is HLA-A2 negative and is positive for HLA-A*29:02. In one embodiment, the transplant host or recipient is HLA-A2 negative and is positive for HLA-A*30:01. In one embodiment, the transplant host or recipient is HLA-A2 negative and is positive for HLA-A*03:01. In one embodiment, the transplant host or recipient is HLA-A2 negative and is positive for HLA-A*31:01. In one embodiment, the transplant host or recipient is HLA-A2 negative and is positive for HLA-A*33:01. In one embodiment, the transplant host or recipient is HLA-A2 negative and is positive for HLA-A*36:01. In one embodiment, the transplant host or recipient is HLA-A2 negative and is positive for HLA-A*68:01. In one embodiment, the transplant is HLA-A2 positive.

In one embodiment, the immune cell is a regulatory immune cell. In one embodiment, the regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the immune cell is a regulatory T cell. In one embodiment, the immune cell is a $CD4^+$ regulatory T cell. In one embodiment, the immune cell is a human immune cell. In another embodiment, the regulatory immune cell is a human regulatory immune cell. In one embodiment, the human regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof. In another embodiment, the immune cell is a human regulatory T cell. In one embodiment, the immune cell is a human $CD4^+$ regulatory T cell.

The CAR-modified immune cells (e.g., the CAR-engineered Treg cells) of the present invention may be used to prevent or treat graft versus host disease (GVHD). In one embodiment, the method comprises administering a CAR-modified immune cell (e.g., the CAR-engineered Treg cells) of the present invention to a subject exposed to a transplanted organ or tissue. In one embodiment, the transplanted organ or tissue may encompass a bone marrow transplant, an organ transplant, a blood transfusion, or any other foreign tissue or cell that is purposefully introduced into a subject. For example, GVHD may occur after heart, heart valve, lung, kidney, liver, pancreas, intestine, skin, blood vessel, bone marrow, stem cell, bone or islet cell transplantation. However, the invention is not limited to a specific type of transplantation. In one embodiment, the GVHD may occur after hematopoietic stem cell transplantation. In one embodiment, there is provided a method of preventing or treating graft versus host disease (GVHD) in a subject, the method comprising administering to the subject a CAR-modified immune cell as described anywhere herein. In one embodiment, there is provided a method of preventing or treating graft versus host disease (GVHD) in a subject, the method comprising administering to the subject a pharmaceutical composition as described anywhere herein. In one embodiment, the invention provides a method of contacting a donor transplant, for example, a biocompatible lattice or a donor tissue, organ or cell, with CAR-modified immune cells of the present invention at the same time as, before, or after the transplantation of the transplant into a recipient. In one embodiment, the CAR-modified immune cells of the present invention may be used to ameliorate, inhibit or reduce an adverse response by the donor transplant against the recipient, thereby preventing or treating GVHD. In one embodiment, the present invention provides a method of preventing or delaying onset of GVHD in a subject, the method comprising administering to the subject a CAR-modified immune cell as described anywhere herein. In one embodiment, the present invention provides a method of preventing or delaying onset of GVHD in a subject, the method comprising administering to the subject a pharmaceutical composition as described anywhere herein. In one embodiment, the onset of GVHD is delayed for 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or the lifetime of the subject. In one embodiment, the subject is not undergoing any immunosuppressant agent therapies. In one embodiment, the subject is undergoing an immunosuppressant therapy. In one embodiment, the immune cells of the invention are administered to the subject with the aim to decrease the therapeutically effective amount of said immunosuppressant therapy. In one embodiment, GVHD may be acute GVHD or chronic GVHD. In one embodiment, the donor transplant may be "preconditioned" or "pretreated" by treating the transplant prior to transplantation into the recipient with CAR-modified immune cells (e.g., the CAR-engineered Treg cells) of the invention in order to reduce the immunogenicity of the transplant against the recipient, thereby reducing or preventing GVHD. In one embodiment, the transplant may be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant may be then further contacted with CAR-modified immune cells (e.g., the CAR-engineered Treg cells) of the present invention to reduce, inhibit or eliminate the activity of the immune effector cells that were activated by the treatment of the cells or tissue from the recipient. Following this treatment of the transplant with CAR-modified immune cells of the present invention, the CAR-modified immune cells may be removed from the transplant prior to transplantation into the recipient. However, some CAR-modified immune cells may adhere to the transplant, and therefore, may be introduced to the recipient with the transplant. In this situation, the CAR-modified immune cells introduced into the recipient may suppress an immune response against the recipient caused by a cell associated with the transplant. In one embodiment, the transplant host or recipient is HLA-A2 negative. In one embodiment, the transplant host or recipient is HLA-A2 negative and is positive for one or two different HLA-A subtypes selected from one or two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for one HLA-A subtype selected from one of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from one or two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from one of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for two different HLA-A subtypes selected from two of HLA-A*03, HLA-A*25, HLA-A*29, HLA-A*30, HLA-A*31, HLA-A*33, HLA-A*36, HLA-A*68. In one embodiment, the transplant host or recipient is HLA-A2 negative and is positive for one or two different HLA-A subtypes selected from one or two of HLA-A*25, HLA-A*29, HLA-A*30. In one embodiment, the transplant host or recipient is HLA-A2 negative and is positive for one HLA-A subtype selected from one of HLA-A*25, HLA-A*29, HLA-A*30. In one embodiment, the transplant host or recipient is HLA-A2 negative and is positive for two different HLA-A subtypes selected from one or two of HLA-A*25, HLA-A*29, HLA-A*30. In one embodiment, the transplant host or recipient is HLA-A2 negative and is positive for two different HLA-A subtypes selected from one of HLA-A*25, HLA-A*29, HLA-A*30. In one embodiment, the transplant host or recipient is HLA-A2 negative and is positive for two different HLA-A subtypes selected from two of HLA-A*25, HLA-A*29, HLA-A*30. In one embodiment, the transplant host or recipient is HLA-A2 negative and is positive for an HLA-A subtype of HLA-A*03. In one embodiment, the transplant host or recipient is HLA-A2 negative and is positive for an HLA-A subtype of HLA-A*25. In one embodiment, the transplant host or recipient is HLA-A2 negative and is positive for an HLA-A subtype of HLA-A*29. In one embodiment, the transplant host or recipient is HLA-A2 negative and is positive for an HLA-A subtype of HLA-A*30. In one embodiment, the transplant host or recipient is HLA-A2 negative and is positive for an HLA-A subtype of HLA-A*31. In one embodiment, the transplant host or recipient is HLA-A2 negative and is positive for an HLA-A subtype of HLA-A*33. In one embodiment, the transplant host or recipient is HLA-A2 negative and is positive for an HLA-A subtype of HLA-A*36. In one embodiment, the transplant host or recipient is HLA-A2 negative and is positive for an HLA-A subtype of HLA-A*68. In one embodiment, the transplant host or recipient is HLA-A2 negative and is positive for one or two of HLA-A*03:01, HLA-A*25:01, HLA-A*29:02, HLA-A*30:01, HLA-A*31:01, HLA-A*33:01, HLA-A*36:01, and HLA-A*68:01. In one embodiment, the transplant host or recipient is HLA-A2 negative and is positive for one of HLA-A*03:01, HLA-A*25:01, HLA-A*29:02, HLA-A*30:01, HLA-A*31:01, HLA-A*33:01, HLA-A*36:01, and HLA-A*68:01. In one embodiment, the transplant host or recipient is HLA-A2 negative and is positive for two of HLA-A*03:01, HLA-A*25:01, HLA-A*29:02, HLA-A*30: 01, HLA-A*31:01, HLA-A*33:01, HLA-A*36:01, and HLA-A*68:01. In one embodiment, the transplant host or recipient is HLA-A2 negative and is positive for one or two of HLA-A*25:01, HLA-A*29:02, and HLA-A*30:01. In one embodiment, the transplant host or recipient is HLA-A2 negative and is positive for one of HLA-A*25:01, HLA-A*29:02, and HLA-A*30:01. In one embodiment, the transplant host or recipient is HLA-A2 negative and is positive for two of HLA-A*25:01, HLA-A*29:02, and HLA-A*30: 01. In one embodiment, the transplant host or recipient is HLA-A2 negative and is positive for HLA-A*25:01. In one embodiment, the transplant host or recipient is HLA-A2 negative and is positive for HLA-A*29:02. In one embodiment, the transplant host or recipient is HLA-A2 negative and is positive for HLA-A*30:01. In one embodiment, the transplant host or recipient is HLA-A2 negative and is positive for HLA-A*03:01. In one embodiment, the transplant host or recipient is HLA-A2 negative and is positive for HLA-A*31:01. In one embodiment, the transplant host or recipient is HLA-A2 negative and is positive for HLA-A*33:01. In one embodiment, the transplant host or recipient is HLA-A2 negative and is positive for HLA-A*36:01. In one embodiment, the transplant host or recipient is HLA-A2 negative and is positive for HLA-A*68:01. In one embodiment, the transplant is HLA-A2 positive. In one embodiment, the immune cell is a regulatory immune cell. In one embodiment, the regulatory immune cell is selected from the group consisting of a regulatory T cell, a CD4$^+$ regulatory T cell, a CD8$^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the immune cell is a regulatory T cell. In one embodiment, the immune cell is a CD4$^+$ regulatory T cell. In one embodiment, the immune cell is a human immune cell. In another embodiment, the regulatory immune cell is a human regulatory immune cell. In one embodiment, the human regulatory immune cell is selected from the group consisting of a regulatory T cell, a CD4$^+$ regulatory T cell, a CD8$^+$ regulatory T cell, a regulatory γδ T cell, a regulatory DN T cell, a regulatory B cell, a regulatory NK cell, a regulatory macrophage, a regulatory dendritic cell, and any combination thereof. In another embodiment, the immune cell is a human regulatory T cell. In one embodiment, the immune cell is a human CD4$^+$ regulatory T cell.

In one embodiment, the present invention provides a method of expanding a population of immune cells in a subject wherein the immune cells are modified to express a chimeric antigen receptor (CAR), the method comprising administering to the subject an immune cell as described anywhere herein, wherein the administered modified immune cell produces a population of progeny immune cells in the subject. In one embodiment, the immune cell is a regulatory immune cell. In one embodiment, the regulatory immune cell is selected from the group consisting of a regulatory T cell, a CD4$^+$ regulatory T cell, a CD8$^+$ regulatory T cell, a regulatory γδ T cell, a regulatory DN T cell, a regulatory B cell, a regulatory NK cell, a regulatory macrophage, a regulatory dendritic cell, and any combination thereof. In one embodiment, the immune cells may be regulatory T cells. In one embodiment, the immune cells may be CD4$^+$ regulatory T cells. In one embodiment, the immune cell is a human immune cell. In another embodiment, the regulatory immune cell is a human regulatory immune cell. In one embodiment, the human regulatory immune cell is selected from the group consisting of a regulatory T cell, a CD4$^+$ regulatory T cell, a CD8$^+$ regulatory T cell, a regulatory γδ T cell, a regulatory DN T cell, a regulatory B cell, a regulatory NK cell, a regulatory macrophage, a regulatory dendritic cell, and any combination thereof. In another embodiment, the immune cell is a human regulatory T cell. In one embodiment, the immune cell is a human CD4$^+$ regulatory T cell. In one embodiment, the CAR-modified Treg cells of the present invention are able to replicate in vivo resulting in long-term persistence that can lead to sustained suppression of an immune response of a targeted cell and immune tolerance. In one embodiment, there is provided a method of generating a persisting population of regulatory T cells in a subject wherein the regulatory T cells are modified to express a chimeric antigen receptor (CAR), the method comprising administering to the subject a regulatory T cell as described anywhere herein, wherein the persisting population of modified regulatory T cells persists in the subject for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 30 days, 40 days, 50 days, 60 days, 70 days, 80 days, 90 days, 100 days, 200 days, 300 days, 400 days, 500 days, 600 days, 700 days, 800 days, 900 days, or 1000 days after administration. In one embodiment, the CAR-Treg cells may be capable of self-renewing and being re-activated in vivo to suppress an immune response of a targeted cell. In one embodiment, the CAR-Treg cells may be memory CAR-Treg cells that can be re-activated to suppress an immune response of a targeted cell.

The immune cells may be obtained from any source. For example, in one embodiment, immune cells may be obtained from the tissue donor, the transplant recipient or an otherwise unrelated source (a different subject or species altogether) for generation of CAR-modified immune cells of the present invention. Accordingly, CAR-modified immune cells of the present invention may be autologous, allogeneic or xenogeneic to the transplant recipient or an otherwise unrelated source. In one embodiment, the CAR-Treg cells of the present invention may be autologous, allogeneic or xenogeneic to the transplant recipient. In one embodiment, the CAR-Treg cells of the present invention may be autologous to the transplant recipient.

In one embodiment, the subject may be a mammal. In one embodiment, the subject may be a human.

In one embodiment, it may be desirable to administer activated T cells to a subject and then subsequently redraw blood (or have an apheresis performed), activate T cells therefrom according to the present invention, and reinfuse the subject with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The CAR-modified immune cells of the present invention may be administered either alone or as a pharmaceutical composition in combination with diluents and/or with other components such as IL-2 or other cytokines or cell populations. In one embodiment, the pharmaceutical composition may comprise a plurality of the modified immune cells as described anywhere herein. In one embodiment, the pharmaceutical compositions of the present invention may comprise a CAR-modified immune cell or cell population as described anywhere herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The pharmaceutical compositions of the present invention may be administered to a subject in any suitable manner, including by aerosol inhalation, injection, ingestion, transfusion, implantation or transplantation. The pharmaceutical compositions described anywhere herein may be administered to a subject by parenteral administration. The pharmaceutical compositions described anywhere herein may be administered to a subject subcutaneously, intradermally, intratumorally, intranodally, intramedullary, intramuscularly, intrastemally, by intravenous (i.v.) injection, by infusion techniques or intraperitoneally. In one embodiment, the CAR-modified immune cell compositions of the present invention may be administered to a subject by intradermal or subcutaneous injection. In another embodiment, the CAR-modified immune cell compositions of the present invention may be administered by i.v. injection. In one embodiment, the compositions of CAR-modified immune cells may be injected directly into a lymph node, site of infection, site of inflammation or site of tissue or organ ejection.

Pharmaceutical compositions of the present invention may be administered in a manner appropriate to the disease to be prevented or treated. The quantity and frequency of administration will be determined by such factors as the condition of the subject, and the type and severity of the subject's disease, although appropriate dosages may be determined by clinical trials.

When an "effective amount" or "therapeutic amount" is indicated, the amount of the compositions of the present invention to be administered may be determined with consideration of individual differences in age, weight, antibody titer, and condition of the subject. It can generally be stated that a pharmaceutical composition comprising the CAR-modified immune cells as described anywhere herein may be administered at a dosage of $1 \times 10^4$ to $1 \times 10^9$ cells/kg body weight. In one embodiment, the CAR-modified immune cells may be administered at a dosage of $1 \times 10^5$ to $100 \times 10^5$ cells/kg body weight, including all integer values within those ranges. CAR-modified immune cell compositions may also be administered multiple times at these dosages. The CAR-modified immune cells can be administered by using infusion techniques that are commonly known in immunotherapy (see, e.g., Rosenberg et al, 1988). The optimal dosage and treatment regime for a particular subject can readily be determined by monitoring the subject for signs of disease and adjusting the treatment accordingly.

In one embodiment, the at least one CAR-engineered immune cell of the invention is administered to the subject in need thereof in combination with another active agent. According to one embodiment, the at least one immune cell population is administered before, at the same time or after the administration of another active agent.

In one embodiment, the CAR-modified immune cells of the present invention may be administered to a subject in conjunction with (e.g., before, simultaneously or following) any number of relevant treatment modalities, including but not limited to treatment with agents such as antiviral therapy, chemotherapy, radiation, immunosuppressive agents, antibodies, immunoablative agents, cytokines, and irradiation. In one embodiment, the CAR-modified immune cells of the present invention may be administered in conjunction with an immunosuppressant agent. Any immunosuppressant agent known in the art may be used. For example, the immunosuppressant agent may be calcineurin inhibitors such as cyclosporine, tacrolimus, azathioprine, methotrexate, methoxsalen, rapamycin, mycophenolate mofetil, mycophenolic acid, mycophenolate sodium, 6-mercaptopurine, 6-thioguanine, rituximab, mTOR inhibitors such as sirolimus, everolimus, basiliximab, daclizumab, belatacept, alemtuzumab, muromonab-CD3, anti-thymocyte globulin, glucorticosteroids, or adrenocortical steroids such as prednisone and prednisolone, or any combination thereof. The CAR-modified immune cells of the present invention may be administered to the subject before, after, or concomitant with the immunosuppressant agent. For example, the CAR-modified immune cells of the present invention may be administered after the immunosuppressant agent is administered to the subject or the CAR-modified immune cells of the invention may be administered before the immunosuppressant agent is administered to the subject. Alternatively, or in addition, the CAR-modified immune cells of the invention may be administered at the same time the immunosuppressant agent is administered to the subject. The CAR-modified immune cells of the present invention and/or the immunosuppressant agent may be administered to the subject after transplantation. Alternatively, or in addition, the CAR-modified immune cells of the present invention and/or the immunosuppressant agent may be administered to the subject before transplantation. The CAR-modified immune cells of the present invention and/or the immunosuppressant agent may be administered to the subject during transplantation surgery. In one embodiment, the method of the invention of administering CAR-modified immune cells to the subject is carried out once immunosuppressive therapy has been initiated. In some embodiments, the method is carried out more than once, e.g., to monitor the transplant recipient over time, and, if applicable, in different immunosuppressive therapy regimes. In some embodiments, immunosuppressive therapy is reduced if the transplant recipient is predicted to be tolerant of the transplant. In some embodiments, no immunosuppressive therapy is prescribed, e.g., immunosuppressive therapy is ceased, if the transplant recipient is predicted to be tolerant of the transplant.

Also provided is a method of preventing or treating organ or tissue transplant rejection in a subject, the method comprising administering to the subject (i) at least one immunosuppressive agent and (ii) CAR-engineered immune cells (e.g., the CAR-engineered Treg cells) of the invention, or a pharmaceutical composition comprising said immune cells.

Another embodiment of the present invention is thus a combination of a CAR-engineered immune cell (e.g., the CAR-engineered Treg cells) of the invention, or a pharmaceutical composition comprising said immune cells, and of at least one immunosuppressive agent, for use in preventing or treating organ or tissue transplant rejection in a subject.

Also provided is a method of increasing the time period of graft survival in a subject, the method comprising administering to the subject at least one immunosuppressive agent and CAR-engineered immune cells (e.g., the CAR-engineered Treg cells) of the present invention, or a pharmaceutical composition comprising the same.

In one embodiment, a combination of at least one immunosuppressive agent with CAR-engineered immune cells (e.g., the CAR-engineered Treg cells) of the present invention is used to prevent or treat graft versus host disease (GVHD). In one embodiment, the GVHD may occur after hematopoietic stem cell transplantation.

Another embodiment of the invention is thus a method of preventing or treating graft versus host disease (GVHD) in a subject, the method comprising administering to the subject at least one immunosuppressive agent and CAR-engineered immune cells (e.g., the CAR-engineered Treg cells) or a pharmaceutical composition as described herein.

In one embodiment, the invention provides a method of contacting a donor transplant, for example, a biocompatible lattice or a donor tissue, organ or cell, with at least one immunosuppressive agent and CAR-engineered immune cells (e.g., the CAR-engineered Treg cells) of the present invention at the same time as, before, or after the transplantation of the transplant into a recipient.

In one embodiment, the combination of at least one immunosuppressive agent with CAR-engineered immune cells (e.g., the CAR-engineered Treg cells) of the present invention may be used to ameliorate, inhibit or reduce an adverse response by the donor transplant against the recipient, thereby preventing or treating GVHD.

Another embodiment of the present invention is thus a method of preventing or delaying onset of GVHD in a subject, the method comprising administering to the subject at least one immunosuppressive agent and CAR-engineered immune cells (e.g., the CAR-engineered Treg cells) or a pharmaceutical composition as described herein.

In one embodiment, the CAR-engineered immune cells of the invention and the at least one immunosuppressive agent are administered simultaneously or sequentially.

In one embodiment, the CAR-engineered immune cells of the present invention, and optionally the at least one other active agent, e.g., immunosuppressive agent, is administered in conjunction with (e.g., before, simultaneously or following) the transplant.

The CAR-modified immune cells of the present invention may be administered following a diagnosis of transplant organ or tissue rejection followed by doses of both the CAR-modified immune cells of the invention and an immunosuppressant agent until symptoms of organ or tissue rejection subside. In a further embodiment, the CAR-modified immune cell compositions of the present invention may be administered to a subject in conjunction with (e.g., before, simultaneously or following) bone marrow transplantation. In another embodiment, the CAR-modified immune cells of the present invention may be administered following B-cell ablative therapy such as agents that react with CD20, e.g., Rituximab. For example, in one embodiment, subjects may undergo standard treatment with high dose chemotherapy followed by peripheral blood stem cell transplantation. In certain embodiments, following the transplant, subjects may receive an infusion of the expanded CAR-modified immune cells of the present invention. In an additional embodiment, expanded CAR-modified immune cells may be administered before or following surgery.

In one embodiment, the subject (e.g., human) receives an initial administration of the at least one immune cell or population of the invention, and one or more subsequent administrations, wherein the one or more subsequent administrations are administered less than 15 days, e.g., 14, 13, 12, 11, 10, 9, 8, 7, 6, 5, 4, 3, or 2 days after the previous administration. In one embodiment, a therapeutically effective amount of immune cells of the invention is administered or is to be administered to the subject. In one embodiment, the amount of immune cells of the at least one immune cell population of the invention administered to the subject is at least of $10^2$, $10^3$, $10^4$, $10^5$, $10^6$, $10^7$, $10^8$ or $10^9$ cells. In one embodiment, the amount of immune cells of the invention administered to the subject ranges from about $10^2$ to about $10^9$, from about $10^3$ to about $10^8$, from about $10^4$ to about $10^7$, or from about $10^5$ to about $10^6$ cells. In another embodiment, the amount of immune cells of the invention administrated to the subject ranges from about $10^6$ to about $10^9$, from about $10^6$ to $10^7$, from about $10^6$ to $10^8$, from about $10^7$ to $10^9$, from about $10^7$ to $10^8$, from about $10^8$ to $10^9$. In another embodiment the amount of immune cells of the invention administrated to the subject is about $10^6$, about $10^7$, about $10^8$, or is about $10^9$. In one embodiment, the amount of immune cells of the at least one immune cell population of the invention administered to the subject is at least of $10^2$, $10^3$, $10^4$, $10^5$, $10^6$, $10^7$, $10^8$ or $10^9$ cells/kg body. In one embodiment, the amount of immune cells of the invention administered to the subject ranges from about $10^4$ to $10^9$ cells/kg body weight or $10^5$ to $10^8$ cells/kg body weight, including all integer values within those ranges. In one embodiment, more than one administration of the at least one immune cell or population of the invention are administered to the subject (e.g., human) per week, e.g., 2, 3, or 4 administrations of the genetically modified immune cell or population of the invention are administered per week.

In some embodiments, it may be desirable to incorporate a suicide gene into the CAR-modified immune cells of the present invention in order to enable selective destruction of CAR-modified immune cells in vivo. In one embodiment, the CAR-modified immune cells of the present invention may further comprise a suicide gene system. In one embodiment, the CAR-modified immune cells of the present invention may further comprise a nucleic acid encoding a suicide gene system. "Suicide gene therapy," "suicide gene" and "suicide gene system" as described herein refer to methods to selectively destroy a cell through apoptosis. Such methods employ a suicide gene that will cause a cell to kill itself by apoptosis. The suicide gene encodes for a product which causes cell death by itself or in the presence of other compounds. The suicide gene may be from any suicide gene system suitable for use in cellular therapy (see, for example, Jones et al., 2014; Wang et al., 2017; Zhang et al., 2017; Casucci et al., 2011; Gargett et al., 2014; Khaleghi, 2012; Philip et al., 2014).

In one embodiment, the suicide gene system may involve a gene-directed enzyme prodrug therapy (GDEPT) where a nontoxic drug (i.e., suicide gene prodrug) is converted to a toxic compound in suicide-gene modified cells. For example, in one embodiment, the suicide gene system may be a herpes simplex virus thymidine kinase (HSV-TK)/ganciclovir (GCV) suicide gene system which uses the thymidine kinase gene from the herpes simplex virus in combination with the prodrug ganciclovir. In other embodiments, the suicide gene system may be a cytosine deaminase/5-fluorocytosine suicide gene system. In some alternatives of the methods provided herein wherein the CAR-modified immune cells comprise a suicide gene system, the methods further comprise administering to the subject a suicide gene prodrug.

In other embodiments, the suicide gene system may involve a dimerization inducing mechanism where apoptotic genes such as caspases destroy cells by inducing apoptosis. Dimerization inducing suicide gene systems may involve chimeric proteins composed of a drug binding domain linked with components of the apoptotic pathway allowing conditional dimerization and apoptosis of the modified immune cells after administration of a chemical inducer of dimerization (CID). For example, in one embodiment, the suicide gene system may be a caspase based suicide gene system. Non-limiting examples of inducible caspase suicide gene systems may include the inducible caspase-9 suicide gene system (iCasp9) and the caspase-8 suicide gene system (iCasp8) where the caspase is activated by the CID, FK506 or an analogue thereof. In some alternatives of the methods provided herein wherein the CAR-modified immune cells comprise a suicide gene system, the methods further comprise administering to the subject a chemical inducer of dimerization.

In other embodiments, the suicide gene system may be mediated by a therapeutic monoclonal antibody. Therapeutic mAb-mediated suicide gene systems involve the expression of proteins at the cell surface which make the modified immune cells sensitive to the therapeutic mAbs. Modified immune cells may be selectively destroyed after administration of the specific therapeutic mAb. Non-limiting examples of therapeutic mAb-mediated suicide gene systems may include the CD20 suicide gene system and the RQR8 suicide gene system where the therapeutic mAb is an anti-CD20 mAb. In some embodiments, the anti-CD20 mAb may be rituximab. In some alternatives of the methods provided herein wherein the CAR-modified immune cells comprise a suicide gene system, the methods further comprise administering to the subject a therapeutic monoclonal antibody.

VIII. Articles of Manufacture and Kits

In another embodiment, the invention provides an article of manufacture containing materials useful for the prevention and/or treatment of transplant rejection or GVHD. The article of manufacture comprises a container and a label or package insert on or associated with the container. Suitable containers include, for example, bottles, vials, syringes, etc. The containers may be formed from a variety of materials such as glass or plastic. The container holds a composition which is effective for preventing and/or treating the immunological condition, such as transplant rejection or GVHD, and may have a sterile access port (for example the container may be an intravenous solution bag or a vial having a stopper pierceable by a hypodermic injection needle). At least one active agent in the composition is a CAR-modified immune cell of the present invention. In one embodiment, the CAR-modified immune cell is a CAR-modified Treg. In one embodiment, the CAR-modified Treg is a CAR-modified human Treg. The label or package insert indicates that the composition is used for preventing or treating transplant rejection or GVHD. The article of manufacture, label or package insert may further comprise instructional material for administering the CAR-modified immune cell composition to the patient. Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes (e.g., for preventing or treating transplant rejection or GVHD). Kits can be provided which contain the CAR-modified immune cells. As with the article of manufacture, the kit comprises a container and a label or package insert on or associated with the container. The container holds a composition comprising at least one CAR-modified immune cell of the present invention. Additional containers may be included that contain, e.g., diluents and buffers. The label or package insert may provide a description of the composition as well as instructions for the intended use. In one embodiment, the CAR-modified immune cells are CAR-modified Tregs. In one embodiment, the CAR-modified Tregs are CAR-modified human Tregs.

The present invention thus further relates to a kit of parts comprising, in a first part, an immune cell or an immune cell population of the present invention, and in a second part, another active agent, including without limitations, antiviral therapy, chemotherapy, radiation, immunosuppressive agents, antibodies, immunoablative agents, cytokines, and irradiation. In some embodiments, the kit of parts of the present invention comprises in a first part, an immune cell or an immune cell population of the present invention, and in a second part, one or more immunosuppressive agents. Examples of immunosuppressive agents that may be present in the kit of the invention include, but are not limited to, calcineurin inhibitors such as cyclosporine, tacrolimus, azathioprine, methotrexate, methoxsalen, rapamycin, mycophenolate mofetil, mycophenolic acid, mycophenolate sodium, 6-mercaptopurine, 6-thioguanine, rituximab, mTOR inhibitors such as sirolimus, everolimus, basiliximab, daclizumab, belatacept, alemtuzumab, muromonab-CD3, anti-thymocyte globulin, glucorticosteroids, or adrenocortical steroids such as prednisone and prednisolone, or any combination thereof.

TABLE 1

|         | Kabat                   | Chothia                 |
|---------|-------------------------|-------------------------|
| VH CDR1 | SYHIQ<br>(SEQ ID NO: 1) | GYTFTSY<br>(SEQ ID NO: 2) |

TABLE 1-continued

|         | Kabat                                  | Chothia                   |
|---------|----------------------------------------|---------------------------|
| VH CDR2 | WIYPGDGSTQYNEKFKG<br>(SEQ ID NO: 3)    | YPGDGS<br>(SEQ ID NO: 4)  |
| VH CDR2 | WIYPGDGSTKYSQKFQG<br>(SEQ ID NO: 5)    | YPGDGS<br>(SEQ ID NO: 4)  |
| VH CDR3 | EGTYYAMDY<br>(SEQ ID NO: 6)            | EGTYYAMDY<br>(SEQ ID NO: 6) |

|         | Kabat                                  | Chothia                                |
|---------|----------------------------------------|----------------------------------------|
| VL CDR1 | RSSQSIVHSNGNTYLE<br>(SEQ ID NO: 7)     | RSSQSIVHSNGNTYLE<br>(SEQ ID NO: 7)     |
| VL CDR2 | KVSNRFS<br>(SEQ ID NO: 8)              | KVSNRFS<br>(SEQ ID NO: 8)              |
| VL CDR3 | FQGSHVPRT<br>(SEQ ID NO: 9)            | FQGSHVPRT<br>(SEQ ID NO: 9)            |

TABLE 3

| SEQ Name | SEQ ID | AA |
|----------|--------|----|
| VH CDR2 (Kabat) | 10 | WIYPGDGSTX$^{10}$YX$^{12}$X$^{13}$KFX$^{16}$G |
| VH FR1 (chothia) | 11 | QVQLVQSGAEVKKPGASVKVSCKAS |
| VH FR1 (kabat) | 12 | QVQLVQSGAEVKKPGASVKVSCKASGYTFT |
| VH FR2 (kabat/kabat variable) | 13 | WVRQAPGQX$^{9}$LEWMGX$^{15}$ |
| VH1/2/5/6 FR2 (kabat/kabat) | 14 | WVRQAPGQRLEWMG |
| VH3 FR2 (kabat/kabat) | 15 | WVRQAPGQGLEWMGI |
| VH4 FR2 (kabat/kabat) | 16 | WVRQAPGQGLEWMG |
| VH FR2 (kabat/chothia variable) | 17 | WVRQAPGQX$^{9}$LEWMGX$^{15}$WI |
| VH1/2/5/6 FR2 (kabat/chothia) | 18 | WVRQAPGQRLEWMGWI |
| VH3 FR2 (kabat/chothia) | 19 | WVRQAPGQGLEWMGIWI |
| VH4 FR2 (kabat/chothia) | 20 | WVRQAPGQGLEWMGWI |
| VH FR2 (chothia/chothia variable) | 21 | HIQWVRQAPGQX$^{12}$LEWMGX$^{18}$WI |

TABLE 3-continued

| SEQ Name | SEQ ID | AA |
| --- | --- | --- |
| VH1/2/5/6 FR2 (chothia/chothia) | 22 | HIQWVRQAPGQRLEWMGWI |
| VH3 FR2 (chothia/chothia) | 23 | HIQWVRQAPGQGLEWMGIWI |
| VH4 FR2 (chothia/chothia) | 24 | HIQWVRQAPGQGLEWMGWI |
| VH FR2 (chothia/kabat variable) | 25 | HIQWVRQAPGQX$^{12}$LEWMGX$^{18}$ |
| VH1/2/5/6 FR2 (chothia/kabat) | 26 | HIQWVRQAPGQRLEWMG |
| VH3 FR2 (chothia/kabat) | 27 | HIQWVRQAPGQGLEWMGI |
| VH4 FR2 (chothia/kabat) | 28 | HIQWVRQAPGQGLEWMG |
| VH FR3 (kabat variable) | 29 | X$^{1}$VTX$^{4}$TX$^{6}$DTSX$^{10}$STAYMX$^{16}$LSX$^{19}$LRSX$^{23}$DX$^{25}$AVYYCAR |
| VH1/6 FR3 (kabat) | 30 | RVTITRDTSASTAYMELSSLRSEDTAVYYCAR |
| VH2 FR3 (kabat) | 31 | RVTITADTSASTAYMLLSSLRSEDTAVYYCAR |
| VH3 FR3 (kabat) | 32 | VTMTRDTSTSTVYMELSSLRSEDTAVYYCAR |
| VH4 FR3 (kabat) | 33 | RVTMTRDTSISTAYMELSRLRSDDTAVYYCAR |
| VH5 FR3 (kabat) | 34 | RVTITRDTSASTAYMELSSLRSEDMAVYYCAR |
| VH FR3 (chothia variable) | 35 | TX$^{2}$YX$^{4}$X$^{5}$KFX$^{8}$GX$^{10}$VTX$^{13}$TX$^{15}$DTSX$^{19}$STAYMX$^{25}$LSX$^{28}$LRSX$^{32}$DX$^{34}$AVYYCAR |
| VH1/2/3/4/5 FR3 (chothia variable) | 36 | TQYNEKFKGX$^{10}$VTX$^{13}$TX$^{15}$DTSX$^{19}$STAYMX$^{25}$LSX$^{28}$LRSX$^{32}$DX$^{34}$AVYYCAR |
| VH6 FR3 (chothia variable) | 37 | TKYSQKFQGX$^{10}$VTX$^{13}$TX$^{15}$DTSX$^{19}$STAYMX$^{25}$LSX$^{28}$LRSX$^{32}$DX$^{34}$AVYYCAR |
| VH 1 FR3 (chothia) | 38 | TQYNEKFKGRVTITRDTSASTAYMELSSLRSEDTAVYYCAR |
| VH 2 FR3 (chothia) | 39 | TQYNEKFKGRVTITADTSASTAYMLLSSLRSEDTAVYYCAR |
| VH 3 FR3 (chothia) | 40 | TQYNEKFKGVTMTRDTSTSTVYMELSSLRSEDTAVYYCAR |
| VH 4 FR3 (chothia) | 41 | TQYNEKFKGRVTMTRDTSISTAYMELSRLRSDDTAVYYCAR |
| VH 5 FR3 (chothia) | 42 | TQYNEKFKGRVTITRDTSASTAYMELSSLRSEDMAVYYCAR |
| VH 6 FR3 (chothia) | 43 | TKYSQKFQGRVTITRDTSASTAYMELSSLRSEDTAVYYCAR |
| VH FR4 | 44 | WGQGTTVTVSS |
| VH | 45 | QVQLVQSGAEVKKPGASVKVSCKASGYTFTSYHIQWVRQAPGQX$^{44}$LEWMGX$^{50}$WIYPGDGSTX$^{60}$YX$^{62}$X$^{63}$KFX$^{66}$GX$^{68}$VTX$^{71}$TX$^{73}$DTSX$^{77}$ |

TABLE 3-continued

| SEQ Name | SEQ ID | AA |
| --- | --- | --- |
| | | STAYMX$^{83}$LSX$^{86}$LRSX$^{90}$DX$^{92}$AVYYCAREGTYYAMDYWGQGTTVTVSS |
| VL FR1 | 46 | DX$^{2}$VMTQX$^{7}$PLSX$^{11}$X$^{12}$VTX$^{15}$GQPASISX$^{23}$ |
| VL1/4 | 47 | DVVMTQSPLSLPVTLGQPASISC |
| VL2 FR1 | 48 | DIVMTQTPLSLSVTPGQPASISC |
| VL3 FR1 | 49 | DIVMTQTPLSSPVTLGQPASISC |
| VL5 FR1 | 50 | DIVMTQTPLSSPVTLGQPASISF |
| VL FR2 | 51 | WX$^{2}$X$^{3}$QX$^{5}$PGQX$^{9}$PX$^{11}$X$^{12}$LIY |
| VL1 FR2 | 52 | WFQQRPGQSPRRLIY |
| VL2 FR2 | 53 | WYLQKPGQSPQLLIY |
| VL3/5 FR2 | 54 | WYQQRPGQPPRLLIY |
| VL4 FR2 | 55 | WYQQRPGQSPRLLIY |
| VL FR3 | 56 | GVPDRFSGSGXHGTDFTLKISRVEAEDVGVYYC |
| VL1/2/4 FR3 | 57 | GVPDRFSGSGSGTDFTLKISRVEAEDVGVYYC |
| VL3/5 FR3 | 58 | GVPDRFSGSGAGTDFTLKISRVEAEDVGVYYC |
| VL FR4 | 59 | FGGGTKVEIK |
| VL | 60 | DX$^{2}$VMTQX$^{7}$PLSX$^{11}$X$^{12}$VTX$^{15}$GQPASISX$^{23}$RSSQSIVHSNGNTYLEWX$^{41}$X$^{42}$QX$^{44}$PGQX$^{48}$PX$^{50}$X$^{51}$LIYKVSNRFSGVPDRFSGSGX$^{72}$GTDFTLKISRVEAEDVGVYYCFQGSHVPRTFGGGTKVEIK |
| H1 (without leader) | 61 | QVQLVQSGAEVKKPGASVKVSCKASGYTFTSYHIQWVRQAPGQRLEWMGWIYPGDGSTQYNEKFKGRVTITRDTSASTAYMELSSLRSEDTAVYYCAREGTYYAMDYWGQGTTVTVSS |
| H2 (without leader) | 62 | QVQLVQSGAEVKKPGASVKVSCKASGYTFTSYHIQWVRQAPGQRLEWMGWIYPGDGSTQYNEKFKGRVTITADTSASTAYMLLSSLRSEDTAVYYCAREGTYYAMDYWGQGTTVTVSS |
| H3 (without leader) | 63 | QVQLVQSGAEVKKPGASVKVSCKASGYTFTSYHIQWVRQAPGQGLEWMGIWIYPGDGSTQYNEKFKGVTMTRDTSTSTVYMELSSLRSEDTAVYYCAREGTYYAMDYWGQGTTVTVSS |
| H4 (without leader) | 64 | QVQLVQSGAEVKKPGASVKVSCKASGYTFTSYHIQWVRQAPGQGLEWMGWIYPGDGSTQYNEKFKGRVTMTRDTSISTAYMELSRLRSDDTAVYYCAREGTYYAMDYWGQGTTVTVSS |
| H5 (without leader) | 65 | QVQLVQSGAEVKKPGASVKVSCKASGYTFTSYHIQWVRQAPGQRLEWMGWIYPGDGSTQYNEKFKGRVTITRDTSASTAYMELSSLRSEDMAVYYCAREGTYYAMDYWGQGTTVTVSS |
| H6 (without leader) | 66 | QVQLVQSGAEVKKPGASVKVSCKASGYTFTSYHIQWVRQAPGQRLEWMGWIYPGDGSTKYSQKFQGRVTITRDTSASTAYMELSSLRSEDTAVYYCAREGTYYAMDYWGQGTTVTVSS |
| K1 | 67 | DVVMTQSPLSLPVTLGQPASISCRSSQSIVHSNGNTYLEWFQQRPGQSPRRLIYKVSNRFSGVPDRFSGSGSGTDFTLKISRVEAEDVGVYYCFQGSHVPRTFGGGTKVEIK |
| K2 | 68 | DIVMTQTPLSLSVTPGQPASISCRSSQSIVHSNGNTYLEWYLQKPGQSPQLLIYKVSNRFSGVPDRFSGSGSGTDFTLKISRVEAEDVGVYYCFQGSHVPRTFGGGTKVEIK |
| K3 | 69 | DIVMTQTPLSSPVTLGQPASISCRSSQSIVHSNGNTYLEWYQQRPGQPPRLLIYKVSNRFSGVPDRFSGSGAGTDFTLKISRVEAEDVGVYYCFQGSHVPRTFGGGTKVEIK |
| K4 | 70 | DVVMTQSPLSLPVTLGQPASISCRSSQSIVHSNGNTYLEWYQQRPGQSPRLLIYKVSNRFSGVPDRFSGSGSGTDFTLKISRVEAEDVGVYYCFQGSHVPRTFGGGTKVEIK |
| K5 | 71 | DIVMTQTPLSSPVTLGQPASISFRSSQSIVHSNGNTYLEWYQQRPGQPPRLLIYKVSNRFSGVPDRFSGSGAGTDFTLKISRVEAEDVGVYYCFQGSHVPRTFGGGTKVEIK |

TABLE 3-continued

| SEQ Name | SEQ ID | AA |
|---|---|---|
| H1_k1_AA (without leader) | 72 | QVQLVQSGAEVKKPGASVKVSCKASGYTFTSYHIQWVRQAPGQR LEWMGWIYPGDGSTQYNEKFKGRVTITRDTSASTAYMELSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWFQQRPGQSPRRLIYKVSNRFSGVPDRFSGSGSGTDFTLKIS RVEAEDVGVYYCFQGSHVPRTFGGGTKVEIK |
| H1_k2_AA (without leader) | 73 | QVQLVQSGAEVKKPGASVKVSCKASGYTFTSYHIQWVRQAPGQR LEWMGWIYPGDGSTQYNEKFKGRVTITRDTSASTAYMELSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H1_k3_AA (without leader) | 74 | QVQLVQSGAEVKKPGASVKVSCKASGYTFTSYHIQWVRQAPGQR LEWMGWIYPGDGSTQYNEKFKGRVTITRDTSASTAYMELSSLRS EDTAVYYCAREGTYYAMDYWGQGTTVTVSSVDSSGGGGSGGGGS GGGGSTSDIVMTQTPLSSPVTLGQPASISCRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H1_k4_AA (without leader) | 75 | QVQLVQSGAEVKKPGASVKVSCKASGYTFTSYHIQWVRQAPGQR LEWMGWIYPGDGSTQYNEKFKGRVTITRDTSASTAYMELSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIK |
| H1_k5_AA (without leader) | 76 | QVQLVQSGAEVKKPGASVKVSCKASGYTFTSYHIQWVRQAPGQR LEWMGWIYPGDGSTQYNEKFKGRVTITRDTSASTAYMELSSLRS EDTAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H2_k1_AA (without leader) | 77 | QVQLVQSGAEVKKPGASVKVSCKASGYTFTSYHIQWVRQAPGQR LEWMGWIYPGDGSTQYNEKFKGRVTITADTSASTAYMLSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWFQQRPGQSPRRLIYKVSNRFSGVPDRFSGSGSGTDFTLKIS RVEAEDVGVYYCFQGSHVPRTFGGGTKVEIK |
| H2_k2_AA (without leader) | 78 | QVQLVQSGAEVKKPGASVKVSCKASGYTFTSYHIQWVRQAPGQR LEWMGWIYPGDGSTQYNEKFKGRVTITADTSASTAYMLSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H3_k2_AA (without leader) | 79 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H3_k3_AA (without leader) | 80 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSSPVTLGQPASISCRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H3_k4_AA (without leader) | 81 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIK |
| H3_k5_AA (without leader) | 82 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |

TABLE 3-continued

| SEQ Name | SEQ ID | AA |
|---|---|---|
| H4_k2_AA (without leader) | 83 | QVQLVQSGAEVKKPGASVKVSCKASGYTFTSYHIQWVRQAPGQG LEWMGWIYPGDGSTQYNEKFKGRVTMTRDTSISTAYMELSRLRS DDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H4_k3_AA (without leader) | 84 | QVQLVQSGAEVKKPGASVKVSCKASGYTFTSYHIQWVRQAPGQG LEWMGWIYPGDGSTQYNEKFKGRVTMTRDTSISTAYMELSRLRS DDTAVYYCAREGTYYAMDYWGQGTTVTVSSVDSSGGGGSGGGGS GGGGSTSDIVMTQTPLSSPVTLGQPASISCRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H4_k4_AA (without leader) | 85 | QVQLVQSGAEVKKPGASVKVSCKASGYTFTSYHIQWVRQAPGQG LEWMGWIYPGDGSTQYNEKFKGRVTMTRDTSISTAYMELSRLRS DDTAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIK |
| H4_k5_AA (without leader) | 86 | QVQLVQSGAEVKKPGASVKVSCKASGYTFTSYHIQWVRQAPGQG LEWMGWIYPGDGSTQYNEKFKGRVTMTRDTSISTAYMELSRLRS DDTAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H5_k2_AA (without leader) | 87 | QVQLVQSGAEVKKPGASVKVSCKASGYTFTSYHIQWVRQAPGQR LEWMGWIYPGDGSTQYNEKFKGRVTITRDTSASTAYMELSSLRS EDMAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H5_k3_AA (without leader) | 88 | QVQLVQSGAEVKKPGASVKVSCKASGYTFTSYHIQWVRQAPGQR LEWMGWIYPGDGSTQYNEKFKGRVTITRDTSASTAYMELSSLRS EDMAVYYCAREGTYYAMDYWGQGTTVTVSSVDSSGGGGSGGGGS GGGGSTSDIVMTQTPLSSPVTLGQPASISCRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H5_k4_AA (without leader) | 89 | QVQLVQSGAEVKKPGASVKVSCKASGYTFTSYHIQWVRQAPGQR LEWMGWIYPGDGSTQYNEKFKGRVTITRDTSASTAYMELSSLRS EDMAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIK |
| H5_k5_AA (without leader) | 90 | QVQLVQSGAEVKKPGASVKVSCKASGYTFTSYHIQWVRQAPGQR LEWMGWIYPGDGSTQYNEKFKGRVTITRDTSASTAYMELSSLRS EDMAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIK |
| H6_k2_AA (without leader) | 91 | QVQLVQSGAEVKKPGASVKVSCKASGYTFTSYHIQWVRQAPGQR LEWMGWIYPGDGSTKYSQKFQGRVTITRDTSASTAYMELSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIK |
| H6 | 92 | QVQLVQSGAEVKKPGASVKVSCKASGYTFTSYHIQWVRQAPGQX$^{44}$ LEWMGX$^{50}$WIYPGDGSTKYSQKFQGX$^{68}$VTX$^{71}$TX$^{73}$DTSX$^{77}$STAY MX$^{83}$LSX$^{86}$LRSX$^{90}$DX$^{92}$AVYYCAREGTYYAMDYWGQGTTVTVSS |
| H1_k1_AA (with leader) | 93 | MDFQVQIFSFLLISASVIMSRASQVQLVQSGAEVKKPGASVKVS CKASGYTFTSYHIQWVRQAPGQRLEWMGWIYPGDGSTQYNEKFK GRVTITRDTSASTAYMELSSLRSEDTAVYYCAREGTYYAMDYWG QGTTVTVSSVDSSGGGGSGGGGSGGGGSTSDVVMTQSPLSLPVT LGQPASISCRSSQSIVHSNGNTYLEWFQQRPGQSPRRLIYKVSN RFSGVPDRFSGSGSGTDFTLKISRVEAEDVGVYYCFQGSHVPRT FGGGTKVEIK |
| H1_k2_AA (with leader) | 94 | MDFQVQIFSFLLISASVIMSRASQVQLVQSGAEVKKPGASVKVS CKASGYTFTSYHIQWVRQAPGQRLEWMGWIYPGDGSTQYNEKFK GRVTITRDTSASTAYMELSSLRSEDTAVYYCAREGTYYAMDYWG |

TABLE 3-continued

| SEQ Name | SEQ ID | AA |
|---|---|---|
| | | QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| H1_k3_AA<br>(with<br>leader) | 95 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDTAVYYCAREGTYYAMDYWG<br>QGTTVTVSSVDSSGGGGSGGGGSGGGGSTSDIVMTQTPLSSPVT<br>LGQPASISCRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H1_k4_AA<br>(with<br>leader) | 96 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDTAVYYCAREGTYYAMDYWG<br>QGTTVTVSSVDSSGGGGSGGGGSGGGGSTSDVVMTQSPLSLPVT<br>LGQPASISCRSSQSIVHSNGNTYLEWYQQRPGQSPRLLIYKVSN<br>RFSGVPDRFSGSGSGTDFTLKISRVEAEDVGVYYCFQGSHVPRT<br>FGGGTKVEIK |
| H1_k5_AA<br>(with<br>leader) | 97 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDTAVYYCAREGTYYAMDYWG<br>QGTTVTVSSVDSSGGGGSGGGGSGGGGSTSDIVMTQTPLSSPVT<br>LGQPASISFRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H2_k1_AA<br>(with<br>leader) | 98 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITADTSASTAYMLLSSLRSEDTAVYYCAREGTYYAMDYWG<br>QGTTVTVSSVDSSGGGGSGGGGSGGGGSTSDVVMTQSPLSLPVT<br>LGQPASISCRSSQSIVHSNGNTYLEWFQQRPGQSPRRLIYKVSN<br>RFSGVPDRFSGSGSGTDFTLKISRVEAEDVGVYYCFQGSHVPRT<br>FGGGTKVEIK |
| H2_k2_AA<br>(with<br>leader) | 99 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITADTSASTAYMLLSSLRSEDTAVYYCAREGTYYAMDYWG<br>QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| H3_k2_AA<br>(with<br>leader) | 100 | MDFQVQIFSFLLISASVIMSRASQVQLVQSGAEVKKPGASVKVS<br>CKASGYTFTSYHIQWVRQAPGQGLEWMGIWIYPGDGSTQYNEKF<br>KGVTMTRDTSTSTVYMELSSLRSEDTAVYYCAREGTYYAMDYWG<br>QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| H3_k3_AA<br>(with<br>leader) | 101 | MDFQVQIFSFLLISASVIMSRASQVQLVQSGAEVKKPGASVKVS<br>CKASGYTFTSYHIQWVRQAPGQGLEWMGIWIYPGDGSTQYNEKF<br>KGVTMTRDTSTSTVYMELSSLRSEDTAVYYCAREGTYYAMDYWG<br>QGTTVTVSSVDSSGGGGSGGGGSGGGGSTSDIVMTQTPLSSPVT<br>LGQPASISCRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H3_k4_AA<br>(with<br>leader) | 102 | MDFQVQIFSFLLISASVIMSRASQVQLVQSGAEVKKPGASVKVS<br>CKASGYTFTSYHIQWVRQAPGQGLEWMGIWIYPGDGSTQYNEKF<br>KGVTMTRDTSTSTVYMELSSLRSEDTAVYYCAREGTYYAMDYWG<br>QGTTVTVSSVDSSGGGGSGGGGSGGGGSTSDVVMTQSPLSLPVT<br>LGQPASISCRSSQSIVHSNGNTYLEWYQQRPGQSPRLLIYKVSN<br>RFSGVPDRFSGSGSGTDFTLKISRVEAEDVGVYYCFQGSHVPRT<br>FGGGTKVEIK |
| H3_k5_AA<br>(with<br>leader) | 103 | MDFQVQIFSFLLISASVIMSRASQVQLVQSGAEVKKPGASVKVS<br>CKASGYTFTSYHIQWVRQAPGQGLEWMGIWIYPGDGSTQYNEKF<br>KGVTMTRDTSTSTVYMELSSLRSEDTAVYYCAREGTYYAMDYWG<br>QGTTVTVSSVDSSGGGGSGGGGSGGGGSTSDIVMTQTPLSSPVT<br>LGQPASISFRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |

TABLE 3-continued

| SEQ Name | SEQ ID | AA |
|---|---|---|
| H4_k2_AA (with leader) | 104 | MDFQVQIFSFLLISASVIMSRASQVQLVQSGAEVKKPGASVKVS<br>CKASGYTFTSYHIQWVRQAPGQGLEWMGWIYPGDGSTQYNEKFK<br>GRVTMTRDTSISTAYMELSRLRSDDTAVYYCAREGTYYAMDYWG<br>QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| H4_k3_AA (with leader) | 105 | MDFQVQIFSFLLISASVIMSRASQVQLVQSGAEVKKPGASVKVS<br>CKASGYTFTSYHIQWVRQAPGQGLEWMGWIYPGDGSTQYNEKFK<br>GRVTMTRDTSISTAYMELSRLRSDDTAVYYCAREGTYYAMDYWG<br>QGTTVTVSSVDSSGGGGSGGGGSGGGGSTSDIVMTQTPLSSPVT<br>LGQPASISCRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H4_k4_AA (with leader) | 106 | MDFQVQIFSFLLISASVIMSRASQVQLVQSGAEVKKPGASVKVS<br>CKASGYTFTSYHIQWVRQAPGQGLEWMGWIYPGDGSTQYNEKFK<br>GRVTMTRDTSISTAYMELSRLRSDDTAVYYCAREGTYYAMDYWG<br>QGTTVTVSSVDSSGGGGSGGGGSGGGGSTSDVVMTQSPLSLPVT<br>LGQPASISCRSSQSIVHSNGNTYLEWYQQRPGQSPRLLIYKVSN<br>RFSGVPDRFSGSGSGTDFTLKISRVEAEDVGVYYCFQGSHVPRT<br>FGGGTKVEIK |
| H4_k5_AA (with leader) | 107 | MDFQVQIFSFLLISASVIMSRASQVQLVQSGAEVKKPGASVKVS<br>CKASGYTFTSYHIQWVRQAPGQGLEWMGWIYPGDGSTQYNEKFK<br>GRVTMTRDTSISTAYMELSRLRSDDTAVYYCAREGTYYAMDYWG<br>QGTTVTVSSVDSSGGGGSGGGGSGGGGSTSDIVMTQTPLSSPVT<br>LGQPASISFRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H5_k2_AA (with leader) | 108 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDMAVYYCAREGTYYAMDYWG<br>QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| H5_k3_AA (with leader) | 109 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDMAVYYCAREGTYYAMDYWG<br>QGTTVTVSSVDSSGGGGSGGGGSGGGGSTSDIVMTQTPLSSPVT<br>LGQPASISCRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H5_k4_AA (with leader) | 110 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDMAVYYCAREGTYYAMDYWG<br>QGTTVTVSSVDSSGGGGSGGGGSGGGGSTSDVVMTQSPLSLPVT<br>LGQPASISCRSSQSIVHSNGNTYLEWYQQRPGQSPRLLIYKVSN<br>RFSGVPDRFSGSGSGTDFTLKISRVEAEDVGVYYCFQGSHVPRT<br>FGGGTKVEIK |
| H5_k5_AA (with leader) | 111 | MDFQVQIFSFLLISASVIMSRASQVQLVQSGAEVKKPGASVKVS<br>CKASGYTFTSYHIQWVRQAPGQRLEWMGWIYPGDGSTQYNEKFK<br>GRVTITRDTSASTAYMELSSLRSEDMAVYYCAREGTYYAMDYWG<br>QGTTVTVSSVDSSGGGGSGGGGSGGGGSTSDIVMTQTPLSSPVT<br>LGQPASISFRSSQSIVHSNGNTYLEWYQQRPGQPPRLLIYKVSN<br>RFSGVPDRFSGSGAGTDFTLKISRVEAEDVGVYYCFQGSHVPRT<br>FGGGTKVEIK |
| H6_k2_AA (with leader) | 112 | MDFQVQIFSFLLISASVIMSRASQVQLVQSGAEVKKPGASVKVS<br>CKASGYTFTSYHIQWVRQAPGQRLEWMGWIYPGDGSTKYSQKFQ<br>GRVTITRDTSASTAYMELSSLRSEDTAVYYCAREGTYYAMDYWG<br>QGTTVTVSSVDSSGGGGSGGGGSGGGGSTSDIVMTQTPLSLSVT<br>PGQPASISCRSSQSIVHSNGNTYLEWYLQKPGQSPQLLIYKVSN<br>RFSGVPDRFSGSGSGTDFTLKISRVEAEDVGVYYCFQGSHVPRT<br>FGGGTKVEIK |
| leader | 113 | MDFQVQIFSFLLISASVIMSRAS |
| linker | 114 | VDSSGGGGSGGGGSGGGGSTS |

TABLE 3-continued

| SEQ Name | SEQ ID | AA |
| --- | --- | --- |
| CD8 hinge | 115 | SALSNSIMYFSHFVPVFLPAKPTTTPAPRPPTPAPTIASQPLSL<br>RPEACRPAAGGAVHTRGLD |
| CD28 TM | 116 | FWVLVVVGGVLACYSLLVTVAFIIFWV |
| CD28 IC | 117 | RSKRSRLLHSDYMNMTPRRPGPTRKHYQPYAPPRDFAAYRS |
| CD3z | 118 | RVKFSRSADAPAYQQGQNQLYNELNLGRREEYDVLDKRRGRDPE<br>MGGKPRRKNPQEGLYNELQKDKMAEAYSEIGMKGERRRGKGHDG<br>LYQGLSTATKDTYDALHMQALPPR |
| CAR_H1_k1_AA<br>(without<br>leader) | 119 | QVQLVQSGAEVKKPGASVKVSCKASGYTFTSYHIQWVRQAPGQR<br>LEWMGWIYPGDSTQYNEKFKGRVTITRDTSASTAYMELSSLRS<br>EDTAVYYCAREGTYYAMDYWGQGTTVTVSSVDSSGGGGSGGGGS<br>GGGGSTSDVVMTQSPLSLPVTLGQPASISCRSSQSIVHSNGNTY<br>LEWFQQRPGQSPRRLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H1_k2_AA<br>(without<br>leader) | 120 | QVQLVQSGAEVKKPGASVKVSCKASGYTFTSYHIQWVRQAPGQR<br>LEWMGWIYPGDSTQYNEKFKGRVTITRDTSASTAYMELSSLRS<br>EDTAVYYCAREGTYYAMDYWGQGTTVTVSSVDSSGGGGSGGGGS<br>GGGGSTSDIVMTQTPLSLSVTPGQPASISCRSSQSIVHSNGNTY<br>LEWYLQKPGQSPQLLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H1_k3_AA<br>(without<br>leader) | 121 | QVQLVQSGAEVKKPGASVKVSCKASGYTFTSYHIQWVRQAPGQR<br>LEWMGWIYPGDSTQYNEKFKGRVTITRDTSASTAYMELSSLRS<br>EDTAVYYCAREGTYYAMDYWGQGTTVTVSSVDSSGGGGSGGGGS<br>GGGGSTSDIVMTQTPLSSPVTLGQPASISCRSSQSIVHSNGNTY<br>LEWYQQRPGQPPRLLIYKVSNRFSGVPDRFSGSGAGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H1_k4_AA<br>(without<br>leader) | 122 | QVQLVQSGAEVKKPGASVKVSCKASGYTFTSYHIQWVRQAPGQR<br>LEWMGWIYPGDSTQYNEKFKGRVTITRDTSASTAYMELSSLRS<br>EDTAVYYCAREGTYYAMDYWGQGTTVTVSSVDSSGGGGSGGGGS<br>GGGGSTSDVVMTQSPLSLPVTLGQPASISCRSSQSIVHSNGNTY<br>LEWYQQRPGQSPRLLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H1_k5_AA<br>(without<br>leader) | 123 | QVQLVQSGAEVKKPGASVKVSCKASGYTFTSYHIQWVRQAPGQR<br>LEWMGWIYPGDSTQYNEKFKGRVTITRDTSASTAYMELSSLRS<br>EDTAVYYCAREGTYYAMDYWGQGTTVTVSSVDSSGGGGSGGGGS<br>GGGGSTSDIVMTQTPLSSPVTLGQPASISFRSSQSIVHSNGNTY<br>LEWYQQRPGQPPRLLIYKVSNRFSGVPDRFSGSGAGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |

TABLE 3-continued

| SEQ Name | SEQ ID | AA |
|---|---|---|
| CAR_H2_k1_AA (without leader) | 124 | QVQLVQSGAEVKKPGASVKVSCKASGYTFTSYHIQWVRQAPGQR LEWMGWIYPGDGSTQYNEKFKGRVTITADTSASTAYMLLSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWFQQRPGQSPRRLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |
| CAR_H2_k2_AA (without leader) | 125 | QVQLVQSGAEVKKPGASVKVSCKASGYTFTSYHIQWVRQAPGQR LEWMGWIYPGDGSTQYNEKFKGRVTITADTSASTAYMLLSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |
| CAR_H3_k2_AA (without leader) | 126 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |
| CAR_H3_k3_AA (without leader) | 127 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSSPVTLGQPASISCRSSQSIVHSNGNTY LEWYQQRPGQPPRLLIYKVSNRFSGVPDRFSGSGAGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |
| CAR_H3_k4_AA (without leader) | 128 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |
| CAR_H3_k5_AA (without leader) | 129 | QVQLVQSGAEVKKPGASVKVSCKASGYTFTSYHIQWVRQAPGQG LEWMGIWIYPGDGSTQYNEKFKGVTMTRDTSTSTVYMELSSLRS EDTAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDMAEAYSEIGMKGERRRGKGH DGLYQGLSTATKDTYDALHMQALPPR |

TABLE 3-continued

| SEQ Name | SEQ ID | AA |
| --- | --- | --- |
| CAR_H4_k2_AA (without leader) | 130 | QVQLVQSGAEVKKPGASVKVSCKASGYTFTSYHIQWVRQAPGQG<br>LEWMGWIYPGDGSTQYNEKFKGRVTMTRDTSISTAYMELSRLRS<br>DDTAVYYCAREGTYYAMDYWGQGTTVTVSSVDSSGGGGSGGGGS<br>GGGGSTSDIVMTQTPLSLSVTPGQPASISCRSSQSIVHSNGNTY<br>LEWYLQKPGQSPQLLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H4_k3_AA (without leader) | 131 | QVQLVQSGAEVKKPGASVKVSCKASGYTFTSYHIQWVRQAPGQG<br>LEWMGWIYPGDGSTQYNEKFKGRVTMTRDTSISTAYMELSRLRS<br>DDTAVYYCAREGTYYAMDYWGQGTTVTVSSVDSSGGGGSGGGGS<br>GGGGSTSDIVMTQTPLSSPVTLGQPASISCRSSQSIVHSNGNTY<br>LEWYQQRPGQPPRLLIYKVSNRFSGVPDRFSGSGAGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H4_k4_AA (without leader) | 132 | QVQLVQSGAEVKKPGASVKVSCKASGYTFTSYHIQWVRQAPGQG<br>LEWMGWIYPGDGSTQYNEKFKGRVTMTRDTSISTAYMELSRLRS<br>DDTAVYYCAREGTYYAMDYWGQGTTVTVSSVDSSGGGGSGGGGS<br>GGGGSTSDVVMTQSPLSLPVTLGQPASISCRSSQSIVHSNGNTY<br>LEWYQQRPGQSPRLLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H4_k5_AA (without leader) | 133 | QVQLVQSGAEVKKPGASVKVSCKASGYTFTSYHIQWVRQAPGQG<br>LEWMGWIYPGDGSTQYNEKFKGRVTMTRDTSISTAYMELSRLRS<br>DDTAVYYCAREGTYYAMDYWGQGTTVTVSSVDSSGGGGSGGGGS<br>GGGGSTSDIVMTQTPLSSPVTLGQPASISFRSSQSIVHSNGNTY<br>LEWYQQRPGQPPRLLIYKVSNRFSGVPDRFSGSGAGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H5_k2_AA (without leader) | 134 | QVQLVQSGAEVKKPGASVKVSCKASGYTFTSYHIQWVRQAPGQR<br>LEWMGWIYPGDGSTQYNEKFKGRVTITRDTSASTAYMELSSLRS<br>EDMAVYYCAREGTYYAMDYWGQGTTVTVSSVDSSGGGGSGGGGS<br>GGGGSTSDIVMTQTPLSLSVTPGQPASISCRSSQSIVHSNGNTY<br>LEWYLQKPGQSPQLLIYKVSNRFSGVPDRFSGSGSGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |
| CAR_H5_k3_AA (without leader) | 135 | QVQLVQSGAEVKKPGASVKVSCKASGYTFTSYHIQWVRQAPGQR<br>LEWMGWIYPGDGSTQYNEKFKGRVTITRDTSASTAYMELSSLRS<br>EDMAVYYCAREGTYYAMDYWGQGTTVTVSSVDSSGGGGSGGGGS<br>GGGGSTSDIVMTQTPLSSPVTLGQPASISCRSSQSIVHSNGNTY<br>LEWYQQRPGQPPRLLIYKVSNRFSGVPDRFSGSGAGTDFTLKIS<br>RVEAEDVGVYYCFQGSHVPRTFGGGTKVEIKNRIRGVTVSSALS<br>NSIMYFSHFVPVFLPAKPTTTPAPRPPTPAPTIASQPLSLRPEA<br>CRPAAGGAVHTRGLDPFGFWVLVVVGGVLACYSLLVTVAFIIFW<br>VRSKRSRLLHSDYMNMTPRRPGPTRKHYQPYAPPRDFAAYRSLE<br>RVRVKFSRSADAPAYQQGQNQLYNELNLGRREEYDVLDKRRGRD<br>PEMGGKPRRKNPQEGLYNELQKDKMAEAYSEIGMKGERRRGKGH<br>DGLYQGLSTATKDTYDALHMQALPPR |

TABLE 3-continued

| SEQ Name | SEQ ID | AA |
| --- | --- | --- |
| CAR_H5_k4_AA (without leader) | 136 | QVQLVQSGAEVKKPGASVKVSCKASGYTFTSYHIQWVRQAPGQR LEWMGWIYPGDSTQYNEKFKGRVTITRDTSASTAYMELSSLRS EDMAVYYCAREGTYYAMDYWGQGTTVTVSSVDSSGGGGSGGGGS GGGGSTSDVVMTQSPLSLPVTLGQPASISCRSSQSIVHSNGNTY LEWYQQRPGQSPRLLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDKMAEAYSEIGMKGERRRGKGH DGLYQGLSTATKDTYDALHMQALPPR |
| CAR_H5_k5_AA (without leader) | 137 | QVQLVQSGAEVKKPGASVKVSCKASGYTFTSYHIQWVRQAPGQR LEWMGWIYPGDSTQYNEKFKGRVTITRDTSASTAYMELSSLRS EDMAVYYCAREGTYYAMDYWGQGTTVTVSSVDSSGGGGSGGGGS GGGGSTSDIVMTQTPLSSPVTLGQPASISFRSSQSIVHSNGNTY LEWYQQRPGQPPRLLIYKVSNRFSGVPDRFSGSGAGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDKMAEAYSEIGMKGERRRGKGH DGLYQGLSTATKDTYDALHMQALPPR |
| CAR_H6_k2_AA (without leader) | 138 | QVQLVQSGAEVKKPGASVKVSCKASGYTFTSYHIQWVRQAPGQR LEWMGWIYPGDSTKYSQKFQGRVTITRDTSASTAYMELSSLRS EDTAVYYCAREGTYYAMDYWGQGTTVTVSSVDSSGGGGSGGGGS GGGGSTSDIVMTQTPLSLSVTPGQPASISCRSSQSIVHSNGNTY LEWYLQKPGQSPQLLIYKVSNRFSGVPDRFSGSGSGTDFTLKIS RVEAEDVGVYYCFQGSHVPRTFGGGTKVEIKNRIRGVTVSSALS NSIMYFSHFVPVFLPAKPTTTPAPRPPTPAPTIASQPLSLRPEA CRPAAGGAVHTRGLDPFGFWVLVVVGGVLACYSLLVTVAFIIFW VRSKRSRLLHSDYMNMTPRRPGPTRKHYQPYAPPRDFAAYRSLE RVRVKFSRSADAPAYQQGQNQLYNELNLGRREEYDVLDKRRGRD PEMGGKPRRKNPQEGLYNELQKDKMAEAYSEIGMKGERRRGKGH DGLYQGLSTATKDTYDALHMQALPPR |
| CAR_H1_k2_AA | 213 | QVQLVQSGAEVKKPGASVKVSCKASGYTFTSYHIQWVRQAPGQR LEWMGWIYPGDSTQYNEKFKGRVTITRDTSASTAYMELSSLRS EDTAVYYCAREGTYYAMDYWGQGTTVTVSSGGGGSGGGGSGGGG SDIVMTQTPLSLSVTPGQPASISCRSSQSIVHSNGNTYLEWYLQ KPGQSPQLLIYKVSNRFSGVPDRFSGSGSGTDFTLKISRVEAED VGVYYCFQGSHVPRTFGGGTKVEIKRTTTPAPRPPTPAPTIASQ PLSLRPEACRPAAGGAVHTRGLDFACDIYIWAPLAGTCGVLLLS LVITLYCRSKRSRLLHSDYMNMTPRRPGPTRKHYQPYAPPRDFA AYRSRVKFSRSADAPAYQQGQNQLYNELNLGRREEYDVLDKRRG RDPEMGGKPRRKNPQEGLYNELQKDKMAEAYSEIGMKGERRRGK GHDGLYQGLSTATKDTYDALHMQALPPR |
| 4-1BB_AA (SEQ ID NO: 23 of U.S. Pat. No. 9,102,760) | 216 | KRGRKKLLYIFKQPFMRPVQTTQEEDGCSCRFPEEEEGGCEL |
| CD8 hinge AA (SEQ ID NO: 21 of U.S. Pat. No. 9,102,760) | 218 | TTTPAPRPPTPAPTIASQPLSLRPEACRPAAGGAVHTRGLDFAC DIY |
| CD8 hinge AA | 219 | TTTPAPRPPTPAPTIASQPLSLRPEACRPAAGGAVHTRGLDFAC D |
| CD8 transmembrane_AA (SEQ ID NO: 22 of U.S. Pat. No. 9,102,760) | 221 | IWAPLAGTCGVLLLSLVITLYC |
| CD8_transmembrane AA | 223 | IYIWAPLAGTCGVLLLSLVITLYC |

TABLE 4

| SEQ Name | SEQ ID | NT |
| --- | --- | --- |
| H1_k1_NT | 139 | ATGGATTTCCAAGTTCAAATCTTCAGTTTCTTGCTTATCAGTGC<br>TTCTGTTATTATGTCACGAGCAAGTCAAGTTCAACTCGTACAGT<br>CTGGAGCCGAGGTGAAAAAACCGGGAGCGTCCGTGAAAGTGAGT<br>TGCAAGGCGAGTGGATACACCTTCACTTCATACCATATACAATG<br>GGTTCGGCAGGCGCCTGGTCAACGGCTGGAATGGATGGGCTGGA<br>TTTATCCCGGAGATGGTTCCACGCAGTACAATGAGAAATTCAAA<br>GGGAGAGTGACAATCACCCGAGATACCAGTGCCTCTACGGCATA<br>TATGGAACTGAGTAGTCTGCGGTCTGAAGATACGGCGGTGTATT<br>ATTGTGCGAGAGAAGGGACGTACTACGCCATGGATTATTGGGGA<br>CAAGGAACAACAGTCACAGTCTCCAGCGTTGATTCCTCAGGCGG<br>GGGCGGAAGTGGGGCGGCGGATCTGGCGGCGGCGGGTCTACGT<br>CTGACGTGGTCATGACCCAATCTCCATTGTCTTTGCCAGTTACT<br>CTGGGACAGCCTGCAAGTATCAGTTGCCGATCCTCCCAATCTAT<br>CGTCCATTCAAACGGGAACACTTATTTGGAATGGTTTCAACAGA<br>GACCTGGGCAAAGTCCGCGCCGACTGATATATAAGGTCAGTAAC<br>CGCTTTTCAGGCGTCCCCGATCGATTCAGTGGATCTGGGTCAGG<br>GACTGACTTCACTCTGAAAATATCAAGAGTCGAAGCTGAAGATG<br>TCGGAGTATATTACTGTTTCCAGGGGTCTCACGTCCCTCGGACG<br>TTTGGAGGCGGAACTAAGGTTGAGATAAAA |
| H1_k2_NT | 140 | ATGGATTTTCAGGTTCAAATCTTTAGCTTTCTCTTGATTTCCGC<br>CTCCGTAATAATGAGTCGGGCCAGTCAGGTACAGCTCGTTCAAT<br>CTGGGGCTGAAGTAAAAAAGCCTGGAGCGTCTGTAAAGGTATCT<br>TGCAAAGCGAGCGGCTACACATTCACAAGTTATCACATCCAATG<br>GGTGAGACAGGCCCCAGGACAACGCTTGGAGTGGATGGGGTGGA<br>TTTACCCTGGCGACGGCAGCACACAGTACAATGAGAAATTTAAA<br>GGCCGGGTGACTATCACTCGGGACACCTCCGCCAGCACGGCTTA<br>TATGGAGCTTAGCAGTTTGAGATCCGAAGATACAGCGGTATATT<br>ACTGCGCGAGAGAAGGAACGTACTACGCTATGGACTATTGGGGT<br>CAGGGCACAACCGTTACAGTCTCCTCTGTGGACAGCTCCGGAGG<br>TGGGGGTTCAGGAGGGGGTGGAAGCGGTGGTGGTGGCAGTACAA<br>GCGATATAGTAATGACCCAAACCCCGCTCTCTCTGAGCGTCACG<br>CCAGGACAACCAGCATCAATCTCTTGCCGCAGTAGTCAATCCAT<br>CGTTCACTCTAATGGAAACACATACCTTGAGTGGTATCTTCAGA<br>AACCAGGTCAGAGCCCTCAGCTCCTCATCTATAAAGTCTCTAAC<br>CGGTTCTCAGGTGTTCCGGACCGGTTCAGTGGTTCCGGCTCAGG<br>AACAGACTTCACCTTGAAGATCAGTGAGTAGAAGCCGAAGACG<br>TGGGTGTATATTATTGCTTTCAGGGTTCCCACGTTCCGCGCACC<br>TTCGGCGGCGGGACCAAAGTTGAGATCAAA |
| H2_k1_NT | 141 | ATGGACTTTCAAGTCCAAATCTTCTCATTCCTCCTGATCTCTGC<br>GTCAGTAATCATGTCCAGAGCGTCACAAGTGCAACTCGTTCAAT<br>CCGGAGCTGAGGTAAAGAAGCCCGGCGCCAGCGTGAAAGTCTCC<br>TGCAAAGCGAGCGGCTACACGTTCACCTCATATCACATTCAATG<br>GGTAAGACAAGCACCTGGGCAACGACTCGAGTGGATGGGGTGGA<br>TCTACCCTGGGGACGGGAGCACGCAGTATAATGAGAAATTCAAA<br>GGCAGGGTTACAATTACAGCCGATACCAGTGCATCTACGGCTTA<br>TATGCTCCTCTCCTCACTCCGGTCTGAGGACACAGCGGTTTATT<br>ATTGCGCACGGGAGGGAACGTACTACGCGATGGACTATTGGGGG<br>CAAGGCACCACAGTTACAGTGAGCTCAGTTGACTCATCAGGAGG<br>CGGAGGATCAGGGGGAGGTGGTAGTGGGGGCGGTGGGAGCACAT<br>CAGATGTTGTCATGACTCAGAGCCCACTTTCTTTGCCGGTGACG<br>CTGGGGCAGCCCGCTTCAATCTCTTGCCGCTCATCACAGTCTAT<br>CGTTCATAGCAATGGTAACACTTACTTGGAATGGTTCCAACAAA<br>GACCGGGTCAAAGTCCACGGCGCTTGATATATAAAGTATCAAAT<br>AGATTTTCAGGGGTGCCTGATCGGTTCAGCGGTTCTGGATCTGG<br>CACCGACTTCACGCTTAAAATAAGTAGGGTAGAAGCCGAAGACG<br>TGGGAGTGTATTATTGTTTCCAGGGGTCACACGTCCCTCGCACG<br>TTCGGCGGAGGCACTAAAGTGGAGATCAAA |
| H2_k2_NT | 142 | ATGGACTTTCAAGTCCAAATCTTCAGCTTTCTCCTTATATCTGC<br>GTCTGTCATTATGAGTAGAGCAAGTCAAGTCCAGCTCGTACAAA<br>GTGGAGCTGAGGTGAAAAAGCCGGGCGCGAGTGTGAAAGTCTCA<br>TGCAAGGCGAGTGGATACACCTTTACCTCTTACCACATTCAATG<br>GGTGCGGCAGGCGCCTGGGCAGCGCTTGGAATGGATGGGCTGGA<br>TATATCCTGCGACGGAAGTACCCAGTACAACGAAAAATTCAAA<br>GGTAGGGTTACCATCACTGCTGATACCTCCGCGTCCACTGCTTA<br>TATGCTTCTTAGCTCCTTGCGAAGCGAGGATACAGCCGTGTATT<br>ATTGTGCCAGAGAGGGGACTTATTATGCCATGGACTATTGGGGT<br>CAGGGTACAACGGTCACTGTCTCATCTGTTGACAGTAGCGGGGG<br>AGGGGGGTCTGGAGGAGGGGGTTCCGGGGGGGGAGGTTCCACGA<br>GCGATATAGTTATGACGCAAACGCCCTTGAGCCTCAGTGTTACA<br>CCCGGTCAACCTGCCTCTATTAGCTGTCGCTCCTCCCAATCAAT<br>TGTGCATAGCAATGGAAATACCTACCTTGAATGGTATCTCCAAA<br>AGCCCGGGCAGAGTCCTCAACTTCTCATCTACAAAGTATCCAAT<br>CGATTCAGTGGCGTTCCTGACAGGTTCAGCGGAAGTGGGTCAGG<br>GACCGATTTTACCCTCAAAATTAGTCGCGTCGAAGCTGAGGATG |

TABLE 4-continued

| SEQ Name | SEQ ID | NT |
|---|---|---|
| | | TTGGGGTGTATTACTGCTTCCAAGGGTCACACGTACCACGCACA<br>TTCGGGGGAGGCACGAAGGTTGAAATTAAG |
| H1_k3_NT | 143 | ATGGATTTCCAAGTCCAAATATTCAGTTTCCTTTTGATAAGTGC<br>TTCAGTTATCATGTCCCGAGCAAGCCAGGTACAGCTTGTGCAAA<br>GCGGGGCGGAAGTTAAGAAACCGGGAGCCTCAGTTAAAGTATCT<br>TGCAAAGCCAGCGGTTATACATTCACTTCATACCACATACAGTG<br>GGTGCGCCAAGCACCGGGGCAGAGACTGGAATGGATGGGATGGA<br>TTTATCCCGGTGATGGTAGTACGCAATACAATGAAAAATTCAAA<br>GGAAGGGTGACTATCACGCGAGACACAAGCGCGTCCACGGCCTA<br>TATGGAACTGAGCAGTCTGAGATCCGAGGACACCGCTGTGTATT<br>ATTGCGCCCGAGAGGGGACCTACTACGCCATGGATTATTGGGGT<br>CAAGGGACCACTGTGACAGTCTCTTCTGTCGATTCCAGCGGCGG<br>AGGAGGGAGTGGAGGGGGTGGGTCCGGGGGGGAGGGTCTACGA<br>GCGACATTGTCATGACACAGACGCCGCTTAGCTCCCCAGTTACA<br>CTCGGACAGCCCGCAAGTATTAGTTGCAGAAGTAGCCAGTCTAT<br>CGTACATTCAAATGGAAACACCTATTTGGAATGGTATCAACAAC<br>GGCCTGGACAGCCGCCCAGGCTGCTCATATACAAAGTCTCCAAC<br>CGCTTCAGCGGAGTACCCGACCGCTTTTCCGGCTCCGGAGCAGG<br>AACTGACTTTACCTTGAAAATTAGTAGGGTCGAAGCAGAGGATG<br>TCGGGGTATATTATTGTTTCCAAGGTAGTCATGTCCCACGGACG<br>TTTGGTGGTGGGACGAAGGTTGAGATCAAA |
| H1_k4_NT | 144 | ATGGACTTCCAGGTGCAGATATTTCCTTTCTTCTCATATCTGC<br>ATCTGTAATAATGTCAAGGGCCAGCCAGGTCCAGCTCGTTCAAA<br>GCGGAGCCGAGGTAAAAAAACCAGGCGCTTCCGTCAAGGTATCA<br>TGCAAAGCGTCCGGCTATACCTTCACAAGTTACCATATCCAATG<br>GGTTCGACAGGCACCCGGACAAAGACTTGAATGGATGGGTTGGA<br>TATACCCCGGAGACGGCTCCACTCAGTATAACGAAAAGTTTAAG<br>GGGAGAGTCACGATCACTAGGGACACATCAGCTTCTACGGCGTA<br>TATGGAACTCAGTTCTTTGCGATCCGAGGATACTGCCGTATATT<br>ACTGCGCCAGAGAAGGCACGTACTACGCAATGGATTACTGGGGG<br>CAAGGGACAACTGTTACCGTCTCAAGCGTCGATTCATCAGGAGG<br>CGGAGGGTCCGGAGGTGGGGGATCTGGCGGTGGGGGTTCTACGT<br>CCGATGTTGTGATGACACAGTCCCCACTCTCTCTTCCAGTGACG<br>CTGGGACAGCCCGCGAGCATCTCCTGTCGCAGCTCTCAGTCCAT<br>AGTACACAGTAATGGTAACACCTATCTTGAGTGGTATCAGCAAC<br>GACCCGGTCAGTCTCCCAGGTTGCTTATTTATAAGGTTAGTAAC<br>CGCTTTTCAGGTGTTCCAGACAGATTTAGCGGGAGTGGTTCCGG<br>TACGGATTTCACATTGAAAATCAGCCGCGTCGAAGCCGAGGACG<br>TGGGTGTTTACTACTGCTTCCAGGGATCTCACGTACCGAGGACC<br>TTCGGCGGAGGAACGAAAGTAGAAATTAAG |
| H1_k5_NT | 145 | ATGGATTTTCAAGTACAAATCTTTTCCTTCCTGCTTATTTCCGC<br>AAGCGTTATTATGAGTAGAGCCAGCCAAGTACAACTGGTACAGT<br>CCGGCGCGGAGGTGAAGAAGCCCGGAGCAAGTGTGAAGGTATCT<br>TGCAAGGCGTCAGGCTATACCTTTACTTCATACCATATACAGTG<br>GGTGCGACAGGCTCCCGGCCAGCGACTCGAATGGATGGGCTGGA<br>TTTATCCCGGAGATGGATCTACGCAGTATAATGAGAAATTCAAG<br>GGTCGGGTCACGATTACACGAGACACGAGTGCTTCCACAGCTTA<br>TATGGAACTTTCTAGCCTGAGGTCTGAGGATACTGCCGTTTACT<br>ATTGTGCACGAGAAGGGACATACTATGCGATGGATTACTGGGGA<br>CAGGGCACCACTGTCACAGTTTCCAGCGTGGACTCAAGTGGAGG<br>CGGTGGATCTGGTGGTGGCGGGTCCGGGGGGGAGGCAGCACCA<br>GTGACATTGTAATGACTCAAACACCTCTCAGTAGCCCAGTCACT<br>CTCGGTCAGCCGGCGAGTATCTCTTTTAGGTCCTCACAATCTAT<br>AGTGCACTCTAACGGCAATACTTATCTTGAATGGTATCAACAAA<br>GACCGGGGCAGCCACCTCGCCTTCTCATCTACAAAGTAAGCAAT<br>CGCTTCTCCGGTGTCCCCGATCGCTTCTCCGGTTCAGGAGCAGG<br>AACTGACTTCACATTGAAGATTTCCAGAGTGGAGGCCGAAGACG<br>TAGGGGTATATTATTGCTTTCAAGGGTCCCATGTGCCCAGAACC<br>TTTGGGGGAGGAACGAAAGTTGAGATTAAA |
| H3_k2_NT | 146 | ATGGATTTCCAAGTGCAGATTTTCTCTTTTCTCCTCATAAGCGC<br>CTCCGTAATTATGTCTAGAGCTAGTCAAGTCCAATTGGTGCAAT<br>CCGGTGCCGAGGTTAAAAAGCCCGGCGCAAGTGTAAAAGTCTCC<br>TGTAAGGCCAGTGGCTACACTTTCACCAGCTACCATATACAGTG<br>GGTGCGGCAGGCGCCTGGTCAGGGTCTGGAGTGGATGGGTATTT<br>GGATTTATCCCGGAGATGGAAGTACTCAATACAATGAGAAATTC<br>AAGGGTGTCACTATGACAAGGGATACGAGCACTTCTACCGTATA<br>TATGGAGTTGTCATCTTTGCGATCAGAGGATACCGCTGTATATT<br>ATTGCGCACGGGAAGGTACATATTATGCCATGGACTACTGGGGC<br>CAAGGAACCACCGTGACGGTAAGCTCTGTCGATTCTAGCGGTGG<br>CGGGGGCTCTGGCGGTGGGGTAGCGGGGGTGGCGGATCTACAT<br>CAGATATTGTAATGACACAGACCCCTCTTTCACTTTCCGTAACG<br>CCAGGACAGCCGGCATCAATAAGTTGCCGATCAAGCCAGTCTAT<br>CGTACACTCCAATGGTAACACATACTTGGAATGGTATCTTCAAA |

TABLE 4-continued

| SEQ Name | SEQ ID | NT |
|---|---|---|
| | | AGCCCGGCCAGAGCCCGCAGCTTTTGATATATAAAGTGTCCAAC AGATTCAGTGGGGTGCCGGACCGCTTTAGTGGATCTGGTTCAGG AACGGACTTCACATTGAAAATTAGTAGAGTTGAAGCGGAAGACG TGGGAGTCTACTACTGTTTCCAGGGTTCACATGTGCCTCGGACC TTTGGGGGAGGCACCAAGGTTGAGATAAAA |
| H3_k3_NT | 147 | ATGGACTTCCAAGTCCAAATCTTTTCTTTTTTGTTGATAAGCGC ATCAGTTATTATGTCTCGCGCCAGTCAAGTACAACTGGTGCAGT CCGGAGCTGAAGTGAAAAAACCAGGAGCAAGCGTGAAAGTAAGT TGTAAGGCAAGTGGTTACACTTTCACAAGCTACCATATTCAATG GGTCCGACAGGCTCCTGGACAGGGCTTGGAGTGGATGGGCATAT GGATTTACCCTGGTGACGGGTCCACCCAGTATAATGAAAAGTTC AAGGGAGTCACGATGACCAGGGACACCTCTACATCTACCGTGTA TATGGAGCTCTCTAGTTTGCGATCCGAAGACACTGCCGTTTATT ACTGTGCAAGAGAAGGAACTTATTACGCGATGGACTACTGGGGT CAGGGGACAACAGTCACCGTTAGCTCCGTCGATTCCAGCGGGGG AGGTGGCTCAGGCGGGGGTGGTTCTGGGGGGGCGGGAGCACTT CAGATATTGTAATGACCCAAACCCCACTGAGTAGTCCAGTCACG CTTGGTCAACCGGCAAGCATTTCTTGCAGGAGCTCTCAGAGTAT TGTCCACTCTAACGGGAATACATATTTGGAGTGGTATCAGCAAA GACCGGGCCAACCACCACGCCTCTTGATTTATAAGGTGAGCAAT AGGTTTTCAGGCGTGCCAGATAGGTTCTCAGGCTCCGGAGCGGG AACCGACTTCACCCTCAAGATAAGTCGGGTGGAAGCCGAAGACG TAGGAGTTTACTACTGCTTTCAAGGATCTCATGTTCCACGAACG TTTGGAGGAGGAACCAAGGTGGAAATAAAA |
| H3_k4_NT | 148 | ATGGACTTTCAGGTCCAAATTTTTTCCTTCTTGCTCATATCCGC GAGTGTCATCATGTCAAGAGCAAGTCAAGTTCAACTCGTTCAAT CAGGAGCTGAGGTGAAAAAACCAGGGGCGTCTGTCAAAGTAAGC TGCAAAGCATCAGGGTATACGTTCACGAGTTATCATATCCAGTG GGTTAGGCAGGCGCCAGGGCAGGGATTGGAATGGATGGGTATCT GGATTTACCCGGGTGACGGCAGCACTCAATACAATGAGAAATTC AAAGGCGTAACAATGACAAGGGACACGAGCACAAGCACAGTGTA CATGGAGCTTAGCTCTTTGAGGTCAGAGGATACCGCTGTTTACT ATTGTGCTCGGGAGGGTACTTACTATGCAATGGACTACTGGGGG CAAGGCACGACCGTTACAGTGAGTAGCGTAGATTCCTCCGGGGG TGGCGGTTCAGGCGGCGGAGGCTCAGGCGGAGGAGGGTCAACAT CCGATGTCGTAATGACTCAGTCCCCTCTGTCATTGCCGGTGACT TTGGGACAGCCAGCGTCTATATCTTGTAGGTCCTCTCAATCAAT AGTGCATTCCAACGGTAACACCTATCTGGAATGGTATCAGCAAA GGCCAGGACAAAGTCCACGCCTGCTTATATATAAGGTGTCTAAT CGATTCAGTGGGGTTCCCGATAGGTTTTCCGGCTCTGGTAGCGG GACTGATTTCACGTTGAAAATATCACGCGTGGAAGCGGAAGATG TTGGGGTCTATTACTGCTTTCAGGGTAGTCATGTCCCTCGAACT TTTGGCGGTGGTACAAAGGTAGAAATCAAA |
| H3_k5_NT | 149 | ATGGATTTTCAGGTACAGATATTCTCATTTCTCCTTATCTCAGC TAGTGTCATAATGTCCAGGGCGAGTCAAGTACAACTTGTCCAGT CAGGCGCAGAGGTCAAGAAGCCGGGCGCAAGCGTTAAGGTTTCC TGCAAAGCATCCGGCTATACATTCACGTCCTATCACATCCAATG GGTCAGGCAAGCACCCGGTCAAGGACTTGAGTGGATGGGCATCT GGATTTACCCTGGAGATGGCAGTACTCAGTACAACGAAAAATTC AAAGGTGTAACCATGACCCGCGACACATCTACTTCCACAGTTTA TATGGAACTCAGCAGTTTGCGGAGCGAAGATACCGCTGTTTACT ACTGTGCCCGAGAGGGAACTTACTACGCCATGGACTATTGGGGT CAAGGAACGACAGTAACAGTTAGTTCTGTAGATTCCAGTGGCGG CGGTGGGAGCGGGGGTGGGGATCTGGCGGAGGCGGAAGTACAA GTGACATCGTTATGACTCAGACACCCCTTAGTAGTCCCGTTACG TTGGGCCAACCCGCGAGCATTTCCTTTCGATCCTCTCAGTCTAT AGTTCACTCAAATGGGAATACTTATTTGGAGTGGTATCAACAGC GCCCCGGACAACCACCAAGGCTCCTGATATACAAGGTGTCCAAT CGATTCTCTGGGGTGCCTGATAGATTTAGCGGAAGTGGAGCCGG TACAGATTTTACCCTGAAAATATCACGGGTAGAAGCCGAAGATG TCGGCGTCTACTACTGTTTCCAGGGTTCCCATGTACCGCGAACG TTCGGGGGCGGAACAAAAGTTGAGATCAAG |
| H4_k2_NT | 150 | ATGGATTTCCAGGTTCAGATATTTAGTTTCCTCTTGATTTCTGC CAGTGTCATCATGAGCAGGGCTTCCCAAGTTCAGTTGGTGCAAA GTGGCGCTGAAGTCAAAAAACCTGGGGCTTCCGTTAAAGTATCT TGCAAGGCGTCCGGCTACACTTTCACATCCTACCACATTCAATG GGTCCGGCAAGCGCCCGGTCAGGGGCTCGAATGGATGGGGTGGA TATACCCAGGAGATGGATCTACTCAGTACAACGAGAAATTTAAA GGACGGGTGACGATGACGCGCGACACTTCAATAAGCACTGCATA CATGGAACTGTCCCGGCTTAGGTCAGATGACACCGCGGTCTACT ATTGTGCGAGAGAGGGTACTTACTATGCTATGGACTACTGGGGG CAAGGCACGACCGGTTACAGTTTCCTCAGTCGATAGTTCAGGCGG AGGCGGCTCCGGGGGCGGTGGTAGTGGAGGGGGTGGATCTACTT |

TABLE 4-continued

| SEQ Name | SEQ ID | NT |
|---|---|---|
| | | CCGACATTGTCATGACCCAGACCCCGTTGAGCCTTTCAGTGACG<br>CCCGGTCAACCCGCCAGCATAAGTTGTCGATCAAGCCAGTCTAT<br>TGTACACTCCAATGGAAACACATATTTGGAGTGGTATCTCCAAA<br>AACCCCGGCCAAAGCCCTCAACTGCTCATCTACAAGGTCTCAAAC<br>AGGTTTAGCGGGGTCCCGGATCGCTTCTCAGGGTCAGGATCTGG<br>TACGGACTTTACACTGAAAATTTCCCGAGTCGAAGCGGAAGACG<br>TGGGTGTATATTACTGCTTCCAGGGGAGTCATGTTCCAAGAACC<br>TTTGGGGGAGGTACAAAGGTCGAAATAAAA |
| H4_k3_NT | 151 | ATGGATTTTCAGGTCCAAATTTTTTCCTTCTTGCTTATCAGCGC<br>AAGTGTAATCATGTCCCGCGCGTCCCAAGTACAACTTGTGCAAT<br>CTGGCGCGGAGGTGAAAAAACCTGGAGCTTCCGTCAAGGTTTCT<br>TGTAAGGCCTCTGGCTACACCTTCACGTCCTACCACATTCAGTG<br>GGTTCGACAGGCGCCGGGCCAAGGACTGGAGTGGATGGGATGGA<br>TATATCCAGGAGATGGTTCTACTCAGTATAATGAGAAATTCAAG<br>GGTCGCGTAACAATGACGAGGGATACATCAATCTCCACCGCGTA<br>CATGGAACTTTCAAGACTCCGGTCAGATGACACGGCGGTTTACT<br>ACTGTGCTCGGGAGGGCACTTACTATGCTATGGACTACTGGGGG<br>CAAGGGACAACGGTAACGGTATCTAGTGTGGATTCTAGTGGCGG<br>CGGCGGTTCAGGAGGAGGTGGTTCAGGCGGGGGGGGTAGTACAA<br>GTGATATTGTGATGACCCAAACACCCCTTTCTAGCCCTGTTACT<br>CTGGGTCAACCCGCGTCCATAAGTTGTCGAAGTAGTCAATCCAT<br>CGTGCATAGCAACGGCAACACTTACCTTGAATGGTATCAACAAC<br>GACCCGGACAGCCCCGCGACTGCTTATCTATAAAGTATCAAAC<br>AGGTTCAGTGGCGTGCCAGATCGATTCTCCGGCTCTGGGCAGG<br>CACAGATTTCACGTTGAAAATTTCTCGGGTCGAGGCCGAGGACG<br>TGGGCGTTTATTACTGTTTCCAGGGGAGTCACGTCCCCAGGACG<br>TTCGGAGGAGGAACTAAAGTCGAAATAAAG |
| H4_k4_NT | 152 | ATGGACTTCCAGGTCCAAATATTCAGCTTCCTCCTCATTTCCGC<br>CAGTGTAATAATGTCCAGAGCCTCACAAGTACAGTTGGTTCAGA<br>GCGGGGCTGAGGTTAAGAAACCAGGCGCGAGCGTCAAGGTATCC<br>TGCAAGGCGAGTGGTTATACTTTCACTAGTTATCACATTCAGTG<br>GGTCCGACAGGCCCCCGGTCAAGGCCTGGAGTGGATGGGGTGGA<br>TATATCCGGGAGATGGTTCTACCCAATATAATGAGAAGTTTAAG<br>GGGAGAGTCACAATGACAAGGGACACCAGTATTAGCACCGCGTA<br>TATGGAGCTTTCCCGCCTGCGATCAGATGACACGGCCGTGTACT<br>ACTGTGCTAGGGAGGGAACCTATTATGCGATGGATTACTGGGGA<br>CAGGGTACTACAGTCACGGTCTCTAGCGTGGACAGTTCCGGGGG<br>CGGTGGAAGCGGTGGTGGCGGTTCAGGTGGAGGAGGCTCTACGA<br>GTGATGTTGTGATGACTCAGTCCCCGCTTTCACTTCCCGTCACC<br>CTTGGGCAACCCGCAAGCATCTCATGCCGATCCTCCCAGTCTAT<br>AGTACATAGTAATGCAACACATATCTTGAATGGTATCAGCAGA<br>GGCCGGGTCAGTCTCCCCGACTCCTTATATATAAAGTGAGCAAC<br>AGATTCTCCGGAGTACCGGATAGATTTTCCGGCTCTGGGAGCGG<br>CACCGACTTTACACTGAAAATTTCACGGGTTGAAGCTGAAGATG<br>TTGGGGTATACTATTGTTTCCAGGGTTCTCACGTCCCGAGGACA<br>TTCGGGGGAGGAACGAAAGTCGAAATAAAG |
| H4_k5-NT | 153 | ATGGATTTTCAGGTACAAATCTTCAGCTTCCTGCTCATCTCCGC<br>GAGCGTAATCATGTCTAGGGCGTCCCAGGTGCAGTTGGTGCAAT<br>CAGGTGCAGAGGTGAAGAAGCCTGGTGCATCCGTTAAAGTAAGT<br>TGTAAGGCAAGCGGATATACTTTTACATCCTATCATATTCAATG<br>GGTCAGACAAGCACCTGGACAGGGTCTTGAGTGGATGGGCTGGA<br>TCTATCCAGGCGATGGCTCAACTCAATATAACGAGAAGTTCAAG<br>GGGAGGGTTACTATGACCAGGGATACGTCTATTTCCACTGCGTA<br>CATGGAACTCTCCAGGTTGAGAAGTGATGATACCGCGGTTTACT<br>ACTGCGCTAGAGAAGGAACGTACTACGCTATGGATTACTGGGGG<br>CAGGGTACAACTGTCACCGTCTCAAGTGTGGATTCTTCTGGGGG<br>TGGGGGATCAGGAGGGGAGGCTCCGGTGGGGCGGGTCAACCA<br>GCGACATTGTCATGACTCAAACCCCCCTGAGCAGCCCTGTCACC<br>CTGGGTCAGCCTGCCTCAATATCCTTTAGAAGCTCCCAAAGCAT<br>CGTCCATTCAAATGGTAATACCTATCTGGAGTGGTATCAGCAAA<br>GGCCTGGTCAACCCCCGCGCCTTCTCATTTACAAGGTGTCAAAC<br>AGGTTCTCCGGCGTACCGGATAGGTTTTCCGGAAGCGGTGCTGG<br>AACCGACTTTACTCTCAAAATCTCTAGGGTGGAAGCTGAGGACG<br>TCGGTGTATACTATTGTTTTCAAGGCTCCCATGTTCCCAGGACA<br>TTTGGTGGGGAACGAAGGTAGAAATCAAG |
| H5_k2_NT | 154 | ATGGACTTTCAGGTTCAGATTTTCTCTTTCTTGTTGATCTCCGC<br>TAGTGTCATAATGTCACGGGCAAGTCAGGTACAACTCGTTCAGA<br>GTGGTGCCGAAGTGAAGAAACCGGGTGCCTCCGTAAAGGTGTCA<br>TGTAAAGCTAGTGGCTATACATTCACAAGTTATCATATCCAATG<br>GGTACGACAAGCACCGGGACAGCGACTGGAATGGATGGGATGGA<br>TCTATCCTGGGGACGGATCTACACAGTACAATGAGAAATTTAAG<br>GGACGGGTCACGATAACCAGGGACACATCTGCTTCCACGGCTTA<br>CATGGAGCTTTCCTCCCTGCGGAGCGAGGACATGGCTGTTTACT |

TABLE 4-continued

| SEQ Name | SEQ ID | NT |
|---|---|---|
| | | ATTGCGCTCGCGAAGGGACATACTACGCAATGGATTATTGGGGC<br>CAAGGCACTACCGTGACGGTCTCTTCTGTCGATAGTTCCGGAGG<br>AGGTGGTTCAGGGGGAGGCGGTTCAGGTGGGGGTGGATCTACCT<br>CAGATATTGTCATGACACAGACACCTTTGTCCTTGAGTGTGACA<br>CCGGGTCAACCGGCGAGTATAAGCTGTCGCAGCTCACAATCTAT<br>TGTGCATAGCAACGGGAATACATATCTCGAATGGTATCTCCAAA<br>AGCCGGGCCAATCCCCCCAACTTCTCATTTACAAAGTTTCTAAT<br>CGATTTTCAGGTGTACCAGATCGGTTTTCCGGGTCTGGCTCAGG<br>TACTGACTTCACCTTGAAAATATCAAGGGTTGAAGCTGAGGATG<br>TAGGTGTGTACTATTGCTTCCAGGGGTCTCACGTTCCTCGGACT<br>TTTGGGGGGGGCACAAAAGTAGAGATTAAA |
| H5_k3_NT | 155 | ATGGATTTCCAGGTGCAAATCTTCTCATTTCTTTTGATAAGTGC<br>GTCAGTGATAATGTCTCGGGCCAGTCAAGTACAGCTTGTCCAAA<br>GTGGCGCTGAAGTCAAGAAGCCGGGAGCCTCAGTTAAGGTTAGC<br>TGCAAGGCCTCAGGGTATACTTTTACCTCCTATCATATACAGTG<br>GGTACGACAAGCACCGGGACAGCGACTGGAGTGGATGGGTTGGA<br>TATATCCGGGAGATGGTTCAACCCAGTATAATGAGAAGTTCAAG<br>GGGCGAGTTACGATAACCCGCGATACGAGTGCATCAACAGCGTA<br>CATGGAGTTGAGTTCCCTCCGCAGCGAGGACATGGCGGATACT<br>ATTGTGCCAGGGAGGGGACTTATTATGCCATGGACTACTGGGGG<br>CAGGGCACAACCGTAACAGTCTCTTCTGTAGACAGTTCAGGAGG<br>GGGCGGAAGTGGAGGTGGCGGATCTGGTGGAGGTGGATCTACTT<br>CCGACATCGTTATGACCCAAACACCACTTTCATCTCCCGTTACT<br>CTCGGGCAACCTGCTAGTATTTCCTGTAGATCCTCACAATCTAT<br>AGTACATAGCAATGGCAATACCTACCTGGAGTGGTATCAACAAC<br>GCCCAGGCCAACCACCTCGCCTGCTTATCTATAAAGTAAGCAAT<br>AGATTCAGTGGTGTACCGGATAGGTTCTCTGGTTCCGGAGCAGG<br>AACTGACTTTACACTCAAAATCAGTAGGGTGGAGGCGGAAGACG<br>TGGGAGTATATTATTGCTTTCAAGGTTCACATGTACCTCGAACA<br>TTTGGCGGAGGAACTAAGGTTGAGATTAAA |
| H5_k4-NT | 156 | ATGGATTTCCAAGTCCAGATATTCAGTTTTCTTTTGATAAGCGC<br>TTCTGTAATCATGTCTCGGGCGTCCCAAGTACAACTGGTGCAAT<br>CAGGGGCAGAAGTGAAAAAACCAGGTGCATCCGTTAAGGTGAGT<br>TGCAAGGCTTCCGGCTATACCTTTACATCATATCATATTCAATG<br>GGTCAGGCAAGCACCTGGTCAGCGATTGGAATGGATGGGTTGGA<br>TATATCCTGGTGATGGGTCTACACAATATAACGAAAAATTCAAG<br>GGGCGAGTGACCATCACAAGAGATACATCAGCGTCAACAGCGTA<br>TATGGAACTGTCATCCCTTAGATCAGAGGACATGGCGGTCTATT<br>ACTGTGCCAGAGAAGGCACTTATTATGCAATGGATTATTGGGGA<br>CAAGGAACCACTGTCACTGTTTCCAGCGTAGACTCCTCCGGTGG<br>TGGTGGAAGTGGCGGCGGTGGGTCAGGAGGGGGTGGGTCAACTT<br>CTGATGTAGTGATGACACAGAGCCCTCTGAGCTTGCCTGTGACC<br>TTGGGTCAGCCGGCCTCAATAAGTTGTCGATCTAGTCAGTCAAT<br>CGTCCATAGTAATGGGAACACATACCTTGAATGGTATCAGCAAA<br>GACCTGGACAATCTCCACGACTCCTTATATACAAAGTTAGCAAC<br>CGATTTAGCGGAGTGCCAGACCGCTTTTCTGGTTCCGGGTCTGG<br>CACAGATTTTACCCTTAAGATCTCCCGCGTGGAGGCGGAAGACG<br>TTGGTGTTTACTATTGCTTCCAGGGGTCACACGTTCCACGCACC<br>TTTGGAGGAGGTACGAAGGTCGAGATTAAG |
| H5_k5_NT | 157 | ATGGATTTTCAAGTACAGATCTTCTCTTTCTTGCTTATTTCAGC<br>GAGCGTAATCATGAGTAGGGCATCTCAAGTTCAACTCGTTCAGT<br>CAGGTGCTGAGGTAAAAAAACCAGGGGCTTCCGTTAAAGTTAGC<br>TGTAAGGCATCTGGGTACACATTTACTAGCTACCATATCCAGTG<br>GGTGCGACAAGCCCCGGGGCAGCGCTTGGAATGGATGGGCTGGA<br>TTTACCCAGGTGACGGCTCCACGCAATATAATGAGAAATTTAAG<br>GGTAGAGTTACTATTACCAGGGACACAAGTGCTTCAACTGCCTA<br>TATGGAACTGAGCAGCCTTCGGAGTGAAGATATGGCCGTATATT<br>ACTGCGCAAGGGAGGGGACTTACTATGCAATGGACTACTGGGGT<br>CAGGGAACGACTGTGACCGTGTCCTCAGTTGACTCCAGCGGTGG<br>TGGCGGCTCTGGAGGTGGGGGTTCCGGCGGAGGCGGAAGCACAT<br>CTGATATAGTGATGACGCAAACGCCTCTTTCTTCCCCGGTAACT<br>CTGGGACAGCCAGCGTCAATTTCATTTAGGTCCTCCCAGTCAAT<br>CGTACATAGTAATGGAAATACTTACCTGGAATGGTATCAACAAC<br>GACCAGGGCAACCGCCCCGATTGTTGATCTATAAAGTGAGCAAT<br>CGCTTTTCTGGCGTGCCCGATCGGTTCTCAGGGTCTGGAGCTGG<br>GACTGACTTCACATTGAAAATTTCCAGGGTTGAGGCCGAGGATG<br>TGGGGGTTATTACTGCTTCCAAGGCTCCCACGTCCCCCGCACC<br>TTCGGAGGGGGAACCAAAGTCGAAATAAAG |
| H6_k2_NT | 158 | ATGGATTTTCAAGTTCAGATATTCTCATTTTTGCTTATATCAGC<br>CTCCGTAATTATGTCACGGGCAAGTCAAGTTCAGTTGGTGCAGT<br>CCGGAGCAGAAGTTAAGAAGCCCGGTGCTTCTGTGAAAGTCTCC<br>TGCAAAGCGTCTGGGTACACCTTCACGAGCTACCATATACAGTG<br>GGTCCGGCAAGCGCCTGGGCAGAGGCTGGAGTGGATGGGCTGGA |

TABLE 4-continued

| SEQ Name | SEQ ID | NT |
|---|---|---|
| | | TTTACCCAGGAGATGGGAGTACAAAGTATAGTCAGAAGTTTCAA<br>GGGCGAGTGACGATAACCAGAGATACGAGTGCAAGTACTGCATA<br>CATGGAACTGAGCTCCTTGAGGTCCGAGGATACAGCGGTGTACT<br>ATTGCGCTCGGGAAGGGACATATTATGCTATGGACTATTGGGGA<br>CAAGGGACAACGGTAACGGTGAGTTCCGTCGATTCCTCAGGTGG<br>CGGAGGCAGTGGGGGCGGGGGTTCCGGCGGTGGCGGGTCCACGA<br>GTGATATAGTTATGACACAGACCCCCCTCAGCCTTTCTGTGACC<br>CCAGGACAACCCGCTAGTATCTCTTGCCGCAGTTCTCAGTCCAT<br>AGTACACAGTAACGGAAATACCTATCTTGAGTGGTATCTTCAAA<br>AGCCCGGCCAGAGCCCTCAACTCTTGATATATAAAGTGTCAAAT<br>CGATTTTCAGGTGTGCCTGATCGATTCTCAGGGTCTGGTTCAGG<br>GACAGATTTCACGCTTAAGATAAGCAGAGTAGAGGCTGAAGACG<br>TGGGAGTCTACTATTGTTTTCAGGGGTCACACGTTCCCCGCACT<br>TTTGGTGGGGGAACCAAGGTGGAAATCAAA |
| CD8 hinge | 159 | TCTTCAGCGCTGAGCAACTCCATCATGTACTTCAGCCACTTCGT<br>GCCGGTCTTCCTGCCAGCGAAGCCCACCACGACGCCAGCGCCGC<br>GACCACCAACACCGGCGCCCACCATCGCGTCGCAGCCCCTGTCC<br>CTGCGCCCAGAGGCGTGCCGGCCAGCGGCGGGGGCGCAGTGCA<br>CACGAGGGGGCTGGAC |
| CD28 TM | 160 | TTTTGGGTGCTGGTGGTGGTTGGTGGAGTCCTGGCTTGCTATAG<br>CTTGCTAGTAACAGTGGCCTTTATTATTTTCTGGGTG |
| CD28 IC | 161 | AGGAGTAAGAGGAGCAGGCTCCTGCACAGTGACTACATGAACAT<br>GACTCCCCGCCGCCCCGGGCCCACCCGCAAGCATTACCAGCCCT<br>ATGCCCCACCACGCGACTTCGCAGCCTATCGCTCC |
| CD3z | 162 | AGAGTGAAGTTCAGCAGGAGCGCAGACGCCCCCGCGTACCAGCA<br>GGGCCAGAACCAGCTCTATAACGAGCTCAATCTAGGACGAAGAG<br>AGGAGTACGATGTTTTGGACAAGAGACGTGGCCGGGACCCTGAG<br>ATGGGGGGAAAGCCGAGAAGGAAGAACCCTCAGGAAGGCCTGTA<br>CAATGAACTGCAGAAAGATAAGATGGCGGAGGCCTACAGTGAGA<br>TTGGGATGAAAGGCGAGCGCCGGAGGGGCAAGGGGCACGATGGC<br>CTTTACCAGGGTCTCAGTACAGCCACCAAGGACACCTACGACGC<br>CCTTCACATGCAGGCCCTGCCCCCTCGC |
| CAR_H1_k1_NT | 163 | ATGGATTTCCAAGTTCAAATCTTCAGTTTCTTGCTTATCAGTGC<br>TTCTGTTATTATGTCACGAGCAAGTCAAGTTCAACTCGTACAGT<br>CTGGAGCCGAGGTGAAAAAACCGGGAGCGTCCGTGAAAGTGAGT<br>TGCAAGGCGAGTGGATACACCTTCACTTCATACCATATACAATG<br>GGTTCGGCAGGCGCCTGGTCAACGGCTGGAATGGATGGGCTGGA<br>TTTATCCCGGAGATGGTTCCACGCAGTACAATGAGAAATTCAA<br>GGGAGAGTGACAATCACCCGAGATACCAGTGCCTCTACGGCATA<br>TATGGAACTGAGTAGTCTGCGGTCTGAAGATACGGCGGTGTATT<br>ATTGTGCGAGAGAAGGGACGTACTACGCCATGGATTATTGGGGA<br>CAAGGAACAACAGTCACAGTCTCCAGCGTTGATTCCTCAGGCGG<br>GGGCGGAAGTGGGGGCGGCGGATCTGGCGGCGGCGGGTCTACGT<br>CTGACGTGGTCATGACCCAATCTCCATTGTCTTTGCCAGTTACT<br>CTGGGACAGCCTGCAAGTATCAGTTGCCGATCCTCCCAATCTAT<br>CGTCCATTCAAACGGGAACACTTATTTGGAATGGTTTCAACAGA<br>GACCTGGGCAAAGTCCGCGCCGACTGATATATAAGGTCAGTAAC<br>CGCTTTTCAGGCGTCCCCGATCGATTCAGTGGATCTGGGTCAGG<br>GACTGACTTCACTCTGAAAATATCAAGAGTCGAAGCTGAAGATG<br>TCGGAGTATATTACTGTTTCCAGGGGTCTCACGTCCCTCGGACG<br>TTTGGAGGCGAACTAAGGTTGAGATAAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>CGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H1_k2_NT | 164 | ATGGATTTTCAGGTTCAAATCTTTAGCTTTCTCTTGATTTCCGC<br>CTCCGTAATAATGAGTCGGGCCAGTCAGGTACAGCTCGTTCAAT |

TABLE 4-continued

| SEQ Name | SEQ ID | NT |
|---|---|---|
| | | CTGGGGCTGAAGTAAAAAAGCCTGGAGCGTCTGTAAAGGTATCT
TGCAAAGCGAGCGGCTACACATTCACAAGTTATCACATCCAATG
GGTGAGACAGGCCCCAGGACAACGCTTGGAGTGGATGGGGTGGA
TTTACCCTGGCGACGGCAGCACACAGTACAATGAGAAATTTAAA
GGCCGGGTGACTATCACTCGGGACACCTCCGCCAGCACGGCTTA
TATGGAGCTTAGCAGTTTGAGATCCGAAGATACAGCGGTATATT
ACTGCGCGAGAGAAGGAACGTACTACGCTATGGACTATTGGGGT
CAGGGCACAACCGTTACAGTCTCCTCTGTGGACAGCTCCGGAGG
TGGGGGTTCAGGAGGGGGTGGAAGCGGTGGTGGTGGCAGTACAA
GCGATATAGTAATGACCCAAACCCCGCTCTCTCTGAGCGTCACG
CCAGGACAACCAGCATCAATCTCTTGCCGCAGTAGTCAATCCAT
CGTTCACTCTAATGGAAACACATACCTTGAGTGGTATCTTCAGA
AACCAGGTCAGAGCCCTCAGCTCCTCATCTATAAAGTCTCTAAC
CGGTTCTCAGGTGTTCCGGACCGGTTCAGTGGTTCCGGCTCAGG
AACAGACTTCACCTTGAAGATCAGTCGAGTAGAAGCCGAAGACG
TGGGTGTATATTATTGCTTTCAGGGTTCCCACGTTCCGCGCACC
TTCGGCGGCGGGACCAAAGTTGAGATCAAAAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CAR_H2_k1_NT | 165 | ATGGACTTTCAAGTCCAAATCTTCTCATTCCTCCTGATCTCTGC
GTCAGTAATCATGTCCAGAGCGTCACAAGTGCAACTCGTTCAAT
CCGGAGCTGAGGTAAAGAAGCCCGGCGCCAGCGTGAAAGTCTCC
TGCAAAGCGAGCGGCTACACGTTCACCTCATATCACATTCAATG
GGTAAGACAAGCACCTGGGCAACGACTCGAGTGGATGGGGTGGA
TCTACCCTGGGACGGGAGCACGCAGTATAATGAGAAATTCAAA
GGCAGGGTTACAATTACAGCCGATACCAGTGCATCTACGGCTTA
TATGCTCCTCTCCTCACTCCGGTCTGAGGACACAGCGGTTTATT
ATTGCGCACGGGAGGGAACGTACTACGCGATGGACTATTGGGGG
CAAGGCACCACAGTTACAGTGAGCTCAGTTGACTCATCAGGAGG
CGGAGGATCAGGGGGAGGTGGTAGTGGGGGCGGTGGGAGCACAT
CAGATGTTGTCATGACTCAGAGCCCACTTTCTTTGCCGGTGACG
CTGGGGCAGCCCGCTTCAATCTCTTGCCGCTCATCACAGTCTAT
CGTTCATAGCAATGGTAACACTTACTTGGAATGGTTCCAACAAA
GACCGGGTCAAAGTCCACGGCGCTTGATATATAAAGTATCAAAT
AGATTTTCAGGGGTGCCTGATCGGTTCAGCGGTTCTGGATCTGG
CACCGACTTCACGCTTAAAATAAGTAGGGTAGAAGCCGAAGACG
TGGGAGTGTATTATTGTTTCCAGGGGTCACACGTCCCTCGCACG
TTCGGCGGAGGCACTAAAGTGGAGATCAAAAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CAR_H2_k2_NT | 166 | ATGGACTTTCAAGTCCAAATCTTCAGCTTTCTCCTTATATCTGC
GTCTGTCATTATGAGTAGAGCAAGTCAAGTCCAGCTCGTACAAA
GTGGAGCTGAGGTGAAAAAGCCGGGCGCGAGTGTGAAAGTCTCA |

TABLE 4-continued

| SEQ Name | SEQ ID | NT |
|---|---|---|
| | | TGCAAGGCGAGTGGATACACCTTTACCTCTTACCACATTCAATG<br>GGTGCGGCAGGCGCCTGGGCAGCGCTTGGAATGGATGGGCTGGA<br>TATATCCTGGCGACGGAAGTACCCAGTACAACGAAAAATTCAAA<br>GGTAGGGTTACCATCACTGCTGATACCTCCGCGTCCACTGCTTA<br>TATGCTTCTTAGCTCCTTGCGAAGCGAGGATACAGCCGTGTATT<br>ATTGTGCCAGAGAGGGGACTTATTATGCCATGGACTATTGGGGT<br>CAGGGTACAACGGTCACTGTCTCATCTGTTGACAGTAGCGGGGG<br>AGGGGGGTCTGGAGGAGGGGGTTCCGGGGGGGGAGGTTCCACGA<br>GCGATATAGTTATGACGCAAACGCCCTTGAGCCTCAGTGTTACA<br>CCCGGTCAACCTGCCTCTATTAGCTGTCGCTCCTCCCAATCAAT<br>TGTGCATAGCAATGGAAATACCTACCTTGAATGGTATCTCCAAA<br>AGCCCGGGCAGAGTCCTCAACTTCTCATCTACAAAGTATCCAAT<br>CGATTCAGTGGCGTTCCTGACAGGTTCAGCGGAAGTGGGTCAGG<br>GACCGATTTTACCCTCAAAATTAGTCGCGTCGAAGCTGAGGATG<br>TTGGGGTGTATTACTGCTTCCAAGGGTCACACGTACCACGCACA<br>TTCGGGGGAGGCACGAAGGTTGAAATTAAGAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H1_k3_NT | 167 | ATGGATTTCCAAGTCCAAATATTCAGTTTCCTTTTGATAAGTGC<br>TTCAGTTATCATGTCCCGAGCAAGCCAGGTACAGCTTGTGCAAA<br>GCGGGGCGGAAGTTAAGAAACCGGGAGCCTCAGTTAAAGTATCT<br>TGCAAAGCCAGCGGTTATACATTCACTTCATACCACATACAGTG<br>GGTGCGCCAAGCACCGGGCAGAGACTGGAATGGATGGGATGGA<br>TTTATCCCGGTGATGGTAGTACGCAATACAATGAAAAATTCAAA<br>GGAAGGGTGACTATCACGCGAGACACAAGCGCGTCCACGGCCTA<br>TATGGAACTGAGCAGTCTGAGATCCGAGGACACCGCTGTGTATT<br>ATTGCGCCCGAGAGGGGACCTACTACGCCATGGATTATTGGGGT<br>CAAGGGACCACTGTGACAGTCTCTTCTGTCGATTCCAGCGGCGG<br>AGGAGGGAGTGGAGGGGGTGGGTCCGGGGGGGAGGGTCTACGA<br>GCGACATTGTCATGACACAGACGCCGCTTAGCTCCCCAGTTACA<br>CTCGGACAGCCCGCAAGTATTAGTTGCAGAAGTAGCCAGTCTAT<br>CGTACATTCAAATGGAAACACCTATTTGGAATGGTATCAACAAC<br>GGCCTGGACAGCCGCCCAGGCTGCTCATATACAAAGTCTCCAAC<br>CGCTTCAGCGGAGTACCCGACCGCTTTTCCGGCTCCGGAGCAGG<br>AACTGACTTTACCTTGAAAATTAGTAGGGTCGAAGCAGAGGATG<br>TCGGGGTATATTATTGTTTCCAAGGTAGTCATGTCCCACGGACG<br>TTTGGTGGTGGGACGAAGGTTGAGATCAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H1_k4_NT | 168 | ATGGACTTCCAGGTGCAGATATTTTCCTTTCTTCTCATATCTGC<br>ATCTGTAATAATGTCAAGGGCCAGCCAGGTCCAGCTCGTTCAAA<br>GCGGAGCCGAGGTAAAAAAACCAGGCGCTTCCGTCAAGGTATCA<br>TGCAAAGCGTCCGGCTATACCTTCACAAGTTACCATATCCAATG |

TABLE 4-continued

| SEQ Name | SEQ ID | NT |
|---|---|---|
| | | GGTTCGACAGGCACCCGGACAAAGACTTGAATGGATGGGTTGGA<br>TATACCCCGGAGACGGCTCCACTCAGTATAACGAAAAGTTTAAG<br>GGGAGAGTCACGATCACTAGGGACACATCAGCTTCTACGGCGTA<br>TATGGAACTCAGTTCTTTGCGATCCGAGGATACTGCCGTATATT<br>ACTGCGCCAGAGAAGGCACGTACTACGCAATGGATTACTGGGGG<br>CAAGGGACAACTGTTACCGTCTCAAGCGTCGATTCATCAGGAGG<br>CGGAGGGTCCGGAGGTGGGGGATCTGGCGGTGGGGGTTCTACGT<br>CCGATGTTGTGATGACACAGTCCCCACTCTCTCTTCCAGTGACG<br>CTGGGACAGCCCGCGAGCATCTCCTGTCGCAGCTCTCAGTCCAT<br>AGTACACAGTAATGGTAACACCTATCTTGAGTGGTATCAGCAAC<br>GACCCGGTCAGTCTCCCAGGTTGCTTATTTATAAGGTTAGTAAC<br>CGCTTTTCAGGTGTTCCAGACAGATTTAGCGGGAGTGGTTCCGG<br>TACGGATTTCACATTGAAAATCAGCCGCGTCGAAGCCGAGGACG<br>TGGGTGTTTACTACTGCTTCCAGGGATCTCACGTACCGAGGACC<br>TTCGGCGGAGGAACGAAAGTAGAAATTAAGAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H1_k5_NT | 169 | ATGGATTTTCAAGTACAAATCTTTTCCTTCCTGCTTATTTCCGC<br>AAGCGTTATTATGAGTAGAGCCAGCCAAGTACAACTGGTACAGT<br>CCGGCGCGGAGGTGAAGAAGCCCGGAGCAAGTGTGAAGGTATCT<br>TGCAAGGCGTCAGGCTATACCTTTACTTCATACCATATACAGTG<br>GGTGCGACAGGCTCCCGGCCAGCGACTCGAATGGATGGGCTGGA<br>TTTATCCCGGAGATGGATCTACGCAGTATAATGAGAAATTCAAG<br>GGTCGGGTCACGATTACACGAGACACGAGTGCTTCCACAGCTTA<br>TATGGAACTTTCTAGCCTGAGGTCTGAGGATACTGCCGTTTACT<br>ATTGTGCACGAGAAGGGACATACTATGCGATGGATTACTGGGGA<br>CAGGGCACCACTGTCACAGTTTCCAGCGTGGACTCAAGTGGAGG<br>CGGTGGATCTGGTGGTGGCGGGTCCGGGGGGGAGGCAGCACCA<br>GTGACATTGTAATGACTCAAACACCTCTCAGTAGCCCAGTCACT<br>CTCGGTCAGCCGGCGAGTATCTCTTTTAGGTCCTCACAATCTAT<br>AGTGCACTCTAACGGCAATACTTATCTTGAATGGTATCAACAAA<br>GACCGGGGCAGCCACCTCGCCTTCTCATCTACAAAGTAAGCAAT<br>CGCTTCTCCGGTGTCCCCGATCGCTTCTCCGGTTCAGGAGCAGG<br>AACTGACTTCACATTGAAGATTTCCAGAGTGGAGGCCGAAGACG<br>TAGGGGTATATTATTGCTTTCAAGGGTCCCATGTGCCCAGAACC<br>TTTGGGGGAGGAACGAAAGTTGAGATTAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H3_k2_NT | 170 | ATGGATTTCCAAGTGCAGATTTTCTCTTTTCTCCTCATAAGCGC<br>CTCCGTAATTATGTCTAGAGCTAGTCAAGTCCAATTGGTGCAAT<br>CCGGTGCCGAGGTTAAAAAGCCCGGCGCAAGTGTAAAAGTCTCC<br>TGTAAGGCCAGTGGCTACACTTTCACCAGCTACCATATACAGTG<br>GGTGCGGCAGGCGCCTGGTCAGGGTCTGGAGTGGATGGGTATTT |

TABLE 4-continued

| SEQ Name | SEQ ID | NT |
|---|---|---|
| | | GGATTTATCCCGGAGATGGAAGTACTCAATACAATGAGAAATTC
AAGGGTGTCACTATGACAAGGGATACGAGCACTTCTACCGTATA
TATGGAGTTGTCATCTTTGCGATCAGAGGATACCGCTGTATATT
ATTGCGCACGGGAAGGTACATATTATGCCATGGACTACTGGGGC
CAAGGAACCACCGTGACGGTAAGCTCTGTCGATTCTAGCGGTGG
CGGGGGCTCTGGCGGTGGGGGTAGCGGGGGTGGCGGATCTACAT
CAGATATTGTAATGACACAGACCCCTCTTTCACTTTCCGTAACG
CCAGGACAGCCGGCATCAATAAGTTGCCGATCAAGCCAGTCTAT
CGTACACTCCAATGGTAACACATACTTGGAATGGTATCTTCAAA
AGCCCGGCCAGAGCCCGCAGCTTTTGATATATAAAGTGTCCAAC
AGATTCAGTGGGGTGCCGGACCGCTTTAGTGGATCTGGTTCAGG
AACGGACTTCACATTGAAAATTAGTAGAGTTGAAGCGGAAGACG
TGGGAGTCTACTACTGTTTCCAGGGTTCACATGTGCCTCGGACC
TTTGGGGGAGGCACCAAGGTTGAGATAAAAAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CA_H3_k3_NT | 171 | ATGGACTTCCAAGTCCAAATCTTTTCTTTTTTGTTGATAAGCGC
ATCAGTTATTATGTCTCGCGCCAGTCAAGTACAACTGGTGCAGT
CCGGAGCTGAAGTGAAAAAACCAGGAGCAAGCGTGAAAGTAAGT
TGTAAGGCAAGTGGTTACACTTTCACAAGCTACCATATTCAATG
GGTCCGACAGGCTCCTGGACAGGGCTTGGAGTGGATGGGCATAT
GGATTTACCCTGGTGACGGGTCCACCCAGTATAATGAAAAGTTC
AAGGGAGTCACGATGACCAGGGACACCTCTACATCTACCGTGTA
TATGGAGCTCTCTAGTTTGCGATCCGAAGACACTGCCGTTTATT
ACTGTGCAAGAGAAGGAACTTATTACGCGATGGACTACTGGGGT
CAGGGGACAACAGTCACCGTTAGCTCCGTCGATTCCAGCGGGGG
AGGTGGCTCAGGCGGGGGTGGTTCTGGGGGGGGCGGGAGCACTT
CAGATATTGTAATGACCCAAACCCCACTGAGTAGTCCAGTCACG
CTTGGTCAACCGGCAAGCATTTCTTGCAGGAGCTCTCAGAGTAT
TGTCCACTCTAACGGGAATACATATTTGGAGTGGTATCAGCAAA
GACCGGGCCAACCACCACGCCTCTTGATTTATAAGGTGAGCAAT
AGGTTTTCAGGCGTGCCAGATAGGTTCTCAGGCTCCGGAGCGGG
AACCGACTTCACCCTCAAGATAAGTCGGGTGGAAGCCGAAGACG
TAGGAGTTTACTACTGCTTTCAAGGATCTCATGTTCCACGAACG
TTTGGAGGAGGAACCAAGGTGGAAATAAAAAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CAR_H3_k4_NT | 172 | ATGGACTTTCAGGTCCAAATTTTTTCCTTCTTGCTCATATCCGC
GAGTGTCATCATGTCAAGAGCAAGTCAAGTTCAACTCGTTCAAT
CAGGAGCTGAGGTGAAAAAACCAGGGGCGTCTGTCAAAGTAAGC
TGCAAAGCATCAGGGTATACGTTCACGAGTTATCATATCCAGTG
GGTTAGGCAGGCGCCAGGGCAGGGATTGGAATGGATGGGTATCT
GGATTTACCCGGGTGACGGCAGCACTCAATACAATGAGAAATTC |

TABLE 4-continued

| SEQ Name | SEQ ID | NT |
|---|---|---|
| | | AAAGGCGTAACAATGACAAGGGACACGAGCACAAGCACAGTGTA<br>CATGGAGCTTAGCTCTTTGAGGTCAGAGGATACCGCTGTTTACT<br>ATTGTGCTCGGGAGGGTACTTACTATGCAATGGACTACTGGGGG<br>CAAGGCACGACCGTTACAGTGAGTAGCGTAGATTCCTCCGGGGG<br>TGGCGGTTCAGGCGGCGGAGGCTCAGGCGGAGGAGGGTCAACAT<br>CCGATGTCGTAATGACTCAGTCCCCTCTGTCATTGCCGGTGACT<br>TTGGGACAGCCAGCGTCTATATCTTGTAGGTCCTCTCAATCAAT<br>AGTGCATTCCAACGGTAACACCTATCTGGAATGGTATCAGCAAA<br>GGCCAGGACAAAGTCCACGCCTGCTTATATATAAGGTGTCTAAT<br>CGATTCAGTGGGGTTCCCGATAGGTTTTCCGGCTCTGGTAGCGG<br>GACTGATTTCACGTTGAAAATATCACGCGTGGAAGCGGAAGATG<br>TTGGGGTCTATTACTGCTTTCAGGGTAGTCATGTCCCTCGAACT<br>TTTTGGCGGTGGTACAAAGGTAGAAATCAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H3_k5_NT | 173 | ATGGATTTTCAGGTACAGATATTCTCATTTCTCCTTATCTCAGC<br>TAGTGTCATAATGTCCAGGGCGAGTCAAGTACAACTTGTCCAGT<br>CAGGCGCAGAGGTCAAGAAGCCGGGCGCAAGCGTTAAGGTTTCC<br>TGCAAAGCATCCGGCTATACATTCACGTCCTATCACATCCAATG<br>GGTCAGGCAAGCACCCGGTCAAGGACTTGAGTGGATGGGCATCT<br>GGATTTACCCTGGAGATGGCAGTACTCAGTACAACGAAAAATTC<br>AAAGGTGTAACCATGACCCGCGCACACATCTACTTCCACAGTTTA<br>TATGGAACTCAGCAGTTTGCGGAGCGAAGATACCGCTGTTTACT<br>ACTGTGCCCGAGAGGGAACTTACTACGCCATGGACTATTGGGGT<br>CAAGGAACGACAGTAACAGTTAGTTCTGTAGATTCCAGTGGCGG<br>CGGTGGGAGCGGGGGTGGGGATCTGGCGGAGGCGGAAGTACAA<br>GTGACATCGTTATGACTCAGACACCCCTTAGTAGTCCCGTTACG<br>TTGGGCCAACCCGCGAGCATTTCCTTTCGATCCTCTCAGTCTAT<br>AGTTCACTCAAATGGGAATACTTATTTGGAGTGGTATCAACAGC<br>GCCCCGGACAACCACCAAGGCTCCTGATATACAAGGTGTCCAAT<br>CGATTCTCTGGGGTGCCTGATAGATTTAGCGGAAGTGGAGCCGG<br>TACAGATTTTACCCTGAAAATATCACGGGTAGAAGCCGAAGATG<br>TCGGCGTCTACTACTGTTTCCAGGGTTCCCATGTACCGCGAACG<br>TTCGGGGGCGGAACAAAAGTTGAGATCAAGAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H4_k2_NT | 174 | ATGGATTTCCAGGTTCAGATATTTAGTTTCCTCTTGATTTCTGC<br>CAGTGTCATCATGAGCAGGGCTTCCCAAGTTCAGTTGGTGCAAA<br>GTGGCGCTGAAGTCAAAAAACCTGGGGCTTCCGTTAAAGTATCT<br>TGCAAGGCGTCCGGCTACACTTTCACATCCTACCACATTCAATG<br>GGTCCGGCAAGCGCCCGGTCAGGGGCTCGAATGGATGGGGTGGA<br>TATACCCAGGAGATGGATCTACTCAGTACAACGAGAAATTTAAA<br>GGACGGGTGACGATGACGCGCGACACTTCAATAAGCACTGCATA |

TABLE 4-continued

| SEQ Name | SEQ ID | NT |
|---|---|---|
| | | CATGGAACTGTCCCGGCTTAGGTCAGATGACACCGCGGTCTACT
ATTGTGCGAGAGAGGGTACTTACTATGCTATGGACTACTGGGGG
CAAGGCACGACGGTTACAGTTTCCTCAGTCGATAGTTCAGGCGG
AGGCGGCTCCGGGGGCGGTGGTAGTGGAGGGGGTGGATCTACTT
CCGACATTGTCATGACCCAGACCCCGTTGAGCCTTTCAGTGACG
CCCGGTCAACCCGCCAGCATAAGTTGTCGATCAAGCCAGTCTAT
TGTACACTCCAATGGAAACACATATTTGGAGTGGTATCTCCAAA
AACCCCGGCCAAAGCCCTCAACTGCTCATCTACAAGGTCTCAAAC
AGGTTTAGCGGGGTCCCGGATCGCTTCTCAGGGTCAGGATCGG
TACGGACTTTACACTGAAAATTTCCCGAGTCGAAGCGGAAGACG
TGGGGTGTATATTACTGCTTCCAGGGGAGTCATGTTCCAAGAACC
TTTGGGGGAGGTACAAAGGTCGAAATAAAAAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CAR_H4_k3_NT | 175 | ATGGATTTTCAGGTCCAAATTTTTTCCTTCTTGCTTATCAGCGC
AAGTGTAATCATGTCCCGCGCGTCCCAAGTACAACTTGTGCAAT
CTGGCGCGGAGGTGAAAAAACCTGGAGCTTCCGTCAAGGTTTCT
TGTAAGGCCTCTGGCTACACCTTCACGTCCTACCACATTCAGTG
GGTTCGACAGGCGCCGGGCCAAGGACTGGAGTGGATGGGATGGA
TATATCCAGGAGATGGTTCTACTCAGTATAATGAGAAATTCAAG
GGTCGCGTAACAATGACGAGGGATACATCAATCTCCACCGCGTA
CATGGAACTTTCAAGACTCCGGTCAGATGACACGGCGGTTTACT
ACTGTGCTCGGGAGGGCACTTACTATGCTATGGACTACTGGGGG
CAAGGGACAACGGTAACGGTATCTAGTGTGGATTCTAGTGGCGG
CGGCGGTTCAGGAGGAGGTGGTTCAGGCGGGGGGGGTAGTACAA
GTGATATTGTGATGACCCAAACACCCCTTTCTAGCCCTGTTACT
CTGGGTCAACCCGCGTCCATAAGTTGTCGAAGTAGTCAATCCAT
CGTGCATAGCAACGGCAACACTTACCTTGAATGGTATCAACAAC
GACCCCGGACAGCCCCCGCGACTGCTTATCTATAAAGTATCAAAC
AGGTTCAGTGGCGTGCCAGATCGATTCTCCGGCTCTGGGGCAGG
CACAGATTTCACGTTGAAAATTTCTCGGGTCGAGGCCGAGGACG
TGGGCGTTTATTACTGTTTCCAGGGGAGTCACGTCCCCAGGACG
TTCGGAGGAGGAACTAAAGTCGAAATAAAGAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCCTCGC |
| CAR_H4_k4_NT | 176 | ATGGACTTCCAGGTCCAAATATTCAGCTTCCTCCTCATTTCCGC
CAGTGTAATAATGTCCAGAGCCTCACAAGTACAGTTGGTTCAGA
GCGGGGCTGAGGTTAAGAAACCAGGCGCGAGCGTCAAGGTATCC
TGCAAGGCGAGTGGTTATACTTTCACTAGTTATCACATTCAGTG
GGTCCGACAGGCCCCCGGTCAAGGCCTGGAGTGGATGGGGTGGA
TATATCCGGGAGATGGTTCTACCCAATATAATGAGAAGTTTAAG
GGGAGAGTCACAATGACAAGGGACACCAGTATTAGCACCGCGTA
TATGGAGCTTTCCCGCCTGCGATCAGATGACACGGCCGTGTACT |

TABLE 4-continued

| SEQ Name | SEQ ID | NT |
|---|---|---|
| | | ACTGTGCTAGGGAGGGAACCTATTATGCGATGGATTACTGGGGA<br>CAGGGTACTACAGTCACGGTCTCTAGCGTGGACAGTTCCGGGGG<br>CGGTGGAAGCGGTGGTGGCGGTTCAGGTGGAGGAGGCTCTACGA<br>GTGATGTTGTGATGACTCAGTCCCCGCTTTCACTTCCCGTCACC<br>CTTGGGCAACCCGCAAGCATCTCATGCCGATCCTCCCAGTCTAT<br>AGTACATAGTAATGGCAACACATATCTTGAATGGTATCAGCAGA<br>GGCCGGGTCAGTCTCCCCGACTCCTTATATATAAAGTGAGCAAC<br>AGATTCTCCGGAGTACCGGATAGATTTTCCGGCTCTGGGAGCGG<br>CACCGACTTTACACTGAAAATTTCACGGGTTGAAGCTGAAGATG<br>TTGGGGTATACTATTGTTTCCAGGGTTCTCACGTCCCGAGGACA<br>TTCGGGGGAGGAACGAAAGTCGAAATAAAGAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCTCGC |
| CAR_H4_k5_NT | 177 | ATGGATTTTCAGGTACAAATCTTCAGCTTCCTGCTCATCTCCGC<br>GAGCGTAATCATGTCTAGGGCGTCCCAGGTGCAGTTGGTGCAAT<br>CAGGTGCAGAGGTGAAGAAGCCTGGTGCATCCGTTAAAGTAAGT<br>TGTAAGGCAAGCGGATATACTTTTACATCCTATCATATTCAATG<br>GGTCAGACAAGCACCTGGACAGGGTCTTGAGTGGATGGGCTGGA<br>TCTATCCAGGCGATGGCTCAACTCAATATAACGAGAAGTTCAAG<br>GGGAGGGTTACTATGACCAGGGATACGTCTATTTCCACTGCGTA<br>CATGGAACTCTCCAGGTTGAGAAGTGATGATACCGCGGTTTACT<br>ACTGCGCTAGAGAAGGAACGTACTACGCTATGGATTACTGGGGG<br>CAGGGTACAACTGTCACCGTCTCAAGTGTGGATTCTTCTGGGGG<br>TGGGGGATCAGGAGGGGGAGGCTCCGGTGGGGCGGGTCAACCA<br>GCGACATTGTCATGACTCAAACCCCCCTGAGCAGCCCTGTCACC<br>CTGGGTCAGCCTGCCTCAATATCCTTTAGAAGCTCCCAAAGCAT<br>CGTCCATTCAAATGGTAATACCTATCTGGAGTGGTATCAGCAAA<br>GGCCTGGTCAACCCCCGCGCCTTCTCATTTACAAGGTGTCAAAC<br>AGGTTCTCCGGCGTACCGGATAGGTTTTCCGGAAGCGGTGCTGG<br>AACCGACTTTACTCTCAAAATCTCTAGGGTGGAAGCTGAGGACG<br>TCGGTGTATACTATTGTTTTCAAGGCTCCCATGTTCCCAGGACA<br>TTTGGTGGGGGAACGAAGGTAGAAATCAAGAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCTCGC |
| CAR_H5_k2_NT | 178 | ATGGACTTTCAGGTTCAGATTTTCTCTTTCTTGTTGATCTCCGC<br>TAGTGTCATAATGTCACGGGCAAGTCAGGTACAACTCGTTCAGA<br>GTGGTGCCGAAGTGAAGAAACCGGGTGCCTCCGTAAAGGTGTCA<br>TGTAAAGCTAGTGGCTATACATTCACAAGTTATCATATCCAATG<br>GGTACGACAAGCACCGGGACAGCGACTGGAATGGATGGGATGGA<br>TCTATCCTGGGGACGGATCTACACAGTACAATGAGAAATTTAAG<br>GGACGGGTCACGATAACCAGGGACACATCTGCTTCCACGGCTTA<br>CATGGAGCTTTCCTCCCTGCGGAGCGAGGACATGGCTGTTTACT<br>ATTGCGCTCGCGAAGGGACATACTACGCAATGGATTATTGGGGC |

TABLE 4-continued

| SEQ Name | SEQ ID | NT |
|---|---|---|
|  |  | CAAGGCACTACCGTGACGGTCTCTTCTGTCGATAGTTCCGGAGG<br>AGGTGGTTCAGGGGGAGGCGGTTCAGGTGGGGGTGGATCTACCT<br>CAGATATTGTCATGACACAGACACCTTTGTCCTTGAGTGTGACA<br>CCGGGTCAACCGGCGAGTATAAGCTGTCGCAGCTCACAATCTAT<br>TGTGCATAGCAACGGGAATACATATCTCGAATGGTATCTCCAAA<br>AGCCGGGCCAATCCCCCCAACTTCTCATTTACAAAGTTTCTAAT<br>CGATTTTCAGGTGTACCAGATCGGTTTTCCGGGTCTGGCTCAGG<br>TACTGACTTCACCTTGAAAATATCAAGGGTTGAAGCTGAGGATG<br>TAGGTGTGTACTATTGCTTCCAGGGGTCTCACGTTCCTCGGACT<br>TTTGGGGGGGCACAAAAGTAGAGATTAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H5_k3_NT | 179 | ATGGATTTCCAGGTGCAAATCTTCTCATTTCTTTTGATAAGTGC<br>GTCAGTGATAATGTCTCGGGCCAGTCAAGTACAGCTTGTCCAAA<br>GTGGCGCTGAAGTCAAGAAGCCGGGAGCCTCAGTTAAGGTTAGC<br>TGCAAGGCCTCAGGGTATACTTTTACCTCCTATCATATACAGTG<br>GGTACGACAAGCACCGGGACAGCGACTGGAGTGGATGGGTTGGA<br>TATATCCGGGAGATGGTTCAACCCAGTATAATGAGAAGTTCAAG<br>GGGCGAGTTACGATAACCCGCGATACGAGTGCATCAACAGCGTA<br>CATGGAGTTGAGTTCCCTCCGCAGCGAGGACATGGCGGATACT<br>ATTGTGCCAGGGAGGGGACTTATTATGCCATGGACTACTGGGGG<br>CAGGGCACAACCGTAACAGTCTCTTCTGTAGACAGTTCAGGAGG<br>GGGCGGAAGTGGAGGTGGCGGATCTGGTGGAGGTGGATCTACTT<br>CCGACATCGTTATGACCCAAACACCACTTTCATCTCCCGTTACT<br>CTCGGGCAACCTGCTAGTATTTCCTGTAGATCCTCACAATCTAT<br>AGTACATAGCAATGGCAATACCTACCTGGAGTGGTATCAACAAC<br>GCCCAGGCCAACCACCTCGCCTGCTTATCTATAAAGTAAGCAAT<br>AGATTCAGTGGTGTACCGGATAGGTTCTCTGGTTCCGGAGCAGG<br>AACTGACTTTACACTCAAAATCAGTAGGGTGGAGGCGGAAGACG<br>TGGGAGTATATTATTGCTTTCAAGGTTCACATGTACCTCGAACA<br>TTTGGCGGAGGAACTAAGGTTGAGATTAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H5_k4_NT | 180 | ATGGATTTCCAAGTCCAGATATTCAGTTTTCTTTTGATAAGCGC<br>TTCTGTAATCATGTCTCGGGCGTCCCAAGTACAACTGGTGCAAT<br>CAGGGGCAGAAGTGAAAAAACCAGGTGCATCCGTTAAGGTGAGT<br>TGCAAGGCTTCCGGCTATACCTTTACATCATATCATATTCAATG<br>GGTCAGGCAAGCACCTGGTCAGCGATTGGAATGGATGGGTTGGA<br>TATATCCTGGTGATGGGTCTACACAATATAACGAAAAATTCAAG<br>GGGCGAGTGACCATCACAAGAGATACATCAGCGTCAACAGCGTA<br>TATGGAACTGTCATCCCTTAGATCAGAGGACATGGCGGTCTATT<br>ACTGTGCCAGAGAAGGCACTTATTATGCAATGGATTATTGGGA<br>CAAGGAACCACTGTCACTGTTTCCAGCGTAGACTCCTCCGGTGG |

TABLE 4-continued

| SEQ Name | SEQ ID | NT |
|---|---|---|
| | | TGGTGGAAGTGGCGGCGGTGGGTCAGGAGGGGGTGGGTCAACTT
CTGATGTAGTGATGACACAGAGCCCTCTGAGCTTGCCTGTGACC
TTGGGTCAGCCGGCCTCAATAAGTTGTCGATCTAGTCAGTCAAT
CGTCCATAGTAATGGGAACACATACCTTGAATGGTATCAGCAAA
GACCTGGACAATCTCCACGACTCCTTATATACAAAGTTAGCAAC
CGATTTAGCGGAGTGCCAGACCGCTTTTCTGGTTCCGGGTCTGG
CACAGATTTTACCCTTAAGATCTCCCGCGTGGAGGCGGAAGACG
TTGGTGTTTACTATTGCTTCCAGGGGTCACACGTTCCACGCACC
TTTGGAGGAGGTACGAAGGTCGAGATTAAGAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCTCGC |
| CAR-H5_k5_NT | 181 | ATGGATTTTCAAGTACAGATCTTCTCTTTCTTGCTTATTTCAGC
GAGCGTAATCATGAGTAGGGCATCTCAAGTTCAACTCGTTCAGT
CAGGTGCTGAGGTAAAAAAACCAGGGGCTTCCGTTAAAGTTAGC
TGTAAGGCATCTGGGTACACATTTACTAGCTACCATATCCAGTG
GGTGCGACAAGCCCCGGGGCAGCGCTTGGAATGGATGGGCTGGA
TTTACCCAGGTGACGGCTCCACGCAATATAATGAGAAATTTAAG
GGTAGAGTTACTATTACCAGGGACACAAGTGCTTCAACTGCCTA
TATGGAACTGAGCAGCCTTCGGAGTGAAGATATGGCCGTATATT
ACTGCGCAAGGGAGGGGACTTACTATGCAATGGACTACTGGGGT
CAGGGAACGACTGTGACCGTGTCCTCAGTTGACTCCAGCGGTGG
TGGCGGCTCTGGAGGTGGGGGTTCCGGCGGAGGCGGAAGCACAT
CTGATATAGTGATGACGCAAACGCCTCTTTCTTCCCCGGTAACT
CTGGGACAGCCAGCGTCAATTTCATTTAGGTCCTCCCAGTCAAT
CGTACATAGTAATGGAAATACTTACCTGGAATGGTATCAACAAC
GACCAGGGCAACCGCCCCGATTGTTGATCTATAAAGTGAGCAAT
CGCTTTTCTGGCGTGCCCGATCGGTTCTCAGGGTCTGGAGCTGG
GACTGACTTCACATTGAAAATTTCCAGGGTTGAGGCCGAGGATG
TGGGGGTTTATTACTGCTTCCAAGGCTCCCACGTCCCCGCACC
TTCGGAGGGGGAACCAAAGTCGAAATAAAGAACCGGATCCGTGG
GGTCACCGTCTCTTCAGCGCTGAGCAACTCCATCATGTACTTCA
GCCACTTCGTGCCGGTCTTCCTGCCAGCGAAGCCCACCACGACG
CCAGCGCCGCGACCACCAACACCGGCGCCCACCATCGCGTCGCA
GCCCCTGTCCCTGCGCCCAGAGGCGTGCCGGCCAGCGGCGGGGG
GCGCAGTGCACACGAGGGGGCTGGACCCCTTTGGGTTTTGGGTG
CTGGTGGTGGTTGGTGGAGTCCTGGCTTGCTATAGCTTGCTAGT
AACAGTGGCCTTTATTATTTTCTGGGTGAGGAGTAAGAGGAGCA
GGCTCCTGCACAGTGACTACATGAACATGACTCCCCGCCGCCCC
GGGCCCACCCGCAAGCATTACCAGCCCTATGCCCCACCACGCGA
CTTCGCAGCCTATCGCTCCCTCGAGAGAGTGAGAGTGAAGTTCA
GCAGGAGCGCAGACGCCCCCGCGTACCAGCAGGGCCAGAACCAG
CTCTATAACGAGCTCAATCTAGGACGAAGAGAGGAGTACGATGT
TTTTGGACAAGAGACGTGGCCGGGACCCTGAGATGGGGGGAAAGC
CGAGAAGGAAGAACCCTCAGGAAGGCCTGTACAATGAACTGCAG
AAAGATAAGATGGCGGAGGCCTACAGTGAGATTGGGATGAAAGG
CGAGCGCCGGAGGGGCAAGGGGCACGATGGCCTTTACCAGGGTC
TCAGTACAGCCACCAAGGACACCTACGACGCCCTTCACATGCAG
GCCCTGCCCCTCGC |
| CAR_H6_k2_NT | 182 | ATGGATTTTCAAGTTCAGATATTCTCATTTTTGCTTATATCAGC
CTCCGTAATTATGTCACGGGCAAGTCAAGTTCAGTTGGTGCAGT
CCGGAGCAGAAGTTAAGAAGCCCGGTGCTTCTGTGAAAGTCTCC
TGCAAAGCGTCTGGGTACACCTTCACGAGCTACCATATACAGTG
GGTCCGGCAAGCGCCTGGGCAGAGGCTGGAGTGGATGGGCTGGA
TTTACCCAGGAGATGGGAGTACAAAGTATAGTCAGAAGTTTCAA
GGGCGAGTGACGATAACCAGAGATACGAGTGCAAGTACTGCATA
CATGGAACTGAGCTCCTTGAGGTCCGAGGATACAGCGGTGTACT
ATTGCGCTCGGGAAGGGACATATTATGCTATGGACTATTGGGGA
CAAGGGACAACGGTAACGGTGAGTTCCGTCGATTCCTCAGGTGG
CGGAGGCAGTGGGGGCGGGGGTTCCGGCGGTGGCGGGTCCACGA |

TABLE 4-continued

| SEQ Name | SEQ ID | NT |
|---|---|---|
| | | GTGATATAGTTATGACACAGACCCCCCTCAGCCTTTCTGTGACC<br>CCAGGACAACCCGCTAGTATCTCTTGCCGCAGTTCTCAGTCCAT<br>AGTACACAGTAACGGAAATACCTATCTTGAGTGGTATCTTCAAA<br>AGCCCGGCCAGAGCCCTCAACTCTTGATATATAAAGTGTCAAAT<br>CGATTTTCAGGTGTGCCTGATCGATTCTCAGGGTCTGGTTCAGG<br>GACAGATTTCACGCTTAAGATAAGCAGAGTAGAGGCTGAAGACG<br>TGGGAGTCTACTATTGTTTTCAGGGGTCACACGTTCCCCGCACT<br>TTTGGTGGGGGAACCAAGGTGGAAATCAAAAACCGGATCCGTGG<br>GGTCACCGTCTCTTCAGCGCTGAGCAACTCCATCATGTACTTCA<br>GCCACTTCGTGCCGGTCTTCCTGCCAGCGAAGCCCACCACGACG<br>CCAGCGCCGCGACCACCAACACCGGCGCCCACCATCGCGTCGCA<br>GCCCCTGTCCCTGCGCCCAGAGGCGTGCCGGCCAGCGGCGGGGG<br>GCGCAGTGCACACGAGGGGGCTGGACCCCTTTGGGTTTTGGGTG<br>CTGGTGGTGGTTGGTGGAGTCCTGGCTTGCTATAGCTTGCTAGT<br>AACAGTGGCCTTTATTATTTTCTGGGTGAGGAGTAAGAGGAGCA<br>GGCTCCTGCACAGTGACTACATGAACATGACTCCCCGCCGCCCC<br>GGGCCCACCCGCAAGCATTACCAGCCCTATGCCCCACCACGCGA<br>CTTCGCAGCCTATCGCTCCCTCGAGAGTGAGAGTGAAGTTCA<br>GCAGGAGCGCAGACGCCCCCGCGTACCAGCAGGGCCAGAACCAG<br>CTCTATAACGAGCTCAATCTAGGACGAAGAGAGGAGTACGATGT<br>TTTGGACAAGAGACGTGGCCGGGACCCTGAGATGGGGGGAAAGC<br>CGAGAAGGAAGAACCCTCAGGAAGGCCTGTACAATGAACTGCAG<br>AAAGATAAGATGGCGGAGGCCTACAGTGAGATTGGGATGAAAGG<br>CGAGCGCCGGAGGGGCAAGGGGCACGATGGCCTTTACCAGGGTC<br>TCAGTACAGCCACCAAGGACACCTACGACGCCCTTCACATGCAG<br>GCCCTGCCCCCTCGC |
| CAR_H1_K2_NT | 214 | ATGGCTCTGCCTGTGACAGCTCTGCTGCTGCCTCTGGCTCTGCT<br>TCTTCATGCCGCCAGACCATCTCAGGTCCAGCTAGTACAAAGCG<br>GCGCCGAAGTAAAGAAACCTGGTGCCTCTGTGAAGGTGAGCTGC<br>AAGGCCAGCGGCTACACCTTCACCAGCTACCACATCCAGTGGGT<br>TCGACAGGCCCCTGGACAGAGACTAGAGTGGATGGGCTGGATCT<br>ATCCTGGCGACGGCAGCACCCAGTACAACGAGAAGTTCAAGGGC<br>AGAGTTACCATCACCCGAGACACCAGCGCCAGCACAGCCTATAT<br>GGAGCTGAGCAGCCTGCGAAGCGAGGACACAGCTGTTTACTATT<br>GTGCCAGAGAGGGCACCTACTACGCAATGGATTATTGGGGCCAG<br>GGGACCACCGTGACCGTTTCTTCTGGAGGCGGAGGTTCTGGCGG<br>CGGAGGAAGTGGTGGCGGAGGCTCAGATATTGTAATGACCCAGA<br>CACCTCTGTCCCTGTCTGTGACACCTGGACAGCCTGCAAGCATC<br>AGCTGTCGGAGCAGCCAGAGCATCGTTCACAGCAACGGCAACAC<br>CTACCTGGAATGGTATCTGCAGAAGCCCGGACAGTCCCCCCAGC<br>TGCTGATCTACAAGGTGTCCAACCGCTTCAGTGGAGTACCCGAT<br>AGATTTTCTGGCAGCGGCTCTGGCACCGACTTCACCCTGAAGAT<br>CTCCAGAGTAGAAGCAGAGGACGTTGGAGTGTACTACTGCTTCC<br>AAGGCAGCCATGTGCCAAGAACCTTTGGTGGAGGCACAAAGGTG<br>GAAATCAAGCGGACAACAACACCTGCTCCTCGGCCTCCTACACC<br>AGCTCCTACAATTGCCAGCCAGCCACTGTCTCTGAGGCCCGAAG<br>CTTGCAGGCCTGCTGCTGGCGGAGCCGTGCATACAAGAGGACTG<br>GATTTCGCCTGCGACATCTACATCTGGGCACCTCTGGCTGGAAC<br>CTGTGGCGTGCTGCTGCTGAGCCTGGTCATCACCCTGTATTGCC<br>GGAGCAAGAGAAGCAGACTGCTGCACAGCGACTACATGAACATG<br>ACCCCTAGACGGCCCGGACCTACCAGAAAGCACTACCAGCCTTA<br>CGCTCCTCCTAGAGACTTCGCCGCCTACAGATCCAGAGTGAAGT<br>TCAGCAGATCCGCCGACGCTCCTGCCTATCAGCAGGGCCAAAAC<br>CAGCTCTACAACGAGCTGAACCTGGGGAGAAGAGAAGAGTACGA<br>CGTGCTGGACAAGCGGAGAGGCAGAGATCCTGAAATGGGCGGCA<br>AGCCCAGACGGAAGAATCCTCAAGAGGGCCTGTATAATGAGCTA<br>CAGAAAGACAAGATGGCAGAGGCCTACAGCGAGATCGGAATGAA<br>GGGCGAGCGCAGAAGAGGCAAGGGACACGATGGACTGTACCAGG<br>GCCTGAGCACCGCCACCAAGGATACCTATGATGCCCTGCACATG<br>CAGGCCCTGCCTCCAAGA |
| 4-1BB NT<br>(SEQ ID<br>NO: 17<br>of U.S.<br>Pat. No<br>9,102,760) | 215 | AAACGGGGCAGAAAGAAACTCCTGTATATATTCAAACAACCATT<br>TATGAGACCAGTACAAACTACTCAAGAGGAAGATGGCTGTAGCT<br>GCCGATTTCCAGAAGAAGAAGAAGGAGGATGTGAACTG |
| CD8 hinge NT<br>(SEQ ID<br>NO: 15<br>of U.S.<br>Pat. No<br>9,102,760) | 217 | ACCACGACGCCAGCGCCGCGACCACCAACACCGGCGCCCACCAT<br>CGCGTCGCAGCCCCTGTCCCTGCGCCCAGAGGCGTGCCGGCCAG<br>CGGCGGGGGGCGCAGTGCACACGAGGGGGCTGGACTTCGCCTGT<br>GAT |

TABLE 4-continued

| SEQ Name | SEQ ID | NT |
| --- | --- | --- |
| CD8_hinge NT | 220 | ACAACAACACCTGCTCCTCGGCCTCCTACACCAGCTCCTACAAT TGCCAGCCAGCCACTGTCTCTGAGGCCCGAAGCTTGCAGGCCTG CTGCTGGCGGAGCCGTGCATACAAGAGGACTGGATTTCGCCTGC GAC |
| CD8 trans-membrane_NT (SEQ ID NO: 16 of U.S. Pat. No. 9,102,760) | 222 | ATCTACATCTGGGCGCCCTTGGCCGGGACTTGTGGGGTCCTTCT CCTGTCACTGGTTATCACCCTTTACTGC |
| CD8trans-membrane_NT | 224 | ATCTACATCTGGGCACCTCTGGCTGGAACCTGTGGCGTGCTGCT GCTGAGCCTGGTCATCACCCTGTATTGC |

TABLE 5

| | Kabat | Chothia |
| --- | --- | --- |
| BB7.2 VH CDR1 | SYHIQ (SEQ ID NO: 183) | GYTFTSY (SEQ ID NO: 184) |
| BB7.2 VH CDR2 | WIYPGDGSTQYNEKFKG (SEQ ID NO: 185) | YPGDGS (SEQ ID NO: 186) |
| BB7.2 VH CDR3 | EGTYYAMDY (SEQ ID NO: 187) | EGTYYAMDY (SEQ ID NO: 187) |

TABLE 6

| | Kabat | Chothia |
| --- | --- | --- |
| BB7.2 VL CDR1 | RSSQSIVHSNGNTYLE (SEQ ID NO: 188) | RSSQSIVHSNGNTYLE (SEQ ID NO: 188) |
| BB7.2 VL CDR2 | KVSNRFS (SEQ ID NO: 189) | KVSNRFS (SEQ ID NO: 189) |
| BB7.2 VL CDR3 | FQGSHVPRT (SEQ ID NO: 190) | FQGSHVPRT (SEQ ID NO: 190) |

TABLE 7

| SEQ Name | SEQ ID | AA |
| --- | --- | --- |
| BB7.2_AA VH | 191 | QVQLQQSGPELVKPGASVKMSCKASGYTFTSYHIQWVKQRPGQGLE WIGWIYPGDGSTQYNEKFKGKTTLTADKSSSTAYMLLSSLTSEDSA IYFCAREGTYYAMDYWGQGTSVTVSS |
| BB7.2_AA VL | 192 | DVLMTQTPLSLPVSLGDQVSISCRSSQSIVHSNGNTYLEWYLQKPG QSPKLLIYKVSNRFSGVPDRFSGSGSGTDFTLKISRVEAEDLGVYY CFQGSHVPRTFGGGTKLEIK |
| BB7.2_AA scFv (without leader) | 193 | QVQLQQSGPELVKPGASVKMSCKASGYTFTSYHIQWVKQRPGQGLE WIGWIYPGDGSTQYNEKFKGKTTLTADKSSSTAYMLLSSLTSEDSA IYFCAREGTYYAMDYWGQGTSVTVSSVDSSGGGGSGGGGSGGGGST SDVLMTQTPLSLPVSLGDQVSISCRSSQSIVHSNGNTYLEWYLQKP GQSPKLLIYKVSNRFSGVPDRFSGSGSGTDFTLKISRVEAEDLGVY YCFQGSHVPRTFGGGTKLEIK |
| BB7.2CAR (without leader) | 194 | QVQLQQSGPELVKPGASVKMSCKASGYTFTSYHIQWVKQRPGQGLE WIGWIYPGDGSTQYNEKFKGKTTLTADKSSSTAYMLLSSLTSEDSA IYFCAREGTYYAMDYWGQGTSVTVSSVDSSGGGGSGGGGSGGGGST SDVLMTQTPLSLPVSLGDQVSISCRSSQSIVHSNGNTYLEWYLQKP GQSPKLLIYKVSNRFSGVPDRFSGSGSGTDFTLKISRVEAEDLGVY YCFQGSHVPRTFGGGTKLEIKLEQKLISEEDLNRIRGVTVSSALSN SIMYFSHFVPVFLPAKPTTTPAPRPPTPAPTIASQPLSLRPEACRP AAGGAVHTRGLDPFGFWVLVVVGGVLACYSLLVTVAFIIFWVRSKR SRLLHSDYMNMTPRRPGPTRKHYQPYAPPRDFAAYRSLERVRVKFS RSADAPAYQQGQNQLYNELNLGRREEYDVLDKRRGRDPEMGGKPRR KNPQEGLYNELQKDKMAEAYSEIGMKGERRRGKGHDGLYQGLSTAT KDTYDALHMQALPPR |
| BB7.2CAR (with leader) | 195 | MDFQVQIFSFLLISASVIMSRASQVQLQQSGPELVKPGASVKMSCK ASGYTFTSYHIQWVKQRPGQGLEWIGWIYPGDGSTQYNEKFKGKTT LTADKSSSTAYMLLSSLTSEDSAIYFCAREGTYYAMDYWGQGTSVT VSSVDSSGGGGSGGGGSGGGGSTSDVLMTQTPLSLPVSLGDQVSIS CRSSQSIVHSNGNTYLEWYLQKPGQSPKLLIYKVSNRFSGVPDRFS GSGSGTDFTLKISRVEAEDLGVYYCFQGSHVPRTFGGGTKLEIKLE QKLISEEDLNRIRGVTVSSALSNSIMYFSHFVPVFLPAKPTTTPAP RPPTPAPTIASQPLSLRPEACRPAAGGAVHTRGLDPFGFWVLVVVG GVLACYSLLVTVAFIIFWVRSKRSRLLHSDYMNMTPRRPGPTRKHY QPYAPPRDFAAYRSLERVRVKFSRSADAPAYQQGQNQLYNELNLGR REEYDVLDKRRGRDPEMGGKPRRKNPQEGLYNELQKDKMAEAYSEI |

TABLE 7-continued

GMKGERRRGKGHDGLYQGLSTATKDTYDALHMQALPPR

| SEQ Name | SEQ ID | NT |
|---|---|---|
| BB7.2CAR (with leader) | 196 | ATGGACTTCCAGGTGCAGATCTTCAGCTTCCTGCTGATCAGCGCCA<br>GCGTGATCATGAGCCGCGCTAGCCAGGTGCAGCTGCAGCAGAGCGG<br>CCCCGAGCTGGTGAAGCCCGGCGCCAGCGTGAAGATGAGCTGCAAG<br>GCCAGCGGCTACACCTTCACCAGCTACCACATCCAGTGGGTGAAGC<br>AGCGCCCCGGCCAGGGCCTGGAGTGGATCGGCTGGATCTACCCCGG<br>CGACGGCAGCACCCAGTACAACGAGAAGTTCAAGGGCAAGACCACC<br>CTGACCGCCGACAAGAGCAGCAGCACCGCCTACATGCTGCTGAGCA<br>GCCTGACCAGCGAGGACAGCGCCATCTACTTCTGCGCCCGCGAGGG<br>CACCTACTACGCCATGGACTACTGGGGCCAGGGCACCAGCGTGACC<br>GTGAGCAGCGTCGACAGCAGCGGCGGCGGCGGCAGCGGCGGCGGCG<br>GCAGCGGCGGCGGCGGCAGCACTAGTGACGTGCTGATGACCCAGAC<br>CCCCCTGAGCCTGCCCGTGAGCCTGGGCGACCAGGTGAGCATCAGC<br>TGCCGCAGCAGCCAGAGCATCGTGCACAGCAACGGCAACACCTACC<br>TGGAGTGGTACCTGCAGAAGCCCGGCCAGAGCCCCAAGCTGCTGAT<br>CTACAAGGTGAGCAACCGCTTCAGCGGCGTGCCCGACCGCTTCAGC<br>GGCAGCGGCAGCGGCACCGACTTCACCCTGAAGATCAGCCGCGTGG<br>AGGCCGAGGACCTGGGCGTGTACTACTGCTTCCAGGGCAGCCACGT<br>GCCCCGCACCTTCGGCGGCGGCACCAAGCTGGAGATCAAGCTCGAG<br>CAGAAGCTGATCAGCGAGGAGGACCTGAACCGGATCCGTGGGGTCA<br>CCGTCTCTTCAGCGCTGAGCAACTCCATCATGTACTTCAGCCACTT<br>CGTGCCGGTCTTCCTGCCAGCGAAGCCCACCACGACGCCAGCGCCG<br>CGACCACCAACACCGGCGCCCACCATCGCGTCGCAGCCCCTGTCCC<br>TGCGCCCAGAGGCGTGCCGGCCAGCGGCGGGGGCGCAGTGCACAC<br>GAGGGGGCTGGACCCCTTTGGGTTTTGGGTGCTGGTGGTGGTTGGT<br>GGAGTCCTGGCTTGCTATAGCTTGCTAGTAACAGTGGCCTTTATTA<br>TTTTCTGGGTGAGGAGTAAGAGGAGCAGGCTCCTGCACAGTGACTA<br>CATGAACATGACTCCCCGCCGCCCCGGGCCCACCCGCAAGCATTAC<br>CAGCCCTATGCCCCACCACGCGACTTCGCAGCCTATCGCTCCCTCG<br>AGAGAGTGAGAGTGAAGTTCAGCAGGAGCGCAGACGCCCCCGCGTA<br>CCAGCAGGGCCAGAACCAGCTCTATAACGAGCTCAATCTAGGACGA<br>AGAGAGGAGTACGATGTTTTGGACAAGAGACGTGGCCGGGACCCTG<br>AGATGGGGGGAAAGCCGAGAAGGAAGAACCCTCAGGAAGGCCTGTA<br>CAATGAACTGCAGAAAGATAAGATGGCGGAGGCCTACAGTGAGATT<br>GGGATGAAAGGCGAGCGCCGGAGGGGCAAGGGGCACGATGGCCTTT<br>ACCAGGGTCTCAGTACAGCCACCAAGGACACCTACGACGCCCTTCA<br>CATGCAGGCCCTGCCCCCTCGCTAA |

EXAMPLES

Methods

Generation of Humanized HLA-A*02-Specific scFvs.

The humanized genes were codon optimized using the codon optimizer from Invitrogen GeneArt Gene Synthesis service using the settings for *Homo sapiens*. gBlocks® Gene Fragments were ordered from Integrated DNA Technologies (Coralville, Iowa) such that the 5' region of the chimeric antigen receptor contained a Kozak sequence, and a 36 NT overlap with a pcDNA3 plasmid. The 3' end contains a BamHI site and an overlap with a CD8 hinge sequence to facilitate Gibson assembly into the plasmid in frame with the CD8 hinge and the intracellular signaling domains of the chimeric antigen receptor.

Generation of hA2-CARs.

Figure 1:
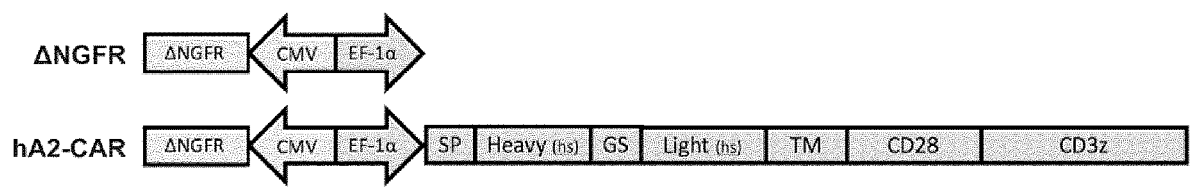
FIG. 1. Construction of humanized anti-HLA-A2 CARs. Schematic representation of the lentiviral constructs. Top: truncated NGFR control construct (no CAR); Bottom: humanized anti-HLA-A2 CAR construct. "SP": signal peptide; "GS": Glycine-Serine linker; "TM": transmembrane region; "hs": humanized.

The scFv variants were fused to a stalk region from human CD8a, the transmembrane and intracellular domains of human CD28, and human CD3 as described (Sadelain et al., 2013). The resulting cDNAs were cloned into a lentiviral vector that encodes cell-surface expression of a truncated nerve-growth-factor (TrkA) receptor (ΔNGFR) as a marker (FIG. 1). Surface expression was determined by flow cytometry with transiently transfected HEK 293T cells (jetPRIME®, Polyplus Transfection). Viral particles were produced as described (Allan et al., 2008).

Generation of HLA-Expressing K562 Cell Lines.

CD64-expressing K562 cells (K562.64) were a gift from James Riley, University of Pennsylvania, Philadelphia, USA. cDNA for HLA-A*02:01 and A*24:02 were isolated from mRNA of peripheral blood mononuclear cells from a donor homozygous for A*02:01 or A*24:02, respectively, on the HLA-A locus using the primer sequences: 5'-TTTTCTA-GACGCGTGCCACCATGGCCGTCATGGCGCC-3' (forward) (SEQ ID NO: 197) and 5'-AAGTCGACGCTAGCT-CACACTTTACAAGCTGTGAGAGACA-3' (reverse) (SEQ ID NO: 198). The resulting sequence was confirmed by Sanger sequencing, aligned to the expected sequences from the IPD and IMGT/HLA Database (Robinson et al., 2015) and transduced into K562 cells, respectively, using a lentiviral expression vector. To generate A25- and A68-K562 cells, HLA sequences for A*25:01, A*68:01 were scraped from the IPD and IMGT/HLA Database (Robinson et al., 2015), codon optimized using the codon optimizer tool (set to *Homo sapiens*) from ThermoFisher Invitrogen GeneArt Gene Synthesis service, then cloned into a lentiviral expression vector and transduced into K562 cells. The resulting K562 cell lines were then sorted on a FACSAria II (BD Biosciences) using anti-HLA-ABC (ThermoFisher, 12-9983-41) to ensure equivalent surface expression of the transduced HLA and anti-HLA-A2 (BB7.2) (ThermoFisher, 17-9876-42) to ensure purity.

Treg Sorting, Transduction, and Expansion.

CD4$^+$ T cells were isolated from HLA-A2$^-$ donors via RosetteSep (Stemcell) and enriched for CD25$^+$ cells (Miltenyi) prior to sorting live CD4$^+$CD25$^+$CD127$^{lo}$Tregs (for in vitro and luciferase experiments) or CD4$^+$CD127$^{lo}$CD25$^{hi}$CD45RA$^+$ Tregs (for xenogeneic GvHD and skin transplant experiments) using a MoFlo® Astrios (Beckman Coulter) or FACSAria II (BD Biosciences), respectively. Sorted Tregs were stimulated with L cells and aCD3 mAb (OKT3; 100 ng/mL) in immunocult-XF T cell expansion media (STEMCELL Technologies) with 1000 U/ml of IL-2 (Proleukin). One day later, cells were transduced with lentivirus at a multiplicity of infection of 10 virus particles:1 cell. At day 7, $\Delta NGFR^+$ cells were purified with magnetic selection (Miltenyi) then used in assays or re-stimulated with L cells as above and expanded for 5 days for in vivo experiments. To test the effects of HLA-A2-mediated stimulation, Tregs were cultured with limiting IL-2 (100 U/mL) for 24 hours, then re-counted and co-cultured with irradiated anti-CD3/anti-CD28 loaded K562.64 cells or HLA-A*02:01, A*24:02, A*25:01 or A*68:01-expressing K562.64 cells at a 1:2 (K562:T cell) ratio for 24 hours.

Flow Cytometry.

For phenotypic analysis, cells were stained with fixable viability dye (FVD, 65-0865-14, ThermoFisher; 423102, Biolegend) and for surface markers before fixation and permeabilization with eBioscience FOXP3/Transcription Factor Staining Buffer Set (ThermoFisher) and staining for intracellular proteins. Samples were read on a Cytoflex (Beckman-Coulter) and results analyzed using FlowJo Software version 9.9.4 and 10.3 (Tree Star).

Surface staining was performed for $\Delta NGFR$ (130-091-885, Miltenyi), CD3 (564465, BD Biosciences), CD4 (317410, Biolegend), CD25 (130-091-024, Miltenyi), LAP (25-9829-42, ThermoFisher), CD69 (310946, Biolegend), CD154 (555702, BD Biosciences), CD71 (BD Biosciences, 563768), and CD127 (48-1278-42, ThermoFisher). Tetramer staining was performed with HLA-A*02:01 monomers made into tetramers with streptavidin-allophycocyanin (PJ27S, Prozyme). Intracellular staining was performed for CTLA-4 (369606, Biolegend).

For in vivo experiments, 50 uL of blood was collected weekly and at endpoints. Ammonium chloride was used for red blood cell lysis. Cells were resuspended in PBS with anti-mouse CD16/32 (ThermoFisher, 14-0161-82) and stained for extracellular markers using fixable viability dye (FVD; ThermoFisher, 65-0865-14), anti-mouse CD45 (ThermoFisher, 25-0451-82), and anti-human CD45 (BD Biosciences, 560777), CD4 (Biolegend, 300554, 317434), CD8 (ThermoFisher, 48-0087-42), anti-human CD271 (NGFR; BD Biosciences, 557196) HLA-A2 (BD Biosciences, 551285). Intracellular staining for FOXP3 (ThermoFisher, 12-4777-42) was done with the eBioscience FOXP3/Transcription Factor Staining Buffer Set (ThermoFisher, 00-5523-00). 10,000 counting beads were added to every sample (ThermoFisher, 01-1234-42). The gating strategies for the xenogeneic GvHD, luciferase and skin transplant experiments are illustrated in FIGS. 8D, 10A and 12A, respectively.

HLA Allele Cross Reactivity Assay.

$0.25 \times 10^6$ CAR Tregs (prepared as above, after 7 days of culture) were incubated with individual FlowPRA Single Antigen Antibody beads panels (FL1HD01, FL1HD02, FL1HD03, FL1HD04, FL1HD06 and FL1HD08, One Lambda) and fixable viability dye (FVD, 65-0865-14, ThermoFisher) for 30 minutes at room temperature, then washed, fixed with 0.5% formaldehyde and analyzed via flow cytometry. Two hundred negative control beads were acquired per sample. For analysis, dead cells were first eliminated using the fixable viability dye. Single beads were then gated after exclusion of dead cells and doublets. Then, the number of beads for each HLA antigen was determined by their respective PE intensity. Data were normalized by dividing the number of negative beads in the sample by the number of negative beads in the Treg-NGFR sample, multiplied by the number of negative beads in the Treg-NGFR specimen. Percent relative binding is the number of beads in the NGFR specimen for one specific HLA minus the normalized number of beads in the specimen for that HLA, divided by the number of beads in the NGFR specimen multiplied by 100.

Suppression of Mixed Lymphocyte Reactions.

Adherent cells from PBMCs from HLA-A2$^+$ healthy donors were differentiated into monocyte-derived dendritic cells as described (Dijke et al., 2015). For mixed lymphocyte reactions, HLA-A2$^-$ PBMC responder cells were labeled with cell proliferation dye eF450 (65-0842-85, ThermoFisher), then plated with $5 \times 10^4$ HLA-A2$^+$ monocyte-derived dendritic cells and increasing ratios of expanded $\Delta NGFR$- or hA2-CAR-expressing Tregs labelled with cell proliferation dye e670 (65-0840-90, ThermoFisher). After 6 days, division of HLA-A2$^-$ CD4$^+$ responder T cells was measured by flow cytometry. Percent suppression was calculated based on the proliferation index of a given cell combination and ratio versus the positive control (HLA-A2$^+$ monocyte-derived dendritic cells with HLA-A2-CD4$^+$ responder T cells only) as described (McMurchy and Levings, 2012). Data were normalized by first calculating percent suppression as follows:

$$\% \text{ suppression} = 100 - 100 \times \frac{\text{proliferation index (sample)}}{\text{proliferation index} (DC + \text{responder control})},$$

then normalizing the resulting values from 0-100%, according to the formula for each independent experiment:

$$\text{normalized } \% \text{ suppression} = 100 - 100 \times \frac{\% \text{ suppression (sample)}}{\% \text{ suppression } (DC + \text{responder control})}.$$

Suppression of Xenogeneic Graft-Versus-Host Disease In Vivo.

8- to 12-week-old female NSG mice (The Jackson Laboratory, bred in house) received whole-body irradiation (150 cGy, RS-2000 Pro Biological System) 1 day before injection of $8 \times 10^6$ HLA-A2$^+$ PBMCs with or without $4 \times 10^6$ hA2-CAR Tregs intravenously into the tail vein. Saline-injected mice served as controls. hA2-CAR Tregs were generated from four different healthy donors. GVHD was scored based on weight, fur texture, posture, activity level, and skin integrity, with 0 to 2 points per category as described (Cooke, et al. 1996; Hill et al. 1997). GVHD scoring was performed by two blinded investigators. Peripheral blood from the saphenous vein was centrifuged; then erythrocytes were lysed and leukocytes were measured by flow cytometry.

Study Approval.

For human PBMCs, healthy volunteers gave written informed consent according to protocols approved by the University of British Columbia Clinical Research Ethics Board and Canadian Blood Services. Samples of human skin discarded from plastic surgery were obtained from the Harvard Skin Resource Centre, Skin Works or the Cambie Surgery Clinic according to University of British Columbia Clinical Research Ethics Board-approved protocols. Animal protocols were approved by the UBC Animal Care Committee.

Skin Transplantation.

To evaluate A2-CAR Treg homing and capacity to inhibit skin rejection, 8- to 12-week-old female NSG mice (The Jackson Laboratory, bred in house) were transplanted with skin from transgenic HLA-A2+ NSG mice (The Jackson Laboratory, bred in house) and NSG skin (HLA-A2 negative), For mouse skin transplants, skin was cut into circular pieces utilizing 8 mm biopsy punch and skin was placed onto fresh plates with PBS and kept at low temperature (4-8° C.) until transplanted (~1-4 hr). HLA-A2 expression of human skin was assessed by flow cytometry and qPCR. Split-thickness explants were generated by trimming fat from the specimen. Explants were rinsed with sterile PBS and stored in RPMI. Quality skin explants were cut into 1 cm² pieces, placed onto fresh plates with PBS and kept at low temperature (4-8° C.) until transplanted (~1-4 hr). For both mouse and human skin transplants, previously shaved mice were anesthetized, dorsal skin was cut near the shoulder and mouse skin of similar size was removed, then grafts were placed on the exposed area and stabilized with steri-strips (3M, Nexcare). Grafts were covered with a Vaseline gauze and wrapped with a 2 cm wide CoFlex bandage (3M, Nexcare) to secure graft for up to 14 days prior to cell injection.

Histology

Human skin graft and surrounding mouse skin was harvested 27 days post-cell injection, fixed overnight at 4° C. in 10% formalin (1:10 v/v ratio of tissue to formalin), and stored in 70% ethanol before paraffin-embedding. Paraffin sections (5-ram thickness) and H&E staining were prepared by BC Children's Hospital Research Institute Histology Services (Vancouver, British Columbia, Canada). For immunostaining, sections were deparaffinized and rehydrated using a series of xylene washes (×3), graded alcohol solutions (2×100% ethanol, 1×95% ethanol and 1×70% ethanol), and 1×PBS. Heat-induced epitope retrieval (HIER) was performed on slides using a microwave to reach 93-95° C. (5 min, high power followed by 20 min, low power) in 10 mM sodium citrate buffer (0.5% Tween-20, pH 6.0). Following HIER, slides were washed using running tap water, deionized water and PBS. Sections were incubated with DAKO® Protein Block, Serum-Free (Dako, Burlington, Canada, X0909) to limit non-specific antibody staining. Sections were then incubated at 4° C. overnight with the following primary antibodies: FOXP3 (Invitrogen, clone PCH101, 14-4776-82), CD45 (eBioscience, clone H130, 17-0459), Ki67 (eBioscience, clone 20Raji, 17-5699), Involucrin (Abcam, ab53112). The following day, sections were gently rinsed with PBS several times, then stained for 1 hour RT with the following secondary antibodies: donkey anti-rat 488 (Life Tech, A11006), goat anti-mouse APC (Invitrogen, 1834696), donkey anti-rabbit 488 (Life Tech, A21206). Finally, sections were counterstained with 4',6-diamidino-2-phenylindole (DAPI) to identify cell nuclei and mounted using VECTASHIELD® Mounting Medium with DAPI (Vector Laboratories, Burlingame, California, USA, H-1200). All antibodies were diluted in Antibody Diluent (Dako, Burlington, Canada, S3022). Images were captured using the Olympus BX61 Fluorescence and Bright Field Automated Upright Microscope with QImaging Retiga Exi camera and Olympus DP71 color camera. Quantitative analysis of fluorescence images performed using Fiji with Olympus viewer Plugin (Schneider et al., 2012; Eliceiri et al., 2012).

H&E-stained slides were evaluated by a blinded clinical pathologist using a scoring system defined by 8 factors each graded from 0 to 3-4; Lerner grade (0, 1—focal or diffuse vacuolar degeneration, 2—dyskeratosis, 3—clefts in basal or superficial layers, 4—frank loss of epidermis), spongiosis (0, 1—basal layer only, 2—up to half way, 3—full thickness), necrotic keratinocytes (0, 1—rare (1/hpf), 2—occasional (2—3/hpf), 3—many (>4/hpf)), necrotic keratinocyte location (0, 1—basal only, 2—up to upper half, 3—full thickness), satellitetosis (0, 1—1 only, 2-2—3/hpf, 3—>4/hpf), exocytosis (0, 1—focal, 2—<50% biopsy, 3—>50% biopsy), adnexal involvement (0, 1—minor involvement of any adnexa, 2—marked involvement of <50% adnexa, 3—marked involvement of >50% adnexa) and lymphoid cuffs in dermis (0, 1—slight, 2—abundant, 3—band like) (Massi et al., 1999; Fischer et al., 2015, Kanitakis et al., 2008).

qPCR.

RNA was harvested from human skin samples according to the manufacturer's instructions (RNeasy Plus Mini Kit; Qiagen) and converted to complementary DNA (cDNA). qPCR was performed using SYBR-green (Biorad) and primers for IL17, IL6, IL1B, DEFB4, IFNg, TNFa, 18S ribosomal RNA (Table 8). Melt curve and SYBR-green emission data were collected. Relative concentrations were calculated using a standard curve and values were normalized to amplification products of 18S ribosomal RNA. $\text{Log}_2(\text{RQ})$ values for each sample were obtained using the double delta Ct ($\Delta\Delta$Ct) method (Schmittgen et al., 2008). Each sample's $\Delta$Ct value was obtained by calculating averaged Ct (gene of interest)–Ct (housekeeping gene). To obtain $\Delta\Delta$Ct, the $\Delta$Ct of the control sample was subtracted from the $\Delta$Ct of the treated sample. Fold gene expression was then calculated by $2^{-(\Delta\Delta Ct)}$.

TABLE 8

Primers used in qPCR analysis

| Oligo name | Direction Forward (FWD) or Reverse (RVS) | Oligo sequence (5' to 3') |
|---|---|---|
| human IL17 | FWD | TCA ACC CGA TTG TCC ACC AT (SEQ ID NO: 199) |
| human IL17 | RVS | GAG TTT AGT CCG AAA TGA GGC TG (SEQ ID NO: 200) |
| human IL6 | FWD | TCC AAA GAT GTA GCC GCC CA (SEQ ID NO: 201) |
| human IL6 | RVS | CCA GTG CCT CTT TGC TGC TTT CA (SEQ ID NO: 202) |
| human IL1B | FWD | CTG AGC TCG CCA GTG AAA TGA TG (SEQ ID NO: 203) |
| human IL1B | RVS | TGC TGT AGT GGT GGT CGG AGA (SEQ ID NO: 204) |
| human DEFB4 | FWD | ACC TGC CTT AAG AGT GGA GCC A (SEQ ID NO: 205) |
| human DEFB4 | RVS | ACA TGT CGC ACG TCT CTG ATG A (SEQ ID NO: 206) |
| human IFNG | FWD | TGC CCA GAG CAT CCA AAA GA (SEQ ID NO: 207) |
| human IFNG | RVS | TGT ATT GCT TTG CGT TGG AC (SEQ ID NO: 208) |
| human TNFA | FWD | AGG CGC TCC CCA AGA AGA CA (SEQ ID NO: 209) |

TABLE 8-continued

Primers used in qPCR analysis

| Oligo name | Direction Forward (FWD) or Reverse (RVS) | Oligo sequence (5' to 3') |
|---|---|---|
| human TNFA | RVS | GGG CTG ATT AGA GAG AGG TCC CT (SEQ ID NO: 210) |
| 18S ribosomal RNA | FWD | CAA GAC GGA CCA GAG CGA AA (SEQ ID NO: 211) |
| 18S ribosomal RNA | RVS | GGC GGG TCA TGG GAA TAA C (SEQ ID NO: 212) |

Luciferase.

To evaluate Treg homing towards HLA-A2-expressing mouse skin grafts in vivo, sorted Tregs (CD4$^+$CD25$^{hi}$CD127$^{lo}$) were stimulated with L-cells as described above. The next day, cells were transduced with HER2-CAR, mA2-CAR or Hlk2 hA2-CAR lentivirus at an MOI of 10 and 8 h later with luciferase-GFP-lentivirus at an MOI of 5. The lentiviral plasmid encoding a beetle luciferase-GFP-fusion protein (pELNS.CBG-T2A-GFP (CBR)) was used as described previously (Barrett et al., 2014). After 7 days of culture, double-transduced GFP+ΔNGFR+Tregs expressing the CAR and luciferase were sorted before restimulation with L-cells as described above. On day 12 of the culture, 1-3×10$^6$ luciferase-CAR Tregs and 6×10$^6$ human allogeneic HLA-A2$^-$ PBMCs were injected intravenously into skin-transplanted NSG mice. For bioluminescent imaging, D-luciferin potassium salt (150 mg/kg, Gold Bio) was injected i.p. immediately before anesthesia with isoflurane and images were acquired within 15-20 min on Ami-X (Spectral Instruments Imaging). Data were analyzed with AmiView software (Spectral Instruments Imaging, version 1.7.06) and the luminescent signal was quantified as the ratio of photons/sec/cm$^2$/steradian in the HLA-A2$^+$ over the HLA-A2$^-$ skin graft. At experimental endpoint, skin-draining axillar lymph nodes and spleen were harvested, placed on a 70 m cell strainer (BD Falcon), then fragmented and filtered through using the plunger of a 1cc syringe. Cells were then stained for flow cytometry.

Statistical Analysis.

All statistics were done using Prism 7.0b. IBM*SPSS Statistics Version 24.0.0.0 was used for FIG. 9.

Results

Construction of Humanized HLA-A2-Specific CARs

The amino acid sequence of the variable regions of the heavy and light chains from the mouse BB7.2 mAbs were aligned to the human immunoglobulin sequences obtained from the international ImMunoGeneTics information System® (IMGT®) database using the IgBLAST tool available from the National Center for Biotechnology Information (NCBI). The V-gene delimitation system was set to the Kabat sequences to obtain the Kabat defined CDRs (Kabat et al., 1991). In addition, the Chothia definition (Chothia et al., 1987) was identified.

A number of different human germline genes were tested as framework sequences for the CDR grafting. In addition to identifying the human germline sequences that were most comparable to the mouse sequence, the CDR lengths were also considered to maintain the structure as much as possible. The human CDRs (Kabat numbering) were replaced with the mouse counterpart CDRs from the BB7.2 antibody. Also, additional CDR amino acids of the heavy chain were replaced by combining the Chothia and Kabat numbering. Ultimately 6 different humanized heavy chains and 5 different humanized light chains were generated, and a total of 20 different chimeric antigen receptors were generated by combining the humanized heavy and light chains.

Expression and Antigen Specificity of Humanized HLA-A2-Specific CARs

Figure 2:
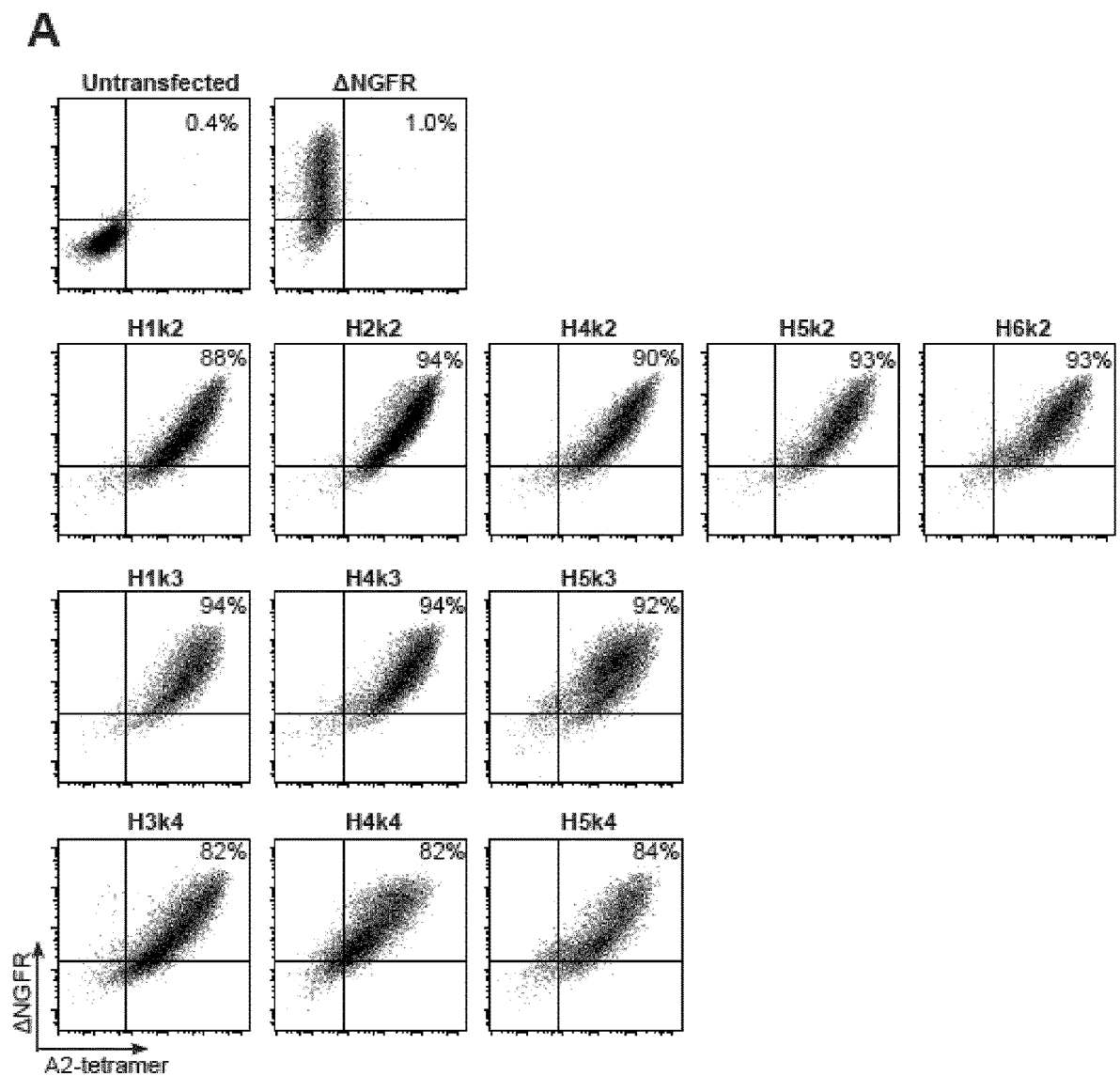
FIG. 2. Cell surface expression and specificity of humanized anti-HLA-A2 CARs. 293T cells were transiently transfected with the indicated construct and after 48 hours expression and antigen specificity was measured by flow cytometric staining with anti-ΔNGFR mAbs and HLA-A2 tetramers. A & B show dot plots for constructs which do, or do not, retain their ability to bind to HLA-A2, respectively. Data are representative of two independent experiments.
Figure 2:
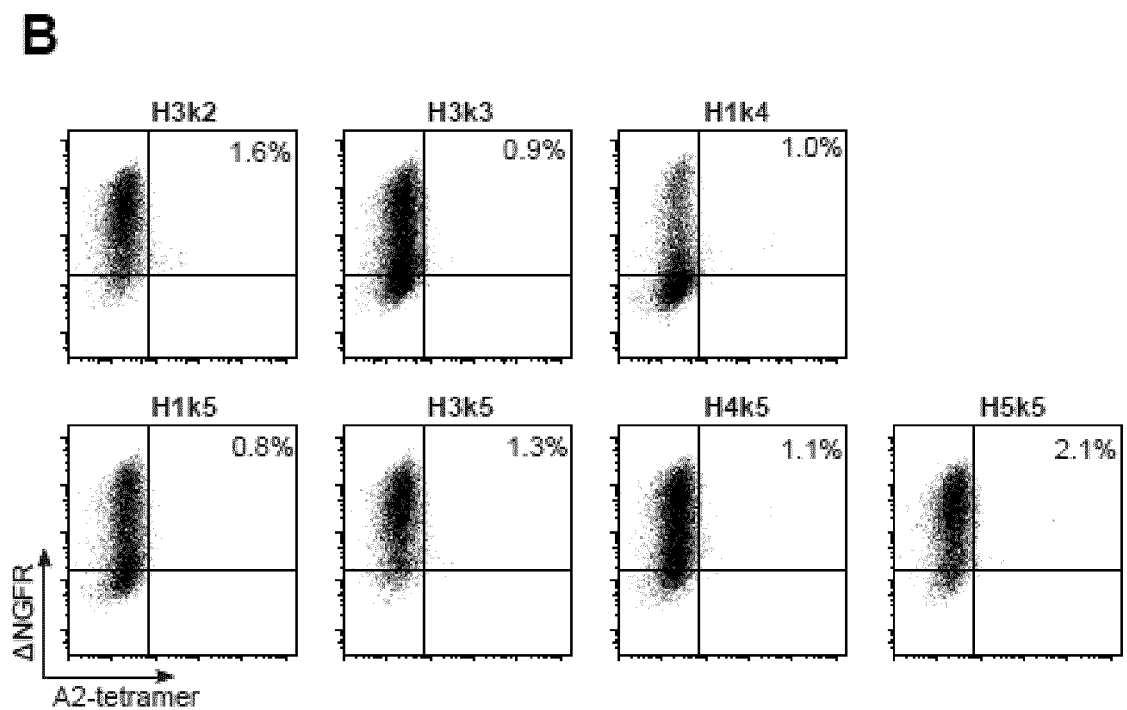

To test for antigen specificity, the various hA2-CAR constructs were transiently transfected into 293T cells, stained with HLA-A*02:01 tetramers and analyzed by flow cytometry. Eleven hA2-CAR constructs were expressed and bound to the A*02:01 tetramer (FIG. 2).

Figure 3:
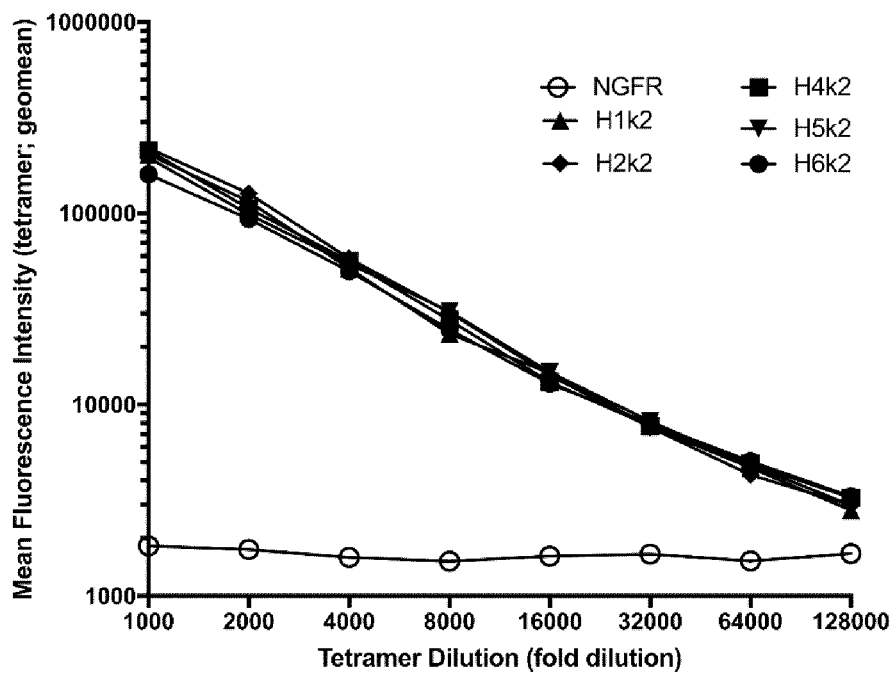
FIG. 3. Comparison of humanized anti-HLA-A2 CAR strength of binding. 293T cells were transfected with the indicated humanized anti-HLA-A2 CAR constructs and stained with the indicated dilutions of HLA-A2 tetramer. A, B & C show graphs depicting the geometric mean fluorescence intensity of HLA-A2 tetramer binding within gated ΔNGFR$^+$ cells, with constructs grouped according to light chain usage.
Figure 3:
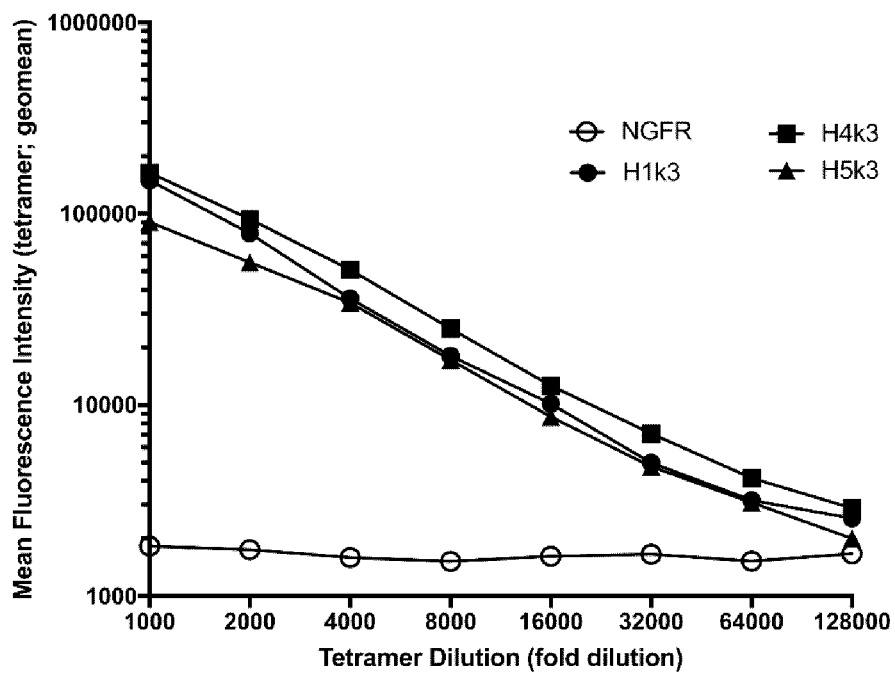
Figure 3:
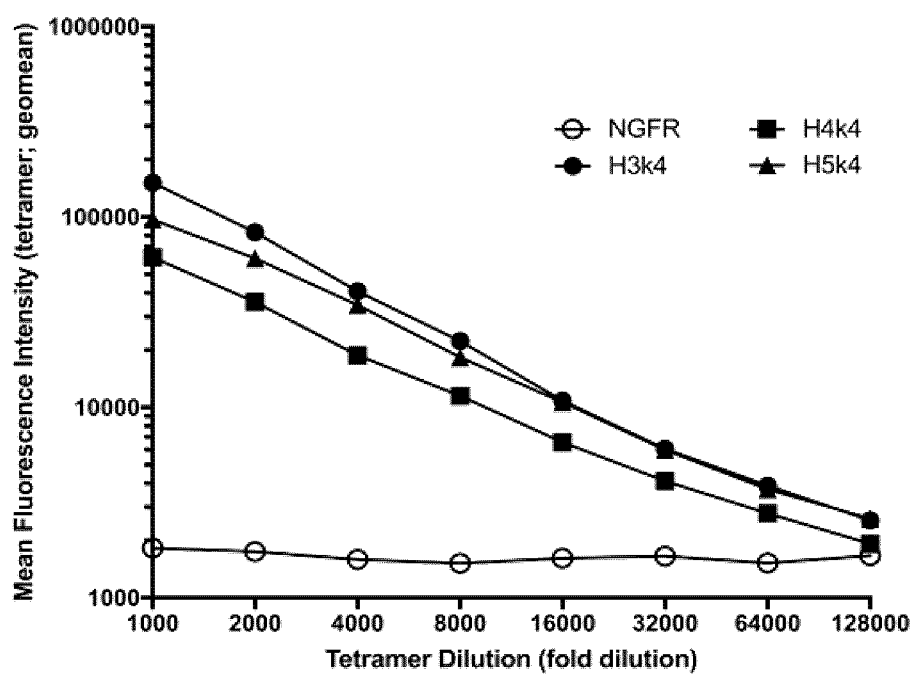

Next we compared the strength of binding of the various hA2-CAR constructs. Transiently transfected 293T cells were stained with increasing dilutions of A*02:01 tetramer, then analyzed by flow cytometry. As shown in FIG. 3 (A, B and C), eleven hA2-CAR constructs bind A*02:01 tetramer to a high degree in a tetramer concentration-dependent manner.

hA2-CAR-Mediated Stimulation Activates Tregs

Figure 4:
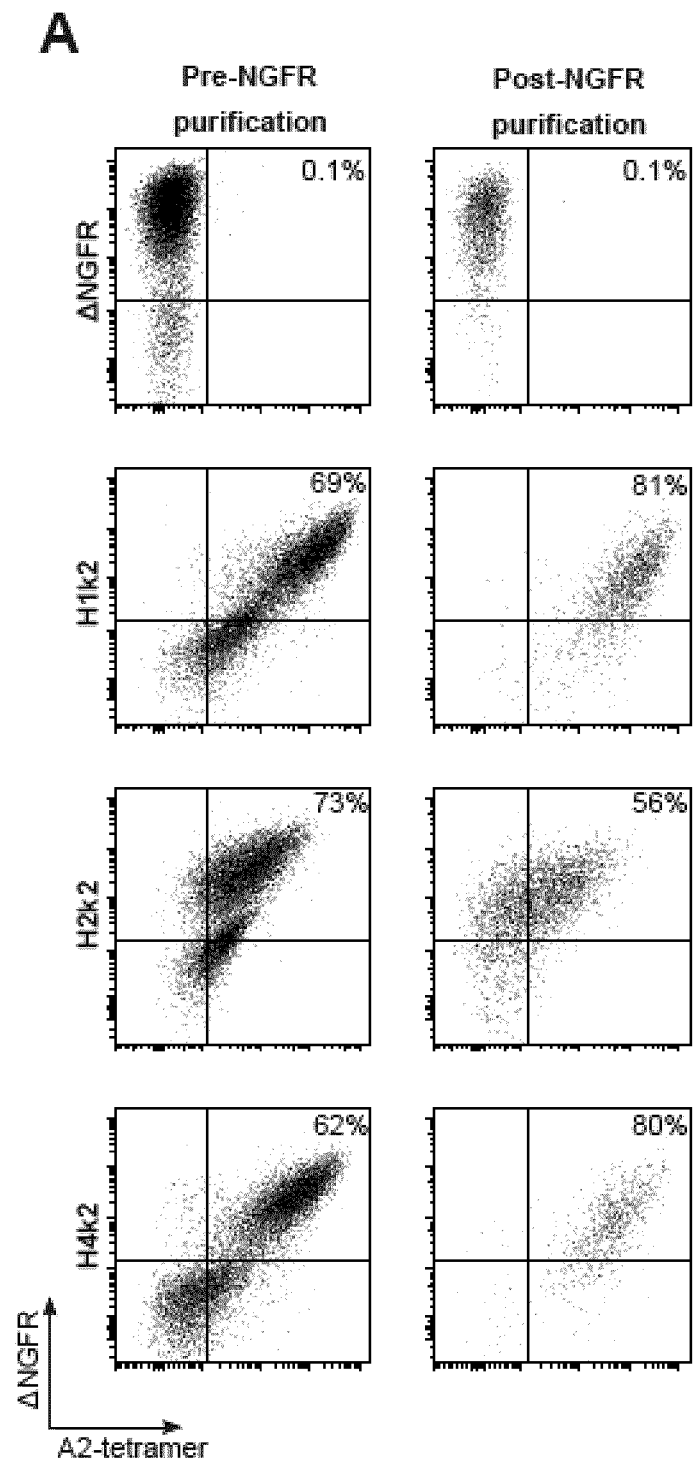
FIG. 4. Expression and specificity of humanized anti-HLA-A2 CARs on Tregs. CD4$^+$CD25$^{hi}$CD127$^{lo}$ Tregs were activated, one day later transduced with the indicated lenti virus, then allowed to expand. Seven days after activation, ΔNGFR-expressing cells were selected by magnetic-bead based separation. Transduction efficiency and HLA-A2 binding was determined by flow cytometry before and after separation of ΔNGFR$^+$ cells (A, B, C & D). Numbers represent the proportion of ΔNGFR$^+$ tetramer$^+$ cells. Data are representative of independent experiments. (E) summarized data of percent or mean fluorescence intensity of A*02:01-tetramer binding.
Figure 4:
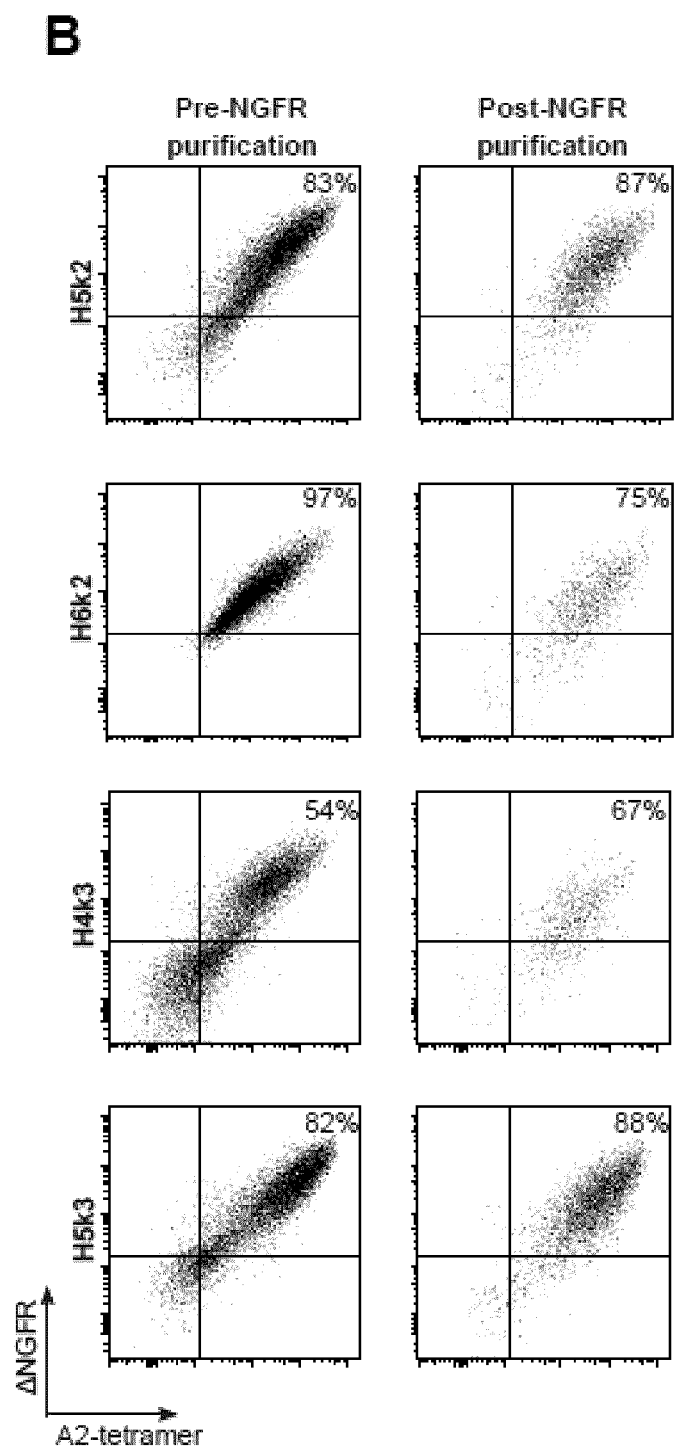
Figure 4:
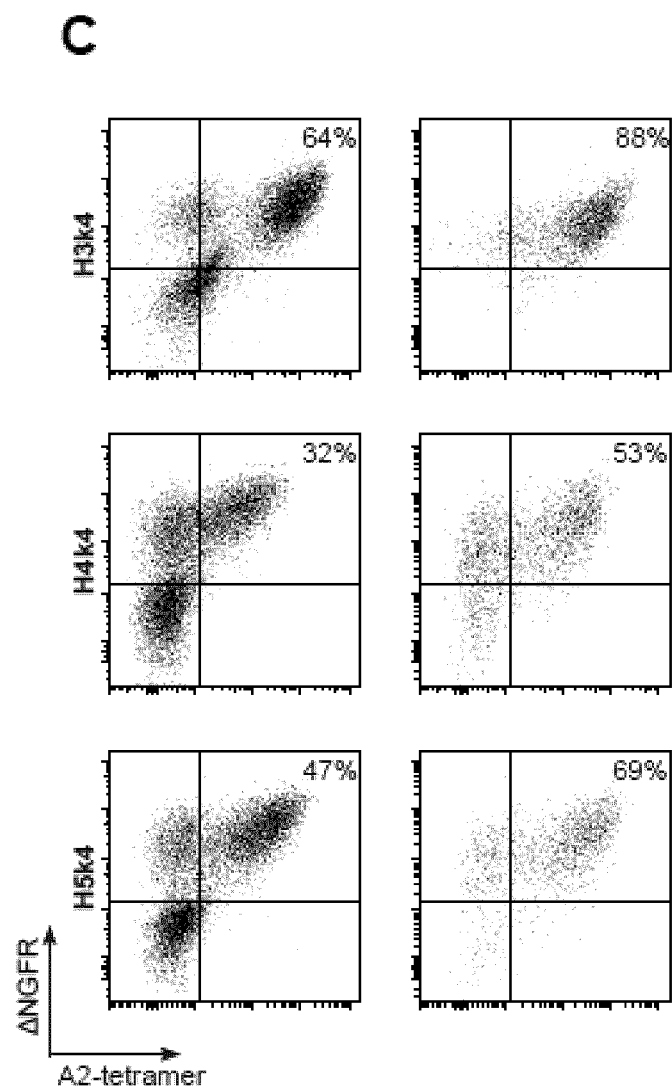
Figure 4:
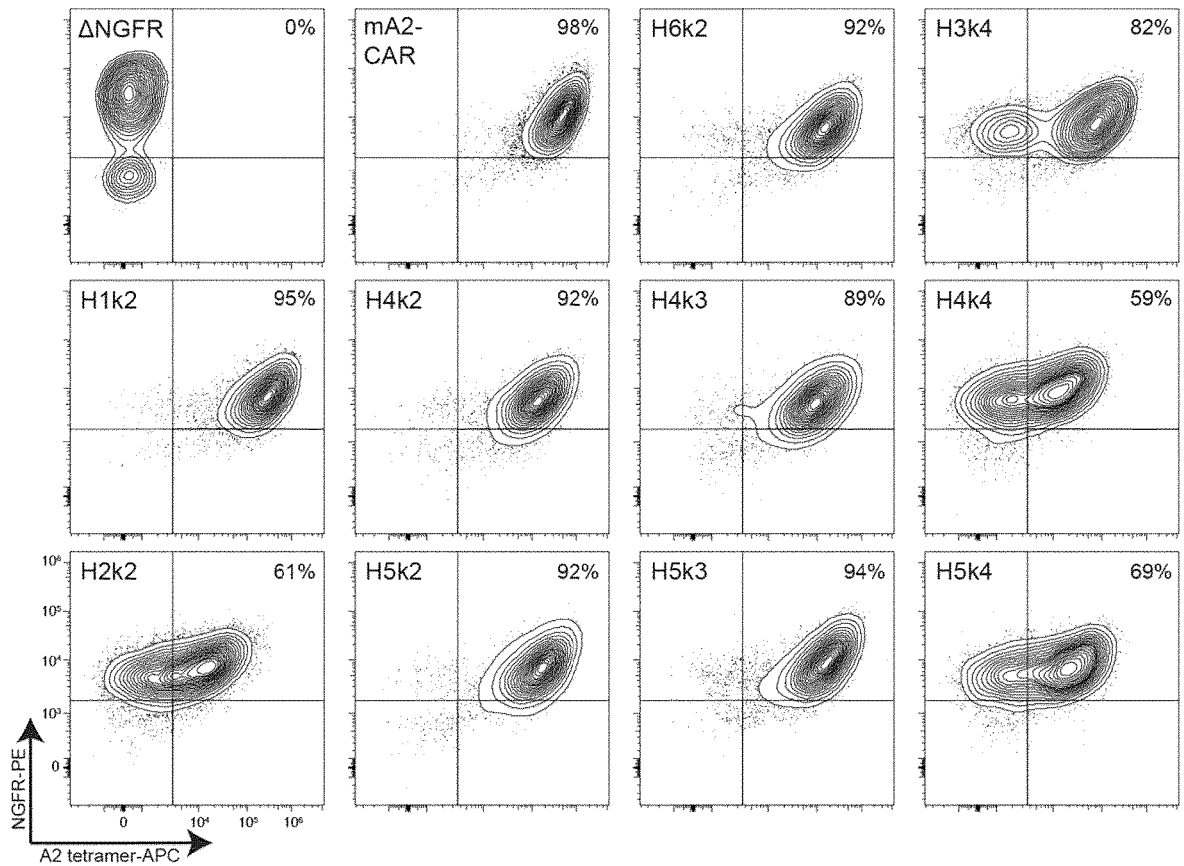
Figure 4:
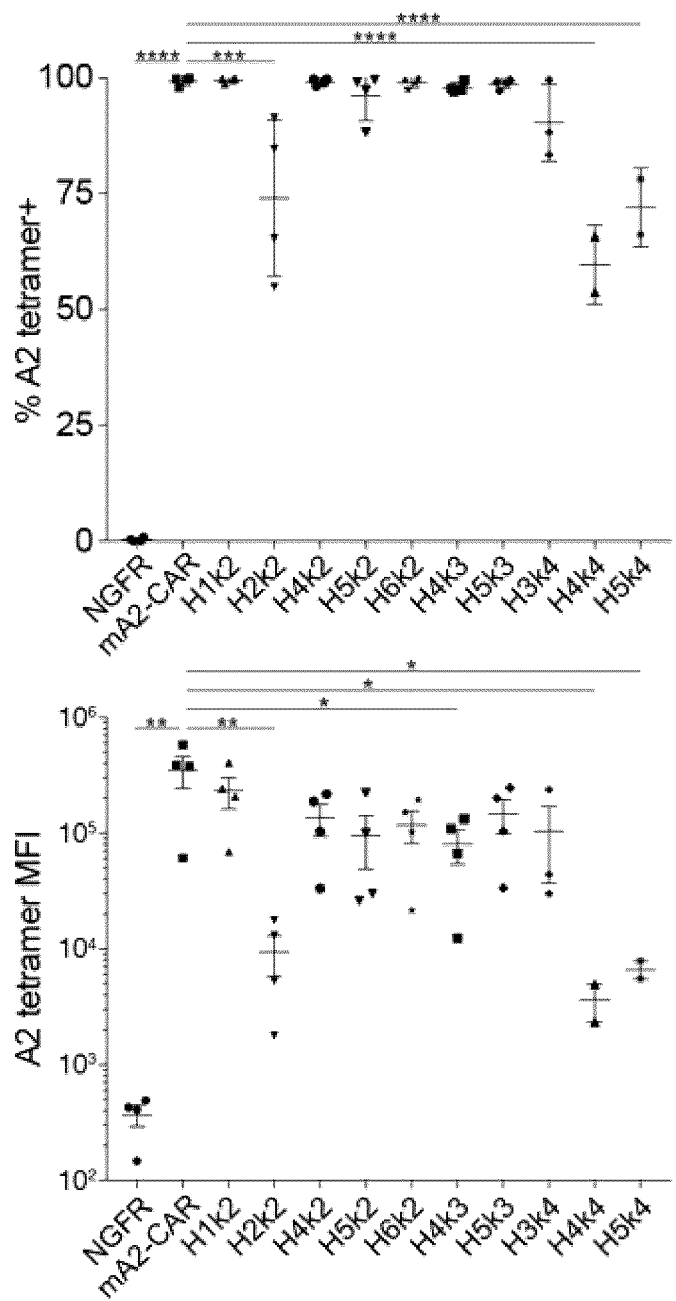
Figure 5:
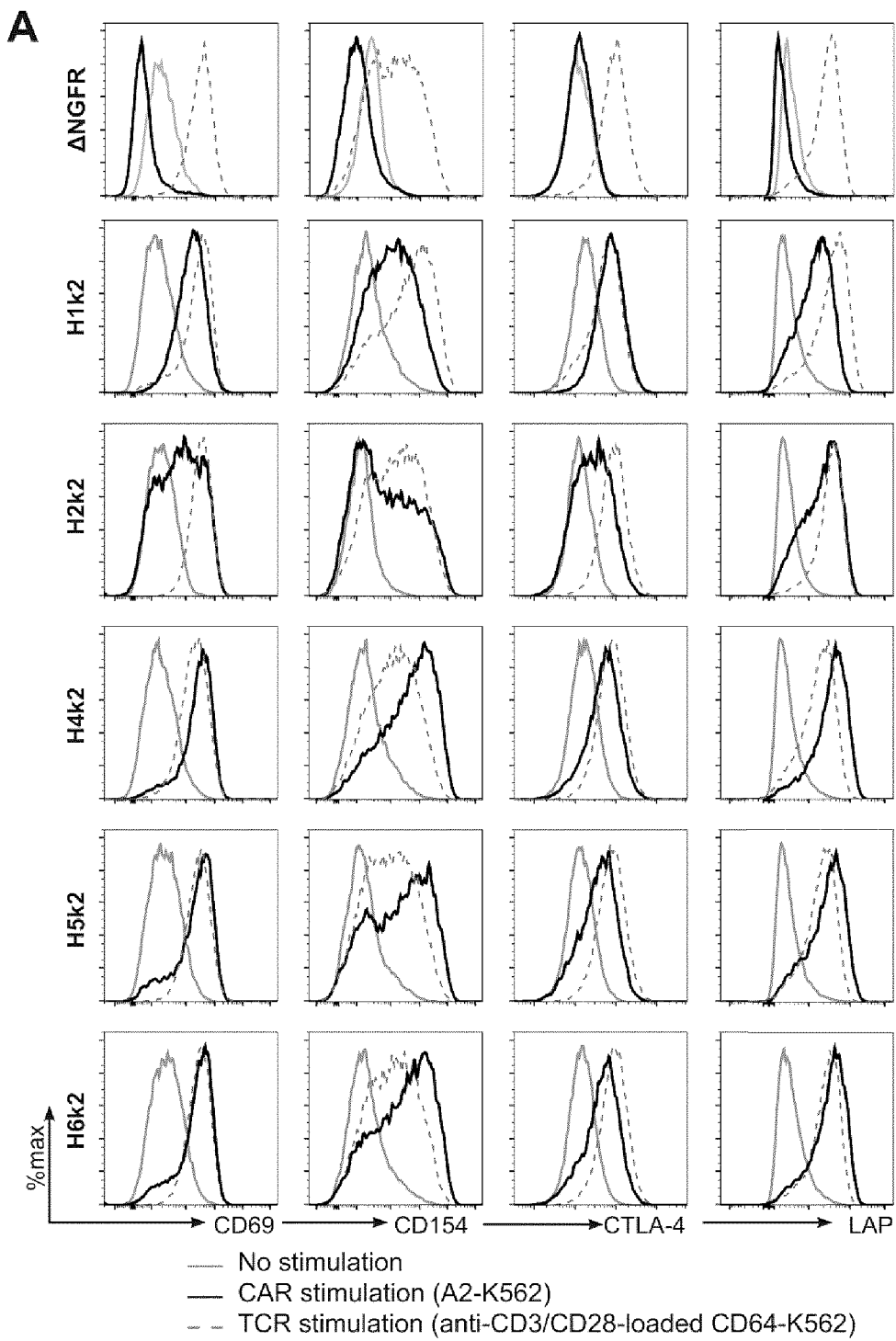
FIG. 5. HLA-A2 CAR-mediated activation of Tregs. CD4$^+$CD25$^{hi}$CD127$^{lo}$ Tregs were activated, transduced with the indicated lentivirus and allowed to expand. After 7 days, the Tregs were rested with 100 U/mL IL-2 overnight then left unstimulated or stimulated by co-culture with a 2:1 (Tregs: K562 cells) ratio of anti-CD3/28-loaded CD64-
Figure 5:
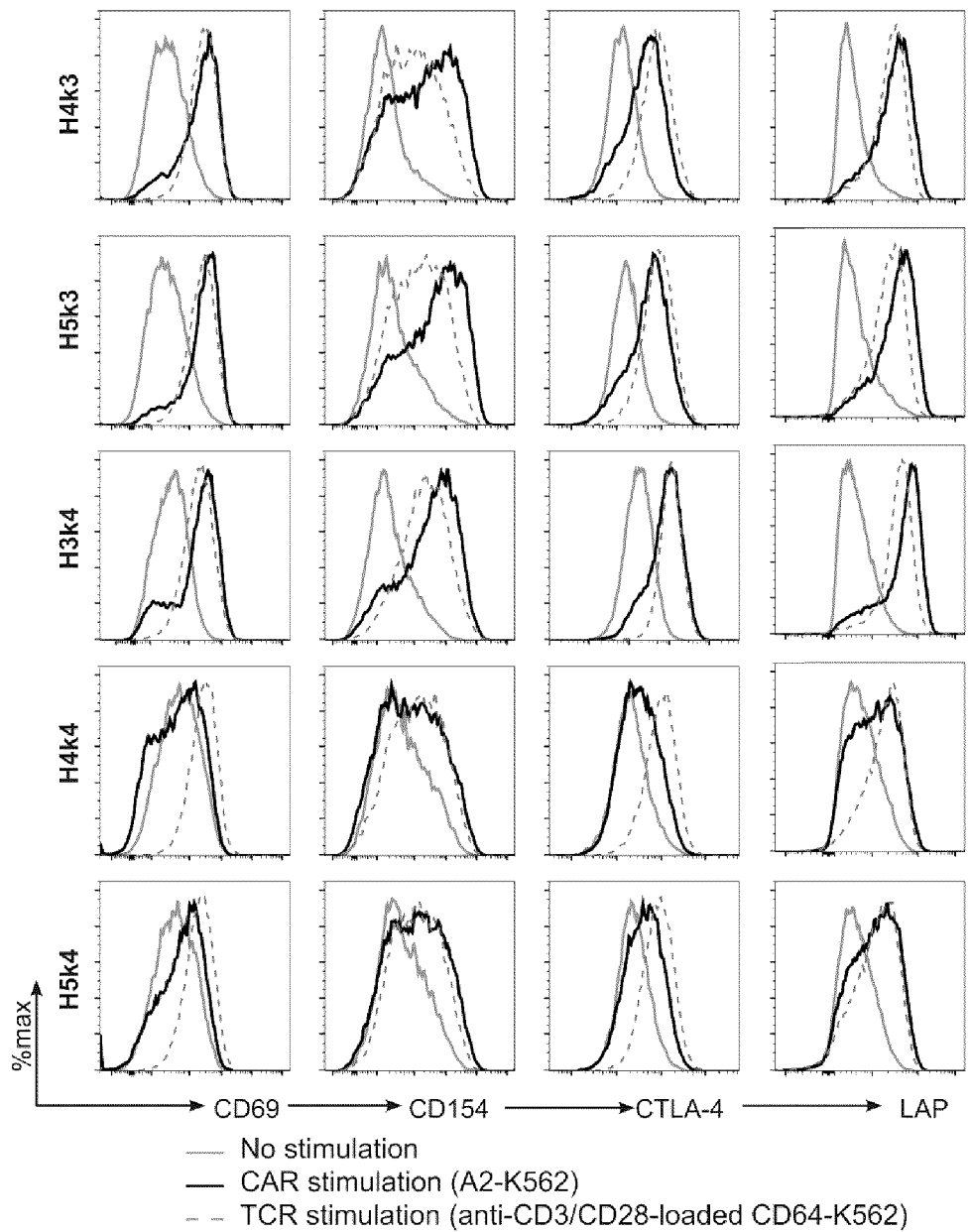
Figure 5:
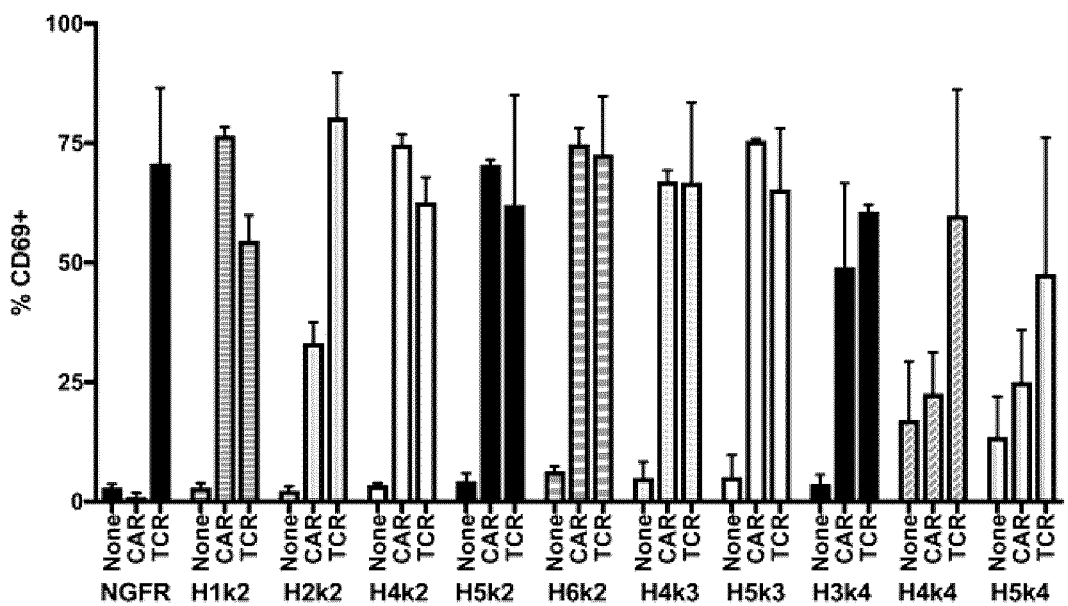
Figure 5:
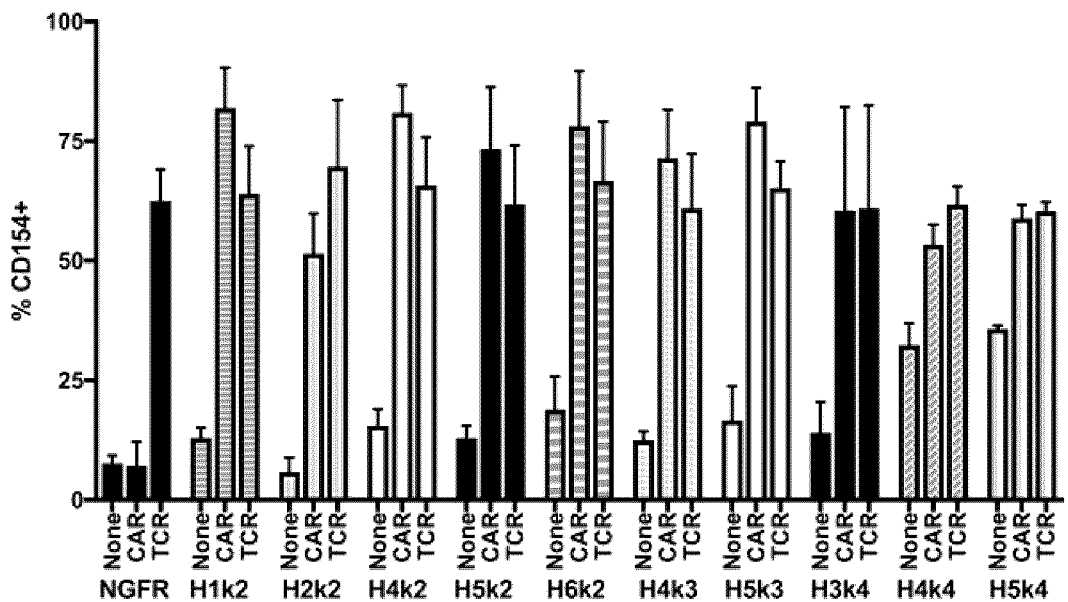
Figure 5:
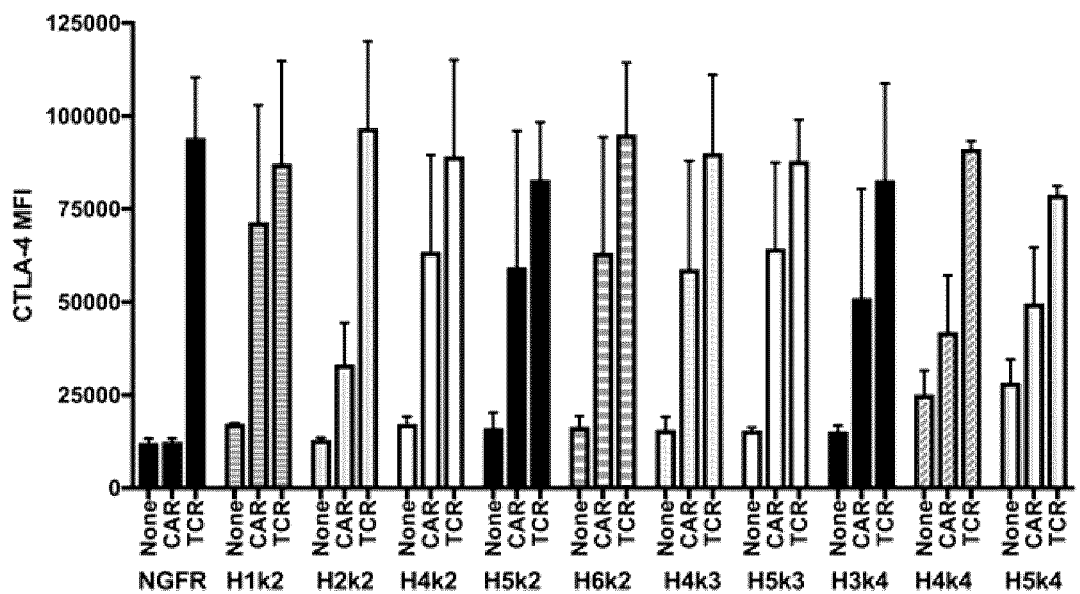
Figure 5:
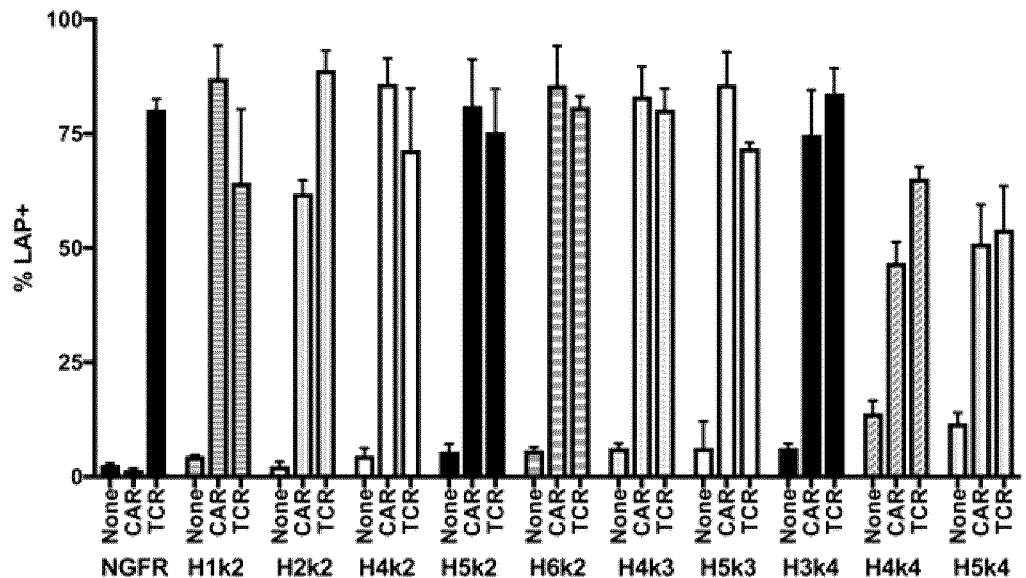
Figure 5:
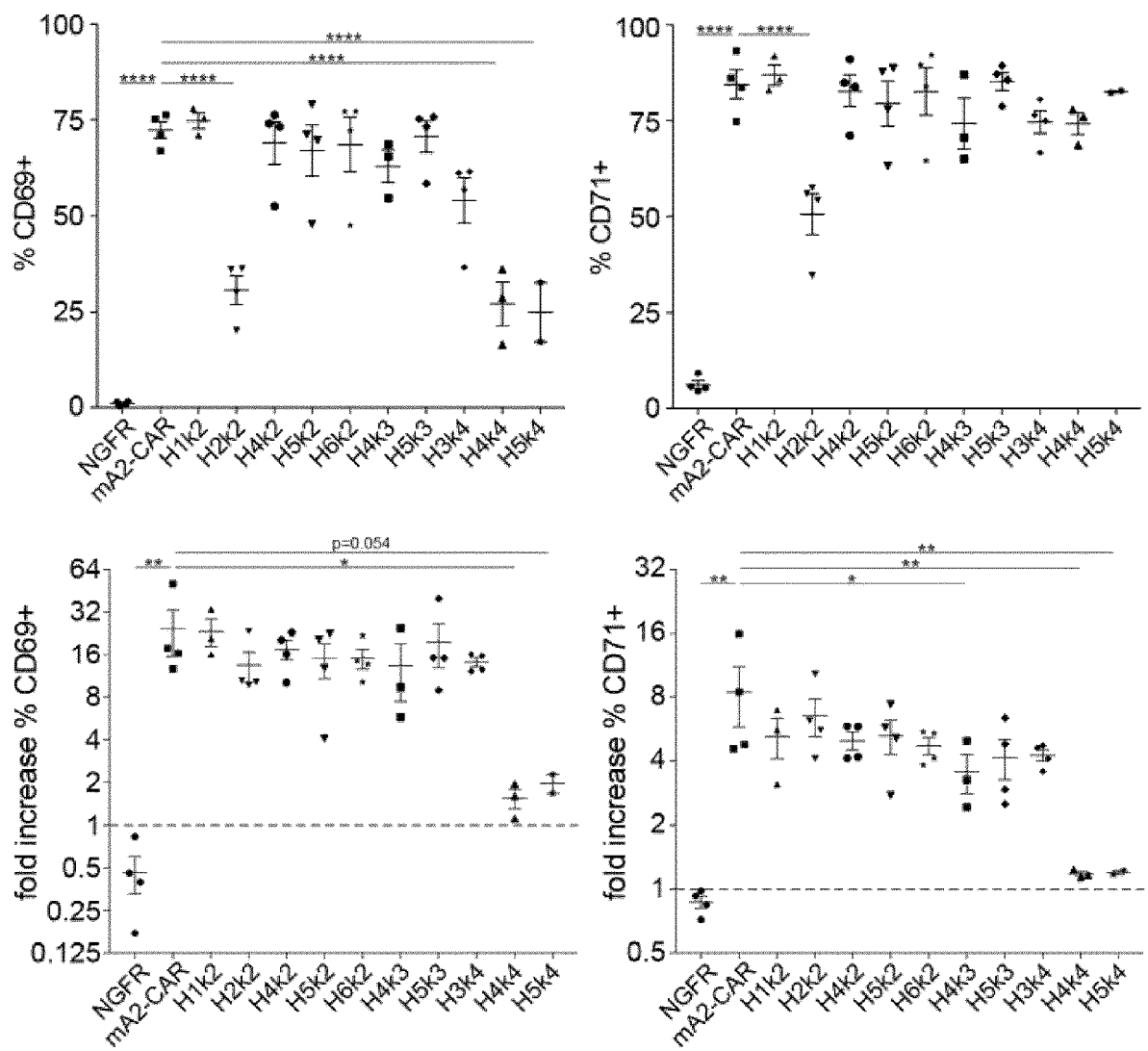
Figure 5:
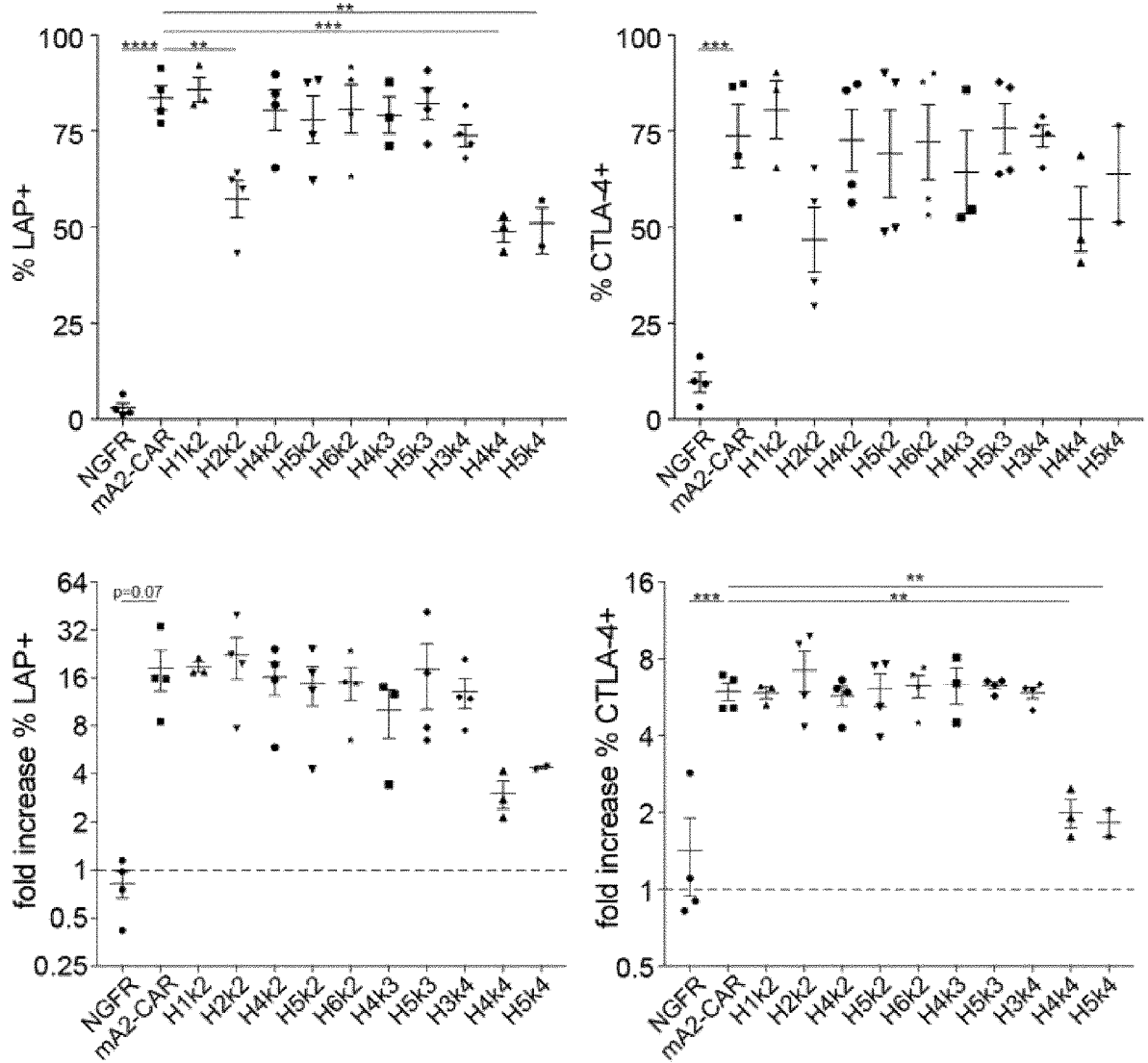

To test the function of the A2-CAR in Tregs, CD4$^+$CD25$^{hi}$CD127$^{lo}$ cells were sorted from peripheral blood. As shown in FIG. 4 (A, B and C), Tregs were stimulated, transduced and cultured for an additional 6-7 days. At the end of 7-8 days of culture, cells were purified as NGFR$^+$ cells and cell surface expression of hA2-CAR variant was tested with flow cytometry. As shown in FIG. 4, Tregs transduced with hA2-CAR constructs showed positive staining by the HLA-A2 tetramer as compared to Tregs transduced with the ΔNGFR control construct, indicating a preservation of antigen specificity for Tregs expressing the hA2-CAR. Technical difficulties were encountered with producing high titer lentivirus for (Hlk3) and this CAR was not tested in Tregs in this experiment. CAR cell surface expression and specificity was tested by staining with an A*02:01 tetramer revealing that H2k2, H4k4 and H5k4 had a bimodal pattern of expression in Tregs, with a lower mean fluorescence intensity (MFI) of A2-tetramer$^+$ cells (FIGS. 4D and 4E).

We next investigated if stimulation via hA2-CAR activated Tregs (hA2-CAR Tregs) in comparison to Tregs expressing only the truncated NGFR transduction marker (NGFR Tregs). NGFR and hA2-CAR Tregs were left unstimulated, stimulated via the CAR with K562 cells expressing HLA-A*02:01 or stimulated via the TCR with K562 cells expressing CD64, a high affinity Fc receptor, that was pre-loaded with anti-CD3/anti-CD28 antibodies. Comparison between NGFR Tregs and hA2-CAR Tregs showed much higher CAR-stimulated expression of CD69 and CD71 in most hA2-CAR Tregs over multiple time points. In contrast, when stimulated via the TCR, both NGFR and hA2-CAR Tregs were able to upregulate CD69, indicating that they retain their ability to signal via the TCR after transduction of CAR DNA (as shown in FIG. 13). hA2-CAR-mediated stimulation of Tregs also caused significantly greater upregulation of proteins associated with Treg function, demonstrating that stimulation through the hA2-CAR preserves the expected high expression of CTLA-4 and LAP (FIGS. 5A-F).

Cross Reactivity of hA2-CAR Constructs on Other Class I HLA Alleles

There are many different alleles of HLA that have evolved over time from a smaller number of ancestor alleles. Consequently, there are allele families that may differ by only a few amino acids and a single anti-HLA antibody may recognize multiple alleles within an evolutionarily-related family. The mouse monoclonal antibody (BB7.2) is known to have cross reactivity to additional HLA-A alleles (Hilton & Parham, 2013.). Specifically, when tested in a solid-phase assay, the BB7.2 antibody was found to recognize five subtypes of HLA-A2 (*02:01, *02:02, *02:03, *02:05, *02:06) and to be cross reactive with HLA-A*69:01, and when tested at high concentrations, also with HLA-A*23:01, A*24:02, A*24:03, A*68:01, and A*68:02 (Hilton & Parham, 2013.). In the context of transplantation, knowledge of alloAg specificity is required to ensure specific targeting to allogenic cells, tissues and/or organs. The traditional way to measure T cell alloreactivity is imprecise and non-quantitative as it involves functional MLRs with large banks of haplotyped PBMCs. To assess the cross reactivity of humanized anti-HLA-A2 antibodies of the invention and compared to the BB7.2 antibody, we adapted the ONE Lambda solid phase assay, which is designed for measuring anti-HLA-antibodies in serum, to measure HLA-coated bead binding to the humanized CARs of interest. The BB7.2 CAR was generated as described in MacDonald, K. G. (2016). NGFR+ Tregs expressing the indicated humanized CARs were incubated with Flow Panel Reactive Single Antigen beads, with binding to a single class of beads quantified as the loss of signal in the bead gate in the forward/side scatter plot (see methods for details). The data were normalized to the number of negative control beads in the sample, and the amount of relative binding to hCAR-expressing Tregs was calculated in relation to the amount of binding by NGFR-control Tregs by the number of negative beads in the NGFR specimen multiplied by the number of negative beads in the NGFR specimen. To validate the methodology, the relative binding of each m/hA2-CAR construct to HLA-A*02:01 as determined by the FlowPRT cell assay (FIG. 6B) was compared to the MFI of tetramer binding (FIG. 6C). This analysis revealed a strong, direct correlation between the two methods of detecting A*02:01 binding. We further asked if amount of A*02:01 binding, as determined by the FlowPRT cell assay, correlated with the biological effect of exposure to A*02:01. Indeed, we found there was a direct correlation between the amount of A*02:01 binding quantified by FlowPRT cell assay and stimulation of Treg activation, as judged by CD69 upregulation following exposure to A*02:01-expressing APCs (FIG. 6D). These data demonstrate the utility of the FlowPRT cell method to measure the ability of alloAg-specific CARs to bind to different HLA alleles.

As shown in FIG. 6 and Table 9, all hA2-CAR constructs significantly bound HLA-A*02:01, confirming the tetramer binding assays. When we tested BB7.2 antibody binding in the single antigen FlowPRA assay, we confirmed high binding to A*69:01 but could not confirm cross-reactivity to A*23:01 or A*24:02 (FIG. 6). When testing the relative ability of the m/hA2-CAR Tregs to bind to various HLA-A alleles, we found the mA2-CAR-Tregs bound significantly to HLA-A*03:01, A*25:01, A*29:02, A*30:01. A*31:01, A*33:01, A*36:01, A*68:01 and A*69:01 (FIG. 6, Table 9). In contrast, all variants of hA2-CAR Tregs surprisingly displayed reduced cross reactivity compared to mA2-CAR Tregs (FIG. 6, Table 9). As expected, all CAR constructs bound to HLA-A*69:01, a variant of A*02:01 differing by only 6 amino acids. None of the CAR-constructs displayed any significant binding to HLA-B (FIG. 6).

The relationship between the degree of CAR-Treg Ag binding and biological activity is unknown. To define the biological significance of HLA cross reactivity we generated APCs expressing HLA-A*24:02, A*25:01 or A*68:01; all cells had comparable levels of HLA-A expression (data not shown). We found that only co-culture with HLA-A*02:01-expressing cells resulted in significant activation of m/hCAR-Tregs, as judged by upregulated expression of CD69, CD71, LAP, CTLA-4 (FIG. 6I) or CD40L (data not shown). These data suggest that effective CAR-mediated activation of Tregs requires high affinity and/or avidity interactions. Accordingly, while some hA2-CARs show binding A*25:01 and A*68:01 in the FlowPRT assay, the strength of binding is insufficient for cellular activation.

TABLE 9

Binding interactions between m/hA2-CARs and HLA-A/B protein found to be statistically significant (2-way ANOVA, Dunnett post-test).

| HLA-Allele | CAR | p value |
|---|---|---|
| A*02:01 | mA2-CAR | 0.0001 |
|  | H1k2 | 0.0001 |
|  | H2K2 | 0.0001 |
|  | H4k2 | 0.0001 |
|  | H5k2 | 0.0001 |
|  | H6k2 | 0.0001 |
|  | H4k3 | 0.0001 |
|  | H5k3 | 0.0001 |
|  | H3k4 | 0.0001 |
|  | H4k4 | 0.0006 |
|  | H5k4 | 0.0001 |
| A*25:01 | mA2-CAR | 0.0001 |
|  | H1K2 | 0.0061 |
| A*69:01 | mA2-CAR | 0.0001 |
|  | H4k2 | 0.0001 |
|  | H5k2 | 0.0001 |
|  | H1k2 | 0.0001 |
|  | H3k4 | 0.0013 |
|  | H2k2 | 0.0084 |
|  | H5k3 | 0.0001 |
|  | H4k3 | 0.0001 |
|  | H6k2 | 0.0060 |
| A*03:01 | mA2-CAR | 0.0315 |
| A*29:02 | mA2-CAR | 0.0001 |
| A*30:01 | mA2-CAR | 0.0001 |
| A*31:01 | mA2-CAR | 0.0001 |
|  | H1k2 | 0.0077 |
| A*33:01 | mA2-CAR | 0.0019 |
| A*36:01 | mA2-CAR | 0.0035 |
|  | H1k2 | 0.0082 |
| A*68:01 | mA2-CAR | 0.0001 |
|  | H1k2 | 0.0001 |
|  | H5k2 | 0.0337 |
|  | H6k2 | 0.0009 |

We developed a new way to systematically test the specificity of CARs for alloantigens, creating a new platform with which to comprehensively identify constructs with defined allele specificity. Surprisingly, we discovered that in comparison to the mA2-CAR, CAR humanization decreased cross-reactivity to several HLA-A allelic variants. hA2-CAR Tregs Mediate HLA-A2-Specific Suppression In Vitro To test the ability of a hA2-CAR to stimulate antigen-specific suppressive activity in Tregs, we used mixed lymphocyte reactions (MLRs) according to the experimental design shown in FIG. 7A. Specifically, proliferation of HLA-A*02:01 negative T cells was stimulated by co-culture with mature HLA-A*02:01-positive dendritic cells in the absence or presence of increasing ratios of Tregs which were either untransduced, or transduced with the control NGFR lentivirus or lentivirus encoding the Hlk2 hA2-CAR. As shown in FIGS. 7B-E, hA2-CAR-expressing Tregs were significantly better able to suppress alloantigen-stimulated proliferation of CD4+ T cells in comparison to control Tregs transduced with the NGFR control lentiviral construct.

hA2-CAR Tregs Mediate HLA-A2-Specific Suppression of Xenogeneic GVHD In Vivo

To test the functional capacity of hA2-CAR Tregs in vivo, we used a mouse model in which human PBMCs engrafted into immunodeficient NSG mice caused xenogeneic GVHD. $8 \times 10^6$ PBMCs from an HLA-A2+ donor were injected into irradiated NSG mice with or without Tregs expressing the Hlk2 hA2-CAR. The ratio of PBMC to hA2-CAR Tregs tested was 1:2 (i.e. $8 \times 10^6$ PBMCs to $4 \times 10^6$ Tregs). Mice were monitored for 7 weeks by clinical score as described in the Methods. In alignment with the in vitro data in FIG. 7, the mice receiving hA2-CAR-expressing Tregs had improved survival, reduced weight loss and delayed onset of xenoGVHD in comparison to mice that did not receive hA2-CAR Tregs (solid grey line) (FIGS. 8A, B and C). While the biological effect of the Tregs was observed, we did not detect circulating m/hA2-CAR Tregs, measured from 14 days post injection (FIGS. 8D and 8E).

hA2-CAR Tregs Traffic to HLA-A2+ Skin Grafts In Vivo

To test how CAR-directed specificity affected Treg trafficking, we performed side-by-side skin transplants from NSG or NSG-A*02:01-transgenic mice onto NSG mice (FIG. 9A). After graft recovery, PBMCs were injected in the absence or presence of m/hA2-CAR Tregs or with HER2-CAR Tregs as a non-specific polyclonal Treg control (MacDonald et al., 2016). In addition to the CAR, Tregs were co-transduced with a lentivirus encoding a luciferase-GFP fusion protein. Bioluminescent imaging was performed after D-luciferin injection up to 21 days post-Treg injection (Barrett et al., 2014). Polyclonal HER2-CAR Tregs showed a directed pattern of trafficking toward the allografts but were equally distributed between the A2-positive and -negative grafts. These polyclonal Tregs may be migrating in response to the inflammatory signals emanating from post-operative skin because in unmanipulated immunodeficient mice, human T cells typically traffic to the lung (Nervi et al. 2007). In contrast to polyclonal HER2-CAR Tregs which trafficked equally to A2-negative and -positive skin, both m/hA2-CAR Tregs rapidly trafficked to the A2-expressing skin. In addition, m/hA2-CAR Tregs persisted longer than non-specific HER2-CAR Tregs. Whereas HER2-CAR Tregs were undetectable by day 21, a strong m/hA2-CAR Tregs signal remained (FIG. 9B). Quantification of the ratio of luminescence in the A2-positive versus A2-negative graft revealed significant Ag-driven trafficking of both Hlk2 and mA2-CAR Tregs to the A2-expressing graft (FIGS. 9C and 9D).

In addition to graft-localized m/hA2-CAR Tregs, at day 21 we noted an adjacent signal consistent with the location of a local draining lymph node. Upon sacrifice, graft draining lymph nodes were collected and flow cytometric analysis revealed a significant proportion of hCD4+FOXP3+ ΔNGFR+ A2-tetramer+ CAR Tregs. In contrast, very few of these cells were detected in the spleen (FIGS. 10B and C). This two-step migratory process from graft to lymph node has previously been reported to be necessary for tolerance induction (Zhang et al. 2009). Importantly, lymph node-homing CAR Tregs maintained expression of FOXP3 and CAR, illustrating their stable phenotype.

hA2-CAR Tregs Prevent Human Skin Allograft Rejection

To evaluate the immunoregulatory potential of hA2-CAR Tregs in a solid organ transplant model, we used a humanized model of skin transplantation in which NSG mice were transplanted with human HLA-A2$^{pos}$ skin grafts. After 6 weeks, mice were injected with HLA-A2$^{neg}$ PBMCs with or without autologous Hlk2 hA2-CAR Tregs. Four weeks after cell injection, mice were sacrificed, and the skin graft was collected for evaluation of pathology and inflammatory cytokine expression. All mice maintained stable body weight, indicating a lack of xenogeneic GvHD (FIG. 11A), with similar levels of human leukocyte engraftment in blood and spleens (FIG. 11B). H&E sections were evaluated using a 25-point scale, revealing a significant decrease in the cumulative pathological rejection score in mice that received Hlk2 hA2-CAR Tregs versus PBMC (FIG. 11C). Immunostaining revealed that in comparison to mice receiving PBMCs alone, mice receiving PBMCs and Hlk2 hA2-CAR Tregs had a significant reduction in Ki67+ keratinocytes, and diminished involucrin destruction (FIG. 11D). qPCR quantification also showed a general reduction in inflammatory cytokines within the graft of Hlk2 hA2-CAR Treg-treated mice (FIG. 11E).

As for the xenogeneic GVHD model, while PBMCs were detectable in blood, CAR Tregs were not (FIG. 12). However, immunostaining revealed that in comparison to mice receiving PBMCs alone, mice receiving PBMCs and Hlk2 hA2-CAR Tregs had a significantly higher proportion of FOXP3+ cells in the graft (FIG. 11F). The presence of FOXP3+ cells was unique to the transplanted skin graft as they were undetectable in the intestine, liver or lung (FIG. 11G). These data show that, as for the model with A2-transgenic NSG skin, Hlk2 hA2-CAR Tregs specifically traffic to human A2+ skin allograft, where they persist indefinitely.

This application contains a sequence listing in electronic form as a text file, "CDRD-003WO_SEQ_LISTING_ST25" created on Sep. 18, 2018 and having a size of 320 KB. The contents of the text file are incorporated by reference herein in their entirety.

REFERENCES

Allan, S. E., A. N. Alstad, N. Merindol, N. K. Crellin, M. Amendola, R. Bacchetta, L. Naldini, M. G. Roncarolo, H. Soudeyns, and M. K. Levings. 2008. Generation of potent and stable human CD4+T regulatory cells by activation-independent expression of FOXP3. Molecular therapy: the journal of the American Society of Gene Therapy 16:194-202.

Barrett, D. M., Singh, N., Liu, X., Jiang, S., June, C. H., Grupp, S. A., and Zhao, Y. 2014. Relation of clinical culture method to T-cell memory status and efficacy in xenograft models of adoptive immunotherapy. Cytotherapy 16: 619-630.

Blat, D., E. Zigmond, Z. Alteber, T. Waks, and Z. Eshhar. 2014. Suppression of murine colitis and its associated cancer by carcinoembryonic antigen-specific regulatory T cells. Molecular therapy: the journal of the American Society of Gene Therapy 22:1018-1028.

Bluestone, J. A., J. H. Buckner, M. Fitch, S. E. Gitelman, S. Gupta, M. K. Hellerstein, K. C. Herold, A. Lares, M. R. Lee, K. Li, W. Liu, S. A. Long, L. M. Masiello, V. Nguyen, A. L. Putnam, M. Rieck, P. H. Sayre, and Q. Tang. 2015. Type 1 diabetes immunotherapy using polyclonal regulatory T cells. Science translational medicine 7:315ra189.

Boardman, D. A., C. Philippeos, G. O. Fruhwirth, M. A. Ibrahim, R. F. Hannen, D. Cooper, F. M. Marelli-Berg, F. M. Watt, R. I. Lechler, J. Maher, L. A. Smyth, and G. Lombardi. 2016. Expression of a Chimeric Antigen Receptor Specific for Donor HLA Class I Enhances the Potency of Human Regulatory T Cells in Preventing Human Skin Transplant Rejection. American journal of transplantation: official journal of the American Society of Transplantation and the American Society of Transplant Surgeons Brunstein, C. G., B. R. Blazar, J. S. Miller, Q. Cao, K. L. Hippen, D. H. McKenna, J. Curtsinger, P. B. McGlave, and J. E. Wagner. 2013. Adoptive transfer of umbilical cord blood-derived regulatory T cells and early viral reactivation. Biology of blood and marrow transplantation: journal of the American Society for Blood and Marrow Transplantation 19:1271-1273.

Brunstein, C. G., J. S. Miller, Q. Cao, D. H. McKenna, K. L. Hippen, J. Curtsinger, T. Defor, B. L. Levine, C. H. June, P. Rubinstein, P. B. McGlave, B. R. Blazar, and J. E. Wagner. 2011. Infusion of ex vivo expanded T regulatory cells in adults transplanted with umbilical cord blood: safety profile and detection kinetics. Blood 117:1061-1070.

Casucci M, Bondanza A. 2011. Suicide Gene Therapy to Increase the Safety of Chimeric Antigen Receptor-Redirected T Lymphocytes. Journal of Cancer, 2:378-382.

Chong, A. S. and S. H. Khiew. Transplantation tolerance: don't forget about the B cells. Clin Exp Immunol. 2017, 189(2):171-180.

Chothia and Lesk J. Mol. Biol. 196:901-917 (1987).

Cooke K R, et al. An experimental model of idiopathic pneumonia syndrome after bone marrow transplantation: I. The roles of minor H antigens and endotoxin. Blood. 1996; 88(8):3230-3239.

Crome, S. Q., Lang, P. A., Lang, K. S., and P. S. Ohashi. Natural killer cells regulate diverse T cell responses. Trends Immunol. 2013 July; 34(7):342-9.

Crome, S. Q., Nguyen, L. T., Lopez-Verges, S., Yang, S. Y., Martin, B., Yam, J. Y., Johnson, D. J., Nie, J., Pniak, M., Yen, P. H., Milea, A., Sowamber, R., Katz, S. R., Bernardini, M. Q., Clarke, B. A., Shaw, P. A., Lang, P. A., Berman, H. K., Pugh, T. J., Lanier, L. L., and P. S. Ohashi. A distinct innate lymphoid cell population regulates tumor-associated T cells. Nat Med. 2017 March; 23(3): 368-375.

Delhove, J. M. K. M. et al., Genome-Edited T Cell Therapies, Curr Stem Cell Rep. 2017; 3(2): 124-136.

Di Ianni, M., F. Falzetti, A. Carotti, A. Terenzi, F. Castellino, E. Bonifacio, B. Del Papa, T. Zei, R. I. Ostini, D. Cecchini, T. Aloisi, K. Perruccio, L. Ruggeri, C. Balucani, A. Pierini, P. Sportoletti, C. Aristei, B. Falini, Y. Reisner, A. Velardi, F. Aversa, and M. F. Martelli. 2011. Tregs prevent GVHD and promote immune reconstitution in HLA-haploidentical transplantation. Blood 117:3921-3928.

Dijke, I. E., R. E. Hoeppli, T. Ellis, J. Pearcey, Q. Huang, A. N. McMurchy, K. Boer, A. M. Peeters, G. Aubert, I. Larsen, D. B. Ross, I. Rebeyka, A. Campbell, C. C. Baan, M. K. Levings, and L. J. West. 2016. Discarded Human Thymus Is a Novel Source of Stable and Long-Lived Therapeutic Regulatory T Cells. American journal of transplantation. 16(1):58-71

Eliceiri, K. W., Berthold, M. R., Goldberg, I. G., Ibanez, L. Manjunath, B. S., Martone, M. E., Murphy, R. F., Peng, H., Plant, A. L., Roysam, B., Stuurman, N., Swedlow, J. R., Tomancak, P., Carpenter, A. E. 2012. Biological imaging software tools. Nature Methods 9: 697-710.

Elinav, E., N. Adam, T. Waks, and Z. Eshhar. 2009. Amelioration of colitis by genetically engineered murine regulatory T cells redirected by antigen-specific chimeric receptor. Gastroenterology 136:1721-1731.

Elinav, E., T. Waks, and Z. Eshhar. 2008. Redirection of regulatory T cells with predetermined specificity for the treatment of experimental colitis in mice. Gastroenterology 134:2014-2024.

Ellis, J. M., Henson, V., Slack, R., Ng, J., Hartzman, R. J., and C. Katovich Hurley. Frequencies of HLA-A2 alleles in five U.S. population groups. Predominance Of A*02011 and identification of HLA-A*0231. Hum Immunol. 61(3):334-40 (2000).

Eyquem, J. et al. Targeting a CAR to the TRAC locus with CRISPR/Cas9 enhances tumour rejection, Nature 543, 113-117 (2017).

Fischer, A., Jakubowski, A. A., Lacouture, M. E., Hollman, T. J., Drucker, A. M., Maloy, M., Prockop, S., Querfeld, C., Busam, K. J., Pulitzer, M. P2015. Histopathologic Features of Cutaneous Acute Graft-Versus-Host Disease in T-Cell-Depleted Peripheral Blood Stem Cell Transplant Recipients. The American Journal ofDdermatopathology 37: 523-529.

Fransson, M., E. Piras, J. Burman, B. Nilsson, M. Essand, B. Lu, R. A. Harris, P. U. Magnusson, E. Brittebo, and A. S. Loskog. 2012. CAR/FoxP3-engineered T regulatory cells target the CNS and suppress EAE upon intranasal delivery. Journal of neuroinflammation 9:112.

Fu, B., Tian, Z., and H. Wei. Subsets of human natural killer cells and their regulatory effects. Immunology. 2014 April; 141(4):483-9.

Gargett T, Brown M P. 2014. The inducible caspase-9 suicide gene system as a "safety switch" to limit on-target, off-tumor toxicities of chimeric antigen receptor T cells. Frontiers in Pharmacology, 5:235.

Ghosh et al., 1991 Glycobiology 5: 505-10.

Gill, S., and C. H. June. 2015. Going viral: chimeric antigen receptor T-cell therapy for hematological malignancies. Immunological reviews 263:68-89.

Golshayan, D., S. Jiang, J. Tsang, M. I. Garin, C. Mottet, and R. I. Lechler. 2007. In vitro-expanded donor alloantigen-specific CD4+CD25+ regulatory T cells promote experimental transplantation tolerance. Blood 109:827-835.

Green, E. A., Y. W. Choi, and R. A. Flavell. 2002. Pancreatic lymph node-derived CD4(+)CD25(+) Treg cells: Highly potent regulators of diabetes that require TRANCE-RANK signals. Immunity 16:183-191.

Guillonneau, C., Picarda, E., and I. Anegon. CD8+ regulatory T cells in solid organ transplantation. Curr Opin Organ Transplant. 2010; 15(6):751-6.

Hill G R, Crawford J M, Cooke K R, Brinson Y S, Pan L, Ferrara J L. Total body irradiation and acute graft-versus-host disease: the role of gastrointestinal damage and inflammatory cytokines. Blood. 1997; 90(8):3204-3213.

Hilton, H. G. & Parham, P. Direct binding to antigen-coated beads refines the specificity and cross-reactivity of four monoclonal antibodies that recognize polymorphic epitopes of HLA class I molecules. Tissue Antigens 81, 212-220 (2013).

Himmel, M. E., K. G. MacDonald, R. V. Garcia, T. S. Steiner, and M. K. Levings. 2013. Helios+ and Helios− cells coexist within the natural FOXP3+T regulatory cell subset in humans. Journal of immunology 190:2001-2008.

Hombach, A. A., D. Kofler, G. Rappl, and H. Abken. 2009. Redirecting human CD4+CD25+ regulatory T cells from the peripheral blood with pre-defined target specificity. Gene therapy 16:1088-1096.

Hutchinson, J. A., Ahrens, N., and E. K. Geissler. MITAP-compliant characterization of human regulatory macrophages. Transpl Int. 2017 August; 30(8):765-775.

Jamnani, F., R., Fatemeh Rahbarizadeh, Mohammad Ali Shokrgozar, Fereidoun Mahboudi, Davoud Ahmadvand, Zahra Sharifzadeh, Ladan Parhamifar, S. Moein Moghimi. 2014. T cells expressing VHH-directed oligoclonal chimeric HER2 antigen receptors: Towards tumor-directed oligoclonal T cell therapy. Biochimica et Biophysica Acta, 1840(1): 378-386.

Joffre, O., T. Santolaria, D. Calise, T. Al Saati, D. Hudrisier, P. Romagnoli, and J. P. van Meerwijk. 2008. Prevention of acute and chronic allograft rejection with CD4+CD25+ Foxp3+ regulatory T lymphocytes. Nature medicine 14:88-92.

Jones, B. S., Lamb, L. S., Goldman, F., and A. Di Stasi. 2014. Improving the safety of cell therapy products by suicide gene transfer. Front Pharmacol. Volume 5, 254.

June, C. H., S. R. Riddell, and T. N. Schumacher. 2015. Adoptive cellular therapy: A race to the finish line. Science translational medicine 7:280-287.

Juvet, S. C. and L. Zhang. Double negative regulatory T cells in transplantation and autoimmunity: recent progress and future directions. J Mol Cell Biol. 2012 February; 4(1):48-58.

Kabat et al., Sequences of Proteins of Immunological Interest, 5th Ed. Public Health Service, National Institutes of Health, Bethesda, MD (1991).

Kanitakis, J. 2008. The challenge of dermatopathological diagnosis of composite tissue allograft rejection: a review. Journal of cutaneous pathology 35: 738-744.

Khaleghi S. 2012. A caspase 8-based suicide switch induces apoptosis in nanobody-directed chimeric receptor expressing T cells. International journal of hematology, 95(4):434.

Konvalinka, A. and K. Tinckam. Utility of HLA Antibody Testing in Kidney Transplantation. J Am Soc Nephrol. 26(7):1489-502 (2015).

Levings, M. K., R. Sangregorio, and M. G. Roncarolo. 2001. Human cd25(+)cd4(+) t regulatory cells suppress naive and memory T cell proliferation and can be expanded in vitro without loss of function. The Journal of experimental medicine 193:1295-1302.

Li, N., Haiying Fu, Stephen M. Hewitt, Dimiter S. Dimitrov, and Mitchell Ho. 2017. Therapeutically targeting glypican-2 via single-domain antibody-based chimeric antigen receptors and immunotoxins in neuroblastoma. PNAS, 114 (32); E6623-E6631.

MacDonald, K. G., R. E. Hoeppli, Q. Huang, J. Gillies, D. S. Luciani, P. C. Orban, R. Broady, and M. K. Levings. 2016. Alloantigen-specific regulatory T cells generated with a chimeric antigen receptor. The Journal of clinical investigation 126:1413-1424.

Marek-Trzonkowska, N., M. Mysliwiec, A. Dobyszuk, M. Grabowska, I. Techmanska, J. Juscinska, M. A. Wujtewicz, P. Witkowski, W. Mlynarski, A. Balcerska, J. Mysliwska, and P. Trzonkowski. 2012. Administration of CD4+CD25highCD127− regulatory T cells preserves beta-cell function in type 1 diabetes in children. Diabetes care 35:1817-1820.

Massi, D., Franchi, A., Pimpinelli, N., Laszlo, D., Bosi, A., Santucci, M. 1999. A reappraisal of the histopathologic criteria for the diagnosis of cutaneous allogeneic acute graft-vs-host disease. American Journal of Clinical Pathology 112: 791-800.

Masteller, E. L., M. R. Warner, Q. Tang, K. V. Tarbell, H. McDevitt, and J. A. Bluestone. 2005. Expansion of functional endogenous antigen-specific CD4+CD25+ regulatory T cells from nonobese diabetic mice. Journal of immunology 175:3053-3059.

McMurchy, A. N. & Levings, M. K. Suppression assays with human T regulatory cells: a technical guide. Eur. J. Immunol. 42, 27-34 (2012).

Nervi, B., Rettig, M. P., Ritchey, J. K., Wang, H. L., Bauer, G., Walker, J., Bonyhadi, M. L., Berenson, R. J., Prior, J. L., Piwnica-Worms, D., Nolta, J. A., DiPersio, J. F. 2007. Factors affecting human T cell engraftment, trafficking, and associated xenogeneic graft-vs-host disease in NOD/SCID beta2mnull mice. Exp Hematol 35: 1823-1838.

Nishimura, E., T. Sakihama, R. Setoguchi, K. Tanaka, and S. Sakaguchi. 2004. Induction of antigen-specific immunologic tolerance by in vivo and in vitro antigen-specific expansion of naturally arising Foxp3+CD25+CD4+ regulatory T cells. International immunology 16:1189-1201.

Noyan, F., K. Zimmermann, M. Hardtke-Wolenski, A. Knoefel, E. Schulde, R. Geffers, M. Hust, J. Huehn, M. Galla, M. Morgan, A. Jokuszies, M. P. Manns, and E. Jaeckel. 2016. Prevention of Allograft Rejection by Use of Regulatory T Cells With an MHC-Specific Chimeric Antigen Receptor. American journal of transplantation: official journal of the American Society of Transplantation and the American Society of Transplant Surgeons Papp, G., Boros, P., Nakken, B., Szodoray, P. and M. Zeher. Regulatory immune cells and functions in autoimmunity and transplantation immunology. Autoimmunity Reviews. Volume 16, Issue 5, 2017, Pages 435-444.

Parham, P. and Brodsky, F M (1981) Hum Immunol 3(4): 277-99.

Brian Philip, Evangelia Kokalaki, Leila Mekkaoui, Simon Thomas, Karin Straathof, Barry Flutter, Virna Marin, Teresa Marafioti, Ronjon Chakraverty, David Linch, Sergio A. Quezada, Karl S. Peggs, and Martin Pule. 2014. A highly compact epitope-based marker/suicide gene for easier and safer T-cell therapy. Blood, 124:1277-1287.

Putnam, A. L., N. Safinia, A. Medvec, M. Laszkowska, M. Wray, M. A. Mintz, E. Trotta, G. L. Szot, W. Liu, A. Lares, K. Lee, A. Laing, R. I. Lechler, J. L. Riley, J. A. Bluestone, G. Lombardi, and Q. Tang. 2013. Clinical grade manufacturing of human alloantigen-reactive regulatory T cells for use in transplantation. American journal of transplantation: official journal of the American Society of Transplantation and the American Society of Transplant Surgeons 13:3010-3020.

Robinson, J. et al. The IPD and IMGT/HLA database: allele variant databases. Nucleic Acids Res 43, D423-431, doi: 10.1093/nar/gku 1161 (2015).

Rosenberg et al, New Eng. J. of Med. 319: 1676, 1988.

Sadelain, M., R. Brentjens, and I. Riviere. 2013. The basic principles of chimeric antigen receptor design. Cancer discovery 3:388-398.

Sagoo, P., N. Ali, G. Garg, F. O. Nestle, R. I. Lechler, and G. Lombardi. 2011. Human regulatory T cells with alloantigen specificity are more potent inhibitors of alloimmune skin graft damage than polyclonal regulatory T cells. Science translational medicine 3:83ra42.

Sambrook et al., 2001, Molecular Cloning: A Laboratory Manual, Cold Spring Harbor Laboratory, New York.

Sanchez-Fueyo, A., S. Sandner, A. Habicht, C. Mariat, J. Kenny, N. Degauque, X. X. Zheng, T. B. Strom, L. A.

Turka, and M. H. Sayegh. 2006. Specificity of CD4+CD25+ regulatory T cell function in alloimmunity. Journal of immunology 176:329-334.

Schneider, C. A., Rasband, W. S. & Eliceiri, K. W. 2012. NIH Image to ImageJ: 25 years of image analysis. Nature Methods 9: 671-675.

Schmittgen, T. D. & Livak, K. J. 2008. Analyzing real-time PCR data by the comparative C(T) method. Nature Protocols 3: 1101-1108.

Stephens, L. A., K. H. Malpass, and S. M. Anderton. 2009. Curing CNS autoimmune disease with myelin-reactive Foxp3+ Treg. European journal of immunology 39:1108-1117.

Tang, Q., K. J. Henriksen, M. Bi, E. B. Finger, G. Szot, J. Ye, E. L. Masteller, H. McDevitt, M. Bonyhadi, and J. A. Bluestone. 2004. In vitro-expanded antigen-specific regulatory T cells suppress autoimmune diabetes. The Journal of experimental medicine 199:1455-1465.

Tarbell, K. V., L. Petit, X. Zuo, P. Toy, X. Luo, A. Mqadmi, H. Yang, M. Suthanthiran, S. Mojsov, and R. M. Steinman. 2007. Dendritic cell-expanded, islet-specific CD4+CD25+CD62L+ regulatory T cells restore normoglycemia in diabetic NOD mice. The Journal of experimental medicine 204:191-201.

Tarbell, K. V., S. Yamazaki, K. Olson, P. Toy, and R. M. Steinman. 2004. CD25+CD4+ T cells, expanded with dendritic cells presenting a single autoantigenic peptide, suppress autoimmune diabetes. The Journal of experimental medicine 199:1467-1477.

Trenado, A., M. Sudres, Q. Tang, S. Maury, F. Charlotte, S. Gregoire, M. Bonyhadi, D. Klatzmann, B. L. Salomon, and J. L. Cohen. 2006. Ex vivo-expanded CD4+CD25+ immunoregulatory T cells prevent graft-versus-host-disease by inhibiting activation/differentiation of pathogenic T cells. Journal of immunology 176:1266-1273.

Trzonkowski, P., M. Bieniaszewska, J. Juscinska, A. Dobyszuk, A. Krzystyniak, N. Marek, J. Mysliwska, and A. Hellmann. 2009. First-in-man clinical results of the treatment of patients with graft versus host disease with human ex vivo expanded CD4+CD25+CD127− T regulatory cells. Clinical immunology 133:22-26.

Tsang, J. Y., Y. Tanriver, S. Jiang, S. A. Xue, K. Ratnasothy, D. Chen, H. J. Stauss, R. P. Bucy, G. Lombardi, and R. Lechler. 2008. Conferring indirect allospecificity on CD4+CD25+Tregs by TCR gene transfer favors transplantation tolerance in mice. The Journal of clinical investigation 118:3619-3628.

Verginis, P., K. A. McLaughlin, K. W. Wucherpfennig, H. von Boehmer, and I. Apostolou. 2008. Induction of antigen-specific regulatory T cells in wild-type mice: visualization and targets of suppression. Proceedings of the National Academy of Sciences of the United States of America 105:3479-3484.

Zhenguang Wang, Zhiqiang Wu, Yang Liu and Weidong Han. 2017. New development in CAR-T cell therapy. Journal of Hematology & Oncology, 10:53.

Watanabe, N., Bajgain, P., Sukumaran, S., Ansari, S., Heslop, H. E., Rooney, C. M., Brenner, M. K., Leen, A. M., Vera, J. F. Fine-tuning the CAR spacer improves T-cell potency. OncoImmunology. 2016, 5(12): e1253656.

Wesch, D., Peters, C., and G. M. Siegers. Human gamma delta T regulatory cells in cancer: fact or fiction? Front Immunol. 2014 Nov. 20; 5:598.

Wood, K. J., Bushell, A., and J. Hester. Regulatory immune cells in transplantation. Nat Rev Immunol. 2012, 12(6): 417-30.

Zhang, E. and Xu, H. J. 2017. A new insight in chimeric antigen receptor-engineered T cells for cancer immunotherapy. Hematol Oncol, 10: 1.

Zhang, N., Schroppel, B., Lal, G., Jakubzick, C., Mao, X., Chen, D., Yin, N., Jessberger, R., Ochando, J. C., Ding, Y., Bromberg, J. S. 2009. Regulatory T cells sequentially migrate from inflamed tissues to draining lymph nodes to suppress the alloimmune response. Immunity. 30: 458-469.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A chimeric antigen receptor (CAR) comprising:
    a) an extracellular domain comprising a humanized anti-HLA-A2 antibody or an antigen-binding fragment thereof that exhibits reduced binding to one or more HLA-A subtypes selected from the group consisting of HLA-A*25, HLA-A*29, and HLA-A*30 as compared to antibody BB7.2 (ATCC Deposit No. HB-82), wherein said humanized anti-HLA-A2 antibody or antigen-binding fragment comprises
        i) a heavy chain variable domain (VH) comprising the amino acid sequence of SEQ ID NO: 61 and a light chain variable domain (VL) comprising the amino acid sequence of SEQ ID NO: 68;
        ii) a VH comprising the amino acid sequence of SEQ ID NO: 64 and a VL comprising the amino acid sequence of SEQ ID NO: 68;
        iii) a VH comprising the amino acid sequence of SEQ ID NO: 65 and a VL comprising the amino acid sequence of SEQ ID NO: 68;
        iv) a VH comprising the amino acid sequence of SEQ ID NO: 66 and a VL comprising the amino acid sequence of SEQ ID NO: 68;
        v) a VH comprising the amino acid sequence of SEQ ID NO: 64 and a VL comprising the amino acid sequence of SEQ ID NO: 69;
        vi) a VH comprising the amino acid sequence of SEQ ID NO: 65 and a VL comprising the amino acid sequence of SEQ ID NO: 69; or
        vii) a VH comprising the amino acid sequence of SEQ ID NO: 63 and a VL comprising the amino acid sequence of SEQ ID NO: 70;
    b) a transmembrane domain; and
    c) a cytoplasmic domain comprising an intracellular signaling domain;
    wherein said CAR is capable of being expressed in an immune cell such that said CAR specifically binds to HLA-A2.

2. The CAR of claim 1, wherein the humanized anti-HLA-A2 antibody or antigen-binding fragment is an scFv comprising an amino acid sequence selected from the group consisting of SEQ ID NOs: 73, 81, 83, 84, 87, 88 and 91.

3. The CAR of claim 1, wherein the humanized anti-HLA-A2 antibody or antigen-binding fragment is an scFv comprising the amino acid sequence of SEQ ID NO: 73.

4. The CAR of claim 1, further comprising a hinge region that comprises a stalk region of CD8α.

5. The CAR of claim 1, wherein the transmembrane domain is a CD8 transmembrane domain and the intracellular signaling domain comprises a CD28 costimulatory domain and a CD3 zeta primary signaling domain.

6. The CAR of claim 1, comprising an amino acid sequence selected from the group consisting of SEQ ID NOs: 120, 128, 130, 131, 134, 135, 138 and 213.

7. A chimeric antigen receptor (CAR) comprising the amino acid sequence of SEQ ID NO: 213.

8. A nucleic acid molecule encoding the CAR of claim 1.

9. An immune cell comprising the CAR of claim 1.

10. The immune cell of claim 9, wherein the immune cell is a regulatory T cell.

11. A pharmaceutical composition comprising the immune cell of claim 9 and a pharmaceutically acceptable excipient.

12. A method for:
    a) preventing or treating organ or tissue transplant rejection in a subject;

b) preventing or treating graft versus host disease (GVHD) in a subject;
c) promoting immune tolerance in a subject in need thereof;
d) inducing tolerance to a transplanted organ or tissue in a subject; or
e) any combination of a)-d);

wherein said method comprises administering an immune cell of claim 9 to the subject.

13. The method of claim 12, wherein the subject is undergoing or has undergone a hematopoietic stem cell transplant.

14. The CAR of claim 1, wherein said transmembrane domain comprises a transmembrane domain of a protein selected from the group consisting of: CD3 gamma, CD3 delta, CD3 epsilon, CD3 zeta, the alpha chain of the T cell receptor, the beta chain of the T cell receptor, the gamma chain of the T cell receptor, the delta chain of the T cell receptor, CD28, CD45, CD4, CD5, CD8, CD9, CD16, CD22, CD33, CD37, CD64, CD80, CD86, CD134, CD137, CD154, and any combination thereof.

15. The CAR of claim 1, wherein said intracellular signaling domain comprises a functional signaling domain of a protein selected from the group consisting of: CD3 gamma, CD3 delta, CD3 epsilon, CD3 zeta, FcR gamma, FcR alpha, FcR epsilon, CD5, CD22, CD79a, CD79b, and CD66d, and any combination thereof.

16. The CAR of claim 1, wherein said intracellular signaling domain comprises a functional signaling domain of CD3 zeta.

17. The CAR of claim 1, wherein said intracellular signaling domain comprises a functional signaling domain and a costimulatory domain, wherein the costimulatory domain comprises a functional signaling domain of a protein selected from the group consisting of OX40, CD27, CD28, lymphocyte function-associated antigen-1 (LFA-1) (CD11a/CD18), TNFR1 (CD120a/TNFRSF1A), TNFR2 (CD120b/TNFRSF1B), CTLA-4 (CD152), CD95, ICOS (CD278), 4-1BB (CD137), CD2, CD30, CD40, PD-1, CD7, LIGHT, NKG2C, B7-H3, ICAM-1, a ligand that specifically binds to CD83, IL2Ra (CD25), IL6Ra (CD126), IL-7Ra (CD127), IL-13RA1, IL-13RA2, IL-33R(IL1RL1), IL-10RA, IL-10RB, IL-4R, IL-5R (CSF2RB), ARHR, BAFF receptor, IL-21R, TGFbR1, TGFbR2, TGFbR3, common gamma chain, and any combination thereof.

18. The CAR of claim 1, wherein said intracellular signaling domain comprises a costimulatory domain, wherein said costimulatory domain comprises a functional signaling domain of a protein selected from CD28 and 4-1BB.

* * * * *

SEQUENCE LISTING

```
<160> NUMBER OF SEQ ID NOS: 224

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Ser Tyr His Ile Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic sequence
```

```
<400> SEQUENCE: 2

Gly Tyr Thr Phe Thr Ser Tyr
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic sequence

<400> SEQUENCE: 3

Trp Ile Tyr Pro Gly Asp Gly Ser Thr Gln Tyr Asn Glu Lys Phe Lys
1               5                   10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Synthetic sequence

<400> SEQUENCE: 4

Tyr Pro Gly Asp Gly Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic sequence

<400> SEQUENCE: 5

Trp Ile Tyr Pro Gly Asp Gly Ser Thr Lys Tyr Ser Gln Lys Phe Gln
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence

<400> SEQUENCE: 6

Glu Gly Thr Tyr Tyr Ala Met Asp Tyr
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic sequence

<400> SEQUENCE: 7

Arg Ser Ser Gln Ser Ile Val His Ser Asn Gly Asn Thr Tyr Leu Glu
1               5                   10                  15

<210> SEQ ID NO 8
<211> LENGTH: 7
<212> TYPE: PRT
<213> ORGANISM: Artificial Sequence
```

```
<220> FEATURE:
<223> OTHER INFORMATION: Synthetic sequence

<400> SEQUENCE: 8

Lys Val Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic sequence

<400> SEQUENCE: 9

Phe Gln Gly Ser His Val Pro Arg Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: Xaa is Q or K
<220> FEATURE:
<221> NAME/KEY: misc_feature
<222> LOCATION: (12)..(12)
<223> OTHER INFORMATION: Xaa is N or S
<220> FEATURE:
<221> NAME/KEY: misc_feature
<222> LOCATION: (13)..(13)
<223> OTHER INFORMATION: Xaa is E or Q
<220> FEATURE:
<221> NAME/KEY: misc_feature
<222> LOCATION: (16)..(16)
<223> OTHER INFORMATION: Xaa is K or Q

<400> SEQUENCE: 10

Trp Ile Tyr Pro Gly Asp Gly Ser Thr Xaa Tyr Xaa Xaa Lys Phe Xaa
1               5                   10                  15

Gly

<210> SEQ ID NO 11
<211> LENGTH: 25
<212> TYPE: PRT
<213> ORGANISM: Artificial Sequence
<220> FEATURE:
<223> OTHER INFORMATION: Synthetic sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 12
<211> LENGTH: 30
<212> TYPE: PRT
<213> ORGANISM: Artificial Sequence
<220> FEATURE:
<223> OTHER INFORMATION: Synthetic sequence

<400> SEQUENCE: 12

Gln Val Gln Leu Val Gln Ser Gly Ala Glu Val Lys Lys Pro Gly Ala
```

```
                1               5                  10                  15
Ser Val Lys Val Ser Cys Lys Ala Ser Gly Tyr Thr Phe Thr
                20                  25                  30

<210> SEQ ID NO 13
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (9)..(9)
<223> OTHER INFORMATION: Xaa is R or G
<220> FEATURE:
<221> NAME/KEY: misc_feature
<222> LOCATION: (15)..(15)
<223> OTHER INFORMATION: Xaa is I or absent

<400> SEQUENCE: 13

Trp Val Arg Gln Ala Pro Gly Gln Xaa Leu Glu Trp Met Gly Xaa
1               5                  10                  15

<210> SEQ ID NO 14
<211> LENGTH: 14
<212> TYPE: PRT
<213> ORGANISM: Artificial Sequence
<220> FEATURE:
<223> OTHER INFORMATION: Synthetic sequence

<400> SEQUENCE: 14

Trp Val Arg Gln Ala Pro Gly Gln Arg Leu Glu Trp Met Gly
1               5                  10

<210> SEQ ID NO 15
<211> LENGTH: 15
<212> TYPE: PRT
<213> ORGANISM: Artificial Sequence
<220> FEATURE:
<223> OTHER INFORMATION: Synthetic sequence

<400> SEQUENCE: 15

Trp Val Arg Gln Ala Pro Gly Gln Gly Leu Glu Trp Met Gly Ile
1               5                  10                  15

<210> SEQ ID NO 16
<211> LENGTH: 14
<212> TYPE: PRT
<213> ORGANISM: Artificial Sequence
<220> FEATURE:
<223> OTHER INFORMATION: Synthetic sequence

<400> SEQUENCE: 16

Trp Val Arg Gln Ala Pro Gly Gln Gly Leu Glu Trp Met Gly
1               5                  10

<210> SEQ ID NO 17
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (9)..(9)
<223> OTHER INFORMATION: Xaa is R or G
<220> FEATURE:
<221> NAME/KEY: misc_feature
<222> LOCATION: (15)..(15)
```

<223> OTHER INFORMATION: Xaa is I or absent

<400> SEQUENCE: 17

Trp Val Arg Gln Ala Pro Gly Gln Xaa Leu Glu Trp Met Gly Xaa Trp
1               5                   10                  15

Ile

<210> SEQ ID NO 18
<211> LENGTH: 16
<212> TYPE: PRT
<213> ORGANISM: Artificial Sequence
<220> FEATURE:
<223> OTHER INFORMATION: Synthetic sequence

<400> SEQUENCE: 18

Trp Val Arg Gln Ala Pro Gly Gln Arg Leu Glu Trp Met Gly Trp Ile
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic sequence

<400> SEQUENCE: 19

Trp Val Arg Gln Ala Pro Gly Gln Gly Leu Glu Trp Met Gly Ile Trp
1               5                   10                  15

Ile

<210> SEQ ID NO 20
<211> LENGTH: 16
<212> TYPE: PRT
<213> ORGANISM: Artificial Sequence
<220> FEATURE:
<223> OTHER INFORMATION: Synthetic sequence

<400> SEQUENCE: 20

Trp Val Arg Gln Ala Pro Gly Gln Gly Leu Glu Trp Met Gly Trp Ile
1               5                   10                  15

<210> SEQ ID NO 21
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (12)..(12)
<223> OTHER INFORMATION: Xaa is R or G
<220> FEATURE:
<221> NAME/KEY: misc_feature
<222> LOCATION: (18)..(18)
<223> OTHER INFORMATION: Xaa is I or absent

<400> SEQUENCE: 21

His Ile Gln Trp Val Arg Gln Ala Pro Gly Gln Xaa Leu Glu Trp Met
1               5                   10                  15

Gly Xaa Trp Ile
            20

<210> SEQ ID NO 22
<211> LENGTH: 19
<212> TYPE: PRT
<213> ORGANISM: Artificial Sequence
<220> FEATURE:
<223> OTHER INFORMATION: Synthetic sequence

<400> SEQUENCE: 22

His Ile Gln Trp Val Arg Gln Ala Pro Gly Gln Arg Leu Glu Trp Met
1               5                   10                  15

Gly Trp Ile

<210> SEQ ID NO 23
<211> LENGTH: 20
<212> TYPE: PRT
<213> ORGANISM: Artificial Sequence
<220> FEATURE:
<223> OTHER INFORMATION: Synthetic sequence

<400> SEQUENCE: 23

His Ile Gln Trp Val Arg Gln Ala Pro Gly Gln Gly Leu Glu Trp Met
1               5                   10                  15

Gly Ile Trp Ile
            20

<210> SEQ ID NO 24
<211> LENGTH: 19
<212> TYPE: PRT
<213> ORGANISM: Artificial Sequence
<220> FEATURE:
<223> OTHER INFORMATION: Synthetic sequence

<400> SEQUENCE: 24

His Ile Gln Trp Val Arg Gln Ala Pro Gly Gln Gly Leu Glu Trp Met
1               5                   10                  15

Gly Trp Ile

<210> SEQ ID NO 25
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (12)..(12)
<223> OTHER INFORMATION: Xaa is R or G
<220> FEATURE:
<221> NAME/KEY: misc_feature
<222> LOCATION: (18)..(18)
<223> OTHER INFORMATION: Xaa is I or absent

<400> SEQUENCE: 25

His Ile Gln Trp Val Arg Gln Ala Pro Gly Gln Xaa Leu Glu Trp Met
1               5                   10                  15

Gly Xaa

<210> SEQ ID NO 26
<211> LENGTH: 17
<212> TYPE: PRT
<213> ORGANISM: Artificial Sequence
<220> FEATURE:
<223> OTHER INFORMATION: Synthetic sequence

<400> SEQUENCE: 26

His Ile Gln Trp Val Arg Gln Ala Pro Gly Gln Arg Leu Glu Trp Met
1               5                   10                  15

Gly

<210> SEQ ID NO 27
<211> LENGTH: 18
<212> TYPE: PRT
<213> ORGANISM: Artificial Sequence
<220> FEATURE:
<223> OTHER INFORMATION: Synthetic sequence

<400> SEQUENCE: 27

His Ile Gln Trp Val Arg Gln Ala Pro Gly Gln Gly Leu Glu Trp Met
1               5                   10                  15

Gly Ile

<210> SEQ ID NO 28
<211> LENGTH: 17
<212> TYPE: PRT
<213> ORGANISM: Artificial Sequence
<220> FEATURE:
<223> OTHER INFORMATION: Synthetic sequence

<400> SEQUENCE: 28

His Ile Gln Trp Val Arg Gln Ala Pro Gly Gln Gly Leu Glu Trp Met
1               5                   10                  15

Gly

<210> SEQ ID NO 29
<211> LENGTH: 32
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is R or absent
<220> FEATURE:
<221> NAME/KEY: misc_feature
<222> LOCATION: (4)..(4)
<223> OTHER INFORMATION: Xaa is I or M
<220> FEATURE:
<221> NAME/KEY: misc_feature
<222> LOCATION: (6)..(6)
<223> OTHER INFORMATION: Xaa is R or A
<220> FEATURE:
<221> NAME/KEY: misc_feature
<222> LOCATION: (10)..(10)
<223> OTHER INFORMATION: Xaa is A, T or I
<220> FEATURE:
<221> NAME/KEY: misc_feature
<222> LOCATION: (16)..(16)
<223> OTHER INFORMATION: Xaa is E or L
<220> FEATURE:
<221> NAME/KEY: misc_feature
<222> LOCATION: (19)..(19)
<223> OTHER INFORMATION: Xaa is S or R
<220> FEATURE:
<221> NAME/KEY: misc_feature
<222> LOCATION: (23)..(23)
<223> OTHER INFORMATION: Xaa is E or D
<220> FEATURE:
<221> NAME/KEY: misc_feature
<222> LOCATION: (25)..(25)
<223> OTHER INFORMATION: Xaa is T or M

<400> SEQUENCE: 29

Xaa Val Thr Xaa Thr Xaa Asp Thr Ser Xaa Ser Thr Ala Tyr Met Xaa
1               5                   10                  15

Leu Ser Xaa Leu Arg Ser Xaa Asp Xaa Ala Val Tyr Tyr Cys Ala Arg
                20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Synthetic sequence

<400> SEQUENCE: 30

Arg Val Thr Ile Thr Arg Asp Thr Ser Ala Ser Thr Ala Tyr Met Glu
 1               5                  10                  15

Leu Ser Ser Leu Arg Ser Glu Asp Thr Ala Val Tyr Tyr Cys Ala Arg
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Synthetic sequence

<400> SEQUENCE: 31

Arg Val Thr Ile Thr Ala Asp Thr Ser Ala Ser Thr Ala Tyr Met Leu
 1               5                  10                  15

Leu Ser Ser Leu Arg Ser Glu Asp Thr Ala Val Tyr Tyr Cys Ala Arg
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic sequence

<400> SEQUENCE: 32

Val Thr Met Thr Arg Asp Thr Ser Thr Ser Val Tyr Met Glu Leu
 1               5                  10                  15

Ser Ser Leu Arg Ser Glu Asp Thr Ala Val Tyr Tyr Cys Ala Arg
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Synthetic sequence

<400> SEQUENCE: 33

Arg Val Thr Met Thr Arg Asp Thr Ser Ile Ser Thr Ala Tyr Met Glu
 1               5                  10                  15

Leu Ser Arg Leu Arg Ser Asp Asp Thr Ala Val Tyr Tyr Cys Ala Arg
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Synthetic sequence

<400> SEQUENCE: 34

Arg Val Thr Ile Thr Arg Asp Thr Ser Ala Ser Thr Ala Tyr Met Glu
 1               5                  10                  15

Leu Ser Ser Leu Arg Ser Glu Asp Met Ala Val Tyr Tyr Cys Ala Arg
            20                  25                  30

```
<210> SEQ ID NO 35
<211> LENGTH: 41
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Q or K
<220> FEATURE:
<221> NAME/KEY: misc_feature
<222> LOCATION: (4)..(4)
<223> OTHER INFORMATION: Xaa is N or S
<220> FEATURE:
<221> NAME/KEY: misc_feature
<222> LOCATION: (5)..(5)
<223> OTHER INFORMATION: Xaa is E or Q
<220> FEATURE:
<221> NAME/KEY: misc_feature
<222> LOCATION: (8)..(8)
<223> OTHER INFORMATION: Xaa is K or Q
<220> FEATURE:
<221> NAME/KEY: misc_feature
<222> LOCATION: (10)..(10)
<223> OTHER INFORMATION: Xaa is R or absent
<220> FEATURE:
<221> NAME/KEY: misc_feature
<222> LOCATION: (13)..(13)
<223> OTHER INFORMATION: Xaa is I or M
<220> FEATURE:
<221> NAME/KEY: misc_feature
<222> LOCATION: (15)..(15)
<223> OTHER INFORMATION: Xaa is R or A
<220> FEATURE:
<221> NAME/KEY: misc_feature
<222> LOCATION: (19)..(19)
<223> OTHER INFORMATION: Xaa is A, T or I
<220> FEATURE:
<221> NAME/KEY: misc_feature
<222> LOCATION: (25)..(25)
<223> OTHER INFORMATION: Xaa is E or L
<220> FEATURE:
<221> NAME/KEY: misc_feature
<222> LOCATION: (28)..(28)
<223> OTHER INFORMATION: Xaa is S or R
<220> FEATURE:
<221> NAME/KEY: misc_feature
<222> LOCATION: (32)..(32)
<223> OTHER INFORMATION: Xaa is E or D
<220> FEATURE:
<221> NAME/KEY: misc_feature
<222> LOCATION: (34)..(34)
<223> OTHER INFORMATION: Xaa is T or M

<400> SEQUENCE: 35

Thr Xaa Tyr Xaa Xaa Lys Phe Xaa Gly Xaa Val Thr Xaa Thr Xaa Asp
 1               5                  10                  15

Thr Ser Xaa Ser Thr Ala Tyr Met Xaa Leu Ser Xaa Leu Arg Ser Xaa
            20                  25                  30

Asp Xaa Ala Val Tyr Tyr Cys Ala Arg
        35                  40

<210> SEQ ID NO 36
<211> LENGTH: 41
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: Xaa is R or absent
<220> FEATURE:
```

```
<221> NAME/KEY: misc_feature
<222> LOCATION: (13)..(13)
<223> OTHER INFORMATION: Xaa is I or M
<220> FEATURE:
<221> NAME/KEY: misc_feature
<222> LOCATION: (15)..(15)
<223> OTHER INFORMATION: Xaa is R or A
<220> FEATURE:
<221> NAME/KEY: misc_feature
<222> LOCATION: (19)..(19)
<223> OTHER INFORMATION: Xaa is A, T or I
<220> FEATURE:
<221> NAME/KEY: misc_feature
<222> LOCATION: (25)..(25)
<223> OTHER INFORMATION: Xaa is E or L
<220> FEATURE:
<221> NAME/KEY: misc_feature
<222> LOCATION: (28)..(28)
<223> OTHER INFORMATION: Xaa is S or R
<220> FEATURE:
<221> NAME/KEY: misc_feature
<222> LOCATION: (32)..(32)
<223> OTHER INFORMATION: Xaa is E or D
<220> FEATURE:
<221> NAME/KEY: misc_feature
<222> LOCATION: (34)..(34)
<223> OTHER INFORMATION: Xaa is T or M

<400> SEQUENCE: 36

Thr Gln Tyr Asn Glu Lys Phe Lys Gly Xaa Val Thr Xaa Thr Xaa Asp
1               5                   10                  15

Thr Ser Xaa Ser Thr Ala Tyr Met Xaa Leu Ser Xaa Leu Arg Ser Xaa
            20                  25                  30

Asp Xaa Ala Val Tyr Tyr Cys Ala Arg
        35                  40

<210> SEQ ID NO 37
<211> LENGTH: 41
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: Xaa is R or absent
<220> FEATURE:
<221> NAME/KEY: misc_feature
<222> LOCATION: (13)..(13)
<223> OTHER INFORMATION: Xaa is I or M
<220> FEATURE:
<221> NAME/KEY: misc_feature
<222> LOCATION: (15)..(15)
<223> OTHER INFORMATION: Xaa is R or A
<220> FEATURE:
<221> NAME/KEY: misc_feature
<222> LOCATION: (19)..(19)
<223> OTHER INFORMATION: Xaa is A, T or I
<220> FEATURE:
<221> NAME/KEY: misc_feature
<222> LOCATION: (25)..(25)
<223> OTHER INFORMATION: Xaa is E or L
<220> FEATURE:
<221> NAME/KEY: misc_feature
<222> LOCATION: (28)..(28)
<223> OTHER INFORMATION: Xaa is S or R
<220> FEATURE:
<221> NAME/KEY: misc_feature
<222> LOCATION: (32)..(32)
<223> OTHER INFORMATION: Xaa is E or D
<220> FEATURE:
<221> NAME/KEY: misc_feature
<222> LOCATION: (34)..(34)
<223> OTHER INFORMATION: Xaa is T or M
```

```
<400> SEQUENCE: 37

Thr Lys Tyr Ser Gln Lys Phe Gln Gly Xaa Val Thr Xaa Thr Xaa Asp
1               5                   10                  15

Thr Ser Xaa Ser Thr Ala Tyr Met Xaa Leu Ser Xaa Leu Arg Ser Xaa
            20                  25                  30

Asp Xaa Ala Val Tyr Tyr Cys Ala Arg
        35                  40

<210> SEQ ID NO 38
<211> LENGTH: 41
<212> TYPE: PRT
<213> ORGANISM: Artificial Sequence
<220> FEATURE:
<223> OTHER INFORMATION: Synthetic sequence

<400> SEQUENCE: 38

Thr Gln Tyr Asn Glu Lys Phe Lys Gly Arg Val Thr Ile Thr Arg Asp
1               5                   10                  15

Thr Ser Ala Ser Thr Ala Tyr Met Glu Leu Ser Ser Leu Arg Ser Glu
            20                  25                  30

Asp Thr Ala Val Tyr Tyr Cys Ala Arg
        35                  40

<210> SEQ ID NO 39
<211> LENGTH: 41
<212> TYPE: PRT
<213> ORGANISM: Artificial Sequence
<220> FEATURE:
<223> OTHER INFORMATION: Synthetic sequence

<400> SEQUENCE: 39

Thr Gln Tyr Asn Glu Lys Phe Lys Gly Arg Val Thr Ile Thr Ala Asp
1               5                   10                  15

Thr Ser Ala Ser Thr Ala Tyr Met Leu Leu Ser Ser Leu Arg Ser Glu
            20                  25                  30

Asp Thr Ala Val Tyr Tyr Cys Ala Arg
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic sequence

<400> SEQUENCE: 40

Thr Gln Tyr Asn Glu Lys Phe Lys Gly Val Thr Met Thr Arg Asp Thr
1               5                   10                  15

Ser Thr Ser Thr Val Tyr Met Glu Leu Ser Ser Leu Arg Ser Glu Asp
            20                  25                  30

Thr Ala Val Tyr Tyr Cys Ala Arg
        35                  40

<210> SEQ ID NO 41
<211> LENGTH: 41
<212> TYPE: PRT
<213> ORGANISM: Artificial Sequence
<220> FEATURE:
<223> OTHER INFORMATION: Synthetic sequence

<400> SEQUENCE: 41

Thr Gln Tyr Asn Glu Lys Phe Lys Gly Arg Val Thr Met Thr Arg Asp
```

```
                1               5                   10                  15
Thr Ser Ile Ser Thr Ala Tyr Met Glu Leu Ser Arg Leu Arg Ser Asp
                20                  25                  30

Asp Thr Ala Val Tyr Tyr Cys Ala Arg
        35                  40

<210> SEQ ID NO 42
<211> LENGTH: 41
<212> TYPE: PRT
<213> ORGANISM: Artificial Sequence
<220> FEATURE:
<223> OTHER INFORMATION: Synthetic sequence

<400> SEQUENCE: 42

Thr Gln Tyr Asn Glu Lys Phe Lys Gly Arg Val Thr Ile Thr Arg Asp
1               5                   10                  15

Thr Ser Ala Ser Thr Ala Tyr Met Glu Leu Ser Ser Leu Arg Ser Glu
                20                  25                  30

Asp Met Ala Val Tyr Tyr Cys Ala Arg
        35                  40

<210> SEQ ID NO 43
<211> LENGTH: 41
<212> TYPE: PRT
<213> ORGANISM: Artificial Sequence
<220> FEATURE:
<223> OTHER INFORMATION: Synthetic sequence

<400> SEQUENCE: 43

Thr Lys Tyr Ser Gln Lys Phe Gln Gly Arg Val Thr Ile Thr Arg Asp
1               5                   10                  15

Thr Ser Ala Ser Thr Ala Tyr Met Glu Leu Ser Ser Leu Arg Ser Glu
                20                  25                  30

Asp Thr Ala Val Tyr Tyr Cys Ala Arg
        35                  40

<210> SEQ ID NO 44
<211> LENGTH: 11
<212> TYPE: PRT
<213> ORGANISM: Artificial Sequence
<220> FEATURE:
<223> OTHER INFORMATION: Synthetic sequence

<400> SEQUENCE: 44

Trp Gly Gln Gly Thr Thr Val Thr Val Ser Ser
1               5                   10

<210> SEQ ID NO 45
<211> LENGTH: 119
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (44)..(44)
<223> OTHER INFORMATION: Xaa is R or G
<220> FEATURE:
<221> NAME/KEY: misc_feature
<222> LOCATION: (50)..(50)
<223> OTHER INFORMATION: Xaa is I or absent
<220> FEATURE:
<221> NAME/KEY: misc_feature
<222> LOCATION: (60)..(60)
<223> OTHER INFORMATION: Xaa is Q or K
<220> FEATURE:
```

```
<221> NAME/KEY: misc_feature
<222> LOCATION: (62)..(62)
<223> OTHER INFORMATION: Xaa is N or S
<220> FEATURE:
<221> NAME/KEY: misc_feature
<222> LOCATION: (63)..(63)
<223> OTHER INFORMATION: Xaa is E or Q
<220> FEATURE:
<221> NAME/KEY: misc_feature
<222> LOCATION: (66)..(66)
<223> OTHER INFORMATION: Xaa is K or Q
<220> FEATURE:
<221> NAME/KEY: misc_feature
<222> LOCATION: (68)..(68)
<223> OTHER INFORMATION: Xaa is R or absent
<220> FEATURE:
<221> NAME/KEY: misc_feature
<222> LOCATION: (71)..(71)
<223> OTHER INFORMATION: Xaa is I or M
<220> FEATURE:
<221> NAME/KEY: misc_feature
<222> LOCATION: (73)..(73)
<223> OTHER INFORMATION: Xaa is R or A
<220> FEATURE:
<221> NAME/KEY: misc_feature
<222> LOCATION: (77)..(77)
<223> OTHER INFORMATION: Xaa is A, T or I
<220> FEATURE:
<221> NAME/KEY: misc_feature
<222> LOCATION: (83)..(83)
<223> OTHER INFORMATION: Xaa is E or L
<220> FEATURE:
<221> NAME/KEY: misc_feature
<222> LOCATION: (86)..(86)
<223> OTHER INFORMATION: Xaa is S or R
<220> FEATURE:
<221> NAME/KEY: misc_feature
<222> LOCATION: (90)..(90)
<223> OTHER INFORMATION: Xaa is E or D
<220> FEATURE:
<221> NAME/KEY: misc_feature
<222> LOCATION: (92)..(92)
<223> OTHER INFORMATION: Xaa is T or M

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Xaa Leu Glu Trp Met
        35                  40                  45

Gly Xaa Trp Ile Tyr Pro Gly Asp Gly Ser Thr Xaa Tyr Xaa Xaa Lys
    50                  55                  60

Phe Xaa Gly Xaa Val Thr Xaa Thr Xaa Asp Thr Ser Xaa Ser Thr Ala
65                  70                  75                  80

Tyr Met Xaa Leu Ser Xaa Leu Arg Ser Xaa Asp Xaa Ala Val Tyr Tyr
                85                  90                  95

Cys Ala Arg Glu Gly Thr Tyr Tyr Ala Met Asp Tyr Trp Gly Gln Gly
            100                 105                 110

Thr Thr Val Thr Val Ser Ser
        115

<210> SEQ ID NO 46
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
```

```
<222> LOCATION: (2)..(2)
<223> OTHER INFORMATION: Xaa is V or I
<220> FEATURE:
<221> NAME/KEY: misc_feature
<222> LOCATION: (7)..(7)
<223> OTHER INFORMATION: Xaa is S or T
<220> FEATURE:
<221> NAME/KEY: misc_feature
<222> LOCATION: (11)..(11)
<223> OTHER INFORMATION: Xaa is L or S
<220> FEATURE:
<221> NAME/KEY: misc_feature
<222> LOCATION: (12)..(12)
<223> OTHER INFORMATION: Xaa is P or S
<220> FEATURE:
<221> NAME/KEY: misc_feature
<222> LOCATION: (15)..(15)
<223> OTHER INFORMATION: Xaa is L or P
<220> FEATURE:
<221> NAME/KEY: misc_feature
<222> LOCATION: (23)..(23)
<223> OTHER INFORMATION: Xaa is C or F

<400> SEQUENCE: 46

Asp Xaa Val Met Thr Gln Xaa Pro Leu Ser Xaa Xaa Val Thr Xaa Gly
1               5                   10                  15

Gln Pro Ala Ser Ile Ser Xaa
            20

<210> SEQ ID NO 47
<211> LENGTH: 23
<212> TYPE: PRT
<213> ORGANISM: Artificial Sequence
<220> FEATURE:
<223> OTHER INFORMATION: Synthetic sequence

<400> SEQUENCE: 47

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic sequence

<400> SEQUENCE: 48

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic sequence

<400> SEQUENCE: 49

Asp Ile Val Met Thr Gln Thr Pro Leu Ser Ser Pro Val Thr Leu Gly
1               5                   10                  15

Gln Pro Ala Ser Ile Ser Cys
            20
```

```
<210> SEQ ID NO 50
<211> LENGTH: 23
<212> TYPE: PRT
<213> ORGANISM: Artificial Sequence
<220> FEATURE:
<223> OTHER INFORMATION: Synthetic sequence

<400> SEQUENCE: 50

Asp Ile Val Met Thr Gln Thr Pro Leu Ser Ser Pro Val Thr Leu Gly
1               5                   10                  15

Gln Pro Ala Ser Ile Ser Phe
            20

<210> SEQ ID NO 51
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is F or Y
<220> FEATURE:
<221> NAME/KEY: misc_feature
<222> LOCATION: (3)..(3)
<223> OTHER INFORMATION: Xaa is Q or L
<220> FEATURE:
<221> NAME/KEY: misc_feature
<222> LOCATION: (5)..(5)
<223> OTHER INFORMATION: Xaa is R or K
<220> FEATURE:
<221> NAME/KEY: misc_feature
<222> LOCATION: (9)..(9)
<223> OTHER INFORMATION: Xaa is S or P
<220> FEATURE:
<221> NAME/KEY: misc_feature
<222> LOCATION: (11)..(11)
<223> OTHER INFORMATION: Xaa is R or Q
<220> FEATURE:
<221> NAME/KEY: misc_feature
<222> LOCATION: (12)..(12)
<223> OTHER INFORMATION: Xaa is R or L

<400> SEQUENCE: 51

Trp Xaa Xaa Gln Xaa Pro Gly Gln Xaa Pro Xaa Xaa Leu Ile Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic sequence

<400> SEQUENCE: 52

Trp Phe Gln Gln Arg Pro Gly Gln Ser Pro Arg Arg Leu Ile Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic sequence

<400> SEQUENCE: 53

Trp Tyr Leu Gln Lys Pro Gly Gln Ser Pro Gln Leu Leu Ile Tyr
1               5                   10                  15
```

-continued

```
<210> SEQ ID NO 54
<211> LENGTH: 15
<212> TYPE: PRT
<213> ORGANISM: Artificial Sequence
<220> FEATURE:
<223> OTHER INFORMATION: Synthetic sequence

<400> SEQUENCE: 54

Trp Tyr Gln Gln Arg Pro Gly Gln Pro Pro Arg Leu Leu Ile Tyr
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic sequence

<400> SEQUENCE: 55

Trp Tyr Gln Gln Arg Pro Gly Gln Ser Pro Arg Leu Leu Ile Tyr
1               5                   10                  15

<210> SEQ ID NO 56
<211> LENGTH: 32
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (11)..(11)
<223> OTHER INFORMATION: Xaa is S or A

<400> SEQUENCE: 56

Gly Val Pro Asp Arg Phe Ser Gly Ser Gly Xaa Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic sequence

<400> SEQUENCE: 57

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic sequence

<400> SEQUENCE: 58

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30
```

```
<210> SEQ ID NO 59
<211> LENGTH: 10
<212> TYPE: PRT
<213> ORGANISM: Artificial Sequence
<220> FEATURE:
<223> OTHER INFORMATION: Synthetic sequence

<400> SEQUENCE: 59

Phe Gly Gly Gly Thr Lys Val Glu Ile Lys
1               5                   10

<210> SEQ ID NO 60
<211> LENGTH: 112
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is V or I
<220> FEATURE:
<221> NAME/KEY: misc_feature
<222> LOCATION: (7)..(7)
<223> OTHER INFORMATION: Xaa is S or T
<220> FEATURE:
<221> NAME/KEY: misc_feature
<222> LOCATION: (11)..(11)
<223> OTHER INFORMATION: Xaa is L or S
<220> FEATURE:
<221> NAME/KEY: misc_feature
<222> LOCATION: (12)..(12)
<223> OTHER INFORMATION: Xaa is P or S
<220> FEATURE:
<221> NAME/KEY: misc_feature
<222> LOCATION: (15)..(15)
<223> OTHER INFORMATION: Xaa is L or P
<220> FEATURE:
<221> NAME/KEY: misc_feature
<222> LOCATION: (23)..(23)
<223> OTHER INFORMATION: Xaa is C or F
<220> FEATURE:
<221> NAME/KEY: misc_feature
<222> LOCATION: (41)..(41)
<223> OTHER INFORMATION: Xaa is F or Y
<220> FEATURE:
<221> NAME/KEY: misc_feature
<222> LOCATION: (42)..(42)
<223> OTHER INFORMATION: Xaa is Q or L
<220> FEATURE:
<221> NAME/KEY: misc_feature
<222> LOCATION: (44)..(44)
<223> OTHER INFORMATION: Xaa is R or K
<220> FEATURE:
<221> NAME/KEY: misc_feature
<222> LOCATION: (48)..(48)
<223> OTHER INFORMATION: Xaa is S or P
<220> FEATURE:
<221> NAME/KEY: misc_feature
<222> LOCATION: (50)..(50)
<223> OTHER INFORMATION: Xaa is R or Q
<220> FEATURE:
<221> NAME/KEY: misc_feature
<222> LOCATION: (51)..(51)
<223> OTHER INFORMATION: Xaa is R or L
<220> FEATURE:
<221> NAME/KEY: misc_feature
<222> LOCATION: (72)..(72)
<223> OTHER INFORMATION: Xaa is S or A

<400> SEQUENCE: 60

Asp Xaa Met Thr Gln Xaa Pro Leu Ser Xaa Xaa Val Thr Xaa Gly
1               5                   10                  15

Gln Pro Ala Ser Ile Ser Xaa Arg Ser Ser Gln Ser Ile Val His Ser
            20                  25                  30
```

Asn Gly Asn Thr Tyr Leu Glu Trp Xaa Xaa Gln Xaa Pro Gly Gln Xaa
         35                  40                  45

Pro Xaa Xaa Leu Ile Tyr Lys Val Ser Asn Arg Phe Ser Gly Val Pro
     50                  55                  60

Asp Arg Phe Ser Gly Ser Gly Xaa Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Arg Thr Phe Gly Gly Gly Thr Lys Val Glu Ile Lys
             100                 105                 110

<210> SEQ ID NO 61
<211> LENGTH: 118
<212> TYPE: PRT
<213> ORGANISM: Artificial Sequence
<220> FEATURE:
<223> OTHER INFORMATION: Synthetic sequence

<400> SEQUENCE: 61

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

His Ile Gln Trp Val Arg Gln Ala Pro Gly Gln Arg Leu Glu Trp Met
             35                  40                  45

Gly Trp Ile Tyr Pro Gly Asp Gly Ser Thr Gln Tyr Asn Glu Lys Phe
         50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Thr Tyr Tyr Ala Met Asp Tyr Trp Gly Gln Gly Thr
             100                 105                 110

Thr Val Thr Val Ser Ser
         115

<210> SEQ ID NO 62
<211> LENGTH: 118
<212> TYPE: PRT
<213> ORGANISM: Artificial Sequence
<220> FEATURE:
<223> OTHER INFORMATION: Synthetic sequence

<400> SEQUENCE: 62

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

His Ile Gln Trp Val Arg Gln Ala Pro Gly Gln Arg Leu Glu Trp Met
             35                  40                  45

Gly Trp Ile Tyr Pro Gly Asp Gly Ser Thr Gln Tyr Asn Glu Lys Phe
         50                  55                  60

Lys Gly Arg Val Thr Ile Thr Ala Asp Thr Ser Ala Ser Thr Ala Tyr
 65                  70                  75                  80

Met Leu Leu Ser Ser Leu Arg Ser Glu Asp Thr Ala Val Tyr Tyr Cys
                 85                  90                  95

Ala Arg Glu Gly Thr Tyr Tyr Ala Met Asp Tyr Trp Gly Gln Gly Thr

Thr Val Thr Val Ser Ser
       115

<210> SEQ ID NO 63
<211> LENGTH: 118
<212> TYPE: PRT
<213> ORGANISM: Artificial Sequence
<220> FEATURE:
<223> OTHER INFORMATION: Synthetic sequence

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Ile Trp Ile Tyr Pro Gly Asp Gly Ser Thr Gln Tyr Asn Glu Lys
        50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser
       115

<210> SEQ ID NO 64
<211> LENGTH: 118
<212> TYPE: PRT
<213> ORGANISM: Artificial Sequence
<220> FEATURE:
<223> OTHER INFORMATION: Synthetic sequence

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Trp Ile Tyr Pro Gly Asp Gly Ser Thr Gln Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser
       115

<210> SEQ ID NO 65
<211> LENGTH: 118
<212> TYPE: PRT
<213> ORGANISM: Artificial Sequence
<220> FEATURE:

<223> OTHER INFORMATION: Synthetic sequence

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser
            115

<210> SEQ ID NO 66
<211> LENGTH: 118
<212> TYPE: PRT
<213> ORGANISM: Artificial Sequence
<220> FEATURE:
<223> OTHER INFORMATION: Synthetic sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser
            115

<210> SEQ ID NO 67
<211> LENGTH: 112
<212> TYPE: PRT
<213> ORGANISM: Artificial Sequence
<220> FEATURE:
<223> OTHER INFORMATION: Synthetic sequence

<400> SEQUENCE: 67

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser

```
                35                  40                  45
Pro Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
               100                 105                 110
```

<210> SEQ ID NO 68
<211> LENGTH: 112
<212> TYPE: PRT
<213> ORGANISM: Artificial Sequence
<220> FEATURE:
<223> OTHER INFORMATION: Synthetic sequence

<400> SEQUENCE: 68

```
Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
               100                 105                 110
```

<210> SEQ ID NO 69
<211> LENGTH: 112
<212> TYPE: PRT
<213> ORGANISM: Artificial Sequence
<220> FEATURE:
<223> OTHER INFORMATION: Synthetic sequence

<400> SEQUENCE: 69

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Ile Val His Ser
                20                  25                  30

Asn Gly Asn Thr Tyr Leu Glu Trp Tyr Gln Gln Arg Pro Gly Gln Pro
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
               100                 105                 110
```

<210> SEQ ID NO 70
<211> LENGTH: 112

```
<212> TYPE: PRT
<213> ORGANISM: Artificial Sequence
<220> FEATURE:
<223> OTHER INFORMATION: Synthetic sequence

<400> SEQUENCE: 70

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthetic sequence

<400> SEQUENCE: 71

Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Ile Val His Ser
            20                  25                  30

Asn Gly Asn Thr Tyr Leu Glu Trp Tyr Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Arg Thr Phe Gly Gly Gly Thr Lys Val Glu Ile Lys
            100                 105                 110

<210> SEQ ID NO 72
<211> LENGTH: 251
<212> TYPE: PRT
<213> ORGANISM: Artificial Sequence
<220> FEATURE:
<223> OTHER INFORMATION: Synthetic sequence

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
```

```
            50                  55                  60
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Ser Gly
                115                 120                 125

Gly Gly Gly Ser Gly Gly Gly Ser Thr Ser Asp Val Val Met Thr
130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Phe Gln Gln Arg Pro Gly Gln Ser Pro Arg Arg Leu Ile
                180                 185                 190

Tyr Lys Val Ser Asn Arg Phe Ser Gly Val Pro Asp Arg Phe Ser Gly
                195                 200                 205

Ser Gly Ser Gly Thr Asp Phe Thr Leu Lys Ile Ser Arg Val Glu Ala
                210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 73
<211> LENGTH: 251
<212> TYPE: PRT
<213> ORGANISM: Artificial Sequence
<220> FEATURE:
<223> OTHER INFORMATION: Synthetic sequence

<400> SEQUENCE: 73

Gln Val Gln Leu Val Gln Ser Gly Ala Glu Val Lys Lys Pro Gly Ala
 1                   5                  10                  15

Ser Val Lys Val Ser Cys Lys Ala Ser Gly Tyr Thr Phe Thr Ser Tyr
                 20                  25                  30

His Ile Gln Trp Val Arg Gln Ala Pro Gly Gln Arg Leu Glu Trp Met
                 35                  40                  45

Gly Trp Ile Tyr Pro Gly Asp Gly Ser Thr Gln Tyr Asn Glu Lys Phe
 50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Ser Gly
                115                 120                 125

Gly Gly Gly Ser Gly Gly Gly Ser Thr Ser Asp Ile Val Met Thr
130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
```

```
                        165                 170                 175
Leu Glu Trp Tyr Leu Gln Lys Pro Gly Gln Ser Pro Gln Leu Leu Ile
                180                 185                 190

Tyr Lys Val Ser Asn Arg Phe Ser Gly Val Pro Asp Arg Phe Ser Gly
            195                 200                 205

Ser Gly Ser Gly Thr Asp Phe Thr Leu Lys Ile Ser Arg Val Glu Ala
        210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 74
<211> LENGTH: 251
<212> TYPE: PRT
<213> ORGANISM: Artificial Sequence
<220> FEATURE:
<223> OTHER INFORMATION: Synthetic sequence

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 75
<211> LENGTH: 251
<212> TYPE: PRT
```

<213> ORGANISM: Artificial Sequence
<220> FEATURE:
<223> OTHER INFORMATION: Synthetic sequence

<400> SEQUENCE: 75

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Val Val Met Thr
    130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Ser Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250
```

<210> SEQ ID NO 76
<211> LENGTH: 251
<212> TYPE: PRT
<213> ORGANISM: Artificial Sequence
<220> FEATURE:
<223> OTHER INFORMATION: Synthetic sequence

<400> SEQUENCE: 76

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
            115                 120                 125

Gly Gly Gly Ser Gly Gly Gly Ser Thr Ser Asp Ile Val Met Thr
            130                 135             140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
        210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 77
<211> LENGTH: 251
<212> TYPE: PRT
<213> ORGANISM: Artificial Sequence
<220> FEATURE:
<223> OTHER INFORMATION: Synthetic sequence

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Thr Ser Ala Ser Thr Ala Tyr
65                  70                  75                  80

Met Leu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
            115                 120                 125

Gly Gly Gly Ser Gly Gly Gly Ser Thr Ser Asp Val Val Met Thr
            130                 135             140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Phe Gln Gln Arg Pro Gly Gln Ser Pro Arg Arg Leu Ile
            180                 185                 190
```

```
Tyr Lys Val Ser Asn Arg Phe Ser Gly Val Pro Asp Arg Phe Ser Gly
            195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 78
<211> LENGTH: 251
<212> TYPE: PRT
<213> ORGANISM: Artificial Sequence
<220> FEATURE:
<223> OTHER INFORMATION: Synthetic sequence

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Thr Ser Ala Ser Thr Ala Tyr
65                  70                  75                  80

Met Leu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 79
<211> LENGTH: 251
<212> TYPE: PRT
<213> ORGANISM: Artificial Sequence
<220> FEATURE:
<223> OTHER INFORMATION: Synthetic sequence

<400> SEQUENCE: 79
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Ile Trp Ile Tyr Pro Gly Asp Gly Ser Thr Gln Tyr Asn Glu Lys
    50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
        130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 80
<211> LENGTH: 251
<212> TYPE: PRT
<213> ORGANISM: Artificial Sequence
<220> FEATURE:
<223> OTHER INFORMATION: Synthetic sequence

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Ile Trp Ile Tyr Pro Gly Asp Gly Ser Thr Gln Tyr Asn Glu Lys
    50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

```
Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
        130                 135                 140

Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Pro Arg Leu Leu Ile
            180                 185                 190

Tyr Lys Val Ser Asn Arg Phe Ser Gly Val Pro Asp Arg Phe Ser Gly
            195                 200                 205

Ser Gly Ala Gly Thr Asp Phe Thr Leu Lys Ile Ser Arg Val Glu Ala
        210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 81
<211> LENGTH: 251
<212> TYPE: PRT
<213> ORGANISM: Artificial Sequence
<220> FEATURE:
<223> OTHER INFORMATION: Synthetic sequence

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Ile Trp Ile Tyr Pro Gly Asp Gly Ser Thr Gln Tyr Asn Glu Lys
        50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Val Val Met Thr
        130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Ser Pro Arg Leu Leu Ile
            180                 185                 190

Tyr Lys Val Ser Asn Arg Phe Ser Gly Val Pro Asp Arg Phe Ser Gly
            195                 200                 205

Ser Gly Ser Gly Thr Asp Phe Thr Leu Lys Ile Ser Arg Val Glu Ala
        210                 215                 220
```

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 82
<211> LENGTH: 251
<212> TYPE: PRT
<213> ORGANISM: Artificial Sequence
<220> FEATURE:
<223> OTHER INFORMATION: Synthetic sequence

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Ile Trp Ile Tyr Pro Gly Asp Gly Ser Thr Gln Tyr Asn Glu Lys
        50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 83
<211> LENGTH: 251
<212> TYPE: PRT
<213> ORGANISM: Artificial Sequence
<220> FEATURE:
<223> OTHER INFORMATION: Synthetic sequence

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                 20                  25                  30
His Ile Gln Trp Val Arg Gln Ala Pro Gly Gln Gly Leu Glu Trp Met
             35                  40                  45

Gly Trp Ile Tyr Pro Gly Asp Gly Ser Thr Gln Tyr Asn Glu Lys Phe
 50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Ser Gly
                115                 120                 125

Gly Gly Gly Ser Gly Gly Gly Ser Thr Ser Asp Ile Val Met Thr
                130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
                180                 185                 190

Tyr Lys Val Ser Asn Arg Phe Ser Gly Val Pro Asp Arg Phe Ser Gly
                195                 200                 205

Ser Gly Ser Gly Thr Asp Phe Thr Leu Lys Ile Ser Arg Val Glu Ala
                210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 84
<211> LENGTH: 251
<212> TYPE: PRT
<213> ORGANISM: Artificial Sequence
<220> FEATURE:
<223> OTHER INFORMATION: Synthetic sequence

<400> SEQUENCE: 84

Gln Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Thr Ser Tyr
                 20                  25                  30

His Ile Gln Trp Val Arg Gln Ala Pro Gly Gln Gly Leu Glu Trp Met
             35                  40                  45

Gly Trp Ile Tyr Pro Gly Asp Gly Ser Thr Gln Tyr Asn Glu Lys Phe
 50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Gly Gly Gly Gly Ser Gly
                115                 120                 125

Gly Gly Gly Ser Gly Gly Gly Gly Ser Thr Ser Asp Ile Val Met Thr
```

```
                     130                 135                 140
Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
                180                 185                 190

Tyr Lys Val Ser Asn Arg Phe Ser Gly Val Pro Asp Arg Phe Ser Gly
                195                 200                 205

Ser Gly Ala Gly Thr Asp Phe Thr Leu Lys Ile Ser Arg Val Glu Ala
                210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 85
<211> LENGTH: 251
<212> TYPE: PRT
<213> ORGANISM: Artificial Sequence
<220> FEATURE:
<223> OTHER INFORMATION: Synthetic sequence

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Trp Ile Tyr Pro Gly Asp Gly Ser Thr Gln Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Gly Ser Gly
            115                 120                 125

Gly Gly Gly Ser Gly Gly Gly Ser Thr Ser Asp Val Val Met Thr
        130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Ser Pro Arg Leu Leu Ile
                180                 185                 190

Tyr Lys Val Ser Asn Arg Phe Ser Gly Val Pro Asp Arg Phe Ser Gly
                195                 200                 205

Ser Gly Ser Gly Thr Asp Phe Thr Leu Lys Ile Ser Arg Val Glu Ala
                210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
```

<210> SEQ ID NO 86
<211> LENGTH: 251
<212> TYPE: PRT
<213> ORGANISM: Artificial Sequence
<220> FEATURE:
<223> OTHER INFORMATION: Synthetic sequence

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250
```

<210> SEQ ID NO 87
<211> LENGTH: 251
<212> TYPE: PRT
<213> ORGANISM: Artificial Sequence
<220> FEATURE:
<223> OTHER INFORMATION: Synthetic sequence

<400> SEQUENCE: 87

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45
```

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
    130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 88
<211> LENGTH: 251
<212> TYPE: PRT
<213> ORGANISM: Artificial Sequence
<220> FEATURE:
<223> OTHER INFORMATION: Synthetic sequence

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
            165                 170                 175

Leu Glu Trp Tyr Gln Gln Arg Pro Gly Gln Pro Pro Arg Leu Leu Ile
        180                 185                 190

Tyr Lys Val Ser Asn Arg Phe Ser Gly Val Pro Asp Arg Phe Ser Gly
    195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 89
<211> LENGTH: 251
<212> TYPE: PRT
<213> ORGANISM: Artificial Sequence
<220> FEATURE:
<223> OTHER INFORMATION: Synthetic sequence

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Ser Gly Gly Gly Ser Thr Ser Asp Val Val Met Thr
    130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
            165                 170                 175

Leu Glu Trp Tyr Gln Gln Arg Pro Gly Gln Ser Pro Arg Leu Leu Ile
        180                 185                 190

Tyr Lys Val Ser Asn Arg Phe Ser Gly Val Pro Asp Arg Phe Ser Gly
    195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 90
<211> LENGTH: 251

```
<212> TYPE: PRT
<213> ORGANISM: Artificial Sequence
<220> FEATURE:
<223> OTHER INFORMATION: Synthetic sequence

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
                245                 250

<210> SEQ ID NO 91
<211> LENGTH: 251
<212> TYPE: PRT
<213> ORGANISM: Artificial Sequence
<220> FEATURE:
<223> OTHER INFORMATION: Synthetic sequence

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Gly Gly Gly Gly Ser Gly
            115                 120                 125

Gly Gly Gly Ser Gly Gly Gly Ser Thr Ser Asp Ile Val Met Thr
        130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
        210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys
            245                 250

<210> SEQ ID NO 92
<211> LENGTH: 119
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (44)..(44)
<223> OTHER INFORMATION: Xaa is R or G
<220> FEATURE:
<221> NAME/KEY: misc_feature
<222> LOCATION: (50)..(50)
<223> OTHER INFORMATION: Xaa is I or absent
<220> FEATURE:
<221> NAME/KEY: misc_feature
<222> LOCATION: (68)..(68)
<223> OTHER INFORMATION: Xaa is R or absent
<220> FEATURE:
<221> NAME/KEY: misc_feature
<222> LOCATION: (71)..(71)
<223> OTHER INFORMATION: Xaa is I or M
<220> FEATURE:
<221> NAME/KEY: misc_feature
<222> LOCATION: (73)..(73)
<223> OTHER INFORMATION: Xaa is R or A
<220> FEATURE:
<221> NAME/KEY: misc_feature
<222> LOCATION: (77)..(77)
<223> OTHER INFORMATION: Xaa is A, T or I
<220> FEATURE:
<221> NAME/KEY: misc_feature
<222> LOCATION: (83)..(83)
<223> OTHER INFORMATION: Xaa is E or L
<220> FEATURE:
<221> NAME/KEY: misc_feature
<222> LOCATION: (86)..(86)
<223> OTHER INFORMATION: Xaa is S or R
<220> FEATURE:
<221> NAME/KEY: misc_feature
<222> LOCATION: (90)..(90)
<223> OTHER INFORMATION: Xaa is E or D
<220> FEATURE:
<221> NAME/KEY: misc_feature

```
<222> LOCATION: (92)..(92)
<223> OTHER INFORMATION: Xaa is T or M

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Xaa Leu Glu Trp Met
        35                  40                  45

Gly Xaa Trp Ile Tyr Pro Gly Asp Gly Ser Thr Lys Tyr Ser Gln Lys
    50                  55                  60

Phe Gln Gly Xaa Val Thr Xaa Thr Xaa Asp Thr Ser Xaa Ser Thr Ala
65                  70                  75                  80

Tyr Met Xaa Leu Ser Xaa Leu Arg Ser Xaa Asp Xaa Ala Val Tyr Tyr
            85                  90                  95

Cys Ala Arg Glu Gly Thr Tyr Tyr Ala Met Asp Tyr Trp Gly Gln Gly
            100                 105                 110

Thr Thr Val Thr Val Ser Ser
            115

<210> SEQ ID NO 93
<211> LENGTH: 274
<212> TYPE: PRT
<213> ORGANISM: Artificial Sequence
<220> FEATURE:
<223> OTHER INFORMATION: Synthetic sequence

<400> SEQUENCE: 93

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
            85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
        130                 135                 140

Ser Gly Gly Gly Ser Gly Gly Gly Ser Gly Gly Gly Ser
145                 150                 155                 160

Thr Ser Asp Val Val Met Thr Gln Ser Pro Leu Ser Leu Pro Val Thr
            165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Phe Gln Gln Arg Pro Gly
            195                 200                 205

Gln Ser Pro Arg Arg Leu Ile Tyr Lys Val Ser Asn Arg Phe Ser Gly
```

```
                210                 215                 220
Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
                260                 265                 270

Ile Lys

<210> SEQ ID NO 94
<211> LENGTH: 274
<212> TYPE: PRT
<213> ORGANISM: Artificial Sequence
<220> FEATURE:
<223> OTHER INFORMATION: Synthetic sequence

<400> SEQUENCE: 94

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Gly Ser Gly Gly Gly Gly Ser Gly Gly Gly Gly Ser
145                 150                 155                 160

Thr Ser Asp Ile Val Met Thr Gln Thr Pro Leu Ser Leu Ser Val Thr
                165                 170                 175

Pro Gly Gln Pro Ala Ser Ile Ser Cys Arg Ser Ser Gln Ser Ile Val
            180                 185                 190

His Ser Asn Gly Asn Thr Tyr Leu Glu Trp Tyr Leu Gln Lys Pro Gly
        195                 200                 205

Gln Ser Pro Gln Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 95
<211> LENGTH: 274
```

```
<212> TYPE: PRT
<213> ORGANISM: Artificial Sequence
<220> FEATURE:
<223> OTHER INFORMATION: Synthetic sequence

<400> SEQUENCE: 95

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Gly Ser Gly Gly Gly Gly Ser Gly Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Pro Pro Arg Leu Leu Ile Tyr Lys Val Ser Asn Arg Phe Ser Gly
    210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 96
<211> LENGTH: 274
<212> TYPE: PRT
<213> ORGANISM: Artificial Sequence
<220> FEATURE:
<223> OTHER INFORMATION: Synthetic sequence

<400> SEQUENCE: 96

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45
```

Gly Tyr Thr Phe Thr Ser Tyr His Ile Gln Trp Val Arg Gln Ala Pro
            50                  55                  60

Gly Gln Arg Leu Glu Trp Met Gly Trp Ile Tyr Pro Gly Asp Gly Ser
 65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
130                 135                 140

Ser Gly Gly Gly Ser Gly Gly Gly Ser Gly Gly Gly Ser
145                 150                 155                 160

Thr Ser Asp Val Val Met Thr Gln Ser Pro Leu Ser Leu Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
            195                 200                 205

Gln Ser Pro Arg Leu Leu Ile Tyr Lys Val Ser Asn Arg Phe Ser Gly
            210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 97
<211> LENGTH: 274
<212> TYPE: PRT
<213> ORGANISM: Artificial Sequence
<220> FEATURE:
<223> OTHER INFORMATION: Synthetic sequence

<400> SEQUENCE: 97

Met Asp Phe Gln Val Gln Ile Phe Ser Phe Leu Leu Ile Ser Ala Ser
 1                5                  10                  15

Val Ile Met Ser Arg Ala Ser Gln Val Gln Leu Val Gln Ser Gly Ala
             20                  25                  30

Glu Val Lys Lys Pro Gly Ala Ser Val Lys Val Ser Cys Lys Ala Ser
             35                  40                  45

Gly Tyr Thr Phe Thr Ser Tyr His Ile Gln Trp Val Arg Gln Ala Pro
            50                  55                  60

Gly Gln Arg Leu Glu Trp Met Gly Trp Ile Tyr Pro Gly Asp Gly Ser
 65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser

```
                130                 135                 140
Ser Gly Gly Gly Ser Gly Gly Gly Ser Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Phe Arg Ser Ser Gln Ser Ile Val
                180                 185                 190

His Ser Asn Gly Asn Thr Tyr Leu Glu Trp Tyr Gln Gln Arg Pro Gly
            195                 200                 205

Gln Pro Pro Arg Leu Leu Ile Tyr Lys Val Ser Asn Arg Phe Ser Gly
210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 98
<211> LENGTH: 274
<212> TYPE: PRT
<213> ORGANISM: Artificial Sequence
<220> FEATURE:
<223> OTHER INFORMATION: Synthetic sequence

<400> SEQUENCE: 98

Met Asp Phe Gln Val Gln Ile Phe Ser Phe Leu Leu Ile Ser Ala Ser
1                   5                  10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
        50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Ala Asp
                85                  90                  95

Thr Ser Ala Ser Thr Ala Tyr Met Leu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Ser
145                 150                 155                 160

Thr Ser Asp Val Val Met Thr Gln Ser Pro Leu Ser Leu Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Phe Gln Gln Arg Pro Gly
        195                 200                 205

Gln Ser Pro Arg Arg Leu Ile Tyr Lys Val Ser Asn Arg Phe Ser Gly
    210                 215                 220
```

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 99
<211> LENGTH: 274
<212> TYPE: PRT
<213> ORGANISM: Artificial Sequence
<220> FEATURE:
<223> OTHER INFORMATION: Synthetic sequence

<400> SEQUENCE: 99

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Ala Asp
                85                  90                  95

Thr Ser Ala Ser Thr Ala Tyr Met Leu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Gly Gly Gly Ser
145                 150                 155                 160

Thr Ser Asp Ile Val Met Thr Gln Thr Pro Leu Ser Leu Ser Val Thr
                165                 170                 175

Pro Gly Gln Pro Ala Ser Ile Ser Cys Arg Ser Ser Gln Ser Ile Val
            180                 185                 190

His Ser Asn Gly Asn Thr Tyr Leu Glu Trp Tyr Leu Gln Lys Pro Gly
        195                 200                 205

Gln Ser Pro Gln Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 100
<211> LENGTH: 274
<212> TYPE: PRT

-continued

```
<213> ORGANISM: Artificial Sequence
<220> FEATURE:
<223> OTHER INFORMATION: Synthetic sequence

<400> SEQUENCE: 100

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Gly Leu Glu Trp Met Gly Ile Trp Ile Tyr Pro Gly Asp Gly
65              70                  75                  80

Ser Thr Gln Tyr Asn Glu Lys Phe Lys Gly Val Thr Met Thr Arg Asp
                85                  90                  95

Thr Ser Thr Ser Thr Val Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Gly Ser Gly Gly Gly Gly Ser Gly Gly Gly Gly Ser
145                 150                 155                 160

Thr Ser Asp Ile Val Met Thr Gln Thr Pro Leu Ser Leu Ser Val Thr
                165                 170                 175

Pro Gly Gln Pro Ala Ser Ile Ser Cys Arg Ser Ser Gln Ser Ile Val
            180                 185                 190

His Ser Asn Gly Asn Thr Tyr Leu Glu Trp Tyr Leu Gln Lys Pro Gly
        195                 200                 205

Gln Ser Pro Gln Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 101
<211> LENGTH: 274
<212> TYPE: PRT
<213> ORGANISM: Artificial Sequence
<220> FEATURE:
<223> OTHER INFORMATION: Synthetic sequence

<400> SEQUENCE: 101

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
```

```
                50                  55                  60
Gly Gln Gly Leu Glu Trp Met Gly Ile Trp Ile Tyr Pro Asp Gly
 65                  70                  75                  80

Ser Thr Gln Tyr Asn Glu Lys Phe Lys Gly Val Thr Met Thr Arg Asp
                 85                  90                  95

Thr Ser Thr Ser Thr Val Tyr Met Glu Leu Ser Ser Leu Arg Ser Glu
                100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
130                 135                 140

Ser Gly Gly Gly Ser Gly Gly Gly Ser Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Pro Pro Arg Leu Leu Ile Tyr Lys Val Ser Asn Arg Phe Ser Gly
210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 102
<211> LENGTH: 274
<212> TYPE: PRT
<213> ORGANISM: Artificial Sequence
<220> FEATURE:
<223> OTHER INFORMATION: Synthetic sequence

<400> SEQUENCE: 102

Met Asp Phe Gln Val Gln Ile Phe Ser Phe Leu Leu Ile Ser Ala Ser
 1               5                  10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
        50                  55                  60

Gly Gln Gly Leu Glu Trp Met Gly Ile Trp Ile Tyr Pro Asp Gly
 65                  70                  75                  80

Ser Thr Gln Tyr Asn Glu Lys Phe Lys Gly Val Thr Met Thr Arg Asp
                 85                  90                  95

Thr Ser Thr Ser Thr Val Tyr Met Glu Leu Ser Ser Leu Arg Ser Glu
                100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
130                 135                 140
```

```
Ser Gly Gly Gly Gly Ser Gly Gly Gly Ser Gly Gly Gly Ser
145                 150                 155                 160

Thr Ser Asp Val Val Met Thr Gln Ser Pro Leu Ser Leu Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Ser Pro Arg Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 103
<211> LENGTH: 274
<212> TYPE: PRT
<213> ORGANISM: Artificial Sequence
<220> FEATURE:
<223> OTHER INFORMATION: Synthetic sequence

<400> SEQUENCE: 103

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
    50                  55                  60

Gly Gln Gly Leu Glu Trp Met Gly Ile Trp Ile Tyr Pro Gly Asp Gly
65                  70                  75                  80

Ser Thr Gln Tyr Asn Glu Lys Phe Lys Gly Val Thr Met Thr Arg Asp
                85                  90                  95

Thr Ser Thr Ser Thr Val Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Gly Ser Gly Gly Gly Gly Ser Gly Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Phe Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Pro Pro Arg Leu Leu Ile Tyr Lys Val Ser Asn Arg Phe Ser Gly
    210                 215                 220
```

```
Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 104
<211> LENGTH: 274
<212> TYPE: PRT
<213> ORGANISM: Artificial Sequence
<220> FEATURE:
<223> OTHER INFORMATION: Synthetic sequence

<400> SEQUENCE: 104

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
50                  55                  60

Gly Gln Gly Leu Glu Trp Met Gly Trp Ile Tyr Pro Gly Asp Gly Ser
65                  70                  75                  80

Thr Gln Tyr Asn Glu Lys Phe Lys Gly Arg Val Thr Met Thr Arg Asp
                85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Gly Gly Gly Ser
145                 150                 155                 160

Thr Ser Asp Ile Val Met Thr Gln Thr Pro Leu Ser Leu Ser Val Thr
                165                 170                 175

Pro Gly Gln Pro Ala Ser Ile Ser Cys Arg Ser Ser Gln Ser Ile Val
            180                 185                 190

His Ser Asn Gly Asn Thr Tyr Leu Glu Trp Tyr Leu Gln Lys Pro Gly
        195                 200                 205

Gln Ser Pro Gln Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 105
<211> LENGTH: 274
<212> TYPE: PRT
<213> ORGANISM: Artificial Sequence
```

<220> FEATURE:
<223> OTHER INFORMATION: Synthetic sequence

<400> SEQUENCE: 105

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Gly Leu Glu Trp Met Gly Trp Ile Tyr Pro Gly Asp Gly Ser
65                  70                  75                  80

Thr Gln Tyr Asn Glu Lys Phe Lys Gly Arg Val Thr Met Thr Arg Asp
                85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Pro Pro Arg Leu Leu Ile Tyr Lys Val Ser Asn Arg Phe Ser Gly
    210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 106
<211> LENGTH: 274
<212> TYPE: PRT
<213> ORGANISM: Artificial Sequence
<220> FEATURE:
<223> OTHER INFORMATION: Synthetic sequence

<400> SEQUENCE: 106

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

```
Gly Gln Gly Leu Glu Trp Met Gly Trp Ile Tyr Pro Gly Asp Gly Ser
 65                  70                  75                  80

Thr Gln Tyr Asn Glu Lys Phe Lys Gly Arg Val Thr Met Thr Arg Asp
                 85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Ser
145                 150                 155                 160

Thr Ser Asp Val Val Met Thr Gln Ser Pro Leu Ser Leu Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Ser Pro Arg Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 107
<211> LENGTH: 274
<212> TYPE: PRT
<213> ORGANISM: Artificial Sequence
<220> FEATURE:
<223> OTHER INFORMATION: Synthetic sequence

<400> SEQUENCE: 107

Met Asp Phe Gln Val Gln Ile Phe Ser Phe Leu Leu Ile Ser Ala Ser
 1               5                  10                  15

Val Ile Met Ser Arg Ala Ser Gln Val Gln Leu Val Gln Ser Gly Ala
                 20                  25                  30

Glu Val Lys Lys Pro Gly Ala Ser Val Lys Val Ser Cys Lys Ala Ser
             35                  40                  45

Gly Tyr Thr Phe Thr Ser Tyr His Ile Gln Trp Val Arg Gln Ala Pro
     50                  55                  60

Gly Gln Gly Leu Glu Trp Met Gly Trp Ile Tyr Pro Gly Asp Gly Ser
 65                  70                  75                  80

Thr Gln Tyr Asn Glu Lys Phe Lys Gly Arg Val Thr Met Thr Arg Asp
                 85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140
```

```
Ser Gly Gly Gly Gly Ser Gly Gly Gly Ser Gly Gly Gly Gly Ser
145                 150                 155                 160

Thr Ser Asp Ile Val Met Thr Gln Thr Pro Leu Ser Ser Pro Val Thr
            165                 170                 175

Leu Gly Gln Pro Ala Ser Ile Ser Phe Arg Ser Ser Gln Ser Ile Val
                180                 185                 190

His Ser Asn Gly Asn Thr Tyr Leu Glu Trp Tyr Gln Gln Arg Pro Gly
            195                 200                 205

Gln Pro Pro Arg Leu Leu Ile Tyr Lys Val Ser Asn Arg Phe Ser Gly
        210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 108
<211> LENGTH: 274
<212> TYPE: PRT
<213> ORGANISM: Artificial Sequence
<220> FEATURE:
<223> OTHER INFORMATION: Synthetic sequence

<400> SEQUENCE: 108

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
    50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Met Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Gly Ser Gly Gly Gly Gly Ser Gly Gly Gly Gly Ser
145                 150                 155                 160

Thr Ser Asp Ile Val Met Thr Gln Thr Pro Leu Ser Leu Ser Val Thr
            165                 170                 175

Pro Gly Gln Pro Ala Ser Ile Ser Cys Arg Ser Ser Gln Ser Ile Val
        180                 185                 190

His Ser Asn Gly Asn Thr Tyr Leu Glu Trp Tyr Leu Gln Lys Pro Gly
            195                 200                 205

Gln Ser Pro Gln Leu Leu Ile Tyr Lys Val Ser Asn Arg Phe Ser Gly
        210                 215                 220

Val Pro Asp Arg Phe Ser Gly Ser Gly Ser Gly Thr Asp Phe Thr Leu
```

```
                225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
                260                 265                 270

Ile Lys

<210> SEQ ID NO 109
<211> LENGTH: 274
<212> TYPE: PRT
<213> ORGANISM: Artificial Sequence
<220> FEATURE:
<223> OTHER INFORMATION: Synthetic sequence

<400> SEQUENCE: 109

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
                35                  40                  45

Gly Tyr Thr Phe Thr Ser Tyr His Ile Gln Trp Val Arg Gln Ala Pro
        50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
                100                 105                 110

Asp Met Ala Val Tyr Tyr Cys Ala Arg Glu Gly Thr Tyr Tyr Ala Met
                115                 120                 125

Asp Tyr Trp Gly Gln Gly Thr Thr Val Thr Val Ser Ser Val Asp Ser
        130                 135                 140

Ser Gly Gly Gly Gly Ser Gly Gly Gly Ser Gly Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Cys Arg Ser Ser Gln Ser Ile Val
                180                 185                 190

His Ser Asn Gly Asn Thr Tyr Leu Glu Trp Tyr Gln Gln Arg Pro Gly
        195                 200                 205

Gln Pro Pro Arg Leu Leu Ile Tyr Lys Val Ser Asn Arg Phe Ser Gly
        210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
                260                 265                 270

Ile Lys

<210> SEQ ID NO 110
<211> LENGTH: 274
<212> TYPE: PRT
<213> ORGANISM: Artificial Sequence
<220> FEATURE:
```

<223> OTHER INFORMATION: Synthetic sequence

<400> SEQUENCE: 110

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

Gly Gln Arg Leu Glu Trp Met Gly Trp Ile Tyr Pro Gly Asp Gly Ser
65                  70                  75                  80

Thr Gln Tyr Asn Glu Lys Phe Lys Gly Arg Val Thr Ile Thr Arg Asp
                85                  90                  95

Thr Ser Ala Ser Thr Ala Tyr Met Glu Leu Ser Ser Leu Arg Ser Glu
            100                 105                 110

Asp Met Ala Val Tyr Tyr Cys Ala Arg Glu Gly Thr Tyr Tyr Ala Met
        115                 120                 125

Asp Tyr Trp Gly Gln Gly Thr Thr Val Thr Val Ser Ser Val Asp Ser
    130                 135                 140

Ser Gly Gly Gly Ser Gly Gly Gly Ser Gly Gly Gly Gly Ser
145                 150                 155                 160

Thr Ser Asp Val Val Met Thr Gln Ser Pro Leu Ser Leu Pro Val Thr
                165                 170                 175

Leu Gly Gln Pro Ala Ser Ile Ser Cys Arg Ser Ser Gln Ser Ile Val
            180                 185                 190

His Ser Asn Gly Asn Thr Tyr Leu Glu Trp Tyr Gln Gln Arg Pro Gly
        195                 200                 205

Gln Ser Pro Arg Leu Leu Ile Tyr Lys Val Ser Asn Arg Phe Ser Gly
    210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 111
<211> LENGTH: 274
<212> TYPE: PRT
<213> ORGANISM: Artificial Sequence
<220> FEATURE:
<223> OTHER INFORMATION: Synthetic sequence

<400> SEQUENCE: 111

Met Asp Phe Gln Val Gln Ile Phe Ser Phe Leu Leu Ile Ser Ala Ser
1               5                   10                  15

Val Ile Met Ser Arg Ala Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr His Ile Gln Trp Val Arg Gln Ala Pro
    50                  55                  60

```
Gly Gln Arg Leu Glu Trp Met Gly Trp Ile Tyr Pro Gly Asp Gly Ser
 65                  70                  75                  80

Thr Gln Tyr Asn Glu Lys Phe Lys Gly Arg Val Thr Ile Thr Arg Asp
                 85                  90                  95

Thr Ser Ala Ser Thr Ala Tyr Met Glu Leu Ser Ser Leu Arg Ser Glu
            100                 105                 110

Asp Met Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
            130                 135                 140

Ser Gly Gly Gly Ser Gly Gly Gly Ser Gly Gly Gly Gly Ser
145                 150                 155                 160

Thr Ser Asp Ile Val Met Thr Gln Thr Pro Leu Ser Ser Pro Val Thr
                165                 170                 175

Leu Gly Gln Pro Ala Ser Ile Ser Phe Arg Ser Ser Gln Ser Ile Val
                180                 185                 190

His Ser Asn Gly Asn Thr Tyr Leu Glu Trp Tyr Gln Gln Arg Pro Gly
            195                 200                 205

Gln Pro Pro Arg Leu Leu Ile Tyr Lys Val Ser Asn Arg Phe Ser Gly
210                 215                 220

Val Pro Asp Arg Phe Ser Gly Ser Gly Ala Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
            260                 265                 270

Ile Lys

<210> SEQ ID NO 112
<211> LENGTH: 274
<212> TYPE: PRT
<213> ORGANISM: Artificial Sequence
<220> FEATURE:
<223> OTHER INFORMATION: Synthetic sequence

<400> SEQUENCE: 112

Met Asp Phe Gln Val Gln Ile Phe Ser Phe Leu Leu Ile Ser Ala Ser
1               5                  10                  15

Val Ile Met Ser Arg Ala Ser Gln Val Gln Leu Val Gln Ser Gly Ala
                20                  25                  30

Glu Val Lys Lys Pro Gly Ala Ser Val Lys Val Ser Cys Lys Ala Ser
            35                  40                  45

Gly Tyr Thr Phe Thr Ser Tyr His Ile Gln Trp Val Arg Gln Ala Pro
        50                  55                  60

Gly Gln Arg Leu Glu Trp Met Gly Trp Ile Tyr Pro Gly Asp Gly Ser
 65                  70                  75                  80

Thr Lys Tyr Ser Gln Lys Phe Gln Gly Arg Val Thr Ile Thr Arg Asp
                 85                  90                  95

Thr Ser Ala Ser Thr Ala Tyr Met Glu Leu Ser Ser Leu Arg Ser Glu
            100                 105                 110

Asp Thr Ala Val Tyr Tyr Cys Ala Arg Glu Gly Thr Tyr Tyr Ala Met
            115                 120                 125

Asp Tyr Trp Gly Gln Gly Thr Thr Val Thr Val Ser Ser Val Asp Ser
            130                 135                 140

Ser Gly Gly Gly Gly Ser Gly Gly Gly Gly Ser Gly Gly Gly Gly Ser
```

```
                145                 150                 155                 160
Thr Ser Asp Ile Val Met Thr Gln Thr Pro Leu Ser Leu Ser Val Thr
                        165                 170                 175

Pro Gly Gln Pro Ala Ser Ile Ser Cys Arg Ser Ser Gln Ser Ile Val
                    180                 185                 190

His Ser Asn Gly Asn Thr Tyr Leu Glu Trp Tyr Leu Gln Lys Pro Gly
                195                 200                 205

Gln Ser Pro Gln Leu Leu Ile Tyr Lys Val Ser Asn Arg Phe Ser Gly
            210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Val Gly Val Tyr Tyr Cys Phe
                245                 250                 255

Gln Gly Ser His Val Pro Arg Thr Phe Gly Gly Gly Thr Lys Val Glu
                260                 265                 270

Ile Lys

<210> SEQ ID NO 113
<211> LENGTH: 23
<212> TYPE: PRT
<213> ORGANISM: Artificial Sequence
<220> FEATURE:
<223> OTHER INFORMATION: Synthetic sequence

<400> SEQUENCE: 113

Met Asp Phe Gln Val Gln Ile Phe Ser Phe Leu Leu Ile Ser Ala Ser
1               5                   10                  15

Val Ile Met Ser Arg Ala Ser
            20

<210> SEQ ID NO 114
<211> LENGTH: 21
<212> TYPE: PRT
<213> ORGANISM: Artificial Sequence
<220> FEATURE:
<223> OTHER INFORMATION: Synthetic sequence

<400> SEQUENCE: 114

Val Asp Ser Ser Gly Gly Gly Ser Gly Gly Gly Ser Gly
1               5                   10                  15

Gly Gly Ser Thr Ser
            20

<210> SEQ ID NO 115
<211> LENGTH: 63
<212> TYPE: PRT
<213> ORGANISM: Artificial Sequence
<220> FEATURE:
<223> OTHER INFORMATION: Synthetic sequence

<400> SEQUENCE: 115

Ser Ala Leu Ser Asn Ser Ile Met Tyr Phe Ser His Phe Val Pro Val
1               5                   10                  15

Phe Leu Pro Ala Lys Pro Thr Thr Thr Pro Ala Pro Arg Pro Pro Thr
                20                  25                  30

Pro Ala Pro Thr Ile Ala Ser Gln Pro Leu Ser Leu Arg Pro Glu Ala
            35                  40                  45

Cys Arg Pro Ala Ala Gly Gly Ala Val His Thr Arg Gly Leu Asp
        50                  55                  60
```

-continued

```
<210> SEQ ID NO 116
<211> LENGTH: 27
<212> TYPE: PRT
<213> ORGANISM: Artificial Sequence
<220> FEATURE:
<223> OTHER INFORMATION: Synthetic sequence

<400> SEQUENCE: 116

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 117
<211> LENGTH: 41
<212> TYPE: PRT
<213> ORGANISM: Artificial Sequence
<220> FEATURE:
<223> OTHER INFORMATION: Synthetic sequence

<400> SEQUENCE: 117

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 118
<211> LENGTH: 112
<212> TYPE: PRT
<213> ORGANISM: Artificial Sequence
<220> FEATURE:
<223> OTHER INFORMATION: Synthetic sequence

<400> SEQUENCE: 118

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 119
<211> LENGTH: 510
<212> TYPE: PRT
<213> ORGANISM: Artificial Sequence
<220> FEATURE:
<223> OTHER INFORMATION: Synthetic sequence

<400> SEQUENCE: 119

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30

His Ile Gln Trp Val Arg Gln Ala Pro Gly Gln Arg Leu Glu Trp Met
         35                  40                  45

Gly Trp Ile Tyr Pro Gly Asp Gly Ser Thr Gln Tyr Asn Glu Lys Phe
     50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
            115                 120                 125

Gly Gly Gly Ser Gly Gly Gly Ser Thr Ser Asp Val Val Met Thr
        130                 135             140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Phe Gln Gln Arg Pro Gly Gln Ser Pro Arg Arg Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
```

```
                 435                 440                 445
Arg Lys Asn Pro Gln Glu Gly Leu Tyr Asn Glu Leu Gln Lys Asp Lys
450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                    485                 490                 495

Asp Thr Tyr Asp Ala Leu His Met Gln Ala Leu Pro Pro Arg
                500                 505                 510

<210> SEQ ID NO 120
<211> LENGTH: 510
<212> TYPE: PRT
<213> ORGANISM: Artificial Sequence
<220> FEATURE:
<223> OTHER INFORMATION: Synthetic sequence

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Arg Leu Glu Trp Met
            35                  40                  45

Gly Trp Ile Tyr Pro Gly Asp Gly Ser Thr Gln Tyr Asn Glu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His
        260                 265                 270

Phe Val Pro Val Phe Leu Pro Ala Lys Pro Thr Thr Thr Pro Ala Pro
    275                 280                 285

Arg Pro Pro Thr Pro Ala Pro Thr Ile Ala Ser Gln Pro Leu Ser Leu
```

```
                290                 295                 300
Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
                355                 360                 365

Thr Pro Arg Arg Pro Gly Pro Thr Arg Lys His Tyr Gln Pro Tyr Ala
                370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
                435                 440                 445

Arg Lys Asn Pro Gln Glu Gly Leu Tyr Asn Glu Leu Gln Lys Asp Lys
                450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 121
<211> LENGTH: 510
<212> TYPE: PRT
<213> ORGANISM: Artificial Sequence
<220> FEATURE:
<223> OTHER INFORMATION: Synthetic sequence

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Arg Leu Glu Trp Met
            35                  40                  45

Gly Trp Ile Tyr Pro Gly Asp Gly Ser Thr Gln Tyr Asn Glu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Gly Gly Gly Gly Ser Gly
            115                 120                 125

Gly Gly Gly Ser Gly Gly Gly Gly Ser Thr Ser Asp Ile Val Met Thr
        130                 135                 140

Gln Thr Pro Leu Ser Ser Pro Val Thr Leu Gly Gln Pro Ala Ser Ile
```

```
            145                 150                 155                 160
Ser Cys Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
                180                 185                 190

Tyr Lys Val Ser Asn Arg Phe Ser Gly Val Pro Asp Arg Phe Ser Gly
                195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
                260                 265                 270

Phe Val Pro Val Phe Leu Pro Ala Lys Pro Thr Thr Thr Pro Ala Pro
            275                 280                 285

Arg Pro Pro Thr Pro Ala Pro Thr Ile Ala Ser Gln Pro Leu Ser Leu
            290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
            370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 122
<211> LENGTH: 510
<212> TYPE: PRT
<213> ORGANISM: Artificial Sequence
<220> FEATURE:
<223> OTHER INFORMATION: Synthetic sequence

<400> SEQUENCE: 122

Gln Val Gln Leu Val Gln Ser Gly Ala Glu Val Lys Lys Pro Gly Ala
```

-continued

| | | | | | | | | | | | | | | | |
|---|---|---|---|---|---|---|---|---|---|---|---|---|---|---|---|

```
  1               5                  10                 15
Ser Val Lys Val Ser Cys Lys Ala Ser Gly Tyr Thr Phe Thr Ser Tyr
                20                 25                 30

His Ile Gln Trp Val Arg Gln Ala Pro Gly Gln Arg Leu Glu Trp Met
                35                 40                 45

Gly Trp Ile Tyr Pro Gly Asp Gly Ser Thr Gln Tyr Asn Glu Lys Phe
         50                 55                 60

Lys Gly Arg Val Thr Ile Thr Arg Asp Thr Ser Ala Ser Thr Ala Tyr
 65                 70                 75                 80

Met Glu Leu Ser Ser Leu Arg Ser Glu Asp Thr Ala Val Tyr Tyr Cys
                85                 90                 95

Ala Arg Glu Gly Thr Tyr Tyr Ala Met Asp Tyr Trp Gly Gln Gly Thr
                100                105                110

Thr Val Thr Val Ser Ser Val Asp Ser Gly Gly Gly Gly Ser Gly
                115                120                125

Gly Gly Gly Ser Gly Gly Gly Ser Thr Ser Asp Val Val Met Thr
         130                135                140

Gln Ser Pro Leu Ser Leu Pro Val Thr Leu Gly Gln Pro Ala Ser Ile
145                150                155                160

Ser Cys Arg Ser Ser Gln Ser Ile Val His Ser Asn Gly Asn Thr Tyr
                165                170                175

Leu Glu Trp Tyr Gln Gln Arg Pro Gly Gln Ser Pro Arg Leu Leu Ile
                180                185                190

Tyr Lys Val Ser Asn Arg Phe Ser Gly Val Pro Asp Arg Phe Ser Gly
                195                200                205

Ser Gly Ser Gly Thr Asp Phe Thr Leu Lys Ile Ser Arg Val Glu Ala
         210                215                220

Glu Asp Val Gly Val Tyr Tyr Cys Phe Gln Gly Ser His Val Pro Arg
225                230                235                240

Thr Phe Gly Gly Gly Thr Lys Val Glu Ile Lys Asn Arg Ile Arg Gly
                245                250                255

Val Thr Val Ser Ser Ala Leu Ser Asn Ser Ile Met Tyr Phe Ser His
                260                265                270

Phe Val Pro Val Phe Leu Pro Ala Lys Pro Thr Thr Thr Pro Ala Pro
                275                280                285

Arg Pro Pro Thr Pro Ala Pro Thr Ile Ala Ser Gln Pro Leu Ser Leu
                290                295                300

Arg Pro Glu Ala Cys Arg Pro Ala Ala Gly Gly Ala Val His Thr Arg
305                310                315                320

Gly Leu Asp Pro Phe Gly Phe Trp Val Leu Val Val Gly Gly Val
                325                330                335

Leu Ala Cys Tyr Ser Leu Leu Val Thr Val Ala Phe Ile Ile Phe Trp
                340                345                350

Val Arg Ser Lys Arg Ser Arg Leu Leu His Ser Asp Tyr Met Asn Met
                355                360                365

Thr Pro Arg Arg Pro Gly Pro Thr Arg Lys His Tyr Gln Pro Tyr Ala
         370                375                380

Pro Pro Arg Asp Phe Ala Ala Tyr Arg Ser Leu Glu Arg Val Arg Val
385                390                395                400

Lys Phe Ser Arg Ser Ala Asp Ala Pro Ala Tyr Gln Gln Gly Gln Asn
                405                410                415

Gln Leu Tyr Asn Glu Leu Asn Leu Gly Arg Arg Glu Glu Tyr Asp Val
                420                425                430
```

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 123
<211> LENGTH: 510
<212> TYPE: PRT
<213> ORGANISM: Artificial Sequence
<220> FEATURE:
<223> OTHER INFORMATION: Synthetic sequence

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

```
Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 124
<211> LENGTH: 510
<212> TYPE: PRT
<213> ORGANISM: Artificial Sequence
<220> FEATURE:
<223> OTHER INFORMATION: Synthetic sequence

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Thr Ser Ala Ser Thr Ala Tyr
65                  70                  75                  80

Met Leu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Val Val Met Thr
            130                 135                 140
```

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
            165                 170                 175

Leu Glu Trp Phe Gln Gln Arg Pro Gly Gln Ser Pro Arg Arg Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
            325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
        370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
        420                 425                 430

Leu Asp Lys Arg Arg Gly Arg Asp Pro Glu Met Gly Gly Lys Pro Arg
    435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 125
<211> LENGTH: 510
<212> TYPE: PRT
<213> ORGANISM: Artificial Sequence
<220> FEATURE:
<223> OTHER INFORMATION: Synthetic sequence

<400> SEQUENCE: 125

```
Gln Val Gln Leu Val Gln Ser Gly Ala Glu Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Thr Ser Ala Ser Thr Ala Tyr
65                  70                  75                  80

Met Leu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
            195                 200                 205

Ser Gly Ser Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
            275                 280                 285

Arg Pro Pro Thr Pro Ala Pro Thr Ile Ala Ser Gln Pro Leu Ser Leu
290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
            325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415
```

Gln Leu Tyr Asn Glu Leu Asn Leu Gly Arg Arg Glu Tyr Asp Val
            420                 425                 430

Leu Asp Lys Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
450                 455                 460

Met Ala Glu Ala Tyr Ser Glu Ile Gly Met Lys Gly Glu Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 126
<211> LENGTH: 510
<212> TYPE: PRT
<213> ORGANISM: Artificial Sequence
<220> FEATURE:
<223> OTHER INFORMATION: Synthetic sequence

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Ile Trp Ile Tyr Pro Gly Asp Gly Ser Thr Gln Tyr Asn Glu Lys
        50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

```
Phe Val Pro Val Phe Leu Pro Ala Lys Pro Thr Thr Thr Pro Ala Pro
                275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
                355                 360                 365

Thr Pro Arg Arg Pro Gly Pro Thr Arg Lys His Tyr Gln Pro Tyr Ala
                370                 375                 380

Pro Pro Arg Asp Phe Ala Ala Tyr Arg Ser Leu Arg Val Lys Phe Ser Arg Ser Ala Asp Ala Pro Ala Tyr Gln Gln Gly Gln Asn
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
                435                 440                 445

Arg Lys Asn Pro Gln Glu Gly Leu Tyr Asn Glu Leu Gln Lys Asp Lys
                450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 127
<211> LENGTH: 510
<212> TYPE: PRT
<213> ORGANISM: Artificial Sequence
<220> FEATURE:
<223> OTHER INFORMATION: Synthetic sequence

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Ile Trp Ile Tyr Pro Gly Asp Gly Ser Thr Gln Tyr Asn Glu Lys
        50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Gly Ser Gly
            115                 120                 125
```

Gly Gly Gly Ser Gly Gly Gly Ser Thr Ser Asp Ile Val Met Thr
130                 135                 140

Gln Thr Pro Leu Ser Ser Pro Val Thr Leu Gly Gln Pro Ala Ser Ile
145                 150                 155                 160

Ser Cys Arg Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
                180                 185                 190

Tyr Lys Val Ser Asn Arg Phe Ser Gly Val Pro Asp Arg Phe Ser Gly
            195                 200                 205

Ser Gly Ala Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
                260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
        370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 128
<211> LENGTH: 510
<212> TYPE: PRT
<213> ORGANISM: Artificial Sequence
<220> FEATURE:
<223> OTHER INFORMATION: Synthetic sequence

<400> SEQUENCE: 128

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ala|
|1| | | |5| | | | |10| | | | |15| |
|Ser|Val|Lys|Val|Ser|Cys|Lys|Ala|Ser|Gly|Tyr|Thr|Phe|Thr|Ser|Tyr|
| | | |20| | | | |25| | | | |30| | |
|His|Ile|Gln|Trp|Val|Arg|Gln|Ala|Pro|Gly|Gln|Gly|Leu|Glu|Trp|Met|
| | |35| | | | |40| | | | |45| | | |
|Gly|Ile|Trp|Ile|Tyr|Pro|Asp|Gly|Ser|Thr|Gln|Tyr|Asn|Glu|Lys|
| |50| | | | |55| | | | |60| | | | |
|Phe|Lys|Gly|Val|Thr|Met|Thr|Arg|Asp|Thr|Ser|Thr|Ser|Thr|Val|Tyr|
|65| | | | |70| | | | |75| | | | |80|
|Met|Glu|Leu|Ser|Ser|Leu|Arg|Ser|Glu|Asp|Thr|Ala|Val|Tyr|Tyr|Cys|
| | | | |85| | | | |90| | | | |95| |
|Ala|Arg|Glu|Gly|Thr|Tyr|Tyr|Ala|Met|Asp|Tyr|Trp|Gly|Gln|Gly|Thr|
| | | |100| | | | |105| | | | |110| | |
|Thr|Val|Thr|Val|Ser|Ser|Val|Asp|Ser|Gly|Gly|Gly|Ser|Gly|
| | | |115| | | | |120| | | | |125| | |
|Gly|Gly|Gly|Ser|Gly|Gly|Gly|Ser|Thr|Ser|Asp|Val|Val|Met|Thr|
| |130| | | | |135| | | | |140| | | | |
|Gln|Ser|Pro|Leu|Ser|Leu|Pro|Val|Thr|Leu|Gly|Gln|Pro|Ala|Ser|Ile|
|145| | | | |150| | | | |155| | | | |160|
|Ser|Cys|Arg|Ser|Ser|Gln|Ser|Ile|Val|His|Ser|Asn|Gly|Asn|Thr|Tyr|
| | | | |165| | | | |170| | | | |175| |
|Leu|Glu|Trp|Tyr|Gln|Gln|Arg|Pro|Gly|Gln|Ser|Pro|Arg|Leu|Leu|Ile|
| | | |180| | | | |185| | | | |190| | |
|Tyr|Lys|Val|Ser|Asn|Arg|Phe|Ser|Gly|Val|Pro|Asp|Arg|Phe|Ser|Gly|
| | |195| | | | |200| | | | |205| | | |
|Ser|Gly|Ser|Gly|Thr|Asp|Phe|Thr|Leu|Lys|Ile|Ser|Arg|Val|Glu|Ala|
| |210| | | | |215| | | | |220| | | | |
|Glu|Asp|Val|Gly|Val|Tyr|Tyr|Cys|Phe|Gln|Gly|Ser|His|Val|Pro|Arg|
|225| | | | |230| | | | |235| | | | |240|
|Thr|Phe|Gly|Gly|Gly|Thr|Lys|Val|Glu|Ile|Lys|Asn|Arg|Ile|Arg|Gly|
| | | | |245| | | | |250| | | | |255| |
|Val|Thr|Val|Ser|Ser|Ala|Leu|Ser|Asn|Ser|Ile|Met|Tyr|Phe|Ser|His|
| | | |260| | | | |265| | | | |270| | |
|Phe|Val|Pro|Val|Phe|Leu|Pro|Ala|Lys|Pro|Thr|Thr|Thr|Pro|Ala|Pro|
| | |275| | | | |280| | | | |285| | | |
|Arg|Pro|Pro|Thr|Pro|Ala|Pro|Thr|Ile|Ala|Ser|Gln|Pro|Leu|Ser|Leu|
| |290| | | | |295| | | | |300| | | | |
|Arg|Pro|Glu|Ala|Cys|Arg|Pro|Ala|Ala|Gly|Gly|Ala|Val|His|Thr|Arg|
|305| | | | |310| | | | |315| | | | |320|
|Gly|Leu|Asp|Pro|Phe|Gly|Phe|Trp|Val|Leu|Val|Val|Gly|Gly|Val|
| | | | |325| | | | |330| | | | |335| |
|Leu|Ala|Cys|Tyr|Ser|Leu|Leu|Val|Thr|Val|Ala|Phe|Ile|Ile|Phe|Trp|
| | | |340| | | | |345| | | | |350| | |
|Val|Arg|Ser|Lys|Arg|Ser|Arg|Leu|Leu|His|Ser|Asp|Tyr|Met|Asn|Met|
| | |355| | | | |360| | | | |365| | | |
|Thr|Pro|Arg|Arg|Pro|Gly|Pro|Thr|Arg|Lys|His|Tyr|Gln|Pro|Tyr|Ala|
| |370| | | | |375| | | | |380| | | | |
|Pro|Pro|Arg|Asp|Phe|Ala|Ala|Tyr|Arg|Ser|Leu|Glu|Arg|Val|Arg|Val|
|385| | | | |390| | | | |395| | | | |400|
|Lys|Phe|Ser|Arg|Ser|Ala|Asp|Ala|Pro|Ala|Tyr|Gln|Gln|Gly|Gln|Asn|

Gln Leu Tyr Asn Glu Leu Asn Leu Gly Arg Arg Glu Tyr Asp Val
                420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 129
<211> LENGTH: 510
<212> TYPE: PRT
<213> ORGANISM: Artificial Sequence
<220> FEATURE:
<223> OTHER INFORMATION: Synthetic sequence

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Ile Trp Ile Tyr Pro Gly Asp Gly Ser Thr Gln Tyr Asn Glu Lys
    50                  55                  60

Phe Lys Gly Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
            165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His

```
                260                 265                 270
Phe Val Pro Val Phe Leu Pro Ala Lys Pro Thr Thr Thr Pro Ala Pro
            275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 130
<211> LENGTH: 510
<212> TYPE: PRT
<213> ORGANISM: Artificial Sequence
<220> FEATURE:
<223> OTHER INFORMATION: Synthetic sequence

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
```

```
            115                 120                 125
Gly Gly Gly Ser Gly Gly Gly Ser Thr Ser Asp Ile Val Met Thr
            130                 135                 140
Gln Thr Pro Leu Ser Leu Ser Val Thr Pro Gly Gln Pro Ala Ser Ile
145                 150                 155                 160
Ser Cys Arg Ser Ser Gln Ser Ile Val His Ser Asn Gly Asn Thr Tyr
                165                 170                 175
Leu Glu Trp Tyr Leu Gln Lys Pro Gly Gln Ser Pro Gln Leu Leu Ile
            180                 185                 190
Tyr Lys Val Ser Asn Arg Phe Ser Gly Val Pro Asp Arg Phe Ser Gly
        195                 200                 205
Ser Gly Ser Gly Thr Asp Phe Thr Leu Lys Ile Ser Arg Val Glu Ala
    210                 215                 220
Glu Asp Val Gly Val Tyr Tyr Cys Phe Gln Gly Ser His Val Pro Arg
225                 230                 235                 240
Thr Phe Gly Gly Gly Thr Lys Val Glu Ile Lys Asn Arg Ile Arg Gly
                245                 250                 255
Val Thr Val Ser Ser Ala Leu Ser Asn Ser Ile Met Tyr Phe Ser His
            260                 265                 270
Phe Val Pro Val Phe Leu Pro Ala Lys Pro Thr Thr Thr Pro Ala Pro
        275                 280                 285
Arg Pro Pro Thr Pro Ala Pro Thr Ile Ala Ser Gln Pro Leu Ser Leu
    290                 295                 300
Arg Pro Glu Ala Cys Arg Pro Ala Ala Gly Gly Ala Val His Thr Arg
305                 310                 315                 320
Gly Leu Asp Pro Phe Gly Phe Trp Val Leu Val Val Gly Gly Val
                325                 330                 335
Leu Ala Cys Tyr Ser Leu Leu Val Thr Val Ala Phe Ile Ile Phe Trp
            340                 345                 350
Val Arg Ser Lys Arg Ser Arg Leu Leu His Ser Asp Tyr Met Asn Met
        355                 360                 365
Thr Pro Arg Arg Pro Gly Pro Thr Arg Lys His Tyr Gln Pro Tyr Ala
    370                 375                 380
Pro Pro Arg Asp Phe Ala Ala Tyr Arg Ser Leu Glu Arg Val Arg Val
385                 390                 395                 400
Lys Phe Ser Arg Ser Ala Asp Ala Pro Ala Tyr Gln Gln Gly Gln Asn
                405                 410                 415
Gln Leu Tyr Asn Glu Leu Asn Leu Gly Arg Arg Glu Glu Tyr Asp Val
            420                 425                 430
Leu Asp Lys Arg Arg Gly Arg Asp Pro Glu Met Gly Gly Lys Pro Arg
        435                 440                 445
Arg Lys Asn Pro Gln Glu Gly Leu Tyr Asn Glu Leu Gln Lys Asp Lys
    450                 455                 460
Met Ala Glu Ala Tyr Ser Glu Ile Gly Met Lys Gly Glu Arg Arg Arg
465                 470                 475                 480
Gly Lys Gly His Asp Gly Leu Tyr Gln Gly Leu Ser Thr Ala Thr Lys
                485                 490                 495
Asp Thr Tyr Asp Ala Leu His Met Gln Ala Leu Pro Pro Arg
            500                 505                 510

<210> SEQ ID NO 131
<211> LENGTH: 510
<212> TYPE: PRT
<213> ORGANISM: Artificial Sequence
```

<220> FEATURE:
<223> OTHER INFORMATION: Synthetic sequence

<400> SEQUENCE: 131

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Leu Glu Arg Val Arg Val
385                 390                 395                 400
```

```
Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Gly Tyr Asp Val
            420                 425                 430

Leu Asp Lys Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 132
<211> LENGTH: 510
<212> TYPE: PRT
<213> ORGANISM: Artificial Sequence
<220> FEATURE:
<223> OTHER INFORMATION: Synthetic sequence

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Val Val Met Thr
    130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Ser Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255
```

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
            275                 280                 285

Arg Pro Pro Thr Pro Ala Pro Thr Ile Ala Ser Gln Pro Leu Ser Leu
            290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
            370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 133
<211> LENGTH: 510
<212> TYPE: PRT
<213> ORGANISM: Artificial Sequence
<220> FEATURE:
<223> OTHER INFORMATION: Synthetic sequence

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Met
            35                  40                  45

Gly Trp Ile Tyr Pro Gly Asp Gly Ser Thr Gln Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Ile Val Met Thr
130                 135                 140

Gln Thr Pro Leu Ser Ser Pro Val Thr Leu Gly Gln Pro Ala Ser Ile
145                 150                 155                 160

Ser Phe Arg Ser Gln Ser Ile Val His Ser Asn Gly Asn Thr Tyr
            165                 170                 175

Leu Glu Trp Tyr Gln Gln Arg Pro Gly Gln Pro Pro Arg Leu Leu Ile
        180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His
        260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
            325                 330                 335

Leu Ala Cys Tyr Ser Leu Leu Val Thr Val Ala Phe Ile Ile Phe Trp
        340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
        370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
        420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
        500                 505                 510

<210> SEQ ID NO 134
<211> LENGTH: 510

<212> TYPE: PRT
<213> ORGANISM: Artificial Sequence
<220> FEATURE:
<223> OTHER INFORMATION: Synthetic sequence

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Ser Gly Gly Gly Ser Thr Ser Asp Ile Val Met Thr
    130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380
```

```
Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
            420                 425                 430

Leu Asp Lys Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 135
<211> LENGTH: 510
<212> TYPE: PRT
<213> ORGANISM: Artificial Sequence
<220> FEATURE:
<223> OTHER INFORMATION: Synthetic sequence

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
            85                  90                  95

Ala Arg Glu Gly Thr Tyr Tyr Ala Met Asp Tyr Trp Gly Gln Gly Thr
        100                 105                 110

Thr Val Thr Val Ser Ser Val Asp Ser Ser Gly Gly Gly Ser Gly
    115                 120                 125

Gly Gly Gly Ser Gly Gly Gly Ser Thr Ser Asp Ile Val Met Thr
130                 135                 140

Gln Thr Pro Leu Ser Ser Pro Val Thr Leu Gly Gln Pro Ala Ser Ile
145                 150                 155                 160

Ser Cys Arg Ser Ser Gln Ser Ile Val His Ser Asn Gly Asn Thr Tyr
            165                 170                 175

Leu Glu Trp Tyr Gln Gln Arg Pro Gly Gln Pro Pro Arg Leu Leu Ile
        180                 185                 190

Tyr Lys Val Ser Asn Arg Phe Ser Gly Val Pro Asp Arg Phe Ser Gly
    195                 200                 205

Ser Gly Ala Gly Thr Asp Phe Thr Leu Lys Ile Ser Arg Val Glu Ala
210                 215                 220

Glu Asp Val Gly Val Tyr Tyr Cys Phe Gln Gly Ser His Val Pro Arg
225                 230                 235                 240
```

Thr Phe Gly Gly Gly Thr Lys Val Glu Ile Lys Asn Arg Ile Arg Gly
            245                 250                 255

Val Thr Val Ser Ser Ala Leu Ser Asn Ser Ile Met Tyr Phe Ser His
        260                 265                 270

Phe Val Pro Val Phe Leu Pro Ala Lys Pro Thr Thr Thr Pro Ala Pro
    275                 280                 285

Arg Pro Pro Thr Pro Ala Pro Thr Ile Ala Ser Gln Pro Leu Ser Leu
290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 136
<211> LENGTH: 510
<212> TYPE: PRT
<213> ORGANISM: Artificial Sequence
<220> FEATURE:
<223> OTHER INFORMATION: Synthetic sequence

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Ser Gly
        115                 120                 125

Gly Gly Gly Ser Gly Gly Gly Ser Thr Ser Asp Val Val Met Thr
        130                 135                 140

Gln Ser Pro Leu Ser Leu Pro Val Thr Leu Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Gln Gln Arg Pro Gly Gln Ser Pro Arg Leu Leu Ile
                180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
        210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
        260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                325                 330                 335

Leu Ala Cys Tyr Ser Leu Leu Val Thr Val Ala Phe Ile Ile Phe Trp
        340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

```
<210> SEQ ID NO 137
<211> LENGTH: 510
<212> TYPE: PRT
<213> ORGANISM: Artificial Sequence
<220> FEATURE:
<223> OTHER INFORMATION: Synthetic sequence

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Val Asp Ser Ser Gly Gly Gly Gly Ser Gly
        115                 120                 125

Gly Gly Gly Ser Gly Gly Gly Ser Thr Ser Asp Ile Val Met Thr
    130                 135                 140

Gln Thr Pro Leu Ser Ser Pro Val Thr Leu Gly Gln Pro Ala Ser Ile
145                 150                 155                 160

Ser Phe Arg Ser Ser Gln Ser Ile Val His Ser Asn Gly Asn Thr Tyr
                165                 170                 175

Leu Glu Trp Tyr Gln Gln Arg Pro Gly Gln Pro Pro Arg Leu Leu Ile
            180                 185                 190

Tyr Lys Val Ser Asn Arg Phe Ser Gly Val Pro Asp Arg Phe Ser Gly
        195                 200                 205

Ser Gly Ala Gly Thr Asp Phe Thr Leu Lys Ile Ser Arg Val Glu Ala
    210                 215                 220

Glu Asp Val Gly Val Tyr Tyr Cys Phe Gln Gly Ser His Val Pro Arg
225                 230                 235                 240

Thr Phe Gly Gly Gly Thr Lys Val Glu Ile Lys Asn Arg Ile Arg Gly
                245                 250                 255

Val Thr Val Ser Ser Ala Leu Ser Asn Ser Ile Met Tyr Phe Ser His
            260                 265                 270

Phe Val Pro Val Phe Leu Pro Ala Lys Pro Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
```

```
                370                 375                 380
Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 138
<211> LENGTH: 510
<212> TYPE: PRT
<213> ORGANISM: Artificial Sequence
<220> FEATURE:
<223> OTHER INFORMATION: Synthetic sequence

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Arg Leu Glu Trp Met
            35                  40                  45

Gly Trp Ile Tyr Pro Gly Asp Gly Ser Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
                100                 105                 110

Thr Val Thr Val Ser Ser Val Asp Ser Ser Gly Gly Gly Ser Gly
            115                 120                 125

Gly Gly Gly Ser Gly Gly Gly Ser Thr Ser Asp Ile Val Met Thr
        130                 135                 140

Gln Thr Pro Leu Ser Leu Ser Val Thr Pro Gly Gln Pro Ala Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Gln Leu Leu Ile
                180                 185                 190

Tyr Lys Val Ser Asn Arg Phe Ser Gly Val Pro Asp Arg Phe Ser Gly
                195                 200                 205

Ser Gly Ser Gly Thr Asp Phe Thr Leu Lys Ile Ser Arg Val Glu Ala
            210                 215                 220

Glu Asp Val Gly Val Tyr Tyr Cys Phe Gln Gly Ser His Val Pro Arg
```

```
                225                 230                 235                 240
Thr Phe Gly Gly Gly Thr Lys Val Glu Ile Lys Asn Arg Ile Arg Gly
                    245                 250                 255

Val Thr Val Ser Ser Ala Leu Ser Asn Ser Ile Met Tyr Phe Ser His
                260                 265                 270

Phe Val Pro Val Phe Leu Pro Ala Lys Pro Thr Thr Thr Pro Ala Pro
            275                 280                 285

Arg Pro Pro Thr Pro Ala Pro Thr Ile Ala Ser Gln Pro Leu Ser Leu
        290                 295                 300

Arg Pro Glu Ala Cys Arg Pro Ala Ala Gly Gly Ala Val His Thr Arg
305                 310                 315                 320

Gly Leu Asp Pro Phe Gly Phe Trp Val Leu Val Val Gly Gly Val
                    325                 330                 335

Leu Ala Cys Tyr Ser Leu Leu Val Thr Val Ala Phe Ile Ile Phe Trp
                340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
        370                 375                 380

Pro Pro Arg Asp Phe Ala Ala Tyr Arg Ser Leu Glu Arg Val Arg Val
385                 390                 395                 400

Lys Phe Ser Arg Ser Ala Asp Ala Pro Ala Tyr Gln Gln Gly Gln Asn
                    405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                    485                 490                 495

Asp Thr Tyr Asp Ala Leu His Met Gln Ala Leu Pro Pro Arg
                500                 505                 510

<210> SEQ ID NO 139
<211> LENGTH: 822
<212> TYPE: DNA
<213> ORGANISM: Artificial Sequence
<220> FEATURE:
<223> OTHER INFORMATION: Synthetic sequence

<400> SEQUENCE: 139
atggatttcc aagttcaaat cttcagtttc ttgcttatca gtgcttctgt tattatgtca      60
cgagcaagtc aagttcaact cgtacagtct ggagccgagg tgaaaaaacc gggagcgtcc     120
gtgaaagtga gttgcaaggc gagtggatac accttcactt cataccatat acaatgggtt     180
cggcaggcgc ctggtcaacg gctggaatgg atgggctgga tttatcccgg agatggttcc     240
acgcagtaca tgagaaatt caaagggaga gtgacaatca cccgagatac cagtgcctct     300
acggcatata tggaactgag tagtctgcgg tctgaagata cggcggtgta ttattgtgcg     360
agagaaggga cgtactacgc catgattat tggggacaag gaacaacagt cacagtctcc     420
agcgttgatt cctcaggcgg gggcggaagt gggggcggcg gatctggcgg cggcgggtct     480
```

| | |
|---|---|
| acgtctgacg tggtcatgac ccaatctcca ttgtctttgc cagttactct gggacagcct | 540 |
| gcaagtatca gttgccgatc ctcccaatct atcgtccatt caaacgggaa cacttatttg | 600 |
| gaatggtttc aacagagacc tgggcaaagt ccgcgccgac tgatatataa ggtcagtaac | 660 |
| cgcttttcag gcgtccccga tcgattcagt ggatctgggt cagggactga cttcactctg | 720 |
| aaaatatcaa gagtcgaagc tgaagatgtc ggagtatatt actgtttcca ggggtctcac | 780 |
| gtccctcgga cgtttggagg cggaactaag gttgagataa aa | 822 |

<210> SEQ ID NO 140
<211> LENGTH: 822
<212> TYPE: DNA
<213> ORGANISM: Artificial Sequence
<220> FEATURE:
<223> OTHER INFORMATION: Synthetic sequence

<400> SEQUENCE: 140

| | |
|---|---|
| atggattttc aggttcaaat ctttagcttt ctcttgattt ccgcctccgt aataatgagt | 60 |
| cgggccagtc aggtacagct cgttcaatct ggggctgaag taaaaaagcc tggagcgtct | 120 |
| gtaaaggtat cttgcaaagc gagcggctac acattcacaa gttatcacat ccaatgggtg | 180 |
| agacaggccc caggacaacg cttggagtgg atggggtgga tttaccctgg cgacggcagc | 240 |
| acacagtaca atgagaaatt taaaggccgg gtgactatca ctcgggacac ctccgccagc | 300 |
| acggcttata tggagcttag cagtttgaga tccgaagata cagcggtata ttactgcgcg | 360 |
| agagaaggaa cgtactacgc tatggactat tggggtcagg gcacaaccgt tacagtctcc | 420 |
| tctgtggaca gctccggagg tggggttca ggaggggtg gaagcggtgg tggtggcagt | 480 |
| acaagcgata tagtaatgac ccaaaccccg ctctctctga gcgtcacgcc aggacaacca | 540 |
| gcatcaatct cttgccgcag tagtcaatcc atcgttcact ctaatggaaa cataccttt | 600 |
| gagtggtatc ttcagaaacc aggtcagagc cctcagctcc tcatctataa agtctctaac | 660 |
| cggttctcag gtgttccga ccggttcagt ggttccggct caggaacaga cttcaccttg | 720 |
| aagatcagtc gagtagaagc cgaagacgtg ggtgtatatt attgctttca gggttcccac | 780 |
| gttccgcgca ccttcggcgg cgggaccaaa gttgagatca aa | 822 |

<210> SEQ ID NO 141
<211> LENGTH: 822
<212> TYPE: DNA
<213> ORGANISM: Artificial Sequence
<220> FEATURE:
<223> OTHER INFORMATION: Synthetic sequence

<400> SEQUENCE: 141

| | |
|---|---|
| atggactttc aagtccaaat cttctcattc ctcctgatct ctgcgtcagt aatcatgtcc | 60 |
| agagcgtcac aagtgcaact cgttcaatcc ggagctgagg taaagaagcc cggcgccagc | 120 |
| gtgaaagtct cctgcaaagc gagcggctac acgttcacct catatcacat tcaatgggta | 180 |
| agacaagcac ctgggcaacg actcgagtgg atggggtgga tctaccctgg ggacgggagc | 240 |
| acgcagtata atgagaaatt caaaggcagg gttacaatta cagccgatac cagtgcatct | 300 |
| acggcttata tgctcctctc ctcactccgg tctgaggaca cagcggttta ttattgcgca | 360 |
| cgggagggaa cgtactacgc gatggactat tgggggcaag gcaccacagt tacagtgagc | 420 |
| tcagttgact catcaggagg cggaggatca gggggaggtg gtagtgggg cggtgggagc | 480 |
| acatcagatg ttgtcatgac tcagagccca ctttctttgc cggtgacgct ggggcagccc | 540 |
| gcttcaatct cttgccgctc atcacagtct atcgttcata gcaatggtaa cacttacttg | 600 |

```
gaatggttcc aacaaagacc gggtcaaagt ccacggcgct tgatatataa agtatcaaat    660
agattttcag gggtgcctga tcggttcagc ggttctggat ctggcaccga cttcacgctt    720
aaaataagta gggtagaagc cgaagacgtg ggagtgtatt attgtttcca ggggtcacac    780
gtccctcgca cgttcggcgg aggcactaaa gtggagatca aa                       822
```

<210> SEQ ID NO 142
<211> LENGTH: 822
<212> TYPE: DNA
<213> ORGANISM: Artificial Sequence
<220> FEATURE:
<223> OTHER INFORMATION: Synthetic sequence

<400> SEQUENCE: 142

```
atggactttc aagtccaaat cttcagcttt ctccttatat ctgcgtctgt cattatgagt     60
agagcaagtc aagtccagct cgtacaaagt ggagctgagg tgaaaaagcc gggcgcgagt    120
gtgaaagtct catgcaaggc gagtggatac acctttacct cttaccacat tcaatgggtg    180
cggcaggcgc ctgggcagcg cttggaatgg atgggctgga tatatcctgg cgacggaagt    240
acccagtaca cgaaaaaatt caaaggtagg gttaccatca ctgctgatac ctccgcgtcc    300
actgcttata tgcttcttag ctccttgcga agcgaggata cagccgtgta ttattgtgcc    360
agagagggga cttattatgc catggactat tggggtcagg gtacaacggt cactgtctca    420
tctgttgaca gtagcggggg aggggggtct ggaggagggg gttccggggg gggaggttcc    480
acgagcgata tagttatgac gcaaacgccc ttgagcctca gtgttacacc cggtcaacct    540
gcctctatta gctgtcgctc ctcccaatca attgtgcata gcaatggaaa tacctacctt    600
gaatggtatc tccaaaagcc cgggcagagt cctcaacttc tcatctacaa agtatccaat    660
cgattcagtg gcgttcctga caggttcagc ggaagtgggt cagggaccga ttttaccctc    720
aaaattagtc gcgtcgaagc tgaggatgtt ggggtgtatt actgcttcca agggtcacac    780
gtaccacgca cattcggggg aggcacgaag gttgaaatta ag                       822
```

<210> SEQ ID NO 143
<211> LENGTH: 822
<212> TYPE: DNA
<213> ORGANISM: Artificial Sequence
<220> FEATURE:
<223> OTHER INFORMATION: Synthetic sequence

<400> SEQUENCE: 143

```
atggatttcc aagtccaaat attcagtttc cttttgataa gtgcttcagt tatcatgtcc     60
cgagcaagcc aggtacagct tgtgcaaagc ggggcggaag ttaagaaacc gggagcctca    120
gttaaagtat cttgcaaagc cagcggttat acattcactt cataccacat acagtgggtg    180
cgccaagcac cggggcagag actggaatgg atgggatgga tttatcccgg tgatggtagt    240
acgcaataca tgaaaaaatt caaggaaggg gtgactatca cgcagacac aagcgcgtcc    300 acggcctata tggaactgag cagtctgaga tccgaggaca ccgctgtgta ttattgcgcc    360
cgagagggga cctactacgc catggattat tggggtcaag gaccactgt gacagtctct    420 tctgtcgatt ccagcggcgg aggagggagt ggaggggtg gtccgggggg gggagggtct    480
acgagcgaca ttgtcatgac acagacgccg cttagctccc cagttacact cggacagccc    540
gcaagtatta gttgcagaag tagccagtct atcgtacatt caaatggaaa cacctatttg    600
gaatggtatc aacaacggcc tggacagccg cccaggctgc tcatatacaa agtctccaac    660
```

| | |
|---|---|
| cgcttcagcg gagtacccga ccgcttttcc ggctccggag caggaactga ctttaccttg | 720 |
| aaaattagta gggtcgaagc agaggatgtc ggggtatatt attgtttcca aggtagtcat | 780 |
| gtcccacgga cgtttggtgg tgggacgaag gttgagatca aa | 822 |

<210> SEQ ID NO 144
<211> LENGTH: 822
<212> TYPE: DNA
<213> ORGANISM: Artificial Sequence
<220> FEATURE:
<223> OTHER INFORMATION: Synthetic sequence

<400> SEQUENCE: 144

| | |
|---|---|
| atggacttcc aggtgcagat attttccttt cttctcatat ctgcatctgt aataatgtca | 60 |
| agggccagcc aggtccagct cgttcaaagc ggagccgagg taaaaaaacc aggcgcttcc | 120 |
| gtcaaggtat catgcaaagc gtccggctat accttcacaa gttaccatat ccaatgggtt | 180 |
| cgacaggcac ccggacaaag acttgaatgg atggggttgga tataccccgg agacggctcc | 240 |
| actcagtata acgaaaagtt taaggggaga gtcacgatca ctaggacac atcagcttct | 300 |
| acggcgtata tggaactcag ttctttgcga tccgaggata ctgccgtata ttactgcgcc | 360 |
| agagaaggca cgtactacgc aatggattac tgggggcaag gacaactgt taccgtctca | 420 |
| agcgtcgatt catcaggagg cggagggtcc ggaggtgggg gatctggcgg tggggggttct | 480 |
| acgtccgatg ttgtgatgac acagtcccca ctctctcttc cagtgacgct gggacagccc | 540 |
| gcgagcatct cctgtcgcag ctctcagtcc atagtacaca gtaatggtaa cacctatctt | 600 |
| gagtggtatc agcaacgacc cggtcagtct cccaggttgc ttatttataa ggttagtaac | 660 |
| cgctttttcag gtgttccaga cagatttagc gggagtggtt ccggtacgga tttcacattg | 720 |
| aaaatcagcc gcgtcgaagc cgaggacgtg ggtgtttact actgcttcca gggatctcac | 780 |
| gtaccgagga ccttcggcgg aggaacgaaa gtagaaatta ag | 822 |

<210> SEQ ID NO 145
<211> LENGTH: 822
<212> TYPE: DNA
<213> ORGANISM: Artificial Sequence
<220> FEATURE:
<223> OTHER INFORMATION: Synthetic sequence

<400> SEQUENCE: 145

| | |
|---|---|
| atggattttc aagtacaaat cttttccttc ctgcttattt ccgcaagcgt tattatgagt | 60 |
| agagccagcc aagtacaact ggtacagtcc ggcgcggagg tgaagaagcc cggagcaagt | 120 |
| gtgaaggtat cttgcaaggc gtcaggctat acctttactt cataccatat acagtgggtg | 180 |
| cgacaggctc ccggccagcg actcgaatgg atgggctgga tttatcccgg agatggatct | 240 |
| acgcagtata tgagaaaatt caagggtcgg gtcacgatta cacgagacac gagtgcttcc | 300 |
| acagcttata tggaactttc tagcctgagg tctgaggata ctgccgttta ctattgtgca | 360 |
| cgagaaggga catactatgc gatggattac tgggacagg gcaccactgt cacagtttcc | 420 |
| agcgtggact caagtggagg cggtggatct ggtggtggcg ggtccggggg ggaggcagc | 480 |
| accagtgaca ttgtaatgac tcaaacacct ctcagtagcc cagtcactct cggtcagccg | 540 |
| gcgagtatct cttttaggtc ctcacaatct atagtgcact ctaacggcaa tacttatctt | 600 |
| gaatggtatc aacaaagacc ggggcagcca cctcgcctt tcatctacaa agtaagcaat | 660 |
| cgcttctccg gtgtccccga tcgcttctcc ggttcaggag caggaactga cttcacattg | 720 |
| aagatttcca gagtggaggc cgaagacgta ggggtatatt attgctttca agggtcccat | 780 |

```
gtgcccagaa cctttgggggg aggaacgaaa gttgagatta aa                822
```

<210> SEQ ID NO 146
<211> LENGTH: 822
<212> TYPE: DNA
<213> ORGANISM: Artificial Sequence
<220> FEATURE:
<223> OTHER INFORMATION: Synthetic sequence

<400> SEQUENCE: 146

```
atggatttcc aagtgcagat tttctctttt ctcctcataa gcgcctccgt aattatgtct    60
agagctagtc aagtccaatt ggtgcaatcc ggtgccgagg ttaaaaagcc cggcgcaagt   120
gtaaaagtct cctgtaaggc cagtggctac actttcacca gctaccatat acagtgggtg   180
cggcaggcgc ctggtcaggg tctggagtgg atgggtattt ggatttatcc cggagatgga   240
agtactcaat acaatgagaa attcaagggt gtcactatga caagggatac gagcacttct   300
accgtatata tggagttgtc atctttgcga tcagaggata ccgctgtata ttattgcgca   360
cgggaaggta catattatgc catggactac tggggccaag aaccaccgt gacggtaagc    420
tctgtcgatt ctagcggtgg cggggggctct ggcggtgggg gtagcggggg tggcggatct  480
acatcagata ttgtaatgac acagacccct ctttcacttt ccgtaacgcc aggacagccg   540
gcatcaataa gttgccgatc aagccagtct atcgtacact ccaatggtaa cacatacttg   600
gaatggtatc ttcaaaagcc cggccagagc ccgcagcttt tgatatataa agtgtccaac   660
agattcagtg gggtgccgga ccgctttagt ggatctggtt caggaacgga cttcacattg   720
aaaattagta gagttgaagc ggaagacgtg ggagtctact actgtttcca gggttcacat   780
gtgcctcgga cctttgggggg aggcaccaag gttgagataa aa                     822
```

<210> SEQ ID NO 147
<211> LENGTH: 822
<212> TYPE: DNA
<213> ORGANISM: Artificial Sequence
<220> FEATURE:
<223> OTHER INFORMATION: Synthetic sequence

<400> SEQUENCE: 147

```
atggacttcc aagtccaaat cttttctttt tgttgataa gcgcatcagt tattatgtct    60
cgcgccagtc aagtacaact ggtgcagtcc ggagctgaag tgaaaaaacc aggagcaagc   120
gtgaaagtaa gttgtaaggc aagtggttac actttcacaa gctaccatat tcaatgggtc   180
cgacaggctc ctggacaggg cttggagtgg atgggcatat ggatttaccc tggtgacggg   240
tccacccagt ataatgaaaa gttcaaggga gtcacgatga ccagggacac ctctacatct   300
accgtgtata tggagctctc tagtttgcga tccgaagaca ctgccgttta ttactgtgca   360
agagaaggaa cttattacgc gatggactac tggggtcagg gacaacagt caccgttagc    420
tccgtcgatt ccagcggggg aggtggctca ggcggggggtg gttctggggg ggcgggagc   480
acttcagata ttgtaatgac ccaaacccca ctgagtagtc cagtcacgct tggtcaaccg   540
gcaagcattt cttgcaggag ctctcagagt attgtccact ctaacgggaa tacatatttg   600
gagtggtatc agcaaagacc gggccaacca ccacgcctct tgatttataa ggtgagcaat   660
aggttttcag gcgtgccaga taggttctca ggctccggag cgggaaccga cttcaccctc   720
aagataagtc gggtggaagc cgaagacgta ggagtttact actgctttca aggatctcat   780
gttccacgaa cgtttggagg aggaaccaag gtggaaataa aa                      822
```

<210> SEQ ID NO 148
<211> LENGTH: 822
<212> TYPE: DNA
<213> ORGANISM: Artificial Sequence
<220> FEATURE:
<223> OTHER INFORMATION: Synthetic sequence

<400> SEQUENCE: 148

```
atggactttc aggtccaaat tttttccttc ttgctcatat ccgcgagtgt catcatgtca      60
agagcaagtc aagttcaact cgttcaatca ggagctgagg tgaaaaaacc aggggcgtct     120
gtcaaagtaa gctgcaaagc atcagggtat acgttcacga gttatcatat ccagtgggtt     180
aggcaggcgc cagggcaggg attggaatgg atgggtatct ggatttaccc gggtgacggc     240
agcactcaat acaatgagaa attcaaaggc gtaacaatga caagggacac gagcacaagc     300
acagtgtaca tggagcttag ctctttgagg tcagaggata ccgctgttta ctattgtgct     360
cgggagggta cttactatgc aatgactac tgggggcaag gcacgaccgt tacagtgagt      420
agcgtagatt cctccggggg tggcggttca ggcggcggag gctcaggcgg aggagggtca     480
acatccgatg tcgtaatgac tcagtcccct ctgtcattgc cggtgacttt gggacagcca     540
gcgtctatat cttgtaggtc ctctcaatca atagtgcatt ccaacggtaa cacctatctg     600
gaatggtatc agcaaaggcc aggacaaagt ccacgcctgc ttatatataa ggtgtctaat     660
cgattcagtg gggttcccga taggttttcc ggctctggta gcgggactga tttcacgttg     720
aaaatatcac gcgtggaagc ggaagatgtt ggggtctatt actgctttca gggtagtcat     780
gtccctcgaa cttttggcgg tggtacaaag gtagaaatca aa                       822
```

<210> SEQ ID NO 149
<211> LENGTH: 822
<212> TYPE: DNA
<213> ORGANISM: Artificial Sequence
<220> FEATURE:
<223> OTHER INFORMATION: Synthetic sequence

<400> SEQUENCE: 149

```
atggatttc aggtacagat attctcattt ctccttatct cagctagtgt cataatgtcc      60
agggcgagtc aagtacaact tgtccagtca ggcgcagagg tcaagaagcc gggcgcaagc    120
gttaaggttt cctgcaaagc atccggctat acattcacgt cctatcacat ccaatgggtc    180
aggcaagcac ccggtcaagg acttgagtgg atgggcatct ggatttaccc tggagatggc    240
agtactcagt acaacgaaaa attcaaaggt gtaaccatga cccgcgacac atctacttcc    300
acagtttata tggaactcag cagtttgcgg agcgaagata ccgctgttta ctactgtgcc    360
cgagagggaa cttactacgc catggactat tggggtcaag aacgacagt aacagttagt      420
tctgtagatt ccagtggcgg cggtgggagc ggggtgggg gatctggcgg aggcggaagt    480
acaagtgaca tcgttatgac tcagacaccc cttagtagtc ccgttacgtt gggccaaccc    540
gcgagcattt cctttcgatc ctctcagtct atagttcact caaatgggaa tacttatttg    600
gagtggtatc aacagcgccc cggacaacca ccaaggctcc tgatatacaa ggtgtccaat    660
cgattctctg gggtgcctga tagatttagc ggaagtggag ccggtacaga ttttaccctg    720
aaaatatcac gggtagaagc cgaagatgtc ggcgtctact actgtttcca gggttcccat    780
gtaccgcgaa cgttcggggg cggaacaaaa gttgagatca ag                       822
```

<210> SEQ ID NO 150
<211> LENGTH: 822

```
<212> TYPE: DNA
<213> ORGANISM: Artificial Sequence
<220> FEATURE:
<223> OTHER INFORMATION: Synthetic sequence

<400> SEQUENCE: 150
atggatttcc aggttcagat atttagtttc ctcttgattt ctgccagtgt catcatgagc      60
agggcttccc aagttcagtt ggtgcaaagt ggcgctgaag tcaaaaaacc tggggcttcc     120
gttaaagtat cttgcaaggc gtccggctac actttcacat cctaccacat tcaatgggtc     180
cggcaagcgc ccgtcaggg gctcgaatgg atggggtgga tatacccagg agatggatct     240
actcagtaca acgagaaatt taaaggacgg gtgacgatga cgcgcgacac ttcaataagc     300
actgcataca tggaactgtc ccggcttagg tcagatgaca ccgcggtcta ctattgtgcg     360
agagagggta cttactatgc tatggactac tgggggcaag gcacgacggt tacagtttcc     420
tcagtcgata gttcaggcgg aggcggctcc ggggcggtg gtagtggagg gggtggatct      480
acttccgaca ttgtcatgac ccagaccccg ttgagccttt cagtgacgcc cggtcaaccc     540
gccagcataa gttgtcgatc aagccagtct attgtacact ccaatggaaa cacatatttg     600
gagtggtatc tccaaaaacc cggccaaagc cctcaactgc tcatctacaa ggtctcaaac     660
aggtttagcg gggtcccgga tcgcttctca gggtcaggat ctggtacgga ctttacactg     720
aaaatttccc gagtcgaagc ggaagacgtg ggtgtatatt actgcttcca ggggagtcat     780
gttccaagaa cctttggggg aggtacaaag gtcgaaataa aa                        822

<210> SEQ ID NO 151
<211> LENGTH: 822
<212> TYPE: DNA
<213> ORGANISM: Artificial Sequence
<220> FEATURE:
<223> OTHER INFORMATION: Synthetic sequence

<400> SEQUENCE: 151
atggattttc aggtccaaat tttttccttc ttgcttatca gcgcaagtgt aatcatgtcc      60
cgcgcgtccc aagtacaact tgtgcaatct ggcgcggagg tgaaaaaacc tggagcttcc     120
gtcaaggttt cttgtaaggc ctctggctac accttcacgt cctaccacat tcagtgggtt     180
cgacaggcgc cgggccaagg actggagtgg atgggatgga tatatccagg agatggttct     240
actcagtata tgagaaatt caagggtcgc gtaacaatga cgagggatac atcaatctcc     300
accgcgtaca tggaactttc aagactccgg tcagatgaca cggcggttta ctactgtgct     360
cgggagggca cttactatgc tatggactac tgggggcaag gacaacggt aacggtatct     420
agtgtggatt ctagtggcgg cggcggttca ggaggaggtg gttcaggcgg ggggggtagt     480
acaagtgata ttgtgatgac ccaaacaccc ctttctagcc ctgttactct gggtcaaccc     540
gcgtccataa gttgtcgaag tagtcaatcc atcgtgcata gcaacggcaa cacttacctt     600
gaatggtatc aacaacgacc cggacagccc ccgcgactgc ttatctataa agtatcaaac     660
aggttcagtg gcgtgccaga tcgattctcc ggctctgggg caggcacaga tttcacgttg     720
aaaatttctc gggtcgaggc cgaggacgtg ggcgtttatt actgtttcca ggggagtcac     780
gtccccagga cgttcggagg aggaactaaa gtcgaaataa ag                        822

<210> SEQ ID NO 152
<211> LENGTH: 822
<212> TYPE: DNA
<213> ORGANISM: Artificial Sequence
<220> FEATURE:
```

<223> OTHER INFORMATION: Synthetic sequence

<400> SEQUENCE: 152

| | | | | | |
|---|---|---|---|---|---|
| atggacttcc | aggtccaaat | attcagcttc | ctcctcattt | ccgccagtgt | aataatgtcc | 60 |
| agagcctcac | aagtacagtt | ggttcagagc | ggggctgagg | ttaagaaacc | aggcgcgagc | 120 |
| gtcaaggtat | cctgcaaggc | gagtggttat | actttcacta | gttatcacat | tcagtgggtc | 180 |
| cgacaggccc | ccggtcaagg | cctggagtgg | atggggtgga | tatatccggg | agatggttct | 240 |
| acccaatata | atgagaagtt | taaggggaga | gtcacaatga | caagggacac | cagtattagc | 300 |
| accgcgtata | tggagctttc | ccgcctgcga | tcagatgaca | cggccgtgta | ctactgtgct | 360 |
| agggagggaa | cctattatgc | gatggattac | tggggacagg | gtactacagt | cacggtctct | 420 |
| agcgtggaca | gttccggggg | cggtggaagc | ggtggtggcg | gttcaggtgg | aggaggctct | 480 |
| acgagtgatg | ttgtgatgac | tcagtccccg | ctttcacttc | ccgtcaccct | ggggcaaccc | 540 |
| gcaagcatct | catgccgatc | tcccagtct | atagtacata | gtaatggcaa | cacatatctt | 600 |
| gaatggtatc | agcagaggcc | gggtcagtct | ccccgactcc | ttatatataa | agtgagcaac | 660 |
| agattctccg | gagtaccgga | tagatttttcc | ggctctggga | gcggcaccga | ctttacactg | 720 |
| aaaatttcac | gggttgaagc | tgaagatgtt | ggggtatact | attgttttcca | gggttctcac | 780 |
| gtcccgagga | cattcggggg | aggaacgaaa | gtcgaaataa | ag | | 822 |

<210> SEQ ID NO 153
<211> LENGTH: 822
<212> TYPE: DNA
<213> ORGANISM: Artificial Sequence
<220> FEATURE:
<223> OTHER INFORMATION: Synthetic sequence

<400> SEQUENCE: 153

| | | | | | |
|---|---|---|---|---|---|
| atggattttc | aggtacaaat | cttcagcttc | tgctcatct | ccgcgagcgt | aatcatgtct | 60 |
| agggcgtccc | aggtgcagtt | ggtgcaatca | ggtgcagagg | tgaagaagcc | tggtgcatcc | 120 |
| gttaaagtaa | gttgtaaggc | aagcggatat | acttttacat | cctatcatat | tcaatgggtc | 180 |
| agacaagcac | ctggacaggg | tcttgagtgg | atgggctgga | tctatccagg | cgatggctca | 240 |
| actcaatata | acgagaagtt | caaggggagg | gttactatga | ccagggatac | gtctatttcc | 300 |
| actgcgtaca | tggaactctc | caggttgaga | agtgatgata | ccgcggttta | ctactgcgct | 360 |
| agagaaggaa | cgtactacgc | tatggattac | tgggggcagg | gtacaactgt | caccgtctca | 420 |
| agtgtggatt | cttctggggg | tggggatca | ggaggggag | gctccggtgg | gggcgggtca | 480 |
| accagcgaca | ttgtcatgac | tcaaaccccc | ctgagcagcc | ctgtcaccct | gggtcagcct | 540 |
| gcctcaatat | cctttagaag | ctcccaaagc | atcgtccatt | caaatggtaa | tacctatctg | 600 |
| gagtggtatc | agcaaaggcc | tggtcaaccc | ccgcgccttc | tcatttacaa | ggtgtcaaac | 660 |
| aggttctccg | gcgtaccgga | taggttttcc | ggaagcggtg | ctggaaccga | ctttactctc | 720 |
| aaaatctcta | gggtggaagc | tgaggacgtc | ggtgtatact | attgttttca | aggctcccat | 780 |
| gttcccagga | catttggtgg | gggaacgaag | gtagaaatca | ag | | 822 |

<210> SEQ ID NO 154
<211> LENGTH: 822
<212> TYPE: DNA
<213> ORGANISM: Artificial Sequence
<220> FEATURE:
<223> OTHER INFORMATION: Synthetic sequence

<400> SEQUENCE: 154

```
atggactttc aggttcagat tttctctttc ttgttgatct ccgctagtgt cataatgtca      60
cgggcaagtc aggtacaact cgttcagagt ggtgccgaag tgaagaaacc gggtgcctcc     120
gtaaaggtgt catgtaaagc tagtggctat acattcacaa gttatcatat ccaatgggta     180
cgacaagcac cgggacagcg actggaatgg atgggatgga tctatcctgg ggacggatct     240
acacagtaca atgagaaatt taagggacgg gtcacgataa ccagggacac atctgcttcc     300
acggcttaca tggagctttc ctccctgcgg agcgaggaca tggctgttta ctattgcgct     360
cgcgaaggga catactacgc aatggattat tggggccaag gcactaccgt gacggtctct     420
tctgtcgata gttccggagg aggtggttca ggggaggcg gttcaggtgg gggtggatct     480
acctcagata ttgtcatgac acagacacct ttgtccttga gtgtgacacc gggtcaaccg     540
gcgagtataa gctgtcgcag ctcacaatct attgtgcata gcaacgggaa tacatatctc     600
gaatggtatc tccaaaagcc gggccaatcc ccccaacttc tcatttacaa agtttctaat     660
cgattttcag gtgtaccaga tcggttttcc gggtctggct caggtactga cttcaccttg     720
aaaatatcaa gggttgaagc tgaggatgta ggtgtgtact attgcttcca ggggtctcac     780
gttcctcgga ctttggggg gggcacaaaa gtagagatta aa                         822

<210> SEQ ID NO 155
<211> LENGTH: 822
<212> TYPE: DNA
<213> ORGANISM: Artificial Sequence
<220> FEATURE:
<223> OTHER INFORMATION: Synthetic sequence

<400> SEQUENCE: 155
atggatttcc aggtgcaaat cttctcattt cttttgataa gtgcgtcagt gataatgtct      60
cgggccagtc aagtacagct tgtccaaagt ggcgctgaag tcaagaagcc gggagcctca     120
gttaaggtta gctgcaaggc ctcagggtat acttttacct cctatcatat acagtgggta     180
cgacaagcac cgggacagcg actggagtgg atggttgga tatatccggg agatggttca     240
acccagtata atgagaagtt caaggggcga gttacgataa cccgcgatac gagtgcatca     300
acagcgtaca tggagttgag ttccctccgc agcgaggaca tggcggtata ctattgtgcc     360
agggagggga cttattatgc catggactac tggggggcagg gcacaaccgt aacagtctct     420
tctgtagaca gttcaggagg gggcggaagt ggaggtggcg gatctggtgg aggtggatct     480
acttccgaca tcgttatgac ccaaacacca cttcatctc ccgttactct cgggcaacct     540
gctagtattt cctgtagatc ctcacaatct atagtacata gcaatggcaa tacctacctg     600
gagtggtatc aacaacgccc aggccaacca cctcgcctgc ttatctataa agtaagcaat     660
agattcagtg gtgtaccgga taggttctct ggttccggag caggaactga ctttacactc     720
aaaatcagta gggtggaggc ggaagacgtg ggagtatatt attgctttca aggttcacat     780
gtacctcgaa catttggcgg aggaactaag gttgagatta aa                        822

<210> SEQ ID NO 156
<211> LENGTH: 822
<212> TYPE: DNA
<213> ORGANISM: Artificial Sequence
<220> FEATURE:
<223> OTHER INFORMATION: Synthetic sequence

<400> SEQUENCE: 156
atggatttcc aagtccagat attcagtttt cttttgataa gcgcttctgt aatcatgtct      60
```

| | |
|---|---|
| cgggcgtccc aagtacaact ggtgcaatca ggggcagaag tgaaaaaacc aggtgcatcc | 120 |
| gttaaggtga gttgcaaggc ttccggctat acctttacat catatcatat tcaatgggtc | 180 |
| aggcaagcac ctggtcagcg attggaatgg atgggttgga tatatcctgg tgatgggtct | 240 |
| acacaatata acgaaaaatt caaggggcga gtgaccatca caagagatac atcagcgtca | 300 |
| acagcgtata tggaactgtc atcccttaga tcagaggaca tggcggtcta ttactgtgcc | 360 |
| agagaaggca cttattatgc aatgattat tggggacaag gaaccactgt cactgtttcc | 420 |
| agcgtagact cctccggtgg tggtggaagt ggcggcggtg ggtcaggagg gggtgggtca | 480 |
| acttctgatg tagtgatgac acagagccct ctgagcttgc ctgtgacctt gggtcagccg | 540 |
| gcctcaataa gttgtcgatc tagtcagtca atcgtccata gtaatgggaa cacatacctt | 600 |
| gaatggtatc agcaaagacc tggacaatct ccacgactcc ttatatacaa agttagcaac | 660 |
| cgatttagcg gagtgccaga ccgcttttct ggttccgggt ctggcacaga ttttacccct | 720 |
| aagatctccc gcgtggaggc ggaagacgtt ggtgtttact attgcttcca ggggtcacac | 780 |
| gttccacgca cctttggagg aggtacgaag gtcgagatta ag | 822 |

<210> SEQ ID NO 157
<211> LENGTH: 822
<212> TYPE: DNA
<213> ORGANISM: Artificial Sequence
<220> FEATURE:
<223> OTHER INFORMATION: Synthetic sequence

<400> SEQUENCE: 157

| | |
|---|---|
| atggattttc aagtacagat cttctctttc ttgcttattt cagcgagcgt aatcatgagt | 60 |
| agggcatctc aagttcaact cgttcagtca ggtgctgagg taaaaaaacc aggggcttcc | 120 |
| gttaaagtta gctgtaaggc atctgggtac acatttacta gctaccatat ccagtgggtg | 180 |
| cgacaagccc cggggcagcg cttggaatgg atgggctgga tttacccagg tgacggctcc | 240 |
| acgcaatata tgagaaaatt taagggtaga gttactatta ccagggacac aagtgcttca | 300 |
| actgcctata tggaactgag cagccttcgg agtgaagata tggccgtata ttactgcgca | 360 |
| agggagggga cttactatgc aatggactac tggggtcagg gaacgactgt gaccgtgtcc | 420 |
| tcagttgact ccagcggtgg tggcggctct ggaggtgggg gttccggcgg aggcggaagc | 480 |
| acatctgata tagtgatgac gcaaacgcct ctttcttccc cggtaactct gggacagcca | 540 |
| gcgtcaattt catttaggtc ctcccagtca atcgtacata gtaatggaaa tacttacctg | 600 |
| gaatggtatc aacaacgacc agggcaaccg ccccgattgt tgatctataa agtgagcaat | 660 |
| cgcttttctg gcgtgcccga tcggttctca gggtctggag ctgggactga cttcacattg | 720 |
| aaaattccca gggttgaggc cgaggatgtg ggggtttatt actgcttcca aggctcccac | 780 |
| gtccccgca ccttcggagg gggaaccaaa gtcgaaataa ag | 822 |

<210> SEQ ID NO 158
<211> LENGTH: 822
<212> TYPE: DNA
<213> ORGANISM: Artificial Sequence
<220> FEATURE:
<223> OTHER INFORMATION: Synthetic sequence

<400> SEQUENCE: 158

| | |
|---|---|
| atggattttc aagttcagat attctcattt ttgcttatat cagcctccgt aattatgtca | 60 |
| cgggcaagtc aagttcagtt ggtgcagtcc ggagcagaag ttaagaagcc cggtgcttct | 120 |
| gtgaaagtct cctgcaaagc gtctgggtac accttcacga gctaccatat acagtgggtc | 180 |

```
cggcaagcgc ctgggcagag gctggagtgg atgggctgga tttacccagg agatgggagt      240
acaaagtata gtcagaagtt tcaagggcga gtgacgataa ccagagatac gagtgcaagt      300
actgcataca tggaactgag ctccttgagg tccgaggata cagcggtgta ctattgcgct      360
cgggaaggga catattatgc tatggactat tggggacaag gacaacggt aacggtgagt       420 tccgtcgatt cctcaggtgg cggaggcagt gggggcgggg gttccggcgg tggcgggtcc      480
acgagtgata tagttatgac acagacccc ctcagccttt ctgtgacccc aggacaaccc       540
gctagtatct cttgccgcag ttctcagtcc atagtacaca gtaacggaaa tacctatctt      600
gagtggtatc ttcaaaagcc cggccagagc cctcaactct tgatatataa agtgtcaaat      660 cgatttcag gtgtgcctga tcgattctca gggtctggtt cagggacaga tttcacgctt       720
aagataagca gagtagaggc tgaagacgtg ggagtctact attgttttca ggggtcacac      780
gttccccgca cttttggtgg gggaaccaag gtggaaatca aa                         822

<210> SEQ ID NO 159
<211> LENGTH: 192
<212> TYPE: DNA
<213> ORGANISM: Artificial Sequence
<220> FEATURE:
<223> OTHER INFORMATION: Synthetic sequence

<400> SEQUENCE: 159
tcttcagcgc tgagcaactc catcatgtac ttcagccact tcgtgccggt cttcctgcca       60
gcgaagccca ccacgacgcc agcgccgcga ccaccaacac cggcgcccac catcgcgtcg      120
cagcccctgt ccctgcgccc agaggcgtgc cggccagcgg cgggggcgc agtgcacacg       180 aggggctgg ac                                                           192

<210> SEQ ID NO 160
<211> LENGTH: 81
<212> TYPE: DNA
<213> ORGANISM: Artificial Sequence
<220> FEATURE:
<223> OTHER INFORMATION: Synthetic sequence

<400> SEQUENCE: 160
ttttgggtgc tggtggtggt tggtggagtc ctggcttgct atagcttgct agtaacagtg       60
gcctttatta ttttctgggt g                                                81

<210> SEQ ID NO 161
<211> LENGTH: 123
<212> TYPE: DNA
<213> ORGANISM: Artificial Sequence
<220> FEATURE:
<223> OTHER INFORMATION: Synthetic sequence

<400> SEQUENCE: 161
aggagtaaga ggagcaggct cctgcacagt gactacatga acatgactcc ccgccgcccc       60
gggcccaccc gcaagcatta ccagccctat gccccaccac gcgacttcgc agcctatcgc      120
tcc                                                                    123

<210> SEQ ID NO 162
<211> LENGTH: 336
<212> TYPE: DNA
<213> ORGANISM: Artificial Sequence
<220> FEATURE:
<223> OTHER INFORMATION: Synthetic sequence
```

<400> SEQUENCE: 162

```
agagtgaagt tcagcaggag cgcagacgcc cccgcgtacc agcagggcca gaaccagctc    60
tataacgagc tcaatctagg acgaagagag gagtacgatg tttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                              336
```

<210> SEQ ID NO 163
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 163

```
atggatttcc aagttcaaat cttcagtttc ttgcttatca gtgcttctgt tattatgtca    60
cgagcaagtc aagttcaact cgtacagtct ggagccgagg tgaaaaaacc gggagcgtcc   120
gtgaaagtga gttgcaaggc gagtggatac accttcactt cataccatat acaatgggtt   180
cggcaggcgc ctggtcaacg gctggaatgg atgggctgga tttatcccgg agatggttcc   240
acgcagtaca tgagaaaatt caaagggaga gtgacaatca cccgagatac cagtgcctct   300
acggcatata tggaactgag tagtctgcgg tctgaagata cggcggtgta ttattgtgcg   360
agagaaggga cgtactacgc catggattat tggggacaag aacaacagt cacagtctcc    420
agcgttgatt cctcaggcgg gggcggaagt gggggcggcg atctggcgg cggcgggtct   480
acgtctgacg tggtcatgac ccaatctcca ttgtctttgc cagttactct gggacagcct   540
gcaagtatca gttgccgatc ctcccaatct atcgtccatt caaacgggaa cacttatttg   600
gaatggtttc aacagagacc tgggcaaagt ccgcgccgac tgatatataa ggtcagtaac   660
cgcttttcag gcgtccccga tcgattcagt ggatctgggt cagggactga cttcactctg   720
aaaatatcaa gagtcgaagc tgaagatgtc ggagtatatt actgttttcca ggggtctcac   780
gtccctcgga cgtttggagg cggaactaag gttgagataa aaaccggat ccgtggggtc    840
accgtctctt cagcgctgag caactccatc atgtacttca gccacttcgt gccggtcttc   900
ctgccagcga agcccaccac gacgccagcg ccgcgaccac caacaccggc gcccaccatc   960
gcgtcgcagc ccctgtccct gcgcccagag gcgtgccggc cagcggcggg gggcgcagtg  1020
cacacgaggg ggctggaccc ctttgggttt tgggtgctgg tggtggttgg tggagtcctg  1080
gcttgctata gcttgctagt aacagtggcc tttattattt tctgggtgag gagtaagagg  1140
agcaggctcc tgcacagtga ctacatgaac atgactcccc gccgccccgg gcccacccgc  1200
aagcattacc agcccatgc cccaccacgc gacttcgcag cctatcgctc cctcgagaga  1260
gtgagagtga agttcagcag gagcgcagac gcccccgcgt accagcaggg ccagaaccag  1320
ctctataacg agctcaatct aggacgaaga gaggagtacg atgtttttgga caagagacgt  1380
ggccgggacc ctgagatggg gggaaagccg agaaggaaga accctcagga aggcctgtac  1440
aatgaactgc agaaagataa gatggcggag gcctacagtg agattgggat gaaaggcgag  1500
cgccggaggg gcaaggggca cgatggcctt taccagggtc tcagtacagc caccaaggac  1560
acctacgacg cccttcacat gcaggccctg cccctcgc                          1599
```

<210> SEQ ID NO 164
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 164

| | | | | | | |
|---|---|---|---|---|---|---|
| atggattttc | aggttcaaat | ctttagcttt | ctcttgattt | ccgcctccgt | aataatgagt | 60 |
| cgggccagtc | aggtacagct | cgttcaatct | ggggctgaag | taaaaaagcc | tggagcgtct | 120 |
| gtaaaggtat | cttgcaaagc | gagcggctac | acattcacaa | gttatcacat | ccaatgggtg | 180 |
| agacaggccc | caggacaacg | cttggagtgg | atggggtgga | tttaccctgg | cgacggcagc | 240 |
| acacagtaca | atgagaaatt | taaaggccgg | gtgactatca | ctcgggacac | ctccgccagc | 300 |
| acggcttata | tggagcttag | cagtttgaga | tccgaagata | cagcggtata | ttactgcgcg | 360 |
| agagaaggaa | cgtactacgc | tatggactat | tggggtcagg | gcacaaccgt | tacagtctcc | 420 |
| tctgtggaca | gctccggagg | tggggttca | ggaggggtg | gaagcggtgg | tggtggcagt | 480 |
| acaagcgata | tagtaatgac | ccaaacccccg | ctctctctga | gcgtcacgcc | aggacaacca | 540 |
| gcatcaatct | cttgccgcag | tagtcaatcc | atcgttcact | ctaatggaaa | cataccttt | 600 |
| gagtggtatc | ttcagaaacc | aggtcagagc | cctcagctcc | tcatctataa | agtctctaac | 660 |
| cggttctcag | tgttccgga | ccggttcagt | ggttccggct | caggaacaga | cttcaccttg | 720 |
| aagatcagtc | gagtagaagc | cgaagacgtg | ggtgtatatt | attgctttca | gggttcccac | 780 |
| gttccgcgca | ccttcggcgg | cgggaccaaa | gttgagatca | aaaaccggat | ccgtggggtc | 840 |
| accgtctctt | cagcgctgag | caactccatc | atgtacttca | gccacttcgt | gccggtcttc | 900 |
| ctgccagcga | agcccaccac | gacgccagcg | ccgcgaccac | caacaccggc | gccaccatc | 960 |
| gcgtcgcagc | ccctgtccct | cgcccagag | gcgtgccggc | cagcggcggg | gggcgcagtg | 1020 |
| cacacgaggg | ggctggaccc | ctttgggttt | tgggtgctgg | tggtggttgg | tggagtcctg | 1080 |
| gcttgctata | gcttgctagt | aacagtggcc | tttattattt | tctgggtgag | gagtaagagg | 1140 |
| agcaggctcc | tgcacagtga | ctacatgaac | atgactcccc | gccgcccggg | gcccacccgc | 1200 |
| aagcattacc | agccctatgc | cccaccacgc | gacttcgcag | cctatcgctc | cctcgagaga | 1260 |
| gtgagagtga | agttcagcag | gagcgcagac | gcccccgcgt | accagcaggg | ccagaaccag | 1320 |
| ctctataacg | agctcaatct | aggacgaaga | gaggagtacg | atgttttgga | caagagacgt | 1380 |
| ggccgggacc | ctgagatggg | gggaaagccg | agaaggaaga | accctcagga | aggcctgtac | 1440 |
| aatgaactgc | agaaagataa | gatggcggag | gcctacagtg | agattggat | gaaaggcgag | 1500 |
| cgccggaggg | gcaaggggca | cgatggcctt | taccagggtc | tcagtacagc | caccaaggac | 1560 |
| acctacgacg | cccttcacat | gcaggccctg | ccccctcgc | | | 1599 |

<210> SEQ ID NO 165
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 165

| | | | | | | |
|---|---|---|---|---|---|---|
| atggactttc | aagtccaaat | cttctcattc | ctcctgatct | ctgcgtcagt | aatcatgtcc | 60 |
| agagcgtcac | aagtgcaact | cgttcaatcc | ggagctgagg | taaagaagcc | cggcgccagc | 120 |
| gtgaaagtct | cctgcaaagc | gagcggctac | acgttcacct | catatcacat | tcaatgggta | 180 |

```
agacaagcac ctgggcaacg actcgagtgg atggggtgga tctaccctgg ggacgggagc      240
acgcagtata atgagaaatt caaaggcagg gttacaatta cagccgatac cagtgcatct      300
acggcttata tgctcctctc ctcactccgg tctgaggaca cagcggttta ttattgcgca      360
cgggagggaa cgtactacgc gatggactat tgggggcaag gcaccacagt tacagtgagc      420
tcagttgact catcaggagg cggaggatca ggggagggtg gtagtggggg cggtgggagc      480
acatcagatg ttgtcatgac tcagagccca cttctttgc cggtgacgct ggggcagccc       540
gcttcaatct cttgccgctc atcacagtct atcgttcata gcaatggtaa cacttacttg      600
gaatggttcc aacaaagacc gggtcaaagt ccacggcgct tgatatataa agtatcaaat      660
agattttcag gggtgcctga tcggttcagc ggttctggat ctggcaccga cttcacgctt      720
aaaataagta gggtagaagc cgaagacgtg gagtgtatt attgtttcca ggggtcacac       780
gtccctcgca cgttcggcgg aggcactaaa gtggagatca aaaaccggat ccgtggggtc      840
accgtctctt cagcgctgag caactccatc atgtacttca gccacttcgt gccggtcttc      900
ctgccagcga agcccaccac gacgccagcg ccgcgaccac caacaccggc gcccaccatc      960
gcgtcgcagc ccctgtccct gcgcccagag gcgtgccggc cagcggcggg gggcgcagtg     1020
cacacgaggg ggctggaccc ctttgggttt tgggtgctgg tggtggttgg tggagtcctg     1080
gcttgctata gcttgctagt aacagtggcc tttattattt tctgggtgag gagtaagagg     1140
agcaggctcc tgcacagtga ctacatgaac atgactcccc gccgcccggg cccacccgc      1200 aagcattacc agccctatgc cccaccacgc gacttcgcag cctatcgctc cctcgagaga     1260
gtgagagtga agttcagcag gagcgcagac gccccccgcgt accagcaggg ccagaaccag    1320
ctctataacg agctcaatct aggacgaaga gaggagtacg atgttttgga caagagacgt     1380
ggccgggacc ctgagatggg gggaaagccg agaaggaaga accctcagga aggcctgtac     1440
aatgaactgc agaaagataa gatggcggag gcctacagtg agattgggat gaaaggcgag     1500
cgccggaggg gcaaggggca cgatggcctt taccagggtc tcagtacagc caccaaggac     1560
acctacgacg cccttcacat gcaggccctg ccccctcgc                            1599

<210> SEQ ID NO 166
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 166
atggactttc aagtccaaat cttcagcttt ctccttatat ctgcgtctgt cattatgagt       60
agagcaagtc aagtccagct cgtacaaagt ggagctgagg tgaaaaagcc gggcgcgagt     120
gtgaaagtct catgcaaggc gagtggatac acctttacct cttaccacat tcaatgggtg     180
cggcaggcgc ctgggcagcg cttggaatgg atgggctgga tatatcctgg cgacggaagt     240
acccagtaca acgaaaaatt caaaggtagg gttaccatca ctgctgatac ctccgcgtcc     300
actgcttata tgcttcttag ctccttgcga agcgaggata cagccgtgta ttattgtgcc     360
agagagggga cttattatgc catggactat tggggtcagg gtacaacggt cactgtctca     420
tctgttgaca gtagcggggg agggggtct ggaggagggg gttccggggg gggaggttcc      480
acgagcgata tagttatgac gcaaacgccc ttgagcctca gtgttacacc cggtcaacct     540
gcctctatta gctgtcgctc ctcccaatca attgtgcata gcaatggaaa tacctacctt     600
gaatggtatc tccaaaagcc cgggcagagt cctcaacttc tcatctacaa agtatccaat     660
```

```
cgattcagtg gcgttcctga caggttcagc ggaagtgggt cagggaccga ttttaccctc    720
aaaattagtc gcgtcgaagc tgaggatgtt ggggtgtatt actgcttcca agggtcacac    780
gtaccacgca cattcggggg aggcacgaag gttgaaatta agaaccggat ccgtggggtc    840
accgtctctt cagcgctgag caactccatc atgtacttca gccacttcgt gccggtcttc    900
ctgccagcga agcccaccac gacgccagcg ccgcgaccac caacaccggc gcccaccatc    960
gcgtcgcagc ccctgtccct gcgcccagag gcgtgccggc cagcggcggg gggcgcagtg   1020
cacacgaggg ggctggaccc ctttgggttt tgggtgctgg tggtggttgg tggagtcctg   1080
gcttgctata gcttgctagt aacagtggcc tttattattt tctgggtgag gagtaagagg   1140
agcaggctcc tgcacagtga ctacatgaac atgactcccc gccgcccgg gcccacccgc    1200 aagcattacc agcccctatgc cccaccacgc gacttcgcag cctatcgctc cctcgagaga   1260
gtgagagtga agttcagcag gagcgcagac gcccccgcgt accagcaggg ccagaaccag   1320
ctctataacg agctcaatct aggacgaaga gaggagtacg atgttttgga caagagacgt   1380
ggccgggacc ctgagatggg gggaaagccg agaaggaaga accctcagga aggcctgtac   1440
aatgaactgc agaaagataa gatggcggag gcctacagtg agattgggat gaaaggcgag   1500
cgccggaggg gcaaggggca cgatggcctt taccagggtc tcagtacagc caccaaggac   1560
acctacgacg cccttcacat gcaggccctg ccccctcgc                           1599

<210> SEQ ID NO 167
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 167
atggatttcc aagtccaaat attcagtttc cttttgataa gtgcttcagt tatcatgtcc     60
cgagcaagcc aggtacagct tgtgcaaagc ggggcggaag ttaagaaacc gggagcctca    120
gttaaagtat cttgcaaagc cagcggttat acattcactt cataccacat acagtgggtg    180
cgccaagcac cggggcagag actggaatgg atgggatgga tttatcccgg tgatggtagt    240
acgcaataca tgaaaaaatt caaaggaagg gtgactatca cgcgagacac aagcgcgtcc    300
acggcctata tggaactgag cagtctgaga tccgaggaca ccgctgtgta ttattgcgcc    360
cgagagggga cctactacgc catggattat tggggtcaag ggaccactgt gacagtctct    420
tctgtcgatt ccagcggcgg aggagggagt ggaggggtg gtccgggggg ggagggtct    480 acgagcgaca ttgtcatgac acagacgccg cttagctccc cagttacact cggacagccc    540
gcaagtatta gttgcagaag tagccagtct atcgtacatt caaatggaaa cacctatttg    600
gaatggtatc aacaacggcc tggacagccg cccaggctgc tcatatacaa agtctccaac    660
cgcttcagcg gagtacccga ccgcttttcc ggctccggag caggaactga ctttaccttg    720
aaaattagta gggtcgaagc agaggatgtc ggggtatatt attgtttcca aggtagtcat    780
gtcccacgga cgtttggtgg tgggacgaag gttgagatca aaaaccggat ccgtggggtc    840
accgtctctt cagcgctgag caactccatc atgtacttca gccacttcgt gccggtcttc    900
ctgccagcga agcccaccac gacgccagcg ccgcgaccac caacaccggc gcccaccatc    960
gcgtcgcagc ccctgtccct gcgcccagag gcgtgccggc cagcggcggg gggcgcagtg   1020
cacacgaggg ggctggaccc ctttgggttt tgggtgctgg tggtggttgg tggagtcctg   1080
```

| | |
|---|---:|
| gcttgctata gcttgctagt aacagtggcc tttattattt tctgggtgag gagtaagagg | 1140 |
| agcaggctcc tgcacagtga ctacatgaac atgactcccc gccgcccggg cccacccgc | 1200 |
| aagcattacc agccctatgc cccaccacgc gacttcgcag cctatcgctc cctcgagaga | 1260 |
| gtgagagtga agttcagcag gagcgcagac gccccgcgt accagcaggg ccagaaccag | 1320 |
| ctctataacg agctcaatct aggacgaaga gaggagtacg atgttttgga caagagacgt | 1380 |
| ggccgggacc ctgagatggg gggaaagccg agaaggaaga accctcagga aggcctgtac | 1440 |
| aatgaactgc agaaagataa gatggcggag gcctacagtg agattgggat gaaaggcgag | 1500 |
| cgccggaggg gcaaggggca cgatggcctt taccagggtc tcagtacagc caccaaggac | 1560 |
| acctacgacg cccttcacat gcaggccctg cccctcgc | 1599 |

<210> SEQ ID NO 168
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 168

| | |
|---|---:|
| atggacttcc aggtgcagat attttccttt cttctcatat ctgcatctgt aataatgtca | 60 |
| agggccagcc aggtccagct cgttcaaagc ggagccgagg taaaaaaacc aggcgcttcc | 120 |
| gtcaaggtat catgcaaagc gtccggctat accttcacaa gttaccatat ccaatgggtt | 180 |
| cgacaggcac ccggacaaag acttgaatgg atgggttgga tatacccggg agacggctcc | 240 |
| actcagtata cgaaaagtt taaggggaga gtcacgatca ctaggacac atcagcttct | 300 |
| acggcgtata tggaactcag ttctttgcga tccgaggata ctgccgtata ttactgcgcc | 360 |
| agagaaggca cgtactacgc aatggattac tgggggcaag gacaactgt taccgtctca | 420 |
| agcgtcgatt catcaggagg cggagggtcc ggaggtgggg atctggcgg tggggttct | 480 |
| acgtccgatg ttgtgatgac acagtcccca ctctctcttc cagtgacgct gggacagccc | 540 |
| gcgagcatct cctgtcgcag ctctcagtcc atagtacaca gtaatggtaa cacctatctt | 600 |
| gagtggtatc agcaacgacc cggtcagtct cccaggttgc ttatttataa ggttagtaac | 660 |
| cgcttttcag gtgttccaga cagatttagc gggagtggtt ccggtacgga tttcacattg | 720 |
| aaaatcagcc gcgtcgaagc cgaggacgtg ggtgttact actgcttcca gggatctcac | 780 |
| gtaccgagga ccttcggcgg aggaacgaaa gtagaaatta gaaccggat ccgtggggtc | 840 |
| accgtctctt cagcgctgag caactccatc atgtacttca gccacttcgt gccggtcttc | 900 |
| ctgccagcga agcccaccac gacgccagcg ccgcgaccac caacaccggc gcccaccatc | 960 |
| gcgtcgcagc ccctgtccct gcgcccagag gcgtgccggc cagcggcggg gggcgcagtg | 1020 |
| cacacgaggg ggctggaccc ctttgggttt tgggtgctgg tggtggttgg tggagtcctg | 1080 |
| gcttgctata gcttgctagt aacagtggcc tttattattt tctgggtgag gagtaagagg | 1140 |
| agcaggctcc tgcacagtga ctacatgaac atgactcccc gccgcccggg cccacccgc | 1200 |
| aagcattacc agccctatgc cccaccacgc gacttcgcag cctatcgctc cctcgagaga | 1260 |
| gtgagagtga agttcagcag gagcgcagac gccccgcgt accagcaggg ccagaaccag | 1320 |
| ctctataacg agctcaatct aggacgaaga gaggagtacg atgttttgga caagagacgt | 1380 |
| ggccgggacc ctgagatggg gggaaagccg agaaggaaga accctcagga aggcctgtac | 1440 |
| aatgaactgc agaaagataa gatggcggag gcctacagtg agattgggat gaaaggcgag | 1500 |
| cgccggaggg gcaaggggca cgatggcctt taccagggtc tcagtacagc caccaaggac | 1560 |

```
acctacgacg cccttcacat gcaggccctg cccccctcgc            1599
```

<210> SEQ ID NO 169
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 169

```
atggattttc aagtacaaat cttttccttc ctgcttattt ccgcaagcgt tattatgagt    60
agagccagcc aagtacaact ggtacagtcc ggcgcgagg tgaagaagcc cggagcaagt   120
gtgaaggtat cttgcaaggc gtcaggctat acctttactt cataccatat acagtgggtg   180
cgacaggctc ccggccagcg actcgaatgg atgggctgga tttatcccgg agatggatct   240
acgcagtata atgagaaatt caagggtcgg gtcacgatta cacgagacac gagtgcttcc   300
acagcttata tggaactttc tagcctgagg tctgaggata ctgccgttta ctattgtgca   360
cgagaaggga catactatgc gatggattac tggggacagg gcaccactgt cacagtttcc   420
agcgtggact caagtggagg cggtggatct ggtggtggcg ggtccggggg gggaggcagc   480
accagtgaca ttgtaatgac tcaaacacct ctcagtagcc cagtcactct cggtcagccg   540
gcgagtatct cttttaggtc ctcacaatct atagtgcact ctaacggcaa tacttatctt   600
gaatggtatc aacaaagacc ggggcagcca cctcgccttc tcatctacaa agtaagcaat   660
cgcttctccg gtgtccccga tcgcttctcc ggttcaggag caggaactga cttcacattg   720
aagatttcca gagtggaggc cgaagacgta ggggtatatt attgctttca agggtcccat   780
gtgcccagaa cctttggggg aggaacgaaa gttgagatta aaaaccggat ccgtggggtc   840
accgtctctt cagcgctgag caactccatc atgtacttca gccacttcgt gccggtcttc   900
ctgccagcga agcccaccac gacgccagcg ccgcgaccac caacaccggc gccaccatc   960
gcgtcgcagc ccctgtccct gcgcccagag gcgtgccggc cagcggcggg gggcgcagtg  1020
cacacgaggg ggctggaccc ctttgggttt tgggtgctgg tggtggttgg tggagtcctg  1080
gcttgctata gcttgctagt aacagtggcc tttattattt tctgggtgag gagtaagagg  1140
agcaggctcc tgcacagtga ctacatgaac atgactcccc gccgcccgg gcccacccgc  1200
aagcattacc agccctatgc cccaccacgc gacttcgcag cctatcgctc cctcgagaga  1260
gtgagagtga agttcagcag gagcgcagac gcccccgcgt accagcaggg ccagaaccag  1320
ctctataacg agctcaatct aggacgaaga gaggagtacg atgttttgga caagagacgt  1380
ggccgggacc ctgagatggg ggaaagccg agaaggaaga accctcagga aggcctgtac  1440
aatgaactgc agaaagataa gatggcgag gcctacagtg agattgggat gaaggcgag  1500
cgccggaggg gcaaggggca cgatggcctt taccagggtc tcagtacagc caccaaggac  1560
acctacgacg cccttcacat gcaggccctg cccccctcgc                        1599
```

<210> SEQ ID NO 170
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 170

```
atggatttcc aagtgcagat tttctctttt ctcctcataa gcgcctccgt aattatgtct    60
```

| | | |
|---|---|---|
| agagctagtc aagtccaatt ggtgcaatcc ggtgccgagg ttaaaaagcc cggcgcaagt | 120 |
| gtaaaagtct cctgtaaggc cagtggctac actttcacca gctaccatat acagtgggtg | 180 |
| cggcaggcgc ctggtcaggg tctggagtgg atgggtattt ggatttatcc cggagatgga | 240 |
| agtactcaat acaatgagaa attcaagggt gtcactatga caagggatac gagcacttct | 300 |
| accgtatata tggagttgtc atctttgcga tcagaggata ccgctgtata ttattgcgca | 360 |
| cgggaaggta catattatgc catggactac tggggccaag gaaccaccgt gacggtaagc | 420 |
| tctgtcgatt ctagcggtgg cggggggctct ggcggtgggg gtagcggggg tggcggatct | 480 |
| acatcagata ttgtaatgac acagacccct ctttcacttt ccgtaacgcc aggacagccg | 540 |
| gcatcaataa gttgccgatc aagccagtct atcgtacact ccaatggtaa cacatacttg | 600 |
| gaatggtatc ttcaaaagcc cggccagagc ccgcagcttt tgatatataa agtgtccaac | 660 |
| agattcagtg gggtgccgga ccgctttagt ggatctggtt caggaacgga cttcacattg | 720 |
| aaaattagta gagttgaagc ggaagacgtg ggagtctact actgttttcca gggttcacat | 780 |
| gtgcctcgga ccttttgggggg aggcaccaag gttgagataa aaaccggat ccgtgggtc | 840 |
| accgtctctt cagcgctgag caactccatc atgtacttca gccacttcgt gccggtcttc | 900 |
| ctgccagcga agcccaccac gacgccacg ccgcgaccac caacaccggc gcccaccatc | 960 |
| gcgtcgcagc ccctgtccct gcgcccagag gcgtgccggc cagcggcggg gggcgcagtg | 1020 |
| cacacgaggg ggctggaccc cttttgggttt tgggtgctgg tggtggttgg tggagtcctg | 1080 |
| gcttgctata gcttgctagt aacagtggcc tttattattt tctgggtgag gagtaagagg | 1140 |
| agcaggctcc tgcacagtga ctacatgaac atgactcccc gccgcccggg cccaccccgc | 1200 |
| aagcattacc agccctatgc cccaccacgc gacttcgcag cctatcgctc cctcgagaga | 1260 |
| gtgagagtga agttcagcag gagcgcagac gccccccgcgt accagcaggg ccagaaccag | 1320 |
| ctctataacg agctcaatct aggacgaaga gaggagtacg atgttttgga caagagacgt | 1380 |
| ggccggggacc ctgagatggg gggaaagccg agaaggaaga accctcagga aggcctgtac | 1440 |
| aatgaactgc agaaagataa gatggcggag gcctacagtg agattgggat gaaaggcgag | 1500 |
| cgccggaggg gcaaggggca cgatggcctt taccagggtc tcagtacagc caccaaggac | 1560 |
| acctacgacg cccttcacat gcaggccctg ccccctcgc | 1599 |

<210> SEQ ID NO 171
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 171

| | | |
|---|---|---|
| atggacttcc aagtccaaat ctttttcttttt ttgttgataa gcgcatcagt tattatgtct | 60 |
| cgcgccagtc aagtacaact ggtgcagtcc ggagctgaag tgaaaaaacc aggagcaagc | 120 |
| gtgaaagtaa gttgtaaggc aagtggttac actttcacaa gctaccatat tcaatgggtc | 180 |
| cgacaggctc ctggacaggg cttggagtgg atgggcatat ggatttaccc tggtgacggg | 240 |
| tccacccagt ataatgaaaa gttcaaggga gtcacgatga ccagggacac ctctacatct | 300 |
| accgtgtata tggagctctc tagtttgcga tccgaagaca ctgccgttta ttactgtgca | 360 |
| agagaaggaa cttattacgc gatggactac tggggtcagg gacaacagt caccgttagc | 420 |
| tccgtcgatt ccagcggggg aggtggctca ggcgggggtg gttctggggg gggcgggagc | 480 |
| acttcagata ttgtaatgac ccaaaccccca ctgagtagtc cagtcacgct tggtcaaccg | 540 |

```
gcaagcattt cttgcaggag ctctcagagt attgtccact ctaacgggaa tacatatttg      600
gagtggtatc agcaaagacc gggccaacca ccacgcctct tgatttataa ggtgagcaat      660
aggttttcag gcgtgccaga taggttctca ggctccggag cgggaaccga cttcaccctc      720
aagataagtc gggtggaagc cgaagacgta ggagtttact actgctttca aggatctcat      780
gttccacgaa cgtttggagg aggaaccaag gtggaaataa aaaaccggat ccgtggggtc      840
accgtctctt cagcgctgag caactccatc atgtacttca gccacttcgt gccggtcttc      900
ctgccagcga agcccaccac gacgccagcg ccgcgaccac caacaccggc gcccaccatc      960
gcgtcgcagc cctgtccct gcgcccagag gcgtgccggc cagcggcggg gggcgcagtg     1020
cacacgaggg ggctggaccc cttttgggttt tgggtgctgg tggtggttgg tggagtcctg     1080
gcttgctata gcttgctagt aacagtggcc tttattattt tctgggtgag gagtaagagg     1140
agcaggctcc tgcacagtga ctacatgaac atgactcccc gccgcccgg gcccacccgc      1200 aagcattacc agcccatgc cccaccacgc gacttcgcag cctatcgctc cctcgagaga     1260
gtgagagtga agttcagcag gagcgcagac gccccgcgt accagcaggg ccagaaccag     1320
ctctataacg agctcaatct aggacgaaga gaggagtacg atgttttgga caagagacgt     1380
ggccgggacc ctgagatggg gggaaagccg agaaggaaga accctcagga aggcctgtac     1440
aatgaactgc agaaagataa gatggcggag gcctacagtg agattgggat gaaaggcgag     1500
cgccggaggg gcaaggggca cgatggcctt taccagggtc tcagtacagc caccaaggac     1560
acctacgacg cccttcacat gcaggccctg ccccctcgc                            1599
```

<210> SEQ ID NO 172
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 172

```
atggactttc aggtccaaat ttttccttc ttgctcatat ccgcgagtgt catcatgtca       60
agagcaagtc aagttcaact cgttcaatca ggagctgagg tgaaaaaacc aggggcgtct     120
gtcaaagtaa gctgcaaagc atcagggtat acgttcacga gttatcatat ccagtgggtt     180
aggcaggcgc cagggcaggg attggaatgg atgggtatct ggatttaccc gggtgacggc     240
agcactcaat acaatgagaa attcaaaggc gtaacaatga caaggggacac gagcacaagc     300 acagtgtaca tggagcttag ctcttttgagg tcagaggata ccgctgttta ctattgtgct     360
cgggagggta cttactatgc aatggactac tgggggcaag gcacgaccgt tacagtgagt     420
agcgtagatt cctccggggg tggcggttca ggcggcggag gctcaggcgg aggagggtca     480
acatccgatg tcgtaatgac tcagtccccct ctgtcattgc cggtgacttt gggacagcca     540
gcgtctatat cttgtaggtc ctctcaatca atagtgcatt ccaacggtaa cacctatctg     600
gaatggtatc agcaaaggcc aggacaaagt ccacgcctgc ttatatataa ggtgtctaat     660
cgattcagtg gggttcccga taggttttcc ggctctggta gcgggactga tttcacgttg     720
aaaatatcac gcgtggaagc ggaagatgtt ggggtctatt actgctttca gggtagtcat     780
gtccctcgaa cttttggcgg tggtacaaag gtagaaatca aaaaccggat ccgtggggtc     840
accgtctctt cagcgctgag caactccatc atgtacttca gccacttcgt gccggtcttc     900
ctgccagcga agcccaccac gacgccagcg ccgcgaccac caacaccggc gcccaccatc     960
```

```
gcgtcgcagc ccctgtccct gcgcccagag gcgtgccggc cagcggcggg gggcgcagtg    1020
cacacgaggg ggctggaccc ctttgggttt tgggtgctgg tggtggttgg tggagtcctg    1080
gcttgctata gcttgctagt aacagtggcc tttattattt tctgggtgag gagtaagagg    1140
agcaggctcc tgcacagtga ctacatgaac atgactcccc gccgcccgg gcccacccgc     1200 aagcattacc agccctatgc cccaccacgc gacttcgcag cctatcgctc cctcgagaga    1260
gtgagagtga agttcagcag gagcgcagac gcccccgcgt accagcaggg ccagaaccag    1320
ctctataacg agctcaatct aggacgaaga gaggagtacg atgttttgga caagagacgt    1380
ggccgggacc ctgagatggg gggaaagccg agaaggaaga accctcagga aggcctgtac    1440
aatgaactgc agaaagataa gatggcggag gcctacagtg agattgggat gaaaggcgag    1500
cgccggaggg gcaaggggca cgatggcctt taccagggtc tcagtacagc caccaaggac    1560
acctacgacg cccttcacat gcaggccctg ccccctcgc                           1599
```

<210> SEQ ID NO 173
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 173

```
atggattttc aggtacagat attctcattt ctccttatct cagctagtgt cataatgtcc      60
agggcgagtc aagtacaact tgtccagtca ggcgcagagg tcaagaagcc gggcgcaagc     120
gttaaggttt cctgcaaagc atccggctat acattcacgt cctatcacat ccaatgggtc     180
aggcaagcac ccggtcaagg acttgagtgg atgggcatct ggatttaccc tggagatggc     240
agtactcagt acaacgaaaa attcaaaggt gtaaccatga cccgcgacac atctacttcc     300
acagtttata tggaactcag cagtttgcgg agcgaagata ccgctgttta ctactgtgcc     360
cgagagggaa cttactacgc catggactat tggggtcaag gaacgacagt aacagttagt     420
tctgtagatt ccagtggcgg cggtgggagc ggggtgggg  gatctggcgg aggcggaagt     480
acaagtgaca tcgttatgac tcagacaccc cttagtagtc cgttacgttt gggccaaccc     540
gcgagcattt cctttcgatc ctctcagtct atagttcact caaatgggaa tacttatttg     600
gagtggtatc aacagcgccc cggacaacca ccaaggctcc tgatatacaa ggtgtccaat     660
cgattctctg gggtgcctga tagatttagc ggaagtggag ccggtacaga ttttaccctg     720
aaaatatcac gggtagaagc cgaagatgtc ggcgtctact actgtttcca gggttcccat     780
gtaccgcgaa cgttcggggg cggaacaaaa gttgagatca agaaccggat ccgtgggtc     840 accgtctctt cagcgctgag caactccatc atgtacttca gccacttcgt gccggtcttc     900
ctgccagcga agcccaccac gacgccagcg ccgcgaccac caacaccggc gcccaccatc     960
gcgtcgcagc ccctgtccct gcgcccagag gcgtgccggc cagcggcggg gggcgcagtg    1020
cacacgaggg ggctggaccc ctttgggttt tgggtgctgg tggtggttgg tggagtcctg    1080
gcttgctata gcttgctagt aacagtggcc tttattattt tctgggtgag gagtaagagg    1140
agcaggctcc tgcacagtga ctacatgaac atgactcccc gccgcccgg gcccacccgc     1200 aagcattacc agccctatgc cccaccacgc gacttcgcag cctatcgctc cctcgagaga    1260
gtgagagtga agttcagcag gagcgcagac gcccccgcgt accagcaggg ccagaaccag    1320
ctctataacg agctcaatct aggacgaaga gaggagtacg atgttttgga caagagacgt    1380
ggccgggacc ctgagatggg gggaaagccg agaaggaaga accctcagga aggcctgtac    1440
```

```
aatgaactgc agaaagataa gatggcggag gcctacagtg agattgggat gaaaggcgag      1500
cgccggaggg gcaaggggca cgatggcctt taccagggtc tcagtacagc caccaaggac      1560
acctacgacg cccttcacat gcaggccctg cccctcgc                              1599
```

<210> SEQ ID NO 174
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 174

```
atggatttcc aggttcagat atttagtttc tcttgatttt ctgccagtgt catcatgagc        60
agggcttccc aagttcagtt ggtgcaaagt ggcgctgaag tcaaaaaacc tggggcttcc       120
gttaaagtat cttgcaaggc gtccggctac actttcacat cctaccacat tcaatgggtc       180
cggcaagcgc ccggtcaggg gctcgaatgg atggggtgga tacccagg agatggatct        240 actcagtaca acgagaaatt taaaggacgg gtgacgatga cgcgcgacac ttcaataagc       300
actgcataca tggaactgtc ccggcttagg tcagatgaca ccgcggtcta ctattgtgcg       360
agagagggta cttactatgc tatggactac tgggggcaag gcacgacggt tacagtttcc       420
tcagtcgata gttcaggcgg aggcggctcc ggggcggtg gtagtggagg gggtggatct       480
acttccgaca ttgtcatgac ccagacccg ttgagccttt cagtgacgcc cggtcaaccc        540
gccagcataa gttgtcgatc aagccagtct attgtacact ccaatggaaa cacatatttg       600
gagtggtatc tccaaaaacc cggccaaagc cctcaactgc tcatctacaa ggtctcaaac       660
aggtttagcg gggtcccgga tcgcttctca gggtcaggat ctggtacgga ctttacactg       720
aaaatttccc gagtcgaagc ggaagacgtg ggtgtatatt actgcttcca ggggagtcat       780
gttccaagaa ccttttgggg aggtacaaag gtcgaaataa aaaaccggat ccgtggggtc       840
accgtctctt cagcgctgag caactccatc atgtacttca gccacttcgt gccggtcttc       900
ctgccagcga agcccaccac gacgccagcg ccgcgaccac caacaccggc gcccaccatc       960
gcgtcgcagc ccctgtccct gcgcccagag gcgtgccggc cagcggcggg gggcgcagtg      1020
cacacgaggg ggctggaccc cttgggtttt tgggtgctgg tggtggttgg tggagtcctg      1080
gcttgctata gcttgctagt aacagtggcc tttattattt tctgggtgag gagtaagagg      1140
agcaggctcc tgcacagtga ctacatgaac atgactcccc gccgccccgg gcccacccgc      1200
aagcattacc agcccatgc cccaccacgc gacttcgcag cctatcgctc cctcgagaga       1260
gtgagagtga agttcagcag gagcgcagac gcccccgcgt accagcaggg ccagaaccag      1320
ctctataacg agctcaatct aggacgaaga gaggagtacg atgttttgga caagagacgt      1380
ggccgggacc ctgagatggg gggaaagccg agaaggaaga accctcagga aggcctgtac      1440
aatgaactgc agaaagataa gatggcggag gcctacagtg agattgggat gaaaggcgag      1500
cgccggaggg gcaaggggca cgatggcctt taccagggtc tcagtacagc caccaaggac      1560
acctacgacg cccttcacat gcaggccctg cccctcgc                              1599
```

<210> SEQ ID NO 175
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 175

```
atggattttc aggtccaaat tttttccttc ttgcttatca gcgcaagtgt aatcatgtcc      60
cgcgcgtccc aagtacaact tgtgcaatct ggcgcggagg tgaaaaaacc tggagcttcc     120
gtcaaggttt cttgtaaggc ctctggctac accttcacgt cctaccacat tcagtgggtt     180
cgacaggcgc cgggccaagg actggagtgg atgggatgga tatatccagg agatggttct     240
actcagtata atgagaaatt caagggtcgc gtaacaatga cgagggatac atcaatctcc     300
accgcgtaca tggaactttc aagactccgg tcagatgaca cggcggttta ctactgtgct     360
cgggagggca cttactatgc tatggactac tggggggcaag ggacaacggt aacggtatct     420
agtgtggatt ctagtggcgg cggcggttca ggaggaggtg gttcaggcgg gggggggtagt    480
acaagtgata ttgtgatgac ccaaacaccc ctttctagcc ctgttactct gggtcaaccc     540
gcgtccataa gttgtcgaag tagtcaatcc atcgtgcata gcaacggcaa cacttacctt     600
gaatggtatc aacaacgacc cggacagccc ccgcgactgc ttatctataa agtatcaaac     660
aggttcagtg gcgtgccaga tcgattctcc ggctctgggg caggcacaga tttcacgttg     720
aaaatttctc gggtcgaggc cgaggacgtg ggcgtttatt actgtttcca ggggagtcac     780
gtccccagga cgttcggagg aggaactaaa gtcgaaataa agaaccggat ccgtgggggtc     840
accgtctctt cagcgctgag caactccatc atgtacttca gccacttcgt gccggtcttc     900
ctgccagcga agcccaccac gacgccacgc cgcgaccac caacaccggc gccaccatc      960
gcgtcgcagc ccctgtccct gcgcccagag gcgtgccggc cagcggcggg gggcgcagtg    1020
cacacgaggg ggctggaccc ctttgggttt gggtgctgg tggtggttgg tggagtcctg    1080
gcttgctata gcttgctagt aacagtggcc tttattattt tctgggtgag gagtaagagg    1140
agcaggctcc tgcacagtga ctacatgaac atgactcccc gccgcccgg gcccaccgc      1200
aagcattacc agccctatgc cccaccacgc gacttcgcag cctatcgctc cctcgagaga    1260
gtgagagtga agttcagcag gagcgcagac gcccccgcgt accagcaggg ccagaaccag    1320
ctctataacg agctcaatct aggacgaaga gaggagtacg atgttttgga caagagacgt    1380
ggccgggacc ctgagatggg gggaaagccg agaaggaaga accctcagga aggcctgtac    1440
aatgaactgc agaaagataa gatggcggag gcctacagtg agattgggat gaaaggcgag    1500
cgccggaggg gcaaggggca cgatggcctt taccagggtc tcagtacagc caccaaggac    1560
acctacgacg cccttcacat gcaggccctg ccccctcgc                          1599
```

<210> SEQ ID NO 176
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 176

```
atggacttcc aggtccaaat attcagcttc ctcctcattt ccgccagtgt aataatgtcc      60
agagcctcac aagtacagtt ggttcagagc ggggctgagg ttaagaaacc aggcgcgagc    120
gtcaaggtat cctgcaaggc gagtggttat actttcacta gttatcacat tcagtgggtc    180
cgacaggccc ccgtcaagg cctggagtgg atggggtgga tatatccggg agatggttct    240
acccaatata atgagaagtt taaggggaga gtcacaatga caagggacac cagtattagc    300
accgcgtata tggagctttc cgcctgcga tcagatgaca cggccgtgta ctactgtgct    360
agggagggaa cctattatgc gatggattac tggggacagg gtactacagt cacggtctct    420
```

```
agcgtggaca gttccggggg cggtggaagc ggtggtggcg gttcaggtgg aggaggctct    480
acgagtgatg ttgtgatgac tcagtccccg ctttcacttc ccgtcaccct tgggcaaccc    540
gcaagcatct catgccgatc ctcccagtct atagtacata gtaatggcaa cacatatctt    600
gaatggtatc agcagaggcc gggtcagtct ccccgactcc ttatatataa agtgagcaac    660
agattctccg gagtaccgga tagatttttc ggctctggga gcggcaccga ctttacactg    720
aaaatttcac gggttgaagc tgaagatgtt ggggtatact attgtttcca gggttctcac    780
gtcccgagga cattcggggg aggaacgaaa gtcgaaataa agaaccggat ccgtggggtc    840
accgtctctt cagcgctgag caactccatc atgtacttca gccacttcgt gccggtcttc    900
ctgccagcga agcccaccac gacgccagcg ccgcgaccac caacaccggc gcccaccatc    960
gcgtcgcagc ccctgtccct gcgcccagag gcgtgccggc cagcggcggg gggcgcagtg   1020
cacacgaggg ggctggaccc ctttgggttt tgggtgctgg tggtggttgg tggagtcctg   1080
gcttgctata gcttgctagt aacagtggcc tttattattt tctgggtgag gagtaagagg   1140
agcaggctcc tgcacagtga ctacatgaac atgactcccc gccgcccggg cccacccgc    1200 aagcattacc agcccatgc cccaccacgc gacttcgcag cctatcgctc cctcgagaga    1260
gtgagagtga agttcagcag gagcgcagac gcccccgcgt accagcaggg ccagaaccag   1320
ctctataacg agctcaatct aggacgaaga gaggagtacg atgttttgga caagagacgt   1380
ggccgggacc ctgagatggg gggaaagccg agaaggaaga accctcagga aggcctgtac   1440
aatgaactgc agaaagataa gatggcggag gcctacagtg agattgggat gaaaggcgag   1500
cgccggaggg gcaaggggca cgatggcctt taccagggtc tcagtacagc caccaaggac   1560
acctacgacg cccttcacat gcaggccctg cccctcgc                          1599

<210> SEQ ID NO 177
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 177
atggattttc aggtacaaat cttcagcttc ctgctcatct ccgcgagcgt aatcatgtct     60
agggcgtccc aggtgcagtt ggtgcaatca ggtgcagagg tgaagaagcc tggtgcatcc    120
gttaaagtaa gttgtaaggc aagcggatat acttttacat cctatcatat tcaatgggtc    180
agacaagcac ctggacaggg tcttgagtgg atgggctgga tctatccagg cgatggctca    240
actcaatata cgagaagtt caaggggagg gttactatga ccagggatac gtctatttcc    300
actgcgtaca tggaactctc caggttgaga agtgatgata ccgcggttta ctactgcgct    360
agagaaggaa cgtactacgc tatggattac tgggggcagg gtacaactgt caccgtctca    420
agtgtggatt cttctggggg tgggggatca ggaggggggag gctccggtgg gggcgggtca    480
accagcgaca ttgtcatgac tcaaaccccc ctgagcagcc ctgtcaccct gggtcagcct    540
gcctcaatat cctttagaag ctcccaaagc atcgtccatt caaatggtaa tacctatctg    600
gagtggtatc agcaaaggcc tggtcaaccc ccgcgccttc tcatttacaa ggtgtcaaac    660
aggttctccg gcgtaccgga taggttttcc ggaagcggtg ctggaaccga ctttactctc    720
aaaatctcta gggtggaagc tgaggacgtc ggtgtatact attgtttcca aggctcccat    780
gttcccagga catttggtgg gggaacgaag gtagaaatca agaaccggat ccgtggggtc    840
```

| | | |
|---|---|---|
| accgtctctt cagcgctgag caactccatc atgtacttca gccacttcgt gccggtcttc | 900 |
| ctgccagcga agcccaccac gacgccagcg ccgcgaccac caacaccggc gcccaccatc | 960 |
| gcgtcgcagc ccctgtccct gcgcccagag gcgtgccggc cagcggcggg gggcgcagtg | 1020 |
| cacacgaggg ggctggaccc ctttgggttt tgggtgctgg tggtggttgg tggagtcctg | 1080 |
| gcttgctata gcttgctagt aacagtggcc tttattattt tctgggtgag gagtaagagg | 1140 |
| agcaggctcc tgcacagtga ctacatgaac atgactcccc gccgcccgg gcccacccgc | 1200 |
| aagcattacc agccctatgc cccaccacgc gacttcgcag cctatcgctc cctcgagaga | 1260 |
| gtgagagtga agttcagcag gagcgcagac gcccccgcgt accagcaggg ccagaaccag | 1320 |
| ctctataacg agctcaatct aggacgaaga gaggagtacg atgttttgga caagagacgt | 1380 |
| ggccgggacc ctgagatggg gggaaagccg agaaggaaga accctcagga aggcctgtac | 1440 |
| aatgaactgc agaaagataa gatggcggag gcctacagtg agattgggat gaaaggcgag | 1500 |
| cgccggaggg gcaaggggca cgatggcctt taccagggtc tcagtacagc caccaaggac | 1560 |
| acctacgacg cccttcacat gcaggccctg cccctcgc | 1599 |

<210> SEQ ID NO 178
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 178

| | | |
|---|---|---|
| atggactttc aggttcagat tttctctttc ttgttgatct ccgctagtgt cataatgtca | 60 |
| cgggcaagtc aggtacaact cgttcagagt ggtgccgaag tgaagaaacc gggtgcctcc | 120 |
| gtaaaggtgt catgtaaagc tagtggctat acattcacaa gttatcatat ccaatgggta | 180 |
| cgacaagcac cgggacagcg actggaatgg atgggatgga tctatcctgg ggacggatct | 240 |
| acacagtaca atgagaaatt taagggacgg gtcacgataa ccaggacaca atctgcttcc | 300 |
| acggcttaca tggagctttc ctccctgcgg agcgaggaca tggctgttta ctattgcgct | 360 |
| cgcgaaggga catactacgc aatgdattat tggggccaag gcactaccgt gacggtctct | 420 |
| tctgtcgata gttccggagg aggtggttca gggggaggcg gttcaggtgg gggtggatct | 480 |
| acctcagata ttgtcatgac acagacacct ttgtccttga gtgtgacacc gggtcaaccg | 540 |
| gcgagtataa gctgtcgcag ctcacaatct attgtgcata gcaacgggaa tacatatctc | 600 |
| gaatggtatc tccaaaagcc gggccaatcc ccccaacttc tcatttacaa gtttctaat | 660 |
| cgattttcag gtgtaccaga tcggttttcc gggtctggct caggtactga cttcaccttg | 720 |
| aaaatatcaa gggttgaagc tgaggatgta gtgtgtact attgcttcca ggggtctcac | 780 |
| gttcctcgga cttttggggg gggcacaaaa gtagagatta aaaccggat ccgtggggtc | 840 |
| accgtctctt cagcgctgag caactccatc atgtacttca gccacttcgt gccggtcttc | 900 |
| ctgccagcga agcccaccac gacgccagcg ccgcgaccac caacaccggc gcccaccatc | 960 |
| gcgtcgcagc ccctgtccct gcgcccagag gcgtgccggc cagcggcggg gggcgcagtg | 1020 |
| cacacgaggg ggctggaccc ctttgggttt tgggtgctgg tggtggttgg tggagtcctg | 1080 |
| gcttgctata gcttgctagt aacagtggcc tttattattt tctgggtgag gagtaagagg | 1140 |
| agcaggctcc tgcacagtga ctacatgaac atgactcccc gccgcccgg gcccacccgc | 1200 |
| aagcattacc agccctatgc cccaccacgc gacttcgcag cctatcgctc cctcgagaga | 1260 |
| gtgagagtga agttcagcag gagcgcagac gcccccgcgt accagcaggg ccagaaccag | 1320 |

```
ctctataacg agctcaatct aggacgaaga gaggagtacg atgttttgga caagagacgt   1380
ggccgggacc ctgagatggg gggaaagccg agaaggaaga accctcagga aggcctgtac   1440
aatgaactgc agaaagataa gatggcggag gcctacagtg agattgggat gaaaggcgag   1500
cgccggaggg gcaaggggca cgatggcctt taccagggtc tcagtacagc caccaaggac   1560
acctacgacg cccttcacat gcaggccctg ccccctcgc                          1599
```

<210> SEQ ID NO 179
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 179

```
atggatttcc aggtgcaaat cttctcattt cttttgataa gtgcgtcagt gataatgtct     60
cgggccagtc aagtacagct tgtccaaagt ggcgctgaag tcaagaagcc gggagcctca    120
gttaaggtta gctgcaaggc ctcagggtat acttttacct cctatcatat acagtgggta    180
cgacaagcac cgggacagcg actggagtgg atgggttgga tatatccggg agatggttca    240
acccagtata atgagaagtt caaggggcga gttacgataa cccgcgatac gagtgcatca    300
acagcgtaca tggagttgag ttccctccgc agcgaggaca tggcggtata ctattgtgcc    360
agggagggga cttattatgc catggactac tgggggcagg gcacaaccgt aacagtctct    420
tctgtagaca gttcaggagg gggcggaagt ggaggtggcg gatctggtgg aggtggatct    480
acttccgaca tcgttatgac ccaaacacca ctttcatctc ccgttactct cgggcaacct    540
gctagtattt cctgtagatc ctcacaatct atagtacata gcaatggcaa tacctacctg    600
gagtggtatc aacaacgccc aggccaacca cctcgcctgc ttatctataa agtaagcaat    660
agattcagtg gtgtaccgga taggttctct ggttccggag caggaactga ctttacactc    720
aaaatcagta gggtggaggc ggaagacgtg ggagtatatt attgctttca aggttcacat    780
gtacctcgaa catttggcgg aggaactaag gttgagatta aaaaccggat ccgtgggtc    840 accgtctctt cagcgctgag caactccatc atgtacttca gccacttcgt gccggtcttc    900
ctgccagcga agcccaccac gacgccagcg ccgcgaccac caacaccggc gccaccatc    960 gcgtcgcagc ccctgtccct gcgcccagag gcgtgccggc cagcggcggg gggcgcagtg   1020
cacacgaggg gcctggaccc ctttgggttt tgggtgctgg tggtggttgg tggagtcctg   1080
gcttgctata gcttgctagt aacagtggcc tttattattt tctgggtgag gagtaagagg   1140
agcaggctcc tgcacagtga ctacatgaac atgactcccc gccgccccgg gcccacccgc   1200
aagcattacc agcccatgc cccaccacgc gacttcgcag cctatcgctc cctcgagaga   1260
gtgagagtga gttcagcag gagcgcagac gcccccgcgt accagcaggg ccagaaccag   1320
ctctataacg agctcaatct aggacgaaga gaggagtacg atgttttgga caagagacgt   1380
ggccgggacc ctgagatggg gggaaagccg agaaggaaga accctcagga aggcctgtac   1440
aatgaactgc agaaagataa gatggcggag gcctacagtg agattgggat gaaaggcgag   1500
cgccggaggg gcaaggggca cgatggcctt taccagggtc tcagtacagc caccaaggac   1560
acctacgacg cccttcacat gcaggccctg ccccctcgc                          1599
```

<210> SEQ ID NO 180
<211> LENGTH: 1599
<212> TYPE: DNA

<213> ORGANISM: Artificial Sequence
<220> FEATURE:
<223> OTHER INFORMATION: Synthetic sequence

<400> SEQUENCE: 180

| | | | | | |
|---|---|---|---|---|---|
| atggatttcc | aagtccagat | attcagtttt | cttttgataa | gcgcttctgt | aatcatgtct | 60 |
| cgggcgtccc | aagtacaact | ggtgcaatca | ggggcagaag | tgaaaaaacc | aggtgcatcc | 120 |
| gttaaggtga | gttgcaaggc | ttccggctat | acctttacat | catatcatat | tcaatgggtc | 180 |
| aggcaagcac | ctggtcagcg | attggaatgg | atgggttgga | tatatcctgg | tgatgggtct | 240 |
| acacaatata | acgaaaaatt | caaggggcga | gtgaccatca | caagagatac | atcagcgtca | 300 |
| acagcgtata | tggaactgtc | atcccttaga | tcagaggaca | tggcggtcta | ttactgtgcc | 360 |
| agagaaggca | cttattatgc | aatggattat | tggggacaag | gaaccactgt | cactgtttcc | 420 |
| agcgtagact | cctccggtgg | tggtggaagt | ggcggcggtg | ggtcaggagg | gggtgggtca | 480 |
| acttctgatg | tagtgatgac | acagagccct | ctgagcttgc | ctgtgacctt | gggtcagccg | 540 |
| gcctcaataa | gttgtcgatc | tagtcagtca | atcgtccata | gtaatgggaa | cacataccct | 600 |
| gaatggtatc | agcaaagacc | tggacaatct | ccacgactcc | ttatatacaa | agttagcaac | 660 |
| cgatttagcg | gagtgccaga | ccgcttttct | ggttccgggt | ctggcacaga | ttttaccctt | 720 |
| aagatctccc | gcgtggaggc | ggaagacgtt | ggtgtttact | attgcttcca | ggggtcacac | 780 |
| gttccacgca | cctttggagg | aggtacgaag | gtcgagatta | gaaccggat | ccgtggggtc | 840 |
| accgtctctt | cagcgctgag | caactccatc | atgtacttca | gccacttcgt | gccggtcttc | 900 |
| ctgccagcga | agcccaccac | gacgccagcg | ccgcgaccac | caacaccggc | gcccaccatc | 960 |
| gcgtcgcagc | ccctgtccct | gcgcccagag | gcgtgccggc | cagcggcggg | gggcgcagtg | 1020 |
| cacacgaggg | ggctggaccc | ctttgggttt | tgggtgctgg | tggtggttgg | tggagtcctg | 1080 |
| gcttgctata | gcttgctagt | aacagtggcc | tttattattt | tctgggtgag | gagtaagagg | 1140 |
| agcaggctcc | tgcacagtga | ctacatgaac | atgactcccc | gccgcccgg | gcccacccgc | 1200 |
| aagcattacc | agccctatgc | cccaccacgc | gacttcgcag | cctatcgctc | cctcgagaga | 1260 |
| gtgagagtga | agttcagcag | gagcgcagac | gcccccgcgt | accagcaggg | ccagaaccag | 1320 |
| ctctataacg | agctcaatct | aggacgaaga | gaggagtacg | atgttttgga | caagagacgt | 1380 |
| ggccgggacc | ctgagatggg | gggaaagccg | agaaggaaga | accctcagga | aggcctgtac | 1440 |
| aatgaactgc | agaaagataa | gatggcggag | gcctacagtg | agattgggat | gaaaggcgag | 1500 |
| cgccggaggg | gcaaggggca | cgatggcctt | taccagggtc | tcagtacagc | caccaaggac | 1560 |
| acctacgacg | cccttcacat | gcaggccctg | cccctcgc | | | 1599 |

<210> SEQ ID NO 181
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 181

| | | | | | |
|---|---|---|---|---|---|
| atggatttc | aagtacagat | cttctctttc | ttgcttattt | cagcgagcgt | aatcatgagt | 60 |
| agggcatctc | aagttcaact | cgttcagtca | ggtgctgagg | taaaaaaacc | aggggcttcc | 120 |
| gttaaagtta | gctgtaaggc | atctgggtac | acatttacta | gctaccatat | ccagtgggtg | 180 |
| cgacaagccc | cggggcagcg | cttggaatgg | atgggctgga | tttacccagg | tgacggctcc | 240 |
| acgcaatata | atgagaaatt | taagggtaga | gttactatta | ccagggacac | aagtgcttca | 300 |

```
actgcctata tggaactgag cagccttcgg agtgaagata tggccgtata ttactgcgca         360
agggagggga cttactatgc aatggactac tggggtcagg gaacgactgt gaccgtgtcc         420
tcagttgact ccagcggtgg tggcggctct ggaggtgggg gttccggcgg aggcggaagc         480
acatctgata tagtgatgac gcaaacgcct ctttcttccc cggtaactct gggacagcca         540
gcgtcaattt catttaggtc ctcccagtca atcgtacata gtaatggaaa tacttacctg         600
gaatggtatc aacaacgacc agggcaaccg ccccgattgt tgatctataa agtgagcaat         660
cgcttttctg gcgtgcccga tcggttctca gggtctggag ctgggactga cttcacattg         720
aaaatttcca gggttgaggc cgaggatgtg ggggtttatt actgcttcca aggctcccac         780
gtcccccgca ccttcggagg gggaaccaaa gtcgaaataa agaaccggat ccgtggggtc         840
accgtctctt cagcgctgag caactccatc atgtacttca gccacttcgt gccggtcttc         900
ctgccagcga agcccaccac gacgccagcg ccgcgaccac caacaccggc gcccaccatc         960
gcgtcgcagc ccctgtccct gcgcccagag gcgtgccggc cagcggcggg gggcgcagtg        1020
cacacgaggg ggctggaccc ctttgggttt tgggtgctgg tggtggttgg tggagtcctg        1080
gcttgctata gcttgctagt aacagtggcc tttattattt tctgggtgag gagtaagagg        1140
agcaggctcc tgcacagtga ctacatgaac atgactcccc gccgccccgg gcccacccgc        1200
aagcattacc agcccatgc cccaccacgc gacttcgcag cctatcgctc cctcgagaga        1260
gtgagagtga agttcagcag gagcgcagac gcccccgcgt accagcaggg ccagaaccag        1320
ctctataacg agctcaatct aggacgaaga gaggagtacg atgttttgga caagagacgt        1380
ggccgggacc ctgagatggg gggaaagccg agaaggaaga accctcagga aggcctgtac        1440
aatgaactgc agaaagataa gatggcggag gcctacagtg agattgggat gaaaggcgag        1500
cgccggaggg gcaaggggca cgatggcctt taccagggtc tcagtacagc caccaaggac        1560
acctacgacg cccttcacat gcaggccctg ccccctcgc                              1599
```

<210> SEQ ID NO 182
<211> LENGTH: 1599
<212> TYPE: DNA
<213> ORGANISM: Artificial Sequence
<220> FEATURE:
<223> OTHER INFORMATION: Synthetic sequence

<400> SEQUENCE: 182

```
atggattttc aagttcagat attctcattt ttgcttatat cagcctccgt aattatgtca          60
cgggcaagtc aagttcagtt ggtgcagtcc ggagcagaag ttaagaagcc cggtgcttct         120
gtgaaagtct cctgcaaagc gtctgggtac accttcacga gctaccatat acagtgggtc         180
cggcaagcgc tgggcagag ctggagtgg atgggctgga tttacccagg agatgggagt          240
acaaagtata gtcagaagtt caagggcga gtgacgataa ccagagatac gagtgcaagt         300
actgcataca tggaactgag ctccttgagg tccgaggata cagcggtgta ctattgcgct         360
cgggaaggga catattatgc tatggactat tggggacaag ggacaacggt aacggtgagt         420
tccgtcgatt cctcaggtgg cggaggcagt ggggcgggg gttccggcgg tggcgggtcc         480
acgagtgata tagttatgac acagacccc ctcagccttt ctgtgacccc aggacaaccc         540
gctagtatct cttgccgcag ttctcagtcc atagtacaca gtaacggaaa tacctatctt         600
gagtggtatc ttcaaaagcc cggccagagc cctcaactct tgatatataa agtgtcaaat         660
cgattttcag gtgtgcctga tcgattctca gggtctggtt cagggacaga tttcacgctt         720
```

```
aagataagca gagtagaggc tgaagacgtg ggagtctact attgttttca ggggtcacac    780
gttccccgca cttttggtgg gggaaccaag gtggaaatca aaaaccggat ccgtggggtc    840
accgtctctt cagcgctgag caactccatc atgtacttca gccacttcgt gccggtcttc    900
ctgccagcga agcccaccac gacgccagcg ccgcgaccac caacaccggc gcccaccatc    960
gcgtcgcagc ccctgtccct cgcccagag gcgtgccggc cagcggcggg gggcgcagtg   1020
cacacgaggg ggctggaccc cttgggtt tgggtgctgg tggtggttgg tggagtcctg   1080
gcttgctata gcttgctagt aacagtggcc tttattattt tctgggtgag gagtaagagg   1140
agcaggctcc tgcacagtga ctacatgaac atgactcccc gccgcccgg gcccacccgc   1200
aagcattacc agccctatgc cccaccacgc gacttcgcag cctatcgctc cctcgagaga   1260
gtgagagtga agttcagcag gagcgcagac gcccccgcgt accagcaggg ccagaaccag   1320
ctctataacg agctcaatct aggacgaaga gaggagtacg atgttttgga caagagacgt   1380
ggccgggacc ctgagatggg gggaaagccg agaaggaaga accctcagga aggcctgtac   1440
aatgaactgc agaaagataa gatggcgag gcctacagtg agattgggat gaaaggcgag   1500
cgccggaggg gcaaggggca cgatggcctt taccagggtc tcagtacagc caccaaggac   1560
acctacgacg cccttcacat gcaggccctg ccccctcgc                          1599
```

<210> SEQ ID NO 183
<211> LENGTH: 5
<212> TYPE: PRT
<213> ORGANISM: Artificial Sequence
<220> FEATURE:
<223> OTHER INFORMATION: Synthetic sequence

<400> SEQUENCE: 183

Ser Tyr His Ile Gln
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic sequence

<400> SEQUENCE: 184

Gly Tyr Thr Phe Thr Ser Tyr
1               5

<210> SEQ ID NO 185
<211> LENGTH: 17
<212> TYPE: PRT
<213> ORGANISM: Artificial Sequence
<220> FEATURE:
<223> OTHER INFORMATION: Synthetic sequence

<400> SEQUENCE: 185

Trp Ile Tyr Pro Gly Asp Gly Ser Thr Gln Tyr Asn Glu Lys Phe Lys
1               5                   10                  15

Gly

<210> SEQ ID NO 186
<211> LENGTH: 6
<212> TYPE: PRT
<213> ORGANISM: Artificial Sequence
<220> FEATURE:
<223> OTHER INFORMATION: Synthetic sequence

```
<400> SEQUENCE: 186

Tyr Pro Gly Asp Gly Ser
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic sequence

<400> SEQUENCE: 187

Glu Gly Thr Tyr Tyr Ala Met Asp Tyr
1               5

<210> SEQ ID NO 188
<211> LENGTH: 16
<212> TYPE: PRT
<213> ORGANISM: Artificial Sequence
<220> FEATURE:
<223> OTHER INFORMATION: Synthetic sequence

<400> SEQUENCE: 188

Arg Ser Ser Gln Ser Ile Val His Ser Asn Gly Asn Thr Tyr Leu Glu
1               5                   10                  15

<210> SEQ ID NO 189
<211> LENGTH: 7
<212> TYPE: PRT
<213> ORGANISM: Artificial Sequence
<220> FEATURE:
<223> OTHER INFORMATION: Synthetic sequence

<400> SEQUENCE: 189

Lys Val Ser Asn Arg Phe Ser
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic sequence

<400> SEQUENCE: 190

Phe Gln Gly Ser His Val Pro Arg Thr
1               5

<210> SEQ ID NO 191
<211> LENGTH: 118
<212> TYPE: PRT
<213> ORGANISM: Artificial Sequence
<220> FEATURE:
<223> OTHER INFORMATION: Synthetic sequence

<400> SEQUENCE: 191

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

His Ile Gln Trp Val Lys Gln Arg Pro Gly Gln Gly Leu Glu Trp Ile
            35                  40                  45

Gly Trp Ile Tyr Pro Gly Asp Gly Ser Thr Gln Tyr Asn Glu Lys Phe
        50                  55                  60
```

```
Lys Gly Lys Thr Thr Leu Thr Ala Asp Lys Ser Ser Thr Ala Tyr
 65                  70                  75                  80

Met Leu Leu Ser Ser Leu Thr Ser Glu Asp Ser Ala Ile Tyr Phe Cys
                 85                  90                  95

Ala Arg Glu Gly Thr Tyr Tyr Ala Met Asp Tyr Trp Gly Gln Gly Thr
            100                 105                 110

Ser Val Thr Val Ser Ser
            115
```

<210> SEQ ID NO 192
<211> LENGTH: 112
<212> TYPE: PRT
<213> ORGANISM: Artificial Sequence
<220> FEATURE:
<223> OTHER INFORMATION: Synthetic sequence

<400> SEQUENCE: 192

```
Asp Val Leu Met Thr Gln Thr Pro Leu Ser Leu Pro Val Ser Leu Gly
 1               5                  10                  15

Asp Gln Val Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Arg Thr Phe Gly Gly Gly Thr Lys Leu Glu Ile Lys
            100                 105                 110
```

<210> SEQ ID NO 193
<211> LENGTH: 251
<212> TYPE: PRT
<213> ORGANISM: Artificial Sequence
<220> FEATURE:
<223> OTHER INFORMATION: Synthetic sequence

<400> SEQUENCE: 193

```
Gln Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                 20                  25                  30

His Ile Gln Trp Val Lys Gln Arg Pro Gly Gln Gly Leu Glu Trp Ile
             35                  40                  45

Gly Trp Ile Tyr Pro Gly Asp Gly Ser Thr Gln Tyr Asn Glu Lys Phe
 50                  55                  60

Lys Gly Lys Thr Thr Leu Thr Ala Asp Lys Ser Ser Thr Ala Tyr
 65                  70                  75                  80

Met Leu Leu Ser Ser Leu Thr Ser Glu Asp Ser Ala Ile Tyr Phe Cys
                 85                  90                  95

Ala Arg Glu Gly Thr Tyr Tyr Ala Met Asp Tyr Trp Gly Gln Gly Thr
            100                 105                 110

Ser Val Thr Val Ser Ser Val Asp Ser Gly Gly Gly Ser Gly
            115                 120                 125

Gly Gly Gly Ser Gly Gly Gly Ser Thr Ser Asp Val Leu Met Thr
            130                 135                 140
```

Gln Thr Pro Leu Ser Leu Pro Val Ser Leu Gly Asp Gln Val Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Lys Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Tyr Cys Phe Gln Gly Ser His Val Pro Arg
225                 230                 235                 240

Thr Phe Gly Gly Gly Thr Lys Leu Glu Ile Lys
                245                 250

<210> SEQ ID NO 194
<211> LENGTH: 521
<212> TYPE: PRT
<213> ORGANISM: Artificial Sequence
<220> FEATURE:
<223> OTHER INFORMATION: Synthetic sequence

<400> SEQUENCE: 194

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

His Ile Gln Trp Val Lys Gln Arg Pro Gly Gln Gly Leu Glu Trp Ile
        35                  40                  45

Gly Trp Ile Tyr Pro Gly Asp Gly Ser Thr Gln Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Ala Arg Glu Gly Thr Tyr Tyr Ala Met Asp Tyr Trp Gly Gln Gly Thr
            100                 105                 110

Ser Val Thr Val Ser Ser Val Asp Ser Gly Gly Gly Gly Ser Gly
        115                 120                 125

Gly Gly Gly Ser Gly Gly Gly Ser Thr Ser Asp Val Leu Met Thr
    130                 135                 140

Gln Thr Pro Leu Ser Leu Pro Val Ser Leu Gly Asp Gln Val Ser Ile
145                 150                 155                 160

Ser Cys Arg Ser Ser Gln Ser Ile Val His Ser Asn Gly Asn Thr Tyr
                165                 170                 175

Leu Glu Trp Tyr Leu Gln Lys Pro Gly Gln Ser Pro Lys Leu Leu Ile
            180                 185                 190

Tyr Lys Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Tyr Cys Phe Gln Gly Ser His Val Pro Arg
225                 230                 235                 240

Thr Phe Gly Gly Gly Thr Lys Leu Glu Ile Lys Leu Glu Gln Lys Leu
                245                 250                 255

```
Ile Ser Glu Glu Asp Leu Asn Arg Ile Arg Gly Val Thr Val Ser Ser
            260                 265                 270

Ala Leu Ser Asn Ser Ile Met Tyr Phe Ser His Phe Val Pro Val Phe
        275                 280                 285

Leu Pro Ala Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Cys
305                 310                 315                 320

Arg Pro Ala Ala Gly Gly Ala Val His Thr Arg Gly Leu Asp Pro Phe
                325                 330                 335

Gly Phe Trp Val Leu Val Val Val Gly Gly Val Leu Ala Cys Tyr Ser
            340                 345                 350

Leu Leu Val Thr Val Ala Phe Ile Ile Phe Trp Val Arg Ser Lys Arg
        355                 360                 365

Ser Arg Leu Leu His Ser Asp Tyr Met Asn Met Thr Pro Arg Arg Pro
    370                 375                 380

Gly Pro Thr Arg Lys His Tyr Gln Pro Tyr Ala Pro Pro Arg Asp Phe
385                 390                 395                 400

Ala Ala Tyr Arg Ser Leu Glu Arg Val Arg Val Lys Phe Ser Arg Ser
                405                 410                 415

Ala Asp Ala Pro Ala Tyr Gln Gln Gly Gln Asn Gln Leu Tyr Asn Glu
            420                 425                 430

Leu Asn Leu Gly Arg Arg Glu Glu Tyr Asp Val Leu Asp Lys Arg Arg
        435                 440                 445

Gly Arg Asp Pro Glu Met Gly Gly Lys Pro Arg Arg Lys Asn Pro Gln
    450                 455                 460

Glu Gly Leu Tyr Asn Glu Leu Gln Lys Asp Lys Met Ala Glu Ala Tyr
465                 470                 475                 480

Ser Glu Ile Gly Met Lys Gly Glu Arg Arg Arg Gly Lys Gly His Asp
                485                 490                 495

Gly Leu Tyr Gln Gly Leu Ser Thr Ala Thr Lys Asp Thr Tyr Asp Ala
            500                 505                 510

Leu His Met Gln Ala Leu Pro Pro Arg
        515                 520

<210> SEQ ID NO 195
<211> LENGTH: 544
<212> TYPE: PRT
<213> ORGANISM: Artificial Sequence
<220> FEATURE:
<223> OTHER INFORMATION: Synthetic sequence

<400> SEQUENCE: 195

Met Asp Phe Gln Val Gln Ile Phe Ser Phe Leu Leu Ile Ser Ala Ser
1               5                   10                  15

Val Ile Met Ser Arg Ala Ser Gln Val Gln Leu Gln Gln Ser Gly Pro
            20                  25                  30

Glu Leu Val Lys Pro Gly Ala Ser Val Lys Met Ser Cys Lys Ala Ser
        35                  40                  45

Gly Tyr Thr Phe Thr Ser Tyr His Ile Gln Trp Val Lys Gln Arg Pro
    50                  55                  60

Gly Gln Gly Leu Glu Trp Ile Gly Trp Ile Tyr Pro Gly Asp Gly Ser
65                  70                  75                  80

Thr Gln Tyr Asn Glu Lys Phe Lys Gly Lys Thr Thr Leu Thr Ala Asp
                85                  90                  95
```

```
Lys Ser Ser Ser Thr Ala Tyr Met Leu Leu Ser Ser Leu Thr Ser Glu
            100                 105                 110

Asp Ser Ala Ile Tyr Phe Cys Ala Arg Glu Gly Thr Tyr Tyr Ala Met
            115                 120                 125

Asp Tyr Trp Gly Gln Gly Thr Ser Val Thr Val Ser Ser Val Asp Ser
130                 135                 140

Ser Gly Gly Gly Ser Gly Gly Gly Ser Gly Gly Gly Ser
145                 150                 155                 160

Thr Ser Asp Val Leu Met Thr Gln Thr Pro Leu Ser Leu Pro Val Ser
            165                 170                 175

Leu Gly Asp Gln Val Ser Ile Ser Cys Arg Ser Ser Gln Ser Ile Val
            180                 185                 190

His Ser Asn Gly Asn Thr Tyr Leu Glu Trp Tyr Leu Gln Lys Pro Gly
            195                 200                 205

Gln Ser Pro Lys Leu Leu Ile Tyr Lys Val Ser Asn Arg Phe Ser Gly
            210                 215                 220

Val Pro Asp Arg Phe Ser Gly Ser Gly Ser Gly Thr Asp Phe Thr Leu
225                 230                 235                 240

Lys Ile Ser Arg Val Glu Ala Glu Asp Leu Gly Val Tyr Tyr Cys Phe
            245                 250                 255

Gln Gly Ser His Val Pro Arg Thr Phe Gly Gly Gly Thr Lys Leu Glu
            260                 265                 270

Ile Lys Leu Glu Gln Lys Leu Ile Ser Glu Glu Asp Leu Asn Arg Ile
            275                 280                 285

Arg Gly Val Thr Val Ser Ser Ala Leu Ser Asn Ser Ile Met Tyr Phe
            290                 295                 300

Ser His Phe Val Pro Val Phe Leu Pro Ala Lys Pro Thr Thr Thr Pro
305                 310                 315                 320

Ala Pro Arg Pro Pro Thr Pro Ala Pro Thr Ile Ala Ser Gln Pro Leu
            325                 330                 335

Ser Leu Arg Pro Glu Ala Cys Arg Pro Ala Ala Gly Gly Ala Val His
            340                 345                 350

Thr Arg Gly Leu Asp Pro Phe Gly Phe Trp Val Leu Val Val Val Gly
            355                 360                 365

Gly Val Leu Ala Cys Tyr Ser Leu Leu Val Thr Val Ala Phe Ile Ile
370                 375                 380

Phe Trp Val Arg Ser Lys Arg Ser Arg Leu Leu His Ser Asp Tyr Met
385                 390                 395                 400

Asn Met Thr Pro Arg Arg Pro Gly Pro Thr Arg Lys His Tyr Gln Pro
            405                 410                 415

Tyr Ala Pro Pro Arg Asp Phe Ala Ala Tyr Arg Ser Leu Glu Arg Val
            420                 425                 430

Arg Val Lys Phe Ser Arg Ser Ala Asp Ala Pro Ala Tyr Gln Gln Gly
            435                 440                 445

Gln Asn Gln Leu Tyr Asn Glu Leu Asn Leu Gly Arg Arg Glu Glu Tyr
            450                 455                 460

Asp Val Leu Asp Lys Arg Arg Gly Arg Asp Pro Glu Met Gly Gly Lys
465                 470                 475                 480

Pro Arg Arg Lys Asn Pro Gln Glu Gly Leu Tyr Asn Glu Leu Gln Lys
            485                 490                 495

Asp Lys Met Ala Glu Ala Tyr Ser Glu Ile Gly Met Lys Gly Glu Arg
            500                 505                 510
```

Arg Arg Gly Lys Gly His Asp Gly Leu Tyr Gln Gly Leu Ser Thr Ala
    515                 520                 525

Thr Lys Asp Thr Tyr Asp Ala Leu His Met Gln Ala Leu Pro Pro Arg
    530                 535                 540

<210> SEQ ID NO 196
<211> LENGTH: 1635
<212> TYPE: DNA
<213> ORGANISM: Artificial Sequence
<220> FEATURE:
<223> OTHER INFORMATION: Synthetic sequence

<400> SEQUENCE: 196

| | | | | | | |
|---|---|---|---|---|---|---|
| atggacttcc | aggtgcagat | cttcagcttc | ctgctgatca | gcgccagcgt | gatcatgagc | 60 |
| cgcgctagcc | aggtgcagct | gcagcagagc | ggccccgagc | tggtgaagcc | cggcgccagc | 120 |
| gtgaagatga | gctgcaaggc | cagcggctac | accttcacca | gctaccacat | ccagtgggtg | 180 |
| aagcagcgcc | ccggccaggg | cctggagtgg | atcggctgga | tctacccggg | cgacggcagc | 240 |
| acccagtaca | acgagaagtt | caagggcaag | gccaccctga | ccgccgacaa | gagcagcagc | 300 |
| accgcctaca | tgctgctgag | cagcctgacc | agcgaggaca | gcgccatcta | cttctgcgcc | 360 |
| cgcgagggca | cctactacgc | catggactac | tggggccagg | gcaccagcgt | gaccgtgagc | 420 |
| agcgtcgaca | gcagcggcgg | cggcggcagc | ggcggcggcg | gcagcggcgg | cggcggcagc | 480 |
| actagtgacg | tgctgatgac | ccagaccccc | ctgagcctgc | ccgtgagcct | gggcgaccag | 540 |
| gtgagcatca | gctgccgcag | cagccagagc | atcgtgcaca | gcaacggcaa | cacctacctg | 600 |
| gagtggtacc | tgcagaagcc | cggccagagc | cccaagctgc | tgatctacaa | ggtgagcaac | 660 |
| cgcttcagcg | gcgtgcccga | ccgcttcagc | ggcagcggca | gcggcaccga | cttcaccctg | 720 |
| aagatcagcc | gcgtggaggc | cgaggacctg | ggcgtgtact | actgcttcca | gggcagccac | 780 |
| gtgccccgca | ccttcggcgg | cggcaccaag | ctggagatca | agctcgagca | gaagctgatc | 840 |
| agcgaggagg | acctgaaccg | gatccgtggg | gtcaccgtct | cttcagcgct | gagcaactcc | 900 |
| atcatgtact | tcagccactt | cgtgccggtc | ttcctgccag | cgaagcccac | cacgacgcca | 960 |
| gcgccgcgac | caccaacacc | ggcgcccacc | atcgcgtcgc | agcccctgtc | cctgcgccca | 1020 |
| gaggcgtgcc | ggccagcggc | ggggggcgca | gtgcacacga | gggggctgga | cccctttggg | 1080 |
| ttttgggtgc | tggtggtggt | tggtggagtc | ctggcttgct | atagcttgct | agtaacagtg | 1140 |
| gcctttatta | ttttctgggt | gaggagtaag | aggagcaggc | tcctgcacag | tgactacatg | 1200 |
| aacatgactc | cccgccgccc | cgggcccacc | cgcaagcatt | accagcccta | tgccccacca | 1260 |
| cgcgacttcg | cagcctatcg | ctccctcgag | agagtgagag | tgaagttcag | caggagcgca | 1320 |
| gacgcccccg | cgtaccagca | gggccagaac | cagctctata | cgagctcaa | tctaggacga | 1380 |
| agagaggagt | acgatgtttt | ggacaagaga | cgtggccggg | accctgagat | gggggaaag | 1440 |
| ccgagaagga | agaaccctca | ggaaggcctg | tacaatgaac | tgcagaaaga | taagatggcg | 1500 |
| gaggcctaca | gtgagattgg | gatgaaaggc | gagcgccgga | ggggcaaggg | gcacgatggc | 1560 |
| ctttaccagg | gtctcagtac | agccaccaag | gacacctacg | acgcccttca | catgcaggcc | 1620 |
| ctgcccccgc | gctaa | | | | | 1635 |

<210> SEQ ID NO 197
<211> LENGTH: 37
<212> TYPE: DNA
<213> ORGANISM: Artificial Sequence
<220> FEATURE:
<223> OTHER INFORMATION: Synthetic sequence

```
<400> SEQUENCE: 197
ttttctagac gcgtgccacc atggccgtca tggcgcc                                37

<210> SEQ ID NO 198
<211> LENGTH: 40
<212> TYPE: DNA
<213> ORGANISM: Artificial Sequence
<220> FEATURE:
<223> OTHER INFORMATION: Synthetic sequence

<400> SEQUENCE: 198
aagtcgacgc tagctcacac tttacaagct gtgagagaca                             40

<210> SEQ ID NO 199
<211> LENGTH: 20
<212> TYPE: DNA
<213> ORGANISM: Artificial Sequence
<220> FEATURE:
<223> OTHER INFORMATION: Synthetic sequence

<400> SEQUENCE: 199
tcaacccgat tgtccaccat                                                   20

<210> SEQ ID NO 200
<211> LENGTH: 23
<212> TYPE: DNA
<213> ORGANISM: Artificial Sequence
<220> FEATURE:
<223> OTHER INFORMATION: Synthetic sequence

<400> SEQUENCE: 200
gagtttagtc cgaaatgagg ctg                                               23

<210> SEQ ID NO 201
<211> LENGTH: 21
<212> TYPE: DNA
<213> ORGANISM: Artificial Sequence
<220> FEATURE:
<223> OTHER INFORMATION: Synthetic sequence

<400> SEQUENCE: 201
tccaaagatg tagccgcccc a                                                 21

<210> SEQ ID NO 202
<211> LENGTH: 23
<212> TYPE: DNA
<213> ORGANISM: Artificial Sequence
<220> FEATURE:
<223> OTHER INFORMATION: Synthetic sequence

<400> SEQUENCE: 202
ccagtgcctc tttgctgctt tca                                               23

<210> SEQ ID NO 203
<211> LENGTH: 23
<212> TYPE: DNA
<213> ORGANISM: Artificial Sequence
<220> FEATURE:
<223> OTHER INFORMATION: Synthetic sequence

<400> SEQUENCE: 203
ctgagctcgc cagtgaaatg atg                                               23

<210> SEQ ID NO 204
```

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 204
tgctgtagtg gtggtcggag a                                             21

<210> SEQ ID NO 205
<211> LENGTH: 22
<212> TYPE: DNA
<213> ORGANISM: Artificial Sequence
<220> FEATURE:
<223> OTHER INFORMATION: Synthetic sequence

<400> SEQUENCE: 205
acctgcctta agagtggagc ca                                            22

<210> SEQ ID NO 206
<211> LENGTH: 22
<212> TYPE: DNA
<213> ORGANISM: Artificial Sequence
<220> FEATURE:
<223> OTHER INFORMATION: Synthetic sequence

<400> SEQUENCE: 206
acatgtcgca cgtctctgat ga                                            22

<210> SEQ ID NO 207
<211> LENGTH: 20
<212> TYPE: DNA
<213> ORGANISM: Artificial Sequence
<220> FEATURE:
<223> OTHER INFORMATION: Synthetic sequence

<400> SEQUENCE: 207
tgcccagagc atccaaaaga                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic sequence

<400> SEQUENCE: 208
tgtattgctt tgcgttggac                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic sequence

<400> SEQUENCE: 209
aggcgctccc caagaagaca                                               20

<210> SEQ ID NO 210
<211> LENGTH: 23
<212> TYPE: DNA
<213> ORGANISM: Artificial Sequence
<220> FEATURE:
<223> OTHER INFORMATION: Synthetic sequence

<400> SEQUENCE: 210
```
gggctgatta gagagaggtc cct                                            23

<210> SEQ ID NO 211
<211> LENGTH: 20
<212> TYPE: DNA
<213> ORGANISM: Artificial Sequence
<220> FEATURE:
<223> OTHER INFORMATION: Synthetic sequence

<400> SEQUENCE: 211
caagacggac cagagcgaaa                                                20

<210> SEQ ID NO 212
<211> LENGTH: 19
<212> TYPE: DNA
<213> ORGANISM: Artificial Sequence
<220> FEATURE:
<223> OTHER INFORMATION: Synthetic sequence

<400> SEQUENCE: 212
ggcgggtcat gggaataac                                                 19

<210> SEQ ID NO 213
<211> LENGTH: 468
<212> TYPE: PRT
<213> ORGANISM: Artificial Sequence
<220> FEATURE:
<223> OTHER INFORMATION: Synthetic sequence

<400> SEQUENCE: 213

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Thr Pro Leu Ser Leu
    130                 135                 140

Ser Val Thr Pro Gly Gln Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Arg Thr Phe Gly Gly Gly Thr
225                 230                 235                 240

Lys Val Glu Ile Lys Arg Thr Thr Thr Pro Ala Pro Arg Pro Pro Thr
            245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 214
<211> LENGTH: 1470
<212> TYPE: DNA
<213> ORGANISM: Artificial Sequence
<220> FEATURE:
<223> OTHER INFORMATION: Synthetic sequence

<400> SEQUENCE: 214
atggctctgc ctgtgacagc tctgctgctg cctctggctc tgcttcttca tgccgccaga    60
ccatctcagg tccagctagt acaaagcggc gccgaagtaa agaaacctgg tgcctctgtg   120
aaggtgagct gcaaggccag cggctacacc ttcaccagct accacatcca gtgggttcga   180
caggcccctg gacagagact agagtggatg ggctggatct atcctggcga cggcagcacc   240
cagtacaacg agaagttcaa gggcagagtt accatcaccc gagacaccag cgccagcaca   300
gcctatatgg agctgagcag cctgcgaagc gaggacacag ctgtttacta ttgtgccaga   360
gagggcaccc tactacgcaat ggattattgg gccaggggga ccaccgtgac cgtttcttct   420
ggaggcggag gttctggcgg cggaggaagt ggtggcggag gctcagatat tgtaatgacc   480
cagacacctc tgtccctgtc tgtgacacct ggacagcctg caagcatcag ctgtcggagc   540
agccagagca tcgttcacag caacggcaac acctacctgg aatggtatct gcagaagccc   600
ggacagtccc cccagctgct gatctacaag gtgtccaacc gcttcagtgg agtacccgat   660

```
agattttctg gcagcggctc tggcaccgac ttcaccctga agatctccag agtagaagca    720
gaggacgttg gagtgtacta ctgcttccaa ggcagccatg tgccaagaac ctttggtgga    780
ggcacaaagg tggaaatcaa gcggacaaca acacctgctc ctcggcctcc tacaccagct    840
cctacaattg ccagccagcc actgtctctg aggcccgaag cttgcaggcc tgctgctggc    900
ggagccgtgc atacaagagg actggatttc gcctgcgaca tctacatctg gcacctctg     960 gctggaacct gtggcgtgct gctgctgagc ctggtcatca ccctgtattg ccggagcaag    1020
agaagcagac tgctgcacag cgactacatg aacatgaccc ctagacggcc cggacctacc    1080
agaaagcact accagcctta cgctcctcct agagacttcg ccgcctacag atccagagtg    1140
aagttcagca gatccgccga cgctcctgcc tatcagcagg gccaaaacca gctctacaac    1200
gagctgaacc tggggagaag agaagagtac gacgtgctgg acaagcggag aggcagagat    1260
cctgaaatgg gcggcaagcc agacggaag aatcctcaag agggcctgta taatgagcta    1320
cagaaagaca gatggcaga ggcctacagc gagatcggaa tgaagggcga gcgcagaaga    1380
ggcaagggac acgatggact gtaccagggc ctgagcaccg ccaccaagga tacctatgat    1440
gccctgcaca tgcaggccct gcctccaaga                                    1470

<210> SEQ ID NO 215
<211> LENGTH: 126
<212> TYPE: DNA
<213> ORGANISM: Artificial Sequence
<220> FEATURE:
<223> OTHER INFORMATION: Synthetic sequence

<400> SEQUENCE: 215
aaacggggca gaaagaaact cctgtatata ttcaaacaac catttatgag accagtacaa    60
actactcaag aggaagatgg ctgtagctgc cgatttccag aagaagaaga aggaggatgt    120
gaactg                                                             126

<210> SEQ ID NO 216
<211> LENGTH: 42
<212> TYPE: PRT
<213> ORGANISM: Artificial Sequence
<220> FEATURE:
<223> OTHER INFORMATION: Synthetic sequence

<400> SEQUENCE: 216

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 217
<211> LENGTH: 135
<212> TYPE: DNA
<213> ORGANISM: Artificial Sequence
<220> FEATURE:
<223> OTHER INFORMATION: Synthetic sequence

<400> SEQUENCE: 217
accacgacgc cagcgccgcg accaccaaca ccggcgccca ccatcgcgtc gcagcccctg    60
tccctgcgcc cagaggcgtg ccggccagcg gcgggggggcg cagtgcacac gagggggctg    120
gacttcgcct gtgat                                                   135
```

<210> SEQ ID NO 218
<211> LENGTH: 47
<212> TYPE: PRT
<213> ORGANISM: Artificial Sequence
<220> FEATURE:
<223> OTHER INFORMATION: Synthetic sequence

<400> SEQUENCE: 218

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 219
<211> LENGTH: 45
<212> TYPE: PRT
<213> ORGANISM: Artificial Sequence
<220> FEATURE:
<223> OTHER INFORMATION: Synthetic sequence

<400> SEQUENCE: 219

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 220
<211> LENGTH: 135
<212> TYPE: DNA
<213> ORGANISM: Artificial Sequence
<220> FEATURE:
<223> OTHER INFORMATION: Synthetic sequence

<400> SEQUENCE: 220

```
acaacaacac ctgctcctcg gcctcctaca ccagctccta caattgccag ccagccactg    60
tctctgaggc ccgaagcttg caggcctgct gctggcggag ccgtgcatac aagaggactg   120
gatttcgcct gcgac                                                    135
```

<210> SEQ ID NO 221
<211> LENGTH: 22
<212> TYPE: PRT
<213> ORGANISM: Artificial Sequence
<220> FEATURE:
<223> OTHER INFORMATION: Synthetic sequence

<400> SEQUENCE: 221

```
Ile Trp Ala Pro Leu Ala Gly Thr Cys Gly Val Leu Leu Leu Ser Leu
1               5                   10                  15

Val Ile Thr Leu Tyr Cys
            20
```

<210> SEQ ID NO 222
<211> LENGTH: 72
<212> TYPE: DNA
<213> ORGANISM: Artificial Sequence
<220> FEATURE:
<223> OTHER INFORMATION: Synthetic sequence

```
<400> SEQUENCE: 222
atctacatct gggcgccctt ggccgggact tgtggggtcc ttctcctgtc actggttatc    60 acccttact gc                                                         72

<210> SEQ ID NO 223
<211> LENGTH: 24
<212> TYPE: PRT
<213> ORGANISM: Artificial Sequence
<220> FEATURE:
<223> OTHER INFORMATION: Synthetic sequence

<400> SEQUENCE: 223

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 224
<211> LENGTH: 72
<212> TYPE: DNA
<213> ORGANISM: Artificial Sequence
<220> FEATURE:
<223> OTHER INFORMATION: Synthetic sequence

<400> SEQUENCE: 224
atctacatct gggcacctct ggctggaacc tgtggcgtgc tgctgctgag cctggtcatc    60
accctgtatt gc                                                        72
```